US009555087B2

(12) United States Patent
Toporik et al.

(10) Patent No.: US 9,555,087 B2
(45) Date of Patent: Jan. 31, 2017

(54) POLYPEPTIDES AND POLYNUCLEOTIDES, AND USES THEREOF AS A DRUG TARGET FOR PRODUCING DRUGS AND BIOLOGICS

(71) Applicant: Compugen Ltd., Tel Aviv-Jaffa (IL)

(72) Inventors: Amir Toporik, Holon (IL); Amit Novik, Binyamina (IL); Anat Cohen-Dayag, Rehovot (IL); Avi Yeshah Rosenberg, Kfar Saba (IL); Cynthia Koifman, Kefar Sava (IL); Dalit Landesman-Milo, Ramat Gan (IL); Eve Montia, Rehovot (IL); Galit Rotman, Herzliyya (IL); Liat Dassa, Yehud (IL); Marina Bubis, Rehovot (IL); Merav Beiman, Tel Aviv-Jaffa (IL); Ofer Levi, Moshav Mesisraelat Zion (IL); Sergey Nemzer, Ra'ananna (IL); Tania Pergam, Rishon LeZiyyon (IL); Yaron Kinar, Tel Aviv-Jaffa (IL); Shirley Sameach- Greenwald, Kfar Saba (IL); Zurit Levine, Herzliyya (IL); Shira Walach, Hod Hasharon (IL)

(73) Assignee: COMPUGEN LTD, Holon (IL)

( * ) Notice: Subject to any disclaimer, the term of this patent is extended or adjusted under 35 U.S.C. 154(b) by 177 days.

(21) Appl. No.: 14/469,546

(22) Filed: Aug. 26, 2014

(65) Prior Publication Data

US 2014/0363446 A1 Dec. 11, 2014

Related U.S. Application Data

(63) Continuation of application No. 13/767,891, filed on Feb. 15, 2013, now Pat. No. 9,107,862, which is a (Continued)

(51) Int. Cl.

| | |
|---|---|
| ***C07K 14/705*** | (2006.01) |
| ***A61K 38/17*** | (2006.01) |
| ***A61K 39/00*** | (2006.01) |
| ***C07K 16/30*** | (2006.01) |
| ***G01N 33/564*** | (2006.01) |
| ***G01N 33/574*** | (2006.01) |

(Continued)

(52) U.S. Cl.

CPC ....... *A61K 39/0008* (2013.01); *A61K 31/7088* (2013.01); *A61K 39/00* (2013.01); *A61K 39/0005* (2013.01); *A61K 39/39* (2013.01); *A61K 39/395* (2013.01); *A61K 39/3955* (2013.01); *A61K 39/39558* (2013.01); *A61K 45/06* (2013.01); *A61K 47/48569* (2013.01); *A61N 5/10* (2013.01); *C07K 14/00* (2013.01); *C07K 14/47* (2013.01); *C07K 14/4702* (2013.01); *C07K 14/705* (2013.01); *C07K 14/70503* (2013.01); *C07K 14/82* (2013.01); *C07K 16/28* (2013.01); *C07K 16/30* (2013.01); *G01N 33/564* (2013.01); *G01N 33/57419* (2013.01); *G01N 33/57423* (2013.01); *G01N 33/57449* (2013.01); *G01N 33/57484* (2013.01); *G01N 33/57492* (2013.01); *A61K 38/00* (2013.01); *A61K 2039/505* (2013.01); *A61K 2039/545* (2013.01); *C07K 2317/21* (2013.01); *C07K 2317/76* (2013.01); *C07K 2319/00* (2013.01); *C07K 2319/30* (2013.01); *C07K 2319/60* (2013.01); *C07K 2319/70* (2013.01); *G01N 2500/04* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,366,241 | A | 12/1982 | Tom |

(Continued)

FOREIGN PATENT DOCUMENTS

| | | |
|---|---|---|
| EP | 0154316 | 9/1985 |
| EP | 0264166 | 4/1988 |

(Continued)

OTHER PUBLICATIONS

Declaration filed on Oct. 20, 2012 in U.S. Appl. No. 12/676,359, 47 pages.*

(Continued)

*Primary Examiner* — Ilia Ouspenski

(74) *Attorney, Agent, or Firm* — Graeser Associates International Inc; Dvorah Graeser

(57) ABSTRACT

This invention relates to a novel target for production of immune and non-immune based therapeutics and for disease diagnosis. More particularly, the invention provides therapeutic antibodies against VSIG1, ILDR1, LOC253012, AI216611, C1ORF32 or FXYD3 antigens, which are predicted co-stimulatory family members and which are differentially expressed in cancers including, lung cancer, ovarian cancer, and colon cancer, and diagnostic and therapeutic usages. The use of these antibodies for modulating B7 costimulation and related therapies such as the treatment of autoimmunity are also provided. This invention further relates to the discovery of extracellular domains of VSIG1 and its variants, FXYD3 and its variants, ILDR1 and its variants, LOC253012 and its variants, AI216611 and its variants, and C1ORF32 and its variants awhich are suitable targets for immunotherapy, cancer therapy, and drug development.

27 Claims, 128 Drawing Sheets

Related U.S. Application Data continuation of application No. 12/676,359, filed as application No. PCT/US2008/075122 on Sep. 3, 2008, now Pat. No. 8,415,455.

(60) Provisional application No. 60/969,865, filed on Sep. 4, 2007, provisional application No. 60/969,799, filed on Sep. 4, 2007, provisional application No. 60/969,780, filed on Sep. 4, 2007, provisional application No. 60/969,806, filed on Sep. 4, 2007, provisional application No. 60/969,769, filed on Sep. 4, 2007, provisional application No. 60/969,788, filed on Sep. 4, 2007.

(51) Int. Cl.

| | |
|---|---|
| ***A61K 31/7088*** | (2006.01) |
| ***C07K 14/47*** | (2006.01) |
| ***C07K 14/82*** | (2006.01) |
| ***A61K 39/395*** | (2006.01) |
| ***A61K 45/06*** | (2006.01) |
| ***C07K 14/00*** | (2006.01) |
| ***C07K 16/28*** | (2006.01) |
| ***A61K 39/39*** | (2006.01) |
| ***A61K 47/48*** | (2006.01) |
| ***A61N 5/10*** | (2006.01) |
| *A61K 38/00* | (2006.01) |

(56) References Cited

U.S. PATENT DOCUMENTS 4,376,110 A 3/1983 David
4,399,216 A 8/1983 Axel
4,439,196 A 3/1984 Higuchi
4,447,224 A 5/1984 DeCant, Jr.
4,447,233 A 5/1984 Mayfield
4,469,863 A 9/1984 Ts'o et al.
4,475,196 A 10/1984 La Zor
4,476,301 A 10/1984 Imbach
4,486,194 A 12/1984 Ferrara
4,487,603 A 12/1984 Harris
4,517,288 A 5/1985 Giegel
4,522,811 A 6/1985 Eppstein
4,596,556 A 6/1986 Morrow
4,634,665 A 1/1987 Axel
4,790,824 A 12/1988 Morrow
4,816,567 A 3/1989 Cabilly
4,837,168 A 6/1989 de Jaeger
4,837,306 A 6/1989 Ling et al.
4,873,316 A 10/1989 Meade
4,881,175 A 11/1989 Ladner
4,941,880 A 7/1990 Burns
4,946,778 A 8/1990 Ladner
4,954,617 A 9/1990 Fanger
5,013,653 A 5/1991 Huston
5,023,243 A 6/1991 Tullis
5,034,506 A 7/1991 Summerton
5,064,413 A 11/1991 McKinnon
5,091,513 A 2/1992 Huston
5,132,405 A 7/1992 Huston
5,166,315 A 11/1992 Summerton
5,177,196 A 1/1993 Meyer, Jr.
5,179,017 A 1/1993 Axel
5,185,444 A 2/1993 Summerton
5,188,897 A 2/1993 Suhadolnik
5,214,134 A 5/1993 Weis
5,216,141 A 6/1993 Benner
5,223,409 A 6/1993 Ladner
5,225,538 A 7/1993 Capon et al.
5,225,539 A 7/1993 Winter
5,235,033 A 8/1993 Summerton
5,258,498 A 11/1993 Huston
5,260,203 A 11/1993 Ladner
5,264,423 A 11/1993 Cohen
5,264,562 A 11/1993 Matteucci
5,264,564 A 11/1993 Matteucci
5,276,019 A 1/1994 Cohen
5,278,302 A 1/1994 Caruthers
5,286,717 A 2/1994 Cohen
5,312,335 A 5/1994 McKinnon
5,321,131 A 6/1994 Agrawal
5,374,548 A 12/1994 Caras
5,383,851 A 1/1995 McKinnon, Jr.
5,399,163 A 3/1995 Peterson
5,399,331 A 3/1995 Loughrey
5,399,676 A 3/1995 Froehler
5,403,484 A 4/1995 Ladner
5,405,938 A 4/1995 Summerton et al.
5,405,939 A 4/1995 Suhadolnik et al.
5,416,016 A 5/1995 Low
5,427,908 A 6/1995 Dower
5,434,257 A 7/1995 Matteucci
5,453,496 A 9/1995 Caruthers
5,455,030 A 10/1995 Ladner
5,455,233 A 10/1995 Spielvogel
5,466,677 A 11/1995 Baxter
5,470,967 A 11/1995 Huie
5,476,786 A 12/1995 Huston
5,476,925 A 12/1995 Letsinger
5,476,996 A 12/1995 Wilson
5,482,858 A 1/1996 Huston
5,489,677 A 2/1996 Sanghvi
5,519,126 A 5/1996 Hecht
5,530,101 A 6/1996 Queen
5,536,821 A 7/1996 Agrawal
5,539,082 A 7/1996 Nielsen
5,541,306 A 7/1996 Agrawal
5,541,307 A 7/1996 Cook
5,545,806 A 8/1996 Lonberg
5,545,807 A 8/1996 Surani
5,550,111 A 8/1996 Suhadolnik
5,561,225 A 10/1996 Maddry
5,563,253 A 10/1996 Agrawal
5,569,825 A 10/1996 Lonberg
5,571,698 A 11/1996 Ladner
5,571,799 A 11/1996 Tkachuk
5,580,717 A 12/1996 Dower
5,585,089 A 12/1996 Queen
5,587,361 A 12/1996 Cook
5,596,086 A 1/1997 Matteucci
5,602,240 A 2/1997 De Mesmaeker
5,608,046 A 3/1997 Cook
5,610,289 A 3/1997 Cook
5,618,704 A 4/1997 Sanghvi
5,623,070 A 4/1997 Cook
5,624,821 A 4/1997 Winter
5,625,050 A 4/1997 Beaton
5,625,126 A 4/1997 Lonberg
5,625,825 A 4/1997 Rostoker
5,633,360 A 5/1997 Bischofberger
5,633,425 A 5/1997 Lonberg
5,648,260 A 7/1997 Winter
5,661,016 A 8/1997 Lonberg
5,663,312 A 9/1997 Chaturvedula
5,677,425 A 10/1997 Bodmer
5,677,437 A 10/1997 Teng
5,677,439 A 10/1997 Weis
5,693,762 A 12/1997 Queen
5,698,767 A 12/1997 Wilson
5,714,331 A 2/1998 Buchardt
5,714,350 A 2/1998 Co
5,719,262 A 2/1998 Buchardt
5,770,429 A 6/1998 Lonberg
5,789,650 A 8/1998 Lonberg
5,814,318 A 9/1998 Lonberg
5,869,046 A 2/1999 Presta
5,874,299 A 2/1999 Lonberg
5,877,397 A 3/1999 Lonberg
5,885,793 A 3/1999 Griffiths
5,939,598 A 8/1999 Kucherlapati
5,969,108 A 10/1999 McCafferty
6,075,181 A 6/2000 Kucherlapati

(56) References Cited

U.S. PATENT DOCUMENTS

| | | | | |
|---|---|---|---|---|
| 6,114,598 | A | 9/2000 | Kucherlapati | |
| 6,121,022 | A | 9/2000 | Presta | |
| 6,150,584 | A | 11/2000 | Kucherlapati | |
| 6,162,963 | A | 12/2000 | Kucherlapati | |
| 6,165,745 | A | 12/2000 | Ward | |
| 6,172,197 | B1 | 1/2001 | McCafferty | |
| 6,180,370 | B1 | 1/2001 | Queen | |
| 6,194,551 | B1 | 2/2001 | Idusogie | |
| 6,277,375 | B1 | 8/2001 | Ward | |
| 6,303,374 | B1 | 10/2001 | Zhang | |
| 6,350,861 | B1 | 2/2002 | Co | |
| 6,521,404 | B1 | 2/2003 | Griffiths | |
| 6,544,731 | B1 | 4/2003 | Griffiths | |
| 6,555,313 | B1 | 4/2003 | Griffiths | |
| 6,582,915 | B1 | 6/2003 | Griffiths | |
| 6,593,081 | B1 | 7/2003 | Griffiths | |
| 6,709,654 | B1 | 3/2004 | Anderson et al. | |
| 7,189,507 | B2 | 3/2007 | Mack | |
| 7,745,391 | B2 | 6/2010 | Mintz et al. | |
| 7,829,084 | B2 | 11/2010 | Ledbetter et al. | |
| 7,842,665 | B2 | 11/2010 | Levin et al. | |
| 7,982,017 | B2 | 7/2011 | Lin et al. | |
| 8,043,616 | B2 | 10/2011 | Anderson et al. | |
| 8,080,246 | B2 | 12/2011 | Lin et al. | |
| 8,183,207 | B2 | 5/2012 | Lin et al. | |
| 8,293,883 | B2 | 10/2012 | Presta | |
| 8,318,159 | B2 | 11/2012 | Adam et al. | |
| 8,318,168 | B2 | 11/2012 | Sass et al. | |
| 8,415,455 | B2 * | 4/2013 | Levine | C07K 14/47 530/350 |
| 9,107,862 | B2 * | 8/2015 | Toporik | C07K 14/47 |
| 2002/0037286 | A1 | 3/2002 | Krause et al. | |
| 2002/0193567 | A1 | 12/2002 | Jacobs | |
| 2004/0009481 | A1 | 1/2004 | Schlegel | |
| 2004/0110704 | A1 | 6/2004 | Yamane | |
| 2006/0034852 | A1 | 2/2006 | Rixon | |
| 2008/0299042 | A1 | 12/2008 | Bechtel et al. | |
| 2011/0151515 | A1 | 6/2011 | Heifetz et al. | |
| 2011/0281302 | A1 | 11/2011 | Williams et al. | |
| 2012/0128672 | A1 | 5/2012 | Keer | |
| 2012/0141573 | A1 | 6/2012 | Ling et al. | |
| 2012/0219559 | A1 | 8/2012 | Chen | |
| 2013/0160150 | A1 | 6/2013 | Leibel et al. | |
| 2014/0170141 | A1 * | 6/2014 | Toporik | C07K 14/70503 424/134.1 |

FOREIGN PATENT DOCUMENTS

| | | | |
|---|---|---|---|
| EP | 0338841 | | 10/1989 |
| EP | 0401384 | | 12/1990 |
| EP | 1176195 | | 1/2002 |
| EP | 2116259 | A1 | 11/2009 |
| EP | 2190469 | A2 | 6/2010 |
| WO | WO 87/04462 | | 7/1987 |
| WO | WO 87/05330 | | 9/1987 |
| WO | WO 88/00052 | | 1/1988 |
| WO | WO 89/01036 | | 2/1989 |
| WO | WO 92/03918 | | 3/1992 |
| WO | WO 93/12227 | | 6/1993 |
| WO | WO 94/10332 | | 5/1994 |
| WO | WO 94/25585 | | 11/1994 |
| WO | WO 94/29351 | | 12/1994 |
| WO | WO 97/13852 | | 4/1997 |
| WO | WO 98/24884 | | 6/1998 |
| WO | WO 99/26972 | | 6/1999 |
| WO | WO 99/45962 | | 9/1999 |
| WO | WO 99/54342 | | 10/1999 |
| WO | WO 99/60020 | | 11/1999 |
| WO | WO 00/42072 | | 7/2000 |
| WO | WO 01/09187 | | 2/2001 |
| WO | WO 01/14424 | | 3/2001 |
| WO | WO 02/26930 | | 4/2002 |
| WO | WO 02/43478 | | 6/2002 |
| WO | WO 02/092780 | | 11/2002 |
| WO | WO 03/000012 | | 1/2003 |
| WO | WO 03/027228 | | 4/2003 |
| WO | WO 03/035835 | | 5/2003 |
| WO | WO 03/074679 | | 9/2003 |
| WO | WO 03/101283 | | 12/2003 |
| WO | WO 2004/037999 | | 5/2004 |
| WO | WO 2004/048550 | | 6/2004 |
| WO | WO 2004/100774 | | 11/2004 |
| WO | WO 2005/108415 | | 11/2005 |
| WO | WO 2006/050247 | | 5/2006 |
| WO | WO 2006/050262 | | 5/2006 |
| WO | 2007014123 | A2 | 2/2007 |
| WO | 2007106056 | A1 | 9/2007 |
| WO | 2008049070 | A2 | 4/2008 |
| WO | 2008131242 | A1 | 10/2008 |
| WO | 2009032845 | A2 | 3/2009 |
| WO | 2009055074 | A2 | 4/2009 |
| WO | 2009076651 | A2 | 6/2009 |
| WO | 2010017198 | A2 | 2/2010 |
| WO | 2012001647 | A2 | 1/2012 |
| WO | 2012006027 | A1 | 1/2012 |
| WO | 2012144692 | | 10/2012 |
| WO | 2013/114367 | | 8/2013 |

OTHER PUBLICATIONS

Sequence alignment, 2016, 2 pages.*

Rentero, Inmaculada, and Christian Heinis. "Screening of large molecule diversities by phage display." CHIMIA International Journal for Chemistry 65.11 (2011): 843-845.

Blast Search results from related U.S. Appl. No. 13/767,891—Oct. 2014.

Extended European Search Report from related EP14162019 mailed on Jul. 28, 2014.

Blast Search results from related U.S. Appl. No. 13/845,420—Dec. 2014.

Lederman, Seth, et al. "A single amino acid substitution in a common African allele of the CD4 molecule ablates binding of the monoclonal antibody, OKT4." Molecular immunology 28.11 (1991): 1171-1181.

Colman, Peter M. "Effects of amino acid sequence changes on antibody-antigen interactions." Research in Immunology 145.1 (1994): 33-36.

Riches et al. 2009. Recent insights into the pathogenesis of hyperuricaemia and gout. Hum Mol Genet.; 18:R177-84.

Masseoud et al. 2005. Overview of hyperuricaemia and gout. Curr Pharm Des.; 11(32):4117-24.

Bencardino and Flassankhani. 2003. Calcium pyrophosphate dihydrate crystal deposition disease. Semin Musculoskelet Radiol.; 7(3):175-85.

Zaka R. and Williams C.J. 2005. Genetics of chondrocalcinosis. OsteoArthritis and Cartilage; 13,745-750.

Langford CA. 2010. Vasculitis. J Allergy Clin Immunol; 125:S216-225.

Khasnis and Langford. 2009. Update on vasculitis. J Allergy Clin Immunol; 123:1226-36.

Miller et al. 2010. An approach to the diagnosis and management of systemic vasculitis. Clinical and Experimental Immunology, 160: 143-160.

Gonzalez et al. 2009. Pediatric Henoch-Schönlein purpura. International Journal of Dermatology; 48: 1157-1165.

Pillebout et al. 2002. Henoch-Schönlein Purpura in Adults: Outcome and Prognostic Factors. J Am Soc Nephrol; 13: 1271-1278.

Genta et al. 2006. Systemic rheumatoid vasculitis: a review. Semin Arthritis Rheum; 36:88-98.

Olivencia-Simmons I. 2007. Wegener's granulomatosis: Symptoms, diagnosis, and treatment. J. of the American Academy of Nurse Practitioners 19:315-320.

Hua et al. 2009. T-Lymphocytes and Disease Mechanisms in Wegener's Granulomatosis. Kidney Blood Press Res; 32:389-398.

Moosig et al. 2008. Wegener's Granulomatosis: The Current View. Clinic Rev Allerg Immunol; 35:19-21.

Khan MA. 2002. Update on spondyloarthropathies. Ann Intern Med.; 136(12):896-907.

(56) References Cited

OTHER PUBLICATIONS

Rostom et al. 2010. New tools for diagnosing spondyloarthropathy. Joint Bone Spine; 77:108-114.
FitzGerald and McInnes. 2006. Spondyloarthropathy: disease at the crossroads of immunity. Best Practice & Research Clinical Rheumatology; 20(5): 949-967.
Brown, 2008. Breakthroughs in genetic studies of ankylosing spondylitis. Rheumatology, vol. 47(2): 132-137.
Brionez and Reveille. 2008. The contribution of genes outside the major histocompatibility complex to susceptibility to ankylosing spondylitis. Curr Opin Rheumatol.; 20(4):384-91.
Kwiatkowska B. and Filipowicz?Sosnowska A. 2009. Reactive arthritis. Pol Arch Med Wewn; 119 (1?2): 60-65.
Rohekar S. and Pope J. 2009. Epidemiologic approaches to infection and immunity: the case of reactive arthritis. Curr Opin Rheumatol.; 21(4):386-90.
Kim et al. 2009. Reactive arthritis: a review. J Adolesc Health; 44(4):309-15.
Gladman et al. 2005. Psoriatic arthritis: epidemiology, clinical features, course, and outcome. Ann Rheum Dis.; 64 (Suppl 2):ii14-ii17.
Leung et al. 2007. Psoriatic arthritis as a distinct disease entity. J Postgrad Med.; 53(1):63-71.
Ho et al. 2008. Investigating the role of the HLA-Cw*06 and HLA-DRB1 genes in susceptibility to psoriatic arthritis: comparison with psoriasis and undifferentiated inflammatory arthritis. Ann Rheum Dis 67(5):677-682.
Wollheim FA. 2001. Enteropathic arthritis: how do the joints talk with the gut? Curr Opin Rheumatol; 13:305-309.
Colombo et al. 2009. Enteropathic spondyloarthropathy: a common genetic background with inflammatory bowel disease? World J Gastroenterol.; 15(20):2456-62.
Nade S. 2003. Septic arthritis. Best Practice & Research Clinical Rheumatology; 17(2): 183-200.
Mathews CJ. and Coakley G. 2008. Septic arthritis: current diagnostic and therapeutic algorithm. Current Opinion in Rheumatology; 20:457-462.
Tarkowski A. 2006. Infectious arthritis. Best Practice & Research Clinical Rheumatology; 20(6): 1029-1044.
Marques AR. 2010. Lyme disease: A Review. Curr Allergy Asthma Rep; 10:13-20.
Murray TS. and Shapiro ED. 2010. Lyme disease. Clin Lab Med.; 30(1):311-28.
Bratton et al. 2008. Diagnosis and treatment of Lyme disease. Mayo Clinic Proceedings; 83(5):566-571.
Jannuzzi et al. 2007. Sarcoidosis. N Engl J Med; 357:2153-2165.
Chen and Moller. 2008. Etiology of sarcoidosis. Clin Chest Med. ;29(3):365-77.
Ben-Chetrit and Touitou L 2009. Familial Mediterranean fever in the world. Arthritis Rheum.; 61(10):1447-53.
Chae et al. 2009. Advances in the understanding of familial Mediterranean fever and possibilities for targeted therapy. Br J Haematol.; 146(5):467-78.
van der Hilst et al. 2008. Long-term follow-up, clinical features, and quality of life in a series of 103 patients with hyperimmunoglobulinemia D syndrome. Medicine; 87(6):301-310.
Simon et al. 2001. Molecular analysis of the mevalonate kinase gene in a cohort of patients with the hyper-IgD and periodic fever syndrome: its application as a diagnostic tool. Ann Intern Med.; 135:338-343.
Rezaei N. 2006. TNF-receptor-associated periodic syndrome (TRAPS): an autosomal dominant multisystem disorder. Clin Rheumatol.; 25(6):773-7.
Kimberley et al. 2007. Falling into TRAPS—receptor misfolding in the TNF receptor 1-associated periodic fever syndrome. Arthritis Research & Therapy; 9(4):217.
Hull et al. 2002. The TNF receptor-associated periodic syndrome (TRAPS): emerging concepts of an autoinflammatory disorder. Medicine (Baltimore); 81(5):349-368.
Mason and Reed. 2005. Update in Juvenile Rheumatoid Arthritis. Arthritis & Rheumatism.; 53 (5): 796-799.
Stastny and Fink. 1979. Different HLA-D associations in adult and juvenile rheumatoid arthritis. J. Clin. Invest.; 53:124-130.
Thomson et al. 2002. Juvenile idiopathic arthritis classi?ed by the ILAR criteria: HLA associations in UK patients. Rheumatology; 41:1183-1189.
Woo P. 2006. Systemic juvenile idiopathic arthritis: Diagnosis, management, and outcome. Nat Clin Pract Rheumatol.;2:28-34.
Buckwalter and Martin. 2006. Osteoarthritis. Adv Drug Deliv Rev.; 20;58(2):150-67.
Brandt et al. 2009. Etiopathogenesis of osteoarthritis. Med Clin North Am.; 93(1):1-24.
Ayonrinde et al. 2008. Clinical perspectives on hereditary hemochromatosis. Critical Reviews in Clinical Laboratory Sciences; 45(5):451-484.
Brissot et al. 2008. Current approach to hemochromatosis. Blood Reviews; 22: 195-210.
Adams PC and Barton JC. 2007. Haemochromatosis. Lancet; 370: 1855-1860.
Teufel et al. 2009. Update on autoimmune hepatitis. World J Gastroenterol; 15(9): 1035-1041.
Foster GR. 2009. Recent advances in viral hepatitis. Clinical Medicine; 9(6): 613-616.
Rizzetto M. 2010. Hepatitis D: clinical features and therapy. Dig Dis.; 28:139-143.
Lucey et al. 2009. Alcoholic Hepatitis. N Engl J Med; 360:2758-2769.
Krasnokutski et al, Osteoarthritis and Cartilage (2008) 16, S1-S3.
Michels, Aaron W, and George S. Eisenbarth. "Immune intervention in type 1 diabetes." Seminars in immunology. vol. 23. No. 3. Academic Press, 2011.
Gillard, Pieter, and Chantal Mathieu. "Immune and cell therapy in type 1 diabetes: too little too late?." Expert opinion on biological therapy 11.5 (2011): 609-621.
Bluestone, Jeffrey A., and Hélène Bour-Jordan. "Current and future immunomodulation strategies to restore tolerance in autoimmune diseases." Cold Spring Harbor perspectives in biology 4.11 (2012): a007542.
Herrath, M., M. Peakman, and B. Roep. "Progress in immune-based therapies for type 1 diabetes." Clinical & Experimental Immunology 172.2 (2013): 186-202.
Coppieters, Ken T., Leonard C. Harrison, and Matthias G. von Herrath. "Trials in type 1 diabetes: Antigen-specific therapies." Clinical Immunology149.3 (2013): 345-355.
Fulpius, Thierry, et al. "Glomerulopathy induced by IgG3 anti-trinitrophenyl monoclonal cryoglobulins derived from non-autoimmune mice." Kidney international 45.4 (1994): 962-971.
Office Action from related AU2013216320 mailed on Mar. 11, 2016.
International Search Report and Written Opinion for PCT/US2008/075122 dated Apr. 9, 2009.
Supplementary European Search Report for EP08829443.4 dated Dec. 14, 2010.
Database UniProt [Online], Jul. 5, 2004, "RecName: Full=Immunoglobin-like-domain-containing receptor 2;" XP002614181 retrieved from EPI Database accession No. Q71H61.
Heidi Schultz, Towards a Comprehensive Description of the Human Retinal Transcriptome:Identification and Characterization of Differentially Expressed Genes, [Online], 2003, PhD Thesis—Würzburg University.
Valeria Roni et al., Mapping of transcription start sites of human retina expressed genes, BMC Genomics, 2007, vol. 8:42.
Office Action for EP08829443.4 dated Feb. 7, 2011.
Markomichelakis, et al., Regression of neovascular age-related macular degeneration following infliximab therapy, American Journal of Ophthalmology, 2005, vol. 139, Issue 3.
Nussenblatt et al., Perspectives: Age Related Macular Degeneration and the Immune Response—Implications for Therapy, American Journal of Ophthalmology, 2007, vol. 144, Issue 4.
Altschul, et al., Basic Local Allignment Search Tool, J Mol. Biol.; 1990; 215:403-10.
Arimochi et al., Interaction of Mat-8 (FXYD-3) with Na/K-ATPase in Colorectal Cancer Cells, Biol. Pharm. Bull., 2007; 30(4) 648-654.

(56) References Cited

OTHER PUBLICATIONS

Bibert et al.; Structural and Functional Properties of Two Human FXYD3 (Mat-8) Isoforms; The Journal of Biological Chemistry; 2006; vol. 281, 51:39142-39151.
Crambert et al.; FXYD3 (Mat-8), a New Regulator of Na,K-ATPase; Molecular Biology of the Cell; 2005; 16:2363-2371.
Fahrlander, P.D. and Klausner A., Amplifying DNA Probe Signals: A 'Christmas Tree' Approach; Bio/Technology; 1988; 6:1165.
Geering; FXYD proteins: new regulators of Na—K-ATPase; AJP—Renal Physiology; 2006; 290:F241-F250.
Gregory SG et al.; The DNA sequence and biological annotation of human chromosome 1; Nature; 2006, 441 (7091):315-321.
Grzmil et al.; Up-regulated expression of the MAT-8 gene in prostate cancer and its siRNA-mediated inhibition of expression induces a decrease in proliferation of human prostate carcinoma cells; International Journal of Oncology; 2004; 24:97-105.
Huston et al.; Protein engineering of antibody binding sites: Recovery of specific activity in an anti-digoxin single-chain Fv analogue produced in *Escherichia coli*; Proc. Natl. Acad. Sci. USA; 1988; 85:5879-5883.
Kayed et al.; FXYD3 is overexpressed in pancreatic ductal adenocarcinoma and influences pancreatic cancer cell growth; Int. J. Cancer:; 2006; 118:43-54.
M. Clark; Chemical Immunol and Antibody Engineering; 1991 Cambridge; pp. 1-31.
Morrison et al.; Mat-8, a Novel Phospholemman-like Protein Expressed in Human Breast Tumors, Induces a Chloride Conductance in Xenopus Oocytes; The Journal of Biological Chemistry ; 1995; 270:2176-2182.
Needleman and Wunsch; A general method applicable to the search for similarities in the amino acid sequence of two proteins; J. Mol. Biol.; 1970; 48:444-453.
Scanlan et al.; Glycoprotein A34, a novel target for antibody-based cancer immunotherapy; Cancer Immunotherapy; 2006; 6:2.
Shields et al.; High Resolution Mapping of the Binding Site on Human IgG1 for FcgRI, FcgRII, FcgRIII, and FcRn and Design of IgG1 Variants with Improved Binding to the FcgR*; The Journal of Biological Chemistry; 2001; 276:6591-6604.
Takebe Y. et al.; SR alpha promoter: an efficient and versatile mammalian cDNA expression system composed of the simian virus 40 early promoter and the R-U5 segment of human T-cell leukemia virus type 1 long terminal repeat; Mol. Cell. Biol.; 1988; 8:466-472.
Umana et al.; Engineered glycoforms of an antineuroblastoma IgG1 with optimized antibodydependent cellular cytotoxic activity; Nat. Biotech.; 1999; 17:176-180.
Urlaub and Chasin; Isolation of Chinese hamster cell mutants deficient in dihydrofolate reductase activity; Proc. Natl. Acad. Sci. USA; 1980; 77:4216-4220.
Altschul et al., Gapped Blast and PSI-Blast: a new generation of protein database search programs; Nucleic Acids Res.; 1997; 25(17):3389-3402.
Baldari, et al.; A novel leader peptide which allows efficient secretion of a fragment of human interleukin 1 beta in *Saccharomyces cerevisiae*; EMBO J.; 1987; 6:229-234.
Byrne et al.; Multiplex gene regulation: A two-tiered approach to transgene regulation in transgenic mice; Proc. Natl. Acad. Sci. USA; 1989; 86:5473-5477.
Chen, J. et al.; B cell development in mice that lack one or both immunoglobulin x light chain genes; EMBO J.; 1993; 12:821-830.
Clark et al; The Secreted Protein Discovery Initiative (SPDI), a Large-Scale Effort to Identify Novel Human Secreted and Transmembrane Proteins: A Bioinformatics Assessment;Genome Res.; 2003; 13: 2265-2270.
Coruzzi et al.; Tissue-specific and light-regulated expression of a pea nuclear gene encoding the small subunit of ribulose-1,5-bisphosphate carboxylase; EMBO J.; 1984; 3:1671-1680.
Karpovsky et al.; Production of Target-Specific Effector Cells Using Hetero-Cross-Linked Aggregates Containing Anti-Target Cell and Anti-Fc3, Receptor Antibodies; J. Exp. Med.; 1984; 160:1686-1701.
Kaufman, et al., Translational efficiency of polycistronic mRNAs and their utilization to express heterologous genes in mammalian cells; EMBO J.; 1987; 6:187-195.
Kwoh et al., Transcription-based amplification system and detection of amplified human immunodeficiency virus type 1 with a bead-based sandwich hybridization format; Proc. Natl. Acad. Sci. USA; 1989; 86:1173-1177.
Liu, M A et al.; Heteroantibody duplexes target cells for lysis by cytotoxic T lymphocytes; Proc. Natl. Acad. Sci. USA; 1985; 82:8648-8652.
Owais et al.; Chloroquine Encapsulated in Malaria-Infected Erythrocyte-Specific Antibody-Bearing Liposomes Effectively Controls Chloroquine-Resistant Plasmodium berghei Infections in Mice†; Antimicrob. Agents Chemother.; 1995; 39:180-184.
Pinkert et al., An albumin enhancer located 10 kb upstream functions along with its promoter to direct efficient, liver-specific expression in transgenic mice; Genes and Development; 1987; 1:268-277.
Queen, C. et al.; A humanized antibody that binds to the interleukin 2 receptor; Proc. Natl. Acad. See. U.S.A.; 1989 86:10029-10033.
Shields, R. L. et al.; Lack of Fucose on Human IgG1 N-Linked Oligosaccharide Improves Binding to Human Fc.GAMA. RIII and Antibody-dependent Cellular Toxicity*; J. Biol. Chem.; 2002; 277:26733-26740.
Singhal et al.; Glutathione, a first line of defense against cadmium toxicity; FASEB J.; 1987; 1:220-223.
Smith, et al., Production of Human Beta Interferon in Insect Cells Infected with a Baculovirus Expression Vector; Mol. Cell. Biol.; 1983; 3:2156-2165.
Takamatsu et al.; Expression of bacterial chloramphenicol acetyltransferase gene in tobacco plants mediated by TMV-RNA; EMBO J.; 1987; 6:307-311.
Taylor, L. et al.; A transgenic mouse that expresses a diversity of human sequence heavy and light chain immunoglobulins; Nucleic Acids Research; 1992; 20:6287-6295.
Tomizuka et al.; Double trans-chromosomic mice: Maintenance of two individual human chromosome fragments containing Ig heavy and k loci and expression of fully human antibodies; Proc. Natl. Acad Sci. USA; 2000; 97:722-727.
Tuaillon et al.; Human immunoglobulin heavy-chain minilocus recombination in transgenic mice: Gene-segment use in ,u and y transcripts; Proc. Natl. Acad. Sci. USA; 1993; 90:3720-3724.
Winoto and Baltimore; A novel, inducible and T cell-specific enhancer located at the 3' end of the T cell receptor alpha locus; EMBO J.; 1989; 8:729-733.
Office Action for IL 204255 dated Jan. 30, 2013.
"Compugen Announces Positive Therapeutic Effects of CGEN 15001 in Aminal Model of Rheumatoid Arthritis", published Dec. 14, 2010, retrieved through the Internet, www.cgen.com.
Office Action for EP08829443.4 dated May 14, 2012.
Office Action for AU2008296361 dated Nov. 26, 2012.
Search report and written opinion for parent PCT application PCT/IB2011/052877, issued Aug. 9, 2012.
"CGEN-15001 an Example of Discovery on Demand", published Jul. 27, 2010, retrieved through the Internet, www.cgen.corn.
"New membrane protein for the treatment of autoimmune diseases", published Feb. 3, 2010, retrieved through the Internet, themspodcast.com.
Gonzalez Rey et al, Arthritis and Rheumatism, vol. 54, Jan. 2006, pp. 864-876.
Gonzalez Rey et al, Ann Rheum Dis, vol. 69, Jan. 1, 2010, pp. 241-248.
IPRP for PCT/1B2011/052877 mailed Jan. 8, 2013.
Office Action for EP08829443.4 dated Oct. 16, 2013.
Office Action for JP2011-505792 dated Feb. 18, 2014.
Office Action for CN201180038162.9 dated Feb. 19, 2014.
Office Action for AU2011272941 dated Feb. 19, 2014.
Crawford et al., Curr Opin Immunol. 2009;21:179-186.
Diepolder and Obst, Expert Rev Vaccines. Mar. 2010;9(3):243-7.
Follicular Helper CD4 T Cells (TFH), Crotty, Annu. Rev. Immunol. 29: 621-663, 2011.
Golden-Mason et al., J Viral. 2009;83:9122-30.

(56) References Cited

OTHER PUBLICATIONS

Ha et al, Immunol Rev. Jun. 2008;223:317-33.
Hofmeyer et al, J. Biomed. & Biotech. 2011, val 2011, The PD-1/PD-L1 (B7-H1) Pathway in Chronic Infection-InducedCytotoxic T Lymphocyte Exhaustion, Art. ID 451694, pp. 1-9.
Kaufmann et al., J Immuno12009;182:5891-5897.
Restoring function in exhausted CDS T cells during chronic viral infection, Barber et al., Nature. 2006;439:682-7.
Rivas et al., J Immunol. 2009 ;183:4284-91.
Sharpe et al., Nat Immunol 2007;8:239-245.
Target-Dependent B7-H1 Regulation Contributes to Clearance of Central Nervous Sysyem Infection and DampensMorbidity, Phares et al., J Immunol. 2009: 182; 5430-5438.
Velu et al., Nature 2009;458:206-210, Enhancing SIV-specific immunity in vivo by PD-1 blockade.
Database Uniprot[Online](Jul. 5, 2007), Accession No. Q71H61.
Taylor et al, Human chromosome 11 DNA sequence and analysis including novel gene identification, Nature, 2006, 440(7083), 497-500.
Yan et al, Genome sequencing and comparison of two nonhuman primate animal models, the cynomolgus and Chinese rhesus macaques, Nature Biotechnology, 2011, 29(11), 1019-1023.
Zimin et al, A whole-genome assembly of the domestic cow, Bos Taurus, Genome Biology, 2009, 10(4), R42.
Strausberg et al, Generation and initial analysis of more than 15,000 full-length human and mouse cDNA sequences, Proceedings of the National Academy of Sciences, 2002, 99(26), 16899-16903.
Li et al, The sequence and de novo assembly of the giant panda genome, Nature, 2010, 463(7279), 311-317.
Skarnes et al, A conditional knockout resource for the genome-wide study of mouse gene function, Nature, 2011, 474 (7351), 337-342.
Kim et al, Genome sequencing reveals insights into physiology and longevity of the naked mole rat, Nature, 2011, 479 (7372), 223-227.
OA for JP2011-505792 mailed Jul. 2, 2013.
GenBank Accession EAW90779, Dec. 2006.
Search report and written opinion for PCT/IB2012/053342 , mailed Sep. 23, 2012.
Fillatreau et al.: "B cells regulate autoimmunity by provision of IL-10" Nature Immunology 3, 944-950 (2002).
Lowes at al.: "Psoriasis vulgaris lesions contain discrete populations of Th1 and Th17 T cells" Jour. of investigative dermatology (2008) vol. 128 p. 1207-1211.
Marija Dokmanovic-Chouinard et al.: "Positional Cloning of "Lisch-like", a Candidate Modifier of Susceptibility to Type 2 Diabetes in Mice", PLoS Genetics, Jul. 25, 2008, vol. 4, Issue 7, e1000137.
Search report from the Singaporean Patent Office, mailed Jun. 12, 2015.
Dong, Haidong, et al. "B7-H1, a third member of the B7 family, co-stimulates T-cell proliferation and interleukin-10 secretion." Nature medicine 5.12 (1999): 1365-1369.
Freeman, Gordon J., et al. "Engagement of the PD-1 immunoinhibitory receptor by a novel B7 family member leads to negative regulation of lymphocyte activation." The Journal of experimental medicine 192.7 (2000): 1027-1034.
Tamura, Hideto, et al. "B7-H1 costimulation preferentially enhances CD28-independent T-helper cell function." Blood 97.6 (2001): 1809-1816.
Latchman, Yvette, et al. "PD-L2 is a second ligand for PD-1 and inhibits T cell activation." Nature immunology 2.3 (2001): 261-268.
Greaves, Paul, and John G. Gribben. "The role of B7 family molecules in hematologic malignancy." Blood 121.5 (2013): 734-744.
Li, Yili, Qian Wang, and Roy A. Mariuzza. "Structure of the human activating natural cytotoxicity receptor NKp30 bound to its tumor cell ligand B7-H6." The Journal of Experimental Medicine 208.4 (2011): 703-714.
Esserman, Laura J., et al. "Vaccination with the extracellular domain of p185 neu prevents mammary tumor development in neu transgenic mice." Cancer Immunology, Immunotherapy 47.6 (1999): 337-342.
Pirker, Robert, et al. "Cetuximab plus chemotherapy in patients with advanced non-small-cell lung cancer (FLEX): an open-label randomised phase III trial." The Lancet 373.9674 (2009): 1525-1531.
Zhao, Jie, et al. "Selective depletion of CD4+ CD25+ Foxp3+ regulatory T cells by low-dose cyclophosphamide is explained by reduced intracellular ATP levels." Cancer research 70.12 (2010): 4850-4858.

* cited by examiner

Alignment of:
AI581519_P4 x known protein(s) NP_872413 and Q86XK7_HUMAN:

```
                        .         .         .         .         .
  1 MVFAFWKVFLILSCLAGQVSVVQVTIPDGFVNVTVGSNVTLICIYTTTVA 50
    ||||||||||||||||||||||||||||||||||||||||||||||||||
  1 MVFAFWKVFLILSCLAGQVSVVQVTIPDGFVNVTVGSNVTLICIYTTTVA 50
                        .         .         .         .         .
 51 SREQLSIQWSFFHKKEMEPISHSSCLSTEGMEEKAVGQCLKMTHVRDARG 100
    |||||||||||||||||||||
 51 SREQLSIQWSFFHKKEMEPIS............................. 71
                        .         .         .         .         .
101 RCSWTSEIYFSQGGQAVAIGQFKDRITGSNDPGNASITISHMQPADSGIY 150
           |||||||||||||||||||||||||||||||||||||||||||
 72 .......IYFSQGGQAVAIGQFKDRITGSNDPGNASITISHMQPADSGIY 114
                        .         .         .         .         .
151 ICDVNNPPDFLGQNQGILNVSVLVKPSKPLCSVQGRPETGHTISLSCLSA 200
    ||||||||||||||||||||||||||||||||||||||||||||||||||
115 ICDVNNPPDFLGQNQGILNVSVLVKPSKPLCSVQGRPETGHTISLSCLSA 164
                        .         .         .         .         .
201 LGTPSPVYYWHKLEGRDIVPVKENFNPTTGILVIGNLTNFEQGYYQCTAI 250
    ||||||||||||||||||||||||||||||||||||||||||||||||||
165 LGTPSPVYYWHKLEGRDIVPVKENFNPTTGILVIGNLTNFEQGYYQCTAI 214
                        .         .         .         .         .
251 NRLGNSSCEIDLTSSHPEVGIIVGALIGSLVGAAIIISVVCFARNKAKAK 300
    ||||||||||||||||||||||||||||||||||||||||||||||||||
215 NRLGNSSCEIDLTSSHPEVGIIVGALIGSLVGAAIIISVVCFARNKAKAK 264
                        .         .         .         .         .
301 AKERNSKTIAELEPMTKINPRGESEAMPREDATQLEVTLPSSIHETGPDT 350
    ||||||||||||||||||||||||||||||||||||||||||||||||||
265 AKERNSKTIAELEPMTKINPRGESEAMPREDATQLEVTLPSSIHETGPDT 314
                        .         .         .         .         .
351 IQEPDYEPKPTQEPAPEPAPGSEPMAVPDLDIELELEPETQSELEPEPEP 400
    ||||||||||||||||||||||||||||||||||||||||||||||||||
315 IQEPDYEPKPTQEPAPEPAPGSEPMAVPDLDIELELEPETQSELEPEPEP 364
                        .         .
401 EPESEPGVVVEPLSEDEKGVVKA 423
    |||||||||||||||||||||||
365 EPESEPGVVVEPLSEDEKGVVKA 387
```

FIG. 3A

Alignment of:
AI581519_P5 x known protein(s) NP_872413 and Q86XK7_HUMAN:

```
              .         .         .         .         .
    1 MVFAFWKVFLILSCLAGQVSVVQVTIPDGFVNVTVGSNVTLICIYTTTVA 50
      ||||||||||||||||||||||||||||||||||||||||||||||||||
    1 MVFAFWKVFLILSCLAGQVSVVQVTIPDGFVNVTVGSNVTLICIYTTTVA 50

              .         .         .         .         .
   51 SREQLSIQWSFFHKKEMEPISHSSCLSTEGMEEKAVGQCLKMTHVRDARG 100
      |||||||||||||||||||||
   51 SREQLSIQWSFFHKKEMEPIS............................. 71

              .         .         .         .         .
  101 RCSWTSESPWEEGKWPDVEAVKGTLDGQQAELQIYFSQGGQAVAIGQFKD 150
                                       |||||||||||||||||
   72 .................................IYFSQGGQAVAIGQFKD 88

              .         .         .         .         .
  151 RITGSNDPGNASITISHMQPADSGIYICDVNNPPDFLGQNQGILNVSVLV 200
      ||||||||||||||||||||||||||||||||||||||||||||||||||
   89 RITGSNDPGNASITISHMQPADSGIYICDVNNPPDFLGQNQGILNVSVLV 138

              .         .         .         .         .
  201 KPSKPLCSVQGRPETGHTISLSCLSALGTPSPVYYWHKLEGRDIVPVKEN 250
      ||||||||||||||||||||||||||||||||||||||||||||||||||
  139 KPSKPLCSVQGRPETGHTISLSCLSALGTPSPVYYWHKLEGRDIVPVKEN 188

              .         .         .         .         .
  251 FNPTTGILVIGNLTNFEQGYYQCTAINRLGNSSCEIDLTSSHPEVGIIVG 300
      ||||||||||||||||||||||||||||||||||||||||||||||||||
  189 FNPTTGILVIGNLTNFEQGYYQCTAINRLGNSSCEIDLTSSHPEVGIIVG 238

              .         .         .         .         .
  301 ALIGSLVGAAIIISVVCFARNKAKAKAKERNSKTIAELEPMTKINPRGES 350
      ||||||||||||||||||||||||||||||||||||||||||||||||||
  239 ALIGSLVGAAIIISVVCFARNKAKAKAKERNSKTIAELEPMTKINPRGES 288

              .         .         .         .         .
  351 EAMPREDATQLEVTLPSSIHETGPDTIQEPDYEPKPTQEPAPEPAPGSEP 400
      ||||||||||||||||||||||||||||||||||||||||||||||||||
  289 EAMPREDATQLEVTLPSSIHETGPDTIQEPDYEPKPTQEPAPEPAPGSEP 338

              .         .         .         .
  401 MAVPDLDIELELEPETQSELEPEPEPEPESEPGVVVEPLSEDEKGVVKA 449
      |||||||||||||||||||||||||||||||||||||||||||||||||
  339 MAVPDLDIELELEPETQSELEPEPEPEPESEPGVVVEPLSEDEKGVVKA 387
```

FIG. 3B

```
Alignment of:
AI581519_P7 x known protein(s) NP_872413 and Q86XK7_HUMAN:

                .         .         .         .         .
    1 MVFAFWKVFLILSCLAGQVSVVQVTIPDGFVNVTVGSNVTLICIYTTTVA 50
      ||||||||||||||||||||||||||||||||||||||||||||||||||
    1 MVFAFWKVFLILSCLAGQVSVVQVTIPDGFVNVTVGSNVTLICIYTTTVA 50
                .         .         .         .         .
   51 SREQLSIQWSFFHKKEMEPISIYFSQGGQAVAIGQFKDRITGSNDP.... 96
      ||||||||||||||||||||||||||||||||||||||||||||||
   51 SREQLSIQWSFFHKKEMEPISIYFSQGGQAVAIGQFKDRITGSNDPGNAS 100
                .         .         .         .         .
   97 .....................................VKPSKPLCSVQGR 109
                                           |||||||||||||
  101 ITISHMQPADSGIYICDVNNPPDFLGQNQGILNVSVLVKPSKPLCSVQGR 150
                .         .         .         .         .
  110 PETGHTISLSCLSALGTPSPVYYWHKLEGRDIVPVKENFNPTTGILVIGN 159
      ||||||||||||||||||||||||||||||||||||||||||||||||||
  151 PETGHTISLSCLSALGTPSPVYYWHKLEGRDIVPVKENFNPTTGILVIGN 200
                .         .         .         .         .
  160 LTNFEQGYYQCTAINRLGNSSCEIDLTSSHPEVGIIVGALIGSLVGAAII 209
      ||||||||||||||||||||||||||||||||||||||||||||||||||
  201 LTNFEQGYYQCTAINRLGNSSCEIDLTSSHPEVGIIVGALIGSLVGAAII 250
                .         .         .         .         .
  210 ISVVCFARNKAKAKAKERNSKTIAELEPMTKINPRGESEAMPREDATQLE 259
      ||||||||||||||||||||||||||||||||||||||||||||||||||
  251 ISVVCFARNKAKAKAKERNSKTIAELEPMTKINPRGESEAMPREDATQLE 300
                .         .         .         .         .
  260 VTLPSSIHETGPDTIQEPDYEPKPTQEPAPEPAPGSEPMAVPDLDIELEL 309
      ||||||||||||||||||||||||||||||||||||||||||||||||||
  301 VTLPSSIHETGPDTIQEPDYEPKPTQEPAPEPAPGSEPMAVPDLDIELEL 350
                .         .         .
  310 EPETQSELEPEPEPEPESEPGVVVEPLSEDEKGVVKA 346
      |||||||||||||||||||||||||||||||||||||
  351 EPETQSELEPEPEPEPESEPGVVVEPLSEDEKGVVKA 387
```

FIG. 3C

```
Alignment of:
AI581519_P9 x known protein(s) NP_872413 and Q86XK7_HUMAN:

                  .         .         .         .         .
      1 MVFAFWKVFLILSCLAGQVSVVQVTIPDGFVNVTVGSNVTLICIYTTTVA 50
        ||||||||||||||||||||||||||||||||||||||||||||||||||
      1 MVFAFWKVFLILSCLAGQVSVVQVTIPDGFVNVTVGSNVTLICIYTTTVA 50

                  .         .         .         .         .
     51 SREQLSIQWSFFHKKEMEPISIYFSQGGQAVAIGQFKDRITGSNDPGNAS 100
        ||||||||||||||||||||||||||||||||||||||||||||||||||
     51 SREQLSIQWSFFHKKEMEPISIYFSQGGQAVAIGQFKDRITGSNDPGNAS 100

                  .         .         .         .         .
    101 ITISHMQPADSGIYICDVNNPPDFLGQNQGILNVSVLVKPSKPLCSVQGR 150
        ||||||||||||||||||||||||||||||||||||||||||||||||||
    101 ITISHMQPADSGIYICDVNNPPDFLGQNQGILNVSVLVKPSKPLCSVQGR 150

                  .         .         .         .         .
    151 PETGHTISLSCLSALGTPSPVYYWHKLEGRDIVPVKENFTNHRDFGHWKS 200
        |||||||||||||||||||||||||||||||||||||||
    151 PETGHTISLSCLSALGTPSPVYYWHKLEGRDIVPVKENF........... 189

                  .         .         .         .         .
    201 DKF                                                203

    189 ...                                                189
```

```
Alignment of:
AI581519_P10 x known protein(s) NP_872413 and Q86XK7_HUMAN:

                 .         .         .         .         .
  1 MVFAFWKVFLILSCLAGQVSVVQVTIPDGFVNVTVGSNVTLICIYTTTVA 50
    ||||||||||||||||||||||||||||||||||||||||||||||||||
  1 MVFAFWKVFLILSCLAGQVSVVQVTIPDGFVNVTVGSNVTLICIYTTTVA 50

                 .         .         .         .         .
 51 SREQLSIQWSFFHKKEMEPISIYFSQGGQAVAIGQFKDRITGSNDPGNAS 100
    ||||||||||||||||||||||||||||||||||||||||||||||||||
 51 SREQLSIQWSFFHKKEMEPISIYFSQGGQAVAIGQFKDRITGSNDPGNAS 100

                 .         .         .         .         .
101 ITISHMQPADSGIYICDVNNPPDFLGQNQGILNVSVLVKPSKPLCSVQGR 150
    ||||||||||||||||||||||||||||||||||||||||||||||||||
101 ITISHMQPADSGIYICDVNNPPDFLGQNQGILNVSVLVKPSKPLCSVQGR 150

                 .         .         .         .         .
151 PETGHTISLSCLSALGTPSPVYYWHKLEGRDIVPVKENFNPTTGILVIGN 200
    ||||||||||||||||||||||||||||||||||||||||||||||||||
151 PETGHTISLSCLSALGTPSPVYYWHKLEGRDIVPVKENFNPTTGILVIGN 200

                 .         .
201 LTNFEQGYYQCTAINRLGNSSCEIDLTSSRQ                    231
    |||||||||||||||||||||||||||||
201 LTNFEQGYYQCTAINRLGNSSCEIDLTSS..                    229
```

FIG. 3E

```
Alignment of:
AA424839_P3 x known protein(s) Q86SU0_HUMAN and NP_787120:
                     .         .         .         .         .
     1 MAWPKLPAPWLLLCTWLPAGCLSLLVTVQHTERYVTLFASIILKCDYTTS 50
       ||||||||||||||||||||||||||||||||||||||||||||||||||
     1 MAWPKLPAPWLLLCTWLPAGCLSLLVTVQHTERYVTLFASIILKCDYTTS 50
                .         .         .         .         .
    51 AQLQDVVVTWRFKSFCKDPIFDYYSASYQAALSLGQDPSNDCNDNQREVR 100
       ||||||||||||||||||||||||||||||||||||||||||||||||||
    51 AQLQDVVVTWRFKSFCKDPIFDYYSASYQAALSLGQDPSNDCNDNQREVR 100
                .         .         .         .         .
   101 IVAQRRGQNEPVLGVDYRQRKITIQNRADLVINEVMWWDHGVYYCTIEAP 150
       ||||||||||||||||||||||||||||||||||||||||||||||||||
   101 IVAQRRGQNEPVLGVDYRQRKITIQNRADLVINEVMWWDHGVYYCTIEAP 150
                .         .         .         .         .
   151 GDTSGDPDKEVKLIVLHWLTVIFIILGALLLLLLIGVCWCQCCPQYCCCY 200
       ||||||||||||||||||||||||||||||||||||||||||||||||||
   151 GDTSGDPDKEVKLIVLHWLTVIFIILGALLLLLLIGVCWCQCCPQYCCCY 200
                .         .         .         .         .
   201 IRCPCCPAHCCCPEEALARHRYMKQAQALGPQMMGKPLYWGADRSSQVSS 250
       |||||||||||||||
   201 IRCPCCPAHCCCPEE................................... 215
                .         .         .         .         .
   251 YPMHPLLQRDLSLPSSLPQMPMTQTTNQPPIANGVLEYLEKELRNLNLAQ 300
                |||||||||||||||||||||||||||||||||||||||||
   216 .........DLSLPSSLPQMPMTQTTNQPPIANGVLEYLEKELRNLNLAQ 256
                .         .         .         .         .
   301 PLPPDLKGRFGHPCSMLSSLGSEVVERRIIHLPPLIRDLSSSRRTSDSLH 350
       ||||||||||||||||||||||||||||||||||||||||||||||||||
   257 PLPPDLKGRFGHPCSMLSSLGSEVVERRIIHLPPLIRDLSSSRRTSDSLH 306
                .         .         .         .         .
   351 QQWLTPIPSRPWDLREGRSHHHYPDFHQELQDRGPKSWALERRELDPSWS 400
       ||||||||||||||||||||||||||||||||||||||||||||||||||
   307 QQWLTPIPSRPWDLREGRSHHHYPDFHQELQDRGPKSWALERRELDPSWS 356
                .         .         .         .         .
   401 GRHRSSRLNGSPIHWSDRDSLSDVPSSSEARWRPSHPPFRSRCQERPRRP 450
       ||||||||||||||||||||||||||||||||||||||||||||||||||
   357 GRHRSSRLNGSPIHWSDRDSLSDVPSSSEARWRPSHPPFRSRCQERPRRP 406
                .         .         .         .         .
   451 SPRESTQRHGRRRRHRSYSPPLPSGLSSWSSEEDKERQPQSWRAHRRGSH 500
       ||||||||||||||||||||||||||||||||||||||||||||||||||
   407 SPRESTQRHGRRRRHRSYSPPLPSGLSSWSSEEDKERQPQSWRAHRRGSH 456
                .         .         .         .
   501 SPHWPEEKPPSYRSLDITPGKNSRKKGSVERRSEKDSSHSGRSVVI     546
       ||||||||||||||||||||||||||||||||||||||||||||||
   457 SPHWPEEKPPSYRSLDITPGKNSRKKGSVERRSEKDSSHSGRSVVI     502
```

FIG. 16A

```
Alignment of:
AA424839_P7 x known protein(s) Q86SU0_HUMAN and NP_787120:

                   .         .         .         .         .
      1 MAWPKLPAPWLLLCTWLPAGCLSLLVTVQHTERYVTLFASIILKCDYTTS 50
        ||||||||||||||||||||||||||||||||||||||||||||||||||
      1 MAWPKLPAPWLLLCTWLPAGCLSLLVTVQHTERYVTLFASIILKCDYTTS 50
                   .         .         .         .         .
     51 AQLQDVVVTWRFKSFCKDPIFDYYSASYQAALSLGQDPSNDCNDNQREVR 100
        ||||||||||||||||||||||||||||||||||||||||||||||||||
     51 AQLQDVVVTWRFKSFCKDPIFDYYSASYQAALSLGQDPSNDCNDNQREVR 100
                   .         .         .         .         .
    101 IVAQRRGQNEPVLGVDYRQRKITIQNPLARHRYMKQAQALGPQMMGKPLY 150
        ||||||||||||||||||||||||||
    101 IVAQRRGQNEPVLGVDYRQRKITIQN........................ 126
                   .         .         .         .         .
    151 WGADRSSQVSSYPMHPLLQR.............................. 170

    127 ....................RADLVINEVMWWDHGVYYCTIEAPGDTSGD 156
                   .         .         .         .         .
        ..................................................

    157 PDKEVKLIVLHWLTVIFIILGALLLLLLIGVCWCQCCPQYCCCYIRCPCC 206
                   .         .         .         .         .
    171 .........DLSLPSSLPQMPMTQTTNQPPIANGVLEYLEKELRNLNLAQ 211
                 |||||||||||||||||||||||||||||||||||||||||
    207 PAHCCCPEEDLSLPSSLPQMPMTQTTNQPPIANGVLEYLEKELRNLNLAQ 256
                   .         .         .         .         .
    212 PLPPDLKGRFGHPCSMLSSLGSEVVERRIIHLPPLIRDLSSSRRTSDSLH 261
        ||||||||||||||||||||||||||||||||||||||||||||||||||
    257 PLPPDLKGRFGHPCSMLSSLGSEVVERRIIHLPPLIRDLSSSRRTSDSLH 306
                   .         .         .         .         .
    262 QQWLTPIPSRPWDLREGRSHHHYPDFHQELQDRGPKSWALERRELDPSWS 311
        ||||||||||||||||||||||||||||||||||||||||||||||||||
    307 QQWLTPIPSRPWDLREGRSHHHYPDFHQELQDRGPKSWALERRELDPSWS 356
                   .         .         .         .         .
    312 GRHRSSRLNGSPIHWSDRDSLSDVPSSSEARWRPSHPPFRSRCQERPRRP 361
        ||||||||||||||||||||||||||||||||||||||||||||||||||
    357 GRHRSSRLNGSPIHWSDRDSLSDVPSSSEARWRPSHPPFRSRCQERPRRP 406
                   .         .         .         .         .
    362 SPRESTQRHGRRRRHRSYSPPLPSGLSSWSSEEDKERQPQSWRAHRRGSH 411
        ||||||||||||||||||||||||||||||||||||||||||||||||||
    407 SPRESTQRHGRRRRHRSYSPPLPSGLSSWSSEEDKERQPQSWRAHRRGSH 456
                   .         .         .         .
    412 SPHWPEEKPPSYRSLDITPGKNSRKKGSVERRSEKDSSHSGRSVVI     457
        ||||||||||||||||||||||||||||||||||||||||||||||
    457 SPHWPEEKPPSYRSLDITPGKNSRKKGSVERRSEKDSSHSGRSVVI     502
```

FIG. 16B

```
Alignment of:
AA424839_1_P11 x known protein(s) Q86SU0_HUMAN and NP_787120:

               .         .         .         .         .
      1 MAWPKLPAPWLLLCTWLPA............................... 18
        |||||||||||||||||||
      1 MAWPKLPAPWLLLCTWLPAGCLSLLVTVQHTERYVTLFASIILKCDYTTS 50

               .         .         .         .         .
     19 ..........................AYQAALSLGQDPSNDCNDNQREVR 43
                                  :|||||||||||||||||||||||
     51 AQLQDVVVTWRFKSFCKDPIFDYYSASYQAALSLGQDPSNDCNDNQREVR 100

               .         .         .         .         .
     44 IVAQRRGQNEPVLGVDYRQRKITIQNRADLVINEVMWWDHGVYYCTIEAP 93
        ||||||||||||||||||||||||||||||||||||||||||||||||||
    101 IVAQRRGQNEPVLGVDYRQRKITIQNRADLVINEVMWWDHGVYYCTIEAP 150

               .         .         .         .         .
     94 GDTSGDPDKEVKLIVLHWLTVIFIILGALLLLLLIGVCWCQCCPQYCCCY 143
        ||||||||||||||||||||||||||||||||||||||||||||||||||
    151 GDTSGDPDKEVKLIVLHWLTVIFIILGALLLLLLIGVCWCQCCPQYCCCY 200

               .         .         .         .         .
    144 IRCPCCPAHCCCPEEALARHRYMKQAQALGPQMMGKPLYWGADRSSQVSS 193
        |||||||||||||||
    201 IRCPCCPAHCCCPEE................................... 215

               .         .         .         .         .
    194 YPMHPLLQRDLSLPSSLPQMPMTQTTNQPPIANGVLEYLEKELRNLNLAQ 243
                 |||||||||||||||||||||||||||||||||||||||||
    216 .........DLSLPSSLPQMPMTQTTNQPPIANGVLEYLEKELRNLNLAQ 256

               .         .         .         .         .
    244 PLPPDLKGRFGHPCSMLSSLGSEVVERRIIHLPPLIRDLSSSRRTSDSLH 293
        ||||||||||||||||||||||||||||||||||||||||||||||||||
    257 PLPPDLKGRFGHPCSMLSSLGSEVVERRIIHLPPLIRDLSSSRRTSDSLH 306

               .         .         .         .         .
    294 QQWLTPIPSRPWDLREGRSHHHYPDFHQELQDRGPKSWALERRELDPSWS 343
        ||||||||||||||||||||||||||||||||||||||||||||||||||
    307 QQWLTPIPSRPWDLREGRSHHHYPDFHQELQDRGPKSWALERRELDPSWS 356

               .         .         .         .         .
    344 GRHRSSRLNGSPIHWSDRGSLSDVPSSSEARWRPSHPPFRSRCQERPRRP 393
        |||||||||||||||||| |||||||||||||||||||||||||||||||
    357 GRHRSSRLNGSPIHWSDRDSLSDVPSSSEARWRPSHPPFRSRCQERPRRP 406

               .         .         .         .         .
    394 SPRESTQRHGRRRRHRSYSPPLPSGLSSWSSEEDKERQPQSWRAHRRGSH 443
        ||||||||||||||||||||||||||||||||||||||||||||||||||
    407 SPRESTQRHGRRRRHRSYSPPLPSGLSSWSSEEDKERQPQSWRAHRRGSH 456

               .         .         .         .
    444 SPHWPEEKPPSYRSLDITPGKNSRKKGSVERRSEKDSSHSGRSVVI 489
        ||||||||||||||||||||||||||||||||||||||||||||||
    457 SPHWPEEKPPSYRSLDITPGKNSRKKGSVERRSEKDSSHSGRSVVI 502
```

FIG. 16C

```
Alignment of:
H68654_1_P7 x known protein(s) NP_937794 and Q6UXI0_HUMAN:

                    .         .         .         .         .
  1 MWLKVFTTFLSFATGACSGLKVTVPSHTVHGVRGQALYLPVHYGFHTPAS 50
    ||||||||||||||||||||||||||||||||||||||||||||||||||
  1 MWLKVFTTFLSFATGACSGLKVTVPSHTVHGVRGQALYLPVHYGFHTPAS 50
                    .         .         .         .         .
 51 DIQIIWLFERPHTMPKYLLGSVNKSVVPDLEYQHKFTMMPPNASLLINPL 100
    ||||||||||||||||||||||||||||||||||||||||||||||||||
 51 DIQIIWLFERPHTMPKYLLGSVNKSVVPDLEYQHKFTMMPPNASLLINPL 100
                    .         .         .         .         .
101 QFPDEGNYIVKVNIQGNGTLSASQKIQVTVDDPVTKPVVQIHPPSGAVEY 150
    ||||||||||||||||||||||||||||||||||||||||||||||||||
101 QFPDEGNYIVKVNIQGNGTLSASQKIQVTVDDPVTKPVVQIHPPSGAVEY 150
                    .         .         .         .         .
151 VGNMTLTCHVEGGTRLAYQWLKNGRPVHTSSTYSFSPQNNTLHIAPVTKE 200
    ||||||||||||||||||||||||||||||||||||||||||||||||||
151 VGNMTLTCHVEGGTRLAYQWLKNGRPVHTSSTYSFSPQNNTLHIAPVTKE 200
                    .         .         .         .         .
201 DIGNYSCLVRNPVSEMESDIIMPIIYYGPYGLQVNSDKGLKVGEVFTVDL 250
    ||||||||||||||||||||||||||||||||||||||||||||||||||
201 DIGNYSCLVRNPVSEMESDIIMPIIYYGPYGLQVNSDKGLKVGEVFTVDL 250
                    .         .         .         .         .
251 GEAILFDCSADSHPPNTYSWIRRTDNTTYIIKHGPRLEVASEKVAQKTMD 300
    ||||||||||||||||||||||||||||||||||||||||||||||||||
251 GEAILFDCSADSHPPNTYSWIRRTDNTTYIIKHGPRLEVASEKVAQKTMD 300
                    .         .         .         .         .
301 YVCCAYNNITGRQDETHFTVIITSVGLEKLAQKGKSLSPLASITGISLFL 350
    ||||||||||||||||||||||||||||||||||||||||||||||||||
301 YVCCAYNNITGRQDETHFTVIITSVGLEKLAQKGKSLSPLASITGISLFL 350
                    .         .         .         .         .
351 IISMCLLFLWKKYQPYKGQKQNTGKLKHFQAMKMLWMTSEYMNLLLFQMF 400
    |||||||||||||||||
351 IISMCLLFLWKKYQPYK................................. 367
                    .         .         .         .         .
401 LVFPGSQAGLFQPLIVYRGKICTVQCMKLFSTSLPSSKTIQSELSWAKQY 450

    ..................................................
                    .         .         .         .         .
451 IRVKF............................................. 455

368 .....VIKQKLEGRPETEYRKAQTFSGHEDALDDFGIYEFVAFPDVSGVS 412
                    .         .         .
    .....................................

413 RIPSRSVPASDCVSGQDLHSTVYEVIQHIPAQQQDHPE             450
```

FIG. 30A

Alignment of:
H68654_1_P7 x known protein(s) NP_001034461:

FIG. 30B

```
              .         .         .         .         .
  1 MWLKVFTTFLSFAT..........................GACSGLKVTV 24
                                            ||||||||||
  1 ..............MGQDAFMEPFGDTLGVFQCKIYLLLFGACSGLKVTV 36
              .         .         .         .         .
 25 PSHTVHGVRGQALYLPVHYGFHTPASDIQIIWLFERPHTMPKYLLGSVNK 74
    ||||||||||||||||||||||||||||||||||||||||||||||||||
 37 PSHTVHGVRGQALYLPVHYGFHTPASDIQIIWLFERPHTMPKYLLGSVNK 86
              .         .         .         .         .
 75 SVVPDLEYQHKFTMMPPNASLLINPLQFPDEGNYIVKVNIQGNGTLSASQ 124
    ||||||||||||||||||||||||||||||||||||||||||||||||||
 87 SVVPDLEYQHKFTMMPPNASLLINPLQFPDEGNYIVKVNIQGNGTLSASQ 136
              .         .         .         .         .
125 KIQVTVDDPVTKPVVQIHPPSGAVEYVGNMTLTCHVEGGTRLAYQWLKNG 174
    ||||||||||||||||||||||||||||||||||||||||||||||||||
137 KIQVTVDDPVTKPVVQIHPPSGAVEYVGNMTLTCHVEGGTRLAYQWLKNG 186
              .         .         .         .         .
175 RPVHTSSTYSFSPQNNTLHIAPVTKEDIGNYSCLVRNPVSEMESDIIMPI 224
    ||||||||||||||||||||||||||||||||||||||||||||||||||
187 RPVHTSSTYSFSPQNNTLHIAPVTKEDIGNYSCLVRNPVSEMESDIIMPI 236
              .         .         .         .         .
225 IYYGPYGLQVNSDKGLKVGEVFTVDLGEAILFDCSADSHPPNTYSWIRRT 274
    ||||||||||||||||||||||||||||||||||||||||||||||||||
237 IYYGPYGLQVNSDKGLKVGEVFTVDLGEAILFDCSADSHPPNTYSWIRRT 286
              .         .         .         .         .
275 DNTTYIIKHGPRLEVASEKVAQKTMDYVCCAYNNITGRQDETHFTVIITS 324
    ||||||||||||||||||||||||||||||||||||||||||||||||||
287 DNTTYIIKHGPRLEVASEKVAQKTMDYVCCAYNNITGRQDETHFTVIITS 336
              .         .         .         .         .
325 VGLEKLAQKGKSLSPLASITGISLFLIISMCLLFLWKKYQPYKGQKQNTG 374
    |||||||||||||||||||||||||||||||||||||||||||
337 VGLEKLAQKGKSLSPLASITGISLFLIISMCLLFLWKKYQPYK....... 379
              .         .         .         .         .
375 KLKHFQAMKMLWMTSEYMNLLLFQMFLVFPGSQAGLFQPLIVYRGKICTV 424

    ..................................................
              .         .         .         .         .
425 QCMKLFSTSLPSSKTIQSELSWAKQYIRVKF................... 455

380 ...............................VIKQKLEGRPETEYRKAQT 398
              .         .         .         .         .
    ..................................................

399 FSGHEDALDDFGIYEFVAFPDVSGVSRIPSRSVPASDCVSGQDLHSTVYE 448
              .
    ..............

449 VIQHIPAQQQDHPE                                     462
```

```
Alignment of:
H68654_1_P12 x known protein(s) NP_937794 and Q6UXI0_HUMAN:

                   .         .         .         .         .
  1 MWLKVFTTFLSFATGACSGLKVTVPSHTVHGVRGQALYLPVHYGFHTPAS 50
    ||||||||||||||||||||||||||||||||||||||||||||||||||
  1 MWLKVFTTFLSFATGACSGLKVTVPSHTVHGVRGQALYLPVHYGFHTPAS 50
                   .         .         .         .         .
 51 DIQIIWLFERPHTMPKYLLGSVNKSVVPDLEYQHKFTMMPPNASLLINPL 100
    ||||||||||||||||||||||||||||||||||||||||||||||||||
 51 DIQIIWLFERPHTMPKYLLGSVNKSVVPDLEYQHKFTMMPPNASLLINPL 100
                   .         .         .         .         .
101 QFPDEGNYIVKVNIQGNGTLSASQKIQVTVDDPVTKPVVQIHPPSGAVEY 150
    ||||||||||||||||||||||||||||||||||||||||||||||||||
101 QFPDEGNYIVKVNIQGNGTLSASQKIQVTVDDPVTKPVVQIHPPSGAVEY 150
                   .         .         .         .         .
151 VGNMTLTCHVEGGTRLAYQWLKNGRPVHTSSTYSFSPQNNTLHIAPVTKE 200
    ||||||||||||||||||||||||||||||||||||||||||||||||||
151 VGNMTLTCHVEGGTRLAYQWLKNGRPVHTSSTYSFSPQNNTLHIAPVTKE 200
                   .         .         .         .         .
201 DIGNYSCLVRNPVSEMESDIIMPIIYYGPYGLQVNSDKGLKVGEVFTVDL 250
    ||||||||||||||||||||||||||||||||||||||||||||||||||
201 DIGNYSCLVRNPVSEMESDIIMPIIYYGPYGLQVNSDKGLKVGEVFTVDL 250
                   .         .         .         .         .
251 GEAILFDCSADSHPPNTYSWIRRTDNTTYIIKHGPRLEVASEKVAQKTMD 300
    ||||||||||||||||||||||||||||||||||||||||||||||||||
251 GEAILFDCSADSHPPNTYSWIRRTDNTTYIIKHGPRLEVASEKVAQKTMD 300
                   .         .         .         .         .
301 YVCCAYNNITGRQDETHFTVIITSVGLEKLAQKGKSLSPLASITGISLFL 350
    ||||||||||||||||||||||||||||||||||||||||||||||||||
301 YVCCAYNNITGRQDETHFTVIITSVGLEKLAQKGKSLSPLASITGISLFL 350
                   .         .         .         .         .
351 IISMCLLFLWKKYQPYKVIKQKLEGRPETEYRKAQTFSGHEDALDDFGIY 400
    ||||||||||||||||||||||||||||||||||||||||||||||||||
351 IISMCLLFLWKKYQPYKVIKQKLEGRPETEYRKAQTFSGHEDALDDFGIY 400
                   .         .         .         .         .
401 EFVAFPDVSGVSRVGFPSG............................... 419
    |||||||||||||
401 EFVAFPDVSGVSR......IPSRSVPASDCVSGQDLHSTVYEVIQHIPAQ 444

    ......

445 QQDHPE                                             450
```

FIG. 30C

Alignment of:
H68654_1_P12 x known protein(s) NP_001034461:

```
                  .         .         .         .         .
  1 MWLKVFTTFLSFAT.........................GACSGLKVTV 24
                                           ||||||||||
  1 ..............MGQDAFMEPFGDTLGVFQCKIYLLLFGACSGLKVTV 36
                  .         .         .         .         .
 25 PSHTVHGVRGQALYLPVHYGFHTPASDIQIIWLFERPHTMPKYLLGSVNK 74
    ||||||||||||||||||||||||||||||||||||||||||||||||||
 37 PSHTVHGVRGQALYLPVHYGFHTPASDIQIIWLFERPHTMPKYLLGSVNK 86
                  .         .         .         .         .
 75 SVVPDLEYQHKFTMMPPNASLLINPLQFPDEGNYIVKVNIQGNGTLSASQ 124
    ||||||||||||||||||||||||||||||||||||||||||||||||||
 87 SVVPDLEYQHKFTMMPPNASLLINPLQFPDEGNYIVKVNIQGNGTLSASQ 136
                  .         .         .         .         .
125 KIQVTVDDPVTKPVVQIHPPSGAVEYVGNMTLTCHVEGGTRLAYQWLKNG 174
    ||||||||||||||||||||||||||||||||||||||||||||||||||
137 KIQVTVDDPVTKPVVQIHPPSGAVEYVGNMTLTCHVEGGTRLAYQWLKNG 186
                  .         .         .         .         .
175 RPVHTSSTYSFSPQNNTLHIAPVTKEDIGNYSCLVRNPVSEMESDIIMPI 224
    ||||||||||||||||||||||||||||||||||||||||||||||||||
187 RPVHTSSTYSFSPQNNTLHIAPVTKEDIGNYSCLVRNPVSEMESDIIMPI 236
                  .         .         .         .         .
225 IYYGPYGLQVNSDKGLKVGEVFTVDLGEAILFDCSADSHPPNTYSWIRRT 274
    ||||||||||||||||||||||||||||||||||||||||||||||||||
237 IYYGPYGLQVNSDKGLKVGEVFTVDLGEAILFDCSADSHPPNTYSWIRRT 286
                  .         .         .         .         .
275 DNTTYIIKHGPRLEVASEKVAQKTMDYVCCAYNNITGRQDETHFTVIITS 324
    ||||||||||||||||||||||||||||||||||||||||||||||||||
287 DNTTYIIKHGPRLEVASEKVAQKTMDYVCCAYNNITGRQDETHFTVIITS 336
                  .         .         .         .         .
325 VGLEKLAQKGKSLSPLASITGISLFLIISMCLLFLWKKYQPYKVIKQKLE 374
    ||||||||||||||||||||||||||||||||||||||||||||||||||
337 VGLEKLAQKGKSLSPLASITGISLFLIISMCLLFLWKKYQPYKVIKQKLE 386
                  .         .         .         .         .
375 GRPETEYRKAQTFSGHEDALDDFGIYEFVAFPDVSGVSRVGFPSG..... 419
    |||||||||||||||||||||||||||||||||||||||
387 GRPETEYRKAQTFSGHEDALDDFGIYEFVAFPDVSGVSR......IPSRS 430
                  .         .         .
    ................................

431 VPASDCVSGQDLHSTVYEVIQHIPAQQQDHPE                   462
```

FIG. 30D

```
Alignment of:
H68654_1_P13 x known protein(s) NP_937794 and Q6UXI0_HUMAN:

             .         .         .         .         .
  1 MWLKVFTTFLSFATGACSGLKVTVPSHTVHGVRGQALYLPVHYGFHTPAS 50
    ||||||||||||||||||||||||||||||||||||||||||||||||||
  1 MWLKVFTTFLSFATGACSGLKVTVPSHTVHGVRGQALYLPVHYGFHTPAS 50

             .         .         .         .         .
 51 DIQIIWLFERPHTMPKYLLGSVNKSVVPDLEYQHKFTMMPPNASLLINPL 100
    ||||||||||||||||||||||||||||||||||||||||||||||||||
 51 DIQIIWLFERPHTMPKYLLGSVNKSVVPDLEYQHKFTMMPPNASLLINPL 100

             .         .         .         .         .
101 QFPDEGNYIVKVNIQGNGTLSASQKIQVTVDDPVTKPVVQIHPPSGAVEY 150
    ||||||||||||||||||||||||||||||||||||||||||||||||||
101 QFPDEGNYIVKVNIQGNGTLSASQKIQVTVDDPVTKPVVQIHPPSGAVEY 150

             .         .         .         .         .
151 VGNMTLTCHVEGGTRLAYQWLKNGRPVHTSSTYSFSPQNNTLHIAPVTKE 200
    ||||||||||||||||||||||||||||||||||||||||||||||||||
151 VGNMTLTCHVEGGTRLAYQWLKNGRPVHTSSTYSFSPQNNTLHIAPVTKE 200

             .         .         .         .         .
201 DIGNYSCLVRNPVSEMESDIIMPIIYYGPYGLQVNSDKGLKVGEVFTVDL 250
    ||||||||||||||||||||||||||||||||||||||||||||||||||
201 DIGNYSCLVRNPVSEMESDIIMPIIYYGPYGLQVNSDKGLKVGEVFTVDL 250

             .         .         .         .         .
251 GEAILFDCSADSHPPNTYSWIRRTDNTTYIIKHGPRLEVASEKVAQKTMD 300
    ||||||||||||||||||||||||||||||||||||||||||||||||||
251 GEAILFDCSADSHPPNTYSWIRRTDNTTYIIKHGPRLEVASEKVAQKTMD 300

             .         .         .         .         .
301 YVCCAYNNITGRQDETHFTVIITSVGLEKLAQKGKSLSPLASITGISLFL 350
    ||||||||||||||||||||||||||||||||||||||||||||||||||
301 YVCCAYNNITGRQDETHFTVIITSVGLEKLAQKGKSLSPLASITGISLFL 350

             .         .         .         .         .
351 IISMCLLFLWKKYQPYKVIKQKLEGR........................ 376
    ||||||||||||||||||||||||||
351 IISMCLLFLWKKYQPYKVIKQKLEGRPETEYRKAQTFSGHEDALDDFGIY 400

             .         .         .         .         .
    ..................................................

401 EFVAFPDVSGVSRIPSRSVPASDCVSGQDLHSTVYEVIQHIPAQQQDHPE 450
```

FIG. 30E

Alignment of:
H68654_1_P13 x known protein(s) NP_001034461:

```
                    .         .         .         .         .
  1 MWLKVFTTFLSFAT.........................GACSGLKVTV 24
                                           ||||||||||
  1 ..............MGQDAFMEPFGDTLGVFQCKIYLLLFGACSGLKVTV 36
                    .         .         .         .         .
 25 PSHTVHGVRGQALYLPVHYGFHTPASDIQIIWLFERPHTMPKYLLGSVNK 74
    ||||||||||||||||||||||||||||||||||||||||||||||||||
 37 PSHTVHGVRGQALYLPVHYGFHTPASDIQIIWLFERPHTMPKYLLGSVNK 86
                    .         .         .         .         .
 75 SVVPDLEYQHKFTMMPPNASLLINPLQFPDEGNYIVKVNIQGNGTLSASQ 124
    ||||||||||||||||||||||||||||||||||||||||||||||||||
 87 SVVPDLEYQHKFTMMPPNASLLINPLQFPDEGNYIVKVNIQGNGTLSASQ 136
                    .         .         .         .         .
125 KIQVTVDDPVTKPVVQIHPPSGAVEYVGNMTLTCHVEGGTRLAYQWLKNG 174
    ||||||||||||||||||||||||||||||||||||||||||||||||||
137 KIQVTVDDPVTKPVVQIHPPSGAVEYVGNMTLTCHVEGGTRLAYQWLKNG 186
                    .         .         .         .         .
175 RPVHTSSTYSFSPQNNTLHIAPVTKEDIGNYSCLVRNPVSEMESDIIMPI 224
    ||||||||||||||||||||||||||||||||||||||||||||||||||
187 RPVHTSSTYSFSPQNNTLHIAPVTKEDIGNYSCLVRNPVSEMESDIIMPI 236
                    .         .         .         .         .
225 IYYGPYGLQVNSDKGLKVGEVFTVDLGEAILFDCSADSHPPNTYSWIRRT 274
    ||||||||||||||||||||||||||||||||||||||||||||||||||
237 IYYGPYGLQVNSDKGLKVGEVFTVDLGEAILFDCSADSHPPNTYSWIRRT 286
                    .         .         .         .         .
275 DNTTYIIKHGPRLEVASEKVAQKTMDYVCCAYNNITGRQDETHFTVIITS 324
    ||||||||||||||||||||||||||||||||||||||||||||||||||
287 DNTTYIIKHGPRLEVASEKVAQKTMDYVCCAYNNITGRQDETHFTVIITS 336
                    .         .         .         .         .
325 VGLEKLAQKGKSLSPLASITGISLFLIISMCLLFLWKKYQPYKVIKQKLE 374
    ||||||||||||||||||||||||||||||||||||||||||||||||||
337 VGLEKLAQKGKSLSPLASITGISLFLIISMCLLFLWKKYQPYKVIKQKLE 386
                    .         .         .         .         .
375 GR................................................ 376
    ||
387 GRPETEYRKAQTFSGHEDALDDFGIYEFVAFPDVSGVSRIPSRSVPASDC 436
                    .         .
    ..........................

437 VSGQDLHSTVYEVIQHIPAQQQDHPE                         462
```

FIG. 30F

Alignment of:
H68654_1_P14 x known protein(s) NP_937794 and Q6UXI0_HUMAN:

```
                .         .         .         .         .
  1 MWLKVFTTFLSFATGACSGLKVTVPSHTVHGVRGQALYLPVHYGFHTPAS 50
    ||||||||||||||||||||||||||||||||||||||||||||||||||
  1 MWLKVFTTFLSFATGACSGLKVTVPSHTVHGVRGQALYLPVHYGFHTPAS 50
                .         .         .         .         .
 51 DIQIIWLFERPHTMPKYLLGSVNKSVVPDLEYQHKFTMMPPNASLLINPL 100
    ||||||||||||||||||||||||||||||||||||||||||||||||||
 51 DIQIIWLFERPHTMPKYLLGSVNKSVVPDLEYQHKFTMMPPNASLLINPL 100
                .         .         .         .         .
101 QFPDEGNYIVKVNIQGNGTLSASQKIQVTVDDPVTKPVVQIHPPSGAVEY 150
    ||||||||||||||||||||||||||||||||||||||||||||||||||
101 QFPDEGNYIVKVNIQGNGTLSASQKIQVTVDDPVTKPVVQIHPPSGAVEY 150
                .         .         .         .         .
151 VGNMTLTCHVEGGTRLAYQWLKNGRPVHTSSTYSFSPQNNTLHIAPVTKE 200
    ||||||||||||||||||||||||||||||||||||||||||||||||||
151 VGNMTLTCHVEGGTRLAYQWLKNGRPVHTSSTYSFSPQNNTLHIAPVTKE 200
                .         .         .         .         .
201 DIGNYSCLVRNPVSEMESDIIMPIIYYGPYGLQVNSDKGLKVGEVFTVDL 250
    ||||||||||||||||||||||||||||||||||||||||||||||||||
201 DIGNYSCLVRNPVSEMESDIIMPIIYYGPYGLQVNSDKGLKVGEVFTVDL 250
                .         .         .         .         .
251 GEAILFDCSADSHPPNTYSWIRRTDNTTYIIKHGPRLEVASEKVAQKTMD 300
    ||||||||||||||||||||||||||||||||||||||||||||||||||
251 GEAILFDCSADSHPPNTYSWIRRTDNTTYIIKHGPRLEVASEKVAQKTMD 300
                .         .         .         .         .
301 YVCCAYNNITGRQDETHFTVIITSVGLEKLAQKGKSLSPLASITGISLFL 350
    ||||||||||||||||||||||||||||||||||||||||||||||||||
301 YVCCAYNNITGRQDETHFTVIITSVGLEKLAQKGKSLSPLASITGISLFL 350
                .         .         .         .         .
351 IISMCLLFLWKKYQPYKVIKQKLEGRPETEYRKAQTFSGFMLAAPSQREE 400
    |||||||||||||||||||||||||||||||||||||||
351 IISMCLLFLWKKYQPYKVIKQKLEGRPETEYRKAQTFSG........... 389
                .         .         .         .         .
401 EKKIWQGPGLLLCPHCNPHYHQY........................... 423

390 .......................HEDALDDFGIYEFVAFPDVSGVSRIPS 416
                .         .         .
    ..................................

417 RSVPASDCVSGQDLHSTVYEVIQHIPAQQQDHPE                 450
```

FIG. 30G

Alignment of:
H68654_1_P14 x known protein(s) NP_001034461:

```
                   .         .         .         .         .
  1 MWLKVFTTFLSFAT..........................GACSGLKVTV 24
                                            ||||||||||
  1 ..............MGQDAFMEPFGDTLGVFQCKIYLLLFGACSGLKVTV 36
                   .         .         .         .         .
 25 PSHTVHGVRGQALYLPVHYGFHTPASDIQIIWLFERPHTMPKYLLGSVNK 74
    ||||||||||||||||||||||||||||||||||||||||||||||||||
 37 PSHTVHGVRGQALYLPVHYGFHTPASDIQIIWLFERPHTMPKYLLGSVNK 86
                   .         .         .         .         .
 75 SVVPDLEYQHKFTMMPPNASLLINPLQFPDEGNYIVKVNIQGNGTLSASQ 124
    ||||||||||||||||||||||||||||||||||||||||||||||||||
 87 SVVPDLEYQHKFTMMPPNASLLINPLQFPDEGNYIVKVNIQGNGTLSASQ 136
                   .         .         .         .         .
125 KIQVTVDDPVTKPVVQIHPPSGAVEYVGNMTLTCHVEGGTRLAYQWLKNG 174
    ||||||||||||||||||||||||||||||||||||||||||||||||||
137 KIQVTVDDPVTKPVVQIHPPSGAVEYVGNMTLTCHVEGGTRLAYQWLKNG 186
                   .         .         .         .         .
175 RPVHTSSTYSFSPQNNTLHIAPVTKEDIGNYSCLVRNPVSEMESDIIMPI 224
    ||||||||||||||||||||||||||||||||||||||||||||||||||
187 RPVHTSSTYSFSPQNNTLHIAPVTKEDIGNYSCLVRNPVSEMESDIIMPI 236
                   .         .         .         .         .
225 IYYGPYGLQVNSDKGLKVGEVFTVDLGEAILFDCSADSHPPNTYSWIRRT 274
    ||||||||||||||||||||||||||||||||||||||||||||||||||
237 IYYGPYGLQVNSDKGLKVGEVFTVDLGEAILFDCSADSHPPNTYSWIRRT 286
                   .         .         .         .         .
275 DNTTYIIKHGPRLEVASEKVAQKTMDYVCCAYNNITGRQDETHFTVIITS 324
    ||||||||||||||||||||||||||||||||||||||||||||||||||
287 DNTTYIIKHGPRLEVASEKVAQKTMDYVCCAYNNITGRQDETHFTVIITS 336
                   .         .         .         .         .
325 VGLEKLAQKGKSLSPLASITGISLFLIISMCLLFLWKKYQPYKVIKQKLE 374
    ||||||||||||||||||||||||||||||||||||||||||||||||||
337 VGLEKLAQKGKSLSPLASITGISLFLIISMCLLFLWKKYQPYKVIKQKLE 386
                   .         .         .         .         .
375 GRPETEYRKAQTFSGFMLAAPSQREEEKKIWQGPGLLLCPHCNPHYHQY. 423
    |||||||||||||||
387 GRPETEYRKAQTFSG..................................H 402
                   .         .         .         .         .
    ..................................................

403 EDALDDFGIYEFVAFPDVSGVSRIPSRSVPASDCVSGQDLHSTVYEVIQH 452
                   .
    ..........

453 IPAQQQDHPE                                         462
```

Alignment of:
H19011_1_P8 x known protein(s) Q71H61_HUMAN and NP_955383:

```
              .         .         .         .         .
  1 MDRVLLRWISLFWLTAMVEGLQVTVPDKKKVAMLFQPTVLRCHFSTSSHQ 50
    ||||||||||||||||||||||||||||||||||||||||||||||||||
  1 MDRVLLRWISLFWLTAMVEGLQVTVPDKKKVAMLFQPTVLRCHFSTSSHQ 50
              .         .         .         .         .
 51 PAVVQWKFKSYCQDRMGESLGMSSTRAQSLSKRNLEWDPYLDCLDSRRTV 100
    ||||||||||||||||||||||||||||||||||||||||||||||||||
 51 PAVVQWKFKSYCQDRMGESLGMSSTRAQSLSKRNLEWDPYLDCLDSRRTV 100
              .         .         .         .         .
101 RVVASKQGSTVTLGDFYRGREITIVHDADLQIGKLMWGDSGLYYCIITTP 150
    ||||||||||||||||||||||||||||||||||||||||||||||||||
101 RVVASKQGSTVTLGDFYRGREITIVHDADLQIGKLMWGDSGLYYCIITTP 150
              .         .         .         .         .
151 DDLEGKNEGSLGLLVLGRTGLLADLLPSFAVEIMPEWVFVGLVLLGVFLF 200
    |||||||| |  ||||||||||||||||||||||||||||||||||||||
151 DDLEGKNEDSVELLVLGRTGLLADLLPSFAVEIMPEWVFVGLVLLGVFLF 200
              .         .         .         .         .
201 FVLVGICWCQCCPHSCCCYVRCPCCPDSCWCPQACEYSDRWGDRAIERNV 250
    ||||||||||||||||||||||||||||| ||||
201 FVLVGICWCQCCPHSCCCYVRCPCCPDSCCCPQA................ 234
              .         .         .         .         .
251 YLST.............................................. 254

235 ....LYEAGKAAKAGYPPSVSGVPGPYSIPSVPLGGAPSSGMLMDKPHPP 280
              .         .         .         .         .
    ..................................................

281 PLAPSDSTGGSHSVRKGYRIQADKERDSMKVLYYVEKELAQFDPARRMRG 330
              .         .         .         .         .
    ..................................................

331 RYNNTISELSSLHEEDSNFRQSFHQMRSKQFPVSGDLESNPDYWSGVMGG 380
              .         .         .         .         .
    ..................................................

381 SSGASRGPSAMEYNKEDRESFRHSQPRSKSEMLSRKNFATGVPAVSMDEL 430
              .         .         .         .         .
    ..................................................

431 AAFADSYGQRPRRADGNSHEARGGSRFERSESRAHSGFYQDDSLEEYYGQ 480
              .         .         .         .         .
    ..................................................

481 RSRSREPLTDADRGWAFSPARRRPAEDAHLPRLVSRTPGTAPKYDHSYLG 530
              .         .         .         .         .
    ..................................................

531 SARERQARPEGASRGGSLETPSKRSAQLGPRSASYYAWSPPGTYKAGSSQ 580
              .         .         .         .         .
    ..................................................

581 DDQEDASDDALPPYSELELTRGPSYRGRDLPYHSNSEKKRKKEPAKKTND 630

    .........

631 FPTRMSLVV                                          639
```

FIG. 38B

```
Alignment of:
H19011_1_P9 x known protein(s) Q71H61_HUMAN and NP_955383:

                 .         .         .         .         .
  1 MDRVLLRWISLFWLTAMVEGLQVTVPDKKKVAMLFQPTVLRCHFSTSSHQ 50
    ||||||||||||||||||||||||||||||||||||||||||||||||||
  1 MDRVLLRWISLFWLTAMVEGLQVTVPDKKKVAMLFQPTVLRCHFSTSSHQ 50
                 .         .         .         .         .
 51 PAVVQWKFKSYCQDRMGESLGMSSTRAQSLSKRNLEWDPYLDCLDSRRTV 100
    ||||||||||||||||||||||||||||||||||||||||||||||||||
 51 PAVVQWKFKSYCQDRMGESLGMSSTRAQSLSKRNLEWDPYLDCLDSRRTV 100
                 .         .         .         .         .
101 RVVASKQGSTVTLGDFYRGREITIVHDADLQIGKLMWGDSGLYYCIITTP 150
    ||||||||||||||||||||||||||||||||||||||||||||||||||
101 RVVASKQGSTVTLGDFYRGREITIVHDADLQIGKLMWGDSGLYYCIITTP 150
                 .         .         .         .         .
151 DDLEGKNEGSLGLLVL...................EWVFVGLVLLGVFLF 181
    |||||||| |  ||||                   |||||||||||||||
151 DDLEGKNEDSVELLVLGRTGLLADLLPSFAVEIMPEWVFVGLVLLGVFLF 200
                 .         .         .         .         .
182 FVLVGICWCQCCPHSCCCYVRCPCCPDSCWCPQACEYSDRWGDRAIERNV 231
    ||||||||||||||||||||||||||||| ||||
201 FVLVGICWCQCCPHSCCCYVRCPCCPDSCCCPQA................ 234
                 .         .         .         .         .
232 YLST.............................................. 235

235 ....LYEAGKAAKAGYPPSVSGVPGPYSIPSVPLGGAPSSGMLMDKPHPP 280
                 .         .         .         .         .
    ..................................................

281 PLAPSDSTGGSHSVRKGYRIQADKERDSMKVLYYVEKELAQFDPARRMRG 330
                 .         .         .         .         .
    ..................................................

331 RYNNTISELSSLHEEDSNFRQSFHQMRSKQFPVSGDLESNPDYWSGVMGG 380
                 .         .         .         .         .
    ..................................................

381 SSGASRGPSAMEYNKEDRESFRHSQPRSKSEMLSRKNFATGVPAVSMDEL 430
                 .         .         .         .         .
    ..................................................

431 AAFADSYGQRPRRADGNSHEARGGSRFERSESRAHSGFYQDDSLEEYYGQ 480
                 .         .         .         .         .
    ..................................................

481 RSRSREPLTDADRGWAFSPARRRPAEDAHLPRLVSRTPGTAPKYDHSYLG 530
                 .         .         .         .         .
    ..................................................

531 SARERQARPEGASRGGSLETPSKRSAQLGPRSASYYAWSPPGTYKAGSSQ 580
                 .         .         .         .         .
    ..................................................

581 DDQEDASDDALPPYSELELTRGPSYRGRDLPYHSNSEKKRKKEPAKKTND 630

    .........

631 FPTRMSLVV                                          639
```

Alignment of:
R31375_P14 x known protein(s) FXYD3_HUMAN, NP_005962 and Q6IB59_HUMAN:

```
                          .         .         .         .         .
      1 MQKVTLGLLVFLAGFPVLDANDLEDKNSPFYYGAPYIFVKRMGGQMKRTQ 50
        ||||||||||||||||||||||||||||||||
      1 MQKVTLGLLVFLAGFPVLDANDLEDKNSPFYY.................. 32

                          .         .         .         .         .
     51 AGTEVPSTFLLDWHSLQVGGLICAGVLCAMGIIIVMSAKCKCKFGQKSGH 100
                   |||||||||||||||||||||||||||||||||||||||
     33 ...........DWHSLQVGGLICAGVLCAMGIIIVMSAKCKCKFGQKSGH 71

                          .
    101 HPGETPPLITPGSAQS                                   116
        ||||||||||||||||
     72 HPGETPPLITPGSAQS                                   87
```

FIG. 49A

Alignment of:
R31375_P31 x known protein(s) FXYD3_HUMAN, NP_005962 and Q6IB59_HUMAN:

```
                          .         .         .         .         .
      1 MQKVTLGLLVFLAGFPVLDANDLEDKNSPFYYDWHSLQVGGLICAGVLCA 50
        ||||||||||||||||||||||||||||||||||||||||||||||||||
      1 MQKVTLGLLVFLAGFPVLDANDLEDKNSPFYYDWHSLQVGGLICAGVLCA 50

                          .         .         .         .         .
     51 MGIIIVMSEWRSSGEQAGRGWGSPPLTTQLSPTGAKCKCKFGQKSG.... 96
        ||||||||                                  ||||||||||||
     51 MGIIIVMS..........................AKCKCKFGQKSGHHPG 74

                          .
        .............

     75 ETPPLITPGSAQS                                      87
```

FIG. 49B

```
Alignment of:
R31375_P31 x known protein(s) NP_068710:

                .         .         .         .         .
      1 MQKVTLGLLVFLAGFPVLDANDLEDKNSPFYYDWHSLQVGGLICAGVLCA 50
        ||||||||||||||||||||||||||||||||||||||||||||||||||
      1 MQKVTLGLLVFLAGFPVLDANDLEDKNSPFYYDWHSLQVGGLICAGVLCA 50
                .         .         .         .         .
     51 MGIIIVMSEWRSSGEQAGRGWGSPPLTTQLSPTGAKCKCKFGQKSG.... 96
        ||||||||||||||||||||||||||||||||||||||||||||||
     51 MGIIIVMSEWRSSGEQAGRGWGSPPLTTQLSPTGAKCKCKFGQKSGHHPG 100
                .
        .............

    101 ETPPLITPGSAQS                                      113
```

FIG. 49C

```
Alignment of:
R31375_P33 x known protein(s) NP_068710:

                .         .         .         .         .
      1 MQKVTLGLLVFLAGFPVLDANDLE........DWHSLQVGGLICAGVLCA 42
        ||||||||||||||||||||||||        ||||||||||||||||||
      1 MQKVTLGLLVFLAGFPVLDANDLEDKNSPFYYDWHSLQVGGLICAGVLCA 50
                .         .         .         .         .
     43 MGIIIVMSEWRSSGEQAGRGWGSPPLTTQLSPTGAKCKCKFGQKSG.... 88
        ||||||||||||||||||||||||||||||||||||||||||||||
     51 MGIIIVMSEWRSSGEQAGRGWGSPPLTTQLSPTGAKCKCKFGQKSGHHPG 100
                .
        .............

    101 ETPPLITPGSAQS                                      113
```

FIG. 49D

Alignment of:
R31375_P33 x known protein(s) NP_068710:

```
                  .         .         .         .         .
  1 MQKVTLGLLVFLAGFPVLDANDLE........DWHSLQVGGLICAGVLCA 42
    ||||||||||||||||||||||||        ||||||||||||||||||
  1 MQKVTLGLLVFLAGFPVLDANDLEDKNSPFYYDWHSLQVGGLICAGVLCA 50
                  .         .         .         .         .
 43 MGIIIVMSEWRSSGEQAGRGWGSPPLTTQLSPTGAKCKCKFGQKSG.... 88
    ||||||||||||||||||||||||||||||||||||||||||||||
 51 MGIIIVMSEWRSSGEQAGRGWGSPPLTTQLSPTGAKCKCKFGQKSGHHPG 100
                  .
    .............

101 ETPPLITPGSAQS                                     113
```

FIG. 49E

FXYD3_T0_P0_EGFP- DNA sequence (996bp)

ATGCAGAAGGTGACCCTGGGCCTGCTTGTGTTCCTGGCAGGCTTTCCTGTCCTGGACGCC
AATGACCTAGAAGATAAAAACAGTCCTTTCTACTATGACTGGCACAGCCTCCAGGTTGGC
GGGCTCATCTGCGCTGGGGTTCTGTGCGCCATGGGCATCATCATCGTCATGAGTGCAAAA
TGCAAATGCAAGTTTGGCCAGAAGTCCGGTCACCATCCAGGGGAGACTCCACCTCTCATC
ACCCCAGGCTCAGCCCAAAGCGGACCGGTCGCCACCATGGTGAGCAAGGGCGAGGAGCTG
TTCACCGGGGTGGTGCCCATCCTGGTCGAGCTGGACGGCGACGTAAACGGCCACAAGTTC
AGCGTGTCCGGCGAGGGCGAGGGCGATGCCACCTACGGCAAGCTGACCCTGAAGTTCATC
TGCACCACCGGCAAGCTGCCCGTGCCCTGGCCCACCCTCGTGACCACCCTGACCTACGGC
GTGCAGTGCTTCAGCCGCTACCCCGACCACATGAAGCAGCACGACTTCTTCAAGTCCGCC
ATGCCCGAAGGCTACGTCCAGGAGCGCACCATCTTCTTCAAGGACGACGGCAACTACAAG
ACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGC
CACAACGTCTATATCATGGCCGACAAGCAGAAGAACGGCATCAAGGTGAACTTCAAGATC
CGCCACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCCCTG
AGCAAAGACCCCAACGAGAAGCGCGATCACATGGTCCTGCTGGAGTTCGTGACCGCCGCC
GGGATCACTCTCGGCATGGACGAGCTGTACAAGTAA

FIG. 56A

FXYD3_T25_P14_EGFP- DNA sequence (1083bp)

ATGCAGAAGGTGACCCTGGGCCTGCTTGTGTTCCTGGCAGGCTTTCCTGTCCTGGACGCC
AATGACCTAGAAGATAAAAACAGTCCTTTCTACTATGGTGCTCCATATATATTTGTCAAG
AGAATGGGGGGACAGATGAAGAGGACACAGGCTGGCACTGAGGTCCCCTCCACTTTCCTC
CTAGACTGGCACAGCCTCCAGGTTGGCGGGCTCATCTGCGCTGGGGTTCTGTGCGCCATG
GGCATCATCATCGTCATGAGTGCAAAATGCAAATGCAAGTTTGGCCAGAAGTCCGGTCAC
CATCCAGGGGAGACTCCACCTCTCATCACCCCAGGCTCAGCCCAAAGCGGACCGGTCGCC
ACCATGGTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGATGCCACC
TACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATG
AAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGGG
CACAAGCTGGAGTACAACTACAACAGCCACAACGTCTATATCATGGCCGACAAGCAGAAG
AACGGCATCAAGGTGAACTTCAAGATCCGCCACAACATCGAGGACGGCAGCGTGCAGCTC
GCCGACCACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGATCACATG
GTCCTGCTGGAGTTCGTGACCGCCGCCGGGATCACTCTCGGCATGGACGAGCTGTACAAG
TAA

FIG. 56B

AI216611_T0_P0_EGFP- DNA sequence (1371bp)

ATGAGGCCTCTGCCCAGCGGGAGGAGGAAGACCCGAGGCATCTCCCTAGGACTCTTCGCC
CTCTGCCTGGCCGCAGCCCGCTGTCTGCAGAGTCAGGGTGTGTCCCTATACATTCCTCAG
GCCACCATCAATGCCACTGTCAAAGAAGACATCCTGCTCTCAGTTGAGTACTCCTGTCAT
GGAGTGCCCACCATCGAATGGACATATTCATCCAATTGGGGAACGCAGAAGATCGTGGAG
TGGAAACCAGGGACTCAGGCCAACATCTCTCAAAGCCACAAGGACAGAGTCTGCACCTTT
GACAACGGCTCCATCCAGCTCTTCAGCGTGGGAGTGAGGGATTCCGGCTACTATGTCATC
ACCGTGACGGAGCGCCTGGGGAGCAGCCAGTTTGGCACCATCGTGCTGCACGTCTCTGAG
ATCCTCTATGAAGACCTGCACTTTGTCGCTGTCATCCTTGCTTTTCTCGCTGCTGTGGCC
GCAGTATTAATCAGCCTCATGTGGGTTTGTAATAAGTGTGCATATAAATTTCAGAGGAAG
AGAAGACACAAACTCAAAGAAAGCACAACTGAGGAGATTGAGCTGGAAGATGTTGAGTGT
CGAATTCTGCAGTCGACGGTACCGCGGGCCCGGGATCCACCGGTCGCCACCATGGTGAGC
AAGGGCGAGGAGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTACGGCAAGCTG
ACCCTGAAGTTCATCTGCACCACCGGCAAGCTGCCCGTGCCCTGGCCCACCCTCGTGACC
ACCCTGACCTACGGCGTGCAGTGCTTCAGCCGCTACCCCGACCACATGAAGCAGCACGAC
TTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAAGCTGGAG
TACAACTACAACAGCCACAACGTCTATATCATGGCCGACAAGCAGAAGAACGGCATCAAG
GTGAACTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTGCTGGAG
TTCGTGACCGCCGCCGGGATCACTCTCGGCATGGACGAGCTGTACAAGTAA

FIG. 56C

AI216611_T1_P1_EGFP- DNA sequence (1332bp)

ATGAGGCCTCTGCCCAGCGGGAGGAGGAAGACCCGAGGCATCTCCCTAGGACTCTTCGCC
CTCTGCCTGGCCGCAGCCCGCTGTCTACAGAGTCAGGGTGTGTCCCTATACATTCCTCAG
GCCACCATCAATGCCACTGTCAAAGAAGACATCCTGCTCTCAGTTGAGTACTCCTGTCAT
GGAGTGCCCACCATCGAATGGACATATTCATCCAATTGGGGAACGCAGAAGATCGTGGAG
TGGAAACCAGGGACTCAGGCCAACATCTCTCAAAGCCACAAGGACAGAGTCTGCACCTTT
GACAACGGCTCCATCCAGCTCTTCAGCGTGGGAGTGAGGGATTCCGGCTACTATGTCATC
ACCGTGACGGAGCGCCTGGGGAGCAGCCAGTTTGGCACCATCGTGCTGCACGTCTCTGAG
ATCCTCTATGAAGACCTGCACTTTGTCGCTGTCATCCTTGCTTTTCTCGCTGCTGTGGCC
GCAGTATTAATCAGCCTCATGTGGGTTTGTAATAAGTGTGCATATAAATTTCAGAGGAAG
AGAAGACACAAACTCAAAGGTAACCCCCTGGGCCTTGTGATAATCCATGAGTGGTTTGGA
CCGGTCGCCACCATGGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGGGC
GATGCCACCTACGGCAAGCTGACCCTGAAGTTCATCTGCACCACCGGCAAGCTGCCCGTG
CCCTGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCAGGAG
CGCACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCAAC
ATCCTGGGGCACAAGCTGGAGTACAACTACAACAGCCACAACGTCTATATCATGGCCGAC
AAGCAGAAGAACGGCATCAAGGTGAACTTCAAGATCCGCCACAACATCGAGGACGGCAGC
GTGCAGCTCGCCGACCACTACCAGCAGAACACCCCCATCGGCGACGGCCCCGTGCTGCTG
CCCGACAACCACTACCTGAGCACCCAGTCCGCCCTGAGCAAAGACCCCAACGAGAAGCGC
GATCACATGGTCCTGCTGGAGTTCGTGACCGCCGCCGGGATCACTCTCGGCATGGACGAG
CTGTACAAGTAA

FIG. 56D

C1ORF32_T8_P8_EGFP- DNA sequence (1533bp)

ATGGATAGGGTCTTGCTGAGGTGGATTTCTCTCTTCTGGCTAACAGCCATGGTCGAAGGC
CTTCAGGTCACAGTGCCCGACAAGAAGAAGGTGGCCATGCTCTTCCAGCCCACTGTGCTT
CGCTGCCACTTCTCAACATCCTCCCATCAGCCTGCAGTTGTGCAGTGGAAGTTCAAGTCC
TACTGCCAGGATCGCATGGGAGAATCCTTGGGCATGTCCTCTACCCGGGCCCAATCTCTC
AGCAAGAGAAACCTGGAATGGGACCCCTACTTGGATTGTTTGGACAGCAGGAGGACTGTT
CGAGTAGTAGCTTCAAAACAGGGCTCGACTGTCACCCTGGGAGATTTCTACAGGGGCAGA
GAGATCACGATTGTTCATGATGCAGATCTTCAAATTGGAAAGCTTATGTGGGGAGACAGC
GGACTCTATTACTGTATTATCACCACCCCAGATGACCTGGAGGGGAAAAATGAGGACTCA
GTGGAACTGCTGGTGTTGGGCAGGACAGGGCTGCTTGCTGATCTCTTGCCCAGTTTTGCT
GTGGAGATTATGCCAGAGTGGGTGTTTGTTGGCCTGGTGCTCCTGGGCGTCTTCCTCTTC
TTCGTCCTGGTGGGGATCTGCTGGTGCCAGTGCTGCCCTCACAGCTGCTGCTGCTATGTC
CGCTGCCCATGCTGCCCAGATTCCTGCTGCTGCCCTCAAGCCTGTGAGTACAGTGACCGC
TGGGGAGACAGAGCGATCGAGAGAAATGTCTACCTCTCTACCCGAATTCTGCAGTCGACG
GTACCGCGGGCCCGGGATCCACCGGTCGCCACCATGGTGAGCAAGGGCGAGGAGCTGTTC
ACCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTGC
ACCACCGGCAAGCTGCCCGTGCCCTGGCCCACCCTCGTGACCACCCTGACCTACGGCGTG
CAGTGCTTCAGCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATC
GGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGG
ATCACTCTCGGCATGGACGAGCTGTACAAGTAA

FIG. 56E

LOC253012_T4_P5_EGFP- DNA sequence (2085bp)

ATGTGGCTCAAGGTCTTCACAACTTTCCTTTCCTTTGCAACAGGTGCTTGCTCGGGGCTG
AAGGTGACAGTGCCATCACACACTGTCCATGGCGTCAGAGGTCAGGCCCTCTACCTACCC
GTCCACTATGGCTTCCACACTCCAGCATCAGACATCCAGATCATATGGCTATTTGAGAGA
CCCCACACAATGCCCAAATACTTACTGGGCTCTGTGAATAAGTCTGTGGTTCCTGACTTG
GAATACCAACACAAGTTCACCATGATGCCACCCAATGCATCTCTGCTTATCAACCCACTG
CAGTTCCCTGATGAAGGCAATTACATCGTGAAGGTCAACATTCAGGGAAATGGAACTCTA
TCTGCCAGTCAGAAGATACAAGTCACGGTTGATGATCCTGTCACAAAGCCAGTGGTGCAG
ATTCATCCTCCCTCTGGGGCTGTGGAGTATGTGGGGAACATGACCCTGACATGCCATGTG
GAAGGGGGCACTCGGCTAGCTTACCAATGGCTAAAAAATGGGAGACCTGTCCACACCAGC
TCCACCTACTCCTTTTCTCCCCAAAACAATACCCTTCATATTGCTCCAGTAACCAAGGAA
GACATTGGGAATTACAGCTGCCTGGTGAGGAACCCTGTCAGTGAAATGGAAAGTGATATC
ATTATGCCCATCATATATTATGGACCTTATGGACTTCAAGTGAATTCTGATAAAGGGCTA
AAAGTAGGGGAAGTGTTTACTGTTGACCTTGGAGAGGCCATCCTATTTGATTGTTCTGCT
GATTCTCATCCCCCCAACACCTACTCCTGGATTAGGAGGACTGACAATACTACATATATC
ATTAAGCATGGGCCTCGCTTAGAAGTTGCATCTGAGAAAGTAGCCCAGAAGACAATGGAC
TATGTGTGCTGTGCTTACAACAACATAACCGGCAGGCAAGATGAAACTCATTTCACAGTT
ATCATCACTTCCGTAGGACTGGAGAAGCTTGCACAGAAAGGAAAATCATTGTCACCTTTA
GCAAGTATAACTGGAATATCACTATTTTTGATTATATCCATGTGTCTTCTCTTCCTATGG
AAAAAATATCAACCCTACAAAGTTATAAAACAGAAACTAGAAGGCAGGCCAGAAACAGAA
TACAGGAAAGCTCAAACATTTTCAGGCCATGAAGATGCTCTGGATGACTTCGGAATATAT
GAATTTGTTGCTTTTCCAGATGTTTCTGGTGTTTCCAGGATCCCAAGCAGGTCTGTTCCA
GCCTCTGATTGTGTATCGGGGCAAGATTTGCACAGTACAGTGTATGAAGTTATTCAGCAC
ATCCCTGCCCAGCAGCAAGACCATCCAGAGGGACCGGTCGCCACCATGGTGAGCAAGGGC
GAGGAGCTGTTCACCGGGGTGGTGCCCATCCTGGTCGAGCTGGACGGCGACGTAAACGGC
CACAAGTTCAGCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTC
AAGTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATCGAG
CTGAAGGGCATCGACTTCAAGGAGGACGGCAACATCCTGGGGCACAAGCTGGAGTACAAC
TACAACAGCCACAACGTCTATATCATGGCCGACAAGCAGAAGAACGGCATCAAGGTGAAC
TTCAAGATCCGCCACAACATCGAGGACGGCAGCGTGCAGCTCGCCGACCACTACCAGCAG
AACACCCCCATCGGCGACGGCCCCGTGCTGCTGCCCGACAACCACTACCTGAGCACCCAG
TCCGCCCTGAGCAAAGACCCCAACGAGAAGCGCGATCACATGGTCCTGCTGGAGTTCGTG
ACCGCCGCCGGGATCACTCTCGGCATGGACGAGCTGTACAAGTAA

FIG. 56F

ILDR1_T0_P3_EGFP- DNA sequence (2373bp)

ATGGCATGGCCCAAACTGCCCGCACCTTGGCTGCTGCTCTGCACCTGGCTCCCAGCAGGG
TGCCTGTCCTTGCTTGTGACGGTCCAGCACACAGAACGCTATGTCACCCTGTTTGCCTCT
ATCATCCTCAAATGTGACTACACCACCTCTGCCCAGCTCCAGGACGTGGTGGTGACATGG
CGCTTCAAGTCCTTCTGCAAGGACCCTATCTTTGACTACTACTCAGCGTCATACCAGGCA
GCTTTATCCCTGGGCCAGGACCCATCCAATGACTGCAACGACAACCAGCGGGAAGTTCGC
ATAGTGGCCCAGCGGCGGGGGCAGAATGAGCCCGTGCTGGGGGTAGATTACCGGCAGCGC
AAGATCACCATCCAGAACCGAGCAGATCTCGTGATAAATGAAGTGATGTGGTGGGACCAT
GGAGTGTATTACTGCACCATTGAGGCTCCAGGGGACACATCAGGAGACCCCGATAAGGAA
GTAAAGCTCATCGTCCTACACTGGCTGACAGTGATCTTCATCATCCTGGGAGCCCTCCTC
CTCCTGCTGCTGATTGGAGTGTGCTGGTGCCAGTGCTGTCCTCAGTATTGCTGCTGCTAT
ATCCGCTGTCCCTGCTGTCCTGCCCACTGCTGCTGTCCTGAGGAAGCCCTGGCCCGCCAC
CGCTACATGAAGCAGGCCCAGGCCCTAGGTCCTCAGATGATGGGAAAACCCCTGTACTGG
GGGGCGGACAGGAGCTCCCAGGTTTCATCTTATCCAATGCACCCGCTGCTGCAGCGAGAT
TTGTCCCTGCGGTCCAGCCTCCCGCAGATGCCAATGACCCAGACCACCAATCAGCCTCCC
ATCGCCAATGGTGTCCTGGAGTATTTGGAGAAAGAACTGCGGAACCTCAACCTGGCCCAG
CCTCTGCCCCCTGACCTCAAAGGCAGATTTGGCCATCCCTGCAGCATGCTGTCCTCCCTG
GGCTCTGAGGTCGTGGAACGCAGAATCATCCACCTGCCCCCACTGATCAGAGACCTGTCA
TCCTCAAGGAGGACCAGTGACTCCCTGCACCAGCAGTGGCTCACCCCAATTCCCTCCAGG
CCCTGGGATCTGAGGGAGGGGAGAAGCCACCACCATTACCCTGATTTCCACCAGGAGCTC
CAGGACCGGGGGCCAAAGTCTTGGGCATTGGAAAGAAGGGAGTTGGACCCATCGTGGAGT
GGAAGGCACCGTAGCTCTAGGCTGAATGGGTCACCCATACACTGGTCAGACAGGGACAGC
CTAAGCGATGTCCCCTCATCCAGTGAGGCACGCTGGCGGCCGAGCCACCCTCCTTTCAGG
AGCCGCTGTCAGGAGAGGCCCCGCAGGCCCAGCCCCCGGGAGAGCACTCAGAGGCACGGG
AGACGACGCAGGCACCGCAGCTACTCTCCTCCCTTGCCCTCCGGCCTCAGTTCCTGGAGC
TCTGAAGAGGACAAGGAGAGGCAGCCCCAGAGCTGGCGGGCCCACCGCCGCGGCTCGCAC
TCCCCACACTGGCCCGAGGAGAAGCCGCCTAGCTACCGCTCACTGGATATCACTCCAGGC
AAGAATAGCAGGAAAAAAGGGAGTGTGGAGAGGCGCTCGGAGAAAGACAGCTCTCATAGT
GGAAGGAGTGTGGTCATTGGACCGGTCGCCACCATGGTGAGCAAGGGCGAGGAGCTGTTC
ACCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTGC
ACCACCGGCAAGCTGCCCGTGCCCTGGCCCACCCTCGTGACCACCCTGACCTACGGCGTG
CAGTGCTTCAGCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATC
GGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGG
ATCACTCTCGGCATGGACGAGCTGTACAAGTAA

FIG. 56G

ILDR1_T2_P5_EGFP- DNA sequence (2241bp)

ATGGCATGGCCCAAACTGCCCGCACCTTGGCTGCTGCTCTGCACCTGGCTCCCAGCAGGG
TGCCTGTCCTTGCTTGTGACGGTCCAGCACACAGAACGCTATGTCACCCTGTTTGCCTCT
ATCATCCTCAAATGTGACTACACCACCTCTGCCCAGCTCCAGGACGTGGTGGTGACATGG
CGCTTCAAGTCCTTCTGCAAGGACCCTATCTTTGACTACTACTCAGCGTCATACCAGGCA
GCTTTATCCCTGGGCCAGGACCCATCCAATGACTGCAACGACAACCAGCGGGAAGTTCGC
ATAGTGGCCCAGCGGCGGGGGCAGAATGAGCCCGTGCTGGGGGTAGATTACCGGCAGCGC
AAGATCACCATCCAGAACCGAGCAGATCTCGTGATAAATGAAGTGATGTGGTGGGACCAT
GGAGTGTATTACTGCACCATTGAGGCTCCAGGGGACACATCAGGAGACCCCGATAAGGAA
GTAAAGCTCATCGTCCTACACTGGCTGACAGTGATCTTCATCATCCTGGGAGCCCTCCTC
CTCCTGCTGCTGATTGGAGTGTGCTGGTGCCAGTGCTGTCCTCAGTATTGCTGCTGCTAT
ATCCGCTGTCCCTGCTGTCCTGCCCACTGCTGCTGTCCTGAGGAAGATTTGTCCCTGCCG
TCCAGCCTCCCGCAGATGCCAATGACCCAGACCACCAATCAGCCTCCCATCGCCAATGGT
GTCCTGGAGTATTTGGAGAAAGAACTGCGGAACCTCAACCTGGCCCAGCCTCTGCCCCCT
GACCTCAAAGGCAGATTTGGCCATCCCTGCAGCATGCTGTCCTCCCTGGGCTCTGAGGTC
GTGGAACGCAGAATCATCCACCTGCCCCCACTGATCAGAGACCTGTCATCCTCAAGGAGG
ACCAGTGACTCCCTGCACCAGCAGTGGCTCACCCCAATTCCCTCCAGGCCCTGGGATCTG
AGGGAGGGGAGAAGCCACCACCATTACCCTGATTTCCACCAGGAGCTCCAGGACCGGGGG
CCAAAGTCTTGGGCATTGGAAAGAAGGGAGTTGGACCCATCGTGGAGTGGAAGGCACCGT
AGCTCTAGGCTGAATGGGTCACCCATACACTGGTCAGACAGGGACAGCCTAAGCGATGTC
CCCTCATCCAGTGAGGCACGCTGGCGGCCGAGCCACCCTCCTTTCAGGAGCCGCTGTCAG
GAGAGGCCCCGCAGGCCCAGCCCCCGGGAGAGCACTCAGAGGCACGGGAGACGACGCAGG
CACCGCAGCTACTCTCCTCCCTTGCCCTCCGGCCTCAGTTCCTGGAGCTCTGAAGAGGAC
AAGGAGAGGCAGCCCCAGAGCTGGCGGGCCCACCGCCGCGGCTCGCACTCCCCACACTGG
CCCGAGGAGAAGCCGCCTAGCTACCGCTCACTGGATATCACTCCAGGCAAGAATAGCAGG
AAAAAAGGGAGTGTGGAGAGGCGCTCGGAGAAAGACAGCTCTCATAGTGGAAGGAGTGTG
GTCATTGGACCGGTCGCCACCATGGTGAGCAAGGGCGAGGAGCTGTTCACCGGGGTGGTG
CCCATCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGGCAAG
CTGCCCGTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAAGGCTAC
GTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAG
GACGGCAACATCCTGGGGCACAAGCTGGAGTACAACTACAACAGCCACAACGTCTATATC
ATGGCCGACAAGCAGAAGAACGGCATCAAGGTGAACTTCAAGATCCGCCACAACATCGAG
GACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAAC
GAGAAGCGCGATCACATGGTCCTGCTGGAGTTCGTGACCGCCGCCGGGATCACTCTCGGC
ATGGACGAGCTGTACAAGTAA

FIG. 56H

VSIG1_T6_P5_EGFP- DNA sequence (2082bp)

ATGGTGTTCGCATTTTGGAAGGTCTTTCTGATCCTAAGCTGCCTTGCAGGTCAGGTTAGT
GTGGTGCAAGTGACCATCCCAGACGGTTTCGTGAACGTGACTGTTGGATCTAATGTCACT
CTCATCTGCATCTACACCACCACTGTGGCCTCCCGAGAACAGCTTTCCATCCAGTGGTCT
TTCTTCCATAAGAAGGAGATGGAGCCAATTTCTCACAGCTCGTGCCTCAGTACTGAGGGT
ATGGAGGAAAAGGCAGTCAGTCAGTGTCTAAAAATGACGCACGCAAGAGACGCTCGGGGA
AGATGTAGCTGGACCTCTGAGTCTCCTTGGGAGGAGGGGAAGTGGCCAGATGTTGAGGCT
GTGAAGGGCACTCTTGATGGACAGCAGGCTGAACTCCAGATTTACTTTTCTCAAGGTGGA
CAAGCTGTAGCCATCGGGCAATTTAAAGATCGAATTACAGGGTCCAACGATCCAGGTAAT
GCATCTATCACTATCTCGCATATGCAGCCAGCAGACAGTGGAATTTACATCTGCGATGTT
AACAACCCCCCAGACTTTCTCGGCCAAAACCAAGGCATCCTCAACGTCAGTGTGTTAGTG
AAACCTTCTAAGCCCCTTTGTAGCGTTCAAGGAAGACCAGAAACTGGCCACACTATTTCC
CTTTCCTGTCTCTCTGCGCTTGGAACACCTTCCCCTGTGTACTACTGGCATAAACTTGAG
GGAAGAGACATCGTGCCAGTGAAAGAAAACTTCAACCCAACCACCGGGATTTTGGTCATT
GGAAATCTGACAAATTTTGAACAAGGTTATTACCAGTGTACTGCCATCAACAGACTTGGC
AATAGTTCCTGCGAAATCGATCTCACTTCTTCACATCCAGAAGTTGGAATCATTGTTGGG
GCCTTGATTGGTAGCCTGGTAGGTGCCGCCATCATCATCTCTGTTGTGTGCTTCGCAAGG
AATAAGGCAAAAGCAAAGGCAAAAGAAAGAAATTCTAAGACCATCGCGGAACTTGAGCCA
ATGACAAAGATAAACCCAAGGGGAGAAAGCGAAGCAATGCCAAGAGAAGACGCTACCCAA
CTAGAAGTAACTCTACCATCTTCCATTCATGAGACTGGCCCTGATACCATCCAAGAACCA
GACTATGAGCCAAAGCCTACTCAGGAGCCTGCCCCAGAGCCTGCCCCAGGATCAGAGCCT
ATGGCAGTGCCTGACCTTGACATCGAGCTGGAGCTGGAGCCAGAAACGCAGTCGGAATTG
GAGCCAGAGCCAGAGCCAGAGCCAGAGTCAGAGCCTGGGGTTGTAGTTGAGCCCTTAAGT
GAAGATGAAAAGGGAGTGGTTAAGGCAGGACCGGTCGCCACCATGGTGAGCAAGGGCGAG
GAGCTGTTCACCGGGGTGGTGCCCATCCTGGTCGAGCTGGACGGCGACGTAAACGGCCAC
AAGTTCAGCGTGTCCGGCGAGGGCGAGGGCGATGCCACCTACGGCAAGCTGACCCTGAAG
TTCATCTGCACCACCGGCAAGCTGCCCGTGCCCTGGCCCACCCTCGTGACCACCCTGACC
TACGGCGTGCAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGACGACGGCAAC
TACAAGACCCGCGCCGAGGTGAAGTTCGAGGGCGACACCCTGGTGAACCGCATCGAGCTG
AAGGGCATCGACTTCAAGGAGGACGGCAACATCCTGGGGCACAAGCTGGAGTACAACTAC
AACAGCCACAACGTCTATATCATGGCCGACAAGCAGAAGAACGGCATCAAGGTGAACTTC
AAGATCCGCCACAACATCGAGGACGGCAGCGTGCAGCTCGCCGACCACTACCAGCAGAAC
ACCCCCATCGGCGACGGCCCCGTGCTGCTGCCCGACAACCACTACCTGAGCACCCAGTCC
GCCCTGAGCAAAGACCCCAACGAGAAGCGCGATCACATGGTCCTGCTGGAGTTCGTGACC
GCCGCCGGGATCACTCTCGGCATGGACGAGCTGTACAAGTAA

FIG. 56I

VSIG1_T5_P4_EGFP- DNA sequence (2004bp)

ATGGTGTTCGCATTTTGGAAGGTCTTTCTGATCCTAAGCTGCCTTGCAGGTCAGGTTAGT
GTGGTGCAAGTGACCATCCCAGACGGTTTCGTGAACGTGACTGTTGGATCTAATGTCACT
CTCATCTGCATCTACACCACCACTGTGGCCTCCCGAGAACAGCTTTCCATCCAGTGGTCT
TTCTTCCATAAGAAGGAGATGGAGCCAATTTCTCACAGCTCGTGCCTCAGTACTGAGGGT
ATGGAGGAAAAGGCAGTCAGTCAGTGTCTAAAAATGACGCACGCAAGAGACGCTCGGGGA
AGATGTAGCTGGACCTCTGAGATTTACTTTTCTCAAGGTGGACAAGCTGTAGCCATCGGG
CAATTTAAAGATCGAATTACAGGGTCCAACGATCCAGGTAATGCATCTATCACTATCTCG
CATATGCAGCCAGCAGACAGTGGAATTTACATCTGCGATGTTAACAACCCCCCAGACTTT
CTCGGCCAAAACCAAGGCATCCTCAACGTCAGTGTGTTAGTGAAACCTTCTAAGCCCCTT
TGTAGCGTTCAAGGAAGACCAGAAACTGGCCACACTATTTCCCTTTCCTGTCTCTCTGCG
CTTGGAACACCTTCCCCTGTGTACTACTGGCATAAACTTGAGGGAAGAGACATCGTGCCA
GTGAAAGAAAACTTCAACCCAACCACCGGGATTTTGGTCATTGGAAATCTGACAAATTTT
GAACAAGGTTATTACCAGTGTACTGCCATCAACAGACTTGGCAATAGTTCCTGCGAAATC
GATCTCACTTCTTCACATCCAGAAGTTGGAATCATTGTTGGGGCCTTGATTGGTAGCCTG
GTAGGTGCCGCCATCATCATCTCTGTTGTGTGCTTCGCAAGGAATAAGGCAAAAGCAAAG
GCAAAAGAAAGAAATTCTAAGACCATCGCGGAACTTGAGCCAATGACAAAGATAAACCCA
AGGGGAGAAAGCGAAGCAATGCCAAGAGAAGACGCTACCCAACTAGAAGTAACTCTACCA
TCTTCCATTCATGAGACTGGCCCTGATACCATCCAAGAACCAGACTATGAGCCAAAGCCT
ACTCAGGAGCCTGCCCCAGAGCCTGCCCCAGGATCAGAGCCTATGGCAGTGCCTGACCTT
GACATCGAGCTGGAGCTGGAGCCAGAAACGCAGTCGGAATTGGAGCCAGAGCCAGAGCCA
GAGCCAGAGTCAGAGCCTGGGGTTGTAGTTGAGCCCTTAAGTGAAGATGAAAAGGGAGTG
GTTAAGGCAGGACCGGTCGCCACCATGGTGAGCAAGGGCGAGGAGCTGTTCACCGGGGTG
GTGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGCTTC
AGCCGCTACCCCGACCACATGAAGCAGCACGACTTCTTCAAGTCCGCCATGCCCGAAGGC
TACGTCCAGGAGCGCACCATCTTCTTCAAGGACGACGGCAACTACAAGACCCGCGCCGAG
GTGAAGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGTCTAT
ATCATGGCCGACAAGCAGAAGAACGGCATCAAGGTGAACTTCAAGATCCGCCACAACATC
GAGGACGGCAGCGTGCAGCTCGCCGACCACTACCAGCAGAACACCCCCATCGGCGACGGC
CCCGTGCTGCTGCCCGACAACCACTACCTGAGCACCCAGTCCGCCCTGAGCAAAGACCCC
AACGAGAAGCGCGATCACATGGTCCTGCTGGAGTTCGTGACCGCCGCCGGGATCACTCTC
GGCATGGACGAGCTGTACAAGTAA

FIG. 56J

FXYD3_P0_EGFP- protein sequence (331aa)

MQKVTLGLLVFLAGFPVLDANDLEDKNSPFYYDWHSLQVGGLICAGVLCA
MGIIIVMSAKCKCKFGQKSGHHPGETPPLITPGSAQSGPVATMVSKGEEL
FTGVVPILVELDGDVNGHKFSVSGEGEGDATYGKLTLKFICTTGKLPVPW
PTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQ
KNGIKVNFKIRHNIEDGSVQLADHYQQNTPIGDGPVLLPDNHYLSTQSAL
SKDPNEKRDHMVLLEFVTAAGITLGMDELYK

FIG. 57A

FXYD3_P14_EGFP- protein sequence (360aa)

MQKVTLGLLVFLAGFPVLDANDLEDKNSPFYYGAPYIFVKRMGGQMKRTQ
AGTEVPSTFLLDWHSLQVGGLICAGVLCAMGIIIVMSAKCKCKFGQKSGH
HPGETPPLITPGSAQSGPVATMVSKGEELFTGVVPILVELDGDVNGHKFS
VSGEGEGDATYGKLTLKFICTTGKLPVPWPTLVTTLTYGVQCFSRYPDHM
KQHDFFKSAMPEGYVQERTIFFKDDGNYKTRAEVKFEGDTLVNRIELKGI
DFKEDGNILGHKLEYNYNSHNVYIMADKQKNGIKVNFKIRHNIEDGSVQL
ADHYQQNTPIGDGPVLLPDNHYLSTQSALSKDPNEKRDHMVLLEFVTAAG
ITLGMDELYK

FIG. 57B

AI216611_P0_EGFP- protein sequence (456aa)

MRPLPSGRRKTRGISLGLFALCLAAARCLQSQGVSLYIPQATINATVKED
ILLSVEYSCHGVPTIEWTYSSNWGTQKIVEWKPGTQANISQSHKDRVCTF
DNGSIQLFSVGVRDSGYYVITVTERLGSSQFGTIVLHVSEILYEDLHFVA
VILAFLAAVAAVLISLMWVCNKCAYKFQRKRRHKLKESTTEEIELEDVEC
RILQSTVPRARDPPVATMVSKGEELFTGVVPILVELDGDVNGHKFSVSGE
GEGDATYGKLTLKFICTTGKLPVPWPTLVTTLTYGVQCFSRYPDHMKQHD
FFKSAMPEGYVQERTIFFKDDGNYKTRAEVKFEGDTLVNRIELKGIDFKE
DGNILGHKLEYNYNSHNVYIMADKQKNGIKVNFKIRHNIEDGSVQLADHY
QQNTPIGDGPVLLPDNHYLSTQSALSKDPNEKRDHMVLLEFVTAAGITLG
MDELYK

FIG. 57C

AI216611_P1_EGFP- protein sequence (443aa)

MRPLPSGRRKTRGISLGLFALCLAAARCLQSQGVSLYIPQATINATVKED
ILLSVEYSCHGVPTIEWTYSSNWGTQKIVEWKPGTQANISQSHKDRVCTF
DNGSIQLFSVGVRDSGYYVITVTERLGSSQFGTIVLHVSEILYEDLHFVA
VILAFLAAVAAVLISLMWVCNKCAYKFQRKRRHKLKGNPLGLVIIHEWFG
PVATMVSKGEELFTGVVPILVELDGDVNGHKFSVSGEGEGDATYGKLTLK
FICTTGKLPVPWPTLVTTLTYGVQCFSRYPDHMKQHDFFKSAMPEGYVQE
RTIFFKDDGNYKTRAEVKFEGDTLVNRIELKGIDFKEDGNILGHKLEYNY
NSHNVYIMADKQKNGIKVNFKIRHNIEDGSVQLADHYQQNTPIGDGPVLL
PDNHYLSTQSALSKDPNEKRDHMVLLEFVTAAGITLGMDELYK

FIG. 57D

C1ORF32_P8_EGFP- protein sequence (510aa)

MDRVLLRWISLFWLTAMVEGLQVTVPDKKKVAMLFQPTVLRCHFSTSSHQ
PAVVQWKFKSYCQDRMGESLGMSSTRAQSLSKRNLEWDPYLDCLDSRRTV
RVVASKQGSTVTLGDFYRGREITIVHDADLQIGKLMWGDSGLYYCIITTP
DDLEGKNEDSVELLVLGRTGLLADLLPSFAVEIMPEWVFVGLVLLGVFLF
FVLVGICWCQCCPHSCCCYVRCPCCPDSCCCPQACEYSDRWGDRAIERNV
YLSTRILQSTVPRARDPPVATMVSKGEELFTGVVPILVELDGDVNGHKFS
VSGEGEGDATYGKLTLKFICTTGKLPVPWPTLVTTLTYGVQCFSRYPDHM
KQHDFFKSAMPEGYVQERTIFFKDDGNYKTRAEVKFEGDTLVNRIELKGI
DFKEDGNILGHKLEYNYNSHNVYIMADKQKNGIKVNFKIRHNIEDGSVQL
ADHYQQNTPIGDGPVLLPDNHYLSTQSALSKDPNEKRDHMVLLEFVTAAG
ITLGMDELYK

FIG. 57E

LOC253012_P5_EGFP- protein sequence (694aa)

MWLKVFTTFLSFATGACSGLKVTVPSHTVHGVRGQALYLPVHYGFHTPAS
DIQIIWLFERPHTMPKYLLGSVNKSVVPDLEYQHKFTMMPPNASLLINPL
QFPDEGNYIVKVNIQGNGTLSASQKIQVTVDDPVTKPVVQIHPPSGAVEY
VGNMTLTCHVEGGTRLAYQWLKNGRPVHTSSTYSFSPQNNTLHIAPVTKE
DIGNYSCLVRNPVSEMESDIIMPIIYYGPYGLQVNSDKGLKVGEVFTVDL
GEAILFDCSADSHPPNTYSWIRRTDNTTYIIKHGPRLEVASEKVAQKTMD
YVCCAYNNITGRQDETHFTVIITSVGLEKLAQKGKSLSPLASITGISLFL
IISMCLLFLWKKYQPYKVIKQKLEGRPETEYRKAQTFSGHEDALDDFGIY
EFVAFPDVSGVSRIPSRSVPASDCVSGQDLHSTVYEVIQHIPAQQQDHPE
GPVATMVSKGEELFTGVVPILVELDGDVNGHKFSVSGEGEGDATYGKLTL
KFICTTGKLPVPWPTLVTTLTYGVQCFSRYPDHMKQHDFFKSAMPEGYVQ
ERTIFFKDDGNYKTRAEVKFEGDTLVNRIELKGIDFKEDGNILGHKLEYN
YNSHNVYIMADKQKNGIKVNFKIRHNIEDGSVQLADHYQQNTPIGDGPVL
LPDNHYLSTQSALSKDPNEKRDHMVLLEFVTAAGITLGMDELYK

FIG. 57F

ILDR1_P3_EGFP protein sequence (790aa)

MAWPKLPAPWLLLCTWLPAGCLSLLVTVQHTERYVTLFASIILKCDYTTS
AQLQDVVVTWRFKSFCKDPIFDYYSASYQAALSLGQDPSNDCNDNQREVR
IVAQRRGQNEPVLGVDYRQRKITIQNRADLVINEVMWWDHGVYYCTIEAP
GDTSGDPDKEVKLIVLHWLTVIFIILGALLLLLLIGVCWCQCCPQYCCCY
IRCPCCPAHCCCPEEALARHRYMKQAQALGPQMMGKPLYWGADRSSQVSS
YPMHPLLQRDLSLRSSLPQMPMTQTTNQPPIANGVLEYLEKELRNLNLAQ
PLPPDLKGRFGHPCSMLSSLGSEVVERRIIHLPPLIRDLSSSRRTSDSLH
QQWLTPIPSRPWDLREGRSHHHYPDFHQELQDRGPKSWALERRELDPSWS
GRHRSSRLNGSPIHWSDRDSLSDVPSSSEARWRPSHPPFRSRCQERPRRP
SPRESTQRHGRRRRHRSYSPPLPSGLSSWSSEEDKERQPQSWRAHRRGSH
SPHWPEEKPPSYRSLDITPGKNSRKKGSVERRSEKDSSHSGRSVVIGPVA
TMVSKGEELFTGVVPILVELDGDVNGHKFSVSGEGEGDATYGKLTLKFIC
TTGKLPVPWPTLVTTLTYGVQCFSRYPDHMKQHDFFKSAMPEGYVQERTI
FFKDDGNYKTRAEVKFEGDTLVNRIELKGIDFKEDGNILGHKLEYNYNSH
NVYIMADKQKNGIKVNFKIRHNIEDGSVQLADHYQQNTPIGDGPVLLPDN
HYLSTQSALSKDPNEKRDHMVLLEFVTAAGITLGMDELYK

FIG. 57G

ILDR1_P5_EGFP- protein sequence (746aa)

MAWPKLPAPWLLLCTWLPAGCLSLLVTVQHTERYVTLFASIILKCDYTTS
AQLQDVVVTWRFKSFCKDPIFDYYSASYQAALSLGQDPSNDCNDNQREVR
IVAQRRGQNEPVLGVDYRQRKITIQNRADLVINEVMWWDHGVYYCTIEAP
GDTSGDPDKEVKLIVLHWLTVIFIILGALLLLLLIGVCWCQCCPQYCCCY
IRCPCCPAHCCCPEEDLSLPSSLPQMPMTQTTNQPPIANGVLEYLEKELR
NLNLAQPLPPDLKGRFGHPCSMLSSLGSEVVERRIIHLPPLIRDLSSSRR
TSDSLHQQWLTPIPSRPWDLREGRSHHHYPDFHQELQDRGPKSWALERRE
LDPSWSGRHRSSRLNGSPIHWSDRDSLSDVPSSSEARWRPSHPPFRSRCQ
ERPRRPSPRESTQRHGRRRRHRSYSPPLPSGLSSWSSEEDKERQPQSWRA
HRRGSHSPHWPEEKPPSYRSLDITPGKNSRKKGSVERRSEKDSSHSGRSV
VIGPVATMVSKGEELFTGVVPILVELDGDVNGHKFSVSGEGEGDATYGKL
TLKFICTTGKLPVPWPTLVTTLTYGVQCFSRYPDHMKQHDFFKSAMPEGY
VQERTIFFKDDGNYKTRAEVKFEGDTLVNRIELKGIDFKEDGNILGHKLE
YNYNSHNVYIMADKQKNGIKVNFKIRHNIEDGSVQLADHYQQNTPIGDGP
VLLPDNHYLSTQSALSKDPNEKRDHMVLLEFVTAAGITLGMDELYK

FIG. 57H

VSIG1_P5_EGFP- protein sequence (693aa)

MVFAFWKVFLILSCLAGQVSVVQVTIPDGFVNVTVGSNVTLICIYTTTVA
SREQLSIQWSFFHKKEMEPISHSSCLSTEGMEEKAVSQCLKMTHARDARG
RCSWTSESPWEEGKWPDVEAVKGTLDGQQAELQIYFSQGGQAVAIGQFKD
RITGSNDPGNASITISHMQPADSGIYICDVNNPPDFLGQNQGILNVSVLV
KPSKPLCSVQGRPETGHTISLSCLSALGTPSPVYYWHKLEGRDIVPVKEN
FNPTTGILVIGNLTNFEQGYYQCTAINRLGNSSCEIDLTSSHPEVGIIVG
ALIGSLVGAAIIISVVCFARNKAKAKAKERNSKTIAELEPMTKINPRGES
EAMPREDATQLEVTLPSSIHETGPDTIQEPDYEPKPTQEPAPEPAPGSEP
MAVPDLDIELELEPETQSELEPEPEPEPESEPGVVVEPLSEDEKGVVKAG
PVATMVSKGEELFTGVVPILVELDGDVNGHKFSVSGEGEGDATYGKLTLK
FICTTGKLPVPWPTLVTTLTYGVQCFSRYPDHMKQHDFFKSAMPEGYVQE
RTIFFKDDGNYKTRAEVKFEGDTLVNRIELKGIDFKEDGNILGHKLEYNY
NSHNVYIMADKQKNGIKVNFKIRHNIEDGSVQLADHYQQNTPIGDGPVLL
PDNHYLSTQSALSKDPNEKRDHMVLLEFVTAAGITLGMDELYK

FIG. 57I

VSIG1_P4_EGFP- protein sequence (667aa)

MVFAFWKVFLILSCLAGQVSVVQVTIPDGFVNVTVGSNVTLICIYTTTVA
SREQLSIQWSFFHKKEMEPISHSSCLSTEGMEEKAVSQCLKMTHARDARG
RCSWTSEIYFSQGGQAVAIGQFKDRITGSNDPGNASITISHMQPADSGIY
ICDVNNPPDFLGQNQGILNVSVLVKPSKPLCSVQGRPETGHTISLSCLSA
LGTPSPVYYWHKLEGRDIVPVKENFNPTTGILVIGNLTNFEQGYYQCTAI
NRLGNSSCEIDLTSSHPEVGIIVGALIGSLVGAAIIISVVCFARNKAKAK
AKERNSKTIAELEPMTKINPRGESEAMPREDATQLEVTLPSSIHETGPDT
IQEPDYEPKPTQEPAPEPAPGSEPMAVPDLDIELELEPETQSELEPEPEP
EPESEPGVVVEPLSEDEKGVVKAGPVATMVSKGEELFTGVVPILVELDGD
VNGHKFSVSGEGEGDATYGKLTLKFICTTGKLPVPWPTLVTTLTYGVQCF
SRYPDHMKQHDFFKSAMPEGYVQERTIFFKDDGNYKTRAEVKFEGDTLVN
RIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLL
EFVTAAGITLGMDELYK

FIG. 57J

FXYD_P14_EGFP

FXYD3_P0_EGFP

C1ORF32_P8_EGFP

LOC253012_P5_EGFP

ILDR1_P5_EGFP

ILDR1_P3_EGFP

FXYD3_T25_P14_ECD-_mFc DNA sequence (924bp)

ATGCAGAAGGTGACCCTGGGCCTGCTTGTGTTCCTGGCAGGCTTTCCTGTCCTGGACGCC
AATGACCTAGAAGATAAAAACAGTCCTTTCTACTATGGTGCTCCATATATATTTGTCAAG
AGAATGGGGGGACAGATGAAGAGGACACAGGCTGGCACTGAGGTCCCCTCCACTTTCCTC
CTAGACTGGGGATCCGAGAACCTGTACTTTCAGGGCAGCGGCGAGCCCAGAGGCCCCACC
ATCAAGCCCTGCCCCCCCTGCAAGTGCCCAGCCCCTAACCTGCTGGGCGGACCCAGCGTG
TTCATCTTCCCCCCCAAGATCAAGGACGTGCTGATGATCAGCCTGAGCCCCATCGTGACC
TGCGTGGTGGTGGACGTGAGCGAGGACGACCCCGACGTGCAGATCAGCTGGTTCGTGAAC
AACGTGGAGGTGCACACCGCCCAGACCCAGACCCACCGGGAGGACTACAACAGCACCCTG
CGGGTGGTGTCCGCCCTGCCCATCCAGCACCAGGACTGGATGAGCGGCAAAGAATTCAAG
TGCAAGGTGAACAACAAGGACCTGCCTGCCCCCATCGAGCGGACCATCAGCAAGCCCAAG
GGCAGCGTGAGAGCCCCCCAGGTGTACGTGCTGCCCCCTCCCGAGGAAGAGATGACCAAG
AAACAGGTGACCCTGACCTGCATGGTGACCGACTTCATGCCCGAGGACATCTACGTGGAG
TGGACCAACAACGGCAAGACCGAGCTGAACTACAAGAACACCGAGCCCGTGCTGGACAGC
GACGGCAGCTACTTCATGTATAGCAAGCTGAGAGTCGAGAAGAAAAACTGGGTGGAGCGG
AACAGCTACAGCTGCAGCGTGGTGCACGAGGGCCTGCACAACCACCACACCACCAAGAGC
TTCAGCCGGACCCCCGGCAAGTGA

FIG. 59A

AI216611_T0_P0_ECD_mFc DNA sequence (1170bp)

ATGAGGCCTCTGCCCAGCGGGAGGAGGAAGACCCGAGGCATCTCCCTAGGACTCTTCGCC
CTCTGCCTGGCCGCAGCCCGCTGTCTGCAGAGTCAGGGTGTGTCCCTATACATTCCTCAG
GCCACCATCAATGCCACTGTCAAAGAAGACATCCTGCTCTCAGTTGAGTACTCCTGTCAT
GGAGTGCCCACCATCGAATGGACATATTCATCCAATTGGGGAACGCAGAAGATCGTGGAG
TGGAAACCAGGGACTCAGGCCAACATCTCTCAAAGCCACAAGGACAGAGTCTGCACCTTT
GACAACGGCTCCATCCAGCTCTTCAGCGTGGGAGTGAGGGATTCCGGCTACTATGTCATC
ACCGTGACGGAGCGCCTGGGGAGCAGCCAGTTTGGCACCATCGTGCTGCACGTCTCTGAG
ATCCTCTATGAAGACGGATCCGAGAACCTGTACTTTCAGGGCAGCGGCGAGCCCAGAGGC
CCCACCATCAAGCCCTGCCCCCCCTGCAAGTGCCCAGCCCCTAACCTGCTGGGCGGACCC
AGCGTGTTCATCTTCCCCCCCAAGATCAAGGACGTGCTGATGATCAGCCTGAGCCCCATC
GTGACCTGCGTGGTGGTGGACGTGAGCGAGGACGACCCCGACGTGCAGATCAGCTGGTTC
GTGAACAACGTGGAGGTGCACACCGCCCAGACCCAGACCCACCGGGAGGACTACAACAGC
ACCCTGCGGGTGGTGTCCGCCCTGCCCATCCAGCACCAGGACTGGATGAGCGGCAAAGAA
TTCAAGTGCAAGGTGAACAACAAGGACCTGCCTGCCCCCATCGAGCGGACCATCAGCAAG
CCCAAGGGCAGCGTGAGAGCCCCCCAGGTGTACGTGCTGCCCCCTCCCGAGGAAGAGATG
ACCAAGAAACAGGTGACCCTGACCTGCATGGTGACCGACTTCATGCCCGAGGACATCTAC
GTGGAGTGGACCAACAACGGCAAGACCGAGCTGAACTACAAGAACACCGAGCCCGTGCTG
GACAGCGACGGCAGCTACTTCATGTATAGCAAGCTGAGAGTCGAGAAGAAAAACTGGGTG
GAGCGGAACAGCTACAGCTGCAGCGTGGTGCACGAGGGCCTGCACAACCACCACACCACC
AAGAGCTTCAGCCGGACCCCCGGCAAGTGA

FIG. 59B

C1ORF32_T8_P8_ECD-_mFc DNA sequence (1287bp)

ATGGATAGGGTCTTGCTGAGGTGGATTTCTCTCTTCTGGCTAACAGCCATGGTCGAAGGC
CTTCAGGTCACAGTGCCCGACAAGAAGAAGGTGGCCATGCTCTTCCAGCCCACTGTGCTT
CGCTGCCACTTCTCAACATCCTCCCATCAGCCTGCAGTTGTGCAGTGGAAGTTCAAGTCC
TACTGCCAGGATCGCATGGGAGAATCCTTGGGCATGTCCTCTACCCGGGCCCAATCTCTC
AGCAAGAGAAACCTGGAATGGGACCCCTACTTGGATTGTTTGGACAGCAGGAGGACTGTT
CGAGTAGTAGCTTCAAAACAGGGCTCGACTGTCACCCTGGGAGATTTCTACAGGGGCAGA
GAGATCACGATTGTTCATGATGCAGATCTTCAAATTGGAAAGCTTATGTGGGGAGACAGC
GGACTCTATTACTGTATTATCACCACCCCAGATGACCTGGAGGGGAAAAATGAGGACTCA
GTGGAACTGCTGGTGTTGGGCAGGACAGGGCTGCTTGCTGATCTCTTGCCCAGTTTTGCT
GTGGAGATTATGGGATCCGAGAACCTGTACTTTCAGGGCAGCGGCGAGCCCAGAGGCCCC
ACCATCAAGCCCTGCCCCCCCTGCAAGTGCCCAGCCCCTAACCTGCTGGGCGGACCCAGC
GTGTTCATCTTCCCCCCCAAGATCAAGGACGTGCTGATGATCAGCCTGAGCCCCATCGTG
ACCTGCGTGGTGGTGGACGTGAGCGAGGACGACCCCGACGTGCAGATCAGCTGGTTCGTG
AACAACGTGGAGGTGCACACCGCCCAGACCCAGACCCACCGGGAGGACTACAACAGCACC
CTGCGGGTGGTGTCCGCCCTGCCCATCCAGCACCAGGACTGGATGAGCGGCAAAGAATTC
AAGTGCAAGGTGAACAACAAGGACCTGCCTGCCCCCATCGAGCGGACCATCAGCAAGCCC
AAGGGCAGCGTGAGAGCCCCCCAGGTGTACGTGCTGCCCCCTCCCGAGGAAGAGATGACC
AAGAAACAGGTGACCCTGACCTGCATGGTGACCGACTTCATGCCCGAGGACATCTACGTG
GAGTGGACCAACAACGGCAAGACCGAGCTGAACTACAAGAACACCGAGCCCGTGCTGGAC
AGCGACGGCAGCTACTTCATGTATAGCAAGCTGAGAGTCGAGAAGAAAAACTGGGTGGAG
CGGAACAGCTACAGCTGCAGCGTGGTGCACGAGGGCCTGCACAACCACCACACCACCAAG
AGCTTCAGCCGGACCCCCGGCAAGTGA

FIG. 59C

LOC253012_T4_P5_ECD_mFc DNA sequence (1740bp)

ATGTGGCTCAAGGTCTTCACAACTTTCCTTTCCTTTGCAACAGGTGCTTGCTCGGGGCTG
AAGGTGACAGTGCCATCACACACTGTCCATGGCGTCAGAGGTCAGGCCCTCTACCTACCC
GTCCACTATGGCTTCCACACTCCAGCATCAGACATCCAGATCATATGGCTATTTGAGAGA
CCCCACACAATGCCCAAATACTTACTGGGCTCTGTGAATAAGTCTGTGGTTCCTGACTTG
GAATACCAACACAAGTTCACCATGATGCCACCCAATGCATCTCTGCTTATCAACCCACTG
CAGTTCCCTGATGAAGGCAATTACATCGTGAAGGTCAACATTCAGGGAAATGGAACTCTA
TCTGCCAGTCAGAAGATACAAGTCACGGTTGATGATCCTGTCACAAAGCCAGTGGTGCAG
ATTCATCCTCCCTCTGGGGCTGTGGAGTATGTGGGGAACATGACCCTGACATGCCATGTG
GAAGGGGGCACTCGGCTAGCTTACCAATGGCTAAAAAATGGGAGACCTGTCCACACCAGC
TCCACCTACTCCTTTTCTCCCCAAAACAATACCCTTCATATTGCTCCAGTAACCAAGGAA
GACATTGGGAATTACAGCTGCCTGGTGAGGAACCCTGTCAGTGAAATGGAAAGTGATATC
ATTATGCCCATCATATATTATGGACCTTATGGACTTCAAGTGAATTCTGATAAAGGGCTA
AAAGTAGGGGAAGTGTTTACTGTTGACCTTGGAGAGGCCATCCTATTTGATTGTTCTGCT
GATTCTCATCCCCCCAACACCTACTCCTGGATTAGGAGGACTGACAATACTACATATATC
ATTAAGCATGGGCCTCGCTTAGAAGTTGCATCTGAGAAAGTAGCCCAGAAGACAATGGAC
TATGTGTGCTGTGCTTACAACAACATAACCGGCAGGCAAGATGAAACTCATTTCACAGTT
ATCATCACTTCCGTAGGACTGGAGAAGCTTGCACAGAAAGGAAAAGGATCCGAGAACCTG
TACTTTCAGGGCAGCGGCGAGCCCAGAGGCCCCACCATCAAGCCCTGCCCCCCCTGCAAG
TGCCCAGCCCCTAACCTGCTGGGCGGACCCAGCGTGTTCATCTTCCCCCCCAAGATCAAG
GACGTGCTGATGATCAGCCTGAGCCCCATCGTGACCTGCGTGGTGGTGGACGTGAGCGAG
GACGACCCCGACGTGCAGATCAGCTGGTTCGTGAACAACGTGGAGGTGCACACCGCCCAG
ACCCAGACCCACCGGGAGGACTACAACAGCACCCTGCGGGTGGTGTCCGCCCTGCCCATC
CAGCACCAGGACTGGATGAGCGGCAAAGAATTCAAGTGCAAGGTGAACAACAAGGACCTG
CCTGCCCCCATCGAGCGGACCATCAGCAAGCCCAAGGGCAGCGTGAGAGCCCCCCAGGTG
TACGTGCTGCCCCCTCCCGAGGAAGAGATGACCAAGAAACAGGTGACCCTGACCTGCATG
GTGACCGACTTCATGCCCGAGGACATCTACGTGGAGTGGACCAACAACGGCAAGACCGAG
CTGAACTACAAGAACACCGAGCCCGTGCTGGACAGCGACGGCAGCTACTTCATGTATAGC
AAGCTGAGAGTCGAGAAGAAAAACTGGGTGGAGCGGAACAGCTACAGCTGCAGCGTGGTG
CACGAGGGCCTGCACAACCACCACACCACCAAGAGCTTCAGCCGGACCCCCGGCAAGTGA

FIG. 59D

ILDR1_T0_P3_ECD_mFc DNA sequence (1167bp)

ATGAACAGCTTCAGCACCAGCGCCTTCGGCCCCGTGGCCTTCAGCCTGGGCCTGCTGCTG
GTGCTGCCTGCCGCCTTCCCTGCCCCCGTGCCCCCCTTCGAAGCCCAGCTCCAGGACGTG
GTGGTGACATGGCGCTTCAAGTCCTTCTGCAAGGACCCTATCTTTGACTACTACTCAGCG
TCATACCAGGCAGCTTTATCCCTGGGCCAGGACCCATCCAATGACTGCAACGACAACCAG
CGGGAAGTTCGCATAGTGGCCCAGCGGCGGGGGCAGAATGAGCCCGTGCTGGGGGTAGAT
TACCGGCAGCGCAAGATCACCATCCAGAACCGAGCAGATCTCGTGATAAATGAAGTGATG
TGGTGGGACCATGGAGTGTATTACTGCACCATTGAGGCTCCAGGGGACACATCAGGAGAC
CCCGATAAGGAAGGATCCGAGAACCTGTACTTTCAGGGCAGCGGCGAGCCCAGAGGCCCC
ACCATCAAGCCCTGCCCCCCCTGCAAGTGCCCAGCCCCTAACCTGCTGGGCGGACCCAGC
GTGTTCATCTTCCCCCCCAAGATCAAGGACGTGCTGATGATCAGCCTGAGCCCCATCGTG
ACCTGCGTGGTGGTGGACGTGAGCGAGGACGACCCCGACGTGCAGATCAGCTGGTTCGTG
AACAACGTGGAGGTGCACACCGCCCAGACCCAGACCCACCGGGAGGACTACAACAGCACC
CTGCGGGTGGTGTCCGCCCTGCCCATCCAGCACCAGGACTGGATGAGCGGCAAAGAATTC
AAGTGCAAGGTGAACAACAAGGACCTGCCTGCCCCCATCGAGCGGACCATCAGCAAGCCC
AAGGGCAGCGTGAGAGCCCCCCAGGTGTACGTGCTGCCCCCTCCCGAGGAAGAGATGACC
AAGAAACAGGTGACCCTGACCTGCATGGTGACCGACTTCATGCCCGAGGACATCTACGTG
GAGTGGACCAACAACGGCAAGACCGAGCTGAACTACAAGAACACCGAGCCCGTGCTGGAC
AGCGACGGCAGCTACTTCATGTATAGCAAGCTGAGAGTCGAGAAGAAAAACTGGGTGGAG
CGGAACAGCTACAGCTGCAGCGTGGTGCACGAGGGCCTGCACAACCACCACACCACCAAG
AGCTTCAGCCGGACCCCCGGCAAGTGA

FIG. 59E

VSIG1_T6_P5_ECD_mFc DNA sequence (1641bp)

ATGAACAGCTTCAGCACCAGCGCCTTCGGCCCCGTGGCCTTCAGCCTGGGCCTGCTGCTG
GTGCTGCCTGCCGCCTTCCCTGCCCCCGTGCCCCCCTTCGAAATCCCAGACGGTTTCGTG
AACGTGACTGTTGGATCTAATGTCACTCTCATCTGCATCTACACCACCACTGTGGCCTCC
CGAGAACAGCTTTCCATCCAGTGGTCTTTCTTCCATAAGAAGGAGATGGAGCCAATTTCT
CACAGCTCGTGCCTCAGTACTGAGGGTATGGAGGAAAAGGCAGTCAGTCAGTGTCTAAAA
ATGACGCACGCAAGAGACGCTCGGGGAAGATGTAGCTGGACCTCTGAGTCTCCTTGGGAG
GAGGGGAAGTGGCCAGATGTTGAGGCTGTGAAGGGCACTCTTGATGGACAGCAGGCTGAA
CTCCAGATTTACTTTTCTCAAGGTGGACAAGCTGTAGCCATCGGGCAATTTAAAGATCGA
ATTACAGGGTCCAACGATCCAGGTAATGCATCTATCACTATCTCGCATATGCAGCCAGCA
GACAGTGGAATTTACATCTGCGATGTTAACAACCCCCCAGACTTTCTCGGCCAAAACCAA
GGCATCCTCAACGTCAGTGTGTTAGTGAAACCTTCTAAGCCCCTTTGTAGCGTTCAAGGA
AGACCAGAAACTGGCCACACTATTTCCCTTTCCTGTCTCTCTGCGCTTGGAACACCTTCC
CCTGTGTACTACTGGCATAAACTTGAGGGAAGAGACATCGTGCCAGTGAAAGAAAACTTC
AACCCAACCACCGGGATTTTGGTCATTGGAAATCTGACAAATTTTGAACAAGGTTATTAC
CAGTGTACTGCCATCAACAGACTTGGCAATAGTTCCTGCGAAATCGATCTCACTTCTTCA
CATCCAGGATCCGAGAACCTGTACTTTCAGGGCAGCGGCGAGCCCAGAGGCCCCACCATC
AAGCCCTGCCCCCCCTGCAAGTGCCCAGCCCCTAACCTGCTGGGCGGACCCAGCGTGTTC
ATCTTCCCCCCCAAGATCAAGGACGTGCTGATGATCAGCCTGAGCCCCATCGTGACCTGC
GTGGTGGTGGACGTGAGCGAGGACGACCCCGACGTGCAGATCAGCTGGTTCGTGAACAAC
GTGGAGGTGCACACCGCCCAGACCCAGACCCACCGGGAGGACTACAACAGCACCCTGCGG
GTGGTGTCCGCCCTGCCCATCCAGCACCAGGACTGGATGAGCGGCAAAGAATTCAAGTGC
AAGGTGAACAACAAGGACCTGCCTGCCCCCATCGAGCGGACCATCAGCAAGCCCAAGGGC
AGCGTGAGAGCCCCCCAGGTGTACGTGCTGCCCCCTCCCGAGGAAGAGATGACCAAGAAA
CAGGTGACCCTGACCTGCATGGTGACCGACTTCATGCCCGAGGACATCTACGTGGAGTGG
ACCAACAACGGCAAGACCGAGCTGAACTACAAGAACACCGAGCCCGTGCTGGACAGCGAC
GGCAGCTACTTCATGTATAGCAAGCTGAGAGTCGAGAAGAAAAACTGGGTGGAGCGGAAC
AGCTACAGCTGCAGCGTGGTGCACGAGGGCCTGCACAACCACCACACCACCAAGAGCTTC
AGCCGGACCCCCGGCAAGTGA

FIG. 59F

FXYD3_T25_P14_ECD-_mFc protein sequence (307aa)
MQKVTLGLLVFLAGFPVLDANDLEDKNSPFYYGAPYIFVKRMGGQMKRTQAGTEVPSTFLLDWGS
ENLYFQGSGEPRGPTIKPCPPCKCPAPNLLGGPSVFIFPPKIKDVLMISLSPIVTCVVVDVSEDD
PDVQISWFVNNVEVHTAQTQTHREDYNSTLRVVSALPIQHQDWMSGKEFKCKVNNKDLPAPIERT
ISKPKGSVRAPQVYVLPPPEEEMTKKQVTLTCMVTDFMPEDIYVEWTNNGKTELNYKNTEPVLDS
GSYFMYSKLRVEKKNWVERNSYSCSVVHEGLHNHHTTKSFSRTPGK

FIG. 60A

AI216611_T0_P0_ECD-_mFc protein sequence (389aa)

MRPLPSGRRKTRGISLGLFALCLAAARCLQSQGVSLYIPQATINATVKEDILLSVEYSCHGVPTI
EWTYSSNWGTQKIVEWKPGTQANISQSHKDRVCTFDNGSIQLFSVGVRDSGYYVITVTERLGSSQ
FGTIVLHVSEILYEDGSENLYFQGSGEPRGPTIKPCPPCKCPAPNLLGGPSVFIFPPKIKDVLMI
SLSPIVTCVVVDVSEDDPDVQISWFVNNVEVHTAQTQTHREDYNSTLRVVSALPIQHQDWMSGKE
FKCKVNNKDLPAPIERTISKPKGSVRAPQVYVLPPPEEEMTKKQVTLTCMVTDFMPEDIYVEWTN
NGKTELNYKNTEPVLDSDGSYFMYSKLRVEKKNWVERNSYSCSVVHEGLHNHHTTKSFSRTPGK

FIG. 60B

C1ORF32_T8_P8_ECD-_mFc protein sequence (428aa)

MDRVLLRWISLFWLTAMVEGLQVTVPDKKKVAMLFQPTVLRCHFSTSSHQPAVVQWKFKSYCQDR
MGESLGMSSTRAQSLSKRNLEWDPYLDCLDSRRTVRVVASKQGSTVTLGDFYRGREITIVHDADL
QIGKLMWGDSGLYYCIITTPDDLEGKNEDSVELLVLGRTGLLADLLPSFAVEIMGSENLYFQGSG
EPRGPTIKPCPPCKCPAPNLLGGPSVFIFPPKIKDVLMISLSPIVTCVVVDVSEDDPDVQISWFV
NNVEVHTAQTQTHREDYNSTLRVVSALPIQHQDWMSGKEFKCKVNNKDLPAPIERTISKPKGSVR
APQVYVLPPPEEEMTKKQVTLTCMVTDFMPEDIYVEWTNNGKTELNYKNTEPVLDSDGSYFMYSK
LRVEKKNWVERNSYSCSVVHEGLHNHHTTKSFSRTPGK

FIG. 60C

LOC253012_T4_P5_ECD-_mFc protein sequence (579aa)

MWLKVFTTFLSFATGACSGLKVTVPSHTVHGVRGQALYLPVHYGFHTPASDIQIIWLFERPHTMP KYLLGSVNKSVVPDLEYQHKFTMMPPNASLLINPLQFPDEGNYIVKVNIQGNGTLSASQKIQVTV DDPVTKPVVQIHPPSGAVEYVGNMTLTCHVEGGTRLAYQWLKNGRPVHTSSTYSFSPQNNTLHIA PVTKEDIGNYSCLVRNPVSEMESDIIMPIIYYGPYGLQVNSDKGLKVGEVFTVDLGEAILFDCSA DSHPPNTYSWIRRTDNTTYIIKHGPRLEVASEKVAQKTMDYVCCAYNNITGRQDETHFTVIITSV GLEKLAQKGKGSENLYFQGSGEPRGPTIKPCPPCKCPAPNLLGGPSVFIFPPKIKDVLMISLSPI VTCVVVDVSEDDPDVQISWFVNNVEVHTAQTQTHREDYNSTLRVVSALPIQHQDWMSGKEFKCKV NNKDLPAPIERTISKPKGSVRAPQVYVLPPPEEEMTKKQVTLTCMVTDFMPEDIYVEWTNNGKTE LNYKNTEPVLDSDGSYFMYSKLRVEKKNWVERNSYSCSVVHEGLHNHHTTKSFSRTPGK

FIG. 60D

ILDR1_T0_P3_ECD-_mFc protein sequence (388aa)

MNSFSTSAFGPVAFSLGLLLVLPAAFPAPVPPFEAQLQDVVVTWRFKSFCKDPIFDYYSASYQAA LSLGQDPSNDCNDNQREVRIVAQRRGQNEPVLGVDYRQRKITIQNRADLVINEVMWWDHGVYYCT IEAPGDTSGDPDKEGSENLYFQGSGEPRGPTIKPCPPCKCPAPNLLGGPSVFIFPPKIKDVLMIS LSPIVTCVVVDVSEDDPDVQISWFVNNVEVHTAQTQTHREDYNSTLRVVSALPIQHQDWMSGKEF KCKVNNKDLPAPIERTISKPKGSVRAPQVYVLPPPEEEMTKKQVTLTCMVTDFMPEDIYVEWTNN GKTELNYKNTEPVLDSDGSYFMYSKLRVEKKNWVERNSYSCSVVHEGLHNHHTTKSFSRTPGK

FIG. 60E

VSIG1_T6_P5_ECD-_mFc protein sequence (546aa)

MNSFSTSAFGPVAFSLGLLLVLPAAFPAPVPPFEIPDGFVNVTVGSNVTLICIYTTTVASREQLS IQWSFFHKKEMEPISHSSCLSTEGMEEKAVSQCLKMTHARDARGRCSWTSESPWEEGKWPDVEAV KGTLDGQQAELQIYFSQGGQAVAIGQFKDRITGSNDPGNASITISHMQPADSGIYICDVNNPPDF LGQNQGILNVSVLVKPSKPLCSVQGRPETGHTISLSCLSALGTPSPVYYWHKLEGRDIVPVKENF NPTTGILVIGNLTNFEQGYYQCTAINRLGNSSCEIDLTSSHPGSENLYFQGSGEPRGPTIKPCPP CKCPAPNLLGGPSVFIFPPKIKDVLMISLSPIVTCVVVDVSEDDPDVQISWFVNNVEVHTAQTQT HREDYNSTLRVVSALPIQHQDWMSGKEFKCKVNNKDLPAPIERTISKPKGSVRAPQVYVLPPPEE EMTKKQVTLTCMVTDFMPEDIYVEWTNNGKTELNYKNTEPVLDSDGSYFMYSKLRVEKKNWVERN SYSCSVVHEGLHNHHTTKSFSRTPGK

FIG. 60F

SEQUENCE LISTING

```
<160> NUMBER OF SEQ ID NOS: 302

<210> SEQ ID NO 1
<211> LENGTH: 3137
<212> TYPE: DNA
<213> ORGANISM: Homo sapiens

<400> SEQUENCE: 1

gtactgaaaa aagtctatac gcaataagta agcccaaaga ggcatgtttg cttggcgatg      60

cccagcagat aagccaggca aacctcggtg tgatcgaaga agccaatttg agactcagcc     120

tagtccaggc aagctactgg cacctgctgc tctcaactaa cctccacaca atggtgttcg     180

cattttggaa ggtctttctg atcctaagct gccttgcagg tcaggttagt gtggtgcaag     240

tgaccatccc agacggtttc gtgaacgtga ctgttggatc taatgtcact ctcatctgca     300

tctacaccac cactgtggcc tcccgagaac agctttccat ccagtggtct ttcttccata     360

agaaggagat ggagccaatt tctatttact ttttctcaagg tggacaagct gtagccatcg    420

ggcaatttaa agatcgaatt acagggtcca acgatccagg taatgcatct atcactatct     480

cgcatatgca gccagcagac agtggaattt acatctgcga tgttaacaac cccccagact     540

ttctcggcca aaaccaaggc atcctcaacg tcagtgtgtt agtgaaacct tctaagcccc     600

tttgtagcgt tcaaggaaga ccagaaactg gccacactat ttccctttcc tgtctctctg     660

cgcttggaac accttcccct gtgtactact ggcataaact tgagggaaga gacatcgtgc     720

cagtgaaaga aaacttcaac ccaaccaccg ggattttggt cattggaaat ctgacaaatt     780

ttgaacaagg ttattaccag tgtactgcca tcaacagact tggcaatagt tcctgcgaaa     840

tcgatctcac ttcttcacat ccagaagttg gaatcattgt tggggccttg attggtagcc     900

tggtaggtgc cgccatcatc atctctgttg tgtgcttcgc aaggaataag gcaaaagcaa     960
```

-continued

```
aggcaaaaga aagaaattct aagaccatcg cggaacttga gccaatgaca aagataaacc   1020
caaggggaga aagcgaagca atgccaagag aagacgctac ccaactagaa gtaactctac   1080
catcttccat tcatgagact ggccctgata ccatccaaga accagactat gagccaaagc   1140
ctactcagga gcctgcccca gagcctgccc caggatcaga gcctatggca gtgcctgacc   1200
ttgacatcga gctggagctg gagccagaaa cgcagtcgga attggagcca gagccagagc   1260
cagagccaga gtcagagcct ggggttgtag ttgagccctt aagtgaagat gaaaagggag   1320
tggttaaggc ataggctggt ggcctaagta cagcattaat cattaaggaa cccattactg   1380
ccatttggaa ttcaaataac ctaaccaacc tccacctcct ccttccattt tgaccaacct   1440
tcttctaaca aggtgctcat tcctactatg aatccagaat aaacacgcca agataacagc   1500
taaatcagca agggttcctg tattaccaat atagaatact aacaatttta ctaacacgta   1560
agcataacaa atgacagggc aagtgatttc taacttagtt gagttttgca acagtacctg   1620
tgttgttatt tcagaaaata ttatttctct ctttttaact actctttttt tttattttgg   1680
acagagtctt gctccgtcgc gcaggctgtg atcgtagtgg tgcgatctcg gctcactgca   1740
gcctccgctc cctgggttca agcgattctc ctgcctgagc ctcctgagta gctgggactg   1800
caggcacgtg ccaccacgcc cggctaattt tttgtatttt tagtagagat ggggtttcac   1860
gttgttggcc aggatggtct ccatctcctg acctcatgat ccgcccacct tggcctccca   1920
aaatgctggg attacaggca tgagccactg cgcccggcct ctttttagct actcttatgt   1980
tccacatgca catatgacaa ggtggcatta attagattca atattatttc taggaatagt   2040
tcctcattca tttttatatt gaccactaag aaaataattc atcagcatta tctcatagat   2100
tggaaaattt tctccaaata caatagagga gaatatgtaa agggtataca ttaattggta   2160
cgtagcattt aaaatcaggt cttataatta atgcttcatt cctcatatta gatttcccaa   2220
gaaatcaccc tggtatccaa tatctgagca tggcaaattt aaaaaataac acaatttctt   2280
gcctgtaacc ctagcacttt gggaggccga ggcaggtgga tcacctgagg tcaggagttc   2340
gagaccagcc tggccggcat ggcgaaaccc cttctctgct gaaaatacag aaattagctg   2400
ggcgtggtgg tgcatgcctg tagtcccagc tacttgggag gctgaggcag gagaatcgct   2460
tgaacccagg aggtggaggt tgcagtgagc cgagattgtg ccactgcact ccaacctggg   2520
tgacagagtg agattccatc tgaaaaacaa aaacaaaaac agaaaacaaa caaacaaaaa   2580
acaaaaaatc cccacaactt tgtcaaataa tgtacaggca aacactttca aatataattt   2640
ccttcagtga atacaaaatg ttgatatcat aggtgatgta caatttagtt ttgaatgagt   2700
tattatgtta tcactgtgtc tgatgttatc tactttgaaa ggcagtccag aaaagtgttc   2760
taagtgaact cttaagatct attttagata atttcaacta attaaataac ctgttttact   2820
gcctgtacat tccacattaa taaagcgata ccaatcttat atgaatgcta atattactaa   2880
aatgcactga tatcacttct tcttcccctg ttgaaaagct ttctcatgat catatttcac   2940
ccacatctca ccttgaagaa acttacaggt agacttacct tttcacttgt ggaattaatc   3000
atatttaaat cttactttaa ggctcaataa ataatactca taatgtctca ttttagtgac   3060
tcctaaggct agtcctttta taaacaactt tttctgacat agcatttatg tataataaac   3120
cagacattta aagtgta                                                  3137
```

<210> SEQ ID NO 2
<211> LENGTH: 3049
<212> TYPE: DNA
<213> ORGANISM: Homo sapiens

<400> SEQUENCE: 2
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360
agaaggagat ggagccaatt tctatttact tttctcaagg tggacaagct gtagccatcg 420
ggcaatttaa agatcgaatt acagggtcca acgatccagg taatgcatct atcactatct 480
cgcatatgca gccagcagac agtggaattt acatctgcga tgttaacaac cccccagact 540
ttctcggcca aaaccaaggc atcctcaacg tcagtgtgtt agtgaaacct tctaagcccc 600
tttgtagcgt tcaaggaaga ccagaaactg gccacactat ttccctttcc tgtctctctg 660
cgcttggaac accttcccct gtgtactact ggcataaact tgagggaaga gacatcgtgc 720
cagtgaaaga aaacttcaac ccaaccaccg ggattttggt cattggaaat ctgacaaatt 780
ttgaacaagg ttattaccag tgtactgcca tcaacagact tggcaatagt tcctgcgaaa 840
tcgatctcac ttcttcacat ccagaagttg gaatcattgt tggggccttg attggtagcc 900
tggtaggtgc cgccatcatc atctctgttg tgtgcttcgc aaggaataag gcaaaagcaa 960
aggcaaaaga aagaaattct aagaccatcg cggaacttga gccaatgaca aagataaacc 1020
caaggggaga aagcgaagca atgccaagag aagacgctac ccaactagaa gtaactctac 1080
catcttccat tcatgagact ggccctgata ccatccaaga accagactat gagccaaagc 1140
ctactcagga gcctgcccca gagcctgccc caggatcaga gcctatggca gtgcctgacc 1200
ttgacatcga gctggagctg gagccagaaa cgcagtcgga attggagcca gagccagagc 1260
cagagccaga gtcagagcct ggggttgtag ttgagccctt aagtgaagat gaaaagggag 1320
tggttaaggc ataggctggt ggcctaagta cagcattaat cattaaggaa cccattactg 1380
ccatttggaa ttcaaataac ctaaccaacc tccacctcct ccttccattt tgaccaacct 1440
tcttctaaca aggtgctcat tcctactatg aatccagaat aaacacgcca agataacagc 1500
taaatcagca agggttcctg tattaccaat atagaatact aacaatttta ctaacacgta 1560
agcataacaa atgacagggc aagtgatttc taacttagtt gagttttgca acagtacctg 1620
tgttgttatt tcagaaaata ttatttctct ctttttaact actctttttt tttattttgg 1680
acagagtctt gctccgtcgc gcaggctgtg atcgtagtgg tgcgatctcg gctcactgca 1740
gcctccgctc cctgggttca agcgattctc ctgcctgagc ctcctgagta gctgggactg 1800
caggcacgtg ccaccacgcc cggctaattt tttgtatttt tagtagagat ggggtttcac 1860
gttgttggcc aggatggtct ccatctcctg acctcatgat ccgcccacct tggcctccca 1920
aaatgctggg attacaggca tgagccactg cgcccggcct ctttttagct actcttatgt 1980
tccacatgca catatgacaa ggtggcatta attagattca atattatttc taggaatagt 2040
tcctcattca tttttatatt gaccactaag aaaataattc atcagcatta tctcatagat 2100
tggaaaattt tctccaaata caatagagga gaatatgtaa agggtataca ttaattggta 2160
cgtagcattt aaaatcaggt cttataatta atgcttcatt cctcatatta gatttcccaa 2220
gaaatcaccc tggtatccaa tatctgagca tggcaaattt aaaaaataac acaatttctt 2280
gcctgtaacc ctagcacttt gggaggccga ggcaggtgga tcacctgagg tcaggagttc 2340
gagaccagcc tggccggcat ggcgaaaccc cttctctgct gaaaatacag aaattagctg 2400
ggcgtggtgg tgcatgcctg tagtcccagc tacttgggag gctgaggcag gagaatcgct 2460
tgaacccagg aggtggaggt tgcagtgagc cgagattgtg ccactgcact ccaacctggg 2520
tgacagagtg agattccatc tgaaaaacaa aaacaaaaac agaaaacaaa caaacaaaaa 2580
acaaaaaatc cccacaactt tgtcaaataa tgtacaggca aacactttca aatataattt 2640
ccttcagtga atacaaaatg ttgatatcat aggtgatgta caatttagtt ttgaatgagt 2700
tattatgtta tcactgtgtc tgatgttatc tactttgaaa ggcagtccag aaaagtgttc 2760
taagtgaact cttaagatct attttagata atttcaacta attaaataac ctgttttact 2820
gcctgtacat tccacattaa taaagcgata ccaatcttat atgaatgcta atattactaa 2880
aatgcactga tatcacttct tcttcccctg ttgaaaagct ttctcatgat catatttcac 2940
ccacatctca ccttgaagaa acttacaggt agacttacct tttcacttgt ggaattaatc 3000
atatttaaat cttactttaa ggctcaataa ataatactca taatgtctc 3049

<210> SEQ ID NO 3
<211> LENGTH: 2448
<212> TYPE: DNA
<213> ORGANISM: Homo sapiens

<400> SEQUENCE: 3
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360
agaaggagat ggagccaatt tctatttact tttctcaagg tggacaagct gtagccatcg 420
ggcaatttaa agatcgaatt acagggtcca acgatccagg taatgcatct atcactatct 480
cgcatatgca gccagcagac agtggaattt acatctgcga tgttaacaac cccccagact 540
ttctcggcca aaaccaaggc atcctcaacg tcagtgtgtt agtgaaacct tctaagcccc 600
tttgtagcgt tcaaggaaga ccagaaactg gccacactat ttccctttcc tgtctctctg 660
cgcttggaac accttcccct gtgtactact ggcataaact tgagggaaga gacatcgtgc 720
cagtgaaaga aaacttcaac ccaaccaccg ggattttggt cattggaaat ctgacaaatt 780
ttgaacaagg ttattaccag tgtactgcca tcaacagact tggcaatagt tcctgcgaaa 840
tcgatctcac ttcttcacat ccagaagttg gaatcattgt tggggccttg attggtagcc 900
tggtaggtgc cgccatcatc atctctgttg tgtgcttcgc aaggaataag gcaaaagcaa 960
aggcaaaaga aagaaattct aagaccatcg cggaacttga gccaatgaca aagataaacc 1020
caaggggaga aagcgaagca atgccaagag aagacgctac ccaactagaa gtaactctac 1080
catcttccat tcatgagact ggccctgata ccatccaaga accagactat gagccaaagc 1140
ctactcagga gcctgcccca gagcctgccc caggatcaga gcctatggca gtgcctgacc 1200
ttgacatcga gctggagctg gagccagaaa cgcagtcgga attggagcca gagccagagc 1260
cagagccaga gtcagagcct ggggttgtag ttgagccctt aagtgaagat gaaaagggag 1320
tggttaaggc ataggctggt ggcctaagta cagcattaat cattaaggaa cccattactg 1380

```
ccatttggaa ttcaaataac ctaaccaacc tccacctcct ccttccattt tgaccaacct   1440
tcttctaaca aggtgctcat tcctactatg aatccagaat aaacacgcca agataacagc   1500
taaatcagca agggttcctg tattaccaat atagaatact aacaatttta ctaacacgta   1560
agcataacaa atgacagggc aagtgatttc taacttagtt gagttttgca acagtacctg   1620
tgttgttatt tcagaaaata ttatttctct ctttttaact actctttttt tttattttgg   1680
acagagtctt gctccgtcgc gcaggctgtg atcgtagtgg tgcgatctcg gctcactgca   1740
gcctccgctc cctgggttca agagaatcgc ttgaacccag gaggtggagg ttgcagtgag   1800
ccgagattgt gccactgcac tccaacctgg gtgacagagt gagattccat ctgaaaaaca   1860
aaaacaaaaa cagaaaacaa acaaacaaaa aacaaaaaat ccccacaact ttgtcaaata   1920
atgtacaggc aaacactttc aaatataatt tccttcagtg aatacaaaat gttgatatca   1980
taggtgatgt acaatttagt tttgaatgag ttattatgtt atcactgtgt ctgatgttat   2040
ctactttgaa aggcagtcca gaaaagtgtt ctaagtgaac tcttaagatc tattttagat   2100
aatttcaact aattaaataa cctgttttac tgcctgtaca ttccacatta ataaagcgat   2160
accaatctta tatgaatgct aatattacta aaatgcactg atatcacttc ttcttcccct   2220
gttgaaaagc tttctcatga tcatatttca cccacatctc accttgaaga aacttacagg   2280
tagacttacc ttttcacttg tggaattaat catatttaaa tcttacttta aggctcaata   2340
aataatactc ataatgtctc attttagtga ctcctaaggc tagtcctttt ataaacaact   2400
ttttctgaca tagcatttat gtataataaa ccagacattt aaagtgta                2448

<210> SEQ ID NO 4
<211> LENGTH: 2368
<212> TYPE: DNA
<213> ORGANISM: Homo sapiens

<400> SEQUENCE: 4

gtactgaaaa aagtctatac gcaataagta agcccaaaga ggcatgtttg cttggcgatg     60
cccagcagat aagccaggca aacctcggtg tgatcgaaga agccaatttg agactcagcc    120
tagtccaggc aagctactgg cacctgctgc tctcaactaa cctccacaca atggtgttcg    180
cattttggaa ggtctttctg atcctaagct gccttgcagg tcaggttagt gtggtgcaag    240
tgaccatccc agacggtttc gtgaacgtga ctgttggatc taatgtcact ctcatctgca    300
tctacaccac cactgtggcc tcccgagaac agctttccat ccagtggtct ttcttccata    360
agaaggagat ggagccaatt tctatttact tttctcaagg tggacaagct gtagccatcg    420
ggcaatttaa agatcgaatt acagggtcca acgatccagg taatgcatct atcactatct    480
cgcatatgca gccagcagac agtggaattt acatctgcga tgttaacaac cccccagact    540
ttctcggcca aaaccaaggc atcctcaacg tcagtgtgtt agtgaaacct tctaagcccc    600
tttgtagcgt tcaaggaaga ccagaaactg gccacactat ttccctttcc tgtctctctg    660
cgcttggaac accttcccct gtgtactact ggcataaact tgagggaaga gacatcgtgc    720
cagtgaaaga aaacttcaac ccaaccaccg ggattttggt cattggaaat ctgacaaatt    780
ttgaacaagg ttattaccag tgtactgcca tcaacagact tggcaatagt tcctgcgaaa    840
tcgatctcac ttcttcacat ccagaagttg gaatcattgt tggggccttg attggtagcc    900
tggtaggtgc cgccatcatc atctctgttg tgtgcttcgc aaggaataag gcaaaagcaa    960
aggcaaaaga aagaaattct aagaccatcg cggaacttga gccaatgaca aagataaacc   1020
```

-continued

```
caaggggaga aagcgaagca atgccaagag aagacgctac ccaactagaa gtaactctac   1080
catcttccat tcatgagact ggccctgata ccatccaaga accagactat gagccaaagc   1140
ctactcagga gcctgcccca gagcctgccc caggatcaga gcctatggca gtgcctgacc   1200
ttgacatcga gctggagctg gagccagaaa cgcagtcgga attggagcca gagccagagc   1260
cagagccaga gtcagagcct ggggttgtag ttgagccctt aagtgaagat gaaaagggag   1320
tggttaaggc ataggctggt ggcctaagta cagcattaat cattaaggaa cccattactg   1380
ccatttggaa ttcaaataac ctaaccaacc tccacctcct ccttccattt tgaccaacct   1440
tcttctaaca aggtgctcat tcctactatg aatccagaat aaacacgcca agataacagc   1500
taaatcagca agggttcctg tattaccaat atagaatact aacaatttta ctaacacgta   1560
agcataacaa atgacagggc aagtgatttc taacttagtt gagttttgca acagtacctg   1620
tgttgttatt tcagaaaata ttatttctct ctttttaact actctttttt tttattttgg   1680
acagagtcgc ttgaacccag gaggtggagg ttgcagtgag ccgagattgt gccactgcac   1740
tccaacctgg gtgacagagt gagattccat ctgaaaaaca aaaacaaaaa cagaaaacaa   1800
acaaacaaaa aacaaaaaat ccccacaact ttgtcaaata atgtacaggc aaacactttc   1860
aaatataatt tccttcagtg aatacaaaat gttgatatca taggtgatgt acaatttagt   1920
tttgaatgag ttattatgtt atcactgtgt ctgatgttat ctactttgaa aggcagtcca   1980
gaaaagtgtt ctaagtgaac tcttaagatc tattttagat aatttcaact aattaaataa   2040
cctgttttac tgcctgtaca ttccacatta ataaagcgat accaatctta tatgaatgct   2100
aatattacta aaatgcactg atatcacttc ttcttcccct gttgaaaagc tttctcatga   2160
tcatatttca cccacatctc accttgaaga aacttacagg tagacttacc ttttcacttg   2220
tggaattaat catatttaaa tcttacttta aggctcaata aataatactc ataatgtctc   2280
attttagtga ctcctaaggc tagtcctttt ataaacaact ttttctgaca tagcatttat   2340
gtataataaa ccagacattt aaagtgta                                       2368
```

<210> SEQ ID NO 5
<211> LENGTH: 1501
<212> TYPE: DNA
<213> ORGANISM: Homo sapiens

<400> SEQUENCE: 5

```
gtactgaaaa aagtctatac gcaataagta agcccaaaga ggcatgtttg cttggcgatg     60
cccagcagat aagccaggca aacctcggtg tgatcgaaga agccaatttg agactcagcc    120
tagtccaggc aagctactgg cacctgctgc tctcaactaa cctccacaca atggtgttcg    180
cattttggaa ggtctttctg atcctaagct gccttgcagg tcaggttagt gtggtgcaag    240
tgaccatccc agacggtttc gtgaacgtga ctgttggatc taatgtcact ctcatctgca    300
tctacaccac cactgtggcc tcccgagaac agctttccat ccagtggtct ttcttccata    360
agaaggagat ggagccaatt tctatttact tttctcaagg tggacaagct gtagccatcg    420
ggcaatttaa agatcgaatt acagggtcca acgatccagg taatgcatct atcactatct    480
cgcatatgca gccagcagac agtggaattt acatctgcga tgttaacaac cccccagact    540
ttctcggcca aaaccaaggc atcctcaacg tcagtgtgtt agtgaaacct tctaagcccc    600
tttgtagcgt tcaaggaaga ccagaaactg gccacactat ttccctttcc tgtctctctg    660
cgcttggaac accttcccct gtgtactact ggcataaact tgagggaaga gacatcgtgc    720
cagtgaaaga aaacttcaac ccaaccaccg ggattttggt cattggaaat ctgacaaatt    780
```

ttgaacaagg ttattaccag tgtactgcca tcaacagact tggcaatagt tcctgcgaaa 840
tcgatctcac ttcttcacat ccagaagttg gaatcattgt tggggccttg attggtagcc 900
tggtaggtgc cgccatcatc atctctgttg tgtgcttcgc aaggaataag gcaaaagcaa 960
aggcaaaaga aagaaattct aagaccatcg cggaacttga gccaatgaca aagataaacc 1020
caaggggaga aagcgaagca atgccaagag aagacgctac ccaactagaa gtaactctac 1080
catcttccat tcatgagact ggccctgata ccatccaaga accagactat gagccaaagc 1140
ctactcagga gcctgcccca gagcctgccc caggatcaga gcctatggca gtgcctgacc 1200
ttgacatcga gctggagctg gagccagaaa cgcagtcgga attggagcca gagccagagc 1260
cagagccaga gtcagagcct ggggttgtag ttgagccctt aagtgaagat gaaaagggag 1320
tggttaaggc ataggctggt ggcctaagta cagcattaat cattaaggaa cccattactg 1380
ccatttggaa ttcaaataac ctaaccaacc tccacctcct ccttccattt tgaccaacct 1440
tcttctaaca aggtgctcat tcctactatg aatccagaat aaacacgcca agataacagc 1500
t 1501

<210> SEQ ID NO 6
<211> LENGTH: 3245
<212> TYPE: DNA
<213> ORGANISM: Homo sapiens

<400> SEQUENCE: 6
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360
agaaggagat ggagccaatt tctcacagct cgtgcctcag tactgagggt atggaggaaa 420
aggcagtcgg tcagtgtcta aaaatgacgc acgtaagaga cgctcgggga agatgtagct 480
ggacctctga gatttacttt tctcaaggtg gacaagctgt agccatcggg caatttaaag 540
atcgaattac agggtccaac gatccaggta atgcatctat cactatctcg catatgcagc 600
cagcagacag tggaatttac atctgcgatg ttaacaaccc cccagacttt ctcggccaaa 660
accaaggcat cctcaacgtc agtgtgttag tgaaaccttc taagcccctt tgtagcgttc 720
aaggaagacc agaaactggc cacactattt ccctttcctg tctctctgcg cttggaacac 780
cttcccctgt gtactactgg cataaacttg agggaagaga catcgtgcca gtgaaagaaa 840
acttcaaccc aaccaccggg attttggtca ttggaaatct gacaaatttt gaacaaggtt 900
attaccagtg tactgccatc aacagacttg gcaatagttc ctgcgaaatc gatctcactt 960
cttcacatcc agaagttgga atcattgttg gggccttgat tggtagcctg gtaggtgccg 1020
ccatcatcat ctctgttgtg tgcttcgcaa ggaataaggc aaaagcaaag gcaaaagaaa 1080
gaaattctaa gaccatcgcg gaacttgagc caatgacaaa gataaaccca aggggagaaa 1140
gcgaagcaat gccaagagaa gacgctaccc aactagaagt aactctacca tcttccattc 1200
atgagactgg ccctgatacc atccaagaac cagactatga gccaaagcct actcaggagc 1260
ctgccccaga gcctgcccca ggatcagagc ctatggcagt gcctgacctt gacatcgagc 1320

-continued

```
tggagctgga gccagaaacg cagtcggaat tggagccaga gccagagcca gagccagagt   1380

cagagcctgg ggttgtagtt gagcccttaa gtgaagatga aaagggagtg gttaaggcat   1440

aggctggtgg cctaagtaca gcattaatca ttaaggaacc cattactgcc atttggaatt   1500

caaataacct aaccaacctc cacctcctcc ttccattttg accaaccttc ttctaacaag   1560

gtgctcattc ctactatgaa tccagaataa acacgccaag ataacagcta aatcagcaag   1620

ggttcctgta ttaccaatat agaatactaa caattttact aacacgtaag cataacaaat   1680

gacagggcaa gtgatttcta acttagttga gttttgcaac agtacctgtg ttgttatttc   1740

agaaaatatt atttctctct ttttaactac tctttttttt tattttggac agagtcttgc   1800

tccgtcgcgc aggctgtgat cgtagtggtg cgatctcggc tcactgcagc ctccgctccc   1860

tgggttcaag cgattctcct gcctgagcct cctgagtagc tgggactgca ggcacgtgcc   1920

accacgcccg gctaattttt tgtattttta gtagagatgg ggtttcacgt tgttggccag   1980

gatggtctcc atctcctgac ctcatgatcc gcccaccttg gcctcccaaa atgctgggat   2040

tacaggcatg agccactgcg cccggcctct ttttagctac tcttatgttc cacatgcaca   2100

tatgacaagg tggcattaat tagattcaat attatttcta ggaatagttc ctcattcatt   2160

tttatattga ccactaagaa aataattcat cagcattatc tcatagattg gaaaattttc   2220

tccaaataca atagaggaga atatgtaaag ggtatacatt aattggtacg tagcatttaa   2280

aatcaggtct tataattaat gcttcattcc tcatattaga tttcccaaga aatcaccctg   2340

gtatccaata tctgagcatg gcaaatttaa aaaataacac aatttcttgc ctgtaaccct   2400

agcactttgg gaggccgagg caggtggatc acctgaggtc aggagttcga gaccagcctg   2460

gccggcatgg cgaaacccct tctctgctga aaatacagaa attagctggg cgtggtggtg   2520

catgcctgta gtcccagcta cttgggaggc tgaggcagga gaatcgcttg aacccaggag   2580

gtggaggttg cagtgagccg agattgtgcc actgcactcc aacctgggtg acagagtgag   2640

attccatctg aaaaacaaaa acaaaaacag aaaacaaaca aacaaaaaac aaaaaatccc   2700

cacaactttg tcaaataatg tacaggcaaa cactttcaaa tataatttcc ttcagtgaat   2760

acaaaatgtt gatatcatag gtgatgtaca atttagtttt gaatgagtta ttatgttatc   2820

actgtgtctg atgttatcta ctttgaaagg cagtccagaa aagtgttcta agtgaactct   2880

taagatctat tttagataat ttcaactaat taaataacct gttttactgc ctgtacattc   2940

cacattaata aagcgatacc aatcttatat gaatgctaat attactaaaa tgcactgata   3000

tcacttcttc ttcccctgtt gaaaagcttt ctcatgatca tatttcaccc acatctcacc   3060

ttgaagaaac ttacaggtag acttaccttt tcacttgtgg aattaatcat atttaaatct   3120

tactttaagg ctcaataaat aatactcata atgtctcatt ttagtgactc ctaaggctag   3180

tccttttata aacaactttt tctgacatag catttatgta taataaacca gacatttaaa   3240

gtgta                                                               3245
```

<210> SEQ ID NO 7
<211> LENGTH: 3323
<212> TYPE: DNA
<213> ORGANISM: Homo sapiens

<400> SEQUENCE: 7

```
gtactgaaaa aagtctatac gcaataagta agcccaaaga ggcatgtttg cttggcgatg     60

cccagcagat aagccaggca aacctcggtg tgatcgaaga agccaatttg agactcagcc    120

tagtccaggc aagctactgg cacctgctgc tctcaactaa cctccacaca atggtgttcg    180
```

-continued

```
cattttggaa ggtctttctg atcctaagct gccttgcagg tcaggttagt gtggtgcaag    240
tgaccatccc agacggtttc gtgaacgtga ctgttggatc taatgtcact ctcatctgca    300
tctacaccac cactgtggcc tcccgagaac agctttccat ccagtggtct ttcttccata    360
agaaggagat ggagccaatt tctcacagct cgtgcctcag tactgagggt atggaggaaa    420
aggcagtcgg tcagtgtcta aaaatgacgc acgtaagaga cgctcgggga agatgtagct    480
ggacctctga gtctccttgg gaggagggga agtggccaga tgttgaggct gtgaagggca    540
ctcttgatgg acagcaggct gaactccaga tttacttttc tcaaggtgga caagctgtag    600
ccatcgggca atttaaagat cgaattacag ggtccaacga tccaggtaat gcatctatca    660
ctatctcgca tatgcagcca gcagacagtg gaatttacat ctgcgatgtt aacaaccccc    720
cagactttct cggccaaaac caaggcatcc tcaacgtcag tgtgttagtg aaaccttcta    780
agcccctttg tagcgttcaa ggaagaccag aaactggcca cactatttcc ctttcctgtc    840
tctctgcgct tggaacacct tcccctgtgt actactggca taaacttgag ggaagagaca    900
tcgtgccagt gaaagaaaac ttcaacccaa ccaccgggat tttggtcatt ggaaatctga    960
caaattttga acaaggttat taccagtgta ctgccatcaa cagacttggc aatagttcct   1020
gcgaaatcga tctcacttct tcacatccag aagttggaat cattgttggg gccttgattg   1080
gtagcctggt aggtgccgcc atcatcatct ctgttgtgtg cttcgcaagg aataaggcaa   1140
aagcaaaggc aaaagaaaga aattctaaga ccatcgcgga acttgagcca atgacaaaga   1200
taaacccaag gggagaaagc gaagcaatgc caagagaaga cgctacccaa ctagaagtaa   1260
ctctaccatc ttccattcat gagactggcc ctgataccat ccaagaacca gactatgagc   1320
caaagcctac tcaggagcct gccccagagc ctgccccagg atcagagcct atggcagtgc   1380
ctgaccttga catcgagctg gagctggagc cagaaacgca gtcggaattg gagccagagc   1440
cagagccaga gccagagtca gagcctgggg ttgtagttga gcccttaagt gaagatgaaa   1500
agggagtggt taaggcatag gctggtggcc taagtacagc attaatcatt aaggaaccca   1560
ttactgccat ttggaattca aataacctaa ccaacctcca cctcctcctt ccattttgac   1620
caaccttctt ctaacaaggt gctcattcct actatgaatc cagaataaac acgccaagat   1680
aacagctaaa tcagcaaggg ttcctgtatt accaatatag aatactaaca attttactaa   1740
cacgtaagca taacaaatga cagggcaagt gatttctaac ttagttgagt tttgcaacag   1800
tacctgtgtt gttatttcag aaaatattat ttctctcttt ttaactactc ttttttttta   1860
ttttggacag agtcttgctc cgtcgcgcag gctgtgatcg tagtggtgcg atctcggctc   1920
actgcagcct ccgctccctg ggttcaagcg attctcctgc ctgagcctcc tgagtagctg   1980
ggactgcagg cacgtgccac cacgcccggc taatttttg tatttttagt agagatgggg    2040
tttcacgttg ttggccagga tggtctccat ctcctgacct catgatccgc ccaccttggc   2100
ctcccaaaat gctgggatta caggcatgag ccactgcgcc cggcctcttt ttagctactc   2160
ttatgttcca catgcacata tgacaaggtg gcattaatta gattcaatat tatttctagg   2220
aatagttcct cattcatttt tatattgacc actaagaaaa taattcatca gcattatctc   2280
atagattgga aaattttctc caaatacaat agaggagaat atgtaaaggg tatacattaa   2340
ttggtacgta gcatttaaaa tcaggtctta taattaatgc ttcattcctc atattagatt   2400
tcccaagaaa tcaccctggt atccaatatc tgagcatggc aaatttaaaa aataacacaa   2460
tttcttgcct gtaaccctag cactttggga ggccgaggca ggtggatcac ctgaggtcag   2520
```

gagttcgaga ccagcctggc cggcatggcg aaaccccttc tctgctgaaa atacagaaat 2580
tagctgggcg tggtggtgca tgcctgtagt cccagctact tgggaggctg aggcaggaga 2640
atcgcttgaa cccaggaggt ggaggttgca gtgagccgag attgtgccac tgcactccaa 2700
cctgggtgac agagtgagat tccatctgaa aaacaaaaac aaaaacagaa aacaaacaaa 2760
caaaaaacaa aaaatcccca caactttgtc aaataatgta caggcaaaca ctttcaaata 2820
taatttcctt cagtgaatac aaaatgttga tatcataggt gatgtacaat ttagttttga 2880
atgagttatt atgttatcac tgtgtctgat gttatctact ttgaaaggca gtccagaaaa 2940
gtgttctaag tgaactctta agatctattt tagataattt caactaatta aataacctgt 3000
tttactgcct gtacattcca cattaataaa gcgataccaa tcttatatga atgctaatat 3060
tactaaaatg cactgatatc acttcttctt cccctgttga aaagctttct catgatcata 3120
tttcacccac atctcacctt gaagaaactt acaggtagac ttaccttttc acttgtggaa 3180
ttaatcatat ttaaatctta ctttaaggct caataaataa tactcataat gtctcatttt 3240
agtgactcct aaggctagtc cttttataaa caactttttc tgacatagca tttatgtata 3300
ataaaccaga catttaaagt gta 3323

<210> SEQ ID NO 8
<211> LENGTH: 3014
<212> TYPE: DNA
<213> ORGANISM: Homo sapiens

<400> SEQUENCE: 8
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360
agaaggagat ggagccaatt tctatttact tttctcaagg tggacaagct gtagccatcg 420
ggcaatttaa agatcgaatt acagggtcca acgatccagt gaaaccttct aagcccttt 480 gtagcgttca aggaagacca gaaactggcc acactatttc cctttcctgt ctctctgcgc 540
ttggaacacc ttcccctgtg tactactggc ataaacttga gggaagagac atcgtgccag 600
tgaaagaaaa cttcaaccca accaccggga ttttggtcat tggaaatctg acaaattttg 660
aacaaggtta ttaccagtgt actgccatca acagacttgg caatagttcc tgcgaaatcg 720
atctcacttc ttcacatcca gaagttggaa tcattgttgg ggccttgatt ggtagcctgg 780
taggtgccgc catcatcatc tctgttgtgt gcttcgcaag gaataaggca aaagcaaagg 840
caaaagaaag aaattctaag accatcgcgg aacttgagcc aatgacaaag ataaacccaa 900
ggggagaaag cgaagcaatg ccaagagaag acgctaccca actagaagta actctaccat 960
cttccattca tgagactggc cctgatacca tccaagaacc agactatgag ccaaagccta 1020
ctcaggagcc tgccccagag cctgccccag gatcagagcc tatggcagtg cctgaccttg 1080
acatcgagct ggagctggag ccagaaacgc agtcggaatt ggagccagag ccagagccag 1140
agccagagtc agagcctggg gttgtagttg agcccttaag tgaagatgaa aagggagtgg 1200
ttaaggcata ggctggtggc ctaagtacag cattaatcat taaggaaccc attactgcca 1260
tttggaattc aaataaccta accaacctcc acctcctcct tccattttga ccaaccttct 1320
tctaacaagg tgctcattcc tactatgaat ccagaataaa cacgccaaga taacagctaa 1380
atcagcaagg gttcctgtat taccaatata gaatactaac aattttacta acacgtaagc 1440
ataacaaatg acagggcaag tgatttctaa cttagttgag ttttgcaaca gtacctgtgt 1500
tgttatttca gaaaatatta tttctctctt tttaactact cttttttttt attttggaca 1560
gagtcttgct ccgtcgcgca ggctgtgatc gtagtggtgc gatctcggct cactgcagcc 1620
tccgctccct gggttcaagc gattctcctg cctgagcctc ctgagtagct gggactgcag 1680
gcacgtgcca ccacgcccgg ctaatttttt gtatttttag tagagatggg gtttcacgtt 1740
gttggccagg atggtctcca tctcctgacc tcatgatccg cccaccttgg cctcccaaaa 1800
tgctgggatt acaggcatga gccactgcgc ccggcctctt tttagctact cttatgttcc 1860
acatgcacat atgacaaggt ggcattaatt agattcaata ttatttctag gaatagttcc 1920
tcattcattt ttatattgac cactaagaaa ataattcatc agcattatct catagattgg 1980
aaaattttct ccaaatacaa tagaggagaa tatgtaaagg gtatacatta attggtacgt 2040
agcatttaaa atcaggtctt ataattaatg cttcattcct catattagat ttcccaagaa 2100
atcaccctgg tatccaatat ctgagcatgg caaatttaaa aaataacaca atttcttgcc 2160
tgtaacccta gcactttggg aggccgaggc aggtggatca cctgaggtca ggagttcgag 2220
accagcctgg ccggcatggc gaaacccctt ctctgctgaa aatacagaaa ttagctgggc 2280
gtggtggtgc atgcctgtag tcccagctac ttgggaggct gaggcaggag aatcgcttga 2340
acccaggagg tggaggttgc agtgagccga gattgtgcca ctgcactcca acctgggtga 2400
cagagtgaga ttccatctga aaaacaaaaa caaaaacaga aaacaaacaa acaaaaaaca 2460
aaaaatcccc acaactttgt caaataatgt acaggcaaac actttcaaat ataatttcct 2520
tcagtgaata caaaatgttg atatcatagg tgatgtacaa tttagttttg aatgagttat 2580
tatgttatca ctgtgtctga tgttatctac tttgaaaggc agtccagaaa agtgttctaa 2640
gtgaactctt aagatctatt ttagataatt tcaactaatt aaataacctg ttttactgcc 2700
tgtacattcc acattaataa agcgatacca atcttatatg aatgctaata ttactaaaat 2760
gcactgatat cacttcttct tcccctgttg aaaagctttc tcatgatcat atttcaccca 2820
catctcacct tgaagaaact tacaggtaga cttacctttt cacttgtgga attaatcata 2880
tttaaatctt actttaaggc tcaataaata atactcataa tgtctcattt tagtgactcc 2940
taaggctagt ccttttataa acaacttttt ctgacatagc atttatgtat aataaaccag 3000
acatttaaag tgta 3014

<210> SEQ ID NO 9
<211> LENGTH: 3135
<212> TYPE: DNA
<213> ORGANISM: Homo sapiens

<400> SEQUENCE: 9
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360

-continued

```
agaaggagat ggagccaatt tctatttact tttctcaagg tggacaagct gtagccatcg    420
ggcaatttaa agatcgaatt acagggtcca acgatccagg taatgcatct atcactatct    480
cgcatatgca gccagcagac agtggaattt acatctgcga tgttaacaac cccccagact    540
ttctcggcca aaaccaaggc atcctcaacg tcagtgtgtt agtgaaacct tctaagcccc    600
tttgtagcgt tcaaggaaga ccagaaactg gccacactat ttccctttcc tgtctctctg    660
cgcttggaac accttcccct gtgtactact ggcataaact tgagggaaga gacatcgtgc    720
cagtgaaaga aaacttcacc aaccaccggg attttggtca ttggaaatct gacaaatttt    780
gaacaaggtt attaccagtg tactgccatc aacagacttg gcaatagttc ctgcgaaatc    840
gatctcactt cttcacatcc agaagttgga atcattgttg gggccttgat tggtagcctg    900
gtaggtgccg ccatcatcat ctctgttgtg tgcttcgcaa ggaataaggc aaaagcaaag    960
gcaaaagaaa gaaattctaa gaccatcgcg gaacttgagc caatgacaaa gataaaccca   1020
aggggagaaa gcgaagcaat gccaagagaa gacgctaccc aactagaagt aactctacca   1080
tcttccattc atgagactgg ccctgatacc atccaagaac cagactatga gccaaagcct   1140
actcaggagc ctgccccaga gcctgcccca ggatcagagc ctatggcagt gcctgacctt   1200
gacatcgagc tggagctgga gccagaaacg cagtcggaat tggagccaga gccagagcca   1260
gagccagagt cagagcctgg ggttgtagtt gagcccttaa gtgaagatga aaagggagtg   1320
gttaaggcat aggctggtgg cctaagtaca gcattaatca ttaaggaacc cattactgcc   1380
atttggaatt caaataacct aaccaacctc cacctcctcc ttccattttg accaaccttc   1440
ttctaacaag gtgctcattc ctactatgaa tccagaataa acacgccaag ataacagcta   1500
aatcagcaag ggttcctgta ttaccaatat agaatactaa caattttact aacacgtaag   1560
cataacaaat gacagggcaa gtgatttcta acttagttga gttttgcaac agtacctgtg   1620
ttgttatttc agaaaatatt atttctctct ttttaactac tctttttttt tattttggac   1680
agagtcttgc tccgtcgcgc aggctgtgat cgtagtggtg cgatctcggc tcactgcagc   1740
ctccgctccc tgggttcaag cgattctcct gcctgagcct cctgagtagc tgggactgca   1800
ggcacgtgcc accacgcccg gctaattttt tgtattttta gtagagatgg ggtttcacgt   1860
tgttggccag gatggtctcc atctcctgac ctcatgatcc gcccaccttg gcctcccaaa   1920
atgctgggat tacaggcatg agccactgcg cccggcctct ttttagctac tcttatgttc   1980
cacatgcaca tatgacaagg tggcattaat tagattcaat attatttcta ggaatagttc   2040
ctcattcatt tttatattga ccactaagaa aataattcat cagcattatc tcatagattg   2100
gaaaattttc tccaaataca atagaggaga atatgtaaag ggtatacatt aattggtacg   2160
tagcatttaa aatcaggtct tataattaat gcttcattcc tcatattaga tttcccaaga   2220
aatcaccctg gtatccaata tctgagcatg gcaaatttaa aaaataacac aatttcttgc   2280
ctgtaaccct agcactttgg gaggccgagg caggtggatc acctgaggtc aggagttcga   2340
gaccagcctg gccggcatgg cgaaacccct tctctgctga aaatacagaa attagctggg   2400
cgtggtggtg catgcctgta gtcccagcta cttgggaggc tgaggcagga gaatcgcttg   2460
aacccaggag gtggaggttg cagtgagccg agattgtgcc actgcactcc aacctgggtg   2520
acagagtgag attccatctg aaaaacaaaa acaaaaacag aaaacaaaca aacaaaaaac   2580
aaaaaatccc cacaactttg tcaaataatg tacaggcaaa cactttcaaa tataatttcc   2640
ttcagtgaat acaaaatgtt gatatcatag gtgatgtaca atttagtttt gaatgagtta   2700
ttatgttatc actgtgtctg atgttatcta ctttgaaagg cagtccagaa aagtgttcta   2760
```

-continued agtgaactct taagatctat tttagataat ttcaactaat taaataacct gttttactgc 2820
ctgtacattc cacattaata aagcgatacc aatcttatat gaatgctaat attactaaaa 2880
tgcactgata tcacttcttc ttcccctgtt gaaaagcttt ctcatgatca tatttcaccc 2940
acatctcacc ttgaagaaac ttacaggtag acttaccttt tcacttgtgg aattaatcat 3000
atttaaatct tactttaagg ctcaataaat aatactcata atgtctcatt ttagtgactc 3060
ctaaggctag tccttttata aacaactttt tctgacatag catttatgta taataaacca 3120
gacatttaaa gtgta 3135

<210> SEQ ID NO 10
<211> LENGTH: 2995
<212> TYPE: DNA
<213> ORGANISM: Homo sapiens

<400> SEQUENCE: 10
gtactgaaaa aagtctatac gcaataagta agcccaaaga ggcatgtttg cttggcgatg 60
cccagcagat aagccaggca aacctcggtg tgatcgaaga agccaatttg agactcagcc 120
tagtccaggc aagctactgg cacctgctgc tctcaactaa cctccacaca atggtgttcg 180
cattttggaa ggtctttctg atcctaagct gccttgcagg tcaggttagt gtggtgcaag 240
tgaccatccc agacggtttc gtgaacgtga ctgttggatc taatgtcact ctcatctgca 300
tctacaccac cactgtggcc tcccgagaac agctttccat ccagtggtct ttcttccata 360
agaaggagat ggagccaatt tctatttact tttctcaagg tggacaagct gtagccatcg 420
ggcaatttaa agatcgaatt acagggtcca acgatccagg taatgcatct atcactatct 480
cgcatatgca gccagcagac agtggaattt acatctgcga tgttaacaac cccccagact 540
ttctcggcca aaaccaaggc atcctcaacg tcagtgtgtt agtgaaacct tctaagcccc 600
tttgtagcgt tcaaggaaga ccagaaactg gccacactat ttccctttcc tgtctctctg 660
cgcttggaac accttcccct gtgtactact ggcataaact tgagggaaga gacatcgtgc 720
cagtgaaaga aaacttcaac ccaaccaccg ggattttggt cattggaaat ctgacaaatt 780
ttgaacaagg ttattaccag tgtactgcca tcaacagact tggcaatagt tcctgcgaaa 840
tcgatctcac ttcttcacgc caatgacaaa gataaaccca aggggagaaa gcgaagcaat 900
gccaagagaa gacgctaccc aactagaagt aactctacca tcttccattc atgagactgg 960
ccctgatacc atccaagaac cagactatga gccaaagcct actcaggagc ctgccccaga 1020
gcctgcccca ggatcagagc ctatggcagt gcctgacctt gacatcgagc tggagctgga 1080
gccagaaacg cagtcggaat tggagccaga gccagagcca gagccagagt cagagcctgg 1140
ggttgtagtt gagcccttaa gtgaagatga aaagggagtg gttaaggcat aggctggtgg 1200
cctaagtaca gcattaatca ttaaggaacc cattactgcc atttggaatt caaataacct 1260
aaccaacctc cacctcctcc ttccattttg accaaccttc ttctaacaag gtgctcattc 1320
ctactatgaa tccagaataa acacgccaag ataacagcta aatcagcaag ggttcctgta 1380
ttaccaatat agaatactaa caattttact aacacgtaag cataacaaat gacagggcaa 1440
gtgatttcta acttagttga gttttgcaac agtacctgtg ttgttatttc agaaaatatt 1500
atttctctct ttttaactac tctttttttt tattttggac agagtcttgc tccgtcgcgc 1560
aggctgtgat cgtagtggtg cgatctcggc tcactgcagc ctccgctccc tgggttcaag 1620
cgattctcct gcctgagcct cctgagtagc tgggactgca ggcacgtgcc accacgcccg 1680

-continued

```
gctaatttt tgtattttta gtagagatgg ggtttcacgt tgttggccag gatggtctcc   1740

atctcctgac ctcatgatcc gcccaccttg gcctcccaaa atgctgggat tacaggcatg   1800

agccactgcg cccggcctct ttttagctac tcttatgttc cacatgcaca tatgacaagg   1860

tggcattaat tagattcaat attatttcta ggaatagttc ctcattcatt tttatattga   1920

ccactaagaa aataattcat cagcattatc tcatagattg gaaaattttc tccaaataca   1980

atagaggaga atatgtaaag ggtatacatt aattggtacg tagcatttaa aatcaggtct   2040

tataattaat gcttcattcc tcatattaga tttcccaaga aatcaccctg gtatccaata   2100

tctgagcatg gcaaatttaa aaaataacac aatttcttgc ctgtaaccct agcactttgg   2160

gaggccgagg caggtggatc acctgaggtc aggagttcga gaccagcctg gccggcatgg   2220

cgaaacccct tctctgctga aaatacagaa attagctggg cgtggtggtg catgcctgta   2280

gtcccagcta cttgggaggc tgaggcagga gaatcgcttg aacccaggag gtggaggttg   2340

cagtgagccg agattgtgcc actgcactcc aacctgggtg acagagtgag attccatctg   2400

aaaaacaaaa acaaaaacag aaaacaaaca aacaaaaaac aaaaaatccc cacaactttg   2460

tcaaataatg tacaggcaaa cactttcaaa tataatttcc ttcagtgaat acaaaatgtt   2520

gatatcatag gtgatgtaca atttagtttt gaatgagtta ttatgttatc actgtgtctg   2580

atgttatcta ctttgaaagg cagtccagaa aagtgttcta agtgaactct taagatctat   2640

tttagataat ttcaactaat taaataacct gttttactgc ctgtacattc cacattaata   2700

aagcgatacc aatcttatat gaatgctaat attactaaaa tgcactgata tcacttcttc   2760

ttcccctgtt gaaaagcttt ctcatgatca tatttcaccc acatctcacc ttgaagaaac   2820

ttacaggtag acttaccttt tcacttgtgg aattaatcat atttaaatct tactttaagg   2880

ctcaataaat aatactcata atgtctcatt ttagtgactc ctaaggctag tccttttata   2940

aacaactttt tctgacatag catttatgta taataaacca gacatttaaa gtgta        2995


<210> SEQ ID NO 11
<211> LENGTH: 387
<212> TYPE: PRT
<213> ORGANISM: Homo sapiens

<400> SEQUENCE: 11

Met Val Phe Ala Phe Trp Lys Val Phe Leu Ile Leu Ser Cys Leu Ala
1               5                   10                  15

Gly Gln Val Ser Val Val Gln Val Thr Ile Pro Asp Gly Phe Val Asn
            20                  25                  30

Val Thr Val Gly Ser Asn Val Thr Leu Ile Cys Ile Tyr Thr Thr Thr
        35                  40                  45

Val Ala Ser Arg Glu Gln Leu Ser Ile Gln Trp Ser Phe Phe His Lys
    50                  55                  60

Lys Glu Met Glu Pro Ile Ser Ile Tyr Phe Ser Gln Gly Gly Gln Ala
65                  70                  75                  80

Val Ala Ile Gly Gln Phe Lys Asp Arg Ile Thr Gly Ser Asn Asp Pro
                85                  90                  95

Gly Asn Ala Ser Ile Thr Ile Ser His Met Gln Pro Ala Asp Ser Gly
            100                 105                 110

Ile Tyr Ile Cys Asp Val Asn Asn Pro Pro Asp Phe Leu Gly Gln Asn
        115                 120                 125

Gln Gly Ile Leu Asn Val Ser Val Leu Val Lys Pro Ser Lys Pro Leu
    130                 135                 140
```

-continued

Cys Ser Val Gln Gly Arg Pro Glu Thr Gly His Thr Ile Ser Leu Ser
145 150 155 160

Cys Leu Ser Ala Leu Gly Thr Pro Ser Pro Val Tyr Tyr Trp His Lys
165 170 175

Leu Glu Gly Arg Asp Ile Val Pro Val Lys Glu Asn Phe Asn Pro Thr
180 185 190

Thr Gly Ile Leu Val Ile Gly Asn Leu Thr Asn Phe Glu Gln Gly Tyr
195 200 205

Tyr Gln Cys Thr Ala Ile Asn Arg Leu Gly Asn Ser Ser Cys Glu Ile
210 215 220

Asp Leu Thr Ser Ser His Pro Glu Val Gly Ile Ile Val Gly Ala Leu
225 230 235 240

Ile Gly Ser Leu Val Gly Ala Ala Ile Ile Ile Ser Val Val Cys Phe
245 250 255

Ala Arg Asn Lys Ala Lys Ala Lys Ala Lys Glu Arg Asn Ser Lys Thr
260 265 270

Ile Ala Glu Leu Glu Pro Met Thr Lys Ile Asn Pro Arg Gly Glu Ser
275 280 285

Glu Ala Met Pro Arg Glu Asp Ala Thr Gln Leu Glu Val Thr Leu Pro
290 295 300

Ser Ser Ile His Glu Thr Gly Pro Asp Thr Ile Gln Glu Pro Asp Tyr
305 310 315 320

Glu Pro Lys Pro Thr Gln Glu Pro Ala Pro Glu Pro Ala Pro Gly Ser
325 330 335

Glu Pro Met Ala Val Pro Asp Leu Asp Ile Glu Leu Glu Leu Glu Pro
340 345 350

Glu Thr Gln Ser Glu Leu Glu Pro Glu Pro Glu Pro Glu Pro Glu Ser
355 360 365

Glu Pro Gly Val Val Val Glu Pro Leu Ser Glu Asp Glu Lys Gly Val
370 375 380

Val Lys Ala
385

<210> SEQ ID NO 12
<211> LENGTH: 423
<212> TYPE: PRT
<213> ORGANISM: Homo sapiens

<400> SEQUENCE: 12

Met Val Phe Ala Phe Trp Lys Val Phe Leu Ile Leu Ser Cys Leu Ala
1 5 10 15

Gly Gln Val Ser Val Val Gln Val Thr Ile Pro Asp Gly Phe Val Asn
20 25 30

Val Thr Val Gly Ser Asn Val Thr Leu Ile Cys Ile Tyr Thr Thr Thr
35 40 45

Val Ala Ser Arg Glu Gln Leu Ser Ile Gln Trp Ser Phe Phe His Lys
50 55 60

Lys Glu Met Glu Pro Ile Ser His Ser Ser Cys Leu Ser Thr Glu Gly
65 70 75 80

Met Glu Glu Lys Ala Val Gly Gln Cys Leu Lys Met Thr His Val Arg
85 90 95

Asp Ala Arg Gly Arg Cys Ser Trp Thr Ser Glu Ile Tyr Phe Ser Gln
100 105 110

Gly Gly Gln Ala Val Ala Ile Gly Gln Phe Lys Asp Arg Ile Thr Gly
115 120 125

```
Ser Asn Asp Pro Gly Asn Ala Ser Ile Thr Ile Ser His Met Gln Pro
    130                 135                 140

Ala Asp Ser Gly Ile Tyr Ile Cys Asp Val Asn Asn Pro Pro Asp Phe
145                 150                 155                 160

Leu Gly Gln Asn Gln Gly Ile Leu Asn Val Ser Val Leu Val Lys Pro
                165                 170                 175

Ser Lys Pro Leu Cys Ser Val Gln Gly Arg Pro Glu Thr Gly His Thr
            180                 185                 190

Ile Ser Leu Ser Cys Leu Ser Ala Leu Gly Thr Pro Ser Pro Val Tyr
        195                 200                 205

Tyr Trp His Lys Leu Glu Gly Arg Asp Ile Val Pro Val Lys Glu Asn
    210                 215                 220

Phe Asn Pro Thr Thr Gly Ile Leu Val Ile Gly Asn Leu Thr Asn Phe
225                 230                 235                 240

Glu Gln Gly Tyr Tyr Gln Cys Thr Ala Ile Asn Arg Leu Gly Asn Ser
                245                 250                 255

Ser Cys Glu Ile Asp Leu Thr Ser Ser His Pro Glu Val Gly Ile Ile
            260                 265                 270

Val Gly Ala Leu Ile Gly Ser Leu Val Gly Ala Ala Ile Ile Ile Ser
        275                 280                 285

Val Val Cys Phe Ala Arg Asn Lys Ala Lys Ala Lys Ala Lys Glu Arg
    290                 295                 300

Asn Ser Lys Thr Ile Ala Glu Leu Glu Pro Met Thr Lys Ile Asn Pro
305                 310                 315                 320

Arg Gly Glu Ser Glu Ala Met Pro Arg Glu Asp Ala Thr Gln Leu Glu
                325                 330                 335

Val Thr Leu Pro Ser Ser Ile His Glu Thr Gly Pro Asp Thr Ile Gln
            340                 345                 350

Glu Pro Asp Tyr Glu Pro Lys Pro Thr Gln Glu Pro Ala Pro Glu Pro
        355                 360                 365

Ala Pro Gly Ser Glu Pro Met Ala Val Pro Asp Leu Asp Ile Glu Leu
    370                 375                 380

Glu Leu Glu Pro Glu Thr Gln Ser Glu Leu Glu Pro Glu Pro Glu Pro
385                 390                 395                 400

Glu Pro Glu Ser Glu Pro Gly Val Val Val Glu Pro Leu Ser Glu Asp
                405                 410                 415

Glu Lys Gly Val Val Lys Ala
            420


<210> SEQ ID NO 13
<211> LENGTH: 449
<212> TYPE: PRT
<213> ORGANISM: Homo sapiens

<400> SEQUENCE: 13

Met Val Phe Ala Phe Trp Lys Val Phe Leu Ile Leu Ser Cys Leu Ala
1               5                   10                  15

Gly Gln Val Ser Val Val Gln Val Thr Ile Pro Asp Gly Phe Val Asn
            20                  25                  30

Val Thr Val Gly Ser Asn Val Thr Leu Ile Cys Ile Tyr Thr Thr Thr
        35                  40                  45

Val Ala Ser Arg Glu Gln Leu Ser Ile Gln Trp Ser Phe Phe His Lys
    50                  55                  60

Lys Glu Met Glu Pro Ile Ser His Ser Ser Cys Leu Ser Thr Glu Gly
```

-continued 65 70 75 80

Met Glu Glu Lys Ala Val Gly Gln Cys Leu Lys Met Thr His Val Arg
85 90 95

Asp Ala Arg Gly Arg Cys Ser Trp Thr Ser Glu Ser Pro Trp Glu Glu
100 105 110

Gly Lys Trp Pro Asp Val Glu Ala Val Lys Gly Thr Leu Asp Gly Gln
115 120 125

Gln Ala Glu Leu Gln Ile Tyr Phe Ser Gln Gly Gly Gln Ala Val Ala
130 135 140

Ile Gly Gln Phe Lys Asp Arg Ile Thr Gly Ser Asn Asp Pro Gly Asn
145 150 155 160

Ala Ser Ile Thr Ile Ser His Met Gln Pro Ala Asp Ser Gly Ile Tyr
165 170 175

Ile Cys Asp Val Asn Asn Pro Pro Asp Phe Leu Gly Gln Asn Gln Gly
180 185 190

Ile Leu Asn Val Ser Val Leu Val Lys Pro Ser Lys Pro Leu Cys Ser
195 200 205

Val Gln Gly Arg Pro Glu Thr Gly His Thr Ile Ser Leu Ser Cys Leu
210 215 220

Ser Ala Leu Gly Thr Pro Ser Pro Val Tyr Tyr Trp His Lys Leu Glu
225 230 235 240

Gly Arg Asp Ile Val Pro Val Lys Glu Asn Phe Asn Pro Thr Thr Gly
245 250 255

Ile Leu Val Ile Gly Asn Leu Thr Asn Phe Glu Gln Gly Tyr Tyr Gln
260 265 270

Cys Thr Ala Ile Asn Arg Leu Gly Asn Ser Ser Cys Glu Ile Asp Leu
275 280 285

Thr Ser Ser His Pro Glu Val Gly Ile Ile Val Gly Ala Leu Ile Gly
290 295 300

Ser Leu Val Gly Ala Ala Ile Ile Ile Ser Val Val Cys Phe Ala Arg
305 310 315 320

Asn Lys Ala Lys Ala Lys Ala Lys Glu Arg Asn Ser Lys Thr Ile Ala
325 330 335

Glu Leu Glu Pro Met Thr Lys Ile Asn Pro Arg Gly Glu Ser Glu Ala
340 345 350

Met Pro Arg Glu Asp Ala Thr Gln Leu Glu Val Thr Leu Pro Ser Ser
355 360 365

Ile His Glu Thr Gly Pro Asp Thr Ile Gln Glu Pro Asp Tyr Glu Pro
370 375 380

Lys Pro Thr Gln Glu Pro Ala Pro Glu Pro Ala Pro Gly Ser Glu Pro
385 390 395 400

Met Ala Val Pro Asp Leu Asp Ile Glu Leu Glu Leu Glu Pro Glu Thr
405 410 415

Gln Ser Glu Leu Glu Pro Glu Pro Glu Pro Glu Pro Glu Ser Glu Pro
420 425 430

Gly Val Val Val Glu Pro Leu Ser Glu Asp Glu Lys Gly Val Val Lys
435 440 445

Ala

<210> SEQ ID NO 14
<211> LENGTH: 346
<212> TYPE: PRT
<213> ORGANISM: Homo sapiens

<400> SEQUENCE: 14

Met Val Phe Ala Phe Trp Lys Val Phe Leu Ile Leu Ser Cys Leu Ala
1 5 10 15

Gly Gln Val Ser Val Val Gln Val Thr Ile Pro Asp Gly Phe Val Asn
20 25 30

Val Thr Val Gly Ser Asn Val Thr Leu Ile Cys Ile Tyr Thr Thr Thr
35 40 45

Val Ala Ser Arg Glu Gln Leu Ser Ile Gln Trp Ser Phe Phe His Lys
50 55 60

Lys Glu Met Glu Pro Ile Ser Ile Tyr Phe Ser Gln Gly Gly Gln Ala
65 70 75 80

Val Ala Ile Gly Gln Phe Lys Asp Arg Ile Thr Gly Ser Asn Asp Pro
85 90 95

Val Lys Pro Ser Lys Pro Leu Cys Ser Val Gln Gly Arg Pro Glu Thr
100 105 110

Gly His Thr Ile Ser Leu Ser Cys Leu Ser Ala Leu Gly Thr Pro Ser
115 120 125

Pro Val Tyr Tyr Trp His Lys Leu Glu Gly Arg Asp Ile Val Pro Val
130 135 140

Lys Glu Asn Phe Asn Pro Thr Thr Gly Ile Leu Val Ile Gly Asn Leu
145 150 155 160

Thr Asn Phe Glu Gln Gly Tyr Tyr Gln Cys Thr Ala Ile Asn Arg Leu
165 170 175

Gly Asn Ser Ser Cys Glu Ile Asp Leu Thr Ser Ser His Pro Glu Val
180 185 190

Gly Ile Ile Val Gly Ala Leu Ile Gly Ser Leu Val Gly Ala Ala Ile
195 200 205

Ile Ile Ser Val Val Cys Phe Ala Arg Asn Lys Ala Lys Ala Lys Ala
210 215 220

Lys Glu Arg Asn Ser Lys Thr Ile Ala Glu Leu Glu Pro Met Thr Lys
225 230 235 240

Ile Asn Pro Arg Gly Glu Ser Glu Ala Met Pro Arg Glu Asp Ala Thr
245 250 255

Gln Leu Glu Val Thr Leu Pro Ser Ser Ile His Glu Thr Gly Pro Asp
260 265 270

Thr Ile Gln Glu Pro Asp Tyr Glu Pro Lys Pro Thr Gln Glu Pro Ala
275 280 285

Pro Glu Pro Ala Pro Gly Ser Glu Pro Met Ala Val Pro Asp Leu Asp
290 295 300

Ile Glu Leu Glu Leu Glu Pro Glu Thr Gln Ser Glu Leu Glu Pro Glu
305 310 315 320

Pro Glu Pro Glu Pro Glu Ser Glu Pro Gly Val Val Val Glu Pro Leu
325 330 335

Ser Glu Asp Glu Lys Gly Val Val Lys Ala
340 345

<210> SEQ ID NO 15
<211> LENGTH: 203
<212> TYPE: PRT
<213> ORGANISM: Homo sapiens

<400> SEQUENCE: 15

Met Val Phe Ala Phe Trp Lys Val Phe Leu Ile Leu Ser Cys Leu Ala
1 5 10 15

```
Gly Gln Val Ser Val Val Gln Val Thr Ile Pro Asp Gly Phe Val Asn
            20                  25                  30

Val Thr Val Gly Ser Asn Val Thr Leu Ile Cys Ile Tyr Thr Thr Thr
        35                  40                  45

Val Ala Ser Arg Glu Gln Leu Ser Ile Gln Trp Ser Phe Phe His Lys
    50                  55                  60

Lys Glu Met Glu Pro Ile Ser Ile Tyr Phe Ser Gln Gly Gly Gln Ala
65                  70                  75                  80

Val Ala Ile Gly Gln Phe Lys Asp Arg Ile Thr Gly Ser Asn Asp Pro
                85                  90                  95

Gly Asn Ala Ser Ile Thr Ile Ser His Met Gln Pro Ala Asp Ser Gly
            100                 105                 110

Ile Tyr Ile Cys Asp Val Asn Asn Pro Pro Asp Phe Leu Gly Gln Asn
        115                 120                 125

Gln Gly Ile Leu Asn Val Ser Val Leu Val Lys Pro Ser Lys Pro Leu
    130                 135                 140

Cys Ser Val Gln Gly Arg Pro Glu Thr Gly His Thr Ile Ser Leu Ser
145                 150                 155                 160

Cys Leu Ser Ala Leu Gly Thr Pro Ser Pro Val Tyr Tyr Trp His Lys
                165                 170                 175

Leu Glu Gly Arg Asp Ile Val Pro Val Lys Glu Asn Phe Thr Asn His
            180                 185                 190

Arg Asp Phe Gly His Trp Lys Ser Asp Lys Phe
        195                 200


<210> SEQ ID NO 16
<211> LENGTH: 231
<212> TYPE: PRT
<213> ORGANISM: Homo sapiens

<400> SEQUENCE: 16

Met Val Phe Ala Phe Trp Lys Val Phe Leu Ile Leu Ser Cys Leu Ala
1               5                   10                  15

Gly Gln Val Ser Val Val Gln Val Thr Ile Pro Asp Gly Phe Val Asn
            20                  25                  30

Val Thr Val Gly Ser Asn Val Thr Leu Ile Cys Ile Tyr Thr Thr Thr
        35                  40                  45

Val Ala Ser Arg Glu Gln Leu Ser Ile Gln Trp Ser Phe Phe His Lys
    50                  55                  60

Lys Glu Met Glu Pro Ile Ser Ile Tyr Phe Ser Gln Gly Gly Gln Ala
65                  70                  75                  80

Val Ala Ile Gly Gln Phe Lys Asp Arg Ile Thr Gly Ser Asn Asp Pro
                85                  90                  95

Gly Asn Ala Ser Ile Thr Ile Ser His Met Gln Pro Ala Asp Ser Gly
            100                 105                 110

Ile Tyr Ile Cys Asp Val Asn Asn Pro Pro Asp Phe Leu Gly Gln Asn
        115                 120                 125

Gln Gly Ile Leu Asn Val Ser Val Leu Val Lys Pro Ser Lys Pro Leu
    130                 135                 140

Cys Ser Val Gln Gly Arg Pro Glu Thr Gly His Thr Ile Ser Leu Ser
145                 150                 155                 160

Cys Leu Ser Ala Leu Gly Thr Pro Ser Pro Val Tyr Tyr Trp His Lys
                165                 170                 175

Leu Glu Gly Arg Asp Ile Val Pro Val Lys Glu Asn Phe Asn Pro Thr
            180                 185                 190
```

```
Thr Gly Ile Leu Val Ile Gly Asn Leu Thr Asn Phe Glu Gln Gly Tyr
        195                 200                 205

Tyr Gln Cys Thr Ala Ile Asn Arg Leu Gly Asn Ser Ser Cys Glu Ile
    210                 215                 220

Asp Leu Thr Ser Ser Arg Gln
225                 230


<210> SEQ ID NO 17
<211> LENGTH: 2888
<212> TYPE: DNA
<213> ORGANISM: Homo sapiens

<400> SEQUENCE: 17

agccgtgggg agcgccgcag gtggggacga gccgggcggc acctgccccg ggaccagagc     60

ggacgctccc tccccgctgc gccgagggag gggaaacccg aggggttcct tggagaaggt    120

ggtgcgtcct ggggcggcag ctgaggaaga aagacgcagt gccccgaagc ccctgagctg    180

aaaagggcca gaaagggggc ggcatggcat ggcccaaact gcccgcacct tggctgctgc    240

tctgcacctg gctcccagca gggtgcctgt ccttgcttgt gacggtccag cacacagaac    300

gctatgtcac cctgtttgcc tctatcatcc tcaaatgtga ctacaccacc tctgcccagc    360

tccaggacgt ggtggtgaca tggcgcttca agtccttctg caaggaccct atctttgact    420

actactcagc gtcataccag gcagctttat ccctgggcca ggacccatcc aatgactgca    480

acgacaacca gcgggaagtt cgcatagtgg cccagcggcg ggggcagaat gagcccgtgc    540

tgggggtaga ttaccggcag cgcaagatca ccatccagaa ccgagcagat ctcgtgataa    600

atgaagtgat gtggtgggac catggagtgt attactgcac cattgaggct ccaggggaca    660

catcaggaga ccccgataag gaagtaaagc tcatcgtcct acactggctg acagtgatct    720

tcatcatcct gggagccctc ctcctcctgc tgctgattgg agtgtgctgg tgccagtgct    780

gtcctcagta ttgctgctgc tatatccgct gtccctgctg tcctgcccac tgctgctgtc    840

ctgaggaagc cctggcccgc caccgctaca tgaagcaggc ccaggcccta ggtcctcaga    900

tgatgggaaa acccctgtac tggggggcgg acaggagctc ccaggtttca tcttatccaa    960

tgcacccgct gctgcagcga gatttgtccc tgccgtccag cctcccgcag atgccaatga   1020

cccagaccac caatcagcct cccatcgcca atggtgtcct ggagtatttg gagaaagaac   1080

tgcggaacct caacctggcc cagcctctgc cccctgacct caaaggcaga tttggccatc   1140

cctgcagcat gctgtcctcc ctgggctctg aggtcgtgga acgcagaatc atccacctgc   1200

ccccactgat cagagacctg tcatcctcaa ggaggaccag tgactccctg caccagcagt   1260

ggctcacccc aattccctcc aggccctggg atctgaggga ggggagaagc caccaccatt   1320

accctgattt ccaccaggag ctccaggacc gggggccaaa gtcttgggca ttggaaagaa   1380

gggagttgga cccatcgtgg agtggaaggc accgtagctc taggctgaat gggtcaccca   1440

tacactggtc agacagggac agcctaagcg atgtcccctc atccagtgag gcacgctggc   1500

ggccgagcca ccctcctttc aggagccgct gtcaggagag gccccgcagg cccagccccc   1560

gggagagcac tcagaggcac gggagacgac gcaggcaccg cagctactct cctcccttgc   1620

cctccggcct cagttcctgg agctctgaag aggacaagga gaggcagccc cagagctggc   1680

gggcccaccg ccgcggctcg cactccccac actggcccga ggagaagccg cctagctacc   1740

gctcactgga tatcactcca ggcaagaata gcaggaaaaa agggagtgtg gagaggcgct   1800

cggagaaaga cagctctcat agtggaagga gtgtggtcat ttagtcacca agcacagcac   1860
```

aacttctgtg gctacttctc ggctcctgtg tgtcatcagc atcacctagg tttccagctg 1920
acttgggaac tgcaagtctg agtctaacag tttttggctt agattctgag aatcaaatag 1980
aagaatttta aatacaagag tttgagattg ggtatagtgg ctcacacctg taatcacagc 2040
actttgggag gctaagaatc acttgagact aggagttcaa gatcagcctg ggaaacatag 2100
tgagaccccg tctctacaaa aaatataaaa attagttagg tgtggtggca tgcacttgta 2160
gtcccagcta ctcaagaggc tgaggcagaa ggatcccttg agcccaggag tgcaaggctg 2220
caatgagcca ggatcccatg atcacacatc tgtattccag cctgggcaat agagcaagtc 2280
cccattacta aaaaacccaa aaggccaaaa aacaaaaaag ttagagttcg aggaattacc 2340
aactgtagtt ttagccttgg ttcatgctct cttgcatatt tatataatct ctgacttgta 2400
atggaccctg actggaatgt gatccctcag gaacttagta gcctgagtct ttcagtagac 2460
tacactgccc agaaccctgg ccattctcaa aatgagaact tgggaatgtt taagaagaaa 2520
tcaaacatgt ttcaggaaaa ggaaatctat ggagtattat agggacattc ccatgggaat 2580
gtatcttcct ccatggcatg tcttgagggt cctttcttgt taggagttta tcctgccagc 2640
ccataaatgg actatttatt gtaagtgtag aaaatcacag agaagcagtt ttgcaccagc 2700
cttattcctg tgccttgttt tcctcttgct cttttttttac ctgtatatct aatttatatt 2760
ttcatatata ttgtgtattg attgaagtca ctttaaatcc ttcttgggaa tgacacagta 2820
tataaataag gaagaaagaa aacatgccaa gctgagcatg ctgctccaaa taaatatctg 2880
ctttccta 2888

<210> SEQ ID NO 18
<211> LENGTH: 2756
<212> TYPE: DNA
<213> ORGANISM: Homo sapiens

<400> SEQUENCE: 18
agccgtgggg agcgccgcag gtggggacga gccgggcggc acctgccccg ggaccagagc 60
ggacgctccc tccccgctgc gccgagggag gggaaacccg aggggttcct tggagaaggt 120
ggtgcgtcct ggggcggcag ctgaggaaga aagacgcagt gccccgaagc ccctgagctg 180
aaaagggcca gaaagggggc ggcatggcat ggcccaaact gcccgcacct tggctgctgc 240
tctgcacctg gctcccagca gggtgcctgt ccttgcttgt gacggtccag cacacagaac 300
gctatgtcac cctgtttgcc tctatcatcc tcaaatgtga ctacaccacc tctgcccagc 360
tccaggacgt ggtggtgaca tggcgcttca agtccttctg caaggaccct atctttgact 420
actactcagc gtcataccag gcagctttat ccctgggcca ggacccatcc aatgactgca 480
acgacaacca gcgggaagtt cgcatagtgg cccagcggcg ggggcagaat gagcccgtgc 540
tgggggtaga ttaccggcag cgcaagatca ccatccagaa ccgagcagat ctcgtgataa 600
atgaagtgat gtggtgggac catggagtgt attactgcac cattgaggct ccaggggaca 660
catcaggaga ccccgataag gaagtaaagc tcatcgtcct acactggctg acagtgatct 720
tcatcatcct gggagccctc ctcctcctgc tgctgattgg agtgtgctgg tgccagtgct 780
gtcctcagta ttgctgctgc tatatccgct gtccctgctg tcctgcccac tgctgctgtc 840
ctgaggaaga tttgtccctg ccgtccagcc tcccgcagat gccaatgacc cagaccacca 900
atcagcctcc catcgccaat ggtgtcctgg agtatttgga gaaagaactg cggaacctca 960
acctggccca gcctctgccc cctgacctca aaggcagatt tggccatccc tgcagcatgc 1020

```
tgtcctccct gggctctgag gtcgtggaac gcagaatcat ccacctgccc ccactgatca   1080

gagacctgtc atcctcaagg aggaccagtg actccctgca ccagcagtgg ctcaccccaa   1140

ttccctccag gccctgggat ctgagggagg ggagaagcca ccaccattac cctgatttcc   1200

accaggagct ccaggaccgg gggccaaagt cttgggcatt ggaaagaagg gagttggacc   1260

catcgtggag tggaaggcac cgtagctcta ggctgaatgg gtcacccata cactggtcag   1320

acagggacag cctaagcgat gtcccctcat ccagtgaggc acgctggcgg ccgagccacc   1380

ctcctttcag gagccgctgt caggagaggc cccgcaggcc cagcccccgg gagagcactc   1440

agaggcacgg gagacgacgc aggcaccgca gctactctcc tcccttgccc tccggcctca   1500

gttcctggag ctctgaagag gacaaggaga ggcagcccca gagctggcgg gcccaccgcc   1560

gcggctcgca ctccccacac tggcccgagg agaagccgcc tagctaccgc tcactggata   1620

tcactccagg caagaatagc aggaaaaaag ggagtgtgga gaggcgctcg gagaaagaca   1680

gctctcatag tggaaggagt gtggtcattt agtcaccaag cacagcacaa cttctgtggc   1740

tacttctcgg ctcctgtgtg tcatcagcat cacctaggtt tccagctgac ttgggaactg   1800

caagtctgag tctaacagtt tttggcttag attctgagaa tcaaatagaa gaattttaaa   1860

tacaagagtt tgagattggg tatagtggct cacacctgta atcacagcac tttgggaggc   1920

taagaatcac ttgagactag gagttcaaga tcagcctggg aaacatagtg agaccccgtc   1980

tctacaaaaa atataaaaat tagttaggtg tggtggcatg cacttgtagt cccagctact   2040

caagaggctg aggcagaagg atcccttgag cccaggagtg caaggctgca atgagccagg   2100

atcccatgat cacacatctg tattccagcc tgggcaatag agcaagtccc cattactaaa   2160

aaacccaaaa ggccaaaaaa caaaaaagtt agagttcgag gaattaccaa ctgtagtttt   2220

agccttggtt catgctctct tgcatattta tataatctct gacttgtaat ggaccctgac   2280

tggaatgtga tccctcagga acttagtagc ctgagtcttt cagtagacta cactgcccag   2340

aaccctggcc attctcaaaa tgagaacttg ggaatgttta agaagaaatc aaacatgttt   2400

caggaaaagg aaatctatgg agtattatag ggacattccc atgggaatgt atcttcctcc   2460

atggcatgtc ttgagggtcc tttcttgtta ggagtttatc ctgccagccc ataaatggac   2520

tatttattgt aagtgtagaa aatcacagag aagcagtttt gcaccagcct tattcctgtg   2580

ccttgttttc ctcttgctct ttttttacct gtatatctaa tttatatttt catatatatt   2640

gtgtattgat tgaagtcact ttaaatcctt cttgggaatg acacagtata taaataagga   2700

agaaagaaaa catgccaagc tgagcatgct gctccaaata aatatctgct ttccta       2756
```

<210> SEQ ID NO 19
<211> LENGTH: 2621
<212> TYPE: DNA
<213> ORGANISM: Homo sapiens

<400> SEQUENCE: 19

```
agccgtgggg agcgccgcag gtggggacga gccgggcggc acctgccccg ggaccagagc     60

ggacgctccc tccccgctgc gccgagggag gggaaacccg aggggttcct tggagaaggt    120

ggtgcgtcct ggggcggcag ctgaggaaga aagacgcagt gccccgaagc ccctgagctg    180

aaaagggcca gaaagggggc ggcatggcat ggcccaaact gcccgcacct tggctgctgc    240

tctgcacctg gctcccagca gggtgcctgt ccttgcttgt gacggtccag cacacagaac    300

gctatgtcac cctgtttgcc tctatcatcc tcaaatgtga ctacaccacc tctgcccagc    360

tccaggacgt ggtggtgaca tggcgcttca agtccttctg caaggaccct atctttgact    420
```

-continued

```
actactcagc gtcataccag gcagctttat ccctgggcca ggacccatcc aatgactgca    480
acgacaacca gcgggaagtt cgcatagtgg cccagcggcg gggcagaat gagcccgtgc     540
tgggggtaga ttaccggcag cgcaagatca ccatccagaa ccccctggcc cgccaccgct    600
acatgaagca ggcccaggcc ctaggtcctc agatgatggg aaaacccctg tactgggggg    660
cggacaggag ctcccaggtt tcatcttatc caatgcaccc gctgctgcag cgagatttgt    720
ccctgccgtc cagcctcccg cagatgccaa tgacccagac caccaatcag cctcccatcg    780
ccaatggtgt cctggagtat ttggagaaag aactgcggaa cctcaacctg gcccagcctc    840
tgccccctga cctcaaaggc agatttggcc atccctgcag catgctgtcc tccctgggct    900
ctgaggtcgt ggaacgcaga atcatccacc tgcccccact gatcagagac ctgtcatcct    960
caaggaggac cagtgactcc ctgcaccagc agtggctcac cccaattccc tccaggccct   1020
gggatctgag ggaggggaga agccaccacc attaccctga tttccaccag gagctccagg   1080
accgggggcc aaagtcttgg gcattggaaa gaagggagtt ggacccatcg tggagtggaa   1140
ggcaccgtag ctctaggctg aatgggtcac ccatacactg gtcagacagg gacagcctaa   1200
gcgatgtccc ctcatccagt gaggcacgct ggcggccgag ccaccctcct ttcaggagcc   1260
gctgtcagga gaggccccgc aggcccagcc cccgggagag cactcagagg cacgggagac   1320
gacgcaggca ccgcagctac tctcctccct tgccctccgg cctcagttcc tggagctctg   1380
aagaggacaa ggagaggcag ccccagagct ggcgggccca ccgccgcggc tcgcactccc   1440
cacactggcc cgaggagaag ccgcctagct accgctcact ggatatcact ccaggcaaga   1500
atagcaggaa aaaagggagt gtggagaggc gctcggagaa agacagctct catagtggaa   1560
ggagtgtggt catttagtca ccaagcacag cacaacttct gtggctactt ctcggctcct   1620
gtgtgtcatc agcatcacct aggtttccag ctgacttggg aactgcaagt ctgagtctaa   1680
cagtttttgg cttagattct gagaatcaaa tagaagaatt ttaaatacaa gagtttgaga   1740
ttgggtatag tggctcacac ctgtaatcac agcactttgg gaggctaaga atcacttgag   1800
actaggagtt caagatcagc ctgggaaaca tagtgagacc ccgtctctac aaaaaatata   1860
aaaattagtt aggtgtggtg gcatgcactt gtagtcccag ctactcaaga ggctgaggca   1920
gaaggatccc ttgagcccag gagtgcaagg ctgcaatgag ccaggatccc atgatcacac   1980
atctgtattc cagcctgggc aatagagcaa gtccccatta ctaaaaaacc caaaaggcca   2040
aaaaacaaaa aagttagagt tcgaggaatt accaactgta gttttagcct tggttcatgc   2100
tctcttgcat atttatataa tctctgactt gtaatggacc ctgactggaa tgtgatccct   2160
caggaactta gtagcctgag tctttcagta gactacactg cccagaaccc tggccattct   2220
caaaatgaga acttgggaat gtttaagaag aaatcaaaca tgtttcagga aaaggaaatc   2280
tatggagtat tatagggaca ttcccatggg aatgtatctt cctccatggc atgtcttgag   2340
ggtcctttct tgttaggagt ttatcctgcc agcccataaa tggactattt attgtaagtg   2400
tagaaaatca cagagaagca gttttgcacc agccttattc ctgtgccttg ttttcctctt   2460
gctctttttt tacctgtata tctaatttat attttcatat atattgtgta ttgattgaag   2520
tcactttaaa tccttcttgg gaatgacaca gtatataaat aaggaagaaa gaaaacatgc   2580
caagctgagc atgctgctcc aaataaatat ctgctttcct a                       2621
```

<210> SEQ ID NO 20
<211> LENGTH: 2717
<212> TYPE: DNA

-continued

<213> ORGANISM: Homo sapiens

<400> SEQUENCE: 20

```
agccgtgggg agcgccgcag gtggggacga gccgggcggc acctgccccg ggaccagagc     60
ggacgctccc tccccgctgc gccgagggag gggaaacccg aggggttcct tggagaaggt    120
ggtgcgtcct ggggcggcag ctgaggaaga aagacgcagt gccccgaagc ccctgagctg    180
aaaagggcca gaaagggggc ggcatggcat ggcccaaact gcccgcacct tggctgctgc    240
tctgcacctg gctcccagca gcataccagg cagctttatc cctgggccag gacccatcca    300
atgactgcaa cgacaaccag cgggaagttc gcatagtggc ccagcggcgg gggcagaatg    360
agcccgtgct gggggtagat taccggcagc gcaagatcac catccagaac cgagcagatc    420
tcgtgataaa tgaagtgatg tggtgggacc atggagtgta ttactgcacc attgaggctc    480
caggggacac atcaggagac cccgataagg aagtaaagct catcgtccta cactggctga    540
cagtgatctt catcatcctg ggagccctcc tcctcctgct gctgattgga gtgtgctggt    600
gccagtgctg tcctcagtat tgctgctgct atatccgctg tccctgctgt cctgcccact    660
gctgctgtcc tgaggaagcc ctggcccgcc accgctacat gaagcaggcc caggccctag    720
gtcctcagat gatgggaaaa cccctgtact gggggggcgga caggagctcc caggtttcat    780
cttatccaat gcacccgctg ctgcagcgag atttgtccct gccgtccagc ctcccgcaga    840
tgccaatgac ccagaccacc aatcagcctc ccatcgccaa tggtgtcctg gagtatttgg    900
agaaagaact gcggaacctc aacctggccc agcctctgcc ccctgacctc aaaggcagat    960
ttggccatcc ctgcagcatg ctgtcctccc tgggctctga ggtcgtggaa cgcagaatca   1020
tccacctgcc cccactgatc agagacctgt catcctcaag gaggaccagt gactccctgc   1080
accagcagtg gctcacccca attccctcca ggccctggga tctgagggag gggagaagcc   1140
accaccatta ccctgatttc caccaggagc tccaggaccg gggggccaaag tcttgggcat   1200
tggaaagaag ggagttggac ccatcgtgga gtggaaggca ccgtagctct aggctgaatg   1260
ggtcacccat acactggtca gacagggaca gcctaagcga tgtcccctca tccagtgagg   1320
cacgctggcg gccgagccac cctcctttca ggagccgctg tcaggagagg ccccgcaggc   1380
ccagcccccg ggagagcact cagaggcacg ggagacgacg caggcaccgc agctactctc   1440
ctcccttgcc ctccggcctc agttcctgga gctctgaaga ggacaaggag aggcagcccc   1500
agagctggcg ggcccaccgc cgcggctcgc actccccaca ctggcccgag gagaagccgc   1560
ctagctaccg ctcactggat atcactccag gcaagaatag caggaaaaaa gggagtgtgg   1620
agaggcgctc ggagaaagac agctctcata gtggaaggag tgtggtcatt tagtcaccaa   1680
gcacagcaca acttctgtgg ctacttctcg gctcctgtgt gtcatcagca tcacctaggt   1740
ttccagctga cttgggaact gcaagtctga gtctaacagt tttggcttta gattctgaga   1800
atcaaataga agaattttaa atacaagagt ttgagattgg gtatagtggc tcacacctgt   1860
aatcacagca ctttgggagg ctaagaatca cttgagacta ggagttcaag atcagcctgg   1920
gaaacatagt gagaccccgt ctctacaaaa aatataaaaa ttagttaggt gtggtggcat   1980
gcacttgtag tcccagctac tcaagaggct gaggcagaag gatcccttga gcccaggagt   2040
gcaaggctgc aatgagccag gatcccatga tcacacatct gtattccagc ctgggcaata   2100
gagcaagtcc ccattactaa aaaacccaaa aggccaaaaa acaaaaaagt tagagttcga   2160
ggaattacca actgtagttt tagccttggt tcatgctctc ttgcatattt atataatctc   2220
tgacttgtaa tggaccctga ctggaatgtg atccctcagg aacttagtag cctgagtctt   2280
```

```
tcagtagact acactgccca gaaccctggc cattctcaaa atgagaactt gggaatgttt   2340

aagaagaaat caaacatgtt tcaggaaaag gaaatctatg gagtattata gggacattcc   2400

catgggaatg tatcttcctc catggcatgt cttgagggtc ctttcttgtt aggagtttat   2460

cctgccagcc cataaatgga ctatttattg taagtgtaga aaatcacaga gaagcagttt   2520

tgcaccagcc ttattcctgt gccttgtttt cctcttgctc ttttttacc tgtatatcta    2580

atttatattt tcatatatat tgtgtattga ttgaagtcac tttaaatcct tcttgggaat   2640

gacacagtat ataaataagg aagaaagaaa acatgccaag ctgagcatgc tgctccaaat   2700

aaatatctgc tttccta                                                  2717
```

```
<210> SEQ ID NO 21
<211> LENGTH: 502
<212> TYPE: PRT
<213> ORGANISM: Homo sapiens

<400> SEQUENCE: 21

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Asp Leu Ser Leu Pro Ser Ser Leu Pro
    210                 215                 220

Gln Met Pro Met Thr Gln Thr Thr Asn Gln Pro Pro Ile Ala Asn Gly
225                 230                 235                 240

Val Leu Glu Tyr Leu Glu Lys Glu Leu Arg Asn Leu Asn Leu Ala Gln
                245                 250                 255

Pro Leu Pro Pro Asp Leu Lys Gly Arg Phe Gly His Pro Cys Ser Met
            260                 265                 270

Leu Ser Ser Leu Gly Ser Glu Val Val Glu Arg Arg Ile Ile His Leu
        275                 280                 285
```

```
Pro Pro Leu Ile Arg Asp Leu Ser Ser Ser Arg Arg Thr Ser Asp Ser
    290                 295                 300

Leu His Gln Gln Trp Leu Thr Pro Ile Pro Ser Arg Pro Trp Asp Leu
305                 310                 315                 320

Arg Glu Gly Arg Ser His His His Tyr Pro Asp Phe His Gln Glu Leu
                325                 330                 335

Gln Asp Arg Gly Pro Lys Ser Trp Ala Leu Glu Arg Arg Glu Leu Asp
            340                 345                 350

Pro Ser Trp Ser Gly Arg His Arg Ser Ser Arg Leu Asn Gly Ser Pro
        355                 360                 365

Ile His Trp Ser Asp Arg Asp Ser Leu Ser Asp Val Pro Ser Ser Ser
    370                 375                 380

Glu Ala Arg Trp Arg Pro Ser His Pro Pro Phe Arg Ser Arg Cys Gln
385                 390                 395                 400

Glu Arg Pro Arg Arg Pro Ser Pro Arg Glu Ser Thr Gln Arg His Gly
                405                 410                 415

Arg Arg Arg Arg His Arg Ser Tyr Ser Pro Pro Leu Pro Ser Gly Leu
            420                 425                 430

Ser Ser Trp Ser Ser Glu Glu Asp Lys Glu Arg Gln Pro Gln Ser Trp
        435                 440                 445

Arg Ala His Arg Arg Gly Ser His Ser Pro His Trp Pro Glu Glu Lys
    450                 455                 460

Pro Pro Ser Tyr Arg Ser Leu Asp Ile Thr Pro Gly Lys Asn Ser Arg
465                 470                 475                 480

Lys Lys Gly Ser Val Glu Arg Arg Ser Glu Lys Asp Ser Ser His Ser
                485                 490                 495

Gly Arg Ser Val Val Ile
            500


<210> SEQ ID NO 22
<211> LENGTH: 546
<212> TYPE: PRT
<213> ORGANISM: Homo sapiens

<400> SEQUENCE: 22

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160
```

```
Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Ala Leu Ala Arg His Arg Tyr Met Lys
    210                 215                 220

Gln Ala Gln Ala Leu Gly Pro Gln Met Met Gly Lys Pro Leu Tyr Trp
225                 230                 235                 240

Gly Ala Asp Arg Ser Ser Gln Val Ser Ser Tyr Pro Met His Pro Leu
                245                 250                 255

Leu Gln Arg Asp Leu Ser Leu Pro Ser Ser Leu Pro Gln Met Pro Met
            260                 265                 270

Thr Gln Thr Thr Asn Gln Pro Pro Ile Ala Asn Gly Val Leu Glu Tyr
        275                 280                 285

Leu Glu Lys Glu Leu Arg Asn Leu Asn Leu Ala Gln Pro Leu Pro Pro
    290                 295                 300

Asp Leu Lys Gly Arg Phe Gly His Pro Cys Ser Met Leu Ser Ser Leu
305                 310                 315                 320

Gly Ser Glu Val Val Glu Arg Arg Ile Ile His Leu Pro Pro Leu Ile
                325                 330                 335

Arg Asp Leu Ser Ser Ser Arg Arg Thr Ser Asp Ser Leu His Gln Gln
            340                 345                 350

Trp Leu Thr Pro Ile Pro Ser Arg Pro Trp Asp Leu Arg Glu Gly Arg
        355                 360                 365

Ser His His His Tyr Pro Asp Phe His Gln Glu Leu Gln Asp Arg Gly
    370                 375                 380

Pro Lys Ser Trp Ala Leu Glu Arg Arg Glu Leu Asp Pro Ser Trp Ser
385                 390                 395                 400

Gly Arg His Arg Ser Ser Arg Leu Asn Gly Ser Pro Ile His Trp Ser
                405                 410                 415

Asp Arg Asp Ser Leu Ser Asp Val Pro Ser Ser Ser Glu Ala Arg Trp
            420                 425                 430

Arg Pro Ser His Pro Pro Phe Arg Ser Arg Cys Gln Glu Arg Pro Arg
        435                 440                 445

Arg Pro Ser Pro Arg Glu Ser Thr Gln Arg His Gly Arg Arg Arg Arg
    450                 455                 460

His Arg Ser Tyr Ser Pro Pro Leu Pro Ser Gly Leu Ser Ser Trp Ser
465                 470                 475                 480

Ser Glu Glu Asp Lys Glu Arg Gln Pro Gln Ser Trp Arg Ala His Arg
                485                 490                 495

Arg Gly Ser His Ser Pro His Trp Pro Glu Glu Lys Pro Pro Ser Tyr
            500                 505                 510

Arg Ser Leu Asp Ile Thr Pro Gly Lys Asn Ser Arg Lys Lys Gly Ser
        515                 520                 525

Val Glu Arg Arg Ser Glu Lys Asp Ser Ser His Ser Gly Arg Ser Val
    530                 535                 540

Val Ile
545
```

<210> SEQ ID NO 23
<211> LENGTH: 457

<212> TYPE: PRT
<213> ORGANISM: Homo sapiens

<400> SEQUENCE: 23

```
Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Pro Leu
        115                 120                 125

Ala Arg His Arg Tyr Met Lys Gln Ala Gln Ala Leu Gly Pro Gln Met
    130                 135                 140

Met Gly Lys Pro Leu Tyr Trp Gly Ala Asp Arg Ser Ser Gln Val Ser
145                 150                 155                 160

Ser Tyr Pro Met His Pro Leu Leu Gln Arg Asp Leu Ser Leu Pro Ser
                165                 170                 175

Ser Leu Pro Gln Met Pro Met Thr Gln Thr Thr Asn Gln Pro Pro Ile
            180                 185                 190

Ala Asn Gly Val Leu Glu Tyr Leu Glu Lys Glu Leu Arg Asn Leu Asn
        195                 200                 205

Leu Ala Gln Pro Leu Pro Pro Asp Leu Lys Gly Arg Phe Gly His Pro
    210                 215                 220

Cys Ser Met Leu Ser Ser Leu Gly Ser Glu Val Val Glu Arg Arg Ile
225                 230                 235                 240

Ile His Leu Pro Pro Leu Ile Arg Asp Leu Ser Ser Ser Arg Arg Thr
                245                 250                 255

Ser Asp Ser Leu His Gln Gln Trp Leu Thr Pro Ile Pro Ser Arg Pro
            260                 265                 270

Trp Asp Leu Arg Glu Gly Arg Ser His His His Tyr Pro Asp Phe His
        275                 280                 285

Gln Glu Leu Gln Asp Arg Gly Pro Lys Ser Trp Ala Leu Glu Arg Arg
    290                 295                 300

Glu Leu Asp Pro Ser Trp Ser Gly Arg His Arg Ser Ser Arg Leu Asn
305                 310                 315                 320

Gly Ser Pro Ile His Trp Ser Asp Arg Asp Ser Leu Ser Asp Val Pro
                325                 330                 335

Ser Ser Ser Glu Ala Arg Trp Arg Pro Ser His Pro Pro Phe Arg Ser
            340                 345                 350

Arg Cys Gln Glu Arg Pro Arg Arg Pro Ser Pro Arg Glu Ser Thr Gln
        355                 360                 365

Arg His Gly Arg Arg Arg Arg His Arg Ser Tyr Ser Pro Pro Leu Pro
    370                 375                 380

Ser Gly Leu Ser Ser Trp Ser Ser Glu Glu Asp Lys Glu Arg Gln Pro
385                 390                 395                 400
```

```
Gln Ser Trp Arg Ala His Arg Arg Gly Ser His Ser Pro His Trp Pro
                405                 410                 415

Glu Glu Lys Pro Pro Ser Tyr Arg Ser Leu Asp Ile Thr Pro Gly Lys
            420                 425                 430

Asn Ser Arg Lys Lys Gly Ser Val Glu Arg Arg Ser Glu Lys Asp Ser
        435                 440                 445

Ser His Ser Gly Arg Ser Val Val Ile
    450                 455


<210> SEQ ID NO 24
<211> LENGTH: 489
<212> TYPE: PRT
<213> ORGANISM: Homo sapiens

<400> SEQUENCE: 24

Met Ala Trp Pro Lys Leu Pro Ala Pro Trp Leu Leu Leu Cys Thr Trp
1               5                   10                  15

Leu Pro Ala Ala Tyr Gln Ala Ala Leu Ser Leu Gly Gln Asp Pro Ser
            20                  25                  30

Asn Asp Cys Asn Asp Asn Gln Arg Glu Val Arg Ile Val Ala Gln Arg
        35                  40                  45

Arg Gly Gln Asn Glu Pro Val Leu Gly Val Asp Tyr Arg Gln Arg Lys
    50                  55                  60

Ile Thr Ile Gln Asn Arg Ala Asp Leu Val Ile Asn Glu Val Met Trp
65                  70                  75                  80

Trp Asp His Gly Val Tyr Tyr Cys Thr Ile Glu Ala Pro Gly Asp Thr
                85                  90                  95

Ser Gly Asp Pro Asp Lys Glu Val Lys Leu Ile Val Leu His Trp Leu
            100                 105                 110

Thr Val Ile Phe Ile Ile Leu Gly Ala Leu Leu Leu Leu Leu Leu Ile
        115                 120                 125

Gly Val Cys Trp Cys Gln Cys Cys Pro Gln Tyr Cys Cys Cys Tyr Ile
    130                 135                 140

Arg Cys Pro Cys Cys Pro Ala His Cys Cys Cys Pro Glu Glu Ala Leu
145                 150                 155                 160

Ala Arg His Arg Tyr Met Lys Gln Ala Gln Ala Leu Gly Pro Gln Met
                165                 170                 175

Met Gly Lys Pro Leu Tyr Trp Gly Ala Asp Arg Ser Ser Gln Val Ser
            180                 185                 190

Ser Tyr Pro Met His Pro Leu Leu Gln Arg Asp Leu Ser Leu Pro Ser
        195                 200                 205

Ser Leu Pro Gln Met Pro Met Thr Gln Thr Thr Asn Gln Pro Pro Ile
    210                 215                 220

Ala Asn Gly Val Leu Glu Tyr Leu Glu Lys Glu Leu Arg Asn Leu Asn
225                 230                 235                 240

Leu Ala Gln Pro Leu Pro Pro Asp Leu Lys Gly Arg Phe Gly His Pro
                245                 250                 255

Cys Ser Met Leu Ser Ser Leu Gly Ser Glu Val Val Glu Arg Arg Ile
            260                 265                 270

Ile His Leu Pro Pro Leu Ile Arg Asp Leu Ser Ser Ser Arg Arg Thr
        275                 280                 285

Ser Asp Ser Leu His Gln Gln Trp Leu Thr Pro Ile Pro Ser Arg Pro
    290                 295                 300

Trp Asp Leu Arg Glu Gly Arg Ser His His His Tyr Pro Asp Phe His
```

```
305                 310                 315                 320

Gln Glu Leu Gln Asp Arg Gly Pro Lys Ser Trp Ala Leu Glu Arg Arg
                325                 330                 335

Glu Leu Asp Pro Ser Trp Ser Gly Arg His Arg Ser Ser Arg Leu Asn
            340                 345                 350

Gly Ser Pro Ile His Trp Ser Asp Arg Asp Ser Leu Ser Asp Val Pro
        355                 360                 365

Ser Ser Ser Glu Ala Arg Trp Arg Pro Ser His Pro Pro Phe Arg Ser
    370                 375                 380

Arg Cys Gln Glu Arg Pro Arg Arg Pro Ser Pro Arg Glu Ser Thr Gln
385                 390                 395                 400

Arg His Gly Arg Arg Arg Arg His Arg Ser Tyr Ser Pro Pro Leu Pro
                405                 410                 415

Ser Gly Leu Ser Ser Trp Ser Ser Glu Glu Asp Lys Glu Arg Gln Pro
            420                 425                 430

Gln Ser Trp Arg Ala His Arg Arg Gly Ser His Ser Pro His Trp Pro
        435                 440                 445

Glu Glu Lys Pro Pro Ser Tyr Arg Ser Leu Asp Ile Thr Pro Gly Lys
    450                 455                 460

Asn Ser Arg Lys Lys Gly Ser Val Glu Arg Arg Ser Glu Lys Asp Ser
465                 470                 475                 480

Ser His Ser Gly Arg Ser Val Val Ile
                485


<210> SEQ ID NO 25
<211> LENGTH: 2148
<212> TYPE: DNA
<213> ORGANISM: Homo sapiens

<400> SEQUENCE: 25

acctcactgc taatttccct agcaaataaa ccagcagctg ctggtccaag ttaccactga     60

gaacagggca ctgcatgcat gggacaggat gctttcatgg agcccttcgg tgacacactt    120

ggggtctttc agtgcaaaat atacctcctt ctcttcggtg cttgctcggg gctgaaggtg    180

acagtgccat cacacactgt ccatggcgtc agaggtcagg ccctctacct acccgtccac    240

tatggcttcc acactccagc atcagacatc cagatcatat ggctatttga gagaccccac    300

acaatgccca aatacttact gggctctgtg aataagtctg tggttcctga cttggaatac    360

caacacaagt tcaccatgat gccacccaat gcatctctgc ttatcaaccc actgcagttc    420

cctgatgaag gcaattacat cgtgaaggtc aacattcagg gaaatggaac tctatctgcc    480

agtcagaaga tacaagtcac ggttgatgat cctgtcacaa agccagtggt gcagattcat    540

cctccctctg ggctgtgga gtatgtgggg aacatgaccc tgacatgcca tgtggaaggg     600

ggcactcggc tagcttacca atggctaaaa aatgggagac ctgtccacac cagctccacc    660

tactcctttt ctccccaaaa caatacctt catattgctc cagtaaccaa ggaagacatt     720

gggaattaca gctgcctggt gaggaaccct gtcagtgaaa tggaaagtga tatcattatg    780

cccatcatat attatggacc ttatggactt caagtgaatt ctgataaagg gctaaaagta    840

ggggaagtgt ttactgttga ccttggagag gccatcctat ttgattgttc tgctgattct    900

catcccccca acacctactc ctggattagg aggactgaca atactacata tatcattaag    960

catgggcctc gcttagaagt tgcatctgag aaagtagccc agaagacaat ggactatgtg   1020

tgctgtgctt acaacaacat aaccggcagg caagatgaaa ctcatttcac agttatcatc   1080
```

-continued acttccgtag gactggagaa gcttgcacag aaaggaaaat cattgtcacc tttagcaagt 1140
ataactggaa tatcactatt tttgattata tccatgtgtc ttctcttcct atggaaaaaa 1200
tatcaaccct acaaagttat aaaacagaaa ctagaaggca ggccagaaac agaatacagg 1260
aaagctcaaa cattttcagg ccatgaagat gctctggatg acttcggaat atatgaattt 1320
gttgcttttc cagatgtttc tggtgtttcc aggatcccaa gcaggtctgt tccagcctct 1380
gattgtgtat cggggcaaga tttgcacagt acagtgtatg aagttattca gcacatccct 1440
gcccagcagc aagaccatcc agagtgaact ttcatgggct aaacagtaca ttcgagtgaa 1500
attctgaaga aacattttaa ggaaaaacag tggaaaagta tattaatctg gaatcagtga 1560
agaaaccaag accaacacct cttactcatt attcctttac atgcagaata gaggcattta 1620
tgcaaattga actgcaggtt tttcagcata tacacaatgt cttgtgcaac agaaaaacat 1680
gttggggaaa tattcctcag tggagagtcg ttctcatgct gacggggaga acgaaagtga 1740
caggggtttc ctcgtaagtt ttgtatgaaa tatctctaca aacctcaatt agttctactc 1800
tacactttca ctatcatcaa cactgagact atcctgtctc acctacaaat gtggaaactt 1860
tacattgttc gatttttcag cagactttgt tttattaaat ttttattagt gttaagaatg 1920
ctaaatttat gtttcaattt tatttccaaa tttctatctt gttatttgta caacaaagta 1980
ataaggatgg ttgtcacaaa aacaaaacta tgccttctct ttttttcaa tcaccagtag 2040 tatttttgag aagacttgtg aacacttaag gaaatgacta ttaaagtctt atttttattt 2100
ttttcaagga aagatggatt caaataaatt attctgtttt tgcttttta 2148

<210> SEQ ID NO 26
<211> LENGTH: 2135
<212> TYPE: DNA
<213> ORGANISM: Homo sapiens

<400> SEQUENCE: 26
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttccaca 240
ctccagcatc agacatccag atcatatggc tatttgagag accccacaca atgcccaaat 300
acttactggg ctctgtgaat aagtctgtgg ttcctgactt ggaataccaa cacaagttca 360
ccatgatgcc acccaatgca tctctgctta tcaacccact gcagttccct gatgaaggca 420
attacatcgt gaaggtcaac attcagggaa atggaactct atctgccagt cagaagatac 480
aagtcacggt tgatgatcct gtcacaaagc cagtggtgca gattcatcct ccctctgggg 540
ctgtggagta tgtggggaac atgaccctga catgccatgt ggaagggggc actcggctag 600
cttaccaatg gctaaaaaat gggagacctg tccacaccag ctccacctac tccttttctc 660
cccaaaacaa taccettcat attgctccag taaccaagga agacattggg aattacagct 720
gcctggtgag gaaccctgtc agtgaaatgg aaagtgatat cattatgccc atcatatatt 780
atggacctta tggacttcaa gtgaattctg ataaagggct aaaagtaggg gaagtgttta 840
ctgttgacct tggagaggcc atcctatttg attgttctgc tgattctcat cccccccaaca 900 cctactcctg gattaggagg actgacaata ctacatatat cattaagcat gggcctcgct 960
tagaagttgc atctgagaaa gtagcccaga agacaatgga ctatgtgtgc tgtgcttaca 1020
acaacataac cggcaggcaa gatgaaactc atttcacagt tatcatcact tccgtaggac 1080
tggagaagct tgcacagaaa ggaaaatcat tgtcaccttt agcaagtata actggaatat 1140
cactattttt gattatatcc atgtgtcttc tcttcctatg gaaaaaatat caaccctaca 1200
aagttataaa acagaaacta gaaggcaggc cagaaacaga atacaggaaa gctcaaacat 1260
tttcaggcca tgaagatgct ctggatgact tcggaatata tgaatttgtt gcttttccag 1320
atgtttctgg tgtttccagg atcccaagca ggtctgttcc agcctctgat tgtgtatcgg 1380
ggcaagattt gcacagtaca gtgtatgaag ttattcagca catccctgcc cagcagcaag 1440
accatccaga gtgaactttc atgggctaaa cagtacattc gagtgaaatt ctgaagaaac 1500
attttaagga aaaacagtgg aaaagtatat taatctggaa tcagtgaaga aaccaagacc 1560
aacacctctt actcattatt cctttacatg cagaatagag gcatttatgc aaattgaact 1620
gcaggttttt cagcatatac acaatgtctt gtgcaacaga aaaacatgtt ggggaaatat 1680
tcctcagtgg agagtcgttc tcatgctgac ggggagaacg aaagtgacag gggtttcctc 1740
gtaagttttg tatgaaatat ctctacaaac ctcaattagt tctactctac actttcacta 1800
tcatcaacac tgagactatc ctgtctcacc tacaaatgtg gaaactttac attgttcgat 1860
ttttcagcag actttgtttt attaaatttt tattagtgtt aagaatgcta aatttatgtt 1920
tcaattttat ttccaaattt ctatcttgtt atttgtacaa caaagtaata aggatggttg 1980
tcacaaaaac aaaactatgc cttctctttt ttttcaatca ccagtagtat ttttgagaag 2040
acttgtgaac acttaaggaa atgactatta aagtcttatt tttatttttt tcaaggaaag 2100
atggattcaa ataaattatt ctgtttttgc tttta 2135

<210> SEQ ID NO 27
<211> LENGTH: 2109
<212> TYPE: DNA
<213> ORGANISM: Homo sapiens

<400> SEQUENCE: 27
acctcactgc taatttccct agcaaataaa ccagcagctg ctggtccaag ttaccactga 60
gaacagggca ctgcatgcat gggacaggat gctttcatgg agcccttcgg tgacacactt 120
ggggtctttc agtgcaaaat atacctcctt ctcttcggtg cttgctcggg gctgaaggtg 180
acagtgccat cacacactgt ccatggcgtc agaggtcagg ccctctacct acccgtccac 240
tatggcttcc acactccagc atcagacatc cagatcatat ggctatttga gagaccccac 300
acaatgccca aatacttact gggctctgtg aataagtctg tggttcctga cttggaatac 360
caacacaagt tcaccatgat gccacccaat gcatctctgc ttatcaaccc actgcagttc 420
cctgatgaag gcaattacat cgtgaaggtc aacattcagg gaaatggaac tctatctgcc 480
agtcagaaga tacaagtcac ggttgatgat cctgtcacaa agccagtggt gcagattcat 540
cctccctctg ggctgtggag gtatgtgggg aacatgaccc tgacatgcca tgtggaaggg 600
ggcactcggc tagcttacca atggctaaaa aatgggagac ctgtccacac cagctccacc 660
tactcctttt ctccccaaaa caatacccttt catattgctc cagtaaccaa ggaagacatt 720
gggaattaca gctgcctggt gaggaaccct gtcagtgaaa tggaaagtga tatcattatg 780
cccatcatat attatggacc ttatggactt caagtgaatt ctgataaagg gctaaaagta 840
ggggaagtgt ttactgttga ccttggagag gccatcctat ttgattgttc tgctgattct 900
catcccccca acacctactc ctggattagg aggactgaca atactacata tatcattaag 960
catgggcctc gcttagaagt tgcatctgag aaagtagccc agaagacaat ggactatgtg 1020
tgctgtgctt acaacaacat aaccggcagg caagatgaaa ctcatttcac agttatcatc 1080
acttccgtag gactggagaa gcttgcacag aaaggaaaat cattgtcacc tttagcaagt 1140
ataactggaa tatcactatt tttgattata tccatgtgtc ttctcttcct atggaaaaaa 1200
tatcaaccct acaaagttat aaaacagaaa ctagaaggca ggccagaaac agaatacagg 1260
aaagctcaaa cattttcagg ccatgaagat gctctggatg acttcggaat atatgaattt 1320
gttgcttttc cagatgtttc tggtgtttcc aggatcccaa gcaggtctgt tccagcctct 1380
gattgtgtat cggggcaaga tttgcacagt acagtgtatg aagttattca gcacatccct 1440
gcccagcagc aagaccatcc agagtgaact ttcatgggct aaacagtaca ttcgagtgaa 1500
attctgaaga aacattttaa ggaaaaacag tggaaaagta tattaatctg gaatcagtga 1560
agaaaccaag accaacacct cttactcatt attcctttac atgcagaata gaggcattta 1620
tgcaaattga actgcaggtt tttcagcata tacacaatgt cttgtgcaac agaaaaacat 1680
gttggggaaa tattcctcag tggagagtcg ttctcatgct gacggggaga acgaaagtga 1740
caggggtttc ctcgtaagtt ttgtatgaaa tatctctaca aacctcaatt agttctactc 1800
tacactttca ctatcatcaa cactgagact atcctgtctc acctacaaat gtggaaactt 1860
tacattgttc gatttttcag cagactttgt tttattaaat ttttattagt gttaagaatg 1920
ctaaatttat gtttcaattt tatttccaaa tttctatctt gttatttgta caacaaagta 1980
ataaggatgg ttgtcacaaa aacaaaacta tgccttctct ttttttcaa tcaccagtag 2040 tatttttgag aagacttgtg aacacttaag gaaatgacta ttaaagtctt atttttattt 2100
ttttcaagg 2109

<210> SEQ ID NO 28
<211> LENGTH: 2110
<212> TYPE: DNA
<213> ORGANISM: Homo sapiens

<400> SEQUENCE: 28
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttcccaca 240 ctccagcatc agacatccag atcatatggc tatttgagag accccacaca atgcccaaat 300
acttactggg ctctgtgaat aagtctgtgg ttcctgactt ggaataccaa cacaagttca 360
ccatgatgcc acccaatgca tctctgctta tcaacccact gcagttccct gatgaaggca 420
attacatcgt gaaggtcaac attcagggaa atggaactct atctgccagt cagaagatac 480
aagtcacggt tgatgatcct gtcacaaagc cagtggtgca gattcatcct ccctctgggg 540
ctgtggagta tgtggggaac atgaccctga catgccatgt ggaaggggggc actcggctag 600 cttaccaatg gctaaaaaat gggagacctg tccacaccag ctccacctac tcctttctc 660 cccaaaacaa taccccttcat attgctccag taaccaagga agacattggg aattacagct 720
gcctggtgag gaaccctgtc agtgaaatgg aaagtgatat cattatgccc atcatatatt 780
atggacctta tggacttcaa gtgaattctg ataaagggct aaaagtaggg gaagtgttta 840
ctgttgacct tggagaggcc atcctatttg attgttctgc tgattctcat ccccccaaca 900
cctactcctg gattaggagg actgacaata ctacatatat cattaagcat gggcctcgct 960
tagaagttgc atctgagaaa gtagcccaga agacaatgga ctatgtgtgc tgtgcttaca 1020
acaacataac cggcaggcaa gatgaaactc atttcacagt tatcatcact tccgtaggac 1080
tggagaagct tgcacagaaa ggaaaatcat tgtcaccttt agcaagtata actggaatat 1140
cactattttt gattatatcc atgtgtcttc tcttcctatg gaaaaaatat caaccctaca 1200
aaggccagaa acagaataca ggaaagctca aacattttca ggccatgaag atgctctgga 1260
tgacttcgga atatatgaat ttgttgcttt tccagatgtt tctggtgttt ccaggatccc 1320
aagcaggtct gttccagcct ctgattgtgt atcggggcaa gatttgcaca gtacagtgta 1380
tgaagttatt cagcacatcc ctgcccagca gcaagaccat ccagagtgaa ctttcatggg 1440
ctaaacagta cattcgagtg aaattctgaa gaaacatttt aaggaaaaac agtggaaaag 1500
tatattaatc tggaatcagt gaagaaacca agaccaacac ctcttactca ttattccttt 1560
acatgcagaa tagaggcatt tatgcaaatt gaactgcagg tttttcagca tatacacaat 1620
gtcttgtgca acagaaaaac atgttgggga aatattcctc agtggagagt cgttctcatg 1680
ctgacgggga gaacgaaagt gacaggggtt tcctcgtaag ttttgtatga aatatctcta 1740
caaacctcaa ttagttctac tctacacttt cactatcatc aacactgaga ctatcctgtc 1800
tcacctacaa atgtggaaac tttacattgt tcgatttttc agcagacttt gttttattaa 1860
atttttatta gtgttaagaa tgctaaattt atgtttcaat tttatttcca aatttctatc 1920
ttgttatttg tacaacaaag taataaggat ggttgtcaca aaaacaaaac tatgccttct 1980 ctttttttc aatcaccagt agtatttttg agaagacttg tgaacactta aggaaatgac 2040
tattaaagtc ttatttttat ttttttcaag gaaagatgga ttcaaataaa ttattctgtt 2100
tttgctttta 2110

<210> SEQ ID NO 29
<211> LENGTH: 2189
<212> TYPE: DNA
<213> ORGANISM: Homo sapiens

<400> SEQUENCE: 29
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttccaca 240
ctccagcatc agacatccag atcatatggc tatttgagag accccacaca atgcccaaat 300
acttactggg ctctgtgaat aagtctgtgg ttcctgactt ggaataccaa cacaagttca 360
ccatgatgcc acccaatgca tctctgctta tcaacccact gcagttccct gatgaaggca 420
attacatcgt gaaggtcaac attcagggaa atggaactct atctgccagt cagaagatac 480
aagtcacggt tgatgatcct gtcacaaagc cagtggtgca gattcatcct ccctctgggg 540
ctgtggagta tgtggggaac atgaccctga catgccatgt ggaagggggc actcggctag 600
cttaccaatg gctaaaaaat gggagacctg tccacaccag ctccacctac tccttttctc 660
cccaaaacaa tacccttcat attgctccag taaccaagga agacattggg aattacagct 720
gcctggtgag gaaccctgtc agtgaaatgg aaagtgatat cattatgccc atcatatatt 780
atggacctta tggacttcaa gtgaattctg ataaagggct aaaagtaggg gaagtgttta 840
ctgttgacct tggagaggcc atcctatttg attgttctgc tgattctcat ccccccaaca 900
cctactcctg gattaggagg actgacaata ctacatatat cattaagcat gggcctcgct 960

```
tagaagttgc atctgagaaa gtagcccaga agacaatgga ctatgtgtgc tgtgcttaca   1020
acaacataac cggcaggcaa gatgaaactc atttcacagt tatcatcact tccgtaggac   1080
tggagaagct tgcacagaaa ggaaaatcat tgtcaccttt agcaagtata actggaatat   1140
cactattttt gattatatcc atgtgtcttc tcttcctatg gaaaaaatat caaccctaca   1200
aagttataaa acagaaacta gaaggcaggc cagaaacaga atacaggaaa gctcaaacat   1260
tttcaggcca tgaagatgct ctggatgact tcggaatata tgaatttgtt gcttttccag   1320
atgtttctgg tgtttccagg gttggttttc ctagtggctg attaaccgag aagtagaatt   1380
ctgcttcacc agagatccca agcaggtctg ttccagcctc tgattgtgta tcggggcaag   1440
atttgcacag tacagtgtat gaagttattc agcacatccc tgcccagcag caagaccatc   1500
cagagtgaac tttcatgggc taaacagtac attcgagtga aattctgaag aaacatttta   1560
aggaaaaaca gtggaaaagt atattaatct ggaatcagtg aagaaaccaa gaccaacacc   1620
tcttactcat tattccttta catgcagaat agaggcattt atgcaaattg aactgcaggt   1680
ttttcagcat atacacaatg tcttgtgcaa cagaaaaaca tgttggggaa atattcctca   1740
gtggagagtc gttctcatgc tgacggggag aacgaaagtg acaggggttt cctcgtaagt   1800
tttgtatgaa atatctctac aaacctcaat tagttctact ctacactttc actatcatca   1860
acactgagac tatcctgtct cacctacaaa tgtggaaact ttacattgtt cgatttttca   1920
gcagactttg ttttattaaa tttttattag tgttaagaat gctaaattta tgtttcaatt   1980
ttatttccaa atttctatct tgttatttgt acaacaaagt aataaggatg gttgtcacaa   2040
aaacaaaact atgccttctc tttttttca atcaccagta gtatttttga gaagacttgt   2100
gaacacttaa ggaaatgact attaaagtct tatttttatt tttttcaagg aaagatggat   2160
tcaaataaat tattctgttt ttgcttttta                                    2189
```

<210> SEQ ID NO 30
<211> LENGTH: 2191
<212> TYPE: DNA
<213> ORGANISM: Homo sapiens

<400> SEQUENCE: 30

```
gtaaccagta ctagaatagt cagtacctag aagccactct tctttgaaaa ggattatcac     60
ctgatcaggt tctctctgca tttgcccctt tagattgtga aatgtggctc aaggtcttca    120
caactttcct ttcctttgca acaggtgctt gctcggggct gaaggtgaca gtgccatcac    180
acactgtcca tggcgtcaga ggtcaggccc tctacctacc cgtccactat ggcttccaca    240
ctccagcatc agacatccag atcatatggc tatttgagag accccacaca atgcccaaat    300
acttactggg ctctgtgaat aagtctgtgg ttcctgactt ggaataccaa cacaagttca    360
ccatgatgcc acccaatgca tctctgctta tcaacccact gcagttccct gatgaaggca    420
attacatcgt gaaggtcaac attcagggaa atggaactct atctgccagt cagaagatac    480
aagtcacggt tgatgatcct gtcacaaagc cagtggtgca gattcatcct ccctctgggg    540
ctgtggagta tgtggggaac atgaccctga catgccatgt ggaagggggc actcggctag    600
cttaccaatg gctaaaaaat gggagacctg tccacaccag ctccacctac tccttttctc    660
cccaaaacaa tacccttcat attgctccag taaccaagga agacattggg aattacagct    720
gcctggtgag gaaccctgtc agtgaaatgg aaagtgatat cattatgccc atcatatatt    780
atggacctta tggacttcaa gtgaattctg ataaagggct aaaagtaggg gaagtgttta    840
ctgttgacct tggagaggcc atcctatttg attgttctgc tgattctcat ccccccaaca    900
```

cctactcctg gattaggagg actgacaata ctacatatat cattaagcat gggcctcgct 960
tagaagttgc atctgagaaa gtagcccaga agacaatgga ctatgtgtgc tgtgcttaca 1020
acaacataac cggcaggcaa gatgaaactc atttcacagt tatcatcact tccgtaggac 1080
tggagaagct tgcacagaaa ggaaaatcat tgtcaccttt agcaagtata actggaatat 1140
cactattttt gattatatcc atgtgtcttc tcttcctatg gaaaaaatat caaccctaca 1200
aagttataaa acagaaacta gaaggcaggc cagaaacaga atacaggaaa gctcaaacat 1260
tttcaggcca tgaagatgct ctggatgact tcggaatata tgaatttgtt gcttttccag 1320
atgtttctgg tgtttccagg gttggttttc ctagtggctg attaaccgag aagtagaatt 1380
ctgcttcacc agaggtatcc caagcaggtc tgttccagcc tctgattgtg tatcggggca 1440
agatttgcac agtacagtgt atgaagttat tcagcacatc cctgcccagc agcaagacca 1500
tccagagtga actttcatgg gctaaacagt acattcgagt gaaattctga agaaacattt 1560
taaggaaaaa cagtggaaaa gtatattaat ctggaatcag tgaagaaacc aagaccaaca 1620
cctcttactc attattcctt tacatgcaga atagaggcat ttatgcaaat tgaactgcag 1680
gtttttcagc atatacacaa tgtcttgtgc aacagaaaaa catgttgggg aaatattcct 1740
cagtggagag tcgttctcat gctgacgggg agaacgaaag tgacaggggt ttcctcgtaa 1800
gttttgtatg aaatatctct acaaacctca attagttcta ctctacactt tcactatcat 1860
caacactgag actatcctgt ctcacctaca aatgtggaaa ctttacattg ttcgattttt 1920
cagcagactt tgttttatta aatttttatt agtgttaaga atgctaaatt tatgtttcaa 1980
ttttatttcc aaatttctat cttgttattt gtacaacaaa gtaataagga tggttgtcac 2040
aaaaacaaaa ctatgccttc tcttttttt caatcaccag tagtattttt gagaagactt 2100
gtgaacactt aaggaaatga ctattaaagt cttattttta tttttttcaa ggaaagatgg 2160
attcaaataa attattctgt ttttgctttt a 2191

<210> SEQ ID NO 31
<211> LENGTH: 2229
<212> TYPE: DNA
<213> ORGANISM: Homo sapiens

<400> SEQUENCE: 31
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttccaca 240
ctccagcatc agacatccag atcatatggc tatttgagag accccacaca atgcccaaat 300
acttactggg ctctgtgaat aagtctgtgg ttcctgactt ggaataccaa cacaagttca 360
ccatgatgcc acccaatgca tctctgctta tcaacccact gcagttccct gatgaaggca 420
attacatcgt gaaggtcaac attcagggaa atggaactct atctgccagt cagaagatac 480
aagtcacggt tgatgatcct gtcacaaagc cagtggtgca gattcatcct ccctctgggg 540
ctgtggagta tgtggggaac atgaccctga catgccatgt ggaagggggc actcggctag 600
cttaccaatg gctaaaaaat gggagacctg tccacaccag ctccacctac tccttttctc 660
cccaaaacaa tacccttcat attgctccag taaccaagga agacattggg aattacagct 720
gcctggtgag gaaccctgtc agtgaaatgg aaagtgatat cattatgccc atcatatatt 780

-continued atggacctta tggacttcaa gtgaattctg ataaagggct aaaagtaggg gaagtgttta 840
ctgttgacct tggagaggcc atcctatttg attgttctgc tgattctcat ccccccaaca 900
cctactcctg gattaggagg actgacaata ctacatatat cattaagcat gggcctcgct 960
tagaagttgc atctgagaaa gtagcccaga agacaatgga ctatgtgtgc tgtgcttaca 1020
acaacataac cggcaggcaa gatgaaactc atttcacagt tatcatcact tccgtaggac 1080
tggagaagct tgcacagaaa ggaaaatcat tgtcaccttt agcaagtata actggaatat 1140
cactattttt gattatatcc atgtgtcttc tcttcctatg gaaaaaatat caaccctaca 1200
aagttataaa acagaaacta gaaggcaggt aatgcatctg tttctatgaa aatagttgtt 1260
ttccttagat gcttattcct caattattat ccctgacaaa aatacctatt ttgtcttttc 1320
aggccagaaa cagaatacag gaaagctcaa acattttcag gccatgaaga tgctctggat 1380
gacttcggaa tatatgaatt tgttgctttt ccagatgttt ctggtgtttc caggatccca 1440
agcaggtctg ttccagcctc tgattgtgta tcggggcaag atttgcacag tacagtgtat 1500
gaagttattc agcacatccc tgcccagcag caagaccatc cagagtgaac tttcatgggc 1560
taaacagtac attcgagtga aattctgaag aaacatttta aggaaaaaca gtggaaaagt 1620
atattaatct ggaatcagtg aagaaaccaa gaccaacacc tcttactcat tattccttta 1680
catgcagaat agaggcattt atgcaaattg aactgcaggt ttttcagcat atacacaatg 1740
tcttgtgcaa cagaaaaaca tgttggggaa atattcctca gtggagagtc gttctcatgc 1800
tgacggggag aacgaaagtg acaggggttt cctcgtaagt tttgtatgaa atatctctac 1860
aaacctcaat tagttctact ctacactttc actatcatca acactgagac tatcctgtct 1920
cacctacaaa tgtggaaact ttacattgtt cgatttttca gcagactttg ttttattaaa 1980
tttttattag tgttaagaat gctaaattta tgtttcaatt ttatttccaa atttctatct 2040
tgttatttgt acaacaaagt aataaggatg gttgtcacaa aaacaaaact atgccttctc 2100 tttttttca atcaccagta gtatttttga gaagacttgt gaacacttaa ggaaatgact 2160
attaaagtct tatttttatt tttttcaagg aaagatggat tcaaataaat tattctgttt 2220
ttgcttta 2229

<210> SEQ ID NO 32
<211> LENGTH: 2229
<212> TYPE: DNA
<213> ORGANISM: Homo sapiens

<400> SEQUENCE: 32
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttccaca 240
ctccagcatc agacatccag atcatatggc tatttgagag accccacaca atgcccaaat 300
acttactggg ctctgtgaat aagtctgtgg ttcctgactt ggaataccaa cacaagttca 360
ccatgatgcc acccaatgca tctctgctta tcaacccact gcagttccct gatgaaggca 420
attacatcgt gaaggtcaac attcagggaa atggaactct atctgccagt cagaagatac 480
aagtcacggt tgatgatcct gtcacaaagc cagtggtgca gattcatcct ccctctgggg 540
ctgtggagta tgtggggaac atgaccctga catgccatgt ggaagggggc actcggctag 600
cttaccaatg gctaaaaaat gggagacctg tccacaccag ctccacctac tccttttctc 660

```
cccaaaacaa taccottcat attgctccag taaccaagga agacattggg aattacagct    720
gcctggtgag gaaccctgtc agtgaaatgg aaagtgatat cattatgccc atcatatatt    780
atggacctta tggacttcaa gtgaattctg ataaagggct aaaagtaggg gaagtgttta    840
ctgttgacct tggagaggcc atcctatttg attgttctgc tgattctcat ccccccaaca    900
cctactcctg gattaggagg actgacaata ctacatatat cattaagcat gggcctcgct    960
tagaagttgc atctgagaaa gtagcccaga agacaatgga ctatgtgtgc tgtgcttaca   1020
acaacataac cggcaggcaa gatgaaactc atttcacagt tatcatcact tccgtaggac   1080
tggagaagct tgcacagaaa ggaaaatcat tgtcaccttt agcaagtata actggaatat   1140
cactattttt gattatatcc atgtgtcttc tcttcctatg gaaaaaatat caaccctaca   1200
aagttataaa acagaaacta gaaggcaggc cagaaacaga atacaggaaa gctcaaacat   1260
tttcaggcca tgaagatgct ctggatgact tcggaatata tgaatttgtt gcttttccag   1320
atgtttctgg tgtttccagg gttggttttc ctagtggctg attaaccgag aagtagaatt   1380
ctgcttcacc agaggtgtaa aaagcatttg tttaagcact gggcagtgtg gtcaaatggc   1440
tgcattaccc attactgcat taagcagtgt tgacttactc cgtaatgaat ggcattgcca   1500
gatttgggaa gctaaagcat cttacttcgc ctttataagt aaagctaaca caaataagga   1560
agttatgcta attcataaat agtctttacc tggtaatctc agtgaagaga gaactaacta   1620
ggttgaaagt caagagaact gaataaacaa gctgggcgtg gtggctcaca tctgtattcc   1680
tagggctttg ggaggctgag atggaaagat cacttgagcc caggagtttg agatcagcct   1740
gggcaaagac cccatcccaa caaatattta aaaattagcc aagcatggtt atgcatgcct   1800
ctggtcccag cttcttggga gaccgaggca ggaggatcat tgagcccagg agttcaaggc   1860
tacagtgagc cgtgatcaca ctaccgcact ccagcctggg cagcagagta agaccctgtc   1920
tcaaataaat aaatactgaa taaacagcgg atcaggagac cctaatttaa gtcattctgc   1980
atcacttggg tgactgcaac ccatcacttt actaaactct ctctgttcct cagttttccc   2040
tttattgccc cctcatatct tttgacaaca ttgcaaagac aattgatcac acccttgaag   2100
atacctcatg cttcaggagg aagttaccat ataggcccaa agtatgcaag tatacatctt   2160
tattattgcc ctaaaggtgc atgagatggc aaaggagctt tcatatagtt gaagtcattt   2220
cagtccgga                                                           2229
```

<210> SEQ ID NO 33
<211> LENGTH: 2323
<212> TYPE: DNA
<213> ORGANISM: Homo sapiens

<400> SEQUENCE: 33

```
gtaaccagta ctagaatagt cagtacctag aagccactct tctttgaaaa ggattatcac     60
ctgatcaggt tctctctgca tttgcccctt tagattgtga aatgtggctc aaggtcttca    120
caactttcct ttcctttgca acaggtgctt gctcggggct gaaggtgaca gtgccatcac    180
acactgtcca tggcgtcaga ggtcaggccc tctacctacc cgtccactat ggcttccaca    240
ctccagcatc agacatccag atcatatggc tatttgagag accccacaca atgcccaaat    300
acttactggg ctctgtgaat aagtctgtgg ttcctgactt ggaataccaa cacaagttca    360
ccatgatgcc acccaatgca tctctgctta tcaacccact gcagttccct gatgaaggca    420
attacatcgt gaaggtcaac attcagggaa atggaactct atctgccagt cagaagatac    480
```

-continued aagtcacggt tgatgatcct gtcacaaagc cagtggtgca gattcatcct ccctctgggg 540
ctgtggagta tgtggggaac atgaccctga catgccatgt ggaagggggc actcggctag 600
cttaccaatg gctaaaaaat gggagacctg tccacaccag ctccacctac tccttttctc 660
cccaaaacaa tacccttcat attgctccag taaccaagga agacattggg aattacagct 720
gcctggtgag gaaccctgtc agtgaaatgg aaagtgatat cattatgccc atcatatatt 780
atggacctta tggacttcaa gtgaattctg ataaagggct aaaagtaggg gaagtgttta 840
ctgttgacct tggagaggcc atcctatttg attgttctgc tgattctcat ccccccaaca 900
cctactcctg gattaggagg actgacaata ctacatatat cattaagcat gggcctcgct 960
tagaagttgc atctgagaaa gtagcccaga agacaatgga ctatgtgtgc tgtgcttaca 1020
acaacataac cggcaggcaa gatgaaactc atttcacagt tatcatcact tccgtaggac 1080
tggagaagct tgcacagaaa ggaaaatcat tgtcaccttt agcaagtata actggaatat 1140
cactattttt gattatatcc atgtgtcttc tcttcctatg gaaaaaatat caaccctaca 1200
aagttataaa acagaaacta gaaggcaggt aatgcatctg tttctatgaa aatagttgtt 1260
ttccttagat gcttattcct caattattat ccctgacaaa aatacctatt ttgtcttttc 1320
aggccagaaa cagaatacag gaaagctcaa acattttcag gccatgaaga tgctctggat 1380
gacttcggaa tatatgaatt tgttgctttt ccagatgttt ctggtgtttc cagggttggt 1440
tttcctagtg gctgattaac cgagaagtag aattctgctt caccagaggt gtaaaaagca 1500
tttgtttaag cactgggcag tgtggtcaaa tggctgcatt acccattact gcattaagca 1560
gtgttgactt actccgtaat gaatggcatt gccagatttg ggaagctaaa gcatcttact 1620
tcgcctttat aagtaaagct aacacaaata aggaagttat gctaattcat aaatagtctt 1680
tacctggtaa tctcagtgaa gagagaacta actaggttga aagtcaagag aactgaataa 1740
acaagctggg cgtggtggct cacatctgta ttcctagggc tttgggaggc tgagatggaa 1800
agatcacttg agcccaggag tttgagatca gcctgggcaa agaccccatc ccaacaaata 1860
tttaaaaatt agccaagcat ggttatgcat gcctctggtc ccagcttctt gggagaccga 1920
ggcaggagga tcattgagcc caggagttca aggctacagt gagccgtgat cacactaccg 1980
cactccagcc tgggcagcag agtaagaccc tgtctcaaat aaataaatac tgaataaaca 2040
gcggatcagg agaccctaat ttaagtcatt ctgcatcact tgggtgactg caacccatca 2100
ctttactaaa ctctctctgt tcctcagttt tccctttatt gccccctcat atcttttgac 2160
aacattgcaa agacaattga tcacaccctt gaagatacct catgcttcag gaggaagtta 2220
ccatataggc ccaaagtatg caagtataca tctttattat tgccctaaag gtgcatgaga 2280
tggcaaagga gctttcatat agttgaagtc atttcagtcc gga 2323

<210> SEQ ID NO 34
<211> LENGTH: 1578
<212> TYPE: DNA
<213> ORGANISM: Homo sapiens

<400> SEQUENCE: 34
gtaaccagta ctagaatagt cagtacctag aagccactct tctttgaaaa ggattatcac 60
ctgatcaggt tctctctgca tttgcccctt tagattgtga aatgtggctc aaggtcttca 120
caactttcct ttcctttgca acaggtgctt gctcggggct gaaggtgaca gtgccatcac 180
acactgtcca tggcgtcaga ggtcaggccc tctacctacc cgtccactat ggcttccaca 240
ctccagcatc agacatccag atcatatggc tatttgagag accccacaca atgcccaaat 300

```
acttactggg ctctgtgaat aagtctgtgg ttcctgactt ggaataccaa cacaagttca    360

ccatgatgcc acccaatgca tctctgctta tcaacccact gcagttccct gatgaaggca    420

attacatcgt gaaggtcaac attcagggaa atggaactct atctgccagt cagaagatac    480

aagtcacggt tgatgatcct gtcacaaagc cagtggtgca gattcatcct ccctctgggg    540

ctgtggagta tgtggggaac atgaccctga catgccatgt ggaagggggc actcggctag    600

cttaccaatg gctaaaaaat gggagacctg tccacaccag ctccacctac tccttttctc    660

cccaaaacaa tacccttcat attgctccag taaccaagga agacattggg aattacagct    720

gcctggtgag gaaccctgtc agtgaaatgg aaagtgatat cattatgccc atcatatatt    780

atggacctta tggacttcaa gtgaattctg ataaagggct aaaagtaggg gaagtgttta    840

ctgttgacct tggagaggcc atcctatttg attgttctgc tgattctcat ccccccaaca    900

cctactcctg gattaggagg actgacaata ctacatatat cattaagcat gggcctcgct    960

tagaagttgc atctgagaaa gtagcccaga agacaatgga ctatgtgtgc tgtgcttaca   1020

acaacataac cggcaggcaa gatgaaactc atttcacagt tatcatcact tccgtaggac   1080

tggagaagct tgcacagaaa ggaaaatcat tgtcaccttt agcaagtata actggaatat   1140

cactattttt gattatatcc atgtgtcttc tcttcctatg gaaaaaatat caaccctaca   1200

aagttataaa acagaaacta gaaggcaggc cagaaacaga atacaggaaa gctcaaacat   1260

tttcaggttt catgctggca gctccatccc aaagagaaga ggaaaagaag atttggcagg   1320

ggccaggatt gcttctttgt ccccactgta accctcatta tcatcaatat tgactgtact   1380

gacttattat aagttaacaa agttttggct caggccacaa aatcacaggg agccaagttt   1440

cagttttatt tcccctcatg tcaccttagg aaaattattt ttcttaaccg caacttcctc   1500

ttctatataa tagggataaa aacttccccc ttaaggttgc tatgagaatt aaataaaatg   1560

atataggtgg agtgcctg                                                 1578
```

<210> SEQ ID NO 35
<211> LENGTH: 462
<212> TYPE: PRT
<213> ORGANISM: Homo sapiens

<400> SEQUENCE: 35

```
Met Gly Gln Asp Ala Phe Met Glu Pro Phe Gly Asp Thr Leu Gly Val
1               5                   10                  15

Phe Gln Cys Lys Ile Tyr Leu Leu Leu Phe Gly Ala Cys Ser Gly Leu
            20                  25                  30

Lys Val Thr Val Pro Ser His Thr Val His Gly Val Arg Gly Gln Ala
        35                  40                  45

Leu Tyr Leu Pro Val His Tyr Gly Phe His Thr Pro Ala Ser Asp Ile
    50                  55                  60

Gln Ile Ile Trp Leu Phe Glu Arg Pro His Thr Met Pro Lys Tyr Leu
65                  70                  75                  80

Leu Gly Ser Val Asn Lys Ser Val Val Pro Asp Leu Glu Tyr Gln His
                85                  90                  95

Lys Phe Thr Met Met Pro Pro Asn Ala Ser Leu Leu Ile Asn Pro Leu
            100                 105                 110

Gln Phe Pro Asp Glu Gly Asn Tyr Ile Val Lys Val Asn Ile Gln Gly
        115                 120                 125

Asn Gly Thr Leu Ser Ala Ser Gln Lys Ile Gln Val Thr Val Asp Asp
    130                 135                 140
```

Pro Val Thr Lys Pro Val Val Gln Ile His Pro Pro Ser Gly Ala Val
145 150 155 160

Glu Tyr Val Gly Asn Met Thr Leu Thr Cys His Val Glu Gly Gly Thr
165 170 175

Arg Leu Ala Tyr Gln Trp Leu Lys Asn Gly Arg Pro Val His Thr Ser
180 185 190

Ser Thr Tyr Ser Phe Ser Pro Gln Asn Asn Thr Leu His Ile Ala Pro
195 200 205

Val Thr Lys Glu Asp Ile Gly Asn Tyr Ser Cys Leu Val Arg Asn Pro
210 215 220

Val Ser Glu Met Glu Ser Asp Ile Ile Met Pro Ile Ile Tyr Tyr Gly
225 230 235 240

Pro Tyr Gly Leu Gln Val Asn Ser Asp Lys Gly Leu Lys Val Gly Glu
245 250 255

Val Phe Thr Val Asp Leu Gly Glu Ala Ile Leu Phe Asp Cys Ser Ala
260 265 270

Asp Ser His Pro Pro Asn Thr Tyr Ser Trp Ile Arg Arg Thr Asp Asn
275 280 285

Thr Thr Tyr Ile Ile Lys His Gly Pro Arg Leu Glu Val Ala Ser Glu
290 295 300

Lys Val Ala Gln Lys Thr Met Asp Tyr Val Cys Cys Ala Tyr Asn Asn
305 310 315 320

Ile Thr Gly Arg Gln Asp Glu Thr His Phe Thr Val Ile Ile Thr Ser
325 330 335

Val Gly Leu Glu Lys Leu Ala Gln Lys Gly Lys Ser Leu Ser Pro Leu
340 345 350

Ala Ser Ile Thr Gly Ile Ser Leu Phe Leu Ile Ile Ser Met Cys Leu
355 360 365

Leu Phe Leu Trp Lys Lys Tyr Gln Pro Tyr Lys Val Ile Lys Gln Lys
370 375 380

Leu Glu Gly Arg Pro Glu Thr Glu Tyr Arg Lys Ala Gln Thr Phe Ser
385 390 395 400

Gly His Glu Asp Ala Leu Asp Asp Phe Gly Ile Tyr Glu Phe Val Ala
405 410 415

Phe Pro Asp Val Ser Gly Val Ser Arg Ile Pro Ser Arg Ser Val Pro
420 425 430

Ala Ser Asp Cys Val Ser Gly Gln Asp Leu His Ser Thr Val Tyr Glu
435 440 445

Val Ile Gln His Ile Pro Ala Gln Gln Gln Asp His Pro Glu
450 455 460

<210> SEQ ID NO 36
<211> LENGTH: 450
<212> TYPE: PRT
<213> ORGANISM: Homo sapiens

<400> SEQUENCE: 36

Met Trp Leu Lys Val Phe Thr Thr Phe Leu Ser Phe Ala Thr Gly Ala
1 5 10 15

Cys Ser Gly Leu Lys Val Thr Val Pro Ser His Thr Val His Gly Val
20 25 30

Arg Gly Gln Ala Leu Tyr Leu Pro Val His Tyr Gly Phe His Thr Pro
35 40 45

Ala Ser Asp Ile Gln Ile Ile Trp Leu Phe Glu Arg Pro His Thr Met

```
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Ile Leu Phe
                245                 250                 255

Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys Ser
                325                 330                 335

Leu Ser Pro Leu Ala Ser Ile Thr Gly Ile Ser Leu Phe Leu Ile Ile
            340                 345                 350

Ser Met Cys Leu Leu Phe Leu Trp Lys Lys Tyr Gln Pro Tyr Lys Val
        355                 360                 365

Ile Lys Gln Lys Leu Glu Gly Arg Pro Glu Thr Glu Tyr Arg Lys Ala
    370                 375                 380

Gln Thr Phe Ser Gly His Glu Asp Ala Leu Asp Asp Phe Gly Ile Tyr
385                 390                 395                 400

Glu Phe Val Ala Phe Pro Asp Val Ser Gly Val Ser Arg Ile Pro Ser
                405                 410                 415

Arg Ser Val Pro Ala Ser Asp Cys Val Ser Gly Gln Asp Leu His Ser
            420                 425                 430

Thr Val Tyr Glu Val Ile Gln His Ile Pro Ala Gln Gln Gln Asp His
        435                 440                 445

Pro Glu
    450

<210> SEQ ID NO 37
```

<211> LENGTH: 455
<212> TYPE: PRT
<213> ORGANISM: Homo sapiens

<400> SEQUENCE: 37

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Gly Phe His Thr Pro
        35                  40                  45

Ala Ser Asp Ile Gln Ile Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Ile Leu Phe
                245                 250                 255

Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys Ser
                325                 330                 335

Leu Ser Pro Leu Ala Ser Ile Thr Gly Ile Ser Leu Phe Leu Ile Ile
            340                 345                 350

Ser Met Cys Leu Leu Phe Leu Trp Lys Lys Tyr Gln Pro Tyr Lys Gly
        355                 360                 365

Gln Lys Gln Asn Thr Gly Lys Leu Lys His Phe Gln Ala Met Lys Met
    370                 375                 380

Leu Trp Met Thr Ser Glu Tyr Met Asn Leu Leu Leu Phe Gln Met Phe

```
385                 390                 395                 400

Leu Val Phe Pro Gly Ser Gln Ala Gly Leu Phe Gln Pro Leu Ile Val
                405                 410                 415

Tyr Arg Gly Lys Ile Cys Thr Val Gln Cys Met Lys Leu Phe Ser Thr
            420                 425                 430

Ser Leu Pro Ser Ser Lys Thr Ile Gln Ser Glu Leu Ser Trp Ala Lys
        435                 440                 445

Gln Tyr Ile Arg Val Lys Phe
    450                 455


<210> SEQ ID NO 38
<211> LENGTH: 419
<212> TYPE: PRT
<213> ORGANISM: Homo sapiens

<400> SEQUENCE: 38

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Gly Phe His Thr Pro
        35                  40                  45

Ala Ser Asp Ile Gln Ile Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Ile Leu Phe
                245                 250                 255

Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300
```

Ala Tyr Asn Asn Ile Thr Gly Arg Gln Asp Glu Thr His Phe Thr Val
305 310 315 320

Ile Ile Thr Ser Val Gly Leu Glu Lys Leu Ala Gln Lys Gly Lys Ser
325 330 335

Leu Ser Pro Leu Ala Ser Ile Thr Gly Ile Ser Leu Phe Leu Ile Ile
340 345 350

Ser Met Cys Leu Leu Phe Leu Trp Lys Lys Tyr Gln Pro Tyr Lys Val
355 360 365

Ile Lys Gln Lys Leu Glu Gly Arg Pro Glu Thr Glu Tyr Arg Lys Ala
370 375 380

Gln Thr Phe Ser Gly His Glu Asp Ala Leu Asp Asp Phe Gly Ile Tyr
385 390 395 400

Glu Phe Val Ala Phe Pro Asp Val Ser Gly Val Ser Arg Val Gly Phe
405 410 415

Pro Ser Gly

<210> SEQ ID NO 39
<211> LENGTH: 376
<212> TYPE: PRT
<213> ORGANISM: Homo sapiens

<400> SEQUENCE: 39

Met Trp Leu Lys Val Phe Thr Thr Phe Leu Ser Phe Ala Thr Gly Ala
1 5 10 15

Cys Ser Gly Leu Lys Val Thr Val Pro Ser His Thr Val His Gly Val
20 25 30

Arg Gly Gln Ala Leu Tyr Leu Pro Val His Tyr Gly Phe His Thr Pro
35 40 45

Ala Ser Asp Ile Gln Ile Ile Trp Leu Phe Glu Arg Pro His Thr Met
50 55 60

Pro Lys Tyr Leu Leu Gly Ser Val Asn Lys Ser Val Val Pro Asp Leu
65 70 75 80

Glu Tyr Gln His Lys Phe Thr Met Met Pro Pro Asn Ala Ser Leu Leu
85 90 95

Ile Asn Pro Leu Gln Phe Pro Asp Glu Gly Asn Tyr Ile Val Lys Val
100 105 110

Asn Ile Gln Gly Asn Gly Thr Leu Ser Ala Ser Gln Lys Ile Gln Val
115 120 125

Thr Val Asp Asp Pro Val Thr Lys Pro Val Val Gln Ile His Pro Pro
130 135 140

Ser Gly Ala Val Glu Tyr Val Gly Asn Met Thr Leu Thr Cys His Val
145 150 155 160

Glu Gly Gly Thr Arg Leu Ala Tyr Gln Trp Leu Lys Asn Gly Arg Pro
165 170 175

Val His Thr Ser Ser Thr Tyr Ser Phe Ser Pro Gln Asn Asn Thr Leu
180 185 190

His Ile Ala Pro Val Thr Lys Glu Asp Ile Gly Asn Tyr Ser Cys Leu
195 200 205

Val Arg Asn Pro Val Ser Glu Met Glu Ser Asp Ile Ile Met Pro Ile
210 215 220

Ile Tyr Tyr Gly Pro Tyr Gly Leu Gln Val Asn Ser Asp Lys Gly Leu
225 230 235 240

Lys Val Gly Glu Val Phe Thr Val Asp Leu Gly Glu Ala Ile Leu Phe
245 250 255

```
Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys Ser
                325                 330                 335

Leu Ser Pro Leu Ala Ser Ile Thr Gly Ile Ser Leu Phe Leu Ile Ile
            340                 345                 350

Ser Met Cys Leu Leu Phe Leu Trp Lys Lys Tyr Gln Pro Tyr Lys Val
        355                 360                 365

Ile Lys Gln Lys Leu Glu Gly Arg
    370                 375
```

```
<210> SEQ ID NO 40
<211> LENGTH: 423
<212> TYPE: PRT
<213> ORGANISM: Homo sapiens

<400> SEQUENCE: 40

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Gly Phe His Thr Pro
        35                  40                  45

Ala Ser Asp Ile Gln Ile Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Ile Leu Phe
                245                 250                 255
```

```
Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys Ser
                325                 330                 335

Leu Ser Pro Leu Ala Ser Ile Thr Gly Ile Ser Leu Phe Leu Ile Ile
            340                 345                 350

Ser Met Cys Leu Leu Phe Leu Trp Lys Lys Tyr Gln Pro Tyr Lys Val
        355                 360                 365

Ile Lys Gln Lys Leu Glu Gly Arg Pro Glu Thr Glu Tyr Arg Lys Ala
    370                 375                 380

Gln Thr Phe Ser Gly Phe Met Leu Ala Ala Pro Ser Gln Arg Glu Glu
385                 390                 395                 400

Glu Lys Lys Ile Trp Gln Gly Pro Gly Leu Leu Leu Cys Pro His Cys
                405                 410                 415

Asn Pro His Tyr His Gln Tyr
            420
```

<210> SEQ ID NO 41
<211> LENGTH: 1520
<212> TYPE: DNA
<213> ORGANISM: Homo sapiens

<400> SEQUENCE: 41

```
atgaggcctc tgcccagcgg gaggaggaag acccgaggca tctccctagg actcttcgcc      60

ctctgcctgg ccgcagcccg ctgtctgcag agtcagggtg tgtccctata cattcctcag     120

gccaccatca atgccactgt caaagaagac atcctgctct cagttgagta ctcctgtcat     180

ggagtgccca ccatcgaatg gacatattca tccaattggg gaacgcagaa gatcgtggag     240

tggaaaccag ggactcaggc caacatctct caaagccaca aggacagagt ctgcaccttt     300

gacaacggct ccatccagct cttcagcgtg ggagtgaggg attccggcta ctatgtcatc     360

accgtgacgg agcgcctggg gagcagccag tttggcacca tcgtgctgca cgtctctgag     420

atcctctatg aagacctgca ctttgtcgct gtcatccttg cttttctcgc tgctgtggcc     480

gcagtattaa tcagcctcat gtgggtttgt aataagtgtg catataaatt tcagaggaag     540

agaagacaca aactcaaaga aagcacaact gaggagattg agctggaaga tgttgagtgt     600

tagccaaggc tgggcctgac tgcattccta cctcaagagg aaaccattct ccaacaaaaa     660

gagcaagcac agctattata cccattgtgt gtggtcctgt tgcagcccgc tcctaacagg     720

acagtgggag attaacaaca ttgactgcat ggagttgagg actgtggatg ggacaaagct     780

agtattagga ctcgcgctaa gttcaaggag aagagtgatt gaggctttga accaggagct     840

tcgcttggct gcagcatcag ggccgtgctg acacataacc aatggcagtc ggaggaacca     900

ggctctgggc caggacagtt tccagtgctg tgaagaaacg aggtgagcag tatccaaggg     960

gctcaaggat aatctgctga tttctttctc gtctttcaca cagagaggcc accagcagga    1020

aagcagtggg agttgggtag ctgctggggc cagcatgtcc tcttccacac tacctgcctt    1080

tcagaactct gctcttccgc ttgtcccgaa gtcagggctg gcaatcttca taatcaaagg    1140
```

ggagttggaa aagaacaccc actaagaggc ctccatggca gatgtcaatt aaattgcccc 1200
cccccccaaa tctcatgaca gtttattcac atcagtagtg tgggaagtta caatgttttt 1260
tttaaaaaaa gcttctttcc ttggctttcc atttctttga aaaaagggtt tcttttgaat 1320
ttttaaagct ctgccatact gaacattcct gtggaaaggt ttaaaatgca gagcctgagg 1380
tttttgcttt tcagaaaaat aaaaatcata gagattagct agtgtaaatg ttaagctata 1440
aattatgttt caaactgtga aaaaaaaaag ttttaaagaa tgaatgaaat aaaacctgaa 1500
aataaagccc tggtcctttg 1520

<210> SEQ ID NO 42
<211> LENGTH: 1650
<212> TYPE: DNA
<213> ORGANISM: Homo sapiens

<400> SEQUENCE: 42
atgaggcctc tgcccagcgg gaggaggaag acccgaggca tctccctagg actcttcgcc 60
ctctgcctgg ccgcagcccg ctgtctgcag agtcagggtg tgtccctata cattcctcag 120
gccaccatca atgccactgt caaagaagac atcctgctct cagttgagta ctcctgtcat 180
ggagtgccca ccatcgaatg gacatattca tccaattggg gaacgcagaa gatcgtggag 240
tggaaaccag ggactcaggc caacatctct caaagccaca aggacagagt ctgcaccttt 300
gacaacggct ccatccagct cttcagcgtg ggagtgaggg attccggcta ctatgtcatc 360
accgtgacgg agcgcctggg gagcagccag tttggcacca tcgtgctgca cgtctctgag 420
atcctctatg aagacctgca ctttgtcgct gtcatccttg cttttctcgc tgctgtggcc 480
gcagtattaa tcagcctcat gtgggtttgt aataagtgtg catataaatt tcagaggaag 540
agaagacaca aactcaaagg taacccccctg ggccttgtga taatccatga gtggttttga 600
ggccagaggt ggcatgtgtt atcttgttct cacgaagaaa gcactatgtg gcttgatttc 660
caactcattg acttgtcttt gctttacaga aagcacaact gaggagattg agctggaaga 720
tgttgagtgt tagccaaggc tgggcctgac tgcattccta cctcaagagg aaaccattct 780
ccaacaaaaa gagcaagcac agctattata cccattgtgt gtggtcctgt tgcagcccgc 840
tcctaacagg acagtgggag attaacaaca ttgactgcat ggagttgagg actgtggatg 900
ggacaaagct agtattagga ctcgcgctaa gttcaaggag aagagtgatt gaggctttga 960
accaggagct tcgcttggct gcagcatcag ggccgtgctg acacataacc aatggcagtc 1020
ggaggaacca ggctctgggc caggacagtt tccagtgctg tgaagaaacg aggtgagcag 1080
tatccaaggg gctcaaggat aatctgctga tttctttctc gtctttcaca cagagaggcc 1140
accagcagga aagcagtggg agttgggtag ctgctggggc cagcatgtcc tcttccacac 1200
tacctgcctt tcagaactct gctcttccgc ttgtcccgaa gtcagggctg gcaatcttca 1260
taatcaaagg ggagttggaa aagaacaccc actaagaggc ctccatggca gatgtcaatt 1320
aaattgcccc cccccccaaa tctcatgaca gtttattcac atcagtagtg tgggaagtta 1380
caatgttttt tttaaaaaaa gcttctttcc ttggctttcc atttctttga aaaaagggtt 1440
tcttttgaat ttttaaagct ctgccatact gaacattcct gtggaaaggt ttaaaatgca 1500
gagcctgagg tttttgcttt tcagaaaaat aaaaatcata gagattagct agtgtaaatg 1560
ttaagctata aattatgttt caaactgtga aaaaaaaaag ttttaaagaa tgaatgaaat 1620
aaaacctgaa aataaagccc tggtcctttg 1650

<210> SEQ ID NO 43
<211> LENGTH: 200
<212> TYPE: PRT
<213> ORGANISM: Homo sapiens

<400> SEQUENCE: 43

```
Met Arg Pro Leu Pro Ser Gly Arg Arg Lys Thr Arg Gly Ile Ser Leu
1               5                   10                  15

Gly Leu Phe Ala Leu Cys Leu Ala Ala Ala Arg Cys Leu Gln Ser Gln
            20                  25                  30

Gly Val Ser Leu Tyr Ile Pro Gln Ala Thr Ile Asn Ala Thr Val Lys
        35                  40                  45

Glu Asp Ile Leu Leu Ser Val Glu Tyr Ser Cys His Gly Val Pro Thr
    50                  55                  60

Ile Glu Trp Thr Tyr Ser Ser Asn Trp Gly Thr Gln Lys Ile Val Glu
65                  70                  75                  80

Trp Lys Pro Gly Thr Gln Ala Asn Ile Ser Gln Ser His Lys Asp Arg
                85                  90                  95

Val Cys Thr Phe Asp Asn Gly Ser Ile Gln Leu Phe Ser Val Gly Val
            100                 105                 110

Arg Asp Ser Gly Tyr Tyr Val Ile Thr Val Thr Glu Arg Leu Gly Ser
        115                 120                 125

Ser Gln Phe Gly Thr Ile Val Leu His Val Ser Glu Ile Leu Tyr Glu
    130                 135                 140

Asp Leu His Phe Val Ala Val Ile Leu Ala Phe Leu Ala Ala Val Ala
145                 150                 155                 160

Ala Val Leu Ile Ser Leu Met Trp Val Cys Asn Lys Cys Ala Tyr Lys
                165                 170                 175

Phe Gln Arg Lys Arg Arg His Lys Leu Lys Glu Ser Thr Thr Glu Glu
            180                 185                 190

Ile Glu Leu Glu Asp Val Glu Cys
        195                 200
```

<210> SEQ ID NO 44
<211> LENGTH: 199
<212> TYPE: PRT
<213> ORGANISM: Homo sapiens

<400> SEQUENCE: 44

```
Met Arg Pro Leu Pro Ser Gly Arg Arg Lys Thr Arg Gly Ile Ser Leu
1               5                   10                  15

Gly Leu Phe Ala Leu Cys Leu Ala Ala Ala Arg Cys Leu Gln Ser Gln
            20                  25                  30

Gly Val Ser Leu Tyr Ile Pro Gln Ala Thr Ile Asn Ala Thr Val Lys
        35                  40                  45

Glu Asp Ile Leu Leu Ser Val Glu Tyr Ser Cys His Gly Val Pro Thr
    50                  55                  60

Ile Glu Trp Thr Tyr Ser Ser Asn Trp Gly Thr Gln Lys Ile Val Glu
65                  70                  75                  80

Trp Lys Pro Gly Thr Gln Ala Asn Ile Ser Gln Ser His Lys Asp Arg
                85                  90                  95

Val Cys Thr Phe Asp Asn Gly Ser Ile Gln Leu Phe Ser Val Gly Val
            100                 105                 110

Arg Asp Ser Gly Tyr Tyr Val Ile Thr Val Thr Glu Arg Leu Gly Ser
        115                 120                 125
```

```
Ser Gln Phe Gly Thr Ile Val Leu His Val Ser Glu Ile Leu Tyr Glu
    130                 135                 140

Asp Leu His Phe Val Ala Val Ile Leu Ala Phe Leu Ala Ala Val Ala
145                 150                 155                 160

Ala Val Leu Ile Ser Leu Met Trp Val Cys Asn Lys Cys Ala Tyr Lys
                165                 170                 175

Phe Gln Arg Lys Arg Arg His Lys Leu Lys Gly Asn Pro Leu Gly Leu
            180                 185                 190

Val Ile Ile His Glu Trp Phe
        195


<210> SEQ ID NO 45
<211> LENGTH: 1407
<212> TYPE: DNA
<213> ORGANISM: Homo sapiens

<400> SEQUENCE: 45

ccggcggcgc gatccagccc ccggccccgc ctgcgcggcc ggcccggcgg gcgctgcgcc     60

cagggacgcc cggtgcccgc cgctccgccg ccgcccgctg ccgcggggtg acagcgatcc    120

ttctgttcca gccatttccc actttcctca ctccgtaatt cggctgggaa gttggggaag    180

atggataggg tcttgctgag gtggatttct ctcttctggc taacagccat ggtcgaaggc    240

cttcaggtca cagtgcccga caagaagaag gtggccatgc tcttccagcc cactgtgctt    300

cgctgccact tctcaacatc ctcccatcag cctgcagttg tgcagtggaa gttcaagtcc    360

tactgccagg atcgcatggg agaatccttg ggcatgtcct ctacccgggc ccaatctctc    420

agcaagagaa acctggaatg ggacccctac ttggattgtt tggacagcag gaggactgtt    480

cgagtagtag cttcaaaaca gggctcgact gtcaccctgg gagatttcta caggggcaga    540

gagatcacga ttgttcatga tgcagatctt caaattggaa agcttatgtg gggagacagc    600

ggactctatt actgtattat caccacccca gatgacctgg aggggaaaaa tgagggctca    660

ctgggactgc tggtgttggg caggacaggg ctgcttgctg atctcttgcc cagttttgct    720

gtggagatta tgccagagtg ggtgtttgtt ggcctggtgc tcctgggcgt cttcctcttc    780

ttcgtcctgg tggggatctg ctggtgccag tgctgccctc acagctgctg ctgctatgtc    840

cgctgcccat gctgcccaga ttcctgctgg tgccctcaag cctgtgagta cagtgaccgc    900

tggggagaca gagcgatcga gagaaatgtc tacctctcta cctgacagct gtgtgcgctg    960

ggttcctcct ccacctcctg tcctgccacc cccaagattg gtcattccag actcttctcc   1020

gctgggtgcc cctggcctca gggatgacca ttctcatttg ccttttcacc tacatacacc   1080

tctccacact tcttatccat atctatcact ccatgcattt ggaattctca tggacactat   1140

tgataaaatg gaagggcagg tttggcgtgg tgaggttgtg gtgtaagact gttccctctc   1200

cctggggcat tcaaactaga ggaaaccttc tctggtcgtt cccttcccat gcagagaagt   1260

tcctttttat atgagaagag tgtgcaaact gtggcctttg ggcacccacc cagccacaga   1320

tttgttttat ttactcccat gatgacatgg gccacaatag ggcctagttc ttatttgagg   1380

attcacaatt tttaccttac tggccaa                                       1407


<210> SEQ ID NO 46
<211> LENGTH: 1350
<212> TYPE: DNA
<213> ORGANISM: Homo sapiens

<400> SEQUENCE: 46
```

-continued

```
ccggcggcgc gatccagccc ccggccccgc ctgcgcggcc ggcccggcgg gcgctgcgcc      60
cagggacgcc cggtgcccgc cgctccgccg ccgcccgctg ccgcggggtg acagcgatcc     120
ttctgttcca gccatttccc actttcctca ctccgtaatt cggctgggaa gttggggaag     180
atggataggg tcttgctgag gtggatttct ctcttctggc taacagccat ggtcgaaggc     240
cttcaggtca cagtgcccga caagaagaag gtggccatgc tcttccagcc cactgtgctt     300
cgctgccact tctcaacatc ctcccatcag cctgcagttg tgcagtggaa gttcaagtcc     360
tactgccagg atcgcatggg agaatccttg ggcatgtcct ctacccgggc ccaatctctc     420
agcaagagaa acctggaatg ggacccctac ttggattgtt tggacagcag gaggactgtt     480
cgagtagtag cttcaaaaca gggctcgact gtcaccctgg gagatttcta caggggcaga     540
gagatcacga ttgttcatga tgcagatctt caaattggaa agcttatgtg gggagacagc     600
ggactctatt actgtattat caccacccca gatgacctgg aggggaaaaa tgagggctca     660
ctgggactgc tggtgttgga gtgggtgttt gttggcctgg tgctcctggg cgtcttcctc     720
ttcttcgtcc tggtggggat ctgctggtgc cagtgctgcc ctcacagctg ctgctgctat     780
gtccgctgcc catgctgccc agattcctgc tggtgccctc aagcctgtga gtacagtgac     840
cgctggggag acagagcgat cgagagaaat gtctacctct ctacctgaca gctgtgtgcg     900
ctgggttcct cctccacctc ctgtcctgcc acccccaaga ttggtcattc cagactcttc     960
tccgctgggt gcccctggcc tcagggatga ccattctcat ttgccttttc acctacatac    1020
acctctccac acttcttatc catatctatc actccatgca tttggaattc tcatggacac    1080
tattgataaa atggaagggc aggtttggcg tggtgaggtt gtggtgtaag actgttccct    1140
ctccctgggg cattcaaact agaggaaacc ttctctggtc gttcccttcc catgcagaga    1200
agttcctttt tatatgagaa gagtgtgcaa actgtggcct ttgggcaccc acccagccac    1260
agatttgttt tatttactcc catgatgaca tgggccacaa tagggcctag ttcttatttg    1320
aggattcaca atttttacct tactggccaa                                     1350
```

```
<210> SEQ ID NO 47
<211> LENGTH: 639
<212> TYPE: PRT
<213> ORGANISM: Homo sapiens

<400> SEQUENCE: 47

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
```

-continued

```
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335

Ser Glu Leu Ser Ser Leu His Glu Glu Asp Ser Asn Phe Arg Gln Ser
            340                 345                 350

Phe His Gln Met Arg Ser Lys Gln Phe Pro Val Ser Gly Asp Leu Glu
        355                 360                 365

Ser Asn Pro Asp Tyr Trp Ser Gly Val Met Gly Gly Ser Ser Gly Ala
    370                 375                 380

Ser Arg Gly Pro Ser Ala Met Glu Tyr Asn Lys Glu Asp Arg Glu Ser
385                 390                 395                 400

Phe Arg His Ser Gln Pro Arg Ser Lys Ser Glu Met Leu Ser Arg Lys
                405                 410                 415

Asn Phe Ala Thr Gly Val Pro Ala Val Ser Met Asp Glu Leu Ala Ala
            420                 425                 430

Phe Ala Asp Ser Tyr Gly Gln Arg Pro Arg Arg Ala Asp Gly Asn Ser
        435                 440                 445

His Glu Ala Arg Gly Gly Ser Arg Phe Glu Arg Ser Glu Ser Arg Ala
    450                 455                 460

His Ser Gly Phe Tyr Gln Asp Asp Ser Leu Glu Glu Tyr Tyr Gly Gln
465                 470                 475                 480

Arg Ser Arg Ser Arg Glu Pro Leu Thr Asp Ala Asp Arg Gly Trp Ala
                485                 490                 495

Phe Ser Pro Ala Arg Arg Arg Pro Ala Glu Asp Ala His Leu Pro Arg
            500                 505                 510

Leu Val Ser Arg Thr Pro Gly Thr Ala Pro Lys Tyr Asp His Ser Tyr
        515                 520                 525

Leu Gly Ser Ala Arg Glu Arg Gln Ala Arg Pro Glu Gly Ala Ser Arg
    530                 535                 540

Gly Gly Ser Leu Glu Thr Pro Ser Lys Arg Ser Ala Gln Leu Gly Pro
545                 550                 555                 560
```

Arg Ser Ala Ser Tyr Tyr Ala Trp Ser Pro Pro Gly Thr Tyr Lys Ala
565 570 575

Gly Ser Ser Gln Asp Asp Gln Glu Asp Ala Ser Asp Asp Ala Leu Pro
580 585 590

Pro Tyr Ser Glu Leu Glu Leu Thr Arg Gly Pro Ser Tyr Arg Gly Arg
595 600 605

Asp Leu Pro Tyr His Ser Asn Ser Glu Lys Lys Arg Lys Lys Glu Pro
610 615 620

Ala Lys Lys Thr Asn Asp Phe Pro Thr Arg Met Ser Leu Val Val
625 630 635

<210> SEQ ID NO 48
<211> LENGTH: 254
<212> TYPE: PRT
<213> ORGANISM: Homo sapiens

<400> SEQUENCE: 48

Met Asp Arg Val Leu Leu Arg Trp Ile Ser Leu Phe Trp Leu Thr Ala
1 5 10 15

Met Val Glu Gly Leu Gln Val Thr Val Pro Asp Lys Lys Lys Val Ala
20 25 30

Met Leu Phe Gln Pro Thr Val Leu Arg Cys His Phe Ser Thr Ser Ser
35 40 45

His Gln Pro Ala Val Val Gln Trp Lys Phe Lys Ser Tyr Cys Gln Asp
50 55 60

Arg Met Gly Glu Ser Leu Gly Met Ser Ser Thr Arg Ala Gln Ser Leu
65 70 75 80

Ser Lys Arg Asn Leu Glu Trp Asp Pro Tyr Leu Asp Cys Leu Asp Ser
85 90 95

Arg Arg Thr Val Arg Val Val Ala Ser Lys Gln Gly Ser Thr Val Thr
100 105 110

Leu Gly Asp Phe Tyr Arg Gly Arg Glu Ile Thr Ile Val His Asp Ala
115 120 125

Asp Leu Gln Ile Gly Lys Leu Met Trp Gly Asp Ser Gly Leu Tyr Tyr
130 135 140

Cys Ile Ile Thr Thr Pro Asp Asp Leu Glu Gly Lys Asn Glu Gly Ser
145 150 155 160

Leu Gly Leu Leu Val Leu Gly Arg Thr Gly Leu Leu Ala Asp Leu Leu
165 170 175

Pro Ser Phe Ala Val Glu Ile Met Pro Glu Trp Val Phe Val Gly Leu
180 185 190

Val Leu Leu Gly Val Phe Leu Phe Phe Val Leu Val Gly Ile Cys Trp
195 200 205

Cys Gln Cys Cys Pro His Ser Cys Cys Cys Tyr Val Arg Cys Pro Cys
210 215 220

Cys Pro Asp Ser Cys Trp Cys Pro Gln Ala Cys Glu Tyr Ser Asp Arg
225 230 235 240

Trp Gly Asp Arg Ala Ile Glu Arg Asn Val Tyr Leu Ser Thr
245 250

<210> SEQ ID NO 49
<211> LENGTH: 254
<212> TYPE: PRT
<213> ORGANISM: Homo sapiens

<400> SEQUENCE: 49

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Cys Glu Tyr Ser Asp Arg
225                 230                 235                 240

Trp Gly Asp Arg Ala Ile Glu Arg Asn Val Tyr Leu Ser Thr
                245                 250


<210> SEQ ID NO 50
<211> LENGTH: 235
<212> TYPE: PRT
<213> ORGANISM: Homo sapiens

<400> SEQUENCE: 50

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
```

```
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Gly Ser
145                 150                 155                 160

Leu Gly Leu Leu Val Leu Glu Trp Val Phe Val Gly Leu Val Leu Leu
                165                 170                 175

Gly Val Phe Leu Phe Phe Val Leu Val Gly Ile Cys Trp Cys Gln Cys
            180                 185                 190

Cys Pro His Ser Cys Cys Cys Tyr Val Arg Cys Pro Cys Cys Pro Asp
        195                 200                 205

Ser Cys Trp Cys Pro Gln Ala Cys Glu Tyr Ser Asp Arg Trp Gly Asp
    210                 215                 220

Arg Ala Ile Glu Arg Asn Val Tyr Leu Ser Thr
225                 230                 235


<210> SEQ ID NO 51
<211> LENGTH: 1621
<212> TYPE: DNA
<213> ORGANISM: Homo sapiens

<400> SEQUENCE: 51

gtggactagg aggcagccgc ccccaccagc acccactctg tagacccagg cgtctggctc      60

ccagcaccca cggaaagagc ctggctagga aactgcagcc tggtgcctgg cagacagttc     120

tcattctccc cagggcaggg agcaggttat gaccaggact aaggtcccag agtccccacc     180

ctgacccctc cctgctgttc cagccgctcc ctcatatcca cccctgcccc atctcctgac     240

tttggtcacg ctagcatctt ctgctgatcc tgaaattgta ccagcggcaa gatgtggcct     300

ggaaggggac tttaagttct ccacaactgc cagcaatcct tccaccaggc aaaacacatc     360

atctaaggaa aagaagtgag gtttgcttag ggcgtggcag cttcggataa acgcaggact     420

ccgcctggca gcccgatttc tcccggaacc tctgctcagc ctggtgaacc acacaggcca     480

gcgctctgac atgcagaagg tgaccctggg cctgcttgtg ttcctggcag gctttcctgt     540

cctggacgcc aatgacctag aagataaaaa cagtcctttc tactatgact ggcacagcct     600

ccaggttggc gggctcatct gcgctggggt tctgtgcgcc atgggcatca tcatcgtcat     660

gagtgcaaaa tgcaaatgca agtttggcca gaagtccggt caccatccag ggagactcc     720

acctctcatc accccaggct cagcccaaag ctgatgagga cagaccagct gaaattgggt     780

ggaggaccgt tctctgtccc caggtcctgt ctctgcacag aaacttgaac tccaggatgg     840

aattcttcct cctctgctgg gactcctttg catggcaggg cctcatctca cctctcgcaa     900

gagggtctct ttgttcaatt ttttttaatc taaaatgatt gtgcctctgc ccaagcagcc     960

tggagacttc ctatgtgtgc attggggtgg ggcttggggc accatgagaa ggttggcgtg    1020

ccctggaggc tgacacagag gctggcactg agcctgcttg ttgggaaaag cccacaggcc    1080

tgttcccttg tggcttggga catggcacag gcccgccctc tgcctcctca gccatgggaa    1140

cctcatatgc aatttgggat ttactagtag ccaaaaggaa tgaaagagag ctctaaccag    1200

atggaacact ggaacattcc agtggaccct ggaccattcc aggaaaactg ggacatagga    1260

tcgtcccgct atgatggaag tgttcagaca gtttataata gtaagcccct gtgaccctct    1320

cacttacccc gagacctcac tttattacaa gatctttcca aatacccaaa tgtccctgca    1380

agcccgttaa ataattccct atgctaccct taataacata caatgaccac atagtgtgag    1440
```

-continued

```
aacttccaac aagcctcaaa gtcccttgag actccccaat acctaataag gcatgcgaaa   1500

tgttctcatg aactacccca caacacgcct aaaactcaaa acacccaaaa atatctcctc   1560

caatgtcctg agacatgaac ccaaaaagag acccacaata aactcgtgac ttgtcccctc   1620

a                                                                   1621


<210> SEQ ID NO 52
<211> LENGTH: 1925
<212> TYPE: DNA
<213> ORGANISM: Homo sapiens

<400> SEQUENCE: 52

gtggactagg aggcagccgc ccccaccagc acccactctg tagacccagg cgtctggctc     60

ccagcaccca cggaaagagc ctggctagga aactgcagcc tggtgcctgg cagacagttc    120

tcattctccc cagggcaggg agcaggttat gaccaggact aaggtcccag agtccccacc    180

ctgacccctc cctgctgttc cagccgctcc ctcatatcca cccctgcccc atctcctgac    240

tttggtcacg ctagcatctt ctgctgatcc tgaaattgta ccagcggcaa gatgtggcct    300

ggaaggggac tttaagttct ccacaactgc cagcaatcct tccaccaggc aaaacacatc    360

atctaaggaa aagaagtgag gtcggaacac caacgcatca tctcactgca tggccctgga    420

ggctctgccg tttaaagacc ccagaacctt ccccattcaa ggtcctctcc tgggcacagg    480

agattggaga aagctcctcc cttaattcca gggaccgagt tccagcccat ccaattctcc    540

gtctcacctg aggctgctgt ggtcctggtg accccaggga gcaacctgcc gcccatggct    600

ggggaggggg tgaagctgtc tctttaagag caggaatgga gcccctgggc ctcagggcat    660

ctgacttgtt ttctacctgc ccaggtttgc ttagggcgtg gcagcttcgg ataaacgcag    720

gactccgcct ggcagcccga tttctcccgg aacctctgct cagcctggtg aaccacacag    780

gccagcgctc tgacatgcag aaggtgaccc tgggcctgct tgtgttcctg gcaggctttc    840

ctgtcctgga cgccaatgac ctagaagata aaaacagtcc tttctactat gactggcaca    900

gcctccaggt tggcgggctc atctgcgctg gggttctgtg cgccatgggc atcatcatcg    960

tcatgagtgc aaaatgcaaa tgcaagtttg gccagaagtc cggtcaccat ccaggggaga   1020

ctccacctct catcacccca ggctcagccc aaagctgatg aggacagacc agctgaaatt   1080

gggtggagga ccgttctctg tccccaggtc ctgtctctgc acagaaactt gaactccagg   1140

atggaattct tcctcctctg ctgggactcc tttgcatggc agggcctcat ctcacctctc   1200

gcaagagggt ctctttgttc aatttttttt aatctaaaat gattgtgcct ctgcccaagc   1260

agcctggaga cttcctatgt gtgcattggg gtggggcttg gggcaccatg agaaggttgg   1320

cgtgccctgg aggctgacac agaggctggc actgagcctg cttgttggga aaagcccaca   1380

ggcctgttcc cttgtggctt gggacatggc acaggcccgc cctctgcctc ctcagccatg   1440

ggaacctcat atgcaatttg ggatttacta gtagccaaaa ggaatgaaag agagctctaa   1500

ccagatggaa cactggaaca ttccagtgga ccctggacca ttccaggaaa actgggacat   1560

aggatcgtcc cgctatgatg gaagtgttca gacagtttat aatagtaagc ccctgtgacc   1620

ctctcactta ccccgagacc tcactttatt acaagatctt tccaaatacc caaatgtccc   1680

tgcaagcccg ttaaataatt ccctatgcta cccttaataa catacaatga ccacatagtg   1740

tgagaacttc caacaagcct caaagtccct tgagactccc caatacctaa taaggcatgc   1800

gaaatgttct catgaactac cccacaacac gcctaaaact caaaacaccc aaaaatatct   1860

cctccaatgt cctgagacat gaacccaaaa agagacccac aataaactcg tgacttgtcc   1920
```

cctca 1925

<210> SEQ ID NO 53
<211> LENGTH: 1808
<212> TYPE: DNA
<213> ORGANISM: Homo sapiens

<400> SEQUENCE: 53
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtcggaacac caacgcatca tctcactgca tggccctgga 420
ggctctgccg tttaaagacc ccagaacctt ccccattcaa ggtcctctcc tgggcacagg 480
agattggaga aagctcctcc cttaattcca gggaccgagt tccagcccat ccaattctcc 540
gtctcacctg aggctgctgt ggtcctggtt tgcttagggc gtggcagctt cggataaacg 600
caggactccg cctggcagcc cgatttctcc cggaacctct gctcagcctg gtgaaccaca 660
caggccagcg ctctgacatg cagaaggtga ccctgggcct gcttgtgttc ctggcaggct 720
ttcctgtcct ggacgccaat gacctagaag ataaaaacag tcctttctac tatgactggc 780
acagcctcca ggttggcggg ctcatctgcg ctggggttct gtgcgccatg ggcatcatca 840
tcgtcatgag tgcaaaatgc aaatgcaagt ttggccagaa gtccggtcac catccagggg 900
agactccacc tctcatcacc ccaggctcag cccaaagctg atgaggacag accagctgaa 960
attgggtgga ggaccgttct ctgtccccag gtcctgtctc tgcacagaaa cttgaactcc 1020
aggatggaat tcttcctcct ctgctgggac tcctttgcat ggcagggcct catctcacct 1080
ctcgcaagag ggtctctttg ttcaattttt tttaatctaa aatgattgtg cctctgccca 1140
agcagcctgg agacttccta tgtgtgcatt ggggtggggc ttggggcacc atgagaaggt 1200
tggcgtgccc tggaggctga cacagaggct ggcactgagc ctgcttgttg ggaaaagccc 1260
acaggcctgt tcccttgtgg cttgggacat ggcacaggcc cgccctctgc ctcctcagcc 1320
atgggaacct catatgcaat ttgggattta ctagtagcca aaaggaatga aagagagctc 1380
taaccagatg gaacactgga acattccagt ggaccctgga ccattccagg aaaactggga 1440
cataggatcg tcccgctatg atggaagtgt tcagacagtt tataatagta agcccctgtg 1500
accctctcac ttaccccgag acctcacttt attacaagat ctttccaaat acccaaatgt 1560
ccctgcaagc ccgttaaata attccctatg ctacccttaa taacatacaa tgaccacata 1620
gtgtgagaac ttccaacaag cctcaaagtc ccttgagact ccccaatacc taataaggca 1680
tgcgaaatgt tctcatgaac taccccacaa cacgcctaaa actcaaaaca cccaaaaata 1740
tctcctccaa tgtcctgaga catgaaccca aaaagagacc cacaataaac tcgtgacttg 1800
tcccctca 1808

<210> SEQ ID NO 54
<211> LENGTH: 1702
<212> TYPE: DNA
<213> ORGANISM: Homo sapiens

<400> SEQUENCE: 54
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtcggaacac caacgcatca tctcactgca tggccctgga 420
ggctctgccg tttaaagacc ccagaacctt ccccattcaa ggtttgctta gggcgtggca 480
gcttcggata aacgcaggac tccgcctggc agcccgattt ctcccggaac ctctgctcag 540
cctggtgaac cacacaggcc agcgctctga catgcagaag gtgaccctgg gcctgcttgt 600
gttcctggca ggctttcctg tcctggacgc caatgaccta gaagataaaa acagtccttt 660
ctactatgac tggcacagcc tccaggttgg cgggctcatc tgcgctgggg ttctgtgcgc 720
catgggcatc atcatcgtca tgagtgcaaa atgcaaatgc aagtttggcc agaagtccgg 780
tcaccatcca ggggagactc cacctctcat caccccaggc tcagcccaaa gctgatgagg 840
acagaccagc tgaaattggg tggaggaccg ttctctgtcc ccaggtcctg tctctgcaca 900
gaaacttgaa ctccaggatg gaattcttcc tcctctgctg ggactccttt gcatggcagg 960
gcctcatctc acctctcgca agagggtctc tttgttcaat ttttttaat ctaaaatgat 1020 tgtgcctctg cccaagcagc ctggagactt cctatgtgtg cattggggtg gggcttgggg 1080
caccatgaga aggttggcgt gccctggagg ctgacacaga ggctggcact gagcctgctt 1140
gttgggaaaa gcccacaggc ctgttccctt gtggcttggg acatggcaca ggcccgccct 1200
ctgcctcctc agccatggga acctcatatg caatttggga tttactagta gccaaaagga 1260
atgaaagaga gctctaacca gatggaacac tggaacattc cagtggaccc tggaccattc 1320
caggaaaact gggacatagg atcgtcccgc tatgatggaa gtgttcagac agtttataat 1380
agtaagcccc tgtgaccctc tcacttaccc cgagacctca ctttattaca agatctttcc 1440
aaatacccaa atgtccctgc aagcccgtta aataattccc tatgctaccc ttaataacat 1500
acaatgacca catagtgtga gaacttccaa caagcctcaa agtcccttga gactccccaa 1560
tacctaataa ggcatgcgaa atgttctcat gaactacccc acaacacgcc taaaactcaa 1620
aacacccaaa aatatctcct ccaatgtcct gagacatgaa cccaaaaaga gacccacaat 1680
aaactcgtga cttgtcccct ca 1702

<210> SEQ ID NO 55
<211> LENGTH: 1705
<212> TYPE: DNA
<213> ORGANISM: Homo sapiens

<400> SEQUENCE: 55
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360

-continued atctaaggaa aagaagtgag gtttgcttag ggcgtggcag cttcggataa acgcaggact 420
ccgcctggca gcccgatttc tcccggaacc tctgctcagc ctggtgaacc acacaggccc 480
gagtttcacc cagtccccac tccacggtgc agctgcggct tatctctcag cccagcgaga 540
tgccagcctt cctgtcccgg gccagcgctc tgacatgcag aaggtgaccc tgggcctgct 600
tgtgttcctg gcaggctttc ctgtcctgga cgccaatgac ctagaagata aaaacagtcc 660
tttctactat gactggcaca gcctccaggt tggcgggctc atctgcgctg gggttctgtg 720
cgccatgggc atcatcatcg tcatgagtgc aaaatgcaaa tgcaagtttg gccagaagtc 780
cggtcaccat ccaggggaga ctccacctct catcacccca ggctcagccc aaagctgatg 840
aggacagacc agctgaaatt gggtggagga ccgttctctg tccccaggtc ctgtctctgc 900
acagaaactt gaactccagg atggaattct tcctcctctg ctgggactcc tttgcatggc 960
agggcctcat ctcacctctc gcaagagggt ctctttgttc aatttttttt aatctaaaat 1020
gattgtgcct ctgcccaagc agcctggaga cttcctatgt gtgcattggg gtggggcttg 1080
gggcaccatg agaaggttgg cgtgccctgg aggctgacac agaggctggc actgagcctg 1140
cttgttggga aaagcccaca ggcctgttcc cttgtggctt gggacatggc acaggcccgc 1200
cctctgcctc ctcagccatg ggaacctcat atgcaatttg ggatttacta gtagccaaaa 1260
ggaatgaaag agagctctaa ccagatggaa cactggaaca ttccagtgga ccctggacca 1320
ttccaggaaa actgggacat aggatcgtcc cgctatgatg gaagtgttca gacagtttat 1380
aatagtaagc ccctgtgacc ctctcactta ccccgagacc tcactttatt acaagatctt 1440
tccaaatacc caaatgtccc tgcaagcccg ttaaataatt ccctatgcta cccttaataa 1500
catacaatga ccacatagtg tgagaacttc caacaagcct caaagtccct tgagactccc 1560
caatacctaa taaggcatgc gaaatgttct catgaactac cccacaacac gcctaaaact 1620
caaaacaccc aaaaatatct cctccaatgt cctgagacat gaacccaaaa agagacccac 1680
aataaactcg tgacttgtcc cctca 1705

<210> SEQ ID NO 56
<211> LENGTH: 1786
<212> TYPE: DNA
<213> ORGANISM: Homo sapiens

<400> SEQUENCE: 56
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtcggaacac caacgcatca tctcactgca tggccctgga 420
ggctctgccg tttaaagacc ccagaacctt ccccattcaa ggtttgctta gggcgtggca 480
gcttcggata aacgcaggac tccgcctggc agcccgattt ctcccggaac ctctgctcag 540
cctggtgaac cacacaggcc cgagtttcac ccagtcccca ctccacggtg cagctgcggc 600
ttatctctca gcccagcgag atgccagcct tcctgtcccg ggccagcgct ctgacatgca 660
gaaggtgacc ctgggcctgc ttgtgttcct ggcaggcttt cctgtcctgg acgccaatga 720

```
cctagaagat aaaaacagtc ctttctacta tgactggcac agcctccagg ttggcgggct    780
catctgcgct ggggttctgt gcgccatggg catcatcatc gtcatgagtg caaaatgcaa    840
atgcaagttt ggccagaagt ccggtcacca tccaggggag actccacctc tcatcacccc    900
aggctcagcc caaagctgat gaggacagac cagctgaaat tgggtggagg accgttctct    960
gtccccaggt cctgtctctg cacagaaact tgaactccag gatggaattc ttcctcctct   1020
gctgggactc ctttgcatgg cagggcctca tctcacctct cgcaagaggg tctctttgtt   1080
caattttttt taatctaaaa tgattgtgcc tctgcccaag cagcctggag acttcctatg   1140
tgtgcattgg ggtggggctt ggggcaccat gagaaggttg gcgtgccctg gaggctgaca   1200
cagaggctgg cactgagcct gcttgttggg aaaagcccac aggcctgttc ccttgtggct   1260
tgggacatgg cacaggcccg ccctctgcct cctcagccat gggaacctca tatgcaattt   1320
gggatttact agtagccaaa aggaatgaaa gagagctcta accagatgga acactggaac   1380
attccagtgg accctggacc attccaggaa aactgggaca taggatcgtc ccgctatgat   1440
ggaagtgttc agacagttta taatagtaag cccctgtgac cctctcactt accccgagac   1500
ctcactttat tacaagatct ttccaaatac ccaaatgtcc ctgcaagccc gttaaataat   1560
tccctatgct acccttaata acatacaatg accacatagt gtgagaactt ccaacaagcc   1620
tcaaagtccc ttgagactcc ccaataccta ataaggcatg cgaaatgttc tcatgaacta   1680
ccccacaaca cgcctaaaac tcaaaacacc caaaaatatc tcctccaatg tcctgagaca   1740
tgaacccaaa aagagaccca caataaactc gtgacttgtc ccctca                  1786
```

<210> SEQ ID NO 57
<211> LENGTH: 1827
<212> TYPE: DNA
<213> ORGANISM: Homo sapiens

<400> SEQUENCE: 57

```
gtggactagg aggcagccgc ccccaccagc acccactctg tagacccagg cgtctggctc     60
ccagcaccca cggaaagagc ctggctagga aactgcagcc tggtgcctgg cagacagttc    120
tcattctccc cagggcaggg agcaggttat gaccaggact aaggtcccag agtccccacc    180
ctgacccctc cctgctgttc cagccgctcc ctcatatcca cccctgcccc atctcctgac    240
tttggtcacg ctagcatctt ctgctgatcc tgaaattgta ccagcggcaa gatgtggcct    300
ggaaggggac tttaagttct ccacaactgc cagcaatcct tccaccaggc aaaacacatc    360
atctaaggaa aagaagtgag gtttgcttag ggcgtggcag cttcggataa acgcaggact    420
ccgcctggca gcccgatttc tcccggaacc tctgctcagc ctggtgaacc acacagaggc    480
tggggcgagg aggataccat ctgtcagtct tggctggatg acatcatggg aagggggtat    540
agtggggcct tgcaggccag aggtggcttg gaggagcccc tggaaagagg cttaagaggc    600
ccgagtttca cccagtcccc actccacggt gcagctgcgg cttatctctc agcccagcga    660
gatgccagcc ttcctgtccc gggccagcgc tctgacatgc agaaggtgac cctgggcctg    720
cttgtgttcc tggcaggctt tcctgtcctg gacgccaatg acctagaaga taaaaacagt    780
cctttctact atgactggca cagcctccag gttggcgggc tcatctgcgc tggggttctg    840
tgcgccatgg gcatcatcat cgtcatgagt gcaaaatgca aatgcaagtt tggccagaag    900
tccggtcacc atccagggga gactccacct ctcatcaccc caggctcagc ccaaagctga    960
tgaggacaga ccagctgaaa ttgggtggag gaccgttctc tgtccccagg tcctgtctct   1020
gcacagaaac ttgaactcca ggatggaatt cttcctcctc tgctgggact cctttgcatg   1080
```

```
gcagggcctc atctcacctc tcgcaagagg gtctctttgt tcaatttttt ttaatctaaa   1140

atgattgtgc ctctgcccaa gcagcctgga gacttcctat gtgtgcattg gggtggggct   1200

tggggcacca tgagaaggtt ggcgtgccct ggaggctgac acagaggctg gcactgagcc   1260

tgcttgttgg gaaaagccca caggcctgtt cccttgtggc ttgggacatg gcacaggccc   1320

gccctctgcc tcctcagcca tgggaacctc atatgcaatt tgggatttac tagtagccaa   1380

aaggaatgaa agagagctct aaccagatgg aacactggaa cattccagtg gaccctggac   1440

cattccagga aaactgggac ataggatcgt cccgctatga tggaagtgtt cagacagttt   1500

ataatagtaa gcccctgtga ccctctcact taccccgaga cctcacttta ttacaagatc   1560

tttccaaata cccaaatgtc cctgcaagcc cgttaaataa ttccctatgc taccccttaat  1620

aacatacaat gaccacatag tgtgagaact tccaacaagc ctcaaagtcc cttgagactc   1680

cccaatacct aataaggcat gcgaaatgtt ctcatgaact accccacaac acgcctaaaa   1740

ctcaaaacac ccaaaaatat ctcctccaat gtcctgagac atgaacccaa aaagagaccc   1800

acaataaact cgtgacttgt cccctca                                       1827
```

<210> SEQ ID NO 58
<211> LENGTH: 3605
<212> TYPE: DNA
<213> ORGANISM: Homo sapiens

<400> SEQUENCE: 58

```
gtggactagg aggcagccgc ccccaccagc acccactctg tagacccagg cgtctggctc     60

ccagcaccca cggaaagagc ctggctagga aactgcagcc tggtgcctgg cagacagttc    120

tcattctccc cagggcaggg agcaggttat gaccaggact aaggtcccag agtccccacc    180

ctgacccctc cctgctgttc cagccgctcc ctcatatcca cccctgcccc atctcctgac    240

tttggtcacg ctagcatctt ctgctgatcc tgaaattgta ccagcggcaa gatgtggcct    300

ggaaggggac tttaagttct ccacaactgc cagcaatcct tccaccaggc aaaacacatc    360

atctaaggaa aagaagtgag gtttgcttag ggcgtggcag cttcggataa acgcaggact    420

ccgcctggca gcccgatttc tcccggaacc tctgctcagc ctggtgaacc acacagaggc    480

tggggcgagg aggataccat ctgtcagtct tggctggatg acatcatggg aagggggtat    540

agtggggcct tgcaggccag aggtggcttg gaggagcccc tggaaagagg cttaagaggt    600

gagactcaac agccatggcg acagagcata gggctttaag atgaatttgc aggggttaca    660

ggattacaac tgcaatgtgg gctaataata gtgccccctg cattaagctg cagagattga    720

gcgagtaagt gggaagctga gaaaatgccc ccatggggta gacactcaat aagcatctgc    780

tgttattacc aggactcgta tggtcatggg tgacagcttc agaccacagg cagtccacct    840

acaacctgtg cccctatcca ccatgccatc ctgcccaccc acccacgcca gctcccccaa    900

cccccaacac ttttggggat cctaaacact tcctgggcct cagtaatgct ccccaaagcc    960

tcaggctttc ttcccgcaaa aaaaggaaaa gaaatggatg ctccaactaa aattgtgagt   1020

tcagcatgtg gaattaactg ggaagctgag aggattccca ggcctggggt gcgcaggcag   1080

agggaggagt ctgtgccaac ctgcaaggac cacccgcacc gttggttgcg ggcaccaccc   1140

tctctcagca tttttgctgt tcgtgaaatg aggacatagt ggacgacgtc ggggattgct   1200

ggggggttaa gtgagtgaga acacggcaag gtcagtgtgc actccagggc aaggtggagg   1260

aagtgccagc tctcgctatc aaaattataa ctaggccagg cgtggtggct cacacctgta   1320
```

-continued

```
atcccagcac tgagggaggc cggggtgggt ggatcacctg aggtcaggag ttggagacca   1380
gcctggccaa cacagtgaaa ccctggctct accaaaaatg caaaaattag ccgagactgg   1440
tggcacacgc ctgtagtctc agctactcag gaggctgagg caggagaatc acttgaaccc   1500
aggaggcaga ggttgcagtg agctgagatt atgccattgc actccagcct gggtgacaga   1560
gtgaaactcc gcctcaaaaa aaaaaaacaa ttatgataac tatgcactca gcatttgggc   1620
agggacaggg cagggacagg gcaggggagg gcatgctcgg aggccagggc ttggtgcagc   1680
cttgcaggct ggtgagaggg caggactgat gccaggtcag gaaggagaga gaaacgagtt   1740
ccttatgctg agcaggtcta cctgggaaag agaaagtgtt tgctgtcacc aggaactctg   1800
ctgggcctag ggtagggtca ggggctgggc tggggacccc ggctaggcag agccagggct   1860
gggaccggga agggcatggg tgtgggatga ggggcaggag gttcgggggga acagagatgg   1920
agctagggct gcagccagga ggtagagtcc ccctctaccc ccagtcccag cctcacgtca   1980
attcctccac acaccacccc acccccaagc agcttgaaga acctgctcag tcctcagcct   2040
gaagtctgca atgtcctggc agggccgggc aggctctgag cggtctacgg agacactcct   2100
gggaagcggg cctcctgccg cctggctccc aatgccccgc ttccccaaac accccaaggc   2160
cctgacagtc cctagttagg agcagctgct ggggagccag gcctggctta aatcctactt   2220
cctggctaga gcacctagtt tcacctctca gagcctcagt ctccccatct gtccagtgag   2280
aacagtgggc agtggcgccc ttgtttggtt gcggggcgat tcccagaaag cctgaagtcc   2340
atgtccagtg agttattatg gctcctcccg cctcaggccc gagtttcacc cagtccccac   2400
tccacggtgc agctgcggct tatctctcag cccagcgaga tgccagcctt cctgtcccgg   2460
gccagcgctc tgacatgcag aaggtgaccc tgggcctgct tgtgttcctg gcaggctttc   2520
ctgtcctgga cgccaatgac ctagaagata aaaacagtcc tttctactat gactggcaca   2580
gcctccaggt tggcgggctc atctgcgctg gggttctgtg cgccatgggc atcatcatcg   2640
tcatgagtgc aaaatgcaaa tgcaagtttg gccagaagtc cggtcaccat ccaggggaga   2700
ctccacctct catcacccca ggctcagccc aaagctgatg aggacagacc agctgaaatt   2760
gggtggagga ccgttctctg tccccaggtc ctgtctctgc acagaaactt gaactccagg   2820
atggaattct tcctcctctg ctgggactcc tttgcatggc agggcctcat ctcacctctc   2880
gcaagagggt ctctttgttc aatttttttt aatctaaaat gattgtgcct ctgcccaagc   2940
agcctggaga cttcctatgt gtgcattggg gtggggcttg gggcaccatg agaaggttgg   3000
cgtgccctgg aggctgacac agaggctggc actgagcctg cttgttggga aaagcccaca   3060
ggcctgttcc cttgtggctt gggacatggc acaggcccgc cctctgcctc ctcagccatg   3120
ggaacctcat atgcaatttg ggatttacta gtagccaaaa ggaatgaaag agagctctaa   3180
ccagatggaa cactggaaca ttccagtgga ccctggacca ttccaggaaa actgggacat   3240
aggatcgtcc cgctatgatg gaagtgttca gacagtttat aatagtaagc ccctgtgacc   3300
ctctcactta ccccgagacc tcactttatt acaagatctt tccaaatacc caaatgtccc   3360
tgcaagcccg ttaaataatt ccctatgcta cccttaataa catacaatga ccacatagtg   3420
tgagaacttc caacaagcct caaagtccct tgagactccc caatacctaa taaggcatgc   3480
gaaatgttct catgaactac cccacaacac gcctaaaact caaaacaccc aaaaatatct   3540
cctccaatgt cctgagacat gaacccaaaa agagacccac aataaactcg tgacttgtcc   3600
cctca                                                               3605
```

<210> SEQ ID NO 59
<211> LENGTH: 2459
<212> TYPE: DNA
<213> ORGANISM: Homo sapiens

<400> SEQUENCE: 59
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacagaggc 480
tggggcgagg aggataccat ctgtcagtct tggctggatg acatcatggg aagggggtat 540
agtggggcct tgcaggccag aggtggcttg gaggagcccc tggaaagagg cttaagaggt 600
gagactcaac agccatggcg acagagcata gggctttaag atgaatttgc aggggttaca 660
ggattacaac tgcaatgtgg gctaataata gtgccccctg cattaagctg cagagattga 720
gcgagtaagt gggaagctga gaaaatgccc ccatggggta gacactcaat aagcatctgc 780
tgttattacc aggactcgta tggtcatggg tgacagcttc agaccacagg cagtccacct 840
acaacctgtg cccctatcca ccatgccatc ctgcccaccc acccacgcca gctcccccaa 900
cccccaacac ttttggggat cctaaacact tcctgggcct cagtaatgct ccccaaagcc 960
tcaggctttc ttcccgcaaa aaaaggaaaa gaaatggatg ctccaactaa aattgtgagt 1020
tcagcatgtg gaattaactg ggaagctgag aggattccca ggcctggggt gcgcaggcag 1080
agggaggagt ctgtgccaac ctgcaaggac cacccgcacc gttggttgcg ggcaccaccc 1140
tctctcagca tttttgctgt tcgtgaaatg aggacatagt ggacgacgtc ggggattgct 1200
ggggggttaa gtgagtgaga acacggcaag gcccgagttt cacccagtcc ccactccacg 1260
gtgcagctgc ggcttatctc tcagcccagc gagatgccag ccttcctgtc ccgggccagc 1320
gctctgacat gcagaaggtg accctgggcc tgcttgtgtt cctggcaggc tttcctgtcc 1380
tggacgccaa tgacctagaa gataaaaaca gtcctttcta ctatgactgg cacagcctcc 1440
aggttggcgg gctcatctgc gctggggttc tgtgcgccat gggcatcatc atcgtcatga 1500
gtgcaaaatg caaatgcaag tttggccaga agtccggtca ccatccaggg gagactccac 1560
ctctcatcac cccaggctca gcccaaagct gatgaggaca gaccagctga aattgggtgg 1620
aggaccgttc tctgtcccca ggtcctgtct ctgcacagaa acttgaactc caggatggaa 1680
ttcttcctcc tctgctggga ctcctttgca tggcagggcc tcatctcacc tctcgcaaga 1740
gggtctcttt gttcaatttt ttttaatcta aaatgattgt gcctctgccc aagcagcctg 1800
gagacttcct atgtgtgcat tggggtgggg cttggggcac catgagaagg ttggcgtgcc 1860
ctggaggctg acacagaggc tggcactgag cctgcttgtt gggaaaagcc cacaggcctg 1920
ttcccttgtg gcttgggaca tggcacaggc ccgccctctg cctcctcagc catgggaacc 1980
tcatatgcaa tttgggattt actagtagcc aaaaggaatg aaagagagct ctaaccagat 2040
ggaacactgg aacattccag tggaccctgg accattccag gaaaactggg acataggatc 2100
gtcccgctat gatggaagtg ttcagacagt ttataatagt aagcccctgt gaccctctca 2160
cttaccccga gacctcactt tattacaaga tctttccaaa tacccaaatg tccctgcaag 2220
cccgttaaat aattccctat gctaccctta ataacataca atgaccacat agtgtgagaa 2280
cttccaacaa gcctcaaagt cccttgagac tccccaatac ctaataaggc atgcgaaatg 2340
ttctcatgaa ctaccccaca acacgcctaa aactcaaaac acccaaaaat atctcctcca 2400
atgtcctgag acatgaaccc aaaaagagac ccacaataaa ctcgtgactt gtcccctca 2459

<210> SEQ ID NO 60
<211> LENGTH: 3716
<212> TYPE: DNA
<213> ORGANISM: Homo sapiens

<400> SEQUENCE: 60
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacagaggc 480
tggggcgagg aggataccat ctgtcagtct tggctggatg acatcatggg aagggggtat 540
agtggggcct tgcaggccag aggtggcttg gaggagcccc tggaaagagg cttaagaggt 600
gagactcaac agccatggcg acagagcata gggctttaag atgaatttgc aggggttaca 660
ggattacaac tgcaatgtgg gctaataata gtgccccctg cattaagctg cagagattga 720
gcgagtaagt gggaagctga gaaaatgccc ccatggggta gacactcaat aagcatctgc 780
tgttattacc aggactcgta tggtcatggg tgacagcttc agaccacagg cagtccacct 840
acaacctgtg cccctatcca ccatgccatc ctgcccaccc acccacgcca gctcccccaa 900
cccccaacac ttttggggat cctaaacact tcctgggcct cagtaatgct ccccaaagcc 960
tcaggctttc ttcccgcaaa aaaaggaaaa gaaatggatg ctccaactaa aattgtgagt 1020
tcagcatgtg gaattaactg ggaagctgag aggattccca ggcctggggt gcgcaggcag 1080
agggaggagt ctgtgccaac ctgcaaggac cacccgcacc gttggttgcg ggcaccaccc 1140
tctctcagca tttttgctgt tcgtgaaatg aggacatagt ggacgacgtc ggggattgct 1200
ggggggttaa gtgagtgaga acacggcaag gtcagtgtgc actccagggc aaggtggagg 1260
aagtgccagc tctcgctatc aaaattataa ctaggccagg cgtggtggct cacacctgta 1320
atcccagcac tgagggaggc cggggtgggt ggatcacctg aggtcaggag ttggagacca 1380
gcctggccaa cacagtgaaa ccctggctct accaaaaatg caaaaattag ccgagactgg 1440
tggcacacgc ctgtagtctc agctactcag gaggctgagg caggagaatc acttgaaccc 1500
aggaggcaga ggttgcagtg agctgagatt atgccattgc actccagcct gggtgacaga 1560
gtgaaactcc gcctcaaaaa aaaaaaacaa ttatgataac tatgcactca gcatttgggc 1620
agggacaggg cagggacagg gcaggggagg gcatgctcgg aggccagggc ttggtgcagc 1680
cttgcaggct ggtgagaggg caggactgat gccaggtcag gaaggagaga gaaacgagtt 1740
ccttatgctg agcaggtcta cctgggaaag agaaagtgtt tgctgtcacc aggaactctg 1800
ctgggcctag ggtagggtca ggggctgggc tggggacccc ggctaggcag agccagggct 1860

```
gggaccggga agggcatggg tgtgggatga ggggcaggag gttcggggga acagagatgg   1920

agctagggct gcagccagga ggtagagtcc ccctctaccc ccagtcccag cctcacgtca   1980

attcctccac acaccacccc acccccaagc agcttgaaga acctgctcag tcctcagcct   2040

gaagtctgca atgtcctggc agggccgggc aggctctgag cggtctacgg agacactcct   2100

gggaagcggg cctcctgccg cctggctccc aatgccccgc ttccccaaac accccaaggc   2160

cctgacagtc cctagttagg agcagctgct ggggagccag gcctggctta aatcctactt   2220

cctggctaga gcacctagtt tcacctctca gagcctcagt ctccccatct gtccagtgag   2280

aacagtgggc agtggcgccc ttgtttggtt gcggggcgat tcccagaaag cctgaagtcc   2340

atgtccagtg agttattatg gctcctcccg cctcaggccc gagtttcacc cagtccccac   2400

tccacggtgc agctgcggct tatctctcag cccagcgaga tgccagcctt cctgtcccgg   2460

gtgagctgcg caccctgcct ggggagcagg ggaggagggt tggggagcca caggcacagg   2520

gccagcctcc cggtggctct gctaaggccg gacctcccgc cacccctcta ggccagcgct   2580

ctgacatgca gaaggtgacc ctgggcctgc ttgtgttcct ggcaggcttt cctgtcctgg   2640

acgccaatga cctagaagat aaaaacagtc ctttctacta tgactggcac agcctccagg   2700

ttggcgggct catctgcgct ggggttctgt gcgccatggg catcatcatc gtcatgagtg   2760

caaaatgcaa atgcaagttt ggccagaagt ccggtcacca tccaggggag actccacctc   2820

tcatcacccc aggctcagcc caaagctgat gaggacagac cagctgaaat tgggtggagg   2880

accgttctct gtccccaggt cctgtctctg cacagaaact tgaactccag gatggaattc   2940

ttcctcctct gctgggactc ctttgcatgg cagggcctca tctcacctct cgcaagaggg   3000

tctctttgtt caattttttt taatctaaaa tgattgtgcc tctgcccaag cagcctggag   3060

acttcctatg tgtgcattgg ggtggggctt ggggcaccat gagaaggttg gcgtgccctg   3120

gaggctgaca cagaggctgg cactgagcct gcttgttggg aaaagcccac aggcctgttc   3180

ccttgtggct tgggacatgg cacaggcccg ccctctgcct cctcagccat gggaacctca   3240

tatgcaattt gggatttact agtagccaaa aggaatgaaa gagagctcta accagatgga   3300

acactggaac attccagtgg accctggacc attccaggaa aactgggaca taggatcgtc   3360

ccgctatgat ggaagtgttc agacagttta taatagtaag cccctgtgac cctctcactt   3420

accccgagac ctcactttat tacaagatct ttccaaatac ccaaatgtcc ctgcaagccc   3480

gttaaataat tccctatgct acccttaata acatacaatg accacatagt gtgagaactt   3540

ccaacaagcc tcaaagtccc ttgagactcc ccaataccta ataaggcatg cgaaatgttc   3600

tcatgaacta ccccacaaca cgcctaaaac tcaaaacacc caaaaatatc tcctccaatg   3660

tcctgagaca tgaacccaaa aagagaccca caataaactc gtgacttgtc ccctca       3716
```

<210> SEQ ID NO 61
<211> LENGTH: 2956
<212> TYPE: DNA
<213> ORGANISM: Homo sapiens

<400> SEQUENCE: 61

```
gtggactagg aggcagccgc ccccaccagc acccactctg tagacccagg cgtctggctc     60

ccagcaccca cggaaagagc ctggctagga aactgcagcc tggtgcctgg cagacagttc    120

tcattctccc cagggcaggg agcaggttat gaccaggact aaggtcccag agtccccacc    180

ctgacccctc cctgctgttc cagccgctcc ctcatatcca cccctgcccc atctcctgac    240
```

-continued

```
tttggtcacg ctagcatctt ctgctgatcc tgaaattgta ccagcggcaa gatgtggcct    300
ggaaggggac tttaagttct ccacaactgc cagcaatcct tccaccaggc aaaacacatc    360
atctaaggaa aagaagtgag gtttgcttag ggcgtggcag cttcggataa acgcaggact    420
ccgcctggca gcccgatttc tcccggaacc tctgctcagc ctggtgaacc acacagaggc    480
tggggcgagg aggataccat ctgtcagtct tggctggatg acatcatggg aaggggggtat    540
agtggggcct tgcaggccag aggtggcttg gaggagcccc tggaaagagg cttaagaggt    600
gagactcaac agccatggcg acagagcata gggctttaag atgaatttgc aggggttaca    660
ggattacaac tgcaatgtgg gctaataata gtgccccctg cattaagctg cagagattga    720
gcgagtaagt gggaagctga gaaaatgccc ccatggggta gacactcaat aagcatctgc    780
tgttattacc aggactcgta tggtcatggg tgacagcttc agaccacagg cagtccacct    840
acaacctgtg cccctatcca ccatgccatc ctgcccaccc acccacgcca gctcccccaa    900
cccccaacac ttttggggat cctaaacact tcctgggcct cagtaatgct ccccaaagcc    960
tcaggctttc ttcccgcaaa aaaaggaaaa gaaatggatg ctccaactaa aattgtgagt   1020
tcagcatgtg gaattaactg ggaagctgag aggattccca ggcctggggt gcgcaggcag   1080
agggaggagt ctgtgccaac ctgcaaggac cacccgcacc gttggttgcg ggcaccaccc   1140
tctctcagca tttttgctgt tcgtgaaatg aggacatagt ggacgacgtc ggggattgct   1200
ggggggttaa gtgagtgaga acacggcaag gtcagtgtgc actccagggc aaggtggagg   1260
aagtgccagc tctcgctatc aaaattataa ctaggccagg cgtggtggct cacacctgta   1320
atcccagcac tgagggaggc cggggtgggt ggatcacctg aggtcaggag ttggagacca   1380
gcctggccaa cacagtgaaa ccctggctct accaaaaatg caaaaattag ccgagactgg   1440
tggcacacgc ctgtagtctc agctactcag gaggctgagg caggagaatc acttgaaccc   1500
aggaggcaga ggttgcagtg agctgagatt atgccattgc actccagcct gggtgacaga   1560
gtgaaactcc gcctcaaaaa aaaaaaacaa ttatgataac tatgcactca gcatttgggc   1620
agggacaggg cagggacagg gcaggggagg gcatgctcgg aggccagggc ttggtgcagc   1680
cttgcaggct ggtgagaggg caggactgat gccaggtcag gaaggagaga gaaacgagtt   1740
ccttatgctg agcaggtcta cctgggaaag agaaagtgtt tgctgtcacc aggaactctg   1800
ctgggcctag ggccagcgct ctgacatgca gaaggtgacc ctgggcctgc ttgtgttcct   1860
ggcaggcttt cctgtcctgg acgccaatga cctagaagat aaaaacagtc ctttctacta   1920
tgactggcac agcctccagg ttggcgggct catctgcgct ggggttctgt gcgccatggg   1980
catcatcatc gtcatgagtg caaaatgcaa atgcaagttt ggccagaagt ccggtcacca   2040
tccaggggag actccacctc tcatcacccc aggctcagcc caaagctgat gaggacagac   2100
cagctgaaat tgggtggagg accgttctct gtccccaggt cctgtctctg cacagaaact   2160
tgaactccag gatggaattc ttcctcctct gctgggactc ctttgcatgg cagggcctca   2220
tctcacctct cgcaagaggg tctctttgtt caattttttt taatctaaaa tgattgtgcc   2280
tctgcccaag cagcctggag acttcctatg tgtgcattgg ggtggggctt ggggcaccat   2340
gagaaggttg gcgtgccctg gaggctgaca cagaggctgg cactgagcct gcttgttggg   2400
aaaagcccac aggcctgttc ccttgtggct tgggacatgg cacaggcccg ccctctgcct   2460
cctcagccat gggaacctca tatgcaattt gggatttact agtagccaaa aggaatgaaa   2520
gagagctcta accagatgga acactggaac attccagtgg accctggacc attccaggaa   2580
aactgggaca taggatcgtc ccgctatgat ggaagtgttc agacagttta taatagtaag   2640
```

cccctgtgac cctctcactt accccgagac ctcactttat tacaagatct ttccaaatac 2700
ccaaatgtcc ctgcaagccc gttaaataat tccctatgct acccttaata acatacaatg 2760
accacatagt gtgagaactt ccaacaagcc tcaaagtccc ttgagactcc ccaataccta 2820
ataaggcatg cgaaatgttc tcatgaacta ccccacaaca cgcctaaaac tcaaaacacc 2880
caaaaatatc tcctccaatg tcctgagaca tgaacccaaa aagagaccca caataaactc 2940
gtgacttgtc ccctca 2956

<210> SEQ ID NO 62
<211> LENGTH: 1743
<212> TYPE: DNA
<213> ORGANISM: Homo sapiens

<400> SEQUENCE: 62
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacagaggc 480
tggggcgagg aggataccat ctgtcagtct tggctggatg acatcatggg aagggggtat 540
agtggggcct tgcaggccag aggtggcttg gaggagcccc tggaaagagg cttaagaggc 600
cagcgctctg acatgcagaa ggtgaccctg ggcctgcttg tgttcctggc aggctttcct 660
gtcctggacg ccaatgacct agaagataaa aacagtcctt tctactatga ctggcacagc 720
ctccaggttg gcgggctcat ctgcgctggg gttctgtgcg ccatgggcat catcatcgtc 780
atgagtgcaa aatgcaaatg caagtttggc cagaagtccg gtcaccatcc aggggagact 840
ccacctctca tcaccccagg ctcagcccaa agctgatgag gacagaccag ctgaaattgg 900
gtggaggacc gttctctgtc cccaggtcct gtctctgcac agaaacttga actccaggat 960
ggaattcttc ctcctctgct gggactcctt tgcatggcag ggcctcatct cacctctcgc 1020
aagagggtct ctttgttcaa ttttttttaa tctaaaatga ttgtgcctct gcccaagcag 1080
cctggagact tcctatgtgt gcattggggt ggggcttggg gcaccatgag aaggttggcg 1140
tgccctggag gctgacacag aggctggcac tgagcctgct tgttgggaaa agcccacagg 1200
cctgttccct tgtggcttgg gacatggcac aggcccgccc tctgcctcct cagccatggg 1260
aacctcatat gcaatttggg atttactagt agccaaaagg aatgaaagag agctctaacc 1320
agatggaaca ctggaacatt ccagtggacc ctggaccatt ccaggaaaac tgggacatag 1380
gatcgtcccg ctatgatgga agtgttcaga cagtttataa tagtaagccc ctgtgaccct 1440
ctcacttacc ccgagacctc actttattac aagatctttc caaataccca aatgtccctg 1500
caagcccgtt aaataattcc ctatgctacc cttaataaca tacaatgacc acatagtgtg 1560
agaacttcca acaagcctca aagtcccttg agactcccca atacctaata aggcatgcga 1620
aatgttctca tgaactaccc cacaacacgc ctaaaactca aaacacccaa aaatatctcc 1680
tccaatgtcc tgagacatga acccaaaaag agacccacaa taaactcgtg acttgtcccc 1740
tca 1743

<210> SEQ ID NO 63
<211> LENGTH: 1841
<212> TYPE: DNA
<213> ORGANISM: Homo sapiens

<400> SEQUENCE: 63
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacaggtga 480
gcagctgggg ccccttcctc caagccctcc ttgtctctgc ccctaaatta ggaagtatct 540
acctgccccc tgaccctgcc ccatagaagc ttttatgtta aagcgcctaa aatcttgtga 600
aatgcttttc tggagccagg agataaacgg aagtcccttc ccctaatgtc cctttcccca 660
ccattctcct ctcagggact tgttgaacca gctgaggcca gcgctctgac atgcagaagg 720
tgaccctggg cctgcttgtg ttcctggcag gctttcctgt cctggacgcc aatgacctag 780
aagataaaaa cagtcctttc tactatgact ggcacagcct ccaggttggc gggctcatct 840
gcgctggggt tctgtgcgcc atgggcatca tcatcgtcat gagtgcaaaa tgcaaatgca 900
agtttggcca gaagtccggt caccatccag ggagagactcc acctctcatc accccaggct 960
cagcccaaag ctgatgagga cagaccagct gaaattgggt ggaggaccgt tctctgtccc 1020
caggtcctgt ctctgcacag aaacttgaac tccaggatgg aattcttcct cctctgctgg 1080
gactcctttg catggcaggg cctcatctca cctctcgcaa gagggtctct ttgttcaatt 1140
ttttttaatc taaaatgatt gtgcctctgc ccaagcagcc tggagacttc ctatgtgtgc 1200
attggggtgg ggcttggggc accatgagaa ggttggcgtg ccctggaggc tgacacagag 1260
gctggcactg agcctgcttg ttgggaaaag cccacaggcc tgttcccttg tggcttggga 1320
catggcacag gcccgccctc tgcctcctca gccatgggaa cctcatatgc aatttgggat 1380
ttactagtag ccaaaaggaa tgaaagagag ctctaaccag atggaacact ggaacattcc 1440
agtggaccct ggaccattcc aggaaaactg ggacatagga tcgtcccgct atgatggaag 1500
tgttcagaca gtttataata gtaagcccct gtgaccctct cacttacccc gagacctcac 1560
tttattacaa gatctttcca aatacccaaa tgtccctgca agcccgttaa ataattccct 1620
atgctaccct taataacata caatgaccac atagtgtgag aacttccaac aagcctcaaa 1680
gtcccttgag actccccaat acctaataag gcatgcgaaa tgttctcatg aactacccca 1740
caacacgcct aaaactcaaa acacccaaaa atatctcctc caatgtcctg agacatgaac 1800
ccaaaaagag acccacaata aactcgtgac ttgtcccctc a 1841

<210> SEQ ID NO 64
<211> LENGTH: 2145
<212> TYPE: DNA
<213> ORGANISM: Homo sapiens

<400> SEQUENCE: 64

-continued

```
gtggactagg aggcagccgc ccccaccagc acccactctg tagacccagg cgtctggctc     60
ccagcaccca cggaaagagc ctggctagga aactgcagcc tggtgcctgg cagacagttc    120
tcattctccc cagggcaggg agcaggttat gaccaggact aaggtcccag agtccccacc    180
ctgacccctc cctgctgttc cagccgctcc ctcatatcca cccctgcccc atctcctgac    240
tttggtcacg ctagcatctt ctgctgatcc tgaaattgta ccagcggcaa gatgtggcct    300
ggaaggggac tttaagttct ccacaactgc cagcaatcct tccaccaggc aaaacacatc    360
atctaaggaa aagaagtgag gtcggaacac caacgcatca tctcactgca tggccctgga    420
ggctctgccg tttaaagacc ccagaacctt ccccattcaa ggtcctctcc tgggcacagg    480
agattggaga aagctcctcc cttaattcca gggaccgagt tccagcccat ccaattctcc    540
gtctcacctg aggctgctgt ggtcctggtg accccaggga gcaacctgcc gcccatggct    600
ggggaggggg tgaagctgtc tctttaagag caggaatgga gcccctgggc ctcagggcat    660
ctgacttgtt ttctacctgc ccaggtttgc ttagggcgtg gcagcttcgg ataaacgcag    720
gactccgcct ggcagcccga tttctcccgg aacctctgct cagcctggtg aaccacacag    780
gtgagcagct ggggcccctt cctccaagcc ctccttgtct ctgcccctaa attaggaagt    840
atctacctgc cccctgaccc tgccccatag aagcttttat gttaaagcgc ctaaaatctt    900
gtgaaatgct tttctggagc caggagataa acggaagtcc cttcccctaa tgtccctttc    960
cccaccattc tcctctcagg gacttgttga accagctgag gccagcgctc tgacatgcag   1020
aaggtgaccc tgggcctgct tgtgttcctg gcaggctttc ctgtcctgga cgccaatgac   1080
ctagaagata aaaacagtcc tttctactat gactggcaca gcctccaggt tggcgggctc   1140
atctgcgctg gggttctgtg cgccatgggc atcatcatcg tcatgagtgc aaaatgcaaa   1200
tgcaagtttg gccagaagtc cggtcaccat ccaggggaga ctccacctct catcacccca   1260
ggctcagccc aaagctgatg aggacagacc agctgaaatt gggtggagga ccgttctctg   1320
tccccaggtc ctgtctctgc acagaaactt gaactccagg atggaattct tcctcctctg   1380
ctgggactcc tttgcatggc agggcctcat ctcacctctc gcaagagggt ctctttgttc   1440
aatttttttt aatctaaaat gattgtgcct ctgcccaagc agcctggaga cttcctatgt   1500
gtgcattggg gtggggcttg gggcaccatg agaaggttgg cgtgccctgg aggctgacac   1560
agaggctggc actgagcctg cttgttggga aaagcccaca ggcctgttcc cttgtggctt   1620
gggacatggc acaggcccgc cctctgcctc ctcagccatg ggaacctcat atgcaatttg   1680
ggatttacta gtagccaaaa ggaatgaaag agagctctaa ccagatggaa cactggaaca   1740
ttccagtgga ccctggacca ttccaggaaa actgggacat aggatcgtcc cgctatgatg   1800
gaagtgttca gacagtttat aatagtaagc ccctgtgacc ctctcactta ccccgagacc   1860
tcactttatt acaagatctt tccaaatacc caaatgtccc tgcaagcccg ttaaataatt   1920
ccctatgcta cccttaataa catacaatga ccacatagtg tgagaacttc caacaagcct   1980
caaagtccct tgagactccc caatacctaa taaggcatgc gaaatgttct catgaactac   2040
cccacaacac gcctaaaact caaaacaccc aaaaatatct cctccaatgt cctgagacat   2100
gaacccaaaa agagacccac aataaactcg tgacttgtcc cctca                   2145
```

<210> SEQ ID NO 65
<211> LENGTH: 1708
<212> TYPE: DNA
<213> ORGANISM: Homo sapiens

<400> SEQUENCE: 65
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacaggcca 480
gcgctctgac atgcagaagg tgaccctggg cctgcttgtg ttcctggcag gctttcctgt 540
cctggacgcc aatgacctag aagataaaaa cagtcctttc tactatggtg ctccatatat 600
atttgtcaag agaatggggg gacagatgaa gaggacacag gctggcactg aggtcccctc 660
cactttcctc ctagactggc acagcctcca ggttggcggg ctcatctgcg ctggggttct 720
gtgcgccatg ggcatcatca tcgtcatgag tgcaaaatgc aaatgcaagt ttggccagaa 780
gtccggtcac catccagggg agactccacc tctcatcacc ccaggctcag cccaaagctg 840
atgaggacag accagctgaa attgggtgga ggaccgttct ctgtccccag gtcctgtctc 900
tgcacagaaa cttgaactcc aggatggaat tcttcctcct ctgctgggac tcctttgcat 960
ggcagggcct catctcacct ctcgcaagag ggtctctttg ttcaattttt tttaatctaa 1020
aatgattgtg cctctgccca agcagcctgg agacttccta tgtgtgcatt ggggtggggc 1080
ttggggcacc atgagaaggt tggcgtgccc tggaggctga cacagaggct ggcactgagc 1140
ctgcttgttg ggaaaagccc acaggcctgt tcccttgtgg cttgggacat ggcacaggcc 1200
cgccctctgc ctcctcagcc atgggaacct catatgcaat ttgggattta ctagtagcca 1260
aaaggaatga aagagagctc taaccagatg gaacactgga acattccagt ggaccctgga 1320
ccattccagg aaaactggga cataggatcg tcccgctatg atggaagtgt tcagacagtt 1380
tataatagta agcccctgtg accctctcac ttaccccgag acctcacttt attacaagat 1440
ctttccaaat acccaaatgt ccctgcaagc ccgttaaata attccctatg ctacccttaa 1500
taacatacaa tgaccacata gtgtgagaac ttccaacaag cctcaaagtc ccttgagact 1560
ccccaatacc taataaggca tgcgaaatgt tctcatgaac taccccacaa cacgcctaaa 1620
actcaaaaca cccaaaaata tctcctccaa tgtcctgaga catgaaccca aaaagagacc 1680
cacaataaac tcgtgacttg tcccctca 1708

<210> SEQ ID NO 66
<211> LENGTH: 1792
<212> TYPE: DNA
<213> ORGANISM: Homo sapiens

<400> SEQUENCE: 66
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacaggccc 480
gagtttcacc cagtccccac tccacggtgc agctgcggct tatctctcag cccagcgaga 540
tgccagcctt cctgtcccgg gccagcgctc tgacatgcag aaggtgaccc tgggcctgct 600
tgtgttcctg gcaggctttc ctgtcctgga cgccaatgac ctagaagata aaaacagtcc 660
tttctactat ggtgctccat atatatttgt caagagaatg gggggacaga tgaagaggac 720
acaggctggc actgaggtcc cctccacttt cctcctagac tggcacagcc tccaggttgg 780
cgggctcatc tgcgctgggg ttctgtgcgc catgggcatc atcatcgtca tgagtgcaaa 840
atgcaaatgc aagtttggcc agaagtccgg tcaccatcca ggggagactc cacctctcat 900
caccccaggc tcagcccaaa gctgatgagg acagaccagc tgaaattggg tggaggaccg 960
ttctctgtcc ccaggtcctg tctctgcaca gaaacttgaa ctccaggatg gaattcttcc 1020
tcctctgctg ggactccttt gcatggcagg gcctcatctc acctctcgca agagggtctc 1080
tttgttcaat ttttttaat ctaaaatgat tgtgcctctg cccaagcagc ctggagactt 1140
cctatgtgtg cattggggtg gggcttgggg caccatgaga aggttggcgt gccctggagg 1200
ctgacacaga ggctggcact gagcctgctt gttgggaaaa gcccacaggc ctgttccctt 1260
gtggcttggg acatggcaca ggcccgccct ctgcctcctc agccatggga acctcatatg 1320
caatttggga tttactagta gccaaaagga atgaaagaga gctctaacca gatggaacac 1380
tggaacattc cagtggaccc tggaccattc caggaaaact gggacatagg atcgtcccgc 1440
tatgatggaa gtgttcagac agtttataat agtaagcccc tgtgaccctc tcacttaccc 1500
cgagacctca ctttattaca agatctttcc aaatacccaa atgtccctgc aagcccgtta 1560
aataattccc tatgctaccc ttaataacat acaatgacca catagtgtga gaacttccaa 1620
caagcctcaa agtcccttga gactccccaa tacctaataa ggcatgcgaa atgttctcat 1680
gaactacccc acaacacgcc taaaactcaa aacacccaaa aatatctcct ccaatgtcct 1740
gagacatgaa cccaaaaaga gacccacaat aaactcgtga cttgtcccct ca 1792

<210> SEQ ID NO 67
<211> LENGTH: 2660
<212> TYPE: DNA
<213> ORGANISM: Homo sapiens

<400> SEQUENCE: 67
gtggactagg aggcagccgc ccccaccagc acccactctg tagacccagg cgtctggctc 60
ccagcaccca cggaaagagc ctggctagga aactgcagcc tggtgcctgg cagacagttc 120
tcattctccc cagggcaggg agcaggttat gaccaggact aaggtcccag agtccccacc 180
ctgacccctc cctgctgttc cagccgctcc ctcatatcca cccctgcccc atctcctgac 240
tttggtcacg ctagcatctt ctgctgatcc tgaaattgta ccagcggcaa gatgtggcct 300
ggaaggggac tttaagttct ccacaactgc cagcaatcct tccaccaggc aaaacacatc 360
atctaaggaa aagaagtgag gtttgcttag ggcgtggcag cttcggataa acgcaggact 420
ccgcctggca gcccgatttc tcccggaacc tctgctcagc ctggtgaacc acacagaggc 480
tggggcgagg aggataccat ctgtcagtct tggctggatg acatcatggg aagggggtat 540
agtggggcct tgcaggccag aggtggcttg gaggagcccc tggaaagagg cttaagaggt 600
gagactcaac agccatggcg acagagcata gggctttaag atgaatttgc aggggttaca 660
ggattacaac tgcaatgtgg gctaataata gtgccccctg cattaagctg cagagattga 720
gcgagtaagt gggaagctga gaaaatgccc ccatggggta gacactcaat aagcatctgc 780
tgttattacc aggactcgta tggtcatggg tgacagcttc agaccacagg cagtccacct 840
acaacctgtg cccctatcca ccatgccatc ctgcccaccc acccacgcca gctcccccaa 900
cccccaacac ttttggggat cctaaacact tcctgggcct cagtaatgct ccccaaagcc 960
tcaggctttc ttcccgcaaa aaaaggaaaa gaaatggatg ctccaactaa aattgtgagt 1020
tcagcatgtg gaattaactg ggaagctgag aggattccca ggcctggggt gcgcaggcag 1080
agggaggagt ctgtgccaac ctgcaaggac cacccgcacc gttggttgcg ggcaccaccc 1140
tctctcagca tttttgctgt tcgtgaaatg aggacatagt ggacgacgtc ggggattgct 1200
ggggggttaa gtgagtgaga acacggcaag gtcagtgtgc actccagggc aaggtggagg 1260
aagtgccagc tctcgctatc aaaattataa ctaggccagg cgtggtggct cacacctgta 1320
atcccagcac tgagggaggc cggggcccga gtttcaccca gtccccactc cacggtgcag 1380
ctgcggctta tctctcagcc cagcgagatg ccagccttcc tgtcccgggc cagcgctctg 1440
acatgcagaa ggtgaccctg ggcctgcttg tgttcctggc aggctttcct gtcctggacg 1500
ccaatgacct agaagataaa aacagtcctt tctactatgg tgctccatat atatttgtca 1560
agagaatggg gggacagatg aagaggacac aggctggcac tgaggtcccc tccactttcc 1620
tcctagactg gcacagcctc caggttggcg ggctcatctg cgctggggtt ctgtgcgcca 1680
tgggcatcat catcgtcatg agtgcaaaat gcaaatgcaa gtttggccag aagtccggtc 1740
accatccagg ggagactcca cctctcatca ccccaggctc agcccaaagc tgatgaggac 1800
agaccagctg aaattgggtg gaggaccgtt ctctgtcccc aggtcctgtc tctgcacaga 1860
aacttgaact ccaggatgga attcttcctc ctctgctggg actcctttgc atggcagggc 1920
ctcatctcac ctctcgcaag agggtctctt tgttcaattt tttttaatct aaaatgattg 1980
tgcctctgcc caagcagcct ggagacttcc tatgtgtgca ttggggtggg gcttggggca 2040
ccatgagaag gttggcgtgc cctggaggct gacacagagg ctggcactga gcctgcttgt 2100
tgggaaaagc ccacaggcct gttcccttgt ggcttgggac atggcacagg cccgccctct 2160
gcctcctcag ccatgggaac ctcatatgca atttgggatt tactagtagc caaaaggaat 2220
gaaagagagc tctaaccaga tggaacactg gaacattcca gtggaccctg gaccattcca 2280
ggaaaactgg gacataggat cgtcccgcta tgatggaagt gttcagacag tttataatag 2340 taagccccctg tgaccctctc acttaccccg agacctcact ttattacaag atctttccaa 2400
atacccaaat gtccctgcaa gcccgttaaa taattcccta tgctaccctt aataacatac 2460
aatgaccaca tagtgtgaga acttccaaca agcctcaaag tcccttgaga ctccccaata 2520
cctaataagg catgcgaaat gttctcatga actaccccac aacacgccta aaactcaaaa 2580
cacccaaaaa tatctcctcc aatgtcctga gacatgaacc caaaaagaga cccacaataa 2640
actcgtgact tgtcccctca 2660

<210> SEQ ID NO 68
<211> LENGTH: 2015
<212> TYPE: DNA
<213> ORGANISM: Homo sapiens

<400> SEQUENCE: 68
gtggactagg aggcagccgc ccccaccagc acccactctg tagacccagg cgtctggctc 60
ccagcaccca cggaaagagc ctggctagga aactgcagcc tggtgcctgg cagacagttc 120

```
tcattctccc cagggcaggg agcaggttat gaccaggact aaggtcccag agtccccacc    180
ctgacccctc cctgctgttc cagccgctcc ctcatatcca cccctgcccc atctcctgac    240
tttggtcacg ctagcatctt ctgctgatcc tgaaattgta ccagcggcaa gatgtggcct    300
ggaaggggac tttaagttct ccacaactgc cagcaatcct tccaccaggc aaaacacatc    360
atctaaggaa aagaagtgag gtttgcttag ggcgtggcag cttcggataa acgcaggact    420
ccgcctggca gcccgatttc tcccggaacc tctgctcagc ctggtgaacc acacaggcca    480
gcgctctgac atgcagaagg tgaccctggg cctgcttgtg ttcctggcag gctttcctgt    540
cctggacgcc aatgacctag aagataaaaa cagtcctttc tactatgact ggcacagcct    600
ccaggttggc gggctcatct gcgctggggt tctgtgcgcc atgggcatca tcatcgtcat    660
gagtgagtgg aggagctcgg gggagcaggc gggccggggc tggggctccc ctcccctgac    720
cactcagctc tccccaacag gtgcaaaatg caaatgcaag tttggccaga agtccgggta    780
agatactgtt ccggcatgcc cgcctcaggc tgactggacg cttttcaggg tgaaagggct    840
aactctccca gcaggagagg cctcggggct ctgcccttta gagttcctgc cgctaagatt    900
tccaggttta ttgtttctag ctggtaatcc ccagggggcc ccaaatcctg aaatgctttg    960
gcccctggga ttgcacaacc ccccaaatgg aaaggcagcc aggaagacat gtctgggcag   1020
gctaagaacc ctctatccgg agggagaggg caaatggggg cggacaccaa tctcaccact   1080
tttgtctcct tagtcaccat ccaggggaga ctccacctct catcacccca ggctcagccc   1140
aaagctgatg aggacagacc agctgaaatt gggtggagga ccgttctctg tccccaggtc   1200
ctgtctctgc acagaaactt gaactccagg atggaattct tcctcctctg ctgggactcc   1260
tttgcatggc agggcctcat ctcacctctc gcaagagggt ctctttgttc aatttttttt   1320
aatctaaaat gattgtgcct ctgcccaagc agcctggaga cttcctatgt gtgcattggg   1380
gtggggcttg gggcaccatg agaaggttgg cgtgccctgg aggctgacac agaggctggc   1440
actgagcctg cttgttggga aaagcccaca ggcctgttcc cttgtggctt gggacatggc   1500
acaggcccgc cctctgcctc ctcagccatg ggaacctcat atgcaatttg ggatttacta   1560
gtagccaaaa ggaatgaaag agagctctaa ccagatggaa cactggaaca ttccagtgga   1620
ccctggacca ttccaggaaa actgggacat aggatcgtcc cgctatgatg gaagtgttca   1680
gacagtttat aatagtaagc ccctgtgacc ctctcactta ccccgagacc tcactttatt   1740
acaagatctt tccaaatacc caaatgtccc tgcaagcccg ttaaataatt ccctatgcta   1800
cccttaataa catacaatga ccacatagtg tgagaacttc caacaagcct caaagtccct   1860
tgagactccc caatacctaa taaggcatgc gaaatgttct catgaactac cccacaacac   1920
gcctaaaact caaaacaccc aaaaatatct cctccaatgt cctgagacat gaacccaaaa   1980
agagacccac aataaactcg tgacttgtcc cctca                              2015
```

<210> SEQ ID NO 69
<211> LENGTH: 1991
<212> TYPE: DNA
<213> ORGANISM: Homo sapiens

<400> SEQUENCE: 69

```
gtggactagg aggcagccgc ccccaccagc acccactctg tagacccagg cgtctggctc     60
ccagcaccca cggaaagagc ctggctagga aactgcagcc tggtgcctgg cagacagttc    120
tcattctccc cagggcaggg agcaggttat gaccaggact aaggtcccag agtccccacc    180
```

-continued

```
ctgacccctc cctgctgttc cagccgctcc ctcatatcca cccctgcccc atctcctgac    240

tttggtcacg ctagcatctt ctgctgatcc tgaaattgta ccagcggcaa gatgtggcct    300

ggaaggggac tttaagttct ccacaactgc cagcaatcct tccaccaggc aaaacacatc    360

atctaaggaa aagaagtgag gtttgcttag ggcgtggcag cttcggataa acgcaggact    420

ccgcctggca gcccgatttc tcccggaacc tctgctcagc ctggtgaacc acacaggcca    480

gcgctctgac atgcagaagg tgaccctggg cctgcttgtg ttcctggcag gctttcctgt    540

cctggacgcc aatgacctag aagactggca cagcctccag gttggcgggc tcatctgcgc    600

tggggttctg tgcgccatgg gcatcatcat cgtcatgagt gagtggagga gctcggggga    660

gcaggcgggc cggggctggg gctcccctcc cctgaccact cagctctccc caacaggtgc    720

aaaatgcaaa tgcaagtttg gccagaagtc cgggtaagat actgttccgg catgcccgcc    780

tcaggctgac tggacgcttt tcagggtgaa agggctaact ctcccagcag gagaggcctc    840

ggggctctgc cctttagagt tcctgccgct aagatttcca ggtttattgt ttctagctgg    900

taatccccag gggccccaa atcctgaaat gctttggccc ctgggattgc acaaccccc     960

aaatggaaag gcagccagga agacatgtct gggcaggcta agaaccctct atccggaggg   1020

agagggcaaa tgggggcgga caccaatctc accacttttg tctccttagt caccatccag   1080

gggagactcc acctctcatc accccaggct cagcccaaag ctgatgagga cagaccagct   1140

gaaattgggt ggaggaccgt tctctgtccc caggtcctgt ctctgcacag aaacttgaac   1200

tccaggatgg aattcttcct cctctgctgg gactcctttg catggcaggg cctcatctca   1260

cctctcgcaa gagggtctct ttgttcaatt ttttttaatc taaaatgatt gtgcctctgc   1320

ccaagcagcc tggagacttc ctatgtgtgc attggggtgg ggcttggggc accatgagaa   1380

ggttggcgtg ccctggaggc tgacacagag gctggcactg agcctgcttg ttgggaaaag   1440

cccacaggcc tgttcccttg tggcttggga catggcacag gcccgccctc tgcctcctca   1500

gccatgggaa cctcatatgc aatttgggat ttactagtag ccaaaaggaa tgaaagagag   1560

ctctaaccag atggaacact ggaacattcc agtggaccct ggaccattcc aggaaaactg   1620

ggacatagga tcgtcccgct atgatggaag tgttcagaca gtttataata gtaagcccct   1680

gtgaccctct cacttacccc gagacctcac tttattacaa gatctttcca aatacccaaa   1740

tgtccctgca agcccgttaa ataattccct atgctaccct taataacata caatgaccac   1800

atagtgtgag aacttccaac aagcctcaaa gtcccttgag actccccaat acctaataag   1860

gcatgcgaaa tgttctcatg aactacccca caacacgcct aaaactcaaa acacccaaaa   1920

atatctcctc caatgtcctg agacatgaac ccaaaaagag acccacaata aactcgtgac   1980

ttgtcccctc a                                                        1991
```

<210> SEQ ID NO 70
<211> LENGTH: 87
<212> TYPE: PRT
<213> ORGANISM: Homo sapiens

<400> SEQUENCE: 70

```
Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Asp Trp His Ser Leu Gln Val Gly Gly Leu Ile Cys Ala Gly Val Leu
        35                  40                  45
```

```
Cys Ala Met Gly Ile Ile Ile Val Met Ser Ala Lys Cys Lys Cys Lys
    50                  55                  60

Phe Gly Gln Lys Ser Gly His His Pro Gly Glu Thr Pro Pro Leu Ile
65                  70                  75                  80

Thr Pro Gly Ser Ala Gln Ser
                85


<210> SEQ ID NO 71
<211> LENGTH: 113
<212> TYPE: PRT
<213> ORGANISM: Homo sapiens

<400> SEQUENCE: 71

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Asp Trp His Ser Leu Gln Val Gly Gly Leu Ile Cys Ala Gly Val Leu
        35                  40                  45

Cys Ala Met Gly Ile Ile Ile Val Met Ser Glu Trp Arg Ser Ser Gly
    50                  55                  60

Glu Gln Ala Gly Arg Gly Trp Gly Ser Pro Pro Leu Thr Thr Gln Leu
65                  70                  75                  80

Ser Pro Thr Gly Ala Lys Cys Lys Cys Lys Phe Gly Gln Lys Ser Gly
                85                  90                  95

His His Pro Gly Glu Thr Pro Pro Leu Ile Thr Pro Gly Ser Ala Gln
            100                 105                 110

Ser


<210> SEQ ID NO 72
<211> LENGTH: 116
<212> TYPE: PRT
<213> ORGANISM: Homo sapiens

<400> SEQUENCE: 72

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Gly Ala Pro Tyr Ile Phe Val Lys Arg Met Gly Gly Gln Met Lys Arg
        35                  40                  45

Thr Gln Ala Gly Thr Glu Val Pro Ser Thr Phe Leu Leu Asp Trp His
    50                  55                  60

Ser Leu Gln Val Gly Gly Leu Ile Cys Ala Gly Val Leu Cys Ala Met
65                  70                  75                  80

Gly Ile Ile Ile Val Met Ser Ala Lys Cys Lys Cys Lys Phe Gly Gln
                85                  90                  95

Lys Ser Gly His His Pro Gly Glu Thr Pro Pro Leu Ile Thr Pro Gly
            100                 105                 110

Ser Ala Gln Ser
        115


<210> SEQ ID NO 73
<211> LENGTH: 96
<212> TYPE: PRT
<213> ORGANISM: Homo sapiens

<400> SEQUENCE: 73
```

Met Gln Lys Val Thr Leu Gly Leu Leu Val Phe Leu Ala Gly Phe Pro
1 5 10 15

Val Leu Asp Ala Asn Asp Leu Glu Asp Lys Asn Ser Pro Phe Tyr Tyr
20 25 30

Asp Trp His Ser Leu Gln Val Gly Gly Leu Ile Cys Ala Gly Val Leu
35 40 45

Cys Ala Met Gly Ile Ile Ile Val Met Ser Glu Trp Arg Ser Ser Gly
50 55 60

Glu Gln Ala Gly Arg Gly Trp Gly Ser Pro Pro Leu Thr Thr Gln Leu
65 70 75 80

Ser Pro Thr Gly Ala Lys Cys Lys Cys Lys Phe Gly Gln Lys Ser Gly
85 90 95

<210> SEQ ID NO 74
<211> LENGTH: 88
<212> TYPE: PRT
<213> ORGANISM: Homo sapiens

<400> SEQUENCE: 74

Met Gln Lys Val Thr Leu Gly Leu Leu Val Phe Leu Ala Gly Phe Pro
1 5 10 15

Val Leu Asp Ala Asn Asp Leu Glu Asp Trp His Ser Leu Gln Val Gly
20 25 30

Gly Leu Ile Cys Ala Gly Val Leu Cys Ala Met Gly Ile Ile Ile Val
35 40 45

Met Ser Glu Trp Arg Ser Ser Gly Glu Gln Ala Gly Arg Gly Trp Gly
50 55 60

Ser Pro Pro Leu Thr Thr Gln Leu Ser Pro Thr Gly Ala Lys Cys Lys
65 70 75 80

Cys Lys Phe Gly Gln Lys Ser Gly
85

<210> SEQ ID NO 75
<211> LENGTH: 139
<212> TYPE: PRT
<213> ORGANISM: Homo sapiens

<400> SEQUENCE: 75

Leu Leu Val Thr Val Gln His Thr Glu Arg Tyr Val Thr Leu Phe Ala
1 5 10 15

Ser Ile Ile Leu Lys Cys Asp Tyr Thr Thr Ser Ala Gln Leu Gln Asp
20 25 30

Val Val Val Thr Trp Arg Phe Lys Ser Phe Cys Lys Asp Pro Ile Phe
35 40 45

Asp Tyr Tyr Ser Ala Ser Tyr Gln Ala Ala Leu Ser Leu Gly Gln Asp
50 55 60

Pro Ser Asn Asp Cys Asn Asp Asn Gln Arg Glu Val Arg Ile Val Ala
65 70 75 80

Gln Arg Arg Gly Gln Asn Glu Pro Val Leu Gly Val Asp Tyr Arg Gln
85 90 95

Arg Lys Ile Thr Ile Gln Asn Arg Ala Asp Leu Val Ile Asn Glu Val
100 105 110

Met Trp Trp Asp His Gly Val Tyr Tyr Cys Thr Ile Glu Ala Pro Gly
115 120 125

Asp Thr Ser Gly Asp Pro Asp Lys Glu Val Lys
130 135

<210> SEQ ID NO 76
<211> LENGTH: 434
<212> TYPE: PRT
<213> ORGANISM: Homo sapiens

<400> SEQUENCE: 76

```
Leu Leu Val Thr Val Gln His Thr Glu Arg Tyr Val Thr Leu Phe Ala
1               5                   10                  15

Ser Ile Ile Leu Lys Cys Asp Tyr Thr Thr Ser Ala Gln Leu Gln Asp
            20                  25                  30

Val Val Val Thr Trp Arg Phe Lys Ser Phe Cys Lys Asp Pro Ile Phe
        35                  40                  45

Asp Tyr Tyr Ser Ala Ser Tyr Gln Ala Ala Leu Ser Leu Gly Gln Asp
    50                  55                  60

Pro Ser Asn Asp Cys Asn Asp Asn Gln Arg Glu Val Arg Ile Val Ala
65                  70                  75                  80

Gln Arg Arg Gly Gln Asn Glu Pro Val Leu Gly Val Asp Tyr Arg Gln
                85                  90                  95

Arg Lys Ile Thr Ile Gln Asn Pro Leu Ala Arg His Arg Tyr Met Lys
            100                 105                 110

Gln Ala Gln Ala Leu Gly Pro Gln Met Met Gly Lys Pro Leu Tyr Trp
        115                 120                 125

Gly Ala Asp Arg Ser Ser Gln Val Ser Ser Tyr Pro Met His Pro Leu
    130                 135                 140

Leu Gln Arg Asp Leu Ser Leu Pro Ser Ser Leu Pro Gln Met Pro Met
145                 150                 155                 160

Thr Gln Thr Thr Asn Gln Pro Pro Ile Ala Asn Gly Val Leu Glu Tyr
                165                 170                 175

Leu Glu Lys Glu Leu Arg Asn Leu Asn Leu Ala Gln Pro Leu Pro Pro
            180                 185                 190

Asp Leu Lys Gly Arg Phe Gly His Pro Cys Ser Met Leu Ser Ser Leu
        195                 200                 205

Gly Ser Glu Val Val Glu Arg Arg Ile Ile His Leu Pro Pro Leu Ile
    210                 215                 220

Arg Asp Leu Ser Ser Ser Arg Arg Thr Ser Asp Ser Leu His Gln Gln
225                 230                 235                 240

Trp Leu Thr Pro Ile Pro Ser Arg Pro Trp Asp Leu Arg Glu Gly Arg
                245                 250                 255

Ser His His His Tyr Pro Asp Phe His Gln Glu Leu Gln Asp Arg Gly
            260                 265                 270

Pro Lys Ser Trp Ala Leu Glu Arg Arg Glu Leu Asp Pro Ser Trp Ser
        275                 280                 285

Gly Arg His Arg Ser Ser Arg Leu Asn Gly Ser Pro Ile His Trp Ser
    290                 295                 300

Asp Arg Asp Ser Leu Ser Asp Val Pro Ser Ser Ser Glu Ala Arg Trp
305                 310                 315                 320

Arg Pro Ser His Pro Pro Phe Arg Ser Arg Cys Gln Glu Arg Pro Arg
                325                 330                 335

Arg Pro Ser Pro Arg Glu Ser Thr Gln Arg His Gly Arg Arg Arg Arg
            340                 345                 350

His Arg Ser Tyr Ser Pro Pro Leu Pro Ser Gly Leu Ser Ser Trp Ser
        355                 360                 365

Ser Glu Glu Asp Lys Glu Arg Gln Pro Gln Ser Trp Arg Ala His Arg
```

-continued

```
    370                 375                 380

Arg Gly Ser His Ser Pro His Trp Pro Glu Glu Lys Pro Pro Ser Tyr
385                 390                 395                 400

Arg Ser Leu Asp Ile Thr Pro Gly Lys Asn Ser Arg Lys Lys Gly Ser
                405                 410                 415

Val Glu Arg Arg Ser Glu Lys Asp Ser Ser His Ser Gly Arg Ser Val
            420                 425                 430

Val Ile


<210> SEQ ID NO 77
<211> LENGTH: 996
<212> TYPE: DNA
<213> ORGANISM: Homo sapiens

<400> SEQUENCE: 77

atgcagaagg tgaccctggg cctgcttgtg ttcctggcag gctttcctgt cctggacgcc      60

aatgacctag aagataaaaa cagtcctttc tactatgact ggcacagcct ccaggttggc     120

gggctcatct gcgctggggt tctgtgcgcc atgggcatca tcatcgtcat gagtgcaaaa     180

tgcaaatgca agtttggcca gaagtccggt caccatccag ggagactccc acctctcatc     240

accccaggct cagcccaaag cggaccggtc gccaccatgg tgagcaaggg cgaggagctg     300

ttcaccgggg tggtgcccat cctggtcgag ctggacggcg acgtaaacgg ccacaagttc     360

agcgtgtccg gcgagggcga gggcgatgcc acctacggca agctgaccct gaagttcatc     420

tgcaccaccg gcaagctgcc cgtgccctgg cccaccctcg tgaccaccct gacctacggc     480

gtgcagtgct tcagccgcta ccccgaccac atgaagcagc acgacttctt caagtccgcc     540

atgcccgaag gctacgtcca ggagcgcacc atcttcttca aggacgacgg caactacaag     600

acccgcgccg aggtgaagtt cgagggcgac accctggtga accgcatcga gctgaagggc     660

atcgacttca aggaggacgg caacatcctg gggcacaagc tggagtacaa ctacaacagc     720

cacaacgtct atatcatggc cgacaagcag aagaacggca tcaaggtgaa cttcaagatc     780

cgccacaaca tcgaggacgg cagcgtgcag ctcgccgacc actaccagca gaacaccccc     840

atcggcgacg gccccgtgct gctgcccgac aaccactacc tgagcaccca gtccgccctg     900

agcaaagacc ccaacgagaa gcgcgatcac atggtcctgc tggagttcgt gaccgccgcc     960

gggatcactc tcggcatgga cgagctgtac aagtaa                               996


<210> SEQ ID NO 78
<211> LENGTH: 1083
<212> TYPE: DNA
<213> ORGANISM: Homo sapiens

<400> SEQUENCE: 78

atgcagaagg tgaccctggg cctgcttgtg ttcctggcag gctttcctgt cctggacgcc      60

aatgacctag aagataaaaa cagtcctttc tactatggtg ctccatatat atttgtcaag     120

agaatggggg gacagatgaa gaggacacag gctggcactg aggtccccctc cactttcctc    180

ctagactggc acagcctcca ggttggcggg ctcatctgcg ctggggttct gtgcgccatg     240

ggcatcatca tcgtcatgag tgcaaaatgc aaatgcaagt ttggccagaa gtccggtcac     300

catccagggg agactccacc tctcatcacc ccaggctcag cccaaagcgg accggtcgcc     360

accatggtga gcaagggcga ggagctgttc accggggtgg tgcccatcct ggtcgagctg     420

gacggcgacg taaacggcca caagttcagc gtgtccggcg agggcgaggg cgatgccacc     480
```

```
tacggcaagc tgaccctgaa gttcatctgc accaccggca agctgcccgt gccctggccc    540

accctcgtga ccaccctgac ctacggcgtg cagtgcttca gccgctaccc cgaccacatg    600

aagcagcacg acttcttcaa gtccgccatg cccgaaggct acgtccagga gcgcaccatc    660

ttcttcaagg acgacggcaa ctacaagacc cgcgccgagg tgaagttcga gggcgacacc    720

ctggtgaacc gcatcgagct gaagggcatc gacttcaagg aggacggcaa catcctgggg    780

cacaagctgg agtacaacta caacagccac aacgtctata tcatggccga caagcagaag    840

aacggcatca aggtgaactt caagatccgc cacaacatcg aggacggcag cgtgcagctc    900

gccgaccact accagcagaa cacccccatc ggcgacggcc ccgtgctgct gcccgacaac    960

cactacctga gcacccagtc cgccctgagc aaagacccca acgagaagcg cgatcacatg   1020

gtcctgctgg agttcgtgac cgccgccggg atcactctcg gcatggacga gctgtacaag   1080

taa                                                                 1083
```

<210> SEQ ID NO 79
<211> LENGTH: 1371
<212> TYPE: DNA
<213> ORGANISM: Homo sapiens

<400> SEQUENCE: 79

```
atgaggcctc tgcccagcgg gaggaggaag acccgaggca tctccctagg actcttcgcc     60

ctctgcctgg ccgcagcccg ctgtctgcag agtcagggtg tgtccctata cattcctcag    120

gccaccatca atgccactgt caaagaagac atcctgctct cagttgagta ctcctgtcat    180

ggagtgccca ccatcgaatg gacatattca tccaattggg gaacgcagaa gatcgtggag    240

tggaaaccag ggactcaggc caacatctct caaagccaca aggacagagt ctgcaccttt    300

gacaacggct ccatccagct cttcagcgtg ggagtgaggg attccggcta ctatgtcatc    360

accgtgacgg agcgcctggg gagcagccag tttggcacca tcgtgctgca cgtctctgag    420

atcctctatg aagacctgca ctttgtcgct gtcatccttg cttttctcgc tgctgtggcc    480

gcagtattaa tcagcctcat gtgggtttgt aataagtgtg catataaatt tcagaggaag    540

agaagacaca aactcaaaga aagcacaact gaggagattg agctggaaga tgttgagtgt    600

cgaattctgc agtcgacggt accgcgggcc cgggatccac cggtcgccac catggtgagc    660

aagggcgagg agctgttcac cggggtggtg cccatcctgg tcgagctgga cggcgacgta    720

aacggccaca agttcagcgt gtccggcgag ggcgagggcg atgccaccta cggcaagctg    780

accctgaagt tcatctgcac caccggcaag ctgcccgtgc cctggcccac cctcgtgacc    840

accctgacct acggcgtgca gtgcttcagc cgctaccccg accacatgaa gcagcacgac    900

ttcttcaagt ccgccatgcc cgaaggctac gtccaggagc gcaccatctt cttcaaggac    960

gacggcaact acaagacccg cgccgaggtg aagttcgagg gcgacaccct ggtgaaccgc   1020

atcgagctga agggcatcga cttcaaggag gacggcaaca tcctggggca caagctggag   1080

tacaactaca acagccacaa cgtctatatc atggccgaca agcagaagaa cggcatcaag   1140

gtgaacttca agatccgcca caacatcgag gacggcagcg tgcagctcgc cgaccactac   1200

cagcagaaca cccccatcgg cgacggcccc gtgctgctgc ccgacaacca ctacctgagc   1260

acccagtccg ccctgagcaa agaccccaac gagaagcgcg atcacatggt cctgctggag   1320

ttcgtgaccg ccgccgggat cactctcggc atggacgagc tgtacaagta a            1371
```

<210> SEQ ID NO 80
<211> LENGTH: 1332

<212> TYPE: DNA
<213> ORGANISM: Homo sapiens

<400> SEQUENCE: 80
atgaggcctc tgcccagcgg gaggaggaag acccgaggca tctccctagg actcttcgcc 60
ctctgcctgg ccgcagcccg ctgtctacag agtcagggtg tgtccctata cattcctcag 120
gccaccatca atgccactgt caaagaagac atcctgctct cagttgagta ctcctgtcat 180
ggagtgccca ccatcgaatg gacatattca tccaattggg gaacgcagaa gatcgtggag 240
tggaaaccag ggactcaggc caacatctct caaagccaca aggacagagt ctgcaccttt 300
gacaacggct ccatccagct cttcagcgtg ggagtgaggg attccggcta ctatgtcatc 360
accgtgacgg agcgcctggg gagcagccag tttggcacca tcgtgctgca cgtctctgag 420
atcctctatg aagacctgca ctttgtcgct gtcatccttg cttttctcgc tgctgtggcc 480
gcagtattaa tcagcctcat gtgggtttgt aataagtgtg catataaatt tcagaggaag 540
agaagacaca aactcaaagg taacccccctg ggccttgtga taatccatga gtggtttgga 600
ccggtcgcca ccatggtgag caagggcgag gagctgttca ccggggtggt gcccatcctg 660
gtcgagctgg acggcgacgt aaacggccac aagttcagcg tgtccggcga gggcgagggc 720
gatgccacct acggcaagct gaccctgaag ttcatctgca ccaccggcaa gctgcccgtg 780
ccctggccca ccctcgtgac caccctgacc tacggcgtgc agtgcttcag ccgctacccc 840
gaccacatga agcagcacga cttcttcaag tccgccatgc ccgaaggcta cgtccaggag 900
cgcaccatct tcttcaagga cgacggcaac tacaagaccc gcgccgaggt gaagttcgag 960
ggcgacaccc tggtgaaccg catcgagctg aagggcatcg acttcaagga ggacggcaac 1020
atcctggggc acaagctgga gtacaactac aacagccaca acgtctatat catggccgac 1080
aagcagaaga acggcatcaa ggtgaacttc aagatccgcc acaacatcga ggacggcagc 1140
gtgcagctcg ccgaccacta ccagcagaac acccccatcg gcgacggccc cgtgctgctg 1200
cccgacaacc actacctgag cacccagtcc gccctgagca aagaccccaa cgagaagcgc 1260
gatcacatgg tcctgctgga gttcgtgacc gccgccggga tcactctcgg catggacgag 1320
ctgtacaagt aa 1332

<210> SEQ ID NO 81
<211> LENGTH: 1533
<212> TYPE: DNA
<213> ORGANISM: Homo sapiens

<400> SEQUENCE: 81
atggataggg tcttgctgag gtggatttct ctcttctggc taacagccat ggtcgaaggc 60
cttcaggtca cagtgcccga caagaagaag gtggccatgc tcttccagcc cactgtgctt 120
cgctgccact tctcaacatc ctcccatcag cctgcagttg tgcagtggaa gttcaagtcc 180
tactgccagg atcgcatggg agaatccttg ggcatgtcct ctacccgggc ccaatctctc 240
agcaagagaa acctggaatg ggacccctac ttggattgtt tggacagcag gaggactgtt 300
cgagtagtag cttcaaaaca gggctcgact gtcaccctgg gagatttcta caggggcaga 360
gagatcacga ttgttcatga tgcagatctt caaattggaa agcttatgtg gggagacagc 420
ggactctatt actgtattat caccacccca gatgacctgg aggggaaaaa tgaggactca 480
gtggaactgc tggtgttggg caggacaggg ctgcttgctg atctcttgcc cagttttgct 540
gtggagatta tgccagagtg ggtgtttgtt ggcctggtgc tcctgggcgt cttcctcttc 600

-continued ttcgtcctgg tggggatctg ctggtgccag tgctgccctc acagctgctg ctgctatgtc 660
cgctgcccat gctgcccaga ttcctgctgc tgccctcaag cctgtgagta cagtgaccgc 720
tggggagaca gagcgatcga gagaaatgtc tacctctcta cccgaattct gcagtcgacg 780
gtaccgcggg cccgggatcc accggtcgcc accatggtga gcaagggcga ggagctgttc 840
accggggtgg tgcccatcct ggtcgagctg gacggcgacg taaacggcca caagttcagc 900
gtgtccggcg agggcgaggg cgatgccacc tacggcaagc tgaccctgaa gttcatctgc 960
accaccggca agctgcccgt gccctggccc accctcgtga ccaccctgac ctacggcgtg 1020
cagtgcttca gccgctaccc cgaccacatg aagcagcacg acttcttcaa gtccgccatg 1080
cccgaaggct acgtccagga gcgcaccatc ttcttcaagg acgacggcaa ctacaagacc 1140
cgcgccgagg tgaagttcga gggcgacacc ctggtgaacc gcatcgagct gaagggcatc 1200
gacttcaagg aggacggcaa catcctgggg cacaagctgg agtacaacta caacagccac 1260
aacgtctata tcatggccga caagcagaag aacggcatca aggtgaactt caagatccgc 1320
cacaacatcg aggacggcag cgtgcagctc gccgaccact accagcagaa cacccccatc 1380
ggcgacggcc ccgtgctgct gcccgacaac cactacctga gcacccagtc cgccctgagc 1440
aaagacccca acgagaagcg cgatcacatg gtcctgctgg agttcgtgac cgccgccggg 1500
atcactctcg gcatggacga gctgtacaag taa 1533

<210> SEQ ID NO 82
<211> LENGTH: 2085
<212> TYPE: DNA
<213> ORGANISM: Homo sapiens

<400> SEQUENCE: 82
atgtggctca aggtcttcac aactttcctt tcctttgcaa caggtgcttg ctcggggctg 60
aaggtgacag tgccatcaca cactgtccat ggcgtcagag gtcaggccct ctacctaccc 120
gtccactatg gcttccacac tccagcatca gacatccaga tcatatggct atttgagaga 180
ccccacacaa tgcccaaata cttactgggc tctgtgaata agtctgtggt tcctgacttg 240
gaataccaac acaagttcac catgatgcca cccaatgcat ctctgcttat caacccactg 300
cagttccctg atgaaggcaa ttacatcgtg aaggtcaaca ttcagggaaa tggaactcta 360
tctgccagtc agaagataca agtcacggtt gatgatcctg tcacaaagcc agtggtgcag 420
attcatcctc cctctggggc tgtggagtat gtggggaaca tgaccctgac atgccatgtg 480
gaagggggca ctcggctagc ttaccaatgg ctaaaaaatg ggagacctgt ccacaccagc 540
tccacctact ccttttctcc ccaaaacaat acccttcata ttgctccagt aaccaaggaa 600
gacattggga attacagctg cctggtgagg aaccctgtca gtgaaatgga aagtgatatc 660
attatgccca tcatatatta tggaccttat ggacttcaag tgaattctga taaagggcta 720
aaagtagggg aagtgtttac tgttgacctt ggagaggcca tcctatttga ttgttctgct 780
gattctcatc cccccaacac ctactcctgg attaggagga ctgacaatac tacatatatc 840
attaagcatg ggcctcgctt agaagttgca tctgagaaag tagcccagaa gacaatggac 900
tatgtgtgct gtgcttacaa caacataacc ggcaggcaag atgaaactca tttcacagtt 960
atcatcactt ccgtaggact ggagaagctt gcacagaaag gaaaatcatt gtcaccttta 1020
gcaagtataa ctggaatatc actatttttg attatatcca tgtgtcttct cttcctatgg 1080
aaaaaatatc aaccctacaa agttataaaa cagaaactag aaggcaggcc agaaacagaa 1140
tacaggaaag ctcaaacatt ttcaggccat gaagatgctc tggatgactt cggaatatat 1200
gaatttgttg cttttccaga tgtttctggt gtttccagga tcccaagcag gtctgttcca 1260
gcctctgatt gtgtatcggg gcaagatttg cacagtacag tgtatgaagt tattcagcac 1320
atccctgccc agcagcaaga ccatccagag ggaccggtcg ccaccatggt gagcaagggc 1380
gaggagctgt tcaccggggt ggtgcccatc ctggtcgagc tggacggcga cgtaaacggc 1440
cacaagttca gcgtgtccgg cgagggcgag ggcgatgcca cctacggcaa gctgaccctg 1500
aagttcatct gcaccaccgg caagctgccc gtgccctggc ccaccctcgt gaccaccctg 1560
acctacggcg tgcagtgctt cagccgctac cccgaccaca tgaagcagca cgacttcttc 1620
aagtccgcca tgcccgaagg ctacgtccag gagcgcacca tcttcttcaa ggacgacggc 1680
aactacaaga cccgcgccga ggtgaagttc gagggcgaca ccctggtgaa ccgcatcgag 1740
ctgaagggca tcgacttcaa ggaggacggc aacatcctgg ggcacaagct ggagtacaac 1800
tacaacagcc acaacgtcta tatcatggcc gacaagcaga agaacggcat caaggtgaac 1860
ttcaagatcc gccacaacat cgaggacggc agcgtgcagc tcgccgacca ctaccagcag 1920
aacaccccca tcggcgacgg ccccgtgctg ctgcccgaca accactacct gagcacccag 1980
tccgccctga gcaaagaccc caacgagaag cgcgatcaca tggtcctgct ggagttcgtg 2040
accgccgccg ggatcactct cggcatggac gagctgtaca agtaa 2085

<210> SEQ ID NO 83
<211> LENGTH: 2373
<212> TYPE: DNA
<213> ORGANISM: Homo sapiens

<400> SEQUENCE: 83
atggcatggc ccaaactgcc cgcaccttgg ctgctgctct gcacctggct cccagcaggg 60
tgcctgtcct tgcttgtgac ggtccagcac acagaacgct atgtcaccct gtttgcctct 120
atcatcctca aatgtgacta caccacctct gcccagctcc aggacgtggt ggtgacatgg 180
cgcttcaagt ccttctgcaa ggaccctatc tttgactact actcagcgtc ataccaggca 240
gctttatccc tgggccagga cccatccaat gactgcaacg acaaccagcg ggaagttcgc 300
atagtggccc agcggcgggg gcagaatgag cccgtgctgg gggtagatta ccggcagcgc 360
aagatcacca tccagaaccg agcagatctc gtgataaatg aagtgatgtg gtgggaccat 420
ggagtgtatt actgcaccat tgaggctcca ggggacacat caggagaccc cgataaggaa 480
gtaaagctca tcgtcctaca ctggctgaca gtgatcttca tcatcctggg agccctcctc 540
ctcctgctgc tgattggagt gtgctggtgc cagtgctgtc ctcagtattg ctgctgctat 600
atccgctgtc cctgctgtcc tgcccactgc tgctgtcctg aggaagccct ggcccgccac 660
cgctacatga agcaggccca ggccctaggt cctcagatga tgggaaaacc cctgtactgg 720
ggggcggaca ggagctccca ggtttcatct tatccaatgc acccgctgct gcagcgagat 780
ttgtccctgc ggtccagcct cccgcagatg ccaatgaccc agaccaccaa tcagcctccc 840
atcgccaatg gtgtcctgga gtatttggag aaagaactgc ggaacctcaa cctggcccag 900
cctctgcccc ctgacctcaa aggcagattt ggccatccct gcagcatgct gtcctccctg 960
ggctctgagg tcgtggaacg cagaatcatc cacctgcccc cactgatcag agacctgtca 1020
tcctcaagga ggaccagtga ctccctgcac cagcagtggc tcaccccaat tccctccagg 1080
ccctgggatc tgagggaggg gagaagccac caccattacc ctgatttcca ccaggagctc 1140
caggaccggg ggccaaagtc ttgggcattg gaaagaaggg agttggaccc atcgtggagt 1200

```
ggaaggcacc gtagctctag gctgaatggg tcacccatac actggtcaga cagggacagc   1260
ctaagcgatg tcccctcatc cagtgaggca cgctggcggc cgagccaccc tcctttcagg   1320
agccgctgtc aggagaggcc ccgcaggccc agcccccggg agagcactca gaggcacggg   1380
agacgacgca ggcaccgcag ctactctcct cccttgccct ccggcctcag ttcctggagc   1440
tctgaagagg acaaggagag gcagccccag agctggcggg cccaccgccg cggctcgcac   1500
tccccacact ggcccgagga gaagccgcct agctaccgct cactggatat cactccaggc   1560
aagaatagca ggaaaaaagg gagtgtggag aggcgctcgg agaaagacag ctctcatagt   1620
ggaaggagtg tggtcattgg accggtcgcc accatggtga gcaagggcga ggagctgttc   1680
accggggtgg tgcccatcct ggtcgagctg gacggcgacg taaacggcca caagttcagc   1740
gtgtccggcg agggcgaggg cgatgccacc tacggcaagc tgaccctgaa gttcatctgc   1800
accaccggca agctgcccgt gccctggccc accctcgtga ccaccctgac ctacggcgtg   1860
cagtgcttca gccgctaccc cgaccacatg aagcagcacg acttcttcaa gtccgccatg   1920
cccgaaggct acgtccagga gcgcaccatc ttcttcaagg acgacggcaa ctacaagacc   1980
cgcgccgagg tgaagttcga gggcgacacc ctggtgaacc gcatcgagct gaagggcatc   2040
gacttcaagg aggacggcaa catcctgggg cacaagctgg agtacaacta caacagccac   2100
aacgtctata tcatggccga caagcagaag aacggcatca aggtgaactt caagatccgc   2160
cacaacatcg aggacggcag cgtgcagctc gccgaccact accagcagaa cacccccatc   2220
ggcgacggcc ccgtgctgct gcccgacaac cactacctga gcacccagtc cgccctgagc   2280
aaagacccca acgagaagcg cgatcacatg gtcctgctgg agttcgtgac cgccgccggg   2340
atcactctcg gcatggacga gctgtacaag taa                                2373
```

<210> SEQ ID NO 84
<211> LENGTH: 2241
<212> TYPE: DNA
<213> ORGANISM: Homo sapiens

<400> SEQUENCE: 84

```
atggcatggc ccaaactgcc cgcaccttgg ctgctgctct gcacctggct cccagcaggg     60
tgcctgtcct tgcttgtgac ggtccagcac acagaacgct atgtcaccct gtttgcctct    120
atcatcctca aatgtgacta caccacctct gcccagctcc aggacgtggt ggtgacatgg    180
cgcttcaagt ccttctgcaa ggaccctatc tttgactact actcagcgtc ataccaggca    240
gctttatccc tgggccagga cccatccaat gactgcaacg acaaccagcg ggaagttcgc    300
atagtggccc agcggcgggg gcagaatgag cccgtgctgg gggtagatta ccggcagcgc    360
aagatcacca tccagaaccg agcagatctc gtgataaatg aagtgatgtg gtgggaccat    420
ggagtgtatt actgcaccat tgaggctcca ggggacacat caggagaccc cgataaggaa    480
gtaaagctca tcgtcctaca ctggctgaca gtgatcttca tcatcctggg agccctcctc    540
ctcctgctgc tgattggagt gtgctggtgc cagtgctgtc ctcagtattg ctgctgctat    600
atccgctgtc cctgctgtcc tgcccactgc tgctgtcctg aggaagattt gtccctgccg    660
tccagcctcc cgcagatgcc aatgacccag accaccaatc agcctcccat cgccaatggt    720
gtcctggagt atttggagaa agaactgcgg aacctcaacc tggcccagcc tctgcccccct    780
gacctcaaag gcagatttgg ccatccctgc agcatgctgt cctccctggg ctctgaggtc    840
gtggaacgca gaatcatcca cctgccccca ctgatcagag acctgtcatc ctcaaggagg    900
accagtgact ccctgcacca gcagtggctc accccaattc cctccaggcc ctgggatctg    960
```

agggagggga gaagccacca ccattaccct gatttccacc aggagctcca ggaccggggg 1020
ccaaagtctt gggcattgga aagaagggag ttggacccat cgtggagtgg aaggcaccgt 1080
agctctaggc tgaatgggtc acccatacac tggtcagaca gggacagcct aagcgatgtc 1140
ccctcatcca gtgaggcacg ctggcggccg agccaccctc ctttcaggag ccgctgtcag 1200
gagaggcccc gcaggcccag cccccgggag agcactcaga ggcacgggag acgacgcagg 1260
caccgcagct actctcctcc cttgccctcc ggcctcagtt cctggagctc tgaagaggac 1320
aaggagaggc agccccagag ctggcgggcc caccgccgcg gctcgcactc cccacactgg 1380
cccgaggaga agccgcctag ctaccgctca ctggatatca ctccaggcaa gaatagcagg 1440
aaaaaaggga gtgtggagag gcgctcggag aaagacagct ctcatagtgg aaggagtgtg 1500
gtcattggac cggtcgccac catggtgagc aagggcgagg agctgttcac cggggtggtg 1560
cccatcctgg tcgagctgga cggcgacgta aacggccaca agttcagcgt gtccggcgag 1620
ggcgagggcg atgccaccta cggcaagctg accctgaagt tcatctgcac caccggcaag 1680
ctgcccgtgc cctggcccac cctcgtgacc accctgacct acggcgtgca gtgcttcagc 1740
cgctaccccg accacatgaa gcagcacgac ttcttcaagt ccgccatgcc cgaaggctac 1800
gtccaggagc gcaccatctt cttcaaggac gacggcaact acaagacccg cgccgaggtg 1860
aagttcgagg gcgacaccct ggtgaaccgc atcgagctga agggcatcga cttcaaggag 1920
gacggcaaca tcctggggca caagctggag tacaactaca acagccacaa cgtctatatc 1980
atggccgaca agcagaagaa cggcatcaag gtgaacttca agatccgcca caacatcgag 2040
gacggcagcg tgcagctcgc cgaccactac cagcagaaca cccccatcgg cgacggcccc 2100
gtgctgctgc ccgacaacca ctacctgagc acccagtccg ccctgagcaa agaccccaac 2160
gagaagcgcg atcacatggt cctgctggag ttcgtgaccg ccgccgggat cactctcggc 2220
atggacgagc tgtacaagta a 2241

<210> SEQ ID NO 85
<211> LENGTH: 2082
<212> TYPE: DNA
<213> ORGANISM: Homo sapiens

<400> SEQUENCE: 85
atggtgttcg cattttggaa ggtctttctg atcctaagct gccttgcagg tcaggttagt 60
gtggtgcaag tgaccatccc agacggtttc gtgaacgtga ctgttggatc taatgtcact 120
ctcatctgca tctacaccac cactgtggcc tcccgagaac agctttccat ccagtggtct 180
ttcttccata agaaggagat ggagccaatt tctcacagct cgtgcctcag tactgagggt 240
atggaggaaa aggcagtcag tcagtgtcta aaaatgacgc acgcaagaga cgctcgggga 300
agatgtagct ggacctctga gtctccttgg gaggagggga agtggccaga tgttgaggct 360
gtgaagggca ctcttgatgg acagcaggct gaactccaga tttacttttc tcaaggtgga 420
caagctgtag ccatcgggca atttaaagat cgaattacag ggtccaacga tccaggtaat 480
gcatctatca ctatctcgca tatgcagcca gcagacagtg gaatttacat ctgcgatgtt 540
aacaaccccc cagactttct cggccaaaac caaggcatcc tcaacgtcag tgtgttagtg 600
aaaccttcta agcccctttg tagcgttcaa ggaagaccag aaactggcca cactatttcc 660
ctttcctgtc tctctgcgct tggaacacct tcccctgtgt actactggca taaacttgag 720
ggaagagaca tcgtgccagt gaaagaaaac ttcaacccaa ccaccgggat tttggtcatt 780

-continued

```
ggaaatctga caaattttga acaaggttat taccagtgta ctgccatcaa cagacttggc    840
aatagttcct gcgaaatcga tctcacttct tcacatccag aagttggaat cattgttggg    900
gccttgattg gtagcctggt aggtgccgcc atcatcatct ctgttgtgtg cttcgcaagg    960
aataaggcaa aagcaaaggc aaaagaaaga aattctaaga ccatcgcgga acttgagcca   1020
atgacaaaga taaacccaag ggagagaaagc gaagcaatgc caagagaaga cgctacccaa   1080
ctagaagtaa ctctaccatc ttccattcat gagactggcc ctgataccat ccaagaacca   1140
gactatgagc caaagcctac tcaggagcct gccccagagc ctgccccagg atcagagcct   1200
atggcagtgc ctgaccttga catcgagctg gagctggagc cagaaacgca gtcggaattg   1260
gagccagagc cagagccaga gccagagtca gagcctgggg ttgtagttga gcccttaagt   1320
gaagatgaaa agggagtggt taaggcagga ccggtcgcca ccatggtgag caagggcgag   1380
gagctgttca ccggggtggt gcccatcctg gtcgagctgg acggcgacgt aaacggccac   1440
aagttcagcg tgtccggcga gggcgagggc gatgccacct acggcaagct gaccctgaag   1500
ttcatctgca ccaccggcaa gctgcccgtg ccctggccca ccctcgtgac caccctgacc   1560
tacggcgtgc agtgcttcag ccgctacccc gaccacatga agcagcacga cttcttcaag   1620
tccgccatgc ccgaaggcta cgtccaggag cgcaccatct tcttcaagga cgacggcaac   1680
tacaagaccc gcgccgaggt gaagttcgag ggcgacaccc tggtgaaccg catcgagctg   1740
aagggcatcg acttcaagga ggacggcaac atcctggggc acaagctgga gtacaactac   1800
aacagccaca acgtctatat catggccgac aagcagaaga acggcatcaa ggtgaacttc   1860
aagatccgcc acaacatcga ggacggcagc gtgcagctcg ccgaccacta ccagcagaac   1920
acccccatcg gcgacggccc cgtgctgctg cccgacaacc actacctgag cacccagtcc   1980
gccctgagca aagaccccaa cgagaagcgc gatcacatgg tcctgctgga gttcgtgacc   2040
gccgccggga tcactctcgg catggacgag ctgtacaagt aa                      2082
```

<210> SEQ ID NO 86
<211> LENGTH: 2004
<212> TYPE: DNA
<213> ORGANISM: Homo sapiens

<400> SEQUENCE: 86

```
atggtgttcg cattttggaa ggtctttctg atcctaagct gccttgcagg tcaggttagt     60
gtggtgcaag tgaccatccc agacggtttc gtgaacgtga ctgttggatc taatgtcact    120
ctcatctgca tctacaccac cactgtggcc tcccgagaac agctttccat ccagtggtct    180
ttcttccata agaaggagat ggagccaatt tctcacagct cgtgcctcag tactgagggt    240
atggaggaaa aggcagtcag tcagtgtcta aaaatgacgc acgcaagaga cgctcgggga    300
agatgtagct ggacctctga gatttacttt tctcaaggtg gacaagctgt agccatcggg    360
caatttaaag atcgaattac agggtccaac gatccaggta atgcatctat cactatctcg    420
catatgcagc cagcagacag tggaatttac atctgcgatg ttaacaaccc cccagacttt    480
ctcggccaaa accaaggcat cctcaacgtc agtgtgttag tgaaaccttc taagcccctt    540
tgtagcgttc aaggaagacc agaaactggc cacactattt ccctttcctg tctctctgcg    600
cttggaacac cttcccctgt gtactactgg cataaacttg agggaagaga catcgtgcca    660
gtgaaagaaa acttcaaccc aaccaccggg attttggtca ttggaaatct gacaaatttt    720
gaacaaggtt attaccagtg tactgccatc aacagacttg gcaatagttc ctgcgaaatc    780
gatctcactt cttcacatcc agaagttgga atcattgttg ggccttgat tggtagcctg    840
```

```
gtaggtgccg ccatcatcat ctctgttgtg tgcttcgcaa ggaataaggc aaaagcaaag    900

gcaaaagaaa gaaattctaa gaccatcgcg gaacttgagc caatgacaaa gataaaccca    960

aggggagaaa gcgaagcaat gccaagagaa gacgctaccc aactagaagt aactctacca   1020

tcttccattc atgagactgg ccctgatacc atccaagaac cagactatga gccaaagcct   1080

actcaggagc ctgccccaga gcctgcccca ggatcagagc ctatggcagt gcctgacctt   1140

gacatcgagc tggagctgga gccagaaacg cagtcggaat tggagccaga gccagagcca   1200

gagccagagt cagagcctgg ggttgtagtt gagcccttaa gtgaagatga aaagggagtg   1260

gttaaggcag gaccggtcgc caccatggtg agcaagggcg aggagctgtt caccggggtg   1320

gtgcccatcc tggtcgagct ggacggcgac gtaaacggcc acaagttcag cgtgtccggc   1380

gagggcgagg gcgatgccac ctacggcaag ctgaccctga agttcatctg caccaccggc   1440

aagctgcccg tgccctggcc caccctcgtg accaccctga cctacggcgt gcagtgcttc   1500

agccgctacc ccgaccacat gaagcagcac gacttcttca agtccgccat gcccgaaggc   1560

tacgtccagg agcgcaccat cttcttcaag gacgacggca actacaagac ccgcgccgag   1620

gtgaagttcg agggcgacac cctggtgaac cgcatcgagc tgaagggcat cgacttcaag   1680

gaggacggca acatcctggg gcacaagctg gagtacaact acaacagcca caacgtctat   1740

atcatggccg acaagcagaa gaacggcatc aaggtgaact tcaagatccg ccacaacatc   1800

gaggacggca gcgtgcagct cgccgaccac taccagcaga acacccccat cggcgacggc   1860

cccgtgctgc tgcccgacaa ccactacctg agcacccagt ccgccctgag caaagacccc   1920

aacgagaagc gcgatcacat ggtcctgctg gagttcgtga ccgccgccgg gatcactctc   1980

ggcatggacg agctgtacaa gtaa                                          2004
```

<210> SEQ ID NO 87
<211> LENGTH: 331
<212> TYPE: PRT
<213> ORGANISM: Homo sapiens

<400> SEQUENCE: 87

```
Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Asp Trp His Ser Leu Gln Val Gly Gly Leu Ile Cys Ala Gly Val Leu
        35                  40                  45

Cys Ala Met Gly Ile Ile Ile Val Met Ser Ala Lys Cys Lys Cys Lys
    50                  55                  60

Phe Gly Gln Lys Ser Gly His His Pro Gly Glu Thr Pro Pro Leu Ile
65                  70                  75                  80

Thr Pro Gly Ser Ala Gln Ser Gly Pro Val Ala Thr Met Val Ser Lys
                85                  90                  95

Gly Glu Glu Leu Phe Thr Gly Val Val Pro Ile Leu Val Glu Leu Asp
            100                 105                 110

Gly Asp Val Asn Gly His Lys Phe Ser Val Ser Gly Glu Gly Glu Gly
        115                 120                 125

Asp Ala Thr Tyr Gly Lys Leu Thr Leu Lys Phe Ile Cys Thr Thr Gly
    130                 135                 140

Lys Leu Pro Val Pro Trp Pro Thr Leu Val Thr Thr Leu Thr Tyr Gly
145                 150                 155                 160
```

```
Val Gln Cys Phe Ser Arg Tyr Pro Asp His Met Lys Gln His Asp Phe
                165                 170                 175

Phe Lys Ser Ala Met Pro Glu Gly Tyr Val Gln Glu Arg Thr Ile Phe
            180                 185                 190

Phe Lys Asp Asp Gly Asn Tyr Lys Thr Arg Ala Glu Val Lys Phe Glu
        195                 200                 205

Gly Asp Thr Leu Val Asn Arg Ile Glu Leu Lys Gly Ile Asp Phe Lys
    210                 215                 220

Glu Asp Gly Asn Ile Leu Gly His Lys Leu Glu Tyr Asn Tyr Asn Ser
225                 230                 235                 240

His Asn Val Tyr Ile Met Ala Asp Lys Gln Lys Asn Gly Ile Lys Val
                245                 250                 255

Asn Phe Lys Ile Arg His Asn Ile Glu Asp Gly Ser Val Gln Leu Ala
            260                 265                 270

Asp His Tyr Gln Gln Asn Thr Pro Ile Gly Asp Gly Pro Val Leu Leu
        275                 280                 285

Pro Asp Asn His Tyr Leu Ser Thr Gln Ser Ala Leu Ser Lys Asp Pro
    290                 295                 300

Asn Glu Lys Arg Asp His Met Val Leu Leu Glu Phe Val Thr Ala Ala
305                 310                 315                 320

Gly Ile Thr Leu Gly Met Asp Glu Leu Tyr Lys
                325                 330


<210> SEQ ID NO 88
<211> LENGTH: 360
<212> TYPE: PRT
<213> ORGANISM: Homo sapiens

<400> SEQUENCE: 88

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Gly Ala Pro Tyr Ile Phe Val Lys Arg Met Gly Gly Gln Met Lys Arg
        35                  40                  45

Thr Gln Ala Gly Thr Glu Val Pro Ser Thr Phe Leu Leu Asp Trp His
    50                  55                  60

Ser Leu Gln Val Gly Gly Leu Ile Cys Ala Gly Val Leu Cys Ala Met
65                  70                  75                  80

Gly Ile Ile Ile Val Met Ser Ala Lys Cys Lys Cys Lys Phe Gly Gln
                85                  90                  95

Lys Ser Gly His His Pro Gly Glu Thr Pro Pro Leu Ile Thr Pro Gly
            100                 105                 110

Ser Ala Gln Ser Gly Pro Val Ala Thr Met Val Ser Lys Gly Glu Glu
        115                 120                 125

Leu Phe Thr Gly Val Val Pro Ile Leu Val Glu Leu Asp Gly Asp Val
    130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
                165                 170                 175

Val Pro Trp Pro Thr Leu Val Thr Thr Leu Thr Tyr Gly Val Gln Cys
            180                 185                 190

Phe Ser Arg Tyr Pro Asp His Met Lys Gln His Asp Phe Phe Lys Ser
        195                 200                 205
```

```
Ala Met Pro Glu Gly Tyr Val Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
                245                 250                 255

Asn Ile Leu Gly His Lys Leu Glu Tyr Asn Tyr Asn Ser His Asn Val
            260                 265                 270

Tyr Ile Met Ala Asp Lys Gln Lys Asn Gly Ile Lys Val Asn Phe Lys
        275                 280                 285

Ile Arg His Asn Ile Glu Asp Gly Ser Val Gln Leu Ala Asp His Tyr
    290                 295                 300

Gln Gln Asn Thr Pro Ile Gly Asp Gly Pro Val Leu Leu Pro Asp Asn
305                 310                 315                 320

His Tyr Leu Ser Thr Gln Ser Ala Leu Ser Lys Asp Pro Asn Glu Lys
                325                 330                 335

Arg Asp His Met Val Leu Leu Glu Phe Val Thr Ala Ala Gly Ile Thr
            340                 345                 350

Leu Gly Met Asp Glu Leu Tyr Lys
        355                 360


<210> SEQ ID NO 89
<211> LENGTH: 456
<212> TYPE: PRT
<213> ORGANISM: Homo sapiens

<400> SEQUENCE: 89

Met Arg Pro Leu Pro Ser Gly Arg Arg Lys Thr Arg Gly Ile Ser Leu
1               5                   10                  15

Gly Leu Phe Ala Leu Cys Leu Ala Ala Ala Arg Cys Leu Gln Ser Gln
            20                  25                  30

Gly Val Ser Leu Tyr Ile Pro Gln Ala Thr Ile Asn Ala Thr Val Lys
        35                  40                  45

Glu Asp Ile Leu Leu Ser Val Glu Tyr Ser Cys His Gly Val Pro Thr
    50                  55                  60

Ile Glu Trp Thr Tyr Ser Ser Asn Trp Gly Thr Gln Lys Ile Val Glu
65                  70                  75                  80

Trp Lys Pro Gly Thr Gln Ala Asn Ile Ser Gln Ser His Lys Asp Arg
                85                  90                  95

Val Cys Thr Phe Asp Asn Gly Ser Ile Gln Leu Phe Ser Val Gly Val
            100                 105                 110

Arg Asp Ser Gly Tyr Tyr Val Ile Thr Val Thr Glu Arg Leu Gly Ser
        115                 120                 125

Ser Gln Phe Gly Thr Ile Val Leu His Val Ser Glu Ile Leu Tyr Glu
    130                 135                 140

Asp Leu His Phe Val Ala Val Ile Leu Ala Phe Leu Ala Ala Val Ala
145                 150                 155                 160

Ala Val Leu Ile Ser Leu Met Trp Val Cys Asn Lys Cys Ala Tyr Lys
                165                 170                 175

Phe Gln Arg Lys Arg Arg His Lys Leu Lys Glu Ser Thr Thr Glu Glu
            180                 185                 190

Ile Glu Leu Glu Asp Val Glu Cys Arg Ile Leu Gln Ser Thr Val Pro
        195                 200                 205

Arg Ala Arg Asp Pro Pro Val Ala Thr Met Val Ser Lys Gly Glu Glu
```

```
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Phe Ile Cys Thr Thr Gly Lys Leu Pro
            260                 265                 270

Val Pro Trp Pro Thr Leu Val Thr Thr Leu Thr Tyr Gly Val Gln Cys
        275                 280                 285

Phe Ser Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Asp Phe Lys Glu Asp Gly
            340                 345                 350

Asn Ile Leu Gly His Lys Leu Glu Tyr Asn Tyr Asn Ser His Asn Val
        355                 360                 365

Tyr Ile Met Ala Asp Lys Gln Lys Asn Gly Ile Lys Val Asn Phe Lys
    370                 375                 380

Ile Arg His Asn Ile Glu Asp Gly Ser Val Gln Leu Ala Asp His Tyr
385                 390                 395                 400

Gln Gln Asn Thr Pro Ile Gly Asp Gly Pro Val Leu Leu Pro Asp Asn
                405                 410                 415

His Tyr Leu Ser Thr Gln Ser Ala Leu Ser Lys Asp Pro Asn Glu Lys
            420                 425                 430

Arg Asp His Met Val Leu Leu Glu Phe Val Thr Ala Ala Gly Ile Thr
        435                 440                 445

Leu Gly Met Asp Glu Leu Tyr Lys
    450                 455
```

<210> SEQ ID NO 90
<211> LENGTH: 443
<212> TYPE: PRT
<213> ORGANISM: Homo sapiens

<400> SEQUENCE: 90

```
Met Arg Pro Leu Pro Ser Gly Arg Arg Lys Thr Arg Gly Ile Ser Leu
1               5                   10                  15

Gly Leu Phe Ala Leu Cys Leu Ala Ala Ala Arg Cys Leu Gln Ser Gln
            20                  25                  30

Gly Val Ser Leu Tyr Ile Pro Gln Ala Thr Ile Asn Ala Thr Val Lys
        35                  40                  45

Glu Asp Ile Leu Leu Ser Val Glu Tyr Ser Cys His Gly Val Pro Thr
    50                  55                  60

Ile Glu Trp Thr Tyr Ser Ser Asn Trp Gly Thr Gln Lys Ile Val Glu
65                  70                  75                  80

Trp Lys Pro Gly Thr Gln Ala Asn Ile Ser Gln Ser His Lys Asp Arg
                85                  90                  95

Val Cys Thr Phe Asp Asn Gly Ser Ile Gln Leu Phe Ser Val Gly Val
            100                 105                 110

Arg Asp Ser Gly Tyr Tyr Val Ile Thr Val Thr Glu Arg Leu Gly Ser
        115                 120                 125
```

Ser Gln Phe Gly Thr Ile Val Leu His Val Ser Glu Ile Leu Tyr Glu
130 135 140

Asp Leu His Phe Val Ala Val Ile Leu Ala Phe Leu Ala Ala Val Ala
145 150 155 160

Ala Val Leu Ile Ser Leu Met Trp Val Cys Asn Lys Cys Ala Tyr Lys
165 170 175

Phe Gln Arg Lys Arg Arg His Lys Leu Lys Gly Asn Pro Leu Gly Leu
180 185 190

Val Ile Ile His Glu Trp Phe Gly Pro Val Ala Thr Met Val Ser Lys
195 200 205

Gly Glu Glu Leu Phe Thr Gly Val Val Pro Ile Leu Val Glu Leu Asp
210 215 220

Gly Asp Val Asn Gly His Lys Phe Ser Val Ser Gly Glu Gly Glu Gly
225 230 235 240

Asp Ala Thr Tyr Gly Lys Leu Thr Leu Lys Phe Ile Cys Thr Thr Gly
245 250 255

Lys Leu Pro Val Pro Trp Pro Thr Leu Val Thr Thr Leu Thr Tyr Gly
260 265 270

Val Gln Cys Phe Ser Arg Tyr Pro Asp His Met Lys Gln His Asp Phe
275 280 285

Phe Lys Ser Ala Met Pro Glu Gly Tyr Val Gln Glu Arg Thr Ile Phe
290 295 300

Phe Lys Asp Asp Gly Asn Tyr Lys Thr Arg Ala Glu Val Lys Phe Glu
305 310 315 320

Gly Asp Thr Leu Val Asn Arg Ile Glu Leu Lys Gly Ile Asp Phe Lys
325 330 335

Glu Asp Gly Asn Ile Leu Gly His Lys Leu Glu Tyr Asn Tyr Asn Ser
340 345 350

His Asn Val Tyr Ile Met Ala Asp Lys Gln Lys Asn Gly Ile Lys Val
355 360 365

Asn Phe Lys Ile Arg His Asn Ile Glu Asp Gly Ser Val Gln Leu Ala
370 375 380

Asp His Tyr Gln Gln Asn Thr Pro Ile Gly Asp Gly Pro Val Leu Leu
385 390 395 400

Pro Asp Asn His Tyr Leu Ser Thr Gln Ser Ala Leu Ser Lys Asp Pro
405 410 415

Asn Glu Lys Arg Asp His Met Val Leu Leu Glu Phe Val Thr Ala Ala
420 425 430

Gly Ile Thr Leu Gly Met Asp Glu Leu Tyr Lys
435 440

<210> SEQ ID NO 91
<211> LENGTH: 510
<212> TYPE: PRT
<213> ORGANISM: Homo sapiens

<400> SEQUENCE: 91

Met Asp Arg Val Leu Leu Arg Trp Ile Ser Leu Phe Trp Leu Thr Ala
1 5 10 15

Met Val Glu Gly Leu Gln Val Thr Val Pro Asp Lys Lys Lys Val Ala
20 25 30

Met Leu Phe Gln Pro Thr Val Leu Arg Cys His Phe Ser Thr Ser Ser
35 40 45

His Gln Pro Ala Val Val Gln Trp Lys Phe Lys Ser Tyr Cys Gln Asp
50 55 60

-continued

Arg Met Gly Glu Ser Leu Gly Met Ser Ser Thr Arg Ala Gln Ser Leu
65 70 75 80

Ser Lys Arg Asn Leu Glu Trp Asp Pro Tyr Leu Asp Cys Leu Asp Ser
85 90 95

Arg Arg Thr Val Arg Val Val Ala Ser Lys Gln Gly Ser Thr Val Thr
100 105 110

Leu Gly Asp Phe Tyr Arg Gly Arg Glu Ile Thr Ile Val His Asp Ala
115 120 125

Asp Leu Gln Ile Gly Lys Leu Met Trp Gly Asp Ser Gly Leu Tyr Tyr
130 135 140

Cys Ile Ile Thr Thr Pro Asp Asp Leu Glu Gly Lys Asn Glu Asp Ser
145 150 155 160

Val Glu Leu Leu Val Leu Gly Arg Thr Gly Leu Leu Ala Asp Leu Leu
165 170 175

Pro Ser Phe Ala Val Glu Ile Met Pro Glu Trp Val Phe Val Gly Leu
180 185 190

Val Leu Leu Gly Val Phe Leu Phe Phe Val Leu Val Gly Ile Cys Trp
195 200 205

Cys Gln Cys Cys Pro His Ser Cys Cys Cys Tyr Val Arg Cys Pro Cys
210 215 220

Cys Pro Asp Ser Cys Cys Cys Pro Gln Ala Cys Glu Tyr Ser Asp Arg
225 230 235 240

Trp Gly Asp Arg Ala Ile Glu Arg Asn Val Tyr Leu Ser Thr Arg Ile
245 250 255

Leu Gln Ser Thr Val Pro Arg Ala Arg Asp Pro Pro Val Ala Thr Met
260 265 270

Val Ser Lys Gly Glu Glu Leu Phe Thr Gly Val Val Pro Ile Leu Val
275 280 285

Glu Leu Asp Gly Asp Val Asn Gly His Lys Phe Ser Val Ser Gly Glu
290 295 300

Gly Glu Gly Asp Ala Thr Tyr Gly Lys Leu Thr Leu Lys Phe Ile Cys
305 310 315 320

Thr Thr Gly Lys Leu Pro Val Pro Trp Pro Thr Leu Val Thr Thr Leu
325 330 335

Thr Tyr Gly Val Gln Cys Phe Ser Arg Tyr Pro Asp His Met Lys Gln
340 345 350

His Asp Phe Phe Lys Ser Ala Met Pro Glu Gly Tyr Val Gln Glu Arg
355 360 365

Thr Ile Phe Phe Lys Asp Asp Gly Asn Tyr Lys Thr Arg Ala Glu Val
370 375 380

Lys Phe Glu Gly Asp Thr Leu Val Asn Arg Ile Glu Leu Lys Gly Ile
385 390 395 400

Asp Phe Lys Glu Asp Gly Asn Ile Leu Gly His Lys Leu Glu Tyr Asn
405 410 415

Tyr Asn Ser His Asn Val Tyr Ile Met Ala Asp Lys Gln Lys Asn Gly
420 425 430

Ile Lys Val Asn Phe Lys Ile Arg His Asn Ile Glu Asp Gly Ser Val
435 440 445

Gln Leu Ala Asp His Tyr Gln Gln Asn Thr Pro Ile Gly Asp Gly Pro
450 455 460

Val Leu Leu Pro Asp Asn His Tyr Leu Ser Thr Gln Ser Ala Leu Ser
465 470 475 480

Lys Asp Pro Asn Glu Lys Arg Asp His Met Val Leu Leu Glu Phe Val
485 490 495

Thr Ala Ala Gly Ile Thr Leu Gly Met Asp Glu Leu Tyr Lys
500 505 510

<210> SEQ ID NO 92
<211> LENGTH: 694
<212> TYPE: PRT
<213> ORGANISM: Homo sapiens

<400> SEQUENCE: 92

Met Trp Leu Lys Val Phe Thr Thr Phe Leu Ser Phe Ala Thr Gly Ala
1 5 10 15

Cys Ser Gly Leu Lys Val Thr Val Pro Ser His Thr Val His Gly Val
20 25 30

Arg Gly Gln Ala Leu Tyr Leu Pro Val His Tyr Gly Phe His Thr Pro
35 40 45

Ala Ser Asp Ile Gln Ile Ile Trp Leu Phe Glu Arg Pro His Thr Met
50 55 60

Pro Lys Tyr Leu Leu Gly Ser Val Asn Lys Ser Val Val Pro Asp Leu
65 70 75 80

Glu Tyr Gln His Lys Phe Thr Met Met Pro Pro Asn Ala Ser Leu Leu
85 90 95

Ile Asn Pro Leu Gln Phe Pro Asp Glu Gly Asn Tyr Ile Val Lys Val
100 105 110

Asn Ile Gln Gly Asn Gly Thr Leu Ser Ala Ser Gln Lys Ile Gln Val
115 120 125

Thr Val Asp Asp Pro Val Thr Lys Pro Val Val Gln Ile His Pro Pro
130 135 140

Ser Gly Ala Val Glu Tyr Val Gly Asn Met Thr Leu Thr Cys His Val
145 150 155 160

Glu Gly Gly Thr Arg Leu Ala Tyr Gln Trp Leu Lys Asn Gly Arg Pro
165 170 175

Val His Thr Ser Ser Thr Tyr Ser Phe Ser Pro Gln Asn Asn Thr Leu
180 185 190

His Ile Ala Pro Val Thr Lys Glu Asp Ile Gly Asn Tyr Ser Cys Leu
195 200 205

Val Arg Asn Pro Val Ser Glu Met Glu Ser Asp Ile Ile Met Pro Ile
210 215 220

Ile Tyr Tyr Gly Pro Tyr Gly Leu Gln Val Asn Ser Asp Lys Gly Leu
225 230 235 240

Lys Val Gly Glu Val Phe Thr Val Asp Leu Gly Glu Ala Ile Leu Phe
245 250 255

Asp Cys Ser Ala Asp Ser His Pro Pro Asn Thr Tyr Ser Trp Ile Arg
260 265 270

Arg Thr Asp Asn Thr Thr Tyr Ile Ile Lys His Gly Pro Arg Leu Glu
275 280 285

Val Ala Ser Glu Lys Val Ala Gln Lys Thr Met Asp Tyr Val Cys Cys
290 295 300

Ala Tyr Asn Asn Ile Thr Gly Arg Gln Asp Glu Thr His Phe Thr Val
305 310 315 320

Ile Ile Thr Ser Val Gly Leu Glu Lys Leu Ala Gln Lys Gly Lys Ser
325 330 335

Leu Ser Pro Leu Ala Ser Ile Thr Gly Ile Ser Leu Phe Leu Ile Ile
340 345 350

```
Ser Met Cys Leu Leu Phe Leu Trp Lys Lys Tyr Gln Pro Tyr Lys Val
        355                 360                 365

Ile Lys Gln Lys Leu Glu Gly Arg Pro Glu Thr Glu Tyr Arg Lys Ala
    370                 375                 380

Gln Thr Phe Ser Gly His Glu Asp Ala Leu Asp Asp Phe Gly Ile Tyr
385                 390                 395                 400

Glu Phe Val Ala Phe Pro Asp Val Ser Gly Val Ser Arg Ile Pro Ser
                405                 410                 415

Arg Ser Val Pro Ala Ser Asp Cys Val Ser Gly Gln Asp Leu His Ser
            420                 425                 430

Thr Val Tyr Glu Val Ile Gln His Ile Pro Ala Gln Gln Gln Asp His
        435                 440                 445

Pro Glu Gly Pro Val Ala Thr Met Val Ser Lys Gly Glu Glu Leu Phe
    450                 455                 460

Thr Gly Val Val Pro Ile Leu Val Glu Leu Asp Gly Asp Val Asn Gly
465                 470                 475                 480

His Lys Phe Ser Val Ser Gly Glu Gly Glu Gly Asp Ala Thr Tyr Gly
                485                 490                 495

Lys Leu Thr Leu Lys Phe Ile Cys Thr Thr Gly Lys Leu Pro Val Pro
            500                 505                 510

Trp Pro Thr Leu Val Thr Thr Leu Thr Tyr Gly Val Gln Cys Phe Ser
        515                 520                 525

Arg Tyr Pro Asp His Met Lys Gln His Asp Phe Phe Lys Ser Ala Met
    530                 535                 540

Pro Glu Gly Tyr Val Gln Glu Arg Thr Ile Phe Phe Lys Asp Asp Gly
545                 550                 555                 560

Asn Tyr Lys Thr Arg Ala Glu Val Lys Phe Glu Gly Asp Thr Leu Val
                565                 570                 575

Asn Arg Ile Glu Leu Lys Gly Ile Asp Phe Lys Glu Asp Gly Asn Ile
            580                 585                 590

Leu Gly His Lys Leu Glu Tyr Asn Tyr Asn Ser His Asn Val Tyr Ile
        595                 600                 605

Met Ala Asp Lys Gln Lys Asn Gly Ile Lys Val Asn Phe Lys Ile Arg
    610                 615                 620

His Asn Ile Glu Asp Gly Ser Val Gln Leu Ala Asp His Tyr Gln Gln
625                 630                 635                 640

Asn Thr Pro Ile Gly Asp Gly Pro Val Leu Leu Pro Asp Asn His Tyr
                645                 650                 655

Leu Ser Thr Gln Ser Ala Leu Ser Lys Asp Pro Asn Glu Lys Arg Asp
            660                 665                 670

His Met Val Leu Leu Glu Phe Val Thr Ala Ala Gly Ile Thr Leu Gly
        675                 680                 685

Met Asp Glu Leu Tyr Lys
    690
```

<210> SEQ ID NO 93
<211> LENGTH: 790
<212> TYPE: PRT
<213> ORGANISM: Homo sapiens

<400> SEQUENCE: 93

```
Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
```

-continued

```
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Ala Leu Ala Arg His Arg Tyr Met Lys
    210                 215                 220

Gln Ala Gln Ala Leu Gly Pro Gln Met Met Gly Lys Pro Leu Tyr Trp
225                 230                 235                 240

Gly Ala Asp Arg Ser Ser Gln Val Ser Ser Tyr Pro Met His Pro Leu
                245                 250                 255

Leu Gln Arg Asp Leu Ser Leu Arg Ser Ser Leu Pro Gln Met Pro Met
            260                 265                 270

Thr Gln Thr Thr Asn Gln Pro Pro Ile Ala Asn Gly Val Leu Glu Tyr
        275                 280                 285

Leu Glu Lys Glu Leu Arg Asn Leu Asn Leu Ala Gln Pro Leu Pro Pro
    290                 295                 300

Asp Leu Lys Gly Arg Phe Gly His Pro Cys Ser Met Leu Ser Ser Leu
305                 310                 315                 320

Gly Ser Glu Val Val Glu Arg Arg Ile Ile His Leu Pro Pro Leu Ile
                325                 330                 335

Arg Asp Leu Ser Ser Ser Arg Arg Thr Ser Asp Ser Leu His Gln Gln
            340                 345                 350

Trp Leu Thr Pro Ile Pro Ser Arg Pro Trp Asp Leu Arg Glu Gly Arg
        355                 360                 365

Ser His His His Tyr Pro Asp Phe His Gln Glu Leu Gln Asp Arg Gly
    370                 375                 380

Pro Lys Ser Trp Ala Leu Glu Arg Arg Glu Leu Asp Pro Ser Trp Ser
385                 390                 395                 400

Gly Arg His Arg Ser Ser Arg Leu Asn Gly Ser Pro Ile His Trp Ser
                405                 410                 415

Asp Arg Asp Ser Leu Ser Asp Val Pro Ser Ser Ser Glu Ala Arg Trp
            420                 425                 430

Arg Pro Ser His Pro Pro Phe Arg Ser Arg Cys Gln Glu Arg Pro Arg
        435                 440                 445
```

Arg Pro Ser Pro Arg Glu Ser Thr Gln Arg His Gly Arg Arg Arg Arg
    450                 455                 460

His Arg Ser Tyr Ser Pro Pro Leu Pro Ser Gly Leu Ser Ser Trp Ser
465                 470                 475                 480

Ser Glu Glu Asp Lys Glu Arg Gln Pro Gln Ser Trp Arg Ala His Arg
                485                 490                 495

Arg Gly Ser His Ser Pro His Trp Pro Glu Glu Lys Pro Pro Ser Tyr
            500                 505                 510

Arg Ser Leu Asp Ile Thr Pro Gly Lys Asn Ser Arg Lys Lys Gly Ser
        515                 520                 525

Val Glu Arg Arg Ser Glu Lys Asp Ser Ser His Ser Gly Arg Ser Val
    530                 535                 540

Val Ile Gly Pro Val Ala Thr Met Val Ser Lys Gly Glu Glu Leu Phe
545                 550                 555                 560

Thr Gly Val Val Pro Ile Leu Val Glu Leu Asp Gly Asp Val Asn Gly
                565                 570                 575

His Lys Phe Ser Val Ser Gly Glu Gly Glu Gly Asp Ala Thr Tyr Gly
            580                 585                 590

Lys Leu Thr Leu Lys Phe Ile Cys Thr Thr Gly Lys Leu Pro Val Pro
        595                 600                 605

Trp Pro Thr Leu Val Thr Thr Leu Thr Tyr Gly Val Gln Cys Phe Ser
    610                 615                 620

Arg Tyr Pro Asp His Met Lys Gln His Asp Phe Phe Lys Ser Ala Met
625                 630                 635                 640

Pro Glu Gly Tyr Val Gln Glu Arg Thr Ile Phe Phe Lys Asp Asp Gly
                645                 650                 655

Asn Tyr Lys Thr Arg Ala Glu Val Lys Phe Glu Gly Asp Thr Leu Val
            660                 665                 670

Asn Arg Ile Glu Leu Lys Gly Ile Asp Phe Lys Glu Asp Gly Asn Ile
        675                 680                 685

Leu Gly His Lys Leu Glu Tyr Asn Tyr Asn Ser His Asn Val Tyr Ile
    690                 695                 700

Met Ala Asp Lys Gln Lys Asn Gly Ile Lys Val Asn Phe Lys Ile Arg
705                 710                 715                 720

His Asn Ile Glu Asp Gly Ser Val Gln Leu Ala Asp His Tyr Gln Gln
                725                 730                 735

Asn Thr Pro Ile Gly Asp Gly Pro Val Leu Leu Pro Asp Asn His Tyr
            740                 745                 750

Leu Ser Thr Gln Ser Ala Leu Ser Lys Asp Pro Asn Glu Lys Arg Asp
        755                 760                 765

His Met Val Leu Leu Glu Phe Val Thr Ala Ala Gly Ile Thr Leu Gly
    770                 775                 780

Met Asp Glu Leu Tyr Lys
785                 790

<210> SEQ ID NO 94
<211> LENGTH: 746
<212> TYPE: PRT
<213> ORGANISM: Homo sapiens

<400> SEQUENCE: 94

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu

```
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Asp Leu Ser Leu Pro Ser Ser Leu Pro
    210                 215                 220

Gln Met Pro Met Thr Gln Thr Thr Asn Gln Pro Pro Ile Ala Asn Gly
225                 230                 235                 240

Val Leu Glu Tyr Leu Glu Lys Glu Leu Arg Asn Leu Asn Leu Ala Gln
                245                 250                 255

Pro Leu Pro Pro Asp Leu Lys Gly Arg Phe Gly His Pro Cys Ser Met
            260                 265                 270

Leu Ser Ser Leu Gly Ser Glu Val Val Glu Arg Arg Ile Ile His Leu
        275                 280                 285

Pro Pro Leu Ile Arg Asp Leu Ser Ser Ser Arg Arg Thr Ser Asp Ser
    290                 295                 300

Leu His Gln Gln Trp Leu Thr Pro Ile Pro Ser Arg Pro Trp Asp Leu
305                 310                 315                 320

Arg Glu Gly Arg Ser His His His Tyr Pro Asp Phe His Gln Glu Leu
                325                 330                 335

Gln Asp Arg Gly Pro Lys Ser Trp Ala Leu Glu Arg Arg Glu Leu Asp
            340                 345                 350

Pro Ser Trp Ser Gly Arg His Arg Ser Ser Arg Leu Asn Gly Ser Pro
        355                 360                 365

Ile His Trp Ser Asp Arg Asp Ser Leu Ser Asp Val Pro Ser Ser Ser
    370                 375                 380

Glu Ala Arg Trp Arg Pro Ser His Pro Pro Phe Arg Ser Arg Cys Gln
385                 390                 395                 400

Glu Arg Pro Arg Arg Pro Ser Pro Arg Glu Ser Thr Gln Arg His Gly
                405                 410                 415

Arg Arg Arg Arg His Arg Ser Tyr Ser Pro Pro Leu Pro Ser Gly Leu
            420                 425                 430

Ser Ser Trp Ser Ser Glu Glu Asp Lys Glu Arg Gln Pro Gln Ser Trp
        435                 440                 445
```

Arg Ala His Arg Arg Gly Ser His Ser Pro His Trp Pro Glu Glu Lys
450 455 460

Pro Pro Ser Tyr Arg Ser Leu Asp Ile Thr Pro Gly Lys Asn Ser Arg
465 470 475 480

Lys Lys Gly Ser Val Glu Arg Arg Ser Glu Lys Asp Ser Ser His Ser
485 490 495

Gly Arg Ser Val Val Ile Gly Pro Val Ala Thr Met Val Ser Lys Gly
500 505 510

Glu Glu Leu Phe Thr Gly Val Val Pro Ile Leu Val Glu Leu Asp Gly
515 520 525

Asp Val Asn Gly His Lys Phe Ser Val Ser Gly Glu Gly Glu Gly Asp
530 535 540

Ala Thr Tyr Gly Lys Leu Thr Leu Lys Phe Ile Cys Thr Thr Gly Lys
545 550 555 560

Leu Pro Val Pro Trp Pro Thr Leu Val Thr Thr Leu Thr Tyr Gly Val
565 570 575

Gln Cys Phe Ser Arg Tyr Pro Asp His Met Lys Gln His Asp Phe Phe
580 585 590

Lys Ser Ala Met Pro Glu Gly Tyr Val Gln Glu Arg Thr Ile Phe Phe
595 600 605

Lys Asp Asp Gly Asn Tyr Lys Thr Arg Ala Glu Val Lys Phe Glu Gly
610 615 620

Asp Thr Leu Val Asn Arg Ile Glu Leu Lys Gly Ile Asp Phe Lys Glu
625 630 635 640

Asp Gly Asn Ile Leu Gly His Lys Leu Glu Tyr Asn Tyr Asn Ser His
645 650 655

Asn Val Tyr Ile Met Ala Asp Lys Gln Lys Asn Gly Ile Lys Val Asn
660 665 670

Phe Lys Ile Arg His Asn Ile Glu Asp Gly Ser Val Gln Leu Ala Asp
675 680 685

His Tyr Gln Gln Asn Thr Pro Ile Gly Asp Gly Pro Val Leu Leu Pro
690 695 700

Asp Asn His Tyr Leu Ser Thr Gln Ser Ala Leu Ser Lys Asp Pro Asn
705 710 715 720

Glu Lys Arg Asp His Met Val Leu Leu Glu Phe Val Thr Ala Ala Gly
725 730 735

Ile Thr Leu Gly Met Asp Glu Leu Tyr Lys
740 745

<210> SEQ ID NO 95
<211> LENGTH: 693
<212> TYPE: PRT
<213> ORGANISM: Homo sapiens

<400> SEQUENCE: 95

Met Val Phe Ala Phe Trp Lys Val Phe Leu Ile Leu Ser Cys Leu Ala
1 5 10 15

Gly Gln Val Ser Val Val Gln Val Thr Ile Pro Asp Gly Phe Val Asn
20 25 30

Val Thr Val Gly Ser Asn Val Thr Leu Ile Cys Ile Tyr Thr Thr Thr
35 40 45

Val Ala Ser Arg Glu Gln Leu Ser Ile Gln Trp Ser Phe Phe His Lys
50 55 60

Lys Glu Met Glu Pro Ile Ser His Ser Ser Cys Leu Ser Thr Glu Gly

```
65                  70                  75                  80

Met Glu Glu Lys Ala Val Ser Gln Cys Leu Lys Met Thr His Ala Arg
                85                  90                  95

Asp Ala Arg Gly Arg Cys Ser Trp Thr Ser Glu Ser Pro Trp Glu Glu
            100                 105                 110

Gly Lys Trp Pro Asp Val Glu Ala Val Lys Gly Thr Leu Asp Gly Gln
        115                 120                 125

Gln Ala Glu Leu Gln Ile Tyr Phe Ser Gln Gly Gly Gln Ala Val Ala
    130                 135                 140

Ile Gly Gln Phe Lys Asp Arg Ile Thr Gly Ser Asn Asp Pro Gly Asn
145                 150                 155                 160

Ala Ser Ile Thr Ile Ser His Met Gln Pro Ala Asp Ser Gly Ile Tyr
                165                 170                 175

Ile Cys Asp Val Asn Asn Pro Pro Asp Phe Leu Gly Gln Asn Gln Gly
            180                 185                 190

Ile Leu Asn Val Ser Val Leu Val Lys Pro Ser Lys Pro Leu Cys Ser
        195                 200                 205

Val Gln Gly Arg Pro Glu Thr Gly His Thr Ile Ser Leu Ser Cys Leu
    210                 215                 220

Ser Ala Leu Gly Thr Pro Ser Pro Val Tyr Tyr Trp His Lys Leu Glu
225                 230                 235                 240

Gly Arg Asp Ile Val Pro Val Lys Glu Asn Phe Asn Pro Thr Thr Gly
                245                 250                 255

Ile Leu Val Ile Gly Asn Leu Thr Asn Phe Glu Gln Gly Tyr Tyr Gln
            260                 265                 270

Cys Thr Ala Ile Asn Arg Leu Gly Asn Ser Ser Cys Glu Ile Asp Leu
        275                 280                 285

Thr Ser Ser His Pro Glu Val Gly Ile Ile Val Gly Ala Leu Ile Gly
    290                 295                 300

Ser Leu Val Gly Ala Ala Ile Ile Ile Ser Val Val Cys Phe Ala Arg
305                 310                 315                 320

Asn Lys Ala Lys Ala Lys Ala Lys Glu Arg Asn Ser Lys Thr Ile Ala
                325                 330                 335

Glu Leu Glu Pro Met Thr Lys Ile Asn Pro Arg Gly Glu Ser Glu Ala
            340                 345                 350

Met Pro Arg Glu Asp Ala Thr Gln Leu Glu Val Thr Leu Pro Ser Ser
        355                 360                 365

Ile His Glu Thr Gly Pro Asp Thr Ile Gln Glu Pro Asp Tyr Glu Pro
    370                 375                 380

Lys Pro Thr Gln Glu Pro Ala Pro Glu Pro Ala Pro Gly Ser Glu Pro
385                 390                 395                 400

Met Ala Val Pro Asp Leu Asp Ile Glu Leu Glu Leu Glu Pro Glu Thr
                405                 410                 415

Gln Ser Glu Leu Glu Pro Glu Pro Glu Pro Glu Pro Glu Ser Glu Pro
            420                 425                 430

Gly Val Val Val Glu Pro Leu Ser Glu Asp Glu Lys Gly Val Val Lys
        435                 440                 445

Ala Gly Pro Val Ala Thr Met Val Ser Lys Gly Glu Glu Leu Phe Thr
    450                 455                 460

Gly Val Val Pro Ile Leu Val Glu Leu Asp Gly Asp Val Asn Gly His
465                 470                 475                 480

Lys Phe Ser Val Ser Gly Glu Gly Glu Gly Asp Ala Thr Tyr Gly Lys
                485                 490                 495
```

Leu Thr Leu Lys Phe Ile Cys Thr Thr Gly Lys Leu Pro Val Pro Trp
500 505 510

Pro Thr Leu Val Thr Thr Leu Thr Tyr Gly Val Gln Cys Phe Ser Arg
515 520 525

Tyr Pro Asp His Met Lys Gln His Asp Phe Phe Lys Ser Ala Met Pro
530 535 540

Glu Gly Tyr Val Gln Glu Arg Thr Ile Phe Phe Lys Asp Asp Gly Asn
545 550 555 560

Tyr Lys Thr Arg Ala Glu Val Lys Phe Glu Gly Asp Thr Leu Val Asn
565 570 575

Arg Ile Glu Leu Lys Gly Ile Asp Phe Lys Glu Asp Gly Asn Ile Leu
580 585 590

Gly His Lys Leu Glu Tyr Asn Tyr Asn Ser His Asn Val Tyr Ile Met
595 600 605

Ala Asp Lys Gln Lys Asn Gly Ile Lys Val Asn Phe Lys Ile Arg His
610 615 620

Asn Ile Glu Asp Gly Ser Val Gln Leu Ala Asp His Tyr Gln Gln Asn
625 630 635 640

Thr Pro Ile Gly Asp Gly Pro Val Leu Leu Pro Asp Asn His Tyr Leu
645 650 655

Ser Thr Gln Ser Ala Leu Ser Lys Asp Pro Asn Glu Lys Arg Asp His
660 665 670

Met Val Leu Leu Glu Phe Val Thr Ala Ala Gly Ile Thr Leu Gly Met
675 680 685

Asp Glu Leu Tyr Lys
690

<210> SEQ ID NO 96
<211> LENGTH: 667
<212> TYPE: PRT
<213> ORGANISM: Homo sapiens

<400> SEQUENCE: 96

Met Val Phe Ala Phe Trp Lys Val Phe Leu Ile Leu Ser Cys Leu Ala
1 5 10 15

Gly Gln Val Ser Val Val Gln Val Thr Ile Pro Asp Gly Phe Val Asn
20 25 30

Val Thr Val Gly Ser Asn Val Thr Leu Ile Cys Ile Tyr Thr Thr Thr
35 40 45

Val Ala Ser Arg Glu Gln Leu Ser Ile Gln Trp Ser Phe Phe His Lys
50 55 60

Lys Glu Met Glu Pro Ile Ser His Ser Ser Cys Leu Ser Thr Glu Gly
65 70 75 80

Met Glu Glu Lys Ala Val Ser Gln Cys Leu Lys Met Thr His Ala Arg
85 90 95

Asp Ala Arg Gly Arg Cys Ser Trp Thr Ser Glu Ile Tyr Phe Ser Gln
100 105 110

Gly Gly Gln Ala Val Ala Ile Gly Gln Phe Lys Asp Arg Ile Thr Gly
115 120 125

Ser Asn Asp Pro Gly Asn Ala Ser Ile Thr Ile Ser His Met Gln Pro
130 135 140

Ala Asp Ser Gly Ile Tyr Ile Cys Asp Val Asn Asn Pro Pro Asp Phe
145 150 155 160

Leu Gly Gln Asn Gln Gly Ile Leu Asn Val Ser Val Leu Val Lys Pro

-continued

```
                165                 170                 175

Ser Lys Pro Leu Cys Ser Val Gln Gly Arg Pro Glu Thr Gly His Thr
            180                 185                 190

Ile Ser Leu Ser Cys Leu Ser Ala Leu Gly Thr Pro Ser Pro Val Tyr
        195                 200                 205

Tyr Trp His Lys Leu Glu Gly Arg Asp Ile Val Pro Val Lys Glu Asn
    210                 215                 220

Phe Asn Pro Thr Thr Gly Ile Leu Val Ile Gly Asn Leu Thr Asn Phe
225                 230                 235                 240

Glu Gln Gly Tyr Tyr Gln Cys Thr Ala Ile Asn Arg Leu Gly Asn Ser
                245                 250                 255

Ser Cys Glu Ile Asp Leu Thr Ser Ser His Pro Glu Val Gly Ile Ile
            260                 265                 270

Val Gly Ala Leu Ile Gly Ser Leu Val Gly Ala Ala Ile Ile Ile Ser
        275                 280                 285

Val Val Cys Phe Ala Arg Asn Lys Ala Lys Ala Lys Ala Lys Glu Arg
    290                 295                 300

Asn Ser Lys Thr Ile Ala Glu Leu Glu Pro Met Thr Lys Ile Asn Pro
305                 310                 315                 320

Arg Gly Glu Ser Glu Ala Met Pro Arg Glu Asp Ala Thr Gln Leu Glu
                325                 330                 335

Val Thr Leu Pro Ser Ser Ile His Glu Thr Gly Pro Asp Thr Ile Gln
            340                 345                 350

Glu Pro Asp Tyr Glu Pro Lys Pro Thr Gln Glu Pro Ala Pro Glu Pro
        355                 360                 365

Ala Pro Gly Ser Glu Pro Met Ala Val Pro Asp Leu Asp Ile Glu Leu
    370                 375                 380

Glu Leu Glu Pro Glu Thr Gln Ser Glu Leu Glu Pro Glu Pro Glu Pro
385                 390                 395                 400

Glu Pro Glu Ser Glu Pro Gly Val Val Val Glu Pro Leu Ser Glu Asp
                405                 410                 415

Glu Lys Gly Val Val Lys Ala Gly Pro Val Ala Thr Met Val Ser Lys
            420                 425                 430

Gly Glu Glu Leu Phe Thr Gly Val Val Pro Ile Leu Val Glu Leu Asp
        435                 440                 445

Gly Asp Val Asn Gly His Lys Phe Ser Val Ser Gly Glu Gly Glu Gly
    450                 455                 460

Asp Ala Thr Tyr Gly Lys Leu Thr Leu Lys Phe Ile Cys Thr Thr Gly
465                 470                 475                 480

Lys Leu Pro Val Pro Trp Pro Thr Leu Val Thr Thr Leu Thr Tyr Gly
                485                 490                 495

Val Gln Cys Phe Ser Arg Tyr Pro Asp His Met Lys Gln His Asp Phe
            500                 505                 510

Phe Lys Ser Ala Met Pro Glu Gly Tyr Val Gln Glu Arg Thr Ile Phe
        515                 520                 525

Phe Lys Asp Asp Gly Asn Tyr Lys Thr Arg Ala Glu Val Lys Phe Glu
    530                 535                 540

Gly Asp Thr Leu Val Asn Arg Ile Glu Leu Lys Gly Ile Asp Phe Lys
545                 550                 555                 560

Glu Asp Gly Asn Ile Leu Gly His Lys Leu Glu Tyr Asn Tyr Asn Ser
                565                 570                 575

His Asn Val Tyr Ile Met Ala Asp Lys Gln Lys Asn Gly Ile Lys Val
            580                 585                 590
```

```
Asn Phe Lys Ile Arg His Asn Ile Glu Asp Gly Ser Val Gln Leu Ala
        595                 600                 605

Asp His Tyr Gln Gln Asn Thr Pro Ile Gly Asp Gly Pro Val Leu Leu
    610                 615                 620

Pro Asp Asn His Tyr Leu Ser Thr Gln Ser Ala Leu Ser Lys Asp Pro
625                 630                 635                 640

Asn Glu Lys Arg Asp His Met Val Leu Leu Glu Phe Val Thr Ala Ala
                645                 650                 655

Gly Ile Thr Leu Gly Met Asp Glu Leu Tyr Lys
            660                 665


<210> SEQ ID NO 97
<211> LENGTH: 924
<212> TYPE: DNA
<213> ORGANISM: Homo sapiens

<400> SEQUENCE: 97

atgcagaagg tgaccctggg cctgcttgtg ttcctggcag gctttcctgt cctggacgcc      60

aatgacctag aagataaaaa cagtcctttc tactatggtg ctccatatat atttgtcaag     120

agaatggggg gacagatgaa gaggacacag gctggcactg aggtcccctc cactttcctc     180

ctagactggg gatccgagaa cctgtacttt cagggcagcg gcgagcccag aggccccacc     240

atcaagccct gccccccctg caagtgccca gcccctaacc tgctgggcgg acccagcgtg     300

ttcatcttcc cccccaagat caaggacgtg ctgatgatca gcctgagccc catcgtgacc     360

tgcgtggtgg tggacgtgag cgaggacgac cccgacgtgc agatcagctg gttcgtgaac     420

aacgtggagg tgcacaccgc ccagacccag acccaccggg aggactacaa cagcaccctg     480

cgggtggtgt ccgccctgcc catccagcac caggactgga tgagcggcaa agaattcaag     540

tgcaaggtga acaacaagga cctgcctgcc cccatcgagc ggaccatcag caagcccaag     600

ggcagcgtga gagcccccca ggtgtacgtg ctgccccctc ccgaggaaga gatgaccaag     660

aaacaggtga ccctgacctg catggtgacc gacttcatgc ccgaggacat ctacgtggag     720

tggaccaaca acggcaagac cgagctgaac tacaagaaca ccgagcccgt gctggacagc     780

gacggcagct acttcatgta tagcaagctg agagtcgaga agaaaaactg ggtggagcgg     840

aacagctaca gctgcagcgt ggtgcacgag ggcctgcaca accaccacac caccaagagc     900

ttcagccgga cccccggcaa gtga                                            924


<210> SEQ ID NO 98
<211> LENGTH: 1170
<212> TYPE: DNA
<213> ORGANISM: Homo sapiens

<400> SEQUENCE: 98

atgaggcctc tgcccagcgg gaggaggaag acccgaggca tctccctagg actcttcgcc      60

ctctgcctgg ccgcagcccg ctgtctgcag agtcagggtg tgtccctata cattcctcag     120

gccaccatca atgccactgt caaagaagac atcctgctct cagttgagta ctcctgtcat     180

ggagtgccca ccatcgaatg gacatattca tccaattggg gaacgcagaa gatcgtggag     240

tggaaaccag ggactcaggc caacatctct caaagccaca aggacagagt ctgcaccttt     300

gacaacggct ccatccagct cttcagcgtg ggagtgaggg attccggcta ctatgtcatc     360

accgtgacgg agcgcctggg gagcagccag tttggcacca tcgtgctgca cgtctctgag     420

atcctctatg aagacggatc cgagaacctg tactttcagg gcagcggcga gcccagaggc     480
```

cccaccatca agccctgccc cccctgcaag tgcccagccc ctaacctgct gggcggaccc 540
agcgtgttca tcttcccccc caagatcaag gacgtgctga tgatcagcct gagccccatc 600
gtgacctgcg tggtggtgga cgtgagcgag gacgaccccg acgtgcagat cagctggttc 660
gtgaacaacg tggaggtgca caccgcccag acccagaccc accgggagga ctacaacagc 720
accctgcggg tggtgtccgc cctgcccatc cagcaccagg actggatgag cggcaaagaa 780
ttcaagtgca aggtgaacaa caaggacctg cctgccccca tcgagcggac catcagcaag 840
cccaagggca gcgtgagagc cccccaggtg tacgtgctgc cccctcccga ggaagagatg 900
accaagaaac aggtgaccct gacctgcatg gtgaccgact tcatgcccga ggacatctac 960
gtggagtgga ccaacaacgg caagaccgag ctgaactaca agaacaccga gcccgtgctg 1020
gacagcgacg gcagctactt catgtatagc aagctgagag tcgagaagaa aaactgggtg 1080
gagcggaaca gctacagctg cagcgtggtg cacgagggcc tgcacaacca ccacaccacc 1140
aagagcttca gccggacccc cggcaagtga 1170

<210> SEQ ID NO 99
<211> LENGTH: 1287
<212> TYPE: DNA
<213> ORGANISM: Homo sapiens

<400> SEQUENCE: 99
atggataggg tcttgctgag gtggatttct ctcttctggc taacagccat ggtcgaaggc 60
cttcaggtca cagtgcccga caagaagaag gtggccatgc tcttccagcc cactgtgctt 120
cgctgccact tctcaacatc ctcccatcag cctgcagttg tgcagtggaa gttcaagtcc 180
tactgccagg atcgcatggg agaatccttg ggcatgtcct ctacccgggc ccaatctctc 240
agcaagagaa acctggaatg ggacccctac ttggattgtt tggacagcag gaggactgtt 300
cgagtagtag cttcaaaaca gggctcgact gtcaccctgg gagatttcta caggggcaga 360
gagatcacga ttgttcatga tgcagatctt caaattggaa agcttatgtg gggagacagc 420
ggactctatt actgtattat caccacccca gatgacctgg aggggaaaaa tgaggactca 480
gtggaactgc tggtgttggg caggacaggg ctgcttgctg atctcttgcc cagttttgct 540
gtggagatta tgggatccga gaacctgtac tttcagggca gcggcgagcc cagaggcccc 600
accatcaagc cctgcccccc ctgcaagtgc ccagccccta acctgctggg cggacccagc 660
gtgttcatct tcccccccaa gatcaaggac gtgctgatga tcagcctgag ccccatcgtg 720
acctgcgtgg tggtggacgt gagcgaggac gaccccgacg tgcagatcag ctggttcgtg 780
aacaacgtgg aggtgcacac cgcccagacc cagacccacc gggaggacta caacagcacc 840
ctgcgggtgg tgtccgccct gcccatccag caccaggact ggatgagcgg caaagaattc 900
aagtgcaagg tgaacaacaa ggacctgcct gcccccatcg agcggaccat cagcaagccc 960
aagggcagcg tgagagcccc ccaggtgtac gtgctgcccc ctcccgagga agagatgacc 1020
aagaaacagg tgaccctgac ctgcatggtg accgacttca tgcccgagga catctacgtg 1080
gagtggacca acaacggcaa gaccgagctg aactacaaga acaccgagcc cgtgctggac 1140
agcgacggca gctacttcat gtatagcaag ctgagagtcg agaagaaaaa ctgggtggag 1200
cggaacagct acagctgcag cgtggtgcac gagggcctgc acaaccacca caccaccaag 1260
agcttcagcc ggacccccgg caagtga 1287

<210> SEQ ID NO 100

-continued

<211> LENGTH: 1740
<212> TYPE: DNA
<213> ORGANISM: Homo sapiens

<400> SEQUENCE: 100
atgtggctca aggtcttcac aactttcctt tcctttgcaa caggtgcttg ctcggggctg 60
aaggtgacag tgccatcaca cactgtccat ggcgtcagag gtcaggccct ctacctaccc 120
gtccactatg gcttccacac tccagcatca gacatccaga tcatatggct atttgagaga 180
ccccacacaa tgcccaaata cttactgggc tctgtgaata agtctgtggt tcctgacttg 240
gaataccaac acaagttcac catgatgcca cccaatgcat ctctgcttat caacccactg 300
cagttccctg atgaaggcaa ttacatcgtg aaggtcaaca ttcagggaaa tggaactcta 360
tctgccagtc agaagataca agtcacggtt gatgatcctg tcacaaagcc agtggtgcag 420
attcatcctc cctctggggc tgtggagtat gtggggaaca tgaccctgac atgccatgtg 480
gaagggggca ctcggctagc ttaccaatgg ctaaaaaatg ggagacctgt ccacaccagc 540
tccacctact ccttttctcc ccaaaacaat acccttcata ttgctccagt aaccaaggaa 600
gacattggga attacagctg cctggtgagg aaccctgtca gtgaaatgga aagtgatatc 660
attatgccca tcatatatta tggaccttat ggacttcaag tgaattctga taaagggcta 720
aaagtagggg aagtgtttac tgttgacctt ggagaggcca tcctatttga ttgttctgct 780
gattctcatc cccccaacac ctactcctgg attaggagga ctgacaatac tacatatatc 840
attaagcatg ggcctcgctt agaagttgca tctgagaaag tagcccagaa gacaatggac 900
tatgtgtgct gtgcttacaa caacataacc ggcaggcaag atgaaactca tttcacagtt 960
atcatcactt ccgtaggact ggagaagctt gcacagaaag gaaaaggatc cgagaacctg 1020
tactttcagg gcagcggcga gcccagaggc cccaccatca agccctgccc cccctgcaag 1080
tgcccagccc ctaacctgct gggcggaccc agcgtgttca tcttcccccc caagatcaag 1140
gacgtgctga tgatcagcct gagccccatc gtgacctgcg tggtggtgga cgtgagcgag 1200
gacgaccccg acgtgcagat cagctggttc gtgaacaacg tggaggtgca caccgcccag 1260
acccagaccc accgggagga ctacaacagc accctgcggg tggtgtccgc cctgcccatc 1320
cagcaccagg actggatgag cggcaaagaa ttcaagtgca aggtgaacaa caaggacctg 1380
cctgccccca tcgagcggac catcagcaag cccaagggca gcgtgagagc cccccaggtg 1440
tacgtgctgc cccctcccga ggaagagatg accaagaaac aggtgaccct gacctgcatg 1500
gtgaccgact tcatgcccga ggacatctac gtggagtgga ccaacaacgg caagaccgag 1560
ctgaactaca agaacaccga gcccgtgctg gacagcgacg gcagctactt catgtatagc 1620
aagctgagag tcgagaagaa aaactgggtg gagcggaaca gctacagctg cagcgtggtg 1680
cacgagggcc tgcacaacca ccacaccacc aagagcttca gccggacccc cggcaagtga 1740

<210> SEQ ID NO 101
<211> LENGTH: 1167
<212> TYPE: DNA
<213> ORGANISM: Homo sapiens

<400> SEQUENCE: 101
atgaacagct tcagcaccag cgccttcggc cccgtggcct tcagcctggg cctgctgctg 60
gtgctgcctg ccgccttccc tgccccccgtg ccccccttcg aagcccagct ccaggacgtg 120
gtggtgacat ggcgcttcaa gtccttctgc aaggacccta tctttgacta ctactcagcg 180
tcataccagg cagctttatc cctgggccag gacccatcca atgactgcaa cgacaaccag 240

-continued

```
cgggaagttc gcatagtggc ccagcggcgg gggcagaatg agcccgtgct gggggtagat    300

taccggcagc gcaagatcac catccagaac cgagcagatc tcgtgataaa tgaagtgatg    360

tggtgggacc atggagtgta ttactgcacc attgaggctc caggggacac atcaggagac    420

cccgataagg aaggatccga gaacctgtac tttcagggca gcggcgagcc cagaggcccc    480

accatcaagc cctgcccccc ctgcaagtgc ccagcccccta acctgctggg cggacccagc    540

gtgttcatct tccccccaa gatcaaggac gtgctgatga tcagcctgag ccccatcgtg    600

acctgcgtgg tggtggacgt gagcgaggac gaccccgacg tgcagatcag ctggttcgtg    660

aacaacgtgg aggtgcacac cgcccagacc cagacccacc gggaggacta caacagcacc    720

ctgcgggtgg tgtccgccct gcccatccag caccaggact ggatgagcgg caaagaattc    780

aagtgcaagg tgaacaacaa ggacctgcct gcccccatcg agcggaccat cagcaagccc    840

aagggcagcg tgagagcccc ccaggtgtac gtgctgcccc ctcccgagga agagatgacc    900

aagaaacagg tgaccctgac ctgcatggtg accgacttca tgcccgagga catctacgtg    960

gagtggacca acaacggcaa gaccgagctg aactacaaga acaccgagcc cgtgctggac   1020

agcgacggca gctacttcat gtatagcaag ctgagagtcg agaagaaaaa ctgggtggag   1080

cggaacagct acagctgcag cgtggtgcac gagggcctgc acaaccacca caccaccaag   1140

agcttcagcc ggacccccgg caagtga                                       1167
```

<210> SEQ ID NO 102
<211> LENGTH: 1641
<212> TYPE: DNA
<213> ORGANISM: Homo sapiens

<400> SEQUENCE: 102

```
atgaacagct tcagcaccag cgccttcggc cccgtggcct tcagcctggg cctgctgctg     60

gtgctgcctg ccgccttccc tgcccccgtg cccccttcg aaatcccaga cggtttcgtg    120

aacgtgactg ttggatctaa tgtcactctc atctgcatct acaccaccac tgtggcctcc    180

cgagaacagc tttccatcca gtggtctttc ttccataaga aggagatgga gccaatttct    240

cacagctcgt gcctcagtac tgagggtatg gaggaaaagg cagtcagtca gtgtctaaaa    300

atgacgcacg caagagacgc tcggggaaga tgtagctgga cctctgagtc tccttgggag    360

gaggggaagt ggccagatgt tgaggctgtg aagggcactc ttgatggaca gcaggctgaa    420

ctccagattt acttttctca aggtggacaa gctgtagcca tcgggcaatt taaagatcga    480

attacagggt ccaacgatcc aggtaatgca tctatcacta tctcgcatat gcagccagca    540

gacagtggaa tttacatctg cgatgttaac aacccccag actttctcgg ccaaaaccaa    600

ggcatcctca acgtcagtgt gttagtgaaa ccttctaagc cccttttgtag cgttcaagga    660

agaccagaaa ctggccacac tatttccctt tcctgtctct ctgcgcttgg aacaccttcc    720

cctgtgtact actggcataa acttgaggga agagacatcg tgccagtgaa agaaaacttc    780

aacccaacca ccgggatttt ggtcattgga aatctgacaa attttgaaca aggttattac    840

cagtgtactg ccatcaacag acttggcaat agttcctgcg aaatcgatct cacttcttca    900

catccaggat ccgagaacct gtactttcag ggcagcggcg agcccagagg ccccaccatc    960

aagccctgcc ccccctgcaa gtgcccagcc cctaacctgc tgggcggacc cagcgtgttc   1020

atcttccccc ccaagatcaa ggacgtgctg atgatcagcc tgagccccat cgtgacctgc   1080

gtggtggtgg acgtgagcga ggacgacccc gacgtgcaga tcagctggtt cgtgaacaac   1140
```

```
gtggaggtgc acaccgccca gacccagacc caccgggagg actacaacag caccctgcgg   1200

gtggtgtccg ccctgcccat ccagcaccag gactggatga gcggcaaaga attcaagtgc   1260

aaggtgaaca acaaggacct gcctgccccc atcgagcgga ccatcagcaa gcccaagggc   1320

agcgtgagag ccccccaggt gtacgtgctg ccccctcccg aggaagagat gaccaagaaa   1380

caggtgaccc tgacctgcat ggtgaccgac ttcatgcccg aggacatcta cgtggagtgg   1440

accaacaacg gcaagaccga gctgaactac aagaacaccg agcccgtgct ggacagcgac   1500

ggcagctact tcatgtatag caagctgaga gtcgagaaga aaaactgggt ggagcggaac   1560

agctacagct gcagcgtggt gcacgagggc ctgcacaacc accacaccac caagagcttc   1620

agccggaccc ccggcaagtg a                                             1641


<210> SEQ ID NO 103
<211> LENGTH: 307
<212> TYPE: PRT
<213> ORGANISM: Homo sapiens

<400> SEQUENCE: 103

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Gly Ala Pro Tyr Ile Phe Val Lys Arg Met Gly Gly Gln Met Lys Arg
        35                  40                  45

Thr Gln Ala Gly Thr Glu Val Pro Ser Thr Phe Leu Leu Asp Trp Gly
    50                  55                  60

Ser Glu Asn Leu Tyr Phe Gln Gly Ser Gly Glu Pro Arg Gly Pro Thr
65                  70                  75                  80

Ile Lys Pro Cys Pro Pro Cys Lys Cys Pro Ala Pro Asn Leu Leu Gly
                85                  90                  95

Gly Pro Ser Val Phe Ile Phe Pro Pro Lys Ile Lys Asp Val Leu Met
            100                 105                 110

Ile Ser Leu Ser Pro Ile Val Thr Cys Val Val Val Asp Val Ser Glu
        115                 120                 125

Asp Asp Pro Asp Val Gln Ile Ser Trp Phe Val Asn Asn Val Glu Val
    130                 135                 140

His Thr Ala Gln Thr Gln Thr His Arg Glu Asp Tyr Asn Ser Thr Leu
145                 150                 155                 160

Arg Val Val Ser Ala Leu Pro Ile Gln His Gln Asp Trp Met Ser Gly
                165                 170                 175

Lys Glu Phe Lys Cys Lys Val Asn Asn Lys Asp Leu Pro Ala Pro Ile
            180                 185                 190

Glu Arg Thr Ile Ser Lys Pro Lys Gly Ser Val Arg Ala Pro Gln Val
        195                 200                 205

Tyr Val Leu Pro Pro Pro Glu Glu Glu Met Thr Lys Lys Gln Val Thr
    210                 215                 220

Leu Thr Cys Met Val Thr Asp Phe Met Pro Glu Asp Ile Tyr Val Glu
225                 230                 235                 240

Trp Thr Asn Asn Gly Lys Thr Glu Leu Asn Tyr Lys Asn Thr Glu Pro
                245                 250                 255

Val Leu Asp Ser Asp Gly Ser Tyr Phe Met Tyr Ser Lys Leu Arg Val
            260                 265                 270

Glu Lys Lys Asn Trp Val Glu Arg Asn Ser Tyr Ser Cys Ser Val Val
        275                 280                 285
```

His Glu Gly Leu His Asn His His Thr Thr Lys Ser Phe Ser Arg Thr
    290                 295                 300

Pro Gly Lys
305

<210> SEQ ID NO 104
<211> LENGTH: 389
<212> TYPE: PRT
<213> ORGANISM: Homo sapiens

<400> SEQUENCE: 104

Met Arg Pro Leu Pro Ser Gly Arg Arg Lys Thr Arg Gly Ile Ser Leu
1               5                   10                  15

Gly Leu Phe Ala Leu Cys Leu Ala Ala Ala Arg Cys Leu Gln Ser Gln
            20                  25                  30

Gly Val Ser Leu Tyr Ile Pro Gln Ala Thr Ile Asn Ala Thr Val Lys
        35                  40                  45

Glu Asp Ile Leu Leu Ser Val Glu Tyr Ser Cys His Gly Val Pro Thr
    50                  55                  60

Ile Glu Trp Thr Tyr Ser Ser Asn Trp Gly Thr Gln Lys Ile Val Glu
65                  70                  75                  80

Trp Lys Pro Gly Thr Gln Ala Asn Ile Ser Gln Ser His Lys Asp Arg
                85                  90                  95

Val Cys Thr Phe Asp Asn Gly Ser Ile Gln Leu Phe Ser Val Gly Val
            100                 105                 110

Arg Asp Ser Gly Tyr Tyr Val Ile Thr Val Thr Glu Arg Leu Gly Ser
        115                 120                 125

Ser Gln Phe Gly Thr Ile Val Leu His Val Ser Glu Ile Leu Tyr Glu
    130                 135                 140

Asp Gly Ser Glu Asn Leu Tyr Phe Gln Gly Ser Gly Glu Pro Arg Gly
145                 150                 155                 160

Pro Thr Ile Lys Pro Cys Pro Pro Cys Lys Cys Pro Ala Pro Asn Leu
                165                 170                 175

Leu Gly Gly Pro Ser Val Phe Ile Phe Pro Pro Lys Ile Lys Asp Val
            180                 185                 190

Leu Met Ile Ser Leu Ser Pro Ile Val Thr Cys Val Val Val Asp Val
        195                 200                 205

Ser Glu Asp Asp Pro Asp Val Gln Ile Ser Trp Phe Val Asn Asn Val
    210                 215                 220

Glu Val His Thr Ala Gln Thr Gln Thr His Arg Glu Asp Tyr Asn Ser
225                 230                 235                 240

Thr Leu Arg Val Val Ser Ala Leu Pro Ile Gln His Gln Asp Trp Met
                245                 250                 255

Ser Gly Lys Glu Phe Lys Cys Lys Val Asn Asn Lys Asp Leu Pro Ala
            260                 265                 270

Pro Ile Glu Arg Thr Ile Ser Lys Pro Lys Gly Ser Val Arg Ala Pro
        275                 280                 285

Gln Val Tyr Val Leu Pro Pro Pro Glu Glu Glu Met Thr Lys Lys Gln
    290                 295                 300

Val Thr Leu Thr Cys Met Val Thr Asp Phe Met Pro Glu Asp Ile Tyr
305                 310                 315                 320

Val Glu Trp Thr Asn Asn Gly Lys Thr Glu Leu Asn Tyr Lys Asn Thr
                325                 330                 335

Glu Pro Val Leu Asp Ser Asp Gly Ser Tyr Phe Met Tyr Ser Lys Leu

```
            340                 345                 350

Arg Val Glu Lys Lys Asn Trp Val Glu Arg Asn Ser Tyr Ser Cys Ser
        355                 360                 365

Val Val His Glu Gly Leu His Asn His His Thr Thr Lys Ser Phe Ser
    370                 375                 380

Arg Thr Pro Gly Lys
385


<210> SEQ ID NO 105
<211> LENGTH: 428
<212> TYPE: PRT
<213> ORGANISM: Homo sapiens

<400> SEQUENCE: 105

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Gly Ser Glu Asn Leu Tyr Phe Gln
            180                 185                 190

Gly Ser Gly Glu Pro Arg Gly Pro Thr Ile Lys Pro Cys Pro Pro Cys
        195                 200                 205

Lys Cys Pro Ala Pro Asn Leu Leu Gly Gly Pro Ser Val Phe Ile Phe
    210                 215                 220

Pro Pro Lys Ile Lys Asp Val Leu Met Ile Ser Leu Ser Pro Ile Val
225                 230                 235                 240

Thr Cys Val Val Val Asp Val Ser Glu Asp Asp Pro Asp Val Gln Ile
                245                 250                 255

Ser Trp Phe Val Asn Asn Val Glu Val His Thr Ala Gln Thr Gln Thr
            260                 265                 270

His Arg Glu Asp Tyr Asn Ser Thr Leu Arg Val Val Ser Ala Leu Pro
        275                 280                 285

Ile Gln His Gln Asp Trp Met Ser Gly Lys Glu Phe Lys Cys Lys Val
    290                 295                 300

Asn Asn Lys Asp Leu Pro Ala Pro Ile Glu Arg Thr Ile Ser Lys Pro
305                 310                 315                 320
```

```
Lys Gly Ser Val Arg Ala Pro Gln Val Tyr Val Leu Pro Pro Pro Glu
            325                 330                 335

Glu Glu Met Thr Lys Lys Gln Val Thr Leu Thr Cys Met Val Thr Asp
            340                 345                 350

Phe Met Pro Glu Asp Ile Tyr Val Glu Trp Thr Asn Asn Gly Lys Thr
        355                 360                 365

Glu Leu Asn Tyr Lys Asn Thr Glu Pro Val Leu Asp Ser Asp Gly Ser
    370                 375                 380

Tyr Phe Met Tyr Ser Lys Leu Arg Val Glu Lys Lys Asn Trp Val Glu
385                 390                 395                 400

Arg Asn Ser Tyr Ser Cys Ser Val Val His Glu Gly Leu His Asn His
            405                 410                 415

His Thr Thr Lys Ser Phe Ser Arg Thr Pro Gly Lys
            420                 425


<210> SEQ ID NO 106
<211> LENGTH: 579
<212> TYPE: PRT
<213> ORGANISM: Homo sapiens

<400> SEQUENCE: 106

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Gly Phe His Thr Pro
        35                  40                  45

Ala Ser Asp Ile Gln Ile Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Ile Leu Phe
                245                 250                 255

Asp Cys Ser Ala Asp Ser His Pro Pro Asn Thr Tyr Ser Trp Ile Arg
            260                 265                 270
```

Arg Thr Asp Asn Thr Thr Tyr Ile Ile Lys His Gly Pro Arg Leu Glu
275 280 285

Val Ala Ser Glu Lys Val Ala Gln Lys Thr Met Asp Tyr Val Cys Cys
290 295 300

Ala Tyr Asn Asn Ile Thr Gly Arg Gln Asp Glu Thr His Phe Thr Val
305 310 315 320

Ile Ile Thr Ser Val Gly Leu Glu Lys Leu Ala Gln Lys Gly Lys Gly
325 330 335

Ser Glu Asn Leu Tyr Phe Gln Gly Ser Gly Glu Pro Arg Gly Pro Thr
340 345 350

Ile Lys Pro Cys Pro Pro Cys Lys Cys Pro Ala Pro Asn Leu Leu Gly
355 360 365

Gly Pro Ser Val Phe Ile Phe Pro Pro Lys Ile Lys Asp Val Leu Met
370 375 380

Ile Ser Leu Ser Pro Ile Val Thr Cys Val Val Val Asp Val Ser Glu
385 390 395 400

Asp Asp Pro Asp Val Gln Ile Ser Trp Phe Val Asn Asn Val Glu Val
405 410 415

His Thr Ala Gln Thr Gln Thr His Arg Glu Asp Tyr Asn Ser Thr Leu
420 425 430

Arg Val Val Ser Ala Leu Pro Ile Gln His Gln Asp Trp Met Ser Gly
435 440 445

Lys Glu Phe Lys Cys Lys Val Asn Asn Lys Asp Leu Pro Ala Pro Ile
450 455 460

Glu Arg Thr Ile Ser Lys Pro Lys Gly Ser Val Arg Ala Pro Gln Val
465 470 475 480

Tyr Val Leu Pro Pro Pro Glu Glu Glu Met Thr Lys Lys Gln Val Thr
485 490 495

Leu Thr Cys Met Val Thr Asp Phe Met Pro Glu Asp Ile Tyr Val Glu
500 505 510

Trp Thr Asn Asn Gly Lys Thr Glu Leu Asn Tyr Lys Asn Thr Glu Pro
515 520 525

Val Leu Asp Ser Asp Gly Ser Tyr Phe Met Tyr Ser Lys Leu Arg Val
530 535 540

Glu Lys Lys Asn Trp Val Glu Arg Asn Ser Tyr Ser Cys Ser Val Val
545 550 555 560

His Glu Gly Leu His Asn His His Thr Thr Lys Ser Phe Ser Arg Thr
565 570 575

Pro Gly Lys

<210> SEQ ID NO 107
<211> LENGTH: 388
<212> TYPE: PRT
<213> ORGANISM: Homo sapiens

<400> SEQUENCE: 107

Met Asn Ser Phe Ser Thr Ser Ala Phe Gly Pro Val Ala Phe Ser Leu
1 5 10 15

Gly Leu Leu Leu Val Leu Pro Ala Ala Phe Pro Ala Pro Val Pro Pro
20 25 30

Phe Glu Ala Gln Leu Gln Asp Val Val Val Thr Trp Arg Phe Lys Ser
35 40 45

Phe Cys Lys Asp Pro Ile Phe Asp Tyr Tyr Ser Ala Ser Tyr Gln Ala
50 55 60

-continued

Ala Leu Ser Leu Gly Gln Asp Pro Ser Asn Asp Cys Asn Asp Asn Gln
65 70 75 80

Arg Glu Val Arg Ile Val Ala Gln Arg Arg Gly Gln Asn Glu Pro Val
85 90 95

Leu Gly Val Asp Tyr Arg Gln Arg Lys Ile Thr Ile Gln Asn Arg Ala
100 105 110

Asp Leu Val Ile Asn Glu Val Met Trp Trp Asp His Gly Val Tyr Tyr
115 120 125

Cys Thr Ile Glu Ala Pro Gly Asp Thr Ser Gly Asp Pro Asp Lys Glu
130 135 140

Gly Ser Glu Asn Leu Tyr Phe Gln Gly Ser Gly Glu Pro Arg Gly Pro
145 150 155 160

Thr Ile Lys Pro Cys Pro Pro Cys Lys Cys Pro Ala Pro Asn Leu Leu
165 170 175

Gly Gly Pro Ser Val Phe Ile Phe Pro Pro Lys Ile Lys Asp Val Leu
180 185 190

Met Ile Ser Leu Ser Pro Ile Val Thr Cys Val Val Val Asp Val Ser
195 200 205

Glu Asp Asp Pro Asp Val Gln Ile Ser Trp Phe Val Asn Asn Val Glu
210 215 220

Val His Thr Ala Gln Thr Gln Thr His Arg Glu Asp Tyr Asn Ser Thr
225 230 235 240

Leu Arg Val Val Ser Ala Leu Pro Ile Gln His Gln Asp Trp Met Ser
245 250 255

Gly Lys Glu Phe Lys Cys Lys Val Asn Asn Lys Asp Leu Pro Ala Pro
260 265 270

Ile Glu Arg Thr Ile Ser Lys Pro Lys Gly Ser Val Arg Ala Pro Gln
275 280 285

Val Tyr Val Leu Pro Pro Pro Glu Glu Glu Met Thr Lys Lys Gln Val
290 295 300

Thr Leu Thr Cys Met Val Thr Asp Phe Met Pro Glu Asp Ile Tyr Val
305 310 315 320

Glu Trp Thr Asn Asn Gly Lys Thr Glu Leu Asn Tyr Lys Asn Thr Glu
325 330 335

Pro Val Leu Asp Ser Asp Gly Ser Tyr Phe Met Tyr Ser Lys Leu Arg
340 345 350

Val Glu Lys Lys Asn Trp Val Glu Arg Asn Ser Tyr Ser Cys Ser Val
355 360 365

Val His Glu Gly Leu His Asn His His Thr Thr Lys Ser Phe Ser Arg
370 375 380

Thr Pro Gly Lys
385

<210> SEQ ID NO 108
<211> LENGTH: 546
<212> TYPE: PRT
<213> ORGANISM: Homo sapiens

<400> SEQUENCE: 108

Met Asn Ser Phe Ser Thr Ser Ala Phe Gly Pro Val Ala Phe Ser Leu
1 5 10 15

Gly Leu Leu Leu Val Leu Pro Ala Ala Phe Pro Ala Pro Val Pro Pro
20 25 30

Phe Glu Ile Pro Asp Gly Phe Val Asn Val Thr Val Gly Ser Asn Val

-continued

```
        35                  40                  45

Thr Leu Ile Cys Ile Tyr Thr Thr Thr Val Ala Ser Arg Glu Gln Leu
    50                  55                  60

Ser Ile Gln Trp Ser Phe Phe His Lys Lys Glu Met Glu Pro Ile Ser
65                  70                  75                  80

His Ser Ser Cys Leu Ser Thr Glu Gly Met Glu Glu Lys Ala Val Ser
                85                  90                  95

Gln Cys Leu Lys Met Thr His Ala Arg Asp Ala Arg Gly Arg Cys Ser
            100                 105                 110

Trp Thr Ser Glu Ser Pro Trp Glu Glu Gly Lys Trp Pro Asp Val Glu
        115                 120                 125

Ala Val Lys Gly Thr Leu Asp Gly Gln Gln Ala Glu Leu Gln Ile Tyr
    130                 135                 140

Phe Ser Gln Gly Gly Gln Ala Val Ala Ile Gly Gln Phe Lys Asp Arg
145                 150                 155                 160

Ile Thr Gly Ser Asn Asp Pro Gly Asn Ala Ser Ile Thr Ile Ser His
                165                 170                 175

Met Gln Pro Ala Asp Ser Gly Ile Tyr Ile Cys Asp Val Asn Asn Pro
            180                 185                 190

Pro Asp Phe Leu Gly Gln Asn Gln Gly Ile Leu Asn Val Ser Val Leu
        195                 200                 205

Val Lys Pro Ser Lys Pro Leu Cys Ser Val Gln Gly Arg Pro Glu Thr
    210                 215                 220

Gly His Thr Ile Ser Leu Ser Cys Leu Ser Ala Leu Gly Thr Pro Ser
225                 230                 235                 240

Pro Val Tyr Tyr Trp His Lys Leu Glu Gly Arg Asp Ile Val Pro Val
                245                 250                 255

Lys Glu Asn Phe Asn Pro Thr Thr Gly Ile Leu Val Ile Gly Asn Leu
            260                 265                 270

Thr Asn Phe Glu Gln Gly Tyr Tyr Gln Cys Thr Ala Ile Asn Arg Leu
        275                 280                 285

Gly Asn Ser Ser Cys Glu Ile Asp Leu Thr Ser Ser His Pro Gly Ser
    290                 295                 300

Glu Asn Leu Tyr Phe Gln Gly Ser Gly Glu Pro Arg Gly Pro Thr Ile
305                 310                 315                 320

Lys Pro Cys Pro Pro Cys Lys Cys Pro Ala Pro Asn Leu Leu Gly Gly
                325                 330                 335

Pro Ser Val Phe Ile Phe Pro Pro Lys Ile Lys Asp Val Leu Met Ile
            340                 345                 350

Ser Leu Ser Pro Ile Val Thr Cys Val Val Val Asp Val Ser Glu Asp
        355                 360                 365

Asp Pro Asp Val Gln Ile Ser Trp Phe Val Asn Asn Val Glu Val His
    370                 375                 380

Thr Ala Gln Thr Gln Thr His Arg Glu Asp Tyr Asn Ser Thr Leu Arg
385                 390                 395                 400

Val Val Ser Ala Leu Pro Ile Gln His Gln Asp Trp Met Ser Gly Lys
                405                 410                 415

Glu Phe Lys Cys Lys Val Asn Asn Lys Asp Leu Pro Ala Pro Ile Glu
            420                 425                 430

Arg Thr Ile Ser Lys Pro Lys Gly Ser Val Arg Ala Pro Gln Val Tyr
        435                 440                 445

Val Leu Pro Pro Pro Glu Glu Glu Met Thr Lys Lys Gln Val Thr Leu
    450                 455                 460
```

```
Thr Cys Met Val Thr Asp Phe Met Pro Glu Asp Ile Tyr Val Glu Trp
465                 470                 475                 480

Thr Asn Asn Gly Lys Thr Glu Leu Asn Tyr Lys Asn Thr Glu Pro Val
                485                 490                 495

Leu Asp Ser Asp Gly Ser Tyr Phe Met Tyr Ser Lys Leu Arg Val Glu
            500                 505                 510

Lys Lys Asn Trp Val Glu Arg Asn Ser Tyr Ser Cys Ser Val Val His
        515                 520                 525

Glu Gly Leu His Asn His His Thr Thr Lys Ser Phe Ser Arg Thr Pro
    530                 535                 540

Gly Lys
545


<210> SEQ ID NO 109
<211> LENGTH: 684
<212> TYPE: PRT
<213> ORGANISM: Homo sapiens

<400> SEQUENCE: 109

Met Ala Arg His Arg Asn Val Arg Gly Tyr Asn Tyr Asp Glu Asp Phe
1               5                   10                  15

Glu Asp Asp Asp Leu Tyr Gly Gln Ser Val Glu Asp Asp Tyr Cys Ile
            20                  25                  30

Ser Pro Ser Thr Ala Ala Gln Phe Ile Tyr Ser Arg Arg Asp Lys Pro
        35                  40                  45

Ser Val Glu Pro Val Glu Glu Tyr Asp Tyr Glu Asp Leu Lys Glu Ser
    50                  55                  60

Ser Asn Ser Val Ser Asn His Gln Leu Ser Gly Phe Asp Gln Ala Arg
65                  70                  75                  80

Leu Tyr Ser Cys Leu Asp His Met Arg Glu Val Leu Gly Asp Ala Val
                85                  90                  95

Pro Asp Glu Ile Leu Ile Glu Ala Val Leu Lys Asn Lys Phe Asp Val
            100                 105                 110

Gln Lys Ala Leu Ser Gly Val Leu Glu Gln Asp Arg Val Gln Ser Leu
        115                 120                 125

Lys Asp Lys Asn Glu Ala Thr Val Ser Thr Gly Lys Ile Ala Lys Gly
    130                 135                 140

Lys Pro Val Asp Ser Gln Thr Ser Arg Ser Glu Ser Glu Ile Val Pro
145                 150                 155                 160

Lys Val Ala Lys Met Thr Val Ser Gly Lys Lys Gln Thr Met Gly Phe
                165                 170                 175

Glu Val Pro Gly Val Ser Ser Glu Glu Asn Gly His Ser Phe His Thr
            180                 185                 190

Pro Gln Lys Gly Pro Pro Ile Glu Asp Ala Ile Ala Ser Ser Asp Val
        195                 200                 205

Leu Glu Thr Ala Ser Lys Ser Ala Asn Pro Pro His Thr Ile Gln Ala
    210                 215                 220

Ser Glu Glu Gln Ser Ser Thr Pro Ala Pro Val Lys Lys Ser Gly Lys
225                 230                 235                 240

Leu Arg Gln Gln Ile Asp Val Lys Ala Glu Leu Glu Lys Arg Gln Gly
                245                 250                 255

Gly Lys Gln Leu Leu Asn Leu Val Val Ile Gly His Val Asp Ala Gly
            260                 265                 270

Lys Ser Thr Leu Met Gly His Met Leu Tyr Leu Leu Gly Asn Ile Asn
```

-continued

```
        275                 280                 285

Lys Arg Thr Met His Lys Tyr Glu Gln Glu Ser Lys Lys Ala Gly Lys
    290                 295                 300

Ala Ser Phe Ala Tyr Ala Trp Val Leu Asp Glu Thr Gly Glu Glu Arg
305                 310                 315                 320

Glu Arg Gly Val Thr Met Asp Val Gly Met Thr Lys Phe Glu Thr Thr
                325                 330                 335

Thr Lys Val Ile Thr Leu Met Asp Ala Pro Gly His Lys Asp Phe Ile
            340                 345                 350

Pro Asn Met Ile Thr Gly Ala Ala Gln Ala Asp Val Ala Val Leu Val
        355                 360                 365

Val Asp Ala Ser Arg Gly Glu Phe Glu Ala Gly Phe Glu Thr Gly Gly
    370                 375                 380

Gln Thr Arg Glu His Gly Leu Leu Val Arg Ser Leu Gly Val Thr Gln
385                 390                 395                 400

Leu Ala Val Ala Val Asn Lys Met Asp Gln Val Asn Trp Gln Gln Glu
                405                 410                 415

Arg Phe Gln Glu Ile Thr Gly Lys Leu Gly His Phe Leu Lys Gln Ala
            420                 425                 430

Gly Phe Lys Glu Ser Asp Val Gly Phe Ile Pro Thr Ser Gly Leu Ser
        435                 440                 445

Gly Glu Asn Leu Ile Thr Arg Ser Gln Ser Ser Glu Leu Thr Lys Trp
    450                 455                 460

Tyr Lys Gly Leu Cys Leu Leu Glu Gln Ile Asp Ser Phe Lys Pro Pro
465                 470                 475                 480

Gln Arg Ser Ile Asp Lys Pro Phe Arg Leu Cys Val Ser Asp Val Phe
                485                 490                 495

Lys Asp Gln Gly Ser Gly Phe Cys Ile Thr Gly Lys Ile Glu Ala Gly
            500                 505                 510

Tyr Ile Gln Thr Gly Asp Arg Leu Leu Ala Met Pro Pro Asn Glu Thr
        515                 520                 525

Cys Thr Val Lys Gly Ile Thr Leu His Asp Glu Pro Val Asp Trp Ala
    530                 535                 540

Ala Ala Gly Asp His Val Ser Leu Thr Leu Val Gly Met Asp Ile Ile
545                 550                 555                 560

Lys Ile Asn Val Gly Cys Ile Phe Cys Gly Pro Lys Val Pro Ile Lys
                565                 570                 575

Ala Cys Thr Arg Phe Arg Ala Arg Ile Leu Ile Phe Asn Ile Glu Ile
            580                 585                 590

Pro Ile Thr Lys Gly Phe Pro Val Leu Leu His Tyr Gln Thr Val Ser
        595                 600                 605

Glu Pro Ala Val Ile Lys Arg Leu Ile Ser Val Leu Asn Lys Ser Thr
    610                 615                 620

Gly Glu Val Thr Lys Lys Lys Pro Lys Phe Leu Thr Lys Gly Gln Asn
625                 630                 635                 640

Ala Leu Val Glu Leu Gln Thr Gln Arg Pro Ile Ala Leu Glu Leu Tyr
                645                 650                 655

Lys Asp Phe Lys Glu Leu Gly Arg Phe Met Leu Arg Tyr Gly Gly Ser
            660                 665                 670

Thr Ile Ala Ala Gly Val Val Thr Glu Ile Lys Glu
        675                 680
```

<210> SEQ ID NO 110

<211> LENGTH: 664
<212> TYPE: PRT
<213> ORGANISM: Homo sapiens

<400> SEQUENCE: 110

Met Ser Gly Val Arg Gly Leu Ser Arg Leu Leu Ser Ala Arg Arg Leu
1 5 10 15

Ala Leu Ala Lys Ala Trp Pro Thr Val Leu Gln Thr Gly Thr Arg Gly
20 25 30

Phe His Phe Thr Val Asp Gly Asn Lys Arg Ala Ser Ala Lys Val Ser
35 40 45

Asp Ser Ile Ser Ala Gln Tyr Pro Val Val Asp His Glu Phe Asp Ala
50 55 60

Val Val Val Gly Ala Gly Gly Ala Gly Leu Arg Ala Ala Phe Gly Leu
65 70 75 80

Ser Glu Ala Gly Phe Asn Thr Ala Cys Val Thr Lys Leu Phe Pro Thr
85 90 95

Arg Ser His Thr Val Ala Ala Gln Gly Gly Ile Asn Ala Ala Leu Gly
100 105 110

Asn Met Glu Glu Asp Asn Trp Arg Trp His Phe Tyr Asp Thr Val Lys
115 120 125

Gly Ser Asp Trp Leu Gly Asp Gln Asp Ala Ile His Tyr Met Thr Glu
130 135 140

Gln Ala Pro Ala Ala Val Val Glu Leu Glu Asn Tyr Gly Met Pro Phe
145 150 155 160

Ser Arg Thr Glu Asp Gly Lys Ile Tyr Gln Arg Ala Phe Gly Gly Gln
165 170 175

Ser Leu Lys Phe Gly Lys Gly Gly Gln Ala His Arg Cys Cys Cys Val
180 185 190

Ala Asp Arg Thr Gly His Ser Leu Leu His Thr Leu Tyr Gly Arg Ser
195 200 205

Leu Arg Tyr Asp Thr Ser Tyr Phe Val Glu Tyr Phe Ala Leu Asp Leu
210 215 220

Leu Met Glu Asn Gly Glu Cys Arg Gly Val Ile Ala Leu Cys Ile Glu
225 230 235 240

Asp Gly Ser Ile His Arg Ile Arg Ala Lys Asn Thr Val Val Ala Thr
245 250 255

Gly Gly Tyr Gly Arg Thr Tyr Phe Ser Cys Thr Ser Ala His Thr Ser
260 265 270

Thr Gly Asp Gly Thr Ala Met Ile Thr Arg Ala Gly Leu Pro Cys Gln
275 280 285

Asp Leu Glu Phe Val Gln Phe His Pro Thr Gly Ile Tyr Gly Ala Gly
290 295 300

Cys Leu Ile Thr Glu Gly Cys Arg Gly Glu Gly Gly Ile Leu Ile Asn
305 310 315 320

Ser Gln Gly Glu Arg Phe Met Glu Arg Tyr Ala Pro Val Ala Lys Asp
325 330 335

Leu Ala Ser Arg Asp Val Val Ser Arg Ser Met Thr Leu Glu Ile Arg
340 345 350

Glu Gly Arg Gly Cys Gly Pro Glu Lys Asp His Val Tyr Leu Gln Leu
355 360 365

His His Leu Pro Pro Glu Gln Leu Ala Thr Arg Leu Pro Gly Ile Ser
370 375 380

Glu Thr Ala Met Ile Phe Ala Gly Val Asp Val Thr Lys Glu Pro Ile 385 390 395 400

Pro Val Leu Pro Thr Val His Tyr Asn Met Gly Gly Ile Pro Thr Asn
405 410 415

Tyr Lys Gly Gln Val Leu Arg His Val Asn Gly Gln Asp Gln Ile Val
420 425 430

Pro Gly Leu Tyr Ala Cys Gly Glu Ala Ala Cys Ala Ser Val His Gly
435 440 445

Ala Asn Arg Leu Gly Ala Asn Ser Leu Leu Asp Leu Val Val Phe Gly
450 455 460

Arg Ala Cys Ala Leu Ser Ile Glu Glu Ser Cys Arg Pro Gly Asp Lys
465 470 475 480

Val Pro Pro Ile Lys Pro Asn Ala Gly Glu Glu Ser Val Met Asn Leu
485 490 495

Asp Lys Leu Arg Phe Ala Asp Gly Ser Ile Arg Thr Ser Glu Leu Arg
500 505 510

Leu Ser Met Gln Lys Ser Met Gln Asn His Ala Ala Val Phe Arg Val
515 520 525

Gly Ser Val Leu Gln Glu Gly Cys Gly Lys Ile Ser Lys Leu Tyr Gly
530 535 540

Asp Leu Lys His Leu Lys Thr Phe Asp Arg Gly Met Val Trp Asn Thr
545 550 555 560

Asp Leu Val Glu Thr Leu Glu Leu Gln Asn Leu Met Leu Cys Ala Leu
565 570 575

Gln Thr Ile Tyr Gly Ala Glu Ala Arg Lys Glu Ser Arg Gly Ala His
580 585 590

Ala Arg Glu Asp Tyr Lys Val Arg Ile Asp Glu Tyr Asp Tyr Ser Lys
595 600 605

Pro Ile Gln Gly Gln Gln Lys Lys Pro Phe Glu Glu His Trp Arg Lys
610 615 620

His Thr Leu Ser Tyr Val Asp Val Gly Thr Gly Lys Val Thr Leu Glu
625 630 635 640

Tyr Arg Pro Val Ile Asp Lys Thr Leu Asn Glu Ala Asp Cys Ala Thr
645 650 655

Val Pro Pro Ala Ile Arg Ser Tyr
660

<210> SEQ ID NO 111
<211> LENGTH: 494
<212> TYPE: PRT
<213> ORGANISM: Homo sapiens

<400> SEQUENCE: 111

Met Pro Arg Val Tyr Ile Gly Arg Leu Ser Tyr Gln Ala Arg Glu Arg
1 5 10 15

Asp Val Glu Arg Phe Phe Lys Gly Tyr Gly Lys Ile Leu Glu Val Asp
20 25 30

Leu Lys Asn Gly Tyr Gly Phe Val Glu Phe Asp Asp Leu Arg Asp Ala
35 40 45

Asp Asp Ala Val Tyr Glu Leu Asn Gly Lys Asp Leu Cys Gly Glu Arg
50 55 60

Val Ile Val Glu His Ala Arg Gly Pro Arg Arg Asp Gly Ser Tyr Gly
65 70 75 80

Ser Gly Arg Ser Gly Tyr Gly Tyr Arg Arg Ser Gly Arg Asp Lys Tyr
85 90 95

-continued

```
Gly Pro Pro Thr Arg Thr Glu Tyr Arg Leu Ile Val Glu Asn Leu Ser
            100                 105                 110

Ser Arg Cys Ser Trp Gln Asp Leu Lys Asp Tyr Met Arg Gln Ala Gly
        115                 120                 125

Glu Val Thr Tyr Ala Asp Ala His Lys Gly Arg Lys Asn Glu Gly Val
    130                 135                 140

Ile Glu Phe Val Ser Tyr Ser Asp Met Lys Arg Ala Leu Glu Lys Leu
145                 150                 155                 160

Asp Gly Thr Glu Val Asn Gly Arg Lys Ile Arg Leu Val Glu Asp Lys
                165                 170                 175

Pro Gly Ser Arg Arg Arg Arg Ser Tyr Ser Arg Ser Arg Ser His Ser
            180                 185                 190

Arg Ser Arg Ser Arg Ser Arg His Ser Arg Lys Ser Arg Ser Arg Ser
        195                 200                 205

Gly Ser Ser Lys Ser Ser His Ser Lys Ser Arg Ser Arg Ser Arg Ser
    210                 215                 220

Gly Ser Arg Ser Arg Ser Lys Ser Arg Ser Arg Ser Gln Ser Arg Ser
225                 230                 235                 240

Arg Ser Lys Lys Glu Lys Ser Arg Ser Pro Ser Lys Glu Lys Ser Arg
                245                 250                 255

Ser Arg Ser His Ser Ala Gly Lys Ser Arg Ser Lys Ser Lys Asp Gln
            260                 265                 270

Ala Glu Glu Lys Ile Gln Asn Asn Asp Asn Val Gly Lys Pro Lys Ser
        275                 280                 285

Arg Ser Pro Ser Arg His Lys Ser Lys Ser Lys Ser Arg Ser Arg Ser
    290                 295                 300

Gln Glu Arg Arg Val Glu Glu Glu Lys Arg Gly Ser Val Ser Arg Gly
305                 310                 315                 320

Arg Ser Gln Glu Lys Ser Leu Arg Gln Ser Arg Ser Arg Ser Arg Ser
                325                 330                 335

Lys Gly Gly Ser Arg Ser Arg Ser Arg Ser Arg Ser Lys Ser Lys Asp
            340                 345                 350

Lys Arg Lys Gly Arg Lys Arg Ser Arg Glu Glu Ser Arg Ser Arg Ser
        355                 360                 365

Arg Ser Arg Ser Lys Ser Glu Arg Ser Arg Lys Arg Gly Ser Lys Arg
    370                 375                 380

Asp Ser Lys Ala Gly Ser Ser Lys Lys Lys Lys Lys Glu Asp Thr Asp
385                 390                 395                 400

Arg Ser Gln Ser Arg Ser Pro Ser Arg Ser Val Ser Lys Glu Arg Glu
                405                 410                 415

His Ala Lys Ser Glu Ser Ser Gln Arg Glu Gly Arg Gly Glu Ser Glu
            420                 425                 430

Asn Ala Gly Thr Asn Gln Glu Thr Arg Ser Arg Ser Arg Ser Asn Ser
        435                 440                 445

Lys Ser Lys Pro Asn Leu Pro Ser Glu Ser Arg Ser Arg Ser Lys Ser
    450                 455                 460

Ala Ser Lys Thr Arg Ser Arg Ser Lys Ser Arg Ser Arg Ser Ala Ser
465                 470                 475                 480

Arg Ser Pro Ser Arg Ser Arg Ser Arg Ser His Ser Arg Ser
                485                 490
```

<210> SEQ ID NO 112
<211> LENGTH: 376
<212> TYPE: PRT

```
<213> ORGANISM: Homo sapiens

<400> SEQUENCE: 112

Thr Phe Pro Arg Glu Trp Leu Cys Asp Arg His Leu Arg Glu Lys Met
1               5                   10                  15

Phe Ser Ser Val Ala His Leu Ala Arg Ala Asn Pro Phe Asn Thr Pro
            20                  25                  30

His Leu Gln Leu Val His Asp Gly Leu Gly Asp Leu Arg Ser Ser Ser
        35                  40                  45

Pro Gly Pro Thr Gly Gln Pro Arg Arg Pro Arg Asn Leu Ala Ala Ala
    50                  55                  60

Ala Val Glu Glu Tyr Ser Cys Glu Phe Gly Ser Ala Lys Tyr Tyr Ala
65                  70                  75                  80

Leu Cys Gly Phe Gly Gly Val Leu Ser Cys Gly Leu Thr His Thr Ala
                85                  90                  95

Val Val Pro Leu Asp Leu Val Lys Cys Arg Met Gln Val Asp Pro Gln
            100                 105                 110

Lys Tyr Lys Gly Ile Phe Asn Gly Phe Ser Val Thr Leu Lys Glu Asp
        115                 120                 125

Gly Val Arg Gly Leu Ala Lys Gly Trp Ala Pro Thr Phe Leu Gly Tyr
    130                 135                 140

Ser Met Gln Gly Leu Cys Lys Phe Gly Phe Tyr Glu Val Phe Lys Val
145                 150                 155                 160

Leu Tyr Ser Asn Met Leu Gly Glu Glu Asn Thr Tyr Leu Trp Arg Thr
                165                 170                 175

Ser Leu Tyr Leu Ala Ala Ser Ala Ser Ala Glu Phe Phe Ala Asp Ile
            180                 185                 190

Ala Leu Ala Pro Met Glu Ala Ala Lys Val Arg Ile Gln Thr Gln Pro
        195                 200                 205

Gly Tyr Ala Asn Thr Leu Arg Asp Ala Ala Pro Lys Met Tyr Lys Glu
    210                 215                 220

Glu Gly Leu Lys Ala Phe Tyr Lys Gly Val Ala Pro Leu Trp Met Arg
225                 230                 235                 240

Gln Ile Pro Tyr Thr Met Met Lys Phe Ala Cys Phe Glu Arg Thr Val
                245                 250                 255

Glu Ala Leu Tyr Lys Phe Val Val Pro Lys Pro Arg Ser Glu Cys Ser
            260                 265                 270

Lys Pro Glu Gln Leu Val Val Thr Phe Val Ala Gly Tyr Ile Ala Gly
        275                 280                 285

Val Phe Cys Ala Ile Val Ser His Pro Ala Asp Ser Val Val Ser Val
    290                 295                 300

Leu Asn Lys Glu Lys Gly Ser Ser Ala Ser Leu Val Leu Lys Arg Leu
305                 310                 315                 320

Gly Phe Lys Gly Val Trp Lys Gly Leu Phe Ala Arg Ile Ile Met Ile
                325                 330                 335

Gly Thr Leu Thr Ala Leu Gln Trp Phe Ile Tyr Asp Ser Val Lys Val
            340                 345                 350

Tyr Phe Arg Leu Pro Arg Pro Pro Pro Pro Glu Met Pro Glu Ser Leu
        355                 360                 365

Lys Lys Lys Leu Gly Leu Thr Gln
    370                 375

<210> SEQ ID NO 113
<211> LENGTH: 748
```

<212> TYPE: DNA
<213> ORGANISM: Homo sapiens

<400> SEQUENCE: 113
gcagataatg ggaggagccg ggcccgagcg agctctttcc tttcgctgct gcggccgcag 60
ccatgagtat gctcaggctt cagaagaggc tcgcctctag tgtcctccgc tgtggcaaga 120
agaaggtctg gttagacccc aatgagacca atgaaatcgc caatgccaac tcccgtcagc 180
agatccggaa gctcatcaaa gatgggctga tcatccgcaa gcctgtgacg gtccattccc 240
gggctcgatg ccggaaaaac accttggccc gccggaaggg caggcacatg ggcataggta 300
agcggaaggg tacagccaat gcccgaatgc cagagaaggt cacatggatg aggagaatga 360
ggattttgcg ccggctgctc agaagatacc gtgaatctaa gaagatcgat cgccacatgt 420
atcacagcct gtacctgaag gtgaagggga atgtgttcaa aaacaagcgg attctcatgg 480
aacacatcca caagctgaag gcagacaagg cccgcaagaa gctcctggct gaccaggctg 540
aggcccgcag gtctaagacc aaggaagcac gcaagcgccg tgaagagcgc ctccaggcca 600
agaaggagga gatcatcaag actttatcca aggaggaaga gaccaagaaa taaaacctcc 660
cactttgtct gtacatactg gcctctgtga ttacatagat cagccattaa aataaaacaa 720
gccttaatct gcaaaaaaaa aaaaaaaa 748

<210> SEQ ID NO 114
<211> LENGTH: 1867
<212> TYPE: DNA
<213> ORGANISM: Homo sapiens

<400> SEQUENCE: 114
ggttcgctgt ggcgggcgcc tgggccgccg gctgtttaac ttcgcttccg ctggcccata 60
gtgatctttg cagtgaccca gcagcatcac tgtttcttgg cgtgtgaaga taacccaagg 120
aattgaggaa gttgctgaga agagtgtgct ggagatgctc taggaaaaaa ttgaatagtg 180
agacgagttc cagcgcaagg gtttctggtt tgccaagaag aaagtgaaca tcatggatca 240
gaacaacagc ctgccacctt acgctcaggg cttggcctcc cctcagggtg ccatgactcc 300
cggaatccct atctttagtc caatgatgcc ttatggcact ggactgaccc cacagcctat 360
tcagaacacc aatagtctgt ctattttgga agagcaacaa aggcagcagc agcaacaaca 420
acagcagcag cagcagcagc agcagcaaca gcaacagcag cagcagcagc agcagcagca 480
gcagcagcag cagcagcagc agcagcagca gcaacaggca gtggcagctg cagccgttca 540
gcagtcaacg tcccagcagg caacacaggg aacctcaggc caggcaccac agctcttcca 600
ctcacagact ctcacaactg caccccttgcc gggcaccact ccactgtatc cctcccccat 660
gactcccatg acccccatca ctcctgccac gccagcttcg gagagttctg ggattgtacc 720
gcagctgcaa aatattgtat ccacagtgaa tcttggttgt aaacttgacc taaagaccat 780
tgcacttcgt gcccgaaacg ccgaatataa tcccaagcgg tttgctgcgg taatcatgag 840
gataagagag ccacgaacca cggcactgat tttcagttct gggaaaatgg tgtgcacagg 900
agccaagagt gaagaacagt ccagactggc agcaagaaaa tatgctagag ttgtacagaa 960
gttgggtttt ccagctaagt tcttggactt caagattcag aatatggtgg ggagctgtga 1020
tgtgaagttt cctataaggt tagaaggcct tgtgctcacc caccaacaat ttagtagtta 1080
tgagccagag ttatttcctg gtttaatcta cagaatgatc aaacccagaa ttgttctcct 1140
tatttttgtt tctggaaaag ttgtattaac aggtgctaaa gtcagagcag aaatttatga 1200

-continued

```
agcatttgaa aacatctacc ctattctaaa gggattcagg aagacgacgt aatggctctc   1260

atgtaccctt gcctccccca cccccttctt ttttttttt taaacaaatc agtttgtttt   1320

ggtaccttta aatggtggtg ttgtgagaag atggatgttg agttgcaggg tgtggcacca   1380

ggtgatgccc ttctgtaagt gcccaccgcg ggatgccggg aaggggcatt atttgtgcac   1440

tgagaacacc gcgcagcgtg actgtgagtt gctcataccg tgctgctatc tgggcagcgc   1500

tgcccattta tttatatgta gattttaaac actgctgttg acaagttggt ttgagggaga   1560

aaactttaag tgttaaagcc acctctataa ttgattggac tttttaattt taatgttttt   1620

ccccatgaac cacagttttt atatttctac cagaaaagta aaaatctttt ttaaaagtgt   1680

tgtttttcta atttataact cctaggggtt atttctgtgc cagacacatt ccacctctcc   1740

agtattgcag gacagaatat atgtgttaat gaaaatgaat ggctgtacat atttttttct   1800

ttcttcagag tactctgtac aataaatgca gtttataaaa gtgttaaaaa aaaaaaaaaa   1860

aaaaaaa                                                             1867
```

<210> SEQ ID NO 115
<211> LENGTH: 2201
<212> TYPE: DNA
<213> ORGANISM: Homo sapiens

<400> SEQUENCE: 115

```
cgggatttgg gtcgcggttc ttgtttgtgg atcgctgtga tcgtcacttg acaatgcaga     60

tcttcgtgaa gactctgact ggtaagacca tcaccctcga ggttgagccc agtgacacca    120

tcgagaatgt caaggcaaag atccaagata aggaaggcat ccctcctgac cagcagaggc    180

tgatctttgc tggaaaacag ctggaagatg ggcgcaccct gtctgactac aacatccaga    240

aagagtccac cctgcacctg gtgctccgtc tcagaggtgg gatgcaaatc ttcgtgaaga    300

cactcactgg caagaccatc acccttgagg tggagcccag tgacaccatc gagaacgtca    360

aagcaaagat ccaggacaag gaaggcattc ctcctgacca gcagaggttg atctttgccg    420

gaaagcagct ggaagatggg cgcaccctgt ctgactacaa catccagaaa gagtctaccc    480

tgcacctggt gctccgtctc agaggtggga tgcagatctt cgtgaagacc ctgactggta    540

agaccatcac cctcgaggtg gagcccagtg acaccatcga gaatgtcaag gcaaagatcc    600

aagataagga aggcattcct cctgatcagc agaggttgat ctttgccgga aaacagctgg    660

aagatggtcg taccctgtct gactacaaca tccagaaaga gtccaccttg cacctggtac    720

tccgtctcag aggtgggatg caaatcttcg tgaagacact cactggcaag accatcaccc    780

ttgaggtcga gcccagtgac actatcgaga acgtcaaagc aaagatccaa gacaaggaag    840

gcattcctcc tgaccagcag aggttgatct ttgccggaaa gcagctggaa gatgggcgca    900

ccctgtctga ctacaacatc cagaaagagt ctaccctgca cctggtgctc cgtctcagag    960

gtgggatgca gatcttcgtg aagaccctga ctggtaagac catcaccctc gaagtggagc   1020

cgagtgacac cattgagaat gtcaaggcaa agatccaaga caaggaaggc atccctcctg   1080

accagcagag gttgatcttt gccggaaaac agctggaaga tggtcgtacc ctgtctgact   1140

acaacatcca gaaagagtcc accttgcacc tggtgctccg tctcagaggt gggatgcaga   1200

tcttcgtgaa gaccctgact ggtaagacca tcactctcga ggtggagccg agtgacacca   1260

ttgagaatgt caaggcaaag atccaagaca aggaaggcat ccctcctgat cagcagaggt   1320

tgatctttgc tgggaaacag ctggaagatg gacgcaccct gtctgactac aacatccaga   1380

aagagtccac cctgcacctg gtgctccgtc ttagaggtgg gatgcagatc ttcgtgaaga   1440
```

ccctgactgg taagaccatc actctcgaag tggagccgag tgacaccatt gagaatgtca 1500
aggcaaagat ccaagacaag gaaggcatcc ctcctgacca gcagaggttg atctttgctg 1560
ggaaacagct ggaagatgga cgcaccctgt ctgactacaa catccagaaa gagtccaccc 1620
tgcacctggt gctccgtctt agaggtggga tgcagatctt cgtgaagacc ctgactggta 1680
agaccatcac tctcgaagtg gagccgagtg acaccattga gaatgtcaag gcaaagatcc 1740
aagacaagga aggcatccct cctgaccagc agaggttgat ctttgctggg aaacagctgg 1800
aagatggacg caccctgtct gactacaaca tccagaaaga gtccaccctg cacctggtgc 1860
tccgtctcag aggtgggatg cagatcttcg tgaagaccct gactggtaag accatcaccc 1920
tcgaggtgga gcccagtgac accatcgaga atgtcaaggc aaagatccaa gataaggaag 1980
gcatccctcc tgatcagcag aggttgatct ttgctgggaa acagctggaa gatggacgca 2040
ccctgtctga ctacaacatc cagaaagagt ccactctgca cttggtcctg cgcttgaggg 2100
ggggtgtcta agtttcccct tttaaggttt caacaaattt cattgcactt tcctttcaat 2160
aaagttgttg cattcccaaa aaaaaaaaaa aaaaaaaaaa a 2201

<210> SEQ ID NO 116
<211> LENGTH: 2405
<212> TYPE: DNA
<213> ORGANISM: Homo sapiens

<400> SEQUENCE: 116
tccggcgtgg tgcgcaggcg cggtatcccc cctcccccgc cagctcgacc ccggtgtggt 60
gcgcaggcgc agtctgcgca gggactggcg ggactgcgcg gcggcaacag cagacatgtc 120
gggggtccgg ggcctgtcgc ggctgctgag cgctcggcgc ctggcgctgg ccaaggcgtg 180
gccaacagtg ttgcaaacag gaacccgagg ttttcacttc actgttgatg ggaacaagag 240
ggcatctgct aaagtttcag attccatttc tgctcagtat ccagtagtgg atcatgaatt 300
tgatgcagtg gtggtaggcg ctggaggggc aggcttgcga gctgcatttg gcctttctga 360
ggcagggttt aatacagcat gtgttaccaa gctgtttcct accaggtcac acactgttgc 420
agcacaggga ggaatcaatg ctgctctggg gaacatggag gaggacaact ggaggtggca 480
tttctacgac accgtgaagg gctccgactg gctgggggac caggatgcca tccactacat 540
gacggagcag gcccccgccg ccgtggtcga gctagaaaat tatggcatgc cgtttagcag 600
aactgaagat gggaagattt atcagcgtgc atttggtgga cagagcctca agtttggaaa 660
gggcgggcag gcccatcggt gctgctgtgt ggctgatcgg actggccact cgctattgca 720
caccttatat ggaaggtctc tgcgatatga taccagctat tttgtggagt attttgcctt 780
ggatctcctg atggagaatg gggagtgccg tggtgtcatc gcactgtgca tagaggacgg 840
gtccatccat cgcataagag caaagaacac tgttgttgcc acaggaggct acgggcgcac 900
ctacttcagc tgcacgtctg cccacaccag cactggcgac ggcacggcca tgatcaccag 960
ggcaggcctt ccttgccagg acctagagtt tgttcagttc caccctacag gcatatatgg 1020
tgctggttgt ctcattacgg aaggatgtcg tggagaggga ggcattctca ttaacagtca 1080
aggcgaaagg tttatggagc gatacgcccc tgtcgcgaag gacctggcgt ctagagatgt 1140
ggtgtctcgg tccatgactc tggagatccg agaaggaaga ggctgtggcc ctgagaaaga 1200
tcacgtctac ctgcagctgc accacctacc tccagagcag ctggccacgc gcctgcctgg 1260
catttcagag acagccatga tcttcgctgg cgtggacgtc acgaaggagc cgatccctgt 1320
cctccccacc gtgcattata acatgggcgg cattcccacc aactacaagg ggcaggtcct 1380
gaggcacgtg aatggccagg atcagattgt gcccggcctg tacgcctgtg gggaggccgc 1440
ctgtgcctcg gtacatggtg ccaaccgcct cggggcaaac tcgctcttgg acctggttgt 1500
ctttggtcgg gcatgtgccc tgagcatcga agagtcatgc aggcctggag ataaagtccc 1560
tccaattaaa ccaaacgctg gggaagaatc tgtcatgaat cttgacaaat tgagatttgc 1620
tgatggaagc ataagaacat cggaactgcg actcagcatg cagaagtcaa tgcaaaatca 1680
tgctgccgtg ttccgtgtgg gaagcgtgtt gcaagaaggt tgtgggaaaa tcagcaagct 1740
ctatggagac ctaaagcacc tgaagacgtt cgaccgggga atggtctgga acacggacct 1800
ggtggagacc ctggagctgc agaacctgat gctgtgtgcg ctgcagacca tctacggagc 1860
agaggcacgg aaggagtcac ggggcgcgca tgccagggaa gactacaagg tgcggattga 1920
tgagtacgat tactccaagc ccatccaggg gcaacagaag aagccctttg aggagcactg 1980
gaggaagcac accctgtcct atgtggacgt tggcactggg aaggtcactc tggaatatag 2040
acccgtgatc gacaaaactt tgaacgaggc tgactgtgcc accgtcccgc cagccattcg 2100
ctcctactga tgagacaaga tgtggtgatg acagaatcag cttttgtaat tatgtataat 2160
agctcatgca tgtgtccatg tcataactgt cttcatacgc ttctgcactc tggggaagaa 2220
ggagtacatt gaagggagat tggcacctag tggctgggag cttgccagga acccagtggc 2280
cagggagcgt ggcacttacc tttgtccctt gcttcattct tgtgagatga taaaactggg 2340
cacagctctt aaataaaata taaatgaaca aactttcttt tatttccaaa aaaaaaaaaa 2400
aaaaa 2405

<210> SEQ ID NO 117
<211> LENGTH: 1536
<212> TYPE: DNA
<213> ORGANISM: Homo sapiens

<400> SEQUENCE: 117
gtgacgcgag gctctgcgga gaccaggagt cagactgtag gacgacctcg ggtcccacgt 60
gtccccggta ctcgccggcc ggagcccccg gcttcccggg gccgggggac cttagcggca 120
cccacacaca gcctactttc caagcggagc catgtctggt aacggcaatg cggctgcaac 180
ggcggaagaa aacagcccaa agatgagagt gattcgcgtg ggtacccgca agagccagct 240
tgctcgcata cagacggaca gtgtggtggc aacattgaaa gcctcgtacc ctggcctgca 300
gtttgaaatc attgctatgt ccaccacagg ggacaagatt cttgatactg cactctctaa 360
gattggagag aaaagcctgt ttaccaagga gcttgaacat gccctggaga agaatgaagt 420
ggacctggtt gttcactcct tgaaggacct gcccactgtg cttcctcctg gcttcaccat 480
cggagccatc tgcaagcggg aaaaccctca tgatgctgtt gtctttcacc caaaatttgt 540
tgggaagacc ctagaaaccc tgccagagaa gagtgtggtg ggaaccagct ccctgcgaag 600
agcagcccag ctgcagagaa agttcccgca tctggagttc aggagtattc ggggaaacct 660
caacacccgg cttcggaagc tggacgagca gcaggagttc agtgccatca tcctggcaac 720
agctggcctg cagcgcatgg gctggcacaa ccgggtgggg cagatcctgc accctgagga 780
atgcatgtat gctgtgggcc agggggcctt gggcgtggaa gtgcgagcca aggaccagga 840
catcttggat ctggtgggtg tgctgcacga tcccgagact ctgcttcgct gcatcgctga 900
aagggccttc ctgaggcacc tggaaggagg ctgcagtgtg ccagtagccg tgcatacagc 960
tatgaaggat gggcaactgt acctgactgg aggagtctgg agtctagacg gctcagatag 1020

-continued

```
catacaagag accatgcagg ctaccatcca tgtccctgcc cagcatgaag atggccctga   1080

ggatgaccca cagttggtag gcatcactgc tcgtaacatt ccacgagggc cccagttggc   1140

tgcccagaac ttgggcatca gcctggccaa cttgttgctg agcaaaggag ccaaaaacat   1200

cctggatgtt gcacggcagc ttaacgatgc ccattaactg gtttgtgggg cacagatgcc   1260

tgggttgctg ctgtccagtg cctacatccc gggcctcagt gccccattct cactgctatc   1320

tggggagtga ttaccccggg agactgaact gcagggttca agccttccag ggatttgcct   1380

caccttgggg ccttgatgac tgccttgcct cctcagtatg tgggggcttc atctctttag   1440

agaagtccaa gcaacagcct ttgaatgtaa ccaatcctac taataaacca gttctgaagg   1500

taaaaaaaaa aaaaaaaaaa aaaaaaaaaa aaaaaa                             1536
```

<210> SEQ ID NO 118
<211> LENGTH: 1435
<212> TYPE: DNA
<213> ORGANISM: Homo sapiens

<400> SEQUENCE: 118

```
ggcggggcct gcttctcctc agcttcaggc ggctgcgacg agccctcagg cgaacctctc     60

ggctttcccg cgcggcgccg cctcttgctg cgcctccgcc tcctcctctg ctccgccacc    120

ggcttcctcc tcctgagcag tcagcccgcg cgccggccgg ctccgttatg gcgacccgca    180

gccctggcgt cgtgattagt gatgatgaac caggttatga ccttgattta ttttgcatac    240

ctaatcatta tgctgaggat ttggaaaggg tgtttattcc tcatggacta attatggaca    300

ggactgaacg tcttgctcga gatgtgatga aggagatggg aggccatcac attgtagccc    360

tctgtgtgct caaggggggc tataaattct ttgctgacct gctggattac atcaaagcac    420

tgaatagaaa tagtgataga tccattccta tgactgtaga ttttatcaga ctgaagagct    480

attgtaatga ccagtcaaca ggggacataa aagtaattgg tggagatgat ctctcaactt    540

taactggaaa gaatgtcttg attgtggaag atataattga cactggcaaa acaatgcaga    600

ctttgctttc cttggtcagg cagtataatc caaagatggt caaggtcgca agcttgctgg    660

tgaaaaggac cccacgaagt gttggatata agccagactt tgttggattt gaaattccag    720

acaagtttgt tgtaggatat gcccttgact ataatgaata cttcagggat ttgaatcatg    780

tttgtgtcat tagtgaaact ggaaaagcaa aatacaaagc ctaagatgag agttcaagtt    840

gagtttggaa acatctggag tcctattgac atcgccagta aaattatcaa tgttctagtt    900

ctgtggccat ctgcttagta gagctttttg catgtatctt ctaagaattt tatctgtttt    960

gtactttaga aatgtcagtt gctgcattcc taaactgttt atttgcacta tgagcctata   1020

gactatcagt tccctttggg cggattgttg tttaacttgt aaatgaaaaa attctcttaa   1080

accacagcac tattgagtga aacattgaac tcatatctgt aagaaataaa gagaagatat   1140

attagttttt taattggtat tttaattttt atatatgcag gaaagaatag aagtgattga   1200

atattgttaa ttataccacc gtgtgttaga aaagtaagaa gcagtcaatt ttcacatcaa   1260

agacagcatc taagaagttt tgttctgtcc tggaattatt ttagtagtgt ttcagtaatg   1320

ttgactgtat tttccaactt gttcaaatta ttaccagtga atctttgtca gcagttccct   1380

tttaaatgca aatcaataaa ttcccaaaaa tttaaaaaaa aaaaaaaaaa aaaaa        1435
```

<210> SEQ ID NO 119
<211> LENGTH: 2395
<212> TYPE: DNA

<213> ORGANISM: Homo sapiens

<400> SEQUENCE: 119
agaggcaggg gctggcctgg gatgcgcgcg cacctgccct cgccccgccc cgcccgcacg 60
aggggtggtg gccgaggccc cgccccgcac gcctcgcctg aggcgggtcc gctcagccca 120
ggcgcccgcc cccgccccg ccgattaaat gggccggcgg ggctcagccc ccggaaacgg 180
tcgtacactt cggggctgcg agcgcggagg gcgacgacga cgaagcgcag acagcgtcat 240
ggcagagcag gtggccctga gccggaccca ggtgtgcggg atcctgcggg aagagctttt 300
ccagggcgat gccttccatc agtcggatac acacatattc atcatcatgg gtgcatcggg 360
tgacctggcc aagaagaaga tctaccccac catctggtgg ctgttccggg atggccttct 420
gcccgaaaac accttcatcg tgggctatgc ccgttcccgc ctcacagtgg ctgacatccg 480
caaacagagt gagcccttct tcaaggccac cccagaggag aagctcaagc tggaggactt 540
ctttgcccgc aactcctatg tggctggcca gtacgatgat gcagcctcct accagcgcct 600
caacagccac atgaatgccc tccacctggg gtcacaggcc aaccgcctct tctacctggc 660
cttgcccccg accgtctacg aggccgtcac caagaacatt cacgagtcct gcatgagcca 720
gataggctgg aaccgcatca tcgtggagaa gcccttcggg agggacctgc agagctctga 780
ccggctgtcc aaccacatct cctccctgtt ccgtgaggac cagatctacc gcatcgacca 840
ctacctgggc aaggagatgg tgcagaacct catggtgctg agatttgcca acaggatctt 900
cggccccatc tggaaccggg acaacatcgc ctgcgttatc ctcaccttca aggagccctt 960
tggcactgag ggtcgcgggg gctatttcga tgaatttggg atcatccggg acgtgatgca 1020
gaaccaccta ctgcagatgc tgtgtctggt ggccatggag aagcccgcct ccaccaactc 1080
agatgacgtc cgtgatgaga aggtcaaggt gttgaaatgc atctcagagg tgcaggccaa 1140
caatgtggtc ctgggccagt acgtggggaa ccccgatgga gagggcgagg ccaccaaagg 1200
gtacctggac gaccccacgg tgccccgcgg gtccaccacc gccacttttg cagccgtcgt 1260
cctctatgtg gagaatgaga ggtgggatgg ggtgcccttc atcctgcgct gcggcaaggc 1320
cctgaacgag cgcaaggccg aggtgaggct gcagttccat gatgtggccg gcgacatctt 1380
ccaccagcag tgcaagcgca acgagctggt gatccgcgtg cagcccaacg aggccgtgta 1440
caccaagatg atgaccaaga agccgggcat gttcttcaac cccgaggagt cggagctgga 1500
cctgacctac ggcaacagat acaagaacgt gaagctccct gacgcctacg agcgcctcat 1560
cctggacgtc ttctgcggga gccagatgca cttcgtgcgc agcgacgagc tccgtgaggc 1620
ctggcgtatt ttcaccccac tgctgcacca gattgagctg gagaagccca agcccatccc 1680
ctatatttat ggcagccgag gccccacgga ggcagacgag ctgatgaaga gagtgggttt 1740
ccagtatgag ggcacctaca agtgggtgaa cccccacaag ctctgagccc tgggcaccca 1800
cctccacccc cgccacggcc accctccttc ccgccgcccg accccgagtc gggaggactc 1860
cgggaccatt gacctcagct gcacattcct ggccccgggc tctggccacc ctggcccgcc 1920
cctcgctgct gctactaccc gagcccagct acattcctca gctgccaagc actcgagacc 1980
atcctggccc ctccagaccc tgcctgagcc caggagctga gtcacctcct ccactcactc 2040
cagcccaaca gaaggaagga ggagggcgcc cattcgtctg tcccagagct tattggccac 2100
tgggtctcac tcctgagtgg ggccagggtg ggagggaggg acaaggggga ggaaaggggc 2160
gagcacccac gtgagagaat ctgcctgtgg ccttgcccgc cagcctcagt gccacttgac 2220
attccttgtc accagcaaca tctcgagccc cctggatgtc ccctgtccca ccaactctgc 2280
actccatggc caccccgtgc cacccgtagg cagcctctct gctataagaa aagcagacgc 2340
agcagctggg accccctccca acctcaatgc cctgccatta aatccgcaaa cagcc 2395

<210> SEQ ID NO 120
<211> LENGTH: 108
<212> TYPE: DNA
<213> ORGANISM: Homo sapiens

<400> SEQUENCE: 120
cacagctcgt gcctcagtac tgagggtatg gaggaaaagg cagtcggtca gtgtctaaaa 60
atgacgcacg taagagacgc tcggggaaga tgtagctgga cctctgag 108

<210> SEQ ID NO 121
<211> LENGTH: 78
<212> TYPE: DNA
<213> ORGANISM: Homo sapiens

<400> SEQUENCE: 121
tctccttggg aggaggggaa gtggccagat gttgaggctg tgaagggcac tcttgatgga 60
cagcaggctg aactccag 78

<210> SEQ ID NO 122
<211> LENGTH: 630
<212> TYPE: DNA
<213> ORGANISM: Homo sapiens

<400> SEQUENCE: 122
gtcgtggaac gcagaatcat ccacctgccc ccactgatca gagacctgtc atcctcaagg 60
aggaccagtg actccctgca ccagcagtgg ctcaccccaa ttccctccag gccctgggat 120
ctgagggagg ggagaagcca ccaccattac cctgatttcc accaggagct ccaggaccgg 180
gggccaaagt cttgggcatt ggaaagaagg gagttggacc catcgtggag tggaaggcac 240
cgtagctcta ggctgaatgg gtcacccata cactggtcag acagggacag cctaagcgat 300
gtcccctcat ccagtgaggc acgctggcgg ccgagccacc ctcctttcag gagccgctgt 360
caggagaggc cccgcaggcc cagcccccgg gagagcactc agaggcacgg gagacgacgc 420
aggcaccgca gctactctcc tcccttgccc tccggcctca gttcctggag ctctgaagag 480
gacaaggaga ggcagcccca gagctggcgg gcccaccgcc gcggctcgca ctccccacac 540
tggcccgagg agaagccgcc tagctaccgc tcactggata tcactccagg caagaatagc 600
aggaaaaaag ggagtgtgga gaggcgctcg 630

<210> SEQ ID NO 123
<211> LENGTH: 351
<212> TYPE: DNA
<213> ORGANISM: Homo sapiens

<400> SEQUENCE: 123
gtgcttgctc ggggctgaag gtgacagtgc catcacacac tgtccatggc gtcagaggtc 60
aggccctcta cctacccgtc cactatggct tccacactcc agcatcagac atccagatca 120
tatggctatt tgagagaccc cacacaatgc ccaaatactt actgggctct gtgaataagt 180
ctgtggttcc tgacttggaa taccaacaca agttcaccat gatgccaccc aatgcatctc 240
tgcttatcaa cccactgcag ttccctgatg aaggcaatta catcgtgaag gtcaacattc 300
agggaaatgg aactctatct gccagtcaga agatacaagt cacggttgat g 351

<210> SEQ ID NO 124
<211> LENGTH: 297
<212> TYPE: DNA
<213> ORGANISM: Homo sapiens

<400> SEQUENCE: 124
atggacctta tggacttcaa gtgaattctg ataaagggct aaaagtaggg gaagtgttta 60
ctgttgacct tggagaggcc atcctatttg attgttctgc tgattctcat ccccccaaca 120
cctactcctg gattaggagg actgacaata ctacatatat cattaagcat gggcctcgct 180
tagaagttgc atctgagaaa gtagcccaga agacaatgga ctatgtgtgc tgtgcttaca 240
acaacataac cggcaggcaa gatgaaactc atttcacagt tatcatcact tccgtag 297

<210> SEQ ID NO 125
<211> LENGTH: 126
<212> TYPE: DNA
<213> ORGANISM: Homo sapiens

<400> SEQUENCE: 125
gactggagaa gcttgcacag aaaggaaaat cattgtcacc tttagcaagt ataactggaa 60
tatcactatt tttgattata tccatgtgtc ttctcttcct atggaaaaaa tatcaaccct 120
acaaag 126

<210> SEQ ID NO 126
<211> LENGTH: 327
<212> TYPE: DNA
<213> ORGANISM: Homo sapiens

<400> SEQUENCE: 126
gtcagggtgt gtccctatac attcctcagg ccaccatcaa tgccactgtc aaagaagaca 60
tcctgctctc agttgagtac tcctgtcatg gagtgcccac catcgaatgg acatattcat 120
ccaattgggg aacgcagaag atcgtggagt ggaaaccagg gactcaggcc aacatctctc 180
aaagccacaa ggacagagtc tgcacctttg acaacggctc catccagctc ttcagcgtgg 240
gagtgaggga ttccggctac tatgtcatca ccgtgacgga gcgcctgggg agcagccagt 300
ttggcaccat cgtgctgcac gtctctg 327

<210> SEQ ID NO 127
<211> LENGTH: 141
<212> TYPE: DNA
<213> ORGANISM: Homo sapiens

<400> SEQUENCE: 127
agatcctcta tgaagacctg cactttgtcg ctgtcatcct tgcttttctc gctgctgtgg 60
ccgcagtatt aatcagcctc atgtgggttt gtaataagtg tgcatataaa tttcagagga 120
agagaagaca caaactcaaa g 141

<210> SEQ ID NO 128
<211> LENGTH: 326
<212> TYPE: DNA
<213> ORGANISM: Homo sapiens

<400> SEQUENCE: 128
aaagcacaac tgaggagatt gagctggaag atgttgagtg ttagccaagg ctgggcctga 60
ctgcattcct acctcaagag gaaaccattc tccaacaaaa agagcaagca cagctattat 120
acccattgtg tgtggtcctg ttgcagcccg ctcctaacag gacagtggga gattaacaac 180
attgactgca tggagttgag gactgtggat gggacaaagc tagtattagg actcgcgcta 240
agttcaagga gaagagtgat tgaggctttg aaccaggagc ttcgcttggc tgcagcatca 300
gggccgtgct gacacataac caatgg 326

<210> SEQ ID NO 129
<211> LENGTH: 524
<212> TYPE: DNA
<213> ORGANISM: Homo sapiens

<400> SEQUENCE: 129
gtgagtacag tgaccgctgg ggagacagag cgatcgagag aaatgtctac ctctctacct 60
gacagctgtg tgcgctgggt tcctcctcca cctcctgtcc tgccaccccc aagattggtc 120
attccagact cttctccgct gggtgcccct ggcctcaggg atgaccattc tcatttgcct 180
tttcacctac atacacctct ccacacttct tatccatatc tatcactcca tgcatttgga 240
attctcatgg acactattga taaaatggaa gggcaggttt ggcgtggtga ggttgtggtg 300
taagactgtt ccctctccct ggggcattca aactagagga aaccttctct ggtcgttccc 360
ttcccatgca gagaagttcc tttttatatg agaagagtgt gcaaactgtg gcctttgggc 420
acccacccag ccacagattt gttttattta ctcccatgat gacatgggcc acaatagggc 480
ctagttctta tttgaggatt cacaattttt accttactgg ccaa 524

<210> SEQ ID NO 130
<211> LENGTH: 57
<212> TYPE: DNA
<213> ORGANISM: Homo sapiens

<400> SEQUENCE: 130
gcaggacagg gctgcttgct gatctcttgc ccagttttgc tgtggagatt atgccag 57

<210> SEQ ID NO 131
<211> LENGTH: 61
<212> TYPE: DNA
<213> ORGANISM: Homo sapiens

<400> SEQUENCE: 131
agtgggtgtt tgttggcctg gtgctcctgg gcgtcttcct cttcttcgtc ctggtgggga 60
t 61

<210> SEQ ID NO 132
<211> LENGTH: 66
<212> TYPE: DNA
<213> ORGANISM: Homo sapiens

<400> SEQUENCE: 132
ctgctggtgc cagtgctgcc ctcacagctg ctgctgctat gtccgctgcc catgctgccc 60
agattc 66

<210> SEQ ID NO 133
<211> LENGTH: 20
<212> TYPE: DNA
<213> ORGANISM: Homo sapiens

<400> SEQUENCE: 133
ctgctggtgc cctcaagcct 20

<210> SEQ ID NO 134

<211> LENGTH: 87
<212> TYPE: DNA
<213> ORGANISM: Homo sapiens

<400> SEQUENCE: 134
gtgctccata tatatttgtc aagagaatgg ggggacagat gaagaggaca caggctggca 60
ctgaggtccc ctccactttc ctcctag 87

<210> SEQ ID NO 135
<211> LENGTH: 44
<212> TYPE: DNA
<213> ORGANISM: Homo sapiens

<400> SEQUENCE: 135
actggcacag cctccaggtt ggcgggctca tctgcgctgg ggtt 44

<210> SEQ ID NO 136
<211> LENGTH: 31
<212> TYPE: DNA
<213> ORGANISM: Homo sapiens

<400> SEQUENCE: 136
ctgtgcgcca tgggcatcat catcgtcatg a 31

<210> SEQ ID NO 137
<211> LENGTH: 37
<212> TYPE: DNA
<213> ORGANISM: Homo sapiens

<400> SEQUENCE: 137
gtgcaaaatg caaatgcaag tttggccaga agtccgg 37

<210> SEQ ID NO 138
<211> LENGTH: 212
<212> TYPE: PRT
<213> ORGANISM: Homo sapiens

<400> SEQUENCE: 138

Gln Val Thr Ile Pro Asp Gly Phe Val Asn Val Thr Val Gly Ser Asn
1 5 10 15

Val Thr Leu Ile Cys Ile Tyr Thr Thr Thr Val Ala Ser Arg Glu Gln
20 25 30

Leu Ser Ile Gln Trp Ser Phe Phe His Lys Lys Glu Met Glu Pro Ile
35 40 45

Ser Ile Tyr Phe Ser Gln Gly Gly Gln Ala Val Ala Ile Gly Gln Phe
50 55 60

Lys Asp Arg Ile Thr Gly Ser Asn Asp Pro Gly Asn Ala Ser Ile Thr
65 70 75 80

Ile Ser His Met Gln Pro Ala Asp Ser Gly Ile Tyr Ile Cys Asp Val
85 90 95

Asn Asn Pro Pro Asp Phe Leu Gly Gln Asn Gln Gly Ile Leu Asn Val
100 105 110

Ser Val Leu Val Lys Pro Ser Lys Pro Leu Cys Ser Val Gln Gly Arg
115 120 125

Pro Glu Thr Gly His Thr Ile Ser Leu Ser Cys Leu Ser Ala Leu Gly
130 135 140

Thr Pro Ser Pro Val Tyr Tyr Trp His Lys Leu Glu Gly Arg Asp Ile
145 150 155 160

Val Pro Val Lys Glu Asn Phe Asn Pro Thr Thr Gly Ile Leu Val Ile

```
                165                 170                 175

Gly Asn Leu Thr Asn Phe Glu Gln Gly Tyr Tyr Gln Cys Thr Ala Ile
            180                 185                 190

Asn Arg Leu Gly Asn Ser Ser Cys Glu Ile Asp Leu Thr Ser Ser His
        195                 200                 205

Pro Glu Val Gly
    210


<210> SEQ ID NO 139
<211> LENGTH: 248
<212> TYPE: PRT
<213> ORGANISM: Homo sapiens

<400> SEQUENCE: 139

Gln Val Thr Ile Pro Asp Gly Phe Val Asn Val Thr Val Gly Ser Asn
1               5                   10                  15

Val Thr Leu Ile Cys Ile Tyr Thr Thr Thr Val Ala Ser Arg Glu Gln
            20                  25                  30

Leu Ser Ile Gln Trp Ser Phe Phe His Lys Lys Glu Met Glu Pro Ile
        35                  40                  45

Ser His Ser Ser Cys Leu Ser Thr Glu Gly Met Glu Glu Lys Ala Val
    50                  55                  60

Gly Gln Cys Leu Lys Met Thr His Val Arg Asp Ala Arg Gly Arg Cys
65                  70                  75                  80

Ser Trp Thr Ser Glu Ile Tyr Phe Ser Gln Gly Gly Gln Ala Val Ala
                85                  90                  95

Ile Gly Gln Phe Lys Asp Arg Ile Thr Gly Ser Asn Asp Pro Gly Asn
            100                 105                 110

Ala Ser Ile Thr Ile Ser His Met Gln Pro Ala Asp Ser Gly Ile Tyr
        115                 120                 125

Ile Cys Asp Val Asn Asn Pro Pro Asp Phe Leu Gly Gln Asn Gln Gly
    130                 135                 140

Ile Leu Asn Val Ser Val Leu Val Lys Pro Ser Lys Pro Leu Cys Ser
145                 150                 155                 160

Val Gln Gly Arg Pro Glu Thr Gly His Thr Ile Ser Leu Ser Cys Leu
                165                 170                 175

Ser Ala Leu Gly Thr Pro Ser Pro Val Tyr Tyr Trp His Lys Leu Glu
            180                 185                 190

Gly Arg Asp Ile Val Pro Val Lys Glu Asn Phe Asn Pro Thr Thr Gly
        195                 200                 205

Ile Leu Val Ile Gly Asn Leu Thr Asn Phe Glu Gln Gly Tyr Tyr Gln
    210                 215                 220

Cys Thr Ala Ile Asn Arg Leu Gly Asn Ser Ser Cys Glu Ile Asp Leu
225                 230                 235                 240

Thr Ser Ser His Pro Glu Val Gly
        245


<210> SEQ ID NO 140
<211> LENGTH: 274
<212> TYPE: PRT
<213> ORGANISM: Homo sapiens

<400> SEQUENCE: 140

Gln Val Thr Ile Pro Asp Gly Phe Val Asn Val Thr Val Gly Ser Asn
1               5                   10                  15

Val Thr Leu Ile Cys Ile Tyr Thr Thr Thr Val Ala Ser Arg Glu Gln
```

```
            20                  25                  30

Leu Ser Ile Gln Trp Ser Phe Phe His Lys Lys Glu Met Glu Pro Ile
        35                  40                  45

Ser His Ser Ser Cys Leu Ser Thr Glu Gly Met Glu Glu Lys Ala Val
    50                  55                  60

Gly Gln Cys Leu Lys Met Thr His Val Arg Asp Ala Arg Gly Arg Cys
65                  70                  75                  80

Ser Trp Thr Ser Glu Ser Pro Trp Glu Glu Gly Lys Trp Pro Asp Val
                85                  90                  95

Glu Ala Val Lys Gly Thr Leu Asp Gly Gln Gln Ala Glu Leu Gln Ile
            100                 105                 110

Tyr Phe Ser Gln Gly Gly Gln Ala Val Ala Ile Gly Gln Phe Lys Asp
        115                 120                 125

Arg Ile Thr Gly Ser Asn Asp Pro Gly Asn Ala Ser Ile Thr Ile Ser
    130                 135                 140

His Met Gln Pro Ala Asp Ser Gly Ile Tyr Ile Cys Asp Val Asn Asn
145                 150                 155                 160

Pro Pro Asp Phe Leu Gly Gln Asn Gln Gly Ile Leu Asn Val Ser Val
                165                 170                 175

Leu Val Lys Pro Ser Lys Pro Leu Cys Ser Val Gln Gly Arg Pro Glu
            180                 185                 190

Thr Gly His Thr Ile Ser Leu Ser Cys Leu Ser Ala Leu Gly Thr Pro
        195                 200                 205

Ser Pro Val Tyr Tyr Trp His Lys Leu Glu Gly Arg Asp Ile Val Pro
    210                 215                 220

Val Lys Glu Asn Phe Asn Pro Thr Thr Gly Ile Leu Val Ile Gly Asn
225                 230                 235                 240

Leu Thr Asn Phe Glu Gln Gly Tyr Tyr Gln Cys Thr Ala Ile Asn Arg
                245                 250                 255

Leu Gly Asn Ser Ser Cys Glu Ile Asp Leu Thr Ser Ser His Pro Glu
            260                 265                 270

Val Gly


<210> SEQ ID NO 141
<211> LENGTH: 171
<212> TYPE: PRT
<213> ORGANISM: Homo sapiens

<400> SEQUENCE: 141

Gln Val Thr Ile Pro Asp Gly Phe Val Asn Val Thr Val Gly Ser Asn
1               5                   10                  15

Val Thr Leu Ile Cys Ile Tyr Thr Thr Thr Val Ala Ser Arg Glu Gln
            20                  25                  30

Leu Ser Ile Gln Trp Ser Phe Phe His Lys Lys Glu Met Glu Pro Ile
        35                  40                  45

Ser Ile Tyr Phe Ser Gln Gly Gly Gln Ala Val Ala Ile Gly Gln Phe
    50                  55                  60

Lys Asp Arg Ile Thr Gly Ser Asn Asp Pro Val Lys Pro Ser Lys Pro
65                  70                  75                  80

Leu Cys Ser Val Gln Gly Arg Pro Glu Thr Gly His Thr Ile Ser Leu
                85                  90                  95

Ser Cys Leu Ser Ala Leu Gly Thr Pro Ser Pro Val Tyr Tyr Trp His
            100                 105                 110

Lys Leu Glu Gly Arg Asp Ile Val Pro Val Lys Glu Asn Phe Asn Pro
```

```
        115                 120                 125

Thr Thr Gly Ile Leu Val Ile Gly Asn Leu Thr Asn Phe Glu Gln Gly
    130                 135                 140

Tyr Tyr Gln Cys Thr Ala Ile Asn Arg Leu Gly Asn Ser Ser Cys Glu
145                 150                 155                 160

Ile Asp Leu Thr Ser Ser His Pro Glu Val Gly
                165                 170


<210> SEQ ID NO 142
<211> LENGTH: 181
<212> TYPE: PRT
<213> ORGANISM: Homo sapiens

<400> SEQUENCE: 142

Gln Val Thr Ile Pro Asp Gly Phe Val Asn Val Thr Val Gly Ser Asn
1               5                   10                  15

Val Thr Leu Ile Cys Ile Tyr Thr Thr Thr Val Ala Ser Arg Glu Gln
            20                  25                  30

Leu Ser Ile Gln Trp Ser Phe Phe His Lys Lys Glu Met Glu Pro Ile
        35                  40                  45

Ser Ile Tyr Phe Ser Gln Gly Gly Gln Ala Val Ala Ile Gly Gln Phe
    50                  55                  60

Lys Asp Arg Ile Thr Gly Ser Asn Asp Pro Gly Asn Ala Ser Ile Thr
65                  70                  75                  80

Ile Ser His Met Gln Pro Ala Asp Ser Gly Ile Tyr Ile Cys Asp Val
                85                  90                  95

Asn Asn Pro Pro Asp Phe Leu Gly Gln Asn Gln Gly Ile Leu Asn Val
            100                 105                 110

Ser Val Leu Val Lys Pro Ser Lys Pro Leu Cys Ser Val Gln Gly Arg
        115                 120                 125

Pro Glu Thr Gly His Thr Ile Ser Leu Ser Cys Leu Ser Ala Leu Gly
    130                 135                 140

Thr Pro Ser Pro Val Tyr Tyr Trp His Lys Leu Glu Gly Arg Asp Ile
145                 150                 155                 160

Val Pro Val Lys Glu Asn Phe Thr Asn His Arg Asp Phe Gly His Trp
                165                 170                 175

Lys Ser Asp Lys Phe
            180


<210> SEQ ID NO 143
<211> LENGTH: 209
<212> TYPE: PRT
<213> ORGANISM: Homo sapiens

<400> SEQUENCE: 143

Gln Val Thr Ile Pro Asp Gly Phe Val Asn Val Thr Val Gly Ser Asn
1               5                   10                  15

Val Thr Leu Ile Cys Ile Tyr Thr Thr Thr Val Ala Ser Arg Glu Gln
            20                  25                  30

Leu Ser Ile Gln Trp Ser Phe Phe His Lys Lys Glu Met Glu Pro Ile
        35                  40                  45

Ser Ile Tyr Phe Ser Gln Gly Gly Gln Ala Val Ala Ile Gly Gln Phe
    50                  55                  60

Lys Asp Arg Ile Thr Gly Ser Asn Asp Pro Gly Asn Ala Ser Ile Thr
65                  70                  75                  80

Ile Ser His Met Gln Pro Ala Asp Ser Gly Ile Tyr Ile Cys Asp Val
```

```
                85                  90                  95

Asn Asn Pro Pro Asp Phe Leu Gly Gln Asn Gln Gly Ile Leu Asn Val
            100                 105                 110

Ser Val Leu Val Lys Pro Ser Lys Pro Leu Cys Ser Val Gln Gly Arg
        115                 120                 125

Pro Glu Thr Gly His Thr Ile Ser Leu Ser Cys Leu Ser Ala Leu Gly
    130                 135                 140

Thr Pro Ser Pro Val Tyr Tyr Trp His Lys Leu Glu Gly Arg Asp Ile
145                 150                 155                 160

Val Pro Val Lys Glu Asn Phe Asn Pro Thr Thr Gly Ile Leu Val Ile
                165                 170                 175

Gly Asn Leu Thr Asn Phe Glu Gln Gly Tyr Tyr Gln Cys Thr Ala Ile
            180                 185                 190

Asn Arg Leu Gly Asn Ser Ser Cys Glu Ile Asp Leu Thr Ser Ser Arg
        195                 200                 205

Gln


<210> SEQ ID NO 144
<211> LENGTH: 312
<212> TYPE: PRT
<213> ORGANISM: Homo sapiens

<400> SEQUENCE: 144

Ser His Thr Val His Gly Val Arg Gly Gln Ala Leu Tyr Leu Pro Val
1               5                   10                  15

His Tyr Gly Phe His Thr Pro Ala Ser Asp Ile Gln Ile Ile Trp Leu
            20                  25                  30

Phe Glu Arg Pro His Thr Met Pro Lys Tyr Leu Leu Gly Ser Val Asn
        35                  40                  45

Lys Ser Val Val Pro Asp Leu Glu Tyr Gln His Lys Phe Thr Met Met
    50                  55                  60

Pro Pro Asn Ala Ser Leu Leu Ile Asn Pro Leu Gln Phe Pro Asp Glu
65                  70                  75                  80

Gly Asn Tyr Ile Val Lys Val Asn Ile Gln Gly Asn Gly Thr Leu Ser
                85                  90                  95

Ala Ser Gln Lys Ile Gln Val Thr Val Asp Asp Pro Val Thr Lys Pro
            100                 105                 110

Val Val Gln Ile His Pro Pro Ser Gly Ala Val Glu Tyr Val Gly Asn
        115                 120                 125

Met Thr Leu Thr Cys His Val Glu Gly Gly Thr Arg Leu Ala Tyr Gln
    130                 135                 140

Trp Leu Lys Asn Gly Arg Pro Val His Thr Ser Ser Thr Tyr Ser Phe
145                 150                 155                 160

Ser Pro Gln Asn Asn Thr Leu His Ile Ala Pro Val Thr Lys Glu Asp
                165                 170                 175

Ile Gly Asn Tyr Ser Cys Leu Val Arg Asn Pro Val Ser Glu Met Glu
            180                 185                 190

Ser Asp Ile Ile Met Pro Ile Ile Tyr Tyr Gly Pro Tyr Gly Leu Gln
        195                 200                 205

Val Asn Ser Asp Lys Gly Leu Lys Val Gly Glu Val Phe Thr Val Asp
    210                 215                 220

Leu Gly Glu Ala Ile Leu Phe Asp Cys Ser Ala Asp Ser His Pro Pro
225                 230                 235                 240

Asn Thr Tyr Ser Trp Ile Arg Arg Thr Asp Asn Thr Thr Tyr Ile Ile
```

-continued

```
                245                 250                 255

Lys His Gly Pro Arg Leu Glu Val Ala Ser Glu Lys Val Ala Gln Lys
            260                 265                 270

Thr Met Asp Tyr Val Cys Cys Ala Tyr Asn Asn Ile Thr Gly Arg Gln
        275                 280                 285

Asp Glu Thr His Phe Thr Val Ile Ile Thr Ser Val Gly Leu Glu Lys
    290                 295                 300

Leu Ala Gln Lys Gly Lys Ser Leu
305                 310


<210> SEQ ID NO 145
<211> LENGTH: 319
<212> TYPE: PRT
<213> ORGANISM: Homo sapiens

<400> SEQUENCE: 145

Gly Leu Lys Val Thr Val Pro Ser His Thr Val His Gly Val Arg Gly
1               5                   10                  15

Gln Ala Leu Tyr Leu Pro Val His Tyr Gly Phe His Thr Pro Ala Ser
            20                  25                  30

Asp Ile Gln Ile Ile Trp Leu Phe Glu Arg Pro His Thr Met Pro Lys
        35                  40                  45

Tyr Leu Leu Gly Ser Val Asn Lys Ser Val Val Pro Asp Leu Glu Tyr
    50                  55                  60

Gln His Lys Phe Thr Met Met Pro Pro Asn Ala Ser Leu Leu Ile Asn
65                  70                  75                  80

Pro Leu Gln Phe Pro Asp Glu Gly Asn Tyr Ile Val Lys Val Asn Ile
                85                  90                  95

Gln Gly Asn Gly Thr Leu Ser Ala Ser Gln Lys Ile Gln Val Thr Val
            100                 105                 110

Asp Asp Pro Val Thr Lys Pro Val Val Gln Ile His Pro Pro Ser Gly
        115                 120                 125

Ala Val Glu Tyr Val Gly Asn Met Thr Leu Thr Cys His Val Glu Gly
    130                 135                 140

Gly Thr Arg Leu Ala Tyr Gln Trp Leu Lys Asn Gly Arg Pro Val His
145                 150                 155                 160

Thr Ser Ser Thr Tyr Ser Phe Ser Pro Gln Asn Asn Thr Leu His Ile
                165                 170                 175

Ala Pro Val Thr Lys Glu Asp Ile Gly Asn Tyr Ser Cys Leu Val Arg
            180                 185                 190

Asn Pro Val Ser Glu Met Glu Ser Asp Ile Ile Met Pro Ile Ile Tyr
        195                 200                 205

Tyr Gly Pro Tyr Gly Leu Gln Val Asn Ser Asp Lys Gly Leu Lys Val
    210                 215                 220

Gly Glu Val Phe Thr Val Asp Leu Gly Glu Ala Ile Leu Phe Asp Cys
225                 230                 235                 240

Ser Ala Asp Ser His Pro Pro Asn Thr Tyr Ser Trp Ile Arg Arg Thr
                245                 250                 255

Asp Asn Thr Thr Tyr Ile Ile Lys His Gly Pro Arg Leu Glu Val Ala
            260                 265                 270

Ser Glu Lys Val Ala Gln Lys Thr Met Asp Tyr Val Cys Cys Ala Tyr
        275                 280                 285

Asn Asn Ile Thr Gly Arg Gln Asp Glu Thr His Phe Thr Val Ile Ile
    290                 295                 300
```

Thr Ser Val Gly Leu Glu Lys Leu Ala Gln Lys Gly Lys Ser Leu
305 310 315

<210> SEQ ID NO 146
<211> LENGTH: 119
<212> TYPE: PRT
<213> ORGANISM: Homo sapiens

<400> SEQUENCE: 146

Leu Gln Ser Gln Gly Val Ser Leu Tyr Ile Pro Gln Ala Thr Ile Asn
1 5 10 15

Ala Thr Val Lys Glu Asp Ile Leu Leu Ser Val Glu Tyr Ser Cys His
20 25 30

Gly Val Pro Thr Ile Glu Trp Thr Tyr Ser Ser Asn Trp Gly Thr Gln
35 40 45

Lys Ile Val Glu Trp Lys Pro Gly Thr Gln Ala Asn Ile Ser Gln Ser
50 55 60

His Lys Asp Arg Val Cys Thr Phe Asp Asn Gly Ser Ile Gln Leu Phe
65 70 75 80

Ser Val Gly Val Arg Asp Ser Gly Tyr Tyr Val Ile Thr Val Thr Glu
85 90 95

Arg Leu Gly Ser Ser Gln Phe Gly Thr Ile Val Leu His Val Ser Glu
100 105 110

Ile Leu Tyr Glu Asp Leu His
115

<210> SEQ ID NO 147
<211> LENGTH: 166
<212> TYPE: PRT
<213> ORGANISM: Homo sapiens

<400> SEQUENCE: 147

Leu Gln Val Thr Val Pro Asp Lys Lys Lys Val Ala Met Leu Phe Gln
1 5 10 15

Pro Thr Val Leu Arg Cys His Phe Ser Thr Ser Ser His Gln Pro Ala
20 25 30

Val Val Gln Trp Lys Phe Lys Ser Tyr Cys Gln Asp Arg Met Gly Glu
35 40 45

Ser Leu Gly Met Ser Ser Thr Arg Ala Gln Ser Leu Ser Lys Arg Asn
50 55 60

Leu Glu Trp Asp Pro Tyr Leu Asp Cys Leu Asp Ser Arg Arg Thr Val
65 70 75 80

Arg Val Val Ala Ser Lys Gln Gly Ser Thr Val Thr Leu Gly Asp Phe
85 90 95

Tyr Arg Gly Arg Glu Ile Thr Ile Val His Asp Ala Asp Leu Gln Ile
100 105 110

Gly Lys Leu Met Trp Gly Asp Ser Gly Leu Tyr Tyr Cys Ile Ile Thr
115 120 125

Thr Pro Asp Asp Leu Glu Gly Lys Asn Glu Gly Ser Leu Gly Leu Leu
130 135 140

Val Leu Gly Arg Thr Gly Leu Leu Ala Asp Leu Leu Pro Ser Phe Ala
145 150 155 160

Val Glu Ile Met Pro Glu
165

<210> SEQ ID NO 148
<211> LENGTH: 149

<212> TYPE: PRT
<213> ORGANISM: Homo sapiens

<400> SEQUENCE: 148

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Gly Ser Leu Gly Leu Leu
    130                 135                 140

Val Leu Glu Trp Val
145

<210> SEQ ID NO 149
<211> LENGTH: 16
<212> TYPE: PRT
<213> ORGANISM: Homo sapiens

<400> SEQUENCE: 149

Asn Asp Leu Glu Asp Lys Asn Ser Pro Phe Tyr Tyr Asp Trp His Ser
1               5                   10                  15

<210> SEQ ID NO 150
<211> LENGTH: 45
<212> TYPE: PRT
<213> ORGANISM: Homo sapiens

<400> SEQUENCE: 150

Asn Asp Leu Glu Asp Lys Asn Ser Pro Phe Tyr Tyr Gly Ala Pro Tyr
1               5                   10                  15

Ile Phe Val Lys Arg Met Gly Gly Gln Met Lys Arg Thr Gln Ala Gly
            20                  25                  30

Thr Glu Val Pro Ser Thr Phe Leu Leu Asp Trp His Ser
        35                  40                  45

<210> SEQ ID NO 151
<211> LENGTH: 5
<212> TYPE: PRT
<213> ORGANISM: Homo sapiens

<400> SEQUENCE: 151

Asn Asp Leu Glu Asp
1               5

<210> SEQ ID NO 152
<211> LENGTH: 21
<212> TYPE: DNA
<213> ORGANISM: Artificial

<220> FEATURE:
<223> OTHER INFORMATION: Synthetic primer

<400> SEQUENCE: 152
gctccaggcc ataaggactt c 21

<210> SEQ ID NO 153
<211> LENGTH: 21
<212> TYPE: DNA
<213> ORGANISM: Artificial
<220> FEATURE:
<223> OTHER INFORMATION: Synthetic primer

<400> SEQUENCE: 153
cagcttcaaa ctctcccctg c 21

<210> SEQ ID NO 154
<211> LENGTH: 103
<212> TYPE: DNA
<213> ORGANISM: Homo sapiens

<400> SEQUENCE: 154
gctccaggcc ataaggactt cattccaaat atgattacag gagcagccca ggcggatgta 60
gctgttttag ttgtagatgc cagcagggga gagtttgaag ctg 103

<210> SEQ ID NO 155
<211> LENGTH: 20
<212> TYPE: DNA
<213> ORGANISM: Artificial
<220> FEATURE:
<223> OTHER INFORMATION: Synthetic primer

<400> SEQUENCE: 155
ttccttgcca ggacctagag 20

<210> SEQ ID NO 156
<211> LENGTH: 20
<212> TYPE: DNA
<213> ORGANISM: Artificial
<220> FEATURE:
<223> OTHER INFORMATION: Synthetic primer

<400> SEQUENCE: 156
cataaacctt tcgccttgac 20

<210> SEQ ID NO 157
<211> LENGTH: 128
<212> TYPE: DNA
<213> ORGANISM: Homo sapiens

<400> SEQUENCE: 157
ttccttgcca ggacctagag tttgttcagt tccaccccac aggcatatat ggtgctggtt 60
gtctcattac ggaaggatgt cgtggagagg gaggcattct cattaacagt caaggcgaaa 120
ggtttatg 128

<210> SEQ ID NO 158
<211> LENGTH: 21
<212> TYPE: DNA
<213> ORGANISM: Artificial
<220> FEATURE:
<223> OTHER INFORMATION: Synthetic primer

<400> SEQUENCE: 158

```
aatttgtcaa gtcggtgcag c                                              21
```

<210> SEQ ID NO 159
<211> LENGTH: 20
<212> TYPE: DNA
<213> ORGANISM: Artificial
<220> FEATURE:
<223> OTHER INFORMATION: Synthetic primer

<400> SEQUENCE: 159

```
tcaccccttc atttttgcgt                                                20
```

<210> SEQ ID NO 160
<211> LENGTH: 106
<212> TYPE: DNA
<213> ORGANISM: Homo sapiens

<400> SEQUENCE: 160

```
aatttgtcaa gtcggtgcag ctggcaagac ctaaaggatt atatgcgtca ggcaggagaa    60

gtgacttatg cagatgctca caagggacgc aaaaatgaag gggtga                  106
```

<210> SEQ ID NO 161
<211> LENGTH: 24
<212> TYPE: DNA
<213> ORGANISM: Artificial
<220> FEATURE:
<223> OTHER INFORMATION: Synthetic primer

<400> SEQUENCE: 161

```
cccaaaatgt ataaggaaga aggc                                           24
```

<210> SEQ ID NO 162
<211> LENGTH: 20
<212> TYPE: DNA
<213> ORGANISM: Artificial
<220> FEATURE:
<223> OTHER INFORMATION: Synthetic primer

<400> SEQUENCE: 162

```
ttcaaagcag gcgaacttca                                                20
```

<210> SEQ ID NO 163
<211> LENGTH: 140
<212> TYPE: DNA
<213> ORGANISM: Homo sapiens

<400> SEQUENCE: 163

```
cagccaggtt atgccaacac tttgagggat gcagctccca aaatgtataa ggaagaaggc    60

ctaaaagcat tctacaaggg ggttgctcct ctctggatga gacagatacc atacaccatg   120

atgaagttcg cctgctttga                                               140
```

<210> SEQ ID NO 164
<211> LENGTH: 23
<212> TYPE: DNA
<213> ORGANISM: Homo sapiens

<400> SEQUENCE: 164

```
tggcaagaag aaggtctggt tag                                            23
```

<210> SEQ ID NO 165
<211> LENGTH: 22
<212> TYPE: DNA
<213> ORGANISM: Homo sapiens

<400> SEQUENCE: 165
tgatcagccc atctttgatg ag 22

<210> SEQ ID NO 166
<211> LENGTH: 101
<212> TYPE: DNA
<213> ORGANISM: Homo sapiens

<400> SEQUENCE: 166
tggcaagaag aaggtctggt tagaccccaa tgagaccaat gaaatcgcca atgccaactc 60
ccgtcagcag atccggaagc tcatcaaaga tgggctgatc a 101

<210> SEQ ID NO 167
<211> LENGTH: 20
<212> TYPE: DNA
<213> ORGANISM: Artificial
<220> FEATURE:
<223> OTHER INFORMATION: Synthetic primer

<400> SEQUENCE: 167
cggtttgctg cggtaatcat 20

<210> SEQ ID NO 168
<211> LENGTH: 21
<212> TYPE: DNA
<213> ORGANISM: Artificial
<220> FEATURE:
<223> OTHER INFORMATION: Synthetic primer

<400> SEQUENCE: 168
tttcttgctg ccagtctgga c 21

<210> SEQ ID NO 169
<211> LENGTH: 122
<212> TYPE: DNA
<213> ORGANISM: Homo sapiens

<400> SEQUENCE: 169
cggtttgctg cggtaatcat gaggataaga gagccacgaa ccacggcact gattttcagt 60
tctgggaaaa tggtgtgcac aggagccaag agtgaagaac agtccagact ggcagcaaga 120
aa 122

<210> SEQ ID NO 170
<211> LENGTH: 19
<212> TYPE: DNA
<213> ORGANISM: Artificial
<220> FEATURE:
<223> OTHER INFORMATION: Synthetic primer

<400> SEQUENCE: 170
atttgggtcg cggttcttg 19

<210> SEQ ID NO 171
<211> LENGTH: 21
<212> TYPE: DNA
<213> ORGANISM: Artificial
<220> FEATURE:
<223> OTHER INFORMATION: Synthetic primer

<400> SEQUENCE: 171
tgccttgaca ttctcgatgg t 21

-continued

<210> SEQ ID NO 172
<211> LENGTH: 133
<212> TYPE: DNA
<213> ORGANISM: Homo sapiens

<400> SEQUENCE: 172
atttgggtcg cggttcttgt ttgtggatcg ctgtgatcgt cacttgacaa tgcagatctt 60
cgtgaagact ctgactggta agaccatcac cctcgaggtt gagcccagtg acaccatcga 120
gaatgtcaag gca 133

<210> SEQ ID NO 173
<211> LENGTH: 20
<212> TYPE: DNA
<213> ORGANISM: Artificial
<220> FEATURE:
<223> OTHER INFORMATION: Synthetic primer

<400> SEQUENCE: 173
tgggaacaag agggcatctg 20

<210> SEQ ID NO 174
<211> LENGTH: 22
<212> TYPE: DNA
<213> ORGANISM: Artificial
<220> FEATURE:
<223> OTHER INFORMATION: Synthetic primer

<400> SEQUENCE: 174
ccaccactgc atcaaattca tg 22

<210> SEQ ID NO 175
<211> LENGTH: 86
<212> TYPE: DNA
<213> ORGANISM: Homo sapiens

<400> SEQUENCE: 175
tgggaacaag agggcatctg ctaaagtttc agattccatt tctgctcagt atccagtagt 60
ggatcatgaa tttgatgcag tggtgg 86

<210> SEQ ID NO 176
<211> LENGTH: 19
<212> TYPE: DNA
<213> ORGANISM: Artificial
<220> FEATURE:
<223> OTHER INFORMATION: Synthetic primer

<400> SEQUENCE: 176
tgagagtgat tcgcgtggg 19

<210> SEQ ID NO 177
<211> LENGTH: 21
<212> TYPE: DNA
<213> ORGANISM: Artificial
<220> FEATURE:
<223> OTHER INFORMATION: Synthetic primer

<400> SEQUENCE: 177
ccagggtacg aggctttcaa t 21

<210> SEQ ID NO 178
<211> LENGTH: 91
<212> TYPE: DNA
<213> ORGANISM: Homo sapiens

<400> SEQUENCE: 178
tgagagtgat tcgcgtgggt acccgcaaga gccagcttgc tcgcatacag acggacagtg 60
tggtggcaac attgaaagcc tcgtaccctg g 91

<210> SEQ ID NO 179
<211> LENGTH: 21
<212> TYPE: DNA
<213> ORGANISM: Artificial
<220> FEATURE:
<223> OTHER INFORMATION: Synthetic primer

<400> SEQUENCE: 179
tgacactggc aaaacaatgc a 21

<210> SEQ ID NO 180
<211> LENGTH: 21
<212> TYPE: DNA
<213> ORGANISM: Artificial
<220> FEATURE:
<223> OTHER INFORMATION: Synthetic primer

<400> SEQUENCE: 180
ggtccttttc accagcaagc t 21

<210> SEQ ID NO 181
<211> LENGTH: 94
<212> TYPE: DNA
<213> ORGANISM: Homo sapiens

<400> SEQUENCE: 181
tgacactggc aaaacaatgc agactttgct ttccttggtc aggcagtata atccaaagat 60
ggtcaaggtc gcaagcttgc tggtgaaaag gacc 94

<210> SEQ ID NO 182
<211> LENGTH: 20
<212> TYPE: DNA
<213> ORGANISM: Artificial
<220> FEATURE:
<223> OTHER INFORMATION: Synthetic primer

<400> SEQUENCE: 182
gaggccgtca ccaagaacat 20

<210> SEQ ID NO 183
<211> LENGTH: 19
<212> TYPE: DNA
<213> ORGANISM: Artificial
<220> FEATURE:
<223> OTHER INFORMATION: Synthetic primer

<400> SEQUENCE: 183
ggacagccgg tcagagctc 19

<210> SEQ ID NO 184
<211> LENGTH: 111
<212> TYPE: DNA
<213> ORGANISM: Homo sapiens

<400> SEQUENCE: 184
gaggccgtca ccaagaacat tcacgagtcc tgcatgagcc agataggctg gaaccgcatc 60
atcgtggaga agcccttcgg gagggacctg cagagctctg accggctgtc c 111

<210> SEQ ID NO 185
<211> LENGTH: 21
<212> TYPE: DNA
<213> ORGANISM: Artificial
<220> FEATURE:
<223> OTHER INFORMATION: Synthetic primer

<400> SEQUENCE: 185
aatgacgcac gtaagagacg c 21

<210> SEQ ID NO 186
<211> LENGTH: 20
<212> TYPE: DNA
<213> ORGANISM: Artificial
<220> FEATURE:
<223> OTHER INFORMATION: Synthetic primer

<400> SEQUENCE: 186
gagtgccctt cacagcctca 20

<210> SEQ ID NO 187
<211> LENGTH: 101
<212> TYPE: DNA
<213> ORGANISM: Homo sapiens

<400> SEQUENCE: 187
aatgacgcac gtaagagacg ctcggggaag atgtagctgg acctctgagt ctccttggga 60
ggaggggaag tggccagatg ttgaggctgt gaagggcact c 101

<210> SEQ ID NO 188
<211> LENGTH: 22
<212> TYPE: DNA
<213> ORGANISM: Artificial
<220> FEATURE:
<223> OTHER INFORMATION: Synthetic primer

<400> SEQUENCE: 188
cacagctcgt gcctcagtac tg 22

<210> SEQ ID NO 189
<211> LENGTH: 20
<212> TYPE: DNA
<213> ORGANISM: Artificial
<220> FEATURE:
<223> OTHER INFORMATION: Synthetic primer

<400> SEQUENCE: 189
agctacatct tccccgagcg 20

<210> SEQ ID NO 190
<211> LENGTH: 97
<212> TYPE: DNA
<213> ORGANISM: Homo sapiens

<400> SEQUENCE: 190
cacagctcgt gcctcagtac tgagggtatg gaggaaaagg cagtcggtca gtgtctaaaa 60
atgacgcacg taagagacgc tcggggaaga tgtagct 97

<210> SEQ ID NO 191
<211> LENGTH: 28
<212> TYPE: DNA
<213> ORGANISM: Artificial
<220> FEATURE:
<223> OTHER INFORMATION: Synthetic primer

<400> SEQUENCE: 191
gaagatgtag ctggacctct gagattta 28

<210> SEQ ID NO 192
<211> LENGTH: 24
<212> TYPE: DNA
<213> ORGANISM: Artificial
<220> FEATURE:
<223> OTHER INFORMATION: Synthetic primer

<400> SEQUENCE: 192
gttggaccct gtaattcgat cttt 24

<210> SEQ ID NO 193
<211> LENGTH: 92
<212> TYPE: DNA
<213> ORGANISM: Homo sapiens

<400> SEQUENCE: 193
gaagatgtag ctggacctct gagatttact tttctcaagg tggacaagct gtagccatcg 60
ggcaatttaa agatcgaatt acagggtcca ac 92

<210> SEQ ID NO 194
<211> LENGTH: 23
<212> TYPE: DNA
<213> ORGANISM: Artificial
<220> FEATURE:
<223> OTHER INFORMATION: Synthetic primer

<400> SEQUENCE: 194
atgacgcacg taagagacgc tcg 23

<210> SEQ ID NO 195
<211> LENGTH: 25
<212> TYPE: DNA
<213> ORGANISM: Artificial
<220> FEATURE:
<223> OTHER INFORMATION: Synthetic primer

<400> SEQUENCE: 195
ggagttcagc ctgctgtcca tcaag 25

<210> SEQ ID NO 196
<211> LENGTH: 124
<212> TYPE: DNA
<213> ORGANISM: Homo sapiens

<400> SEQUENCE: 196
atgacgcacg taagagacgc tcggggaaga tgtagctgga cctctgagtc tccttgggag 60
gaggggaagt ggccagatgt tgaggctgtg aagggcactc ttgatggaca gcaggctgaa 120
ctcc 124

<210> SEQ ID NO 197
<211> LENGTH: 20
<212> TYPE: DNA
<213> ORGANISM: Artificial
<220> FEATURE:
<223> OTHER INFORMATION: Synthetic primer

<400> SEQUENCE: 197
agccaccacc attaccctga 20

<210> SEQ ID NO 198
<211> LENGTH: 19
<212> TYPE: DNA
<213> ORGANISM: Artificial
<220> FEATURE:
<223> OTHER INFORMATION: Synthetic primer

<400> SEQUENCE: 198
tgccttccac tccacgatg 19

<210> SEQ ID NO 199
<211> LENGTH: 104
<212> TYPE: DNA
<213> ORGANISM: Homo sapiens

<400> SEQUENCE: 199
agccaccacc attaccctga tttccaccag gagctccagg accgggggcc aaagtcttgg 60
gcattggaaa gaagggagtt ggacccatcg tggagtggaa ggca 104

<210> SEQ ID NO 200
<211> LENGTH: 19
<212> TYPE: DNA
<213> ORGANISM: Artificial
<220> FEATURE:
<223> OTHER INFORMATION: Synthetic primer

<400> SEQUENCE: 200
gccaccgcta catgaagca 19

<210> SEQ ID NO 201
<211> LENGTH: 19
<212> TYPE: DNA
<213> ORGANISM: Artificial
<220> FEATURE:
<223> OTHER INFORMATION: Synthetic primer

<400> SEQUENCE: 201
ctggacggca gggacaaat 19

<210> SEQ ID NO 202
<211> LENGTH: 142
<212> TYPE: DNA
<213> ORGANISM: Homo sapiens

<400> SEQUENCE: 202
gccaccgcta catgaagcag gcccaggccc taggtcctca gatgatggga aaacccctgt 60 actgggggc ggacaggagc tcccaggttt catcttatcc aatgcacccg ctgctgcagc 120
gagatttgtc cctgccgtcc ag 142

<210> SEQ ID NO 203
<211> LENGTH: 21
<212> TYPE: DNA
<213> ORGANISM: Artificial
<220> FEATURE:
<223> OTHER INFORMATION: Synthetic primer

<400> SEQUENCE: 203
tcctcctcct gctgctgatt g 21

<210> SEQ ID NO 204
<211> LENGTH: 20
<212> TYPE: DNA
<213> ORGANISM: Artificial

<220> FEATURE:
<223> OTHER INFORMATION: Synthetic primer

<400> SEQUENCE: 204
tgggcctgct tcatgtagcg 20

<210> SEQ ID NO 205
<211> LENGTH: 145
<212> TYPE: DNA
<213> ORGANISM: Homo sapiens

<400> SEQUENCE: 205
tcctcctcct gctgctgatt ggagtgtgct ggtgccagtg ctgtcctcag tattgctgct 60
gctatatccg ctgtccctgc tgtcctgccc actgctgctg tcctgaggaa gccctggccc 120
gccaccgcta catgaagcag gccca 145

<210> SEQ ID NO 206
<211> LENGTH: 23
<212> TYPE: DNA
<213> ORGANISM: Artificial
<220> FEATURE:
<223> OTHER INFORMATION: Synthetic primer

<400> SEQUENCE: 206
ccgcagtatt aatcagcctc atg 23

<210> SEQ ID NO 207
<211> LENGTH: 25
<212> TYPE: DNA
<213> ORGANISM: Artificial
<220> FEATURE:
<223> OTHER INFORMATION: Synthetic primer

<400> SEQUENCE: 207
aatctcctca gttgtgcttt ctttg 25

<210> SEQ ID NO 208
<211> LENGTH: 101
<212> TYPE: DNA
<213> ORGANISM: Homo sapiens

<400> SEQUENCE: 208
ccgcagtatt aatcagcctc atgtgggttt gtaataagtg tgcatataaa tttcagagga 60
agagaagaca caaactcaaa gaaagcacaa ctgaggagat t 101

<210> SEQ ID NO 209
<211> LENGTH: 21
<212> TYPE: DNA
<213> ORGANISM: Artificial
<220> FEATURE:
<223> OTHER INFORMATION: Synthetic primer

<400> SEQUENCE: 209
gaacgcagaa gatcgtggag t 21

<210> SEQ ID NO 210
<211> LENGTH: 20
<212> TYPE: DNA
<213> ORGANISM: Artificial
<220> FEATURE:
<223> OTHER INFORMATION: Synthetic primer

<400> SEQUENCE: 210
ctgaagagct ggatggagcc 20

<210> SEQ ID NO 211
<211> LENGTH: 106
<212> TYPE: DNA
<213> ORGANISM: Homo sapiens

<400> SEQUENCE: 211
gaacgcagaa gatcgtggag tggaaaccag ggactcaggc caacatctct caaagccaca 60
aggacagagt ctgcaccttt gacaacggct ccatccagct cttcag 106

<210> SEQ ID NO 212
<211> LENGTH: 21
<212> TYPE: DNA
<213> ORGANISM: Artificial
<220> FEATURE:
<223> OTHER INFORMATION: Synthetic primer

<400> SEQUENCE: 212
ctgcactttg tcgctgtcat c 21

<210> SEQ ID NO 213
<211> LENGTH: 26
<212> TYPE: DNA
<213> ORGANISM: Artificial
<220> FEATURE:
<223> OTHER INFORMATION: Synthetic primer

<400> SEQUENCE: 213
caatctcctc agttgtgctt tctttg 26

<210> SEQ ID NO 214
<211> LENGTH: 145
<212> TYPE: DNA
<213> ORGANISM: Homo sapiens

<400> SEQUENCE: 214
ctgcactttg tcgctgtcat ccttgctttt ctcgctgctg tggccgcagt attaatcagc 60
ctcatgtggg tttgtaataa gtgtgcatat aaatttcaga ggaagagaag acacaaactc 120
aaagaaagca caactgagga gattg 145

<210> SEQ ID NO 215
<211> LENGTH: 21
<212> TYPE: DNA
<213> ORGANISM: Artificial
<220> FEATURE:
<223> OTHER INFORMATION: Synthetic primer

<400> SEQUENCE: 215
tgctgcacgt ctctgagatc c 21

<210> SEQ ID NO 216
<211> LENGTH: 23
<212> TYPE: DNA
<213> ORGANISM: Artificial
<220> FEATURE:
<223> OTHER INFORMATION: Synthetic primer

<400> SEQUENCE: 216
cacctctggc ctcaaaacca ctc 23

<210> SEQ ID NO 217
<211> LENGTH: 208

<212> TYPE: DNA
<213> ORGANISM: Homo sapiens

<400> SEQUENCE: 217
tgctgcacgt ctctgagatc ctctatgaag acctgcactt tgtcgctgtc atccttgctt 60
ttctcgctgc tgtggccgca gtattaatca gcctcatgtg ggtttgtaat aagtgtgcat 120
ataaatttca gaggaagaga agacacaaac tcaaaggtaa ccccctgggc cttgtgataa 180
tccatgagtg gttttgaggc cagaggtg 208

<210> SEQ ID NO 218
<211> LENGTH: 21
<212> TYPE: DNA
<213> ORGANISM: Artificial
<220> FEATURE:
<223> OTHER INFORMATION: Synthetic primer

<400> SEQUENCE: 218
gctgcacgtc tctgagatcc t 21

<210> SEQ ID NO 219
<211> LENGTH: 20
<212> TYPE: DNA
<213> ORGANISM: Artificial
<220> FEATURE:
<223> OTHER INFORMATION: Synthetic primer

<400> SEQUENCE: 219
cacctctggc ctcaaaacca 20

<210> SEQ ID NO 220
<211> LENGTH: 207
<212> TYPE: DNA
<213> ORGANISM: Homo sapiens

<400> SEQUENCE: 220
gctgcacgtc tctgagatcc tctatgaaga cctgcacttt gtcgctgtca tccttgcttt 60
tctcgctgct gtggccgcag tattaatcag cctcatgtgg gtttgtaata agtgtgcata 120
taaatttcag aggaagagaa gacacaaact caaaggtaac cccctgggcc ttgtgataat 180
ccatgagtgg ttttgaggcc agaggtg 207

<210> SEQ ID NO 221
<211> LENGTH: 21
<212> TYPE: DNA
<213> ORGANISM: Artificial
<220> FEATURE:
<223> OTHER INFORMATION: Synthetic primer

<400> SEQUENCE: 221
atgggcctcg cttagaagtt g 21

<210> SEQ ID NO 222
<211> LENGTH: 22
<212> TYPE: DNA
<213> ORGANISM: Artificial
<220> FEATURE:
<223> OTHER INFORMATION: Synthetic primer

<400> SEQUENCE: 222
ttctgtgcaa gcttctccag tc 22

<210> SEQ ID NO 223

<211> LENGTH: 151
<212> TYPE: DNA
<213> ORGANISM: Homo sapiens

<400> SEQUENCE: 223
atgggcctcg cttagaagtt gcatctgaga aagtagccca gaagacaatg gactatgtgt 60
gctgtgctta caacaacata accggcaggc aagatgaaac tcatttcaca gttatcatca 120
cttccgtagg actggagaag cttgcacaga a 151

<210> SEQ ID NO 224
<211> LENGTH: 21
<212> TYPE: DNA
<213> ORGANISM: Artificial
<220> FEATURE:
<223> OTHER INFORMATION: Synthetic primer

<400> SEQUENCE: 224
atcacacact gtccatggcg t 21

<210> SEQ ID NO 225
<211> LENGTH: 26
<212> TYPE: DNA
<213> ORGANISM: Artificial
<220> FEATURE:
<223> OTHER INFORMATION: Synthetic primer

<400> SEQUENCE: 225
gtctctcaaa tagccatatg atctgg 26

<210> SEQ ID NO 226
<211> LENGTH: 107
<212> TYPE: DNA
<213> ORGANISM: Homo sapiens

<400> SEQUENCE: 226
atcacacact gtccatggcg tcagaggtca ggccctctac ctacccgtcc actatggctt 60
ccacactcca gcatcagaca tccagatcat atggctattt gagagac 107

<210> SEQ ID NO 227
<211> LENGTH: 19
<212> TYPE: DNA
<213> ORGANISM: Artificial
<220> FEATURE:
<223> OTHER INFORMATION: Synthetic primer

<400> SEQUENCE: 227
gctttcatgg agcccttcg 19

<210> SEQ ID NO 228
<211> LENGTH: 18
<212> TYPE: DNA
<213> ORGANISM: Artificial
<220> FEATURE:
<223> OTHER INFORMATION: Synthetic primer

<400> SEQUENCE: 228
gcctgacctc tgacgcca 18

<210> SEQ ID NO 229
<211> LENGTH: 131
<212> TYPE: DNA
<213> ORGANISM: Homo sapiens

<400> SEQUENCE: 229
gctttcatgg agcccttcgg tgacacactt ggggtctttc agtgcaaaat atacctcctt 60
ctcttcggtg cttgctcggg gctgaaggtg acagtgccat cacacactgt ccatggcgtc 120
agaggtcagg c 131

<210> SEQ ID NO 230
<211> LENGTH: 21
<212> TYPE: DNA
<213> ORGANISM: Artificial
<220> FEATURE:
<223> OTHER INFORMATION: Synthetic primer

<400> SEQUENCE: 230
ctctgcattt gcccctttag a 21

<210> SEQ ID NO 231
<211> LENGTH: 21
<212> TYPE: DNA
<213> ORGANISM: Artificial
<220> FEATURE:
<223> OTHER INFORMATION: Synthetic primer

<400> SEQUENCE: 231
gatggcactg tcaccttcag c 21

<210> SEQ ID NO 232
<211> LENGTH: 105
<212> TYPE: DNA
<213> ORGANISM: Homo sapiens

<400> SEQUENCE: 232
ctctgcattt gcccctttag attgtgaaat gtggctcaag gtcttcacaa ctttcctttc 60
ctttgcaaca ggtgcttgct cggggctgaa ggtgacagtg ccatc 105

<210> SEQ ID NO 233
<211> LENGTH: 21
<212> TYPE: DNA
<213> ORGANISM: Artificial
<220> FEATURE:
<223> OTHER INFORMATION: Synthetic primer

<400> SEQUENCE: 233
gtgagtacag tgaccgctgg g 21

<210> SEQ ID NO 234
<211> LENGTH: 23
<212> TYPE: DNA
<213> ORGANISM: Artificial
<220> FEATURE:
<223> OTHER INFORMATION: Synthetic primer

<400> SEQUENCE: 234
ggagaagagt ctggaatgac caa 23

<210> SEQ ID NO 235
<211> LENGTH: 137
<212> TYPE: DNA
<213> ORGANISM: Homo sapiens

<400> SEQUENCE: 235
gtgagtacag tgaccgctgg ggagacagag cgatcgagag aaatgtctac ctctctacct 60
gacagctgtg tgcgctgggt tcctcctcca cctcctgtcc tgccaccccc aagattggtc 120
attccagact cttctcc 137

<210> SEQ ID NO 236
<211> LENGTH: 20
<212> TYPE: DNA
<213> ORGANISM: Artificial
<220> FEATURE:
<223> OTHER INFORMATION: Synthetic primer

<400> SEQUENCE: 236
gcccagtttt gctgtggaga 20

<210> SEQ ID NO 237
<211> LENGTH: 24
<212> TYPE: DNA
<213> ORGANISM: Artificial
<220> FEATURE:
<223> OTHER INFORMATION: Synthetic primer

<400> SEQUENCE: 237
ggtagacatt tctctcgatc gctc 24

<210> SEQ ID NO 238
<211> LENGTH: 227
<212> TYPE: DNA
<213> ORGANISM: Homo sapiens

<400> SEQUENCE: 238
gcccagtttt gctgtggaga ttatgccaga gtgggtgttt gttggcctgg tgctcctggg 60
cgtcttcctc ttcttcgtcc tggtggggat ctgctggtgc cagtgctgcc ctcacagctg 120
ctgctgctat gtccgctgcc catgctgccc agattcctgc tggtgccctc aagcctgtga 180
gtacagtgac cgctggggag acagagcgat cgagagaaat gtctacc 227

<210> SEQ ID NO 239
<211> LENGTH: 22
<212> TYPE: DNA
<213> ORGANISM: Artificial
<220> FEATURE:
<223> OTHER INFORMATION: Synthetic primer

<400> SEQUENCE: 239
tgtggagatt atgccagagt gg 22

<210> SEQ ID NO 240
<211> LENGTH: 23
<212> TYPE: DNA
<213> ORGANISM: Artificial
<220> FEATURE:
<223> OTHER INFORMATION: Synthetic primer

<400> SEQUENCE: 240
gacatttctc tcgatcgctc tgt 23

<210> SEQ ID NO 241
<211> LENGTH: 211
<212> TYPE: DNA
<213> ORGANISM: Homo sapiens

<400> SEQUENCE: 241
tgtggagatt atgccagagt gggtgtttgt tggcctggtg ctcctgggcg tcttcctctt 60
cttcgtcctg gtggggatct gctggtgcca gtgctgccct cacagctgct gctgctatgt 120
ccgctgccca tgctgcccag attcctgctg gtgccctcaa gcctgtgagt acagtgaccg 180
ctggggagac agagcgatcg agagaaatgt c 211

<210> SEQ ID NO 242
<211> LENGTH: 29
<212> TYPE: DNA
<213> ORGANISM: Artificial
<220> FEATURE:
<223> OTHER INFORMATION: Synthetic primer

<400> SEQUENCE: 242
actctattac tgtattatca ccaccccag 29

<210> SEQ ID NO 243
<211> LENGTH: 21
<212> TYPE: DNA
<213> ORGANISM: Artificial
<220> FEATURE:
<223> OTHER INFORMATION: Synthetic primer

<400> SEQUENCE: 243
ccaacaaaca cccactccaa c 21

<210> SEQ ID NO 244
<211> LENGTH: 93
<212> TYPE: DNA
<213> ORGANISM: Homo sapiens

<400> SEQUENCE: 244
actctattac tgtattatca ccaccccaga tgacctggag gggaaaaatg agggctcact 60
gggactgctg gtgttggagt gggtgtttgt tgg 93

<210> SEQ ID NO 245
<211> LENGTH: 29
<212> TYPE: DNA
<213> ORGANISM: Homo sapiens

<400> SEQUENCE: 245
gtgctccata tatatttgtc aagagaatg 29

<210> SEQ ID NO 246
<211> LENGTH: 20
<212> TYPE: DNA
<213> ORGANISM: Artificial
<220> FEATURE:
<223> OTHER INFORMATION: Synthetic primer

<400> SEQUENCE: 246
ggaggctgtg ccagtctagg 20

<210> SEQ ID NO 247
<211> LENGTH: 102
<212> TYPE: DNA
<213> ORGANISM: Homo sapiens

<400> SEQUENCE: 247
gtgctccata tatatttgtc aagagaatgg ggggacagat gaagaggaca caggctggca 60
ctgaggtccc ctccactttc ctcctagact ggcacagcct cc 102

<210> SEQ ID NO 248
<211> LENGTH: 18
<212> TYPE: DNA
<213> ORGANISM: Artificial
<220> FEATURE:

<223> OTHER INFORMATION: Synthetic primer

<400> SEQUENCE: 248
actggcacag cctccagg 18

<210> SEQ ID NO 249
<211> LENGTH: 21
<212> TYPE: DNA
<213> ORGANISM: Artificial
<220> FEATURE:
<223> OTHER INFORMATION: Synthetic primer

<400> SEQUENCE: 249
catttgcatt ttgcactcat g 21

<210> SEQ ID NO 250
<211> LENGTH: 91
<212> TYPE: DNA
<213> ORGANISM: Homo sapiens

<400> SEQUENCE: 250
actggcacag cctccaggtt ggcgggctca tctgcgctgg ggttctgtgc gccatgggca 60
tcatcatcgt catgagtgca aaatgcaaat g 91

<210> SEQ ID NO 251
<211> LENGTH: 20
<212> TYPE: DNA
<213> ORGANISM: Artificial
<220> FEATURE:
<223> OTHER INFORMATION: Synthetic primer

<400> SEQUENCE: 251
ttgtgttcct ggcaggcttt 20

<210> SEQ ID NO 252
<211> LENGTH: 20
<212> TYPE: DNA
<213> ORGANISM: Artificial
<220> FEATURE:
<223> OTHER INFORMATION: Synthetic primer

<400> SEQUENCE: 252
tcatctgtcc ccccattctc 20

<210> SEQ ID NO 253
<211> LENGTH: 114
<212> TYPE: DNA
<213> ORGANISM: Homo sapiens

<400> SEQUENCE: 253
ttgtgttcct ggcaggcttt cctgtcctgg acgccaatga cctagaagat aaaaacagtc 60
ctttctacta tggtgctcca tatatatttg tcaagagaat ggggggacag atga 114

<210> SEQ ID NO 254
<211> LENGTH: 31
<212> TYPE: DNA
<213> ORGANISM: Artificial
<220> FEATURE:
<223> OTHER INFORMATION: Synthetic primer

<400> SEQUENCE: 254
ctagctagcc accatgcaga aggtgaccct g 31

<210> SEQ ID NO 255
<211> LENGTH: 30
<212> TYPE: DNA
<213> ORGANISM: Artificial
<220> FEATURE:
<223> OTHER INFORMATION: Synthetic primer

<400> SEQUENCE: 255
cgcgaccggt ccgctttggg ctgagcctgg 30

<210> SEQ ID NO 256
<211> LENGTH: 21
<212> TYPE: DNA
<213> ORGANISM: Artificial
<220> FEATURE:
<223> OTHER INFORMATION: Synthetic primer

<400> SEQUENCE: 256
cctgtgtcct cttcatctgt c 21

<210> SEQ ID NO 257
<211> LENGTH: 21
<212> TYPE: DNA
<213> ORGANISM: Artificial
<220> FEATURE:
<223> OTHER INFORMATION: Synthetic primer

<400> SEQUENCE: 257
gacagatgaa gaggacacag g 21

<210> SEQ ID NO 258
<211> LENGTH: 32
<212> TYPE: DNA
<213> ORGANISM: Artificial
<220> FEATURE:
<223> OTHER INFORMATION: Synthetic primer

<400> SEQUENCE: 258
ctagctagcc accatgaggc ctctgcccag cg 32

<210> SEQ ID NO 259
<211> LENGTH: 31
<212> TYPE: DNA
<213> ORGANISM: Artificial
<220> FEATURE:
<223> OTHER INFORMATION: Synthetic primer

<400> SEQUENCE: 259
cgcgaattcg acactcaaca tcttccagct c 31

<210> SEQ ID NO 260
<211> LENGTH: 18
<212> TYPE: DNA
<213> ORGANISM: Artificial
<220> FEATURE:
<223> OTHER INFORMATION: Synthetic primer

<400> SEQUENCE: 260
aaggctgcat aggagctg 18

<210> SEQ ID NO 261
<211> LENGTH: 23
<212> TYPE: DNA
<213> ORGANISM: Artificial
<220> FEATURE:
<223> OTHER INFORMATION: Synthetic primer

<400> SEQUENCE: 261
caatgagttg gaaatcaagc cac 23

<210> SEQ ID NO 262
<211> LENGTH: 70
<212> TYPE: DNA
<213> ORGANISM: Artificial
<220> FEATURE:
<223> OTHER INFORMATION: Synthetic primer

<400> SEQUENCE: 262
cgcgaccggt ccaaaccact catggattat cacaaggccc agggggttac ctttgagttt 60
gtgtcttctc 70

<210> SEQ ID NO 263
<211> LENGTH: 33
<212> TYPE: DNA
<213> ORGANISM: Artificial
<220> FEATURE:
<223> OTHER INFORMATION: Synthetic primer

<400> SEQUENCE: 263
ctagctagcc accatggata gggtcttgct gag 33

<210> SEQ ID NO 264
<211> LENGTH: 30
<212> TYPE: DNA
<213> ORGANISM: Artificial
<220> FEATURE:
<223> OTHER INFORMATION: Synthetic primer

<400> SEQUENCE: 264
cgcgaattcg ggtagagagg tagacatttc 30

<210> SEQ ID NO 265
<211> LENGTH: 36
<212> TYPE: DNA
<213> ORGANISM: Artificial
<220> FEATURE:
<223> OTHER INFORMATION: Synthetic primer

<400> SEQUENCE: 265
gcgcttcgaa gccaccatgt ggctcaaggt cttcac 36

<210> SEQ ID NO 266
<211> LENGTH: 33
<212> TYPE: DNA
<213> ORGANISM: Artificial
<220> FEATURE:
<223> OTHER INFORMATION: Synthetic primer

<400> SEQUENCE: 266
cgcgaccggt ccctctggat ggtcttgctg ctg 33

<210> SEQ ID NO 267
<211> LENGTH: 33
<212> TYPE: DNA
<213> ORGANISM: Artificial
<220> FEATURE:
<223> OTHER INFORMATION: Synthetic primer

<400> SEQUENCE: 267
ctagctagcc accatggcat ggcccaaact gcc 33

<210> SEQ ID NO 268
<211> LENGTH: 34
<212> TYPE: DNA
<213> ORGANISM: Artificial
<220> FEATURE:
<223> OTHER INFORMATION: Synthetic primer

<400> SEQUENCE: 268
cgcgaccggt ccaatgacca cactccttcc acta 34

<210> SEQ ID NO 269
<211> LENGTH: 34
<212> TYPE: DNA
<213> ORGANISM: Artificial
<220> FEATURE:
<223> OTHER INFORMATION: Synthetic primer

<400> SEQUENCE: 269
ctagctagcc accatggtgt tcgcattttg gaag 34

<210> SEQ ID NO 270
<211> LENGTH: 29
<212> TYPE: DNA
<213> ORGANISM: Artificial
<220> FEATURE:
<223> OTHER INFORMATION: Synthetic primer

<400> SEQUENCE: 270
ctggagttca gcctgctgtc catcaagag 29

<210> SEQ ID NO 271
<211> LENGTH: 29
<212> TYPE: DNA
<213> ORGANISM: Artificial
<220> FEATURE:
<223> OTHER INFORMATION: Synthetic primer

<400> SEQUENCE: 271
ctcttgatgg acagcaggct gaactccag 29

<210> SEQ ID NO 272
<211> LENGTH: 33
<212> TYPE: DNA
<213> ORGANISM: Artificial
<220> FEATURE:
<223> OTHER INFORMATION: Synthetic primer

<400> SEQUENCE: 272
cgcgaccggt cctgccttaa ccactccctt ttc 33

<210> SEQ ID NO 273
<211> LENGTH: 25
<212> TYPE: DNA
<213> ORGANISM: Artificial
<220> FEATURE:
<223> OTHER INFORMATION: Synthetic primer

<400> SEQUENCE: 273
cctcagtact gaggcacgag ctgtg 25

<210> SEQ ID NO 274
<211> LENGTH: 20
<212> TYPE: DNA
<213> ORGANISM: Artificial
<220> FEATURE:
<223> OTHER INFORMATION: Synthetic primer

<400> SEQUENCE: 274
cctcagtact gagggtatgg 20

<210> SEQ ID NO 275
<211> LENGTH: 29
<212> TYPE: DNA
<213> ORGANISM: Artificial
<220> FEATURE:
<223> OTHER INFORMATION: Synthetic primer

<400> SEQUENCE: 275
cgcggatccc cagtctagga ggaaagtgg 29

<210> SEQ ID NO 276
<211> LENGTH: 29
<212> TYPE: DNA
<213> ORGANISM: Artificial
<220> FEATURE:
<223> OTHER INFORMATION: Synthetic primer

<400> SEQUENCE: 276
cgcggatccg tcttcataga ggatctcag 29

<210> SEQ ID NO 277
<211> LENGTH: 29
<212> TYPE: DNA
<213> ORGANISM: Artificial
<220> FEATURE:
<223> OTHER INFORMATION: Synthetic primer

<400> SEQUENCE: 277
cgcggatccc ataatctcca cagcaaaac 29

<210> SEQ ID NO 278
<211> LENGTH: 33
<212> TYPE: DNA
<213> ORGANISM: Artificial
<220> FEATURE:
<223> OTHER INFORMATION: Synthetic primer

<400> SEQUENCE: 278
aaccggtgcc accatgtggc tcaaggtctt cac 33

<210> SEQ ID NO 279
<211> LENGTH: 29
<212> TYPE: DNA
<213> ORGANISM: Artificial
<220> FEATURE:
<223> OTHER INFORMATION: Synthetic primer

<400> SEQUENCE: 279
cgcggatcct tttcctttct gtgcaagct 29

<210> SEQ ID NO 280
<211> LENGTH: 30
<212> TYPE: DNA
<213> ORGANISM: Artificial
<220> FEATURE:
<223> OTHER INFORMATION: Synthetic primer

<400> SEQUENCE: 280
gcgttcgaag cccagctcca ggacgtggtg 30

<210> SEQ ID NO 281
<211> LENGTH: 29

<212> TYPE: DNA
<213> ORGANISM: Artificial
<220> FEATURE:
<223> OTHER INFORMATION: Synthetic primer

<400> SEQUENCE: 281
cgcggatcct tccttatcgg ggtctcctg 29

<210> SEQ ID NO 282
<211> LENGTH: 28
<212> TYPE: DNA
<213> ORGANISM: Artificial
<220> FEATURE:
<223> OTHER INFORMATION: Synthetic primer

<400> SEQUENCE: 282
gcgcttcgaa atcccagacg gtttcgtg 28

<210> SEQ ID NO 283
<211> LENGTH: 29
<212> TYPE: DNA
<213> ORGANISM: Artificial
<220> FEATURE:
<223> OTHER INFORMATION: Synthetic primer

<400> SEQUENCE: 283
cgcggatcct ggatgtgaag aagtgagat 29

<210> SEQ ID NO 284
<211> LENGTH: 36
<212> TYPE: PRT
<213> ORGANISM: Homo sapiens

<400> SEQUENCE: 284

His Ser Ser Cys Leu Ser Thr Glu Gly Met Glu Glu Lys Ala Val Gly
1 5 10 15

Gln Cys Leu Lys Met Thr His Val Arg Asp Ala Arg Gly Arg Cys Ser
20 25 30

Trp Thr Ser Glu
35

<210> SEQ ID NO 285
<211> LENGTH: 62
<212> TYPE: PRT
<213> ORGANISM: Homo sapiens

<400> SEQUENCE: 285

His Ser Ser Cys Leu Ser Thr Glu Gly Met Glu Glu Lys Ala Val Gly
1 5 10 15

Gln Cys Leu Lys Met Thr His Val Arg Asp Ala Arg Gly Arg Cys Ser
20 25 30

Trp Thr Ser Glu Ser Pro Trp Glu Glu Gly Lys Trp Pro Asp Val Glu
35 40 45

Ala Val Lys Gly Thr Leu Asp Gly Gln Gln Ala Glu Leu Gln
50 55 60

<210> SEQ ID NO 286
<211> LENGTH: 14
<212> TYPE: PRT
<213> ORGANISM: Homo sapiens

<400> SEQUENCE: 286

Thr Asn His Arg Asp Phe Gly His Trp Lys Ser Asp Lys Phe 1 5 10

<210> SEQ ID NO 287
<211> LENGTH: 2
<212> TYPE: PRT
<213> ORGANISM: Homo sapiens

<400> SEQUENCE: 287

Arg Gln
1

<210> SEQ ID NO 288
<211> LENGTH: 44
<212> TYPE: PRT
<213> ORGANISM: Homo sapiens

<400> SEQUENCE: 288

Ala Leu Ala Arg His Arg Tyr Met Lys Gln Ala Gln Ala Leu Gly Pro
1 5 10 15

Gln Met Met Gly Lys Pro Leu Tyr Trp Gly Ala Asp Arg Ser Ser Gln
20 25 30

Val Ser Ser Tyr Pro Met His Pro Leu Leu Gln Arg
35 40

<210> SEQ ID NO 289
<211> LENGTH: 14
<212> TYPE: PRT
<213> ORGANISM: Homo sapiens

<400> SEQUENCE: 289

Met Trp Leu Lys Val Phe Thr Thr Phe Leu Ser Phe Ala Thr
1 5 10

<210> SEQ ID NO 290
<211> LENGTH: 88
<212> TYPE: PRT
<213> ORGANISM: Homo sapiens

<400> SEQUENCE: 290

Gly Gln Lys Gln Asn Thr Gly Lys Leu Lys His Phe Gln Ala Met Lys
1 5 10 15

Met Leu Trp Met Thr Ser Glu Tyr Met Asn Leu Leu Leu Phe Gln Met
20 25 30

Phe Leu Val Phe Pro Gly Ser Gln Ala Gly Leu Phe Gln Pro Leu Ile
35 40 45

Val Tyr Arg Gly Lys Ile Cys Thr Val Gln Cys Met Lys Leu Phe Ser
50 55 60

Thr Ser Leu Pro Ser Ser Lys Thr Ile Gln Ser Glu Leu Ser Trp Ala
65 70 75 80

Lys Gln Tyr Ile Arg Val Lys Phe
85

<210> SEQ ID NO 291
<211> LENGTH: 6
<212> TYPE: PRT
<213> ORGANISM: Homo sapiens

<400> SEQUENCE: 291

Val Gly Phe Pro Ser Gly
1 5

<210> SEQ ID NO 292
<211> LENGTH: 34
<212> TYPE: PRT
<213> ORGANISM: Homo sapiens

<400> SEQUENCE: 292

```
Phe Met Leu Ala Ala Pro Ser Gln Arg Glu Glu Glu Lys Lys Ile Trp
1               5                   10                  15

Gln Gly Pro Gly Leu Leu Leu Cys Pro His Cys Asn Pro His Tyr His
            20                  25                  30

Gln Tyr
```

<210> SEQ ID NO 293
<211> LENGTH: 20
<212> TYPE: PRT
<213> ORGANISM: Homo sapiens

<400> SEQUENCE: 293

```
Cys Glu Tyr Ser Asp Arg Trp Gly Asp Arg Ala Ile Glu Arg Asn Val
1               5                   10                  15

Tyr Leu Ser Thr
            20
```

<210> SEQ ID NO 294
<211> LENGTH: 29
<212> TYPE: PRT
<213> ORGANISM: Homo sapiens

<400> SEQUENCE: 294

```
Gly Ala Pro Tyr Ile Phe Val Lys Arg Met Gly Gly Gln Met Lys Arg
1               5                   10                  15

Thr Gln Ala Gly Thr Glu Val Pro Ser Thr Phe Leu Leu
            20                  25
```

<210> SEQ ID NO 295
<211> LENGTH: 26
<212> TYPE: PRT
<213> ORGANISM: Homo sapiens

<400> SEQUENCE: 295

```
Glu Trp Arg Ser Ser Gly Glu Gln Ala Gly Arg Gly Trp Gly Ser Pro
1               5                   10                  15

Pro Leu Thr Thr Gln Leu Ser Pro Thr Gly
            20                  25
```

<210> SEQ ID NO 296
<211> LENGTH: 82
<212> TYPE: PRT
<213> ORGANISM: Homo sapiens

<400> SEQUENCE: 296

```
Ala Leu Ser Leu Gly Gln Asp Pro Ser Asn Asp Cys Asn Asp Asn Gln
1               5                   10                  15

Arg Glu Val Arg Ile Val Ala Gln Arg Arg Gly Gln Asn Glu Pro Val
            20                  25                  30

Leu Gly Val Asp Tyr Arg Gln Arg Lys Ile Thr Ile Gln Asn Arg Ala
        35                  40                  45

Asp Leu Val Ile Asn Glu Val Met Trp Trp Asp His Gly Val Tyr Tyr
    50                  55                  60

Cys Thr Ile Glu Ala Pro Gly Asp Thr Ser Gly Asp Pro Asp Lys Glu
65                  70                  75                  80
```

Val Lys

<210> SEQ ID NO 297
<211> LENGTH: 63
<212> TYPE: PRT
<213> ORGANISM: Homo sapiens

<400> SEQUENCE: 297

Met Gln Lys Val Thr Leu Gly Leu Leu Val Phe Leu Ala Gly Phe Pro
1 5 10 15

Val Leu Asp Ala Asn Asp Leu Glu Asp Lys Asn Ser Pro Phe Tyr Tyr
20 25 30

Gly Ala Pro Tyr Ile Phe Val Lys Arg Met Gly Gly Gln Met Lys Arg
35 40 45

Thr Gln Ala Gly Thr Glu Val Pro Ser Thr Phe Leu Leu Asp Trp
50 55 60

<210> SEQ ID NO 298
<211> LENGTH: 145
<212> TYPE: PRT
<213> ORGANISM: Homo sapiens

<400> SEQUENCE: 298

Met Arg Pro Leu Pro Ser Gly Arg Arg Lys Thr Arg Gly Ile Ser Leu
1 5 10 15

Gly Leu Phe Ala Leu Cys Leu Ala Ala Ala Arg Cys Leu Gln Ser Gln
20 25 30

Gly Val Ser Leu Tyr Ile Pro Gln Ala Thr Ile Asn Ala Thr Val Lys
35 40 45

Glu Asp Ile Leu Leu Ser Val Glu Tyr Ser Cys His Gly Val Pro Thr
50 55 60

Ile Glu Trp Thr Tyr Ser Ser Asn Trp Gly Thr Gln Lys Ile Val Glu
65 70 75 80

Trp Lys Pro Gly Thr Gln Ala Asn Ile Ser Gln Ser His Lys Asp Arg
85 90 95

Val Cys Thr Phe Asp Asn Gly Ser Ile Gln Leu Phe Ser Val Gly Val
100 105 110

Arg Asp Ser Gly Tyr Tyr Val Ile Thr Val Thr Glu Arg Leu Gly Ser
115 120 125

Ser Gln Phe Gly Thr Ile Val Leu His Val Ser Glu Ile Leu Tyr Glu
130 135 140

Asp
145

<210> SEQ ID NO 299
<211> LENGTH: 184
<212> TYPE: PRT
<213> ORGANISM: Homo sapiens

<400> SEQUENCE: 299

Met Asp Arg Val Leu Leu Arg Trp Ile Ser Leu Phe Trp Leu Thr Ala
1 5 10 15

Met Val Glu Gly Leu Gln Val Thr Val Pro Asp Lys Lys Lys Val Ala
20 25 30

Met Leu Phe Gln Pro Thr Val Leu Arg Cys His Phe Ser Thr Ser Ser
35 40 45

His Gln Pro Ala Val Val Gln Trp Lys Phe Lys Ser Tyr Cys Gln Asp

```
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met
            180


<210> SEQ ID NO 300
<211> LENGTH: 335
<212> TYPE: PRT
<213> ORGANISM: Homo sapiens

<400> SEQUENCE: 300

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Gly Phe His Thr Pro
        35                  40                  45

Ala Ser Asp Ile Gln Ile Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile His Pro Pro
    130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
            180                 185                 190

His Ile Ala Pro Val Thr Lys Glu Asp Ile Gly Asn Tyr Ser Cys Leu
        195                 200                 205

Val Arg Asn Pro Val Ser Glu Met Glu Ser Asp Ile Ile Met Pro Ile
    210                 215                 220

Ile Tyr Tyr Gly Pro Tyr Gly Leu Gln Val Asn Ser Asp Lys Gly Leu
225                 230                 235                 240
```

```
Lys Val Gly Glu Val Phe Thr Val Asp Leu Gly Glu Ala Ile Leu Phe
                245                 250                 255

Asp Cys Ser Ala Asp Ser His Pro Pro Asn Thr Tyr Ser Trp Ile Arg
            260                 265                 270

Arg Thr Asp Asn Thr Thr Tyr Ile Ile Lys His Gly Pro Arg Leu Glu
        275                 280                 285

Val Ala Ser Glu Lys Val Ala Gln Lys Thr Met Asp Tyr Val Cys Cys
    290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys
                325                 330                 335


<210> SEQ ID NO 301
<211> LENGTH: 110
<212> TYPE: PRT
<213> ORGANISM: Homo sapiens

<400> SEQUENCE: 301

Ala Gln Leu Gln Asp Val Val Val Thr Trp Arg Phe Lys Ser Phe Cys
1               5                   10                  15

Lys Asp Pro Ile Phe Asp Tyr Tyr Ser Ala Ser Tyr Gln Ala Ala Leu
            20                  25                  30

Ser Leu Gly Gln Asp Pro Ser Asn Asp Cys Asn Asp Asn Gln Arg Glu
        35                  40                  45

Val Arg Ile Val Ala Gln Arg Arg Gly Gln Asn Glu Pro Val Leu Gly
    50                  55                  60

Val Asp Tyr Arg Gln Arg Lys Ile Thr Ile Gln Asn Arg Ala Asp Leu
65                  70                  75                  80

Val Ile Asn Glu Val Met Trp Trp Asp His Gly Val Tyr Tyr Cys Thr
                85                  90                  95

Ile Glu Ala Pro Gly Asp Thr Ser Gly Asp Pro Asp Lys Glu
            100                 105                 110


<210> SEQ ID NO 302
<211> LENGTH: 268
<212> TYPE: PRT
<213> ORGANISM: Homo sapiens

<400> SEQUENCE: 302

Ile Pro Asp Gly Phe Val Asn Val Thr Val Gly Ser Asn Val Thr Leu
1               5                   10                  15

Ile Cys Ile Tyr Thr Thr Thr Val Ala Ser Arg Glu Gln Leu Ser Ile
            20                  25                  30

Gln Trp Ser Phe Phe His Lys Lys Glu Met Glu Pro Ile Ser His Ser
        35                  40                  45

Ser Cys Leu Ser Thr Glu Gly Met Glu Glu Lys Ala Val Ser Gln Cys
    50                  55                  60

Leu Lys Met Thr His Ala Arg Asp Ala Arg Gly Arg Cys Ser Trp Thr
65                  70                  75                  80

Ser Glu Ser Pro Trp Glu Glu Gly Lys Trp Pro Asp Val Glu Ala Val
                85                  90                  95

Lys Gly Thr Leu Asp Gly Gln Gln Ala Glu Leu Gln Ile Tyr Phe Ser
            100                 105                 110

Gln Gly Gly Gln Ala Val Ala Ile Gly Gln Phe Lys Asp Arg Ile Thr
        115                 120                 125
```

-continued

```
Gly Ser Asn Asp Pro Gly Asn Ala Ser Ile Thr Ile Ser His Met Gln
    130                 135                 140

Pro Ala Asp Ser Gly Ile Tyr Ile Cys Asp Val Asn Asn Pro Pro Asp
145                 150                 155                 160

Phe Leu Gly Gln Asn Gln Gly Ile Leu Asn Val Ser Val Leu Val Lys
                165                 170                 175

Pro Ser Lys Pro Leu Cys Ser Val Gln Gly Arg Pro Glu Thr Gly His
            180                 185                 190

Thr Ile Ser Leu Ser Cys Leu Ser Ala Leu Gly Thr Pro Ser Pro Val
        195                 200                 205

Tyr Tyr Trp His Lys Leu Glu Gly Arg Asp Ile Val Pro Val Lys Glu
    210                 215                 220

Asn Phe Asn Pro Thr Thr Gly Ile Leu Val Ile Gly Asn Leu Thr Asn
225                 230                 235                 240

Phe Glu Gln Gly Tyr Tyr Gln Cys Thr Ala Ile Asn Arg Leu Gly Asn
                245                 250                 255

Ser Ser Cys Glu Ile Asp Leu Thr Ser Ser His Pro
            260                 265
```

POLYPEPTIDES AND POLYNUCLEOTIDES, AND USES THEREOF AS A DRUG TARGET FOR PRODUCING DRUGS AND BIOLOGICS

FIELD OF THE INVENTION

This invention relates to the discovery of certain proteins that are differentially expressed in specific tissues and their use as therapeutic and diagnostic targets. More specifically the invention relates to a protein VSIG1 and its variants, FXYD3 and its variants, ILDR1 and its variants, LOC253012 and its variants, AI216611 and its variants, and C1ORF32 and its variants, which are differentially expressed by some cancers, and therefore are suitable targets for immunotherapy, cancer therapy, and drug development. This invention further relates to the discovery of extracellular domains of VSIG1 and its variants, FXYD3 and its variants, ILDR1 and its variants, LOC253012 and its variants, AI216611 and its variants, and C1ORF32 and its variants which are suitable targets for immunotherapy, cancer therapy, and drug development Additionally, because some of the proteins of this invention, based on their B7-like structure, are believed to play a role in immune costimulation, the invention further relates to the use of these proteins, or drugs which modulate these proteins (agonistic and antagonistic), as immune modulators and for immune therapy, especially for treating cancer and immune related disorders such as cancers and autoimmune disorders. Also, the invention more specifically relates to therapeutic and diagnostic antibodies and therapies and diagnostic methods using same antibodies and antibody fragments that specifically bind to proteins of invention or a soluble or secreted portion thereof, especially the ectodomain.

BACKGROUND OF THE INVENTION

Tumor antigens are ideally positioned as biomarkers and drug targets, and they play a critical role in the development of novel strategies for active and passive immunotherapy agents, to be used as stand-alone therapies or in conjunction with conventional therapies for cancer. Tumor antigens can be classified as either tumor-specific antigens (TSAs) where the antigens are expressed only in tumor cells and not in normal tissues, or tumor-associated antigens (TAAs) where the antigens are overexpressed in tumor cells but nonetheless also present at low levels in normal tissues.

TAAs and TSAs are validated as targets for passive (antibody) therapy as well as active immunotherapy using strategies to break immune tolerance and stimulate the immune system. The antigenic epitopes that are targeted by these therapeutic approaches are present at the cell surface, overexpressed in tumor cells compared to non-tumor cells, and are targeted by antibodies that block functional activity, inhibit cell prohliferation, or induce cell death.

There are growing number of tumor-associated antigens against which monoclonal antibodies have been tested or are in use as treatment for cancer. The identification and molecular characterization of novel tumor antigens expressed by human malignancies is an active field in tumor immunology. Several approaches have been used to identify tumor-associated antigens as target candidates for immunotherapy, including high throughput bioinformatic approaches, based on genomics and proteomics. The identification of novel TAAs or TSAs expands the spectrum of tumor antigen targets available for immune recognition and provides new target molecules for the development of therapeutic agents for passive immunotherapy, including monoclonal antibodies, whether unmodified or armed. Such novel antigens may also point the way to more effective therapeutic vaccines for active or adoptive immunotherapy.

Cancer vaccination involves the administration of tumor antigens and is used to break immune tolerance and induce an active T-cell response to the tumor. Vaccine therapy includes the use of naked DNA, peptides, recombinant protein, and whole cell therapy, where the patient's own tumor cells are used as the source of the vaccine. With the identification of specific tumor antigens, vaccinations are more often carried out by dendritic cell therapy, whereby dendritic cells are loaded with the relevant protein or peptide, or transfected with vector DNA or RNA.

The major applications of anti-TAA antibodies for treatment of cancer are therapy with naked antibody, therapy with a drug-conjugated antibody, and fusion therapy with cellular immunity. Ever since their discovery, antibodies were envisioned as "magic bullets" that would deliver toxic agents, such as drugs, toxins, enzymes and radioisotopes, specifically to the diseased site and leaving the non-target normal tissues unaffected. Indeed, antibodies, and in particular antibody fragments, can function as carriers of cytotoxic substances such as radioisotopes, drugs and toxins. Immunotherapy with such immunoconjugates is more effective than with the naked antibody.

In contrast to the overwhelming success of naked (such as Rituxan and Campath) and conjugated antibodies (such as Bexxar and Zevalin) in treating hematological malignancies, only modest success has been achieved in the immunotherapy of solid tumors. One of the major limitations in successful application of immunotherapy to solid tumors is the large molecular size of the intact immunoglobulin that results in prolonged serum half-life but in poor tumor penetration and uptake. Indeed, only a very small amount of administered antibody (as low as 0.01%) reaches the tumor. In addition to their size, antibodies encounter other impediments before reaching their target antigens expressed on the cell surface of solid tumors. Some of the barriers include poor blood flow in large tumors, permeability of vascular endothelium, elevated interstitial fluid pressure of tumor stroma, and heterogenous antigen expression.

With the advent of antibody engineering, small molecular weight antibody fragments exhibiting improved tumor penetration have been generated. Such antibody fragments are often conjugated to specific cytotoxic molecules and are designed to selectively deliver them to cancer cells. Still, solid tumors remain a formidable challenge for therapy, even with immunoconjugated antibody fragments.

The new wave of optimization strategies involves the use of biological modifiers to modulate the impediments posed by solid tumors. Thus, in combination to antibodies or their conjugated antibody fragments, various agents are being used to improve the tumor blood flow, enhance vascular permeability, lower tumor interstitial fluid pressure by modulating stromal cells and extracellular matrix components, upregulate expression of target antigens and improve penetration and retention of the therapeutic agent.

Immunotherapy with antibodies represents an exciting opportunity for combining with standard modalities, such as chemotherapy, as well as combinations with diverse biological agents to obtain a synergistic activity. Indeed, unconjugated mAbs are more effective when used in combination with other therapeutic agents, including other antibodies.

Another component of the immune system response to immunotherapy is the cellular response, specifically—the T cell response and activation of cytotoxic T cells (CTLs). The efficiency of the immune system in mediating tumor regression depends on the induction of antigen-specific T-cell responses through physiologic immune surveillance, priming by vaccination, or following adoptive transfer of T-cells. Although a variety of tumor-associated antigens have been identified and many immunotherapeutic strategies have been tested, objective clinical responses are rare. The reasons for this include the inability of current immunotherapy approaches to generate efficient T-cell responses, the presence of regulatory cells that inhibit T-cell responses, and other escape mechanisms that tumors develop, such as inactivation of cytolytic T-cells through expression of negative costimulatory molecules. Effective immunotherapy for cancer will require the use of appropriate tumor-specific antigens; the optimization of the interaction between the antigenic peptide, the APC and the T cell; and the simultaneous blockade of negative regulatory mechanisms that impede immunotherapeutic effects.

T-cell activation plays a central role in driving both protective and pathogenic immune responses, and it requires the completion of a carefully orchestrated series of specific steps that can be preempted or disrupted by any number of critical events. Naïve T cells must receive two independent signals from antigen-presenting cells (APC) in order to become productively activated. The first, Signal 1, is antigen-specific and occurs when T cell antigen receptors encounter the appropriate antigen-MHC complex on the APC. A second, antigen-independent signal (Signal 2) is delivered through a T cell costimulatory molecule that engages its APC-expressed ligand. In the absence of a costimulatory signal, T-cell activation is impaired or aborted, which may lead to a state of antigen-specific unresponsiveness (known as T-cell anergy), or may result in T-cell apoptotic death.

Costimulatory signals can be either stimulatory (positive costimulation) or inhibitory (negative costimulation or coinhibition). Positive costimulation is required for optimal activation of naïve T cells, while negative costimulation is required for the acquisition of immunologic tolerance to self, as well as the termination of effector T cell functions. Costimulatory signals, particularly positive costimulatory signals, also play a role in the modulation of B cell activity. For example, B cell activation and the survival of germinal center B cells require T cell-derived signals in addition to stimulation by antigen.

Both positive and negative costimulatory signals play critical roles in the regulation of cell-mediated immune responses, and molecules that mediate these signals have proven to be effective targets for immunomodulation. Based on this knowledge, several therapeutic approaches that involve targeting of costimulatory molecules have been developed, and were shown to be useful for prevention and treatment of cancer and autoimmune diseases, as well as rejection of allogenic transplantation, each by turning on, or preventing the turning off, of immune responses in subjects with these pathological conditions.

Costimulatory molecule pairs usually consist of ligands expressed on APCs and their cognate receptors expressed on T cells. The well characterized B7/CD28 and CD40/CD40L costimulatory molecules are critical in primary T-cell activation. In recent years, several additional costimulatory molecules have been identified, that belong to the B7/CD28 or the TNF/TNF-R gene families. The effects of costimulatory TNFR family members can often be functionally, temporally, or spatially segregated from those of CD28 family members and from each other. The sequential and transient regulation of T cell activation/survival signals by different costimulators may function to allow longevity of the response while maintaining tight control of T cell survival.

The B7 family consists of structurally related, cell-surface protein ligands, which bind to receptors on lymphocytes that regulate immune responses. Interaction of B7-family members with their respective costimulatory receptor, usually a member of the CD28-related family, augments immune responses, while interaction with coinhibitory receptors, such as CTLA4, attenuates immune responses. Members of the B7 family share 20-40% amino-acid identity and are structurally related, with the extracellular domain containing tandem domains related to variable and constant immunoglobulin domains.

There are currently seven known members of the family: B7.1 (CD80), B7.2 (CD86), B7-H1 (PD-L1), B7-H2 (ICOS-L), B7-DC (PD-L2), B7-H3, and B7-H4, each with unique, yet often overlapping functions. Clearly, each B7 molecule has developed its own indispensable niche in the immune system. As specific niches of B7 family members continue to be dissected, their diagnostic and therapeutic potential becomes ever more apparent. Many of the B7 superfamily members were initially characterized as T cell costimulatory molecules. However, more recently it has become clear they can also coinhibit T cell responses. Thus, B7 family members may have opposing effects on an immune response.

Central to the normal function of the immune system is its ability to distinguish between self and non-self, since failure to do so could provoke the onset of autoimmune disease. Most autoimmune disorders are known to involve autoreactive T cells and/or autoantibodies. Thus, agents that are capable of inhibiting or eliminating autoreactive lymphocytes have a promising therapeutic potential. Furthermore, the use of agents that exhibit such immunosuppressive activity should also be beneficial in order to inhibit normal immune responses to alloantigens in patients receiving a transplant. Thus, novel agents that are capable of modulating costimulatory signals, without compromising the immune system's ability to defend against pathogens, are highly advantageous for treatment and prevention of such pathological conditions.

The importance of the B7 family members in regulating immune responses to self and allo-antigens was demonstrated by the development of immunodeficiency and autoimmune diseases in mice with mutations in B7-family genes. Accordingly, manipulation of the signals delivered by B7 ligands has shown potential in the treatment of autoimmunity, inflammatory diseases, and transplant rejection. This approach relies, at least partially, on the eventual deletion of auto- or allo-reactive T cells, presumably because in the absence of costimulation (which induces cell survival genes) T cells become highly susceptible to induction of apoptosis.

Harnessing the immune system to treat chronic diseases is a major goal of immunotherapy. Active and passive immunotherapies are proving themselves as effective therapeutic strategies. Passive immunotherapy, using monoclonal antibodies or receptor Fc-fusion proteins, has come of age and has shown great clinical success. A growing number of such therapeutic agents have been approved or are in clinical trials to prevent allograft rejection or to treat autoimmune diseases and cancer. Active immunotherapy (i.e. vaccines) has been effective against agents that normally cause acute self-limiting infectious diseases followed by immunity and has been at the forefront of efforts to prevent the infectious diseases that plague humankind. However, active immunotherapy has been much less effective against cancer or chronic infectious diseases primarily because these have developed strategies to escape normal immune responses. Among these are negative costimulators of the B7 family, such as B7-H1 and B7-H4, which are highly expressed in certain tumors, and afford local protection from immune cells-mediated attack.

The efficiency of the immune system in mediating tumor regression depends on the induction of antigen-specific T-cell responses through physiologic immune surveillance, priming by vaccination, or following adoptive transfer of T-cells. Although a variety of tumor-associated antigens have been identified and many immunotherapeutic strategies have been tested, objective clinical responses are rare. The reasons for this include the inability of current immunotherapy approaches to generate efficient T-cell responses, the presence of regulatory cells that inhibit T-cell responses, and other escape mechanisms that tumors develop, such as inactivation of cytolytic T-cells through expression of negative costimulatory molecules. Effective immunotherapy for cancer will require the use of appropriate tumor-specific antigens; the optimization of the interaction between the antigenic peptide, the APC and the T cell; and the simultaneous blockade of negative regulatory mechanisms that impede immunotherapeutic effects.

Costimulators of the B7 family play a critical role in activation and inhibition of antitumor immune responses. Novel agents targeting these molecules could find significant use in the modulation of immune responses and the improvement of cancer immunotherapy. Such agents could be administered in conjunction with tumor-specific antigens, as an adjuvant that serves to enhance the immune response to the antigen in the patient. In addition, such agents could be of use in other types of cancer immunotherapy, such as adoptive immunotherapy, in which tumor-specific T cell populations are expanded and directed to attack and kill tumor cells. Agents capable of augmenting such anti-tumor response have great therapeutic potential and may be of value in the attempt to overcome the obstacles to tumor immunotherapy.

Passive tumor immunotherapy uses the exquisite specificity and lytic capability of the immune system to target tumor specific antigens and treat malignant disease with a minimum of damage to normal tissue. Several approaches have been used to identify tumor-associated antigens as target candidates for immunotherapy. The identification of novel tumor specific antigens expands the spectrum of tumor antigen targets available for immune recognition and provides new target molecules for the development of therapeutic agents for passive immunotherapy, including monoclonal antibodies, whether unmodified or armed. Such novel antigens may also point the way to more effective therapeutic vaccines for active or adoptive immunotherapy.

Clinical development of costimulation blockade came to fruition with the approval of CTLA4Ig (abatacept) for rheumatoid arthritis. This soluble fusion protein, which acts as competitive inhibitor of the B7/CD28 costimulatory pathway, is also in clinical trials for other immune diseases such as psoriasis and multiple sclerosis, and for transplant rejection. Promising results have also been obtained in a phase II clinical trial in kidney transplantation with belatacept, a re-engineered CTLA4Ig with enhanced binding affinity to its ligands, B7.1 and B7.2 (CD80 and CD86, respectively). Two fully human anti-CTLA4 monoclonal antibodies, Ipilimumab and tremelimumab, abrogate the CTLA4/B7 inhibitory interaction, and are in clinical phase III for metastatic melanoma and other cancers, as well as HIV infection. Galiximab is a primatized monoclonal antibody targeting CD80, in Phase II for rheumatoid arthritis, psoriasis and Non-Hodgkin's lymphoma.

It is important to point out that strategies that use single agents to block costimulation have often proved to be insufficient. Given the diversity of the different costimulation molecules, future strategies may involve the simultaneous blockade of several selected pathways or combination therapy with conventional drugs, such as immunosuppressants for immune-related disorders or cytotoxic drugs for cancer.

Despite recent progress in the understanding of cancer biology and cancer treatment, as well as better understanding of the molecules involved in immune responses, the success rate for cancer therapy and for the treatment of autoimmune diseases remains low. Therefore, there is an unmet need for new therapies which can successfully treat both cancer and autoimmune disorders.

BRIEF SUMMARY OF THE INVENTION

It is an object of the invention to provide novel therapeutic and diagnostic compositions containing at least one of the VSIG1, ILDR1, LOC253012, AI216611, C1ORF32, or FXYD3 proteins or one of the novel splice variants disclosed herein as well as to provide these novel VSIG1 splice variants; specifically ILDR1 splice variants; LOC253012 splice variants; AI216611 splice variants, C1ORF32 splice variants; and FXYD3 splice variants, and nucleic acid sequences encoding for same or fragments thereof especially the ectodomain or secreted forms of VSIG1, ILDR1, LOC253012, AI216611, C1ORF32, FXYD3 proteins and/or splice variants.

It is another object of the invention to use said proteins, splice variants and nucleic acid sequences as novel targets for development of drugs which specifically bind to the VSIG1, ILDR1, LOC253012, AI216611, C1ORF32, FXYD3 proteins and/or splice variants, and/or drugs which agonize or antagonize the binding of other moieties to the VSIG1, ILDR1, LOC253012, AI216611, C1ORF32, FXYD3 proteins and/or splice variants.

It is still another object of the invention to provide drugs which modulate (agonize or antagonize) at least one VSIG1, ILDR1, LOC253012, AI216611, C1ORF32 or FXYD3 related biological activity. Such drugs include by way of example antibodies, small molecules, peptides, ribozymes, antisense molecules, siRNA's and the like. These molecules may directly bind or modulate an activity elicited by the VSIG1, ILDR1, LOC253012, AI216611, C1ORF32, FXYD3 proteins or VSIG1, ILDR1, LOC253012, AI216611, C1ORF32, FXYD3 DNA or portions or variants thereof or may indirectly modulate a VSIG1, ILDR1, LOC253012, AI216611, C1ORF32, FXYD3 associated activity or binding of molecules to VSIG1, ILDR1, LOC253012, AI216611, C1ORF32, FXYD3 and portions and variants thereof such as by modulating the binding of VSIG1, ILDR1, LOC253012, AI216611, C1ORF32, FXYD3 to its counterreceptor or endogenous ligand.

In more specific embodiments, the present invention provides novel splice variants of a known protein V-set and immunoglobulin domain containing 1 (SEQ ID NO:11) (RefSeq accession identifier NP_872413, synonyms: RP5-889N15.1, 1700062D20Rik, GPA34, MGC44287, dJ889N15.1) or a polynucleotide encoding same, which can be used as diagnostic markers and/or therapeutic agents which agonize or antagonize the binding of other moieties to the VSIG1 proteins and/or which modulate (agonize or antagonize) at least one VSIG1 related biological activity.

According to one more specific embodiment, the novel splice variant is an isolated polynucleotide comprising a nucleic acid having a nucleic acid sequence as set forth in any one of AI581519_T10 (SEQ ID NO:9), AI581519_T11 (SEQ ID NO:10), or a sequence homologous thereto. According to another embodiment, the isolated polynucleotide is at least 95% homologous to any one of AI581519_T10 (SEQ ID NO:9), AI581519_T11 (SEQ ID NO:10).

According to yet another more specific embodiment, the novel splice variant is an isolated protein or polypeptide having an amino acid sequence as set forth in any one of AI581519_P9 (SEQ ID NO:15), AI581519_P10 (SEQ ID NO:16), or a sequence homologous thereto. According to another embodiment, the isolated polypeptide is at least 95% homologous to any one of AI581519_P9 (SEQ ID NO:15), AI581519_P10 (SEQ ID NO:16).

It is another specific object of the invention to provide molecules and isolated polypeptides comprising the soluble ectodomain (ECD) of the VSIG1 proteins and fragments thereof as well as nucleic acid sequences encoding said soluble ectodomain, as well as fragments thereof and conjugates and the use thereof as therapeutics including their use in immunotherapy (promoting or inhibiting immune costimulation).

In more specific embodiments the present invention provides discrete portions of the VSIG1 proteins including different portions of the extracellular domain corresponding to residues 23-234 of the VSIG1 protein sequence contained in the sequence of AI581519_P3 (SEQ ID NO:11), corresponding to amino acid sequence depicted in SEQ ID NO:138, or residues 23-270 of the of the VSIG1 protein sequence contained in the sequence of AI581519_P4 (SEQ ID NO:12), corresponding to amino acid sequence depicted in SEQ ID NO:139, or residues 23-296 of the VSIG1 protein sequence contained in the sequence of AI581519_P5 (SEQ ID NO:13), corresponding to amino acid sequence depicted in SEQ ID NO:140, or residues 23-193 of the VSIG1 protein sequence contained in the sequence of AI581519_P7 (SEQ ID NO:14) corresponding to amino acid sequence depicted in SEQ ID NO:141, or residues 23-203 of the VSIG1 protein sequence contained in the of AI581519_P9 (SEQ ID NO:15) corresponding to amino acid sequence depicted in SEQ ID NO:142, or residues 23-231 of the VSIG1 protein sequence contained in the sequence of AI581519_P10 (SEQ ID NO:16), corresponding to amino acid sequence depicted in SEQ ID NO:143, or residues 26-293 of the VSIG1 protein sequence contained in the sequence of AI581519_P5 (SEQ ID NO:13), corresponding to amino acid sequence depicted in SEQ ID NO:302, or variants thereof possessing at least 80% sequence identity, more preferably at least 90% sequence identity therewith and even more preferably at least 95, 96, 97, 98 or 99% sequence identity therewith.

According to other more specific embodiments, the present invention provides novel splice variants of a known protein immunoglobulin-like domain containing receptor 1 (SEQ ID NO:21) (RefSeq accession identifier NP_787120, also known as ILDR1alpha, ILDR1beta, ILDR1), or a polynucleotide encoding same, which can be used as diagnostic markers and/or therapeutic agents which agonize or antagonize the binding of other moieties to the ILDR1 proteins and/or which modulate (agonize or antagonize) at least one ILDR1 related biological activity.

In one specific embodiment, the novel splice variant is an isolated polynucleotide comprising a nucleic acid having a nucleic acid sequence as set forth in AA424839_1_T7 (SEQ ID NO:20), or a sequence homologous thereto. According to another embodiment, the isolated polynucleotide is at least 95, 96, 97, 98 or 99% homologous to AA424839_1_T7 (SEQ ID NO:20).

According to yet another specific embodiment, the novel splice variant is an isolated protein or polypeptide having an amino acid sequence as set forth in AA424839_1_P11 (SEQ ID NO:24), or a sequence homologous there, i.e., which possesses at least 80, or 90% sequence identity therewith. According to another related embodiment, the isolated polypeptide is at least 95, 96, 97, 98 or 99% homologous to AA424839_1_P11 (SEQ ID NO:24).

It is another embodiment of the invention to provide molecules and isolated polypeptides comprising the soluble ectodomain (ECD) of the ILDR1 proteins and fragments thereof as well as nucleic acid sequences encoding said soluble ectodomain, as well as fragments thereof and conjugates and the use thereof as therapeutics including their use in immunotherapy (promoting or inhibiting immune costimulation).

According to yet further embodiments the present invention provides discrete portions of the ILDR1 proteins including different portions of the extracellular domain corresponding to residues 24-162 of sequences AA424839_P3 (SEQ ID NO:22) and AA424839_P5 (SEQ ID NO:21), corresponding to amino acid sequence depicted in SEQ ID NO:75, or residues 24-457 of AA424839_P7 (SEQ ID NO:23), corresponding to amino acid sequence depicted in SEQ ID NO:76, or residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301, or variants thereof possessing at least 80% sequence identity, more preferably at least 90% sequence identity therewith and even more preferably at least 95, 96, 97, 98 or 99% sequence identity therewith.

It is another embodiment of the invention to provide an isolated or purified soluble protein or nucleic acid sequence having or encoding the extracellular domain of the ILDR1 protein which optionally may be directly or indirectly attached to a non-ILDR1 protein or nucleic acid sequence such as a soluble immunoglobulin domain or fragment.

According to certain embodiments, the present invention provides novel splice variants of a known hypothetical protein LOC253012 isoform 1 (SEQ ID NO:35) (RefSeq accession identifier NP_001034461) or a polynucleotide encoding same, and their use as diagnostic markers and/or as therapeutic agents which agonize or antagonize the binding of other moieties to the LOC253012 proteins and/or which modulate (agonize or antagonize) at least one LOC253012 related biological activity.

According to one embodiment, the novel LOC253012 splice variant is an isolated polynucleotide comprising a nucleic acid having a nucleic acid sequence as set forth in any one of H68654_1_T8 (SEQ ID NO:28), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), or H68654_1_T20 (SEQ ID NO:34) or a sequence homologous thereto. According to another embodiment, the isolated polynucleotide is at least 95% homologous to any one of H68654_1_T8 (SEQ ID NO:28), H68654_1_T15 (SEQ ID NO:29), H68654_1_T16 (SEQ ID NO:30), H68654_1_T17

(SEQ ID NO:31), H68654_1_T18 (SEQ ID NO:32), H68654_1_T19 (SEQ ID NO:33), or H68654_1_T20 (SEQ ID NO:34).

According to yet another embodiment, the novel LOC253012 splice variant is an isolated protein or polypeptide having an amino acid sequence as set forth in any one of H68654_1_P7 (SEQ ID NO:37), H68654_1_P12 (SEQ ID NO:38), H68654_1_P13 (SEQ ID NO:39), H68654_1_P14 (SEQ ID NO:40) or a sequence homologous thereto. According to another embodiment, the isolated polypeptide is at least 95, 96, 97, 98 or 99% homologous to any one of H68654_1_P7 (SEQ ID NO:37), H68654_1_P12 (SEQ ID NO:38), H68654_1_P13 (SEQ ID NO:39), H68654_1_P14 (SEQ ID NO:40).

It is another object of the invention to provide molecules and isolated polypeptides comprising the soluble ectodomain (ECD) of the LOC253012 proteins and fragments thereof as well as nucleic acid sequences encoding said soluble ectodomain, as well as fragments thereof and conjugates and the use thereof as therapeutics including their use in immunotherapy (promoting or inhibiting immune costimulation).

According to yet further embodiments of the present invention there are discrete portions of the LOC253012 proteins including different portions of the extracellular domain corresponding to residues 38-349 of the sequence H68654_1_P2 (SEQ ID NO:35), corresponding to amino acid sequence depicted in SEQ ID NO:144, or residues 19-337 of the sequences H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300, or variants thereof possessing at least 80% sequence identity, more preferably at least 90% sequence identity therewith and even more preferably at least 95, 96, 97, 98 or 99% sequence identity therewith.

It is another object of the invention to provide an isolated or purified soluble protein or nucleic acid sequence encoding having or encoding the extracellular domain of the LOC253012 protein which optionally may be directly or indirectly attached to a non-LOC253012 protein or nucleic acid sequence such as a soluble immunoglobulin domain or fragment.

According to certain embodiments, the present invention provides novel splice variants of AI216611, or a polynucleotide encoding same, which can be used as diagnostic markers and/or therapeutic agents which agonize or antagonize the binding of other moieties to the AI216611 proteins and/or which modulate (agonize or antagonize) at least one AI216611 related biological activity.

According to one embodiment, the novel AI216611 splice variant is an isolated polynucleotide comprising a nucleic acid having a nucleic acid sequence as set forth in AI216611_T1 (SEQ ID NO:42), or a sequence homologous thereto. According to another embodiment, the isolated polynucleotide is at least 95, 96, 97, 98 or 99% homologous to AI216611_T1 (SEQ ID NO:42).

According to yet another embodiment, the novel AI216611 splice variant is an isolated protein or polypeptide having an amino acid sequence as set forth in AI216611_P1 (SEQ ID NO:44) or a sequence homologous thereto. According to another embodiment, the isolated polypeptide is at least 95, 96, 97, 98 or 99% homologous to AI216611_P1 (SEQ ID NO:44).

It is another object of the invention to provide molecules and isolated polypeptides comprising the soluble ectodomain (ECD) of the AI216611 proteins and fragments thereof as well as nucleic acid sequences encoding said soluble ectodomain, as well as fragments thereof and conjugates and the use thereof as therapeutics including their use in immunotherapy (such as promoting or inhibiting immune costimulation). According to yet further embodiments of the present invention there are discrete portions of the AI216611 proteins including different portions of the extracellular domain corresponding to residues 29-147 of the sequence AI216611_P0 (SEQ ID NO:43) or AI216611_P1 (SEQ ID NO:44), corresponding to amino acid sequence depicted in SEQ ID NO:146, or residues 1-145 of the sequence AI216611_P0 (SEQ ID NO:43), corresponding to amino acid sequence depicted in SEQ ID NO:298, or variants thereof possessing at least 80% sequence identity, more preferably at least 90% sequence identity therewith and even more preferably at least 95, 96, 97, 98 or 99% sequence identity therewith.

It is another object of the invention to provide an isolated or purified soluble protein or nucleic acid sequence having or encoding the extracellular domain of the AI216611 protein which optionally may be directly or indirectly attached to a non-AI216611 protein or nucleic acid sequence such as a soluble immunoglobulin domain or fragment.

It is another object of the invention to provide vectors such as plasmids and recombinant viral vectors and host cells containing that express AI216611, its secreted or soluble form and/or the ECD of the AI216611 protein and variants thereof or polypeptide conjugates containing any of the foregoing.

According to certain embodiments, the present invention provides novel splice variants of a known hypothetical protein LOC387597 (SEQ ID NO:47) (RefSeq accession identifier NP_955383, synonyms: NP_955383; LISCH-like; C1ORF32; RP4-782G3.2; dJ782G3.1) or a polynucleotide encoding same, which can be used as diagnostic markers and/or therapeutic agents which agonize or antagonize the binding of other moieties to the C1ORF32 proteins and/or which modulate (agonize or antagonize) at least one C1ORF32 related biological activity.

According to one embodiment, the novel LOC387597 splice variant is an isolated polynucleotide comprising a nucleic acid having a nucleic acid sequence as set forth in any one of H19011_1_T8 (SEQ ID NO:45), H19011_1_T9 (SEQ ID NO:46), or a sequence homologous thereto. According to another embodiment, the isolated polynucleotide is at least 95, 96, 97, 98 or 99% homologous to any one of H19011_1_T8 (SEQ ID NO:45), H19011_1_T9 (SEQ ID NO:46).

According to yet another embodiment, the novel splice LOC387597 variant is an isolated protein or polypeptide having an amino acid sequence as set forth in any one of H19011_1_P8 (SEQ ID NO:48), H19011_1_P9 (SEQ ID NO:50) or a sequence homologous thereto. According to another embodiment, the isolated polypeptide is at least 95, 96, 97, 98 or 99% homologous to any one of H19011_1_P8 (SEQ ID NO:48), H19011_1_P9 (SEQ ID NO:50).

It is another object of the invention to provide molecules and isolated polypeptides comprising the soluble ectodomain (ECD) of the C1ORF32 proteins and fragments thereof as well as nucleic acid sequences encoding said soluble ectodomain, as well as fragments thereof and conjugates and the use thereof as therapeutics including their use in immunotherapy (promoting or inhibiting immune costimulation).

According to yet further embodiments of the present invention there are discrete portions of the C1ORF32 proteins including different portions of the extracellular domain corresponding to residues 21-186 of the sequence H19011_1_P8 (SEQ ID NO:48), corresponding to amino acid sequence depicted in SEQ ID NO:147, or residues 21-169 of the sequence H19011_1_P9 (SEQ ID NO:50), corresponding to amino acid sequence depicted in SEQ ID NO:148, or residues 1-184 of the sequence H19011_1_P8 (SEQ ID NO:48), corresponding to amino acid sequence depicted in SEQ ID NO:299 (with non-silent SNPs as given in Table 94) or variants thereof possessing at least 80% sequence identity, more preferably at least 90% sequence identity therewith and even more preferably at least 95, 96, 97, 98 or 99% sequence identity therewith.

It is another object of the invention to provide an isolated or purified soluble protein or nucleic acid sequence encoding having or encoding the extracellular domain of the C1ORF32 protein which optionally may be directly or indirectly attached to a non-C1ORF32 protein or nucleic acid sequence such as a soluble immunoglobulin domain or fragment.

According to certain embodiments, the present invention provides novel splice variants of known protein FXYD3, FXYD domain-containing ion transport regulator 3 precursor (SEQ ID NO:70) (SwissProt accession identifier FXYD3 HUMAN; known also according to the synonyms Chloride conductance inducer protein Mat-8; Mammary tumor 8 kDa protein; Phospholemman-like) or a polynucleotide encoding same, which can be used as diagnostic markers and/or therapeutic agents which agonize or antagonize the binding of other moieties to the FXYD3 proteins and/or which modulate (agonize or antagonize) at least one FXYD3 related biological activity.

According to one embodiment, the novel FXYD3 splice variant is an isolated polynucleotide comprising a nucleic acid having a nucleic acid sequence as set forth in any one of R31375_T19 (SEQ ID NO:65), R31375_T25 (SEQ ID NO:66), R31375_T26 (SEQ ID NO:67), R31375_T29 (SEQ ID NO:68), R31375_T39 (SEQ ID NO:69), or a sequence homologous thereto. According to another embodiment, the isolated polynucleotide is at least 95, 96, 97, 98 or 99% homologous to any one of R31375_T19 (SEQ ID NO:65), R31375_T25 (SEQ ID NO:66), R31375_T26 (SEQ ID NO:67), R31375_T29 (SEQ ID NO:68), R31375_T39 (SEQ ID NO:69).

According to yet another embodiment, the novel FXYD3 splice variant is an isolated protein or polypeptide having an amino acid sequence as set forth in any one of R31375_P14 (SEQ ID NO:72), R31375_P31 (SEQ ID NO:73), R31375_P33 (SEQ ID NO:74) or a sequence homologous thereto. According to another embodiment, the isolated polypeptide is at least 95, 96, 97, 98 or 99% homologous to any one of R31375_P14 (SEQ ID NO:72), R31375_P31 (SEQ ID NO:73), R31375_P33 (SEQ ID NO:74).

It is another object of the invention to provide molecules and isolated polypeptides comprising the soluble ectodomain (ECD) of the FXYD3 proteins and fragments thereof as well as nucleic acid sequences encoding said soluble ectodomain, as well as fragments thereof and conjugates and the use thereof as therapeutics including their use in cancer immunotherapy.

According to yet further embodiments of the present invention there are discrete portions of the FXYD3 proteins including different portions of the extracellular domain corresponding to residues 21-36 of the sequence R31375_P0 (SEQ ID NO:70) or R31375_P31 (SEQ ID NO:73), corresponding to amino acid sequence depicted in SEQ ID NO:149, or residues 21-65 of the sequence R31375_P14 (SEQ ID NO:72), corresponding to amino acid sequence depicted in SEQ ID NO:150, or residues 21-25 of the sequence R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297, or variants thereof possessing at least 80% sequence identity, more preferably at least 90% sequence identity therewith and even more preferably at least 95, 96, 97, 98 or 99% sequence identity therewith.

It is another object of the invention to provide an isolated or purified soluble protein or nucleic acid sequence encoding having or encoding the extracellular domain of any one of the VSIG1, ILDR1, LOC253012, AI216611, C1ORF32 or FXYD3 proteins which optionally may be directly or indirectly attached to a non-VSIG1, non-ILDR1, non-LOC253012, non-AI216611, non-C1ORF32 or non-FXYD3 protein or nucleic acid sequence, respectively, such as a soluble immunoglobulin domain or fragment.

It is another object of the invention to provide molecules and isolated polypeptides comprising edge portion, tail or head portion, of any one of the VSIG1, ILDR1, LOC253012, AI216611, C1ORF32, FXYD3 novel variants of the invention, or a homologue or a fragment thereof as well as nucleic acid sequences encoding said edge portion, tail or head portion, as well as fragments thereof and conjugates and the use thereof as therapeutics and/or for diagnostics.

It is further object of the invention to provide molecules and isolated polypeptides comprising a bridge, edge portion, tail or head portion, as depicted in any one of SEQ. ID NOs: 284-295, or a homologue or a fragment thereof as well as nucleic acid sequences encoding said edge portion, tail or head portion, as well as fragments thereof and conjugates and the use thereof as therapeutics and/or for diagnostics.

It is another object of the invention to provide vectors such as plasmids and recombinant viral vectors and host cells containing the vectors that express any one of VSIG1, ILDR1, LOC253012, AI216611, C1ORF32, FXYD3, its secreted or soluble form and/or the ECD of the VSIG1, ILDR1, LOC253012, AI216611, C1ORF32 or FXYD3 protein and variants thereof or polypeptide conjugates containing any of the foregoing.

It is another object of the invention to use these vectors such as plasmids and recombinant viral vectors and host cells containing that express any one of VSIG1, ILDR1, LOC253012, AI216611, C1ORF32, FXYD3, its secreted or soluble form and/or the ECD of the VSIG1, ILDR1, LOC253012, AI216611, C1ORF32, FXYD3 protein and variants thereof or polypeptide conjugates containing any of the foregoing to produce said VSIG1, ILDR1, LOC253012, AI216611, C1ORF32, FXYD3 protein, fragments or variants thereof and/or conjugates containing any one of the foregoing.

It is another object of the invention to provide pharmaceutical or diagnostic compositions containing any of the foregoing.

It is another object of the invention to provide and use compounds including VSIG1 ectodomain or fragments or variants thereof, which are suitable for treatment or prevention of cancer, autoimmune disorders, transplant rejection, graft versus host disease, and/or for blocking or promoting immune costimulation mediated by the VSIG1, ILDR1, LOC253012, AI216611, FXYD3 or C1ORF32 polypeptide.

It is a specific object of the invention to develop novel monoclonal or polyclonal antibodies and antibody fragments and conjugates containing that specifically bind the full length VSIG1, ILDR1, LOC253012, AI216611, C1ORF32 or FXYD3 antigen, selected from the group consisting of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), its secreted form and/or the ECD thereof or conjugates or fragments thereof. These antibodies are potentially useful as therapeutics and/or diagnostic agents (both in vitro and in vivo diagnostic methods). Included in particular are antibodies and fragments that are immune activating or immune suppressing such as antibodies or fragments that target cells via ADCC (antibody dependent cellular cytotoxicity) or CDC (complement dependent cytotoxicity) activities.

It is another object of the invention to provide diagnostic methods that include the use of any of the foregoing including by way of example immunohistochemical assay, radioimaging assays, in-vivo imaging, radioimmunoassay (RIA), ELISA, slot blot, competitive binding assays, fluorimetric imaging assays, Western blot, FACS, and the like. In particular this includes assays which use chimeric or non-human antibodies or fragments that specifically bind the intact VSIG1, ILDR1, LOC253012, AI216611, C1ORF32 or FXYD3 protein, selected from the group consisting of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), its soluble form, its ECD, and or conjugates, fragments or variants thereof.

It is another object of the invention to use novel therapeutically effective polyclonal or monoclonal antibodies against anyone of the VSIG1, ILDR1, LOC253012, AI216611, C1ORF32 or FXYD3 antigen, selected from the group consisting of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), and fragments, conjugates, and variants thereof for treating conditions wherein the VSIG1, ILDR1, LOC253012, AI216611, C1ORF32 or FXYD3 antigen or its secreted or soluble form or ECD and/or portions or variants thereof are differentially expressed including various cancers and malignancies including non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer is non-metastatic, invasive or metastatic.

It is another object of the invention to use novel therapeutically effective polyclonal or monoclonal antibodies against anyone of the VSIG1, ILDR1, LOC253012, AI216611, C1ORF32 or FXYD3 antigen, selected from the group consisting of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), and fragments, conjugates and variants thereof for treating non-malignant disorders such as immune disorders including but not limited to autoimmune diseases, transplant rejection and graft versus host disease.

It is a specific object of the invention to use antibodies and antibody fragments against VSIG1 antigen, its secreted or soluble form or ECD and/or variants, conjugates, or fragments thereof and fragments and variants thereof for treating and diagnosing lung cancer and/or ovarian cancer, wherein this antigen is differentially expressed.

It is a specific embodiment of the invention to use antibodies and antibody fragments against ILDR1 antigen, its secreted or soluble form or ECD and/or variants, conjugates, or fragments thereof and fragments and variants thereof for treating and diagnosing colon and/or ovarian cancers wherein this antigen is differentially expressed.

It is a specific object of the invention to use antibodies and antibody fragments against LOC253012 or C1ORF32 antigen, its secreted or soluble form or ECD and/or variants, conjugates, or fragments thereof and fragments and variants thereof for treating and diagnosing lung cancer, particularly small cell lung carcinoma, wherein this antigen is differentially expressed.

It is a specific object of the invention to use antibodies and antibody fragments against AI216611 antigen, its secreted or soluble form or ECD and/or variants, conjugates, or fragments thereof and fragments and variants thereof for treating and diagnosing colon cancer, wherein this antigen is differentially expressed.

It is a specific object of the invention to use antibodies and antibody fragments against FXYD3 wild type antigen (R31375_P0 (SEQ ID NO:70)), or antibodies and antibody fragments against its secreted or soluble form or ECD and conjugates containing for treating and diagnosing ovarian cancer, wherein this antigen is differentially expressed.

It is another object of the invention to use antibodies and antibody fragments, and conjugates containing, against the VSIG1, ILDR1, LOC253012, AI216611, C1ORF32 or FXYD3 antigen, selected from the group consisting of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74) in modulating (enhancing or inhibiting) immunity including antibodies that activate or suppress the immune co-stimulation in particular B7 related immune costimulation and are capable of treating related therapeutic applications, through positive stimulation of T cell activity against cancer cells, and negative stimulation of T cell activity for the treatment of autoimmunity and other immune disorders.

It is another specific object of the invention to produce antibodies and antibody fragments against discrete portions of the VSIG1 proteins including different portions of the extracellular domain corresponding to residues 23-234 of the VSIG1 protein sequence contained in the sequence of AI581519_P3 (SEQ ID NO:11) corresponding to amino acid sequence depicted in SEQ ID NO:138, or residues 23-270 of the VSIG1 protein sequence contained in the sequence of AI581519_P4 (SEQ ID NO:12) corresponding to amino acid sequence depicted in SEQ ID NO:139, or residues 23-296 of the VSIG1 protein sequence contained in the sequence of AI581519_P5 (SEQ ID NO:13) corresponding to amino acid sequence depicted in SEQ ID NO:140, or residues 23-193 of the VSIG1 protein sequence contained in the sequence of AI581519_P7 (SEQ ID NO:14) corresponding to amino ac, id sequence depicted in SEQ ID NO:141, or residues 23-203 of the VSIG1 protein sequence contained in the sequence of AI581519_P9 (SEQ ID NO:15) corresponding to amino acid sequence depicted in SEQ ID NO:142, or residues 23-231 of the VSIG1 protein sequence contained in the sequence of AI581519_P10 (SEQ ID NO:16), corresponding to amino acid sequence depicted in SEQ ID NO:143, or residues 26-293 of the VSIG1 protein sequence contained in the sequence of AI581519_P5 (SEQ ID NO:13), corresponding to amino acid sequence depicted in SEQ ID NO:302.

It is another specific embodiment of the invention to produce antibodies and antibody fragments against discrete portions of the ILDR1 proteins including different portions of the extracellular domain corresponding to residues 24-162 of sequences AA424839_P3 (SEQ ID NO:22) and AA424839_P5 (SEQ ID NO:21), corresponding to amino acid sequence depicted in SEQ ID NO:75, residues 24-457 of AA424839_P7 (SEQ ID NO:23), corresponding to amino acid sequence depicted in SEQ ID NO:76, and residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301 of the ILDR1 protein sequences disclosed herein.

It is another specific object of the invention to produce antibodies and antibody fragments against discrete portions of the LOC253012 proteins including different portions of the extracellular domain corresponding to residues 38-349 of the sequence H68654_1_P2 (SEQ ID NO:35), corresponding to amino acid sequence depicted in SEQ ID NO:144, or residues 19-337 of the sequences H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), or residues 1-335 of the sequences H68654_1_P5 (SEQ ID NO:36), corresponding to amino acid sequence depicted in SEQ ID NO:300, of the LOC253012 protein sequences disclosed herein.

It is another specific object of the invention to produce antibodies and antibody fragments against discrete portions of the AI216611 proteins including different portions of the extracellular domain corresponding to residues 29-147 of the sequence AI216611_P0 (SEQ ID NO:43) or AI216611_P1 (SEQ ID NO:44), corresponding to amino acid sequence depicted in SEQ ID NO:146, or residues 1-145 of the sequence AI216611_P0 (SEQ ID NO:43), corresponding to amino acid sequence depicted in SEQ ID NO:298 sequence disclosed herein.

It is another specific object of the invention to produce antibodies and antibody fragments against discrete portions of the C1ORF32 proteins including different portions of the extracellular domain corresponding to residues 21-186 of the C1ORF32 protein sequence contained in the sequence of H19011_1_P8 (SEQ ID NO:48), corresponding to amino acid sequence depicted in SEQ ID NO:147, or residues 21-169 of the C1ORF32 protein sequence contained in the sequence of H19011_1_P9 (SEQ ID NO:50), corresponding to amino acid sequence depicted in SEQ ID NO:148, or residues 1-184 of the sequence H19011_1_P8 (SEQ ID NO:48), corresponding to amino acid sequence depicted in SEQ ID NO:299 (with non-silent SNPs as given in Table 94).

It is another specific object of the invention to produce antibodies and antibody fragments against discrete portions of the FXYD3 proteins including different portions of the extracellular domain corresponding to residues 21-36 of the FXYD3 protein sequence contained in the sequence of R31375_P0 (SEQ ID NO:70) or R31375_P31 (SEQ ID NO:73), corresponding to amino acid sequence depicted in SEQ ID NO:149, or residues 21-65 of the FXYD3 protein sequence contained in the sequence of R31375_P14 (SEQ ID NO:72), corresponding to amino acid sequence depicted in SEQ ID NO:150, or residues 21-25 of the FXYD3 protein sequence contained in the sequence of R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297.

It is a specific object of the invention to provide polyclonal and monoclonal antibodies and fragments thereof or an antigen binding fragment thereof comprising an antigen bindings site that binds specifically to the VSIG1, ILDR1, LOC253012, AI216611, C1ORF32 or FXYD3 proteins, its soluble forms, the ECD thereof and/or variants and fragments thereof.

It is a specific object of the invention to use such antibodies and fragments thereof for treatment or prevention of cancer and/or for modulating (activating or blocking) the activity of the target in the immune co-stimulatory system.

It is a related object of the invention to select monoclonal and polyclonal antibodies and fragments thereof against VSIG1, ILDR1, LOC253012, AI216611, C1ORF32 or FXYD3 which are suitable for treatment or prevention of autoimmune disorders, transplant rejection, GVHD, and/or for blocking or enhancing immune costimulation mediated by the VSIG1, ILDR1, LOC253012, AI216611, C1ORF32 or FXYD3 polypeptide.

It is a specific object of the invention to use antibodies against anyone of the VSIG1, ILDR1, LOC253012, AI216611, C1ORF32 or FXYD3 antigen, soluble form, ECD or fragment or variant thereof for the treatment and diagnosis of cancers including by way of example lung cancer, ovarian cancer, colon cancer, as well as other non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, spleen, kidney, bladder, head and neck, uterus, testicles, stomach, cervix, liver, bone, skin, pancreas, brain and wherein the cancer is non-metastatic, invasive or metastatic.

With regard to lung cancer, the disease is selected from the group consisting of squamous cell lung carcinoma, lung adenocarcinoma, carcinoid, small cell lung cancer or non-small cell lung cancer.

It is another object of the invention to provide and use antibodies and antibody fragments against anyone of the VSIG1, ILDR1, LOC253012, AI216611, C1ORF32 or FXYD3 antigen, its soluble form, or ECD and variants or fragments thereof as well as soluble polypeptides containing the ectodomain of the VSIG1, ILDR1, LOC253012, AI216611, C1ORF32 or FXYD3 antigen or a portion thereof which are useful for immune modulation, including treatment of autoimmunity and preferably for treating an autoimmune disease selected from autoimmune diseases: Multiple sclerosis; Psoriasis; Rheumatoid arthritis; Systemic lupus erythematosus; Ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

It is another object of the invention to provide and use compounds including drugs such as small molecules, peptides, antibodies and fragments that bind anyone of the VSIG1, ILDR1, LOC253012, AI216611, C1ORF32 or FXYD3 antigen, as well as ribozymes or antisense or siRNAs which target the VSIG1, ILDR1, LOC253012, AI216611, C1ORF32 or FXYD3 nucleic acid sequence or fragments or variants thereof which are useful for treatment or prevention of cancer, autoimmune disorders, transplant rejection, GVHD, and/or for blocking or enhancing immune costimulation mediated by the VSIG1, ILDR1, LOC253012, AI216611, C1ORF32 or FXYD3 polypeptide.

It is another object of the invention to provide and use compounds including drugs such as small molecules, peptides, antibodies and fragments that bind the VSIG1, ILDR1, LOC253012, AI216611, C1ORF32 or FXYD3 antigen, as well as ribozymes or antisense or siRNAs which target the FXYD3 nucleic acid sequence or fragments or variants thereof which are useful for treatment or prevention of cancer.

It is a preferred object to provide therapeutic and diagnostic antibodies and fragments and conjugates containing useful in treating or diagnosing any of the foregoing that specifically bind to amino-acids residues 23-234 of the sequence AI581519_P3 (SEQ ID NO:11), corresponding to amino acid sequence depicted in SEQ ID NO:138, or residues 23-270 of the sequence AI581519_P4 (SEQ ID NO:12), corresponding to amino acid sequence depicted in SEQ ID NO:139, or residues 23-296 of the sequence AI581519_P5 (SEQ ID NO:13), corresponding to amino acid sequence depicted in SEQ ID NO:140, or residues 23-193 of the sequence AI581519_P7 (SEQ ID NO:14), corresponding to amino acid sequence depicted in SEQ ID NO:141, or residues 23-203 of the sequence AI581519_P9 (SEQ ID NO:15), corresponding to amino acid sequence depicted in SEQ ID NO:144, or residues 23-231 of the sequence AI581519_P10 (SEQ ID NO:16), corresponding to amino acid sequence depicted in SEQ ID NO:143, or residues 26-293 of the sequence AI581519_P5 (SEQ ID NO:13), corresponding to amino acid sequence depicted in SEQ ID NO:302 of the VSIG1 protein sequences disclosed herein.

It is a preferred embodiment to provide therapeutic and diagnostic antibodies and fragments and conjugates containing useful in treating or diagnosing any of the foregoing that specifically bind to amino-acids residues 24-162 of the ILDR1 protein sequence contained in the sequence of AA424839_P3 (SEQ ID NO:22) and AA424839_P5 (SEQ ID NO:21), corresponding to amino acid sequence depicted in SEQ ID NO:75, residues 24-457 of the ILDR1 protein sequence contained in the sequence of AA424839_P7 (SEQ ID NO:23), corresponding to amino acid sequence depicted in SEQ ID NO:76, and residues 24-105 of the ILDR1 protein sequence contained in the sequence of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301.

It is a preferred object to provide therapeutic and diagnostic antibodies and fragments and conjugates containing useful in treating or diagnosing any of the foregoing that specifically bind to amino-acids residues 38-349 of the LOC253012 protein sequence contained in the sequence of H68654_1_P2 (SEQ ID NO:35), corresponding to amino acid sequence depicted in SEQ ID NO:144, or residues 19-337 of the of the LOC253012 protein sequence contained in the sequences of H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300.

It is a preferred object to provide therapeutic and diagnostic antibodies and fragments and conjugates containing useful in treating or diagnosing any of the foregoing that specifically bind to amino-acids residues 29-147 of the AI216611 protein sequence contained in the sequence of AI216611_P0 (SEQ ID NO:43) or AI216611_P1 (SEQ ID NO:44), corresponding to amino acid sequence depicted in SEQ ID NO:146, or residues 1-145 of the sequence AI216611_P0 (SEQ ID NO:43), corresponding to amino acid sequence depicted in SEQ ID NO:298.

It is a preferred object to provide therapeutic and diagnostic antibodies and fragments and conjugates containing useful in treating or diagnosing any of the foregoing that specifically bind to amino-acids residues 21-186 of the C1ORF32 protein sequence contained in the sequence of H19011_1_P8 (SEQ ID NO:48), corresponding to amino acid sequence depicted in SEQ ID NO:147, or residues 21-169 of the sequence of the C1ORF32 protein sequence contained in the sequence of H19011_1_P9 (SEQ ID NO:50), corresponding to amino acid sequence depicted in SEQ ID NO:149, or residues 1-184 of the sequence H19011_1_P8 (SEQ ID NO:48), corresponding to amino acid sequence depicted in SEQ ID NO:299 (with non-silent SNPs as given in Table 94).

It is a preferred object to provide therapeutic and diagnostic antibodies and fragments and conjugates containing useful in treating or diagnosing any of the foregoing that specifically bind to amino-acids residues 21-36 of the FXYD3 protein sequence contained in the sequence of R31375_P0 (SEQ ID NO:70), or R31375_P31 (SEQ ID NO:73), corresponding to amino acid sequence depicted in SEQ ID NO:149 or residues 21-65 of the FXYD3 protein sequence contained in the sequence of R31375_P14 (SEQ ID NO:72), corresponding to amino acid sequence depicted in SEQ ID NO:150, or residues or residues 21-25 of the FXYD3 protein sequence contained in the sequence of R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297.

It is also a preferred object to provide antibodies and fragments thereof that bind to VSIG1, ILDR1, LOC253012, AI216611, C1ORF32 or FXYD3 and the specific residues above-identified and fragments thereof, wherein the antibody is a chimeric, humanized, fully human antibody and/or is an antibody or antibody fragment having CDC or ADCC activities on target cells.

It is also a preferred object to provide chimeric and human antibodies and fragments thereof and conjugates containing that bind to VSIG1, ILDR1, LOC253012, AI216611, C1ORF32 or FXYD3 and the specific residues above-identified and fragments thereof.

It is another specific object of the invention to provide antibody fragments and conjugates containing useful in the foregoing therapies and related diagnostic methods including but not limited to Fab, F(ab')2, Fv or scFv fragment.

It is also an object of the invention to directly or indirectly attach the subject antibodies and fragments to markers and other effector moieties such as a detectable marker, or to an effector moiety such as an enzyme, a toxin, a therapeutic agent, or a chemotherapeutic agent.

In a preferred embodiment the inventive antibodies or fragments may be attached directly or indirectly to a radioisotope, a metal chelator, an enzyme, a fluorescent compound, a bioluminescent compound or a chemiluminescent compound.

It is also an object of the invention to provide pharmaceutical and diagnostic compositions that comprise a therapeutically or diagnostically effective form of an antibody or antibody fragment according to the invention.

It is another specific object of the invention to inhibit the growth of cells that express VSIG1 in a subject, comprising: administering to said subject an antibody that specifically binds to the antigen referred to herein as AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16) or VSIG1.

It is another specific object of the invention to provide methods for treating or preventing cancer, comprising administering to a patient an effective amount of a monoclonal antibody that specifically bind AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16) or VSIG1.

It is a more preferred object of the invention to use these antibodies for treating cancers selected from the group consisting of lung cancer, and ovarian cancer, and wherein the lung cancer or the ovarian cancer is non-metastatic, invasive or metastatic, wherein preferably the antibody has an antigen-binding region specific for the extracellular domain of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16).

It is another object of the invention to provide methods for treating or preventing autoimmune diseases, comprising administering to a patient an effective amount of a polyclonal or monoclonal antibody or fragment or a conjugate containing that specifically bind AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16).

It is another specific embodiment of the invention to inhibit the growth of cells that express ILDR1 in a subject, comprising: administering to said subject an antibody that specifically binds to the antigen referred to herein as AA424839_P3 (SEQ ID NO:22), AA424839_P5 (SEQ ID NO:21), AA424839_P7 (SEQ ID NO:23), AA424839_1_P11 (SEQ ID NO:24) or ILDR1.

It is another specific embodiment of the invention to provide methods for treating or preventing cancer, comprising administering to a patient an effective amount of a monoclonal antibody that specifically binds to AA424839_P3 (SEQ ID NO:22), AA424839_P5 (SEQ ID NO:21), AA424839_P7 (SEQ ID NO:23), AA424839_1_P11 (SEQ ID NO:24) or ILDR1.

It is a more preferred embodiment of the invention to use these antibodies for treating cancers selected from the group consisting of colon cancer or ovarian cancer, and wherein the colon cancer or the ovarian cancer is non-metastatic, invasive or metastatic wherein preferably the antibody has an antigen-binding region specific for the extracellular domain of AA424839_P3 (SEQ ID NO:22), AA424839_P5 (SEQ ID NO:21), AA424839_P7 (SEQ ID NO:23) or AA424839_1_P11 (SEQ ID NO:24).

It is another embodiment of the invention to provide methods for treating or preventing autoimmune diseases, comprising administering to a patient an effective amount of a polyclonal or monoclonal antibody or fragment that specifically binds AA424839_P3 (SEQ ID NO:22), AA424839_P5 (SEQ ID NO:21), AA424839_P7 (SEQ ID NO:23), or AA424839_1_P11 (SEQ ID NO:24).

It is another specific object of the invention to inhibit the growth of cells that express LOC253012 in a subject, comprising: administering to said subject an antibody that specifically binds to the antigen referred to herein as H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40) or LOC253012.

It is another specific object of the invention to provide methods for treating or preventing cancer, comprising administering to a patient an effective amount of a monoclonal antibody that specifically bind H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40) or LOC253012.

It is a more preferred object of the invention to use these antibodies for treating cancers selected from the group consisting of lung cancer, especially small cell lung carcinoma, and wherein the lung cancer is non-metastatic, invasive or metastatic wherein preferably the antibody has an antigen-binding region specific for the extracellular domain of H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40).

It is another object of the invention to provide methods for treating or preventing autoimmune diseases, comprising administering to a patient an effective amount of a polyclonal or monoclonal antibody or fragment that specifically bind H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40).

It is another specific object of the invention to provide methods for treating or preventing cancer, comprising administering to a patient an effective amount of a monoclonal antibody that specifically binds to AI216611_P0 (SEQ ID NO:43) or AI216611_P1 (SEQ ID NO:44).

It is another object of the invention to provide methods for treating or preventing autoimmune diseases, comprising administering to a patient an effective amount of a polyclonal or monoclonal antibody or fragment or a conjugate containing that specifically bind AI216611_P0 (SEQ ID NO:43) or AI216611_P1 (SEQ ID NO:44).

It is another specific object of the invention to inhibit the growth of cells that express C1ORF32 in a subject, comprising: administering to said subject an antibody that specifically binds to the antigen referred to herein as H19011_1_P8 (SEQ ID NO:48), H19011_1_P9 (SEQ ID NO:50), or C1ORF32.

It is another specific object of the invention to provide methods for treating or preventing cancer, comprising administering to a patient an effective amount of a monoclonal antibody that specifically binds to H19011_1_P8 (SEQ ID NO:48), H19011_1_P9 (SEQ ID NO:50) or C1ORF32.

It is a more preferred object of the invention to use these antibodies for treating cancers selected from the group consisting of lung cancer, particularly lung small cell carcinoma, and wherein the lung cancer is non-metastatic, invasive or metastatic, wherein preferably the antibody has an antigen-binding region specific for the extracellular domain of H19011_1_P8 (SEQ ID NO:48), H19011_1_P9 (SEQ ID NO:50).

It is another object of the invention to provide methods for treating or preventing autoimmune diseases, comprising administering to a patient an effective amount of a polyclonal or monoclonal antibody or fragment that specifically bind H19011_1_P8 (SEQ ID NO:48), H19011_1_P9 (SEQ ID NO:50).

It is another specific object of the invention to inhibit the growth of cells that express FXYD3 in a subject, comprising: administering to said subject an antibody that specifically binds to the antigen referred to herein as R31375_P0 (SEQ ID NO:70), R31375_P14 (SEQ ID NO:72), R31375_P31 (SEQ ID NO:73), R31375_P33 (SEQ ID NO:74).

It is another specific object of the invention to use part or all of the ectodomain of VSIG1, ILDR1, LOC253012, AI216611, C1ORF32, FXYD3 or its variants and conjugates containing for administration as an anti-cancer vaccine, for immunotherapy of cancer, including but not limited to ovarian cancer.

It is another specific object of the invention to provide methods for treating or preventing cancer, comprising administering to a patient an effective amount of a monoclonal antibody that specifically binds to R31375_P0 (SEQ ID NO:70), R31375_P14 (SEQ ID NO:72), R31375_P31 (SEQ ID NO:73), R31375_P33 (SEQ ID NO:74).

It is a more preferred object of the invention to use these antibodies for treating ovarian cancer, and wherein the ovarian cancer is non-metastatic, invasive or metastatic, wherein preferably the antibody has an antigen-binding region specific for the extracellular domain of R31375_P0 (SEQ ID NO:70), R31375_P14 (SEQ ID NO:72), R31375_P31 (SEQ ID NO:73), R31375_P33 (SEQ ID NO:74).

In another embodiment of the invention the cancer is selected from the group consisting of non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the lung, ovary, breast, prostate, colon, spleen, kidney, bladder, head and neck, uterus, testicles, stomach, cervix, liver, bone, skin, pancreas, brain and wherein the cancer may be non-metastatic, invasive or metastatic.

In a preferred embodiment the autoimmune diseases include Multiple sclerosis; Psoriasis; Rheumatoid arthritis; Systemic lupus erythematosus; Ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

It is a specific object of the invention to provide methods for treating or preventing rejection of any organ transplant and/or graft versus host disease, comprising administering to a patient an effective amount of an antibody that specifically bind AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74). It is also preferred in the foregoing methods that the antibody possess an antigen-binding region specific for the extracellular domain of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO: 74).

According to the present invention, each one of the following: the VSIG1 ectodomain, ILDR1 ectodomain, LOC253012 ectodomain, AI216611 ectodomain, C1ORF32 ectodomain or FXYD3 ectodomain of the present invention, antibodies and fragments that bind the VSIG1, ILDR1, LOC253012, AI216611, C1ORF32 of FXYD3 antigen, the compounds including drugs such as small molecules, peptides, as well as ribozymes or antisense or siRNAs which target the VSIG1, ILDR1, LOC253012, AI216611, C1ORF32 or FXYD3 nucleic acid sequence or fragments or variants thereof which are useful for treatment or prevention of cancer, autoimmune disorders, transplant rejection, GVHD, and/or for blocking or enhancing immune co-stimulation mediated by the VSIG1, ILDR1, LOC253012, AI216611, C1ORF32 or FXYD3 polypeptide, can be used with simultaneous blockade of several co-stimulatory pathways or in combination therapy with conventional drugs, such as immunosuppressants or cytotoxic drugs for cancer.

It is another object of the invention to provide assays for detecting the presence of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74) protein in vitro or in vivo in a biological sample or individual comprising contacting the sample with an antibody having specificity for AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74) polypeptides, or a combination thereof, and detecting the binding of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74) protein in the sample.

It is another object of the invention to provide methods for detecting a disease, diagnosing a disease, monitoring disease progression or treatment efficacy or relapse of a disease, or selecting a therapy for a disease, comprising detecting expression of a AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74).

In a related object the detected diseases will include cancers such as lung cancer, ovarian cancer, colon cancer, as well as other non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, spleen, kidney, bladder, head and neck, uterus, testicles, stomach, cervix, liver, bone, skin, pancreas, brain and wherein the cancer is non-metastatic, invasive or metastatic.

With regard to lung cancer, the disease is selected from the group consisting of non-metastatic, invasive or metastatic lung cancer; squamous cell lung carcinoma, lung adenocarcinoma, carcinoid, small cell lung cancer or non-small cell lung cancer; detection of overexpression in lung metastasis (vs. primary tumor); detection of overexpression in lung cancer, for example non small cell lung cancer, for example adenocarcinoma, squamous cell cancer or carcinoid, or large cell carcinoma; identification of a metastasis of unknown origin which originated from a primary lung cancer; assessment of a malignant tissue residing in the lung that is from a non-lung origin, including but not limited to: osteogenic and soft tissue sarcomas; colorectal, uterine, cervix and corpus tumors; head and neck, breast, testis and salivary gland cancers; melanoma; and bladder and kidney tumors; distinguishing between different types of lung cancer, therefore potentially affecting treatment choice (e.g. small cell vs. non small cell tumors); analysis of unexplained dyspnea and/or chronic cough and/or hemoptysis; differential diagnosis of the origin of a pleural effusion; diagnosis of conditions which have similar symptoms, signs and complications as lung cancer and where the differential diagnosis between them and lung cancer is of clinical importance including but not limited to: non-malignant causes of lung symptoms and signs, including but not limited to: lung lesions and infiltrates, wheeze, stridor, tracheal obstruction, esophageal compression, dysphagia, recurrent laryngeal nerve paralysis, hoarseness, phrenic nerve paralysis with elevation of the hemidiaphragm and Horner syndrome; or detecting a cause of any condition suggestive of a malignant tumor including but not limited to anorexia, cachexia, weight loss, fever, hypercalcemia, hypophosphatemia, hyponatremia, syndrome of inappropriate secretion of antidiuretic hormone, elevated ANP, elevated ACTH, hypokalemia, clubbing, neurologic-myopathic syndromes and thrombophlebitis.

With regard to ovarian cancer, the compounds of the present invention can be used in the diagnosis, treatment or prognostic assessment of non-metastatic, invasive or metastatic ovarian cancer; correlating stage and malignant potential; identification of a metastasis of unknown origin which originated from a primary ovarian cancer; differential diagnosis between benign and malignant ovarian cysts; diagnosing a cause of infertility, for example differential diagnosis of various causes thereof; detecting of one or more non-ovarian cancer conditions that may elevate serum levels of ovary related markers, including but not limited to: cancers of the endometrium, cervix, fallopian tubes, pancreas, breast, lung and colon; nonmalignant conditions such as pregnancy, endometriosis, pelvic inflammatory disease and uterine fibroids; diagnosing conditions which have similar symptoms, signs and complications as ovarian cancer and where the differential diagnosis between them and ovarian cancer is of clinical importance including but not limited to: non-malignant causes of pelvic mass, including, but not limited to: benign (functional) ovarian cyst, uterine fibroids, endometriosis, benign ovarian neoplasms and inflammatory bowel lesions; determining a cause of any condition suggestive of a malignant tumor including but not limited to anorexia, cachexia, weight loss, fever, hypercalcemia, skeletal or abdominal pain, paraneoplastic syndrome, or ascites.

In another related object the detected diseases will include autoimmune and neoplastic disorders selected from the group consisting of Multiple sclerosis; Psoriasis; Rheumatoid arthritis; Systemic lupus erythematosus; Ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another related object the detected diseases will include rejection of any organ transplant and/or Graft versus host disease.

In a related aspect the foregoing assays will detect cells affected by the disease using the antibody that binds specifically to the AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74) protein wherein the assays may be effected in vitro or in vivo, and include RIA, ELISA, fluorimetric assays, FACS, slot blot, Western blot, immunohistochemical assays, radioimaging assays and the like. In some embodiments, this invention provides a method for diagnosing a disease in a subject, comprising detecting in the subject or in a sample obtained from said subject at least one polypeptide or polynucleotide selected from the group consisting of:

a polypeptide comprising an amino acid sequence as set forth in any one of SEQ ID NOs: 11-16, 21-34, 35-40, 43-44, 48-50, 70-76, 138-151, 296, 298-302;

a polypeptide comprising a bridge, edge portion, tail or head portion, of any one of SEQ. ID NOs: 284-295, or a homologue or a fragment thereof;

a polynucleotide comprising a nucleic acid sequence as set forth in any one of SEQ ID NOs: 1-10, 17-20, 25-34, 41-42, 45-46, 51-69;

a polynucleotide comprising a nucleic acid sequence encoding a polypeptide comprising a bridge, edge portion, tail or head portion, of any one of SEQ. ID NOs: 284-295;

an oligonucleotide having a nucleic acid sequence as set forth in SEQ. ID NOs: 187, 190, 193, 196, 199, 202, 205, 208, 211, 214, 217, 220, 223, 226, 229, 232, 235, 238, 241, 244, 247, 250, 253.

According to further embodiment, detecting a polypeptide of the invention comprises employing an antibody capable of specifically binding to at least one epitope of a polypeptide comprising an amino acid sequence of a polypeptide comprising a bridge, edge portion, tail, or head portion of any one of SEQ. ID NOs: 284-295. According to one embodiment, detecting the presence of the polypeptide or polynucleotide is indicative of the presence of the disease and/or its severity and/or its progress. According to another embodiment, a change in the expression and/or the level of the polynucleotide or polypeptide compared to its expression and/or level in a healthy subject or a sample obtained therefrom is indicative of the presence of the disease and/or its severity and/or its progress. According to a further embodiment, a change in the expression and/or level of the polynucleotide or polypeptide compared to its level and/or expression in said subject or in a sample obtained therefrom at earlier stage is indicative of the progress of the disease. According to still further embodiment, detecting the presence and/or relative change in the expression and/or level of the polynucleotide or polypeptide is useful for selecting a treatment and/or monitoring a treatment of the disease.

According to one embodiment, detecting a polynucleotide of the invention comprises employing a primer pair, comprising a pair of isolated oligonucleotides capable of specifically hybridizing to at least a portion of a polynucleotide having a nucleic acid sequence as set forth in SEQ. ID NOs: 187, 190, 193, 196, 199, 202, 205, 208, 211, 214, 217, 220, 223, 226, 229, 232, 235, 238, 241, 244, 247, 250, 253, or polynucleotides homologous thereto.

According to another embodiment, detecting a polynucleotide of the invention comprises employing a primer pair, comprising a pair of isolated oligonucleotides as set forth in SEQ. ID NOs:185-186, 188-189, 191-192, 194-195, 197-198, 200-201, 203-204, 206-207, 209-210, 212-213, 215-216, 218-219, 221-222, 224-225, 227-228, 230-231, 233-234, 236-237, 239-240, 242-243, 245-246, 248-249, 251-252.

The invention also includes the following specific embodiments.

In one embodiment the invention includes an isolated polypeptide selected from AI581519_P9 (SEQ ID NO:15), AI581519_P10 (SEQ ID NO:16), AA424839_1_P11 (SEQ ID NO:24), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P1 (SEQ ID NO:44), H19011_1_P8 (SEQ ID NO:48), H19011_1_P9 (SEQ ID NO:50), R31375_P14 (SEQ ID NO:72), R31375_P31 (SEQ ID NO:73), R31375_P33 (SEQ ID NO:74) or a fragment or variant thereof that possesses at least 95, 96, 97, 98 or 99% sequence identity therewith.

In another embodiment the invention includes a fragment or conjugate comprising any one of the foregoing polypeptides.

In another embodiment the invention includes any one of the foregoing polypeptides fused to an immunoglobulin domain.

In another embodiment the invention includes any of the foregoing polypeptides attached to a detectable or therapeutic moiety.

In another embodiment the invention includes a nucleic acid sequence encoding any of the foregoing polypeptides.

In another embodiment the invention includes any of the nucleic acid sequences selected from AI581519_T10 (SEQ ID NO:9), AI581519_T11 (SEQ ID NO:10), AA424839_1_T7 (SEQ ID NO:20), H68654_1_T8 (SEQ ID NO:28), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), H68654_1_T20 (SEQ ID NO:34), AI216611_T1 (SEQ ID NO:42), H19011_1_T8 (SEQ ID NO:45), H19011_1_T9 (SEQ ID NO:46), R31375_T19 (SEQ ID NO:65); R31375_T25 (SEQ ID NO:66), R31375_T26 (SEQ ID NO:67), R31375_T29 (SEQ ID NO:68), R31375_T39 (SEQ ID NO:69), or a fragment or variant and conjugates containing that possesses at least 95, 96, 97, 98 or 99% sequence identity therewith.

In another embodiment the invention includes an isolated VSIG1, ILDR1, LOC253012, AI216611, C1ORF32 or FXYD3 ectodomain polypeptide, or fragment or conjugate thereof.

In another embodiment the invention includes any of the foregoing polypeptides, comprising a sequence of amino acid residues having at least 95, 96, 97, 98 or 99% sequence identity with amino acid residues 23-234 of AI581519_P3 (SEQ ID NO:11), corresponding to amino acid sequence depicted in SEQ ID NO:138, or amino acid residues 23-270 of AI581519_P4 (SEQ ID NO:12), corresponding to amino acid sequence depicted in SEQ ID NO:139, or amino acid residues 23-296 of AI581519_P5 (SEQ ID NO:13), corresponding to amino acid sequence depicted in SEQ ID NO:140, or amino acid residues 23-193 of AI581519_P7 (SEQ ID NO:14), corresponding to amino acid sequence depicted in SEQ ID NO:141, or amino acid residues 23-203 of AI581519_P9 (SEQ ID NO:15), corresponding to amino acid sequence depicted in SEQ ID NO:142, or amino acid residues 23-231 of AI581519_P10 (SEQ ID NO:16), corresponding to amino acid sequence depicted in SEQ ID NO:143, or residues 26-293 of AI581519_P5 (SEQ ID NO:13), corresponding to amino acid sequence depicted in SEQ ID NO:302, or amino acid residues 24-162 of AA424839_P3 (SEQ ID NO:22), or AA424839_P5 (SEQ ID NO:21), corresponding to amino acid sequence depicted in SEQ ID NO:75, or amino acid residues 24-456 of AA424839_P7 (SEQ ID NO:23), corresponding to amino acid sequence depicted in SEQ ID NO:76, or amino acid residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301, or amino acid residues 38-349 of H68654_1_P2 (SEQ ID NO:35), corresponding to amino acid sequence depicted in SEQ ID NO:144, or residues 19-337 of H68654_1_P5 (SEQ ID NO:36), H68654_1_P7 (SEQ ID NO:37), H68654_1_P12 (SEQ ID NO:38), H68654_1_P13 (SEQ ID NO:39), or H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300, or amino acid residues 29-147 of the sequence AI216611_P0 (SEQ ID NO:43) or AI216611_P1 (SEQ ID NO:44), or residues 1-145 of the sequence AI216611_P0 (SEQ ID NO:43), corresponding to amino acid sequence depicted in SEQ ID NO:298, corresponding to amino acid sequence depicted in SEQ ID NO:146, or amino acid residues 21-186 of H19011_1_P8 (SEQ ID NO:48), corresponding to amino acid sequence depicted in SEQ ID NO:147, or residues 21-169 of H19011_1_P9 (SEQ ID NO:50), corresponding to amino acid sequence depicted in SEQ ID NO:148, or residues 1-184 of the sequence H19011_1_P8 (SEQ ID NO:48), corresponding to amino acid sequence depicted in SEQ ID NO:299 (with non-silent SNPs as given in Table 94), or amino acid residues 21-36 of R31375_P0 (SEQ ID NO:70) or R31375_P31 (SEQ ID NO:73), corresponding to amino acid sequence depicted in SEQ ID NO:149, or residues 21-65 of R31375_P14 (SEQ ID NO:72), corresponding to amino acid sequence depicted in SEQ ID NO:150, or residues 21-25 of R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297.

In another embodiment the invention includes any of the foregoing polypeptides, comprising the extracellular domain of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74).

In another embodiment the invention includes any of the foregoing polypeptides, attached to a detectable or therapeutic moiety.

In another embodiment the invention includes any of the foregoing nucleic acid sequences encoding any one of the VSIG1, ILDR1, LOC253012, AI216611, C1ORF32, FXYD3 ectodomain polypeptides and conjugates containing.

In another embodiment the invention includes an expression vector containing any of the foregoing nucleic acid sequences.

In another embodiment the invention includes a host cell comprising the foregoing expression vector or a virus containing a nucleic acid sequence encoding the VSIG1, ILDR1, LOC253012, AI216611, C1ORF32, FXYD3 ectodomain polypeptide, or fragment or conjugate thereof, wherein the cell expresses the polypeptide encoded by the DNA segment.

In another embodiment the invention includes a method of producing anyone of the VSIG1, ILDR1, LOC253012, AI216611, C1ORF32, FXYD3 ectodomain polypeptides, or fragment or conjugate thereof, comprising culturing the foregoing host cell, wherein the cell expresses the polypeptide encoded by the DNA segment or nucleic acid and recovering said polypeptide.

In another embodiment the invention includes any of the foregoing isolated soluble VSIG1, ILDR1, LOC253012, AI216611, C1ORF32, FXYD3 ectodomain wherein said polypeptide blocks or inhibits the interaction of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof with a corresponding functional counterpart.

In another embodiment the invention includes the foregoing isolated soluble VSIG1, ILDR1, LOC253012, AI216611, C1ORF32, FXYD3 ectodomains, wherein said polypeptide replaces or augments the interaction of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74), or a fragment or variant or conjugate thereof with a corresponding functional counterpart.

In another embodiment the invention includes a fusion protein comprising any of the foregoing isolated soluble VSIG1, ILDR1, LOC253012, AI216611, C1ORF32, FXYD3 ectodomain joined to a non-VSIG1, non-ILDR1, non-LOC253012, non-AI216611, non-C1ORF32, non-FXYD3 protein sequence, correspondingly.

In another embodiment the invention includes any of the foregoing fusion proteins, wherein the non-VSIG1, non-ILDR1, non-LOC253012, non-AI216611, non-C1ORF32, non-FXYD3 protein is at least a portion of an immunoglobulin molecule.

In another embodiment the invention includes any of the foregoing fusion proteins, wherein a polyalkyl oxide moiety such as polyethylene glycol is attached to the polypeptide.

In another embodiment the invention includes any of the foregoing fusion proteins, wherein the immunoglobulin heavy chain constant region is an Fc fragment.

In another embodiment the invention includes any one of the protein sequences of the VSIG1, ILDR1, LOC253012, AI216611, C1ORF32 and FXYD3 ECDs fused to mouse Fc, as set forth in any one of amino acid sequences as depicted in SEQ ID NOs: 103-108, or nucleic acid sequences encoding the VSIG1, ILDR1, LOC253012, AI216611, C1ORF32 and FXYD3 ECDs fused to mouse Fc. The invention further includes the nucleic acid sequences encoding the VSIG1, ILDR1, LOC253012, AI216611, C1ORF32 and FXYD3 ECDs fused to mouse Fc, as set forth in any one of nucleic acid sequences depicted in SEQ ID NOs:97-102.

In another embodiment the invention includes any of the foregoing fusion proteins wherein the immunoglobulin heavy chain constant region is an isotype selected from the group consisting of an IgG1, IgG2, IgG3, IgG4, IgM, IgE, IgA and IgD.

In another embodiment the invention includes any of the foregoing fusion proteins, wherein the polypeptide is fused to a VASP domain.

In another embodiment the invention includes any of the foregoing fusion proteins, wherein the fusion protein modulates lymphocyte activation.

In another embodiment the invention includes a pharmaceutical composition comprising any of the foregoing polynucleotide sequences and further comprising a pharmaceutically acceptable diluent or carrier.

In another embodiment the invention includes a pharmaceutical composition comprising the foregoing vector and further comprising a pharmaceutically acceptable diluent or carrier.

In another embodiment the invention includes a pharmaceutical composition comprising the foregoing host cell and further comprising a pharmaceutically acceptable diluent or carrier.

In another embodiment the invention includes a pharmaceutical composition comprising any of the foregoing VSIG1, ILDR1, LOC253012, AI216611, C1ORF32, FXYD3 ectodomains and further comprising a pharmaceutically acceptable diluent or carrier.

In another embodiment the invention includes a pharmaceutical composition comprising any of the foregoing polypeptides and further comprising a pharmaceutically acceptable diluent or carrier.

In another embodiment the invention includes a pharmaceutical composition comprising the foregoing fusion protein and further comprising a pharmaceutically acceptable diluent or carrier.

In another embodiment the invention includes a method for treating or preventing cancer, comprising administering to a subject in need thereof a pharmaceutical composition comprising: a soluble molecule having the extracellular domain of VSIG1, ILDR1, LOC253012, AI216611, C1ORF32, FXYD3 polypeptide, or fragment or conjugate thereof; or polypeptide, comprising a sequence of amino acid residues having at least 95, 96, 97, 98 or 99% sequence identity with amino acid residues 23-234 of AI581519_P3 (SEQ ID NO:11), corresponding to amino acid sequence depicted in SEQ ID NO:138, or amino acid residues 23-270 of AI581519_P4 (SEQ ID NO:12), corresponding to amino acid sequence depicted in SEQ ID NO:139, or amino acid residues 23-296 of AI581519_P5 (SEQ ID NO:13), corresponding to amino acid sequence depicted in SEQ ID NO:140, or amino acid residues 23-193 of AI581519_P7 (SEQ ID NO:14), corresponding to amino acid sequence depicted in SEQ ID NO:141, or amino acid residues 23-203 of AI581519_P9 (SEQ ID NO:15), corresponding to amino acid sequence depicted in SEQ ID NO:142, or amino acid residues 23-231 of AI581519_P10 (SEQ ID NO:16), corresponding to amino acid sequence depicted in SEQ ID NO:143, or residues 26-293 of AI581519_P5 (SEQ ID NO:13), corresponding to amino acid sequence depicted in SEQ ID NO:302, or amino acid residues 24-162 of AA424839_P3 (SEQ ID NO:22), or AA424839_P5 (SEQ ID NO:21), corresponding to amino acid sequence depicted in SEQ ID NO:75, or amino acid residues 24-456 of AA424839_P7 (SEQ ID NO:23), corresponding to amino acid sequence depicted in SEQ ID NO:76, or amino acid residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301, or amino acid residues 38-349 of H68654_1_P2 (SEQ ID NO:35), corresponding to amino acid sequence depicted in SEQ ID NO:144, or residues 19-337 of H68654_1_P5 (SEQ ID NO:36), H68654_1_P7 (SEQ ID NO:37), H68654_1_P12 (SEQ ID NO:38), H68654_1_P13 (SEQ ID NO:39), or H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300, or amino acid residues 29-147 of the sequence AI216611_P0 (SEQ ID NO:43) or AI216611_P1 (SEQ ID NO:44), or residues 1-145 of the sequence AI216611_P0 (SEQ ID NO:43), corresponding to amino acid sequence depicted in SEQ ID NO:298, corresponding to amino acid sequence depicted in SEQ ID NO:146, or amino acid residues 21-186 of H19011_1_P8 (SEQ ID NO:48), corresponding to amino acid sequence depicted in SEQ ID NO:147, or residues 21-169 of H19011_1_P9 (SEQ ID NO:50), corresponding to amino acid sequence depicted in SEQ ID NO:148, or residues 1-184 of the sequence H19011_1_P8 (SEQ ID NO:48), corresponding to amino acid sequence depicted in SEQ ID NO:299 (with non-silent SNPs as given in Table 94), or amino acid residues 21-36 of R31375_P0 (SEQ ID NO:70) or R31375_P31 (SEQ ID NO:73), corresponding to amino acid sequence depicted in SEQ ID NO:149, or residues 21-65 of R31375_P14 (SEQ ID NO:72), corresponding to amino acid sequence depicted in SEQ ID NO:150, or residues 21-25 of R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297, or a nucleic acid sequence encoding the same.

In another embodiment the invention includes the foregoing method, wherein the cancer is selected from a group consisting of hematological malignancies such as acute lymphocytic leukemia, chronic lymphocytic leukemia, acute myelogenous leukemia, chronic myelogenous leukemia, multiple myeloma, Hodgkin's lymphoma, Non-Hodgkin's lymphoma, and soft or solid tumors such as cancer of breast, prostate, lung, ovary, colon, spleen, kidney, bladder, head and neck, uterus, testicles, stomach, cervix, liver, bone, skin, pancreas, brain and wherein the cancer is non-metastatic, invasive or metastatic.

In another embodiment the invention includes the foregoing method wherein the cancer is selected from the group consisting of lung cancer, ovarian cancer or colon cancer, and wherein the lung cancer, the ovarian cancer or the colon cancer is non-metastatic, invasive or metastatic.

In another embodiment the invention includes a method for treating or preventing immune related conditions, such as autoimmune diseases or transplant rejection, comprising administering to a subject in need thereof a pharmaceutical composition comprising: a soluble molecule having the extracellular domain of VSIG1, ILDR1, LOC253012, AI216611, C1ORF32, FXYD3 polypeptide, or fragment or conjugate thereof; or polypeptide, comprising a sequence of amino acid residues having at least 95, 96, 97, 98 or 99% sequence identity with amino acid residues 23-234 of AI581519_P3 (SEQ ID NO:11), corresponding to amino acid sequence depicted in SEQ ID NO:138, or amino acid residues 23-270 of AI581519_P4 (SEQ ID NO:12), corresponding to amino acid sequence depicted in SEQ ID NO:139, or amino acid residues 23-296 of AI581519_P5 (SEQ ID NO:13), corresponding to amino acid sequence depicted in SEQ ID NO:140, or amino acid residues 23-193 of AI581519_P7 (SEQ ID NO:14), corresponding to amino acid sequence depicted in SEQ ID NO:141, or amino acid residues 23-203 of AI581519_P9 (SEQ ID NO:15), corresponding to amino acid sequence depicted in SEQ ID NO:142, or amino acid residues 23-231 of AI581519_P10 (SEQ ID NO:16), corresponding to amino acid sequence depicted in SEQ ID NO:143, or residues 26-293 of AI581519_P5 (SEQ ID NO:13), corresponding to amino acid sequence depicted in SEQ ID NO:302, or amino acid residues 24-162 of AA424839_P3 (SEQ ID NO:22), or AA424839_P5 (SEQ ID NO:21), corresponding to amino acid sequence depicted in SEQ ID NO:75, or amino acid residues 24-456 of AA424839_P7 (SEQ ID NO:23), corresponding to amino acid sequence depicted in SEQ ID NO:76, or amino acid residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301, or amino acid residues 38-349 of H68654_1_P2 (SEQ ID NO:35), corresponding to amino acid sequence depicted in SEQ ID NO:144, or residues 19-337 of H68654_1_P5 (SEQ ID NO:36), H68654_1_P7 (SEQ ID NO:37), H68654_1_P12 (SEQ ID NO:38), H68654_1_P13 (SEQ ID NO:39), or H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300, or amino acid residues 29-147 of the sequence AI216611_P0 (SEQ ID NO:43) or AI216611_P1 (SEQ ID NO:44), or residues 1-145 of the sequence AI216611_P0 (SEQ ID NO:43), corresponding to amino acid sequence depicted in SEQ ID NO:298, corresponding to amino acid sequence depicted in SEQ ID NO:146, or amino acid residues 21-186 of H19011_1_P8 (SEQ ID NO:48), corresponding to amino acid sequence depicted in SEQ ID NO:147, or residues 21-169 of H19011_1_P9 (SEQ ID NO:50), corresponding to amino acid sequence depicted in SEQ ID NO:148, residues 1-184 of the sequence H19011_1_P8 (SEQ ID NO:48), corresponding to amino acid sequence depicted in SEQ ID NO:299 (with non-silent SNPs as given in Table 94), or residues 21-36 of R31375_P0 (SEQ ID NO:70) or R31375_P31 (SEQ ID NO:73), corresponding to amino acid sequence depicted in SEQ ID NO:149, or residues 21-65 of R31375_P14 (SEQ ID NO:72), corresponding to amino acid sequence depicted in SEQ ID NO:150, or residues 21-25 of R31375_P33 (SEQ ID NO:74), corresponding to amino acid sequence depicted in SEQ ID NO:151, or residues 1-63 of R31375_P14 (SEQ ID NO:72), corresponding to amino acid sequence depicted in SEQ ID NO:297, or a nucleic acid sequence encoding the same.

In another embodiment the invention includes the foregoing method, wherein the autoimmune diseases are selected from a group consisting of multiple sclerosis; psoriasis; rheumatoid arthritis; systemic lupus erythematosus; ulcerative colitis; Crohn's disease; immune disorders associated with graft transplantation rejection; benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another embodiment the invention includes the foregoing method, wherein the immune related disorders are selected from transplant rejection or graft versus host disease.

In another embodiment the invention includes an siRNA, antisense RNA, or ribozyme that binds the transcript encoding any one of the VSIG1, ILDR1, LOC253012, AI216611, C1ORF32, FXYD3 polypeptides, selected from AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or a variant thereof, and inhibits its expression.

In another embodiment the invention includes a polyclonal or monoclonal antibody that specifically binds and/or modulates an activity elicited by any one of the VSIG1, ILDR1, LOC253012, AI216611, C1ORF32, FXYD3 polypeptides, selected from AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or a variant thereof and conjugates containing.

In another embodiment the invention includes a monoclonal or polyclonal antibody or an antigen binding fragment thereof comprising an antigen binding site that binds specifically to any one of the VSIG1, ILDR1, LOC253012, AI216611, C1ORF32, FXYD3 polypeptides comprised in AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or fragment or variant thereof that is at least 80% identical thereto.

In another embodiment the invention includes any of the foregoing antibodies or fragments thereof, wherein said antibody blocks or inhibits the interaction of one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8

(SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof with a counterpart activity or function.

In another embodiment the invention includes any of the foregoing antibodies or fragments wherein said antibody replaces or augments the interaction of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof with a counterpart function or activity.

In another embodiment the invention includes a method for modulating lymphocyte activity, comprising contacting a AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74) positive lymphocyte with a bioactive agent capable of modulating VSIG1-mediated, ILDR1-mediated, LOC253012-mediated, AI216611-mediated, C1ORF32-mediated, or FXYD3-mediated signaling in an amount effective to modulate at least one lymphocyte activity.

In another embodiment the invention includes the foregoing method, wherein said agent comprises an antagonist of VSIG1-mediated, ILDR1-mediated, LOC253012-mediated, AI216611-mediated, C1ORF32-mediated signaling, or FXYD3-mediated signaling and wherein said contacting inhibits the attenuation of lymphocyte activity mediated by such signaling.

In another embodiment the invention includes the foregoing method, wherein said contacting increases lymphocyte activity.

In another embodiment the invention includes the foregoing method wherein said antagonist comprises a blocking agent capable of interfering with the functional interaction of VSIG1, ILDR1, LOC253012, AI216611, C1ORF32, FXYD3 antigen and its counterpart.

In another embodiment the invention includes the foregoing antibody or fragment which is suitable for treatment or prevention of cancer by modulating the activity of any one of the VSIG1, ILDR1, LOC253012, AI216611, C1ORF32, FXYD3 proteins in a B7-like co-stimulatory system.

In another embodiment the invention includes the foregoing method wherein the administered antibody or fragment inhibits negative stimulation of T cell activity against cancer cells.

In another embodiment the invention includes any of the foregoing antibodies or fragments, wherein the cancer is selected from the group consisting of hematological malignancies such as acute lymphocytic leukemia, chronic lymphocytic leukemia, acute myelogenous leukemia, chronic myelogenous leukemia, multiple myeloma, Hodgkin's lymphoma, Non-Hodgkin's lymphoma, and soft tissue or solid tumors such as cancer of breast, prostate, lung, ovary, colon, spleen, kidney, bladder, head and neck, uterus, testicles, stomach, cervix, liver, bone, skin, pancreas, brain and wherein the cancer is non-metastatic, invasive or metastatic.

In another embodiment the invention includes any of the foregoing antibodies or fragments, which are suitable for treatment or prevention of immune related disorders, such as autoimmune diseases or transplant rejection, by modulating the activity of anyone of the VSIG1, ILDR1, LOC253012, AI216611, C1ORF32, FXYD3 proteins in a B7-like co-stimulatory system.

In another embodiment the invention includes any of the foregoing antibodies or fragments, which are suitable for treating an autoimmune disease selected from multiple sclerosis; psoriasis; rheumatoid arthritis; Systemic lupus erythematosus; ulcerative colitis; Crohn's disease, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another embodiment the invention includes any of the foregoing antibodies or fragments, suitable for treating transplant rejection or graft versus host disease.

In another embodiment the invention includes any of the foregoing antibodies or fragments, that specifically binds to amino-acids: 23-234 of AI581519_P3 (SEQ ID NO:11), corresponding to amino acid sequence depicted in SEQ ID NO:138, or amino acid residues 23-270 of AI581519_P4 (SEQ ID NO:12), corresponding to amino acid sequence depicted in SEQ ID NO:139, or amino acid residues 23-296 of AI581519_P5 (SEQ ID NO:13), corresponding to amino acid sequence depicted in SEQ ID NO:140, or amino acid residues 23-193 of AI581519_P7 (SEQ ID NO:14), corresponding to amino acid sequence depicted in SEQ ID NO:141, or amino acid residues 23-203 of AI581519_P9 (SEQ ID NO:15), corresponding to amino acid sequence depicted in SEQ ID NO:142, or amino acid residues 23-231 of AI581519_P10 (SEQ ID NO:16), corresponding to amino acid sequence depicted in SEQ ID NO:143, or residues 26-293 of AI581519_P5 (SEQ ID NO:13), corresponding to amino acid sequence depicted in SEQ ID NO:302, or amino acid residues 24-162 of AA424839_P3 (SEQ ID NO:22), or AA424839_P5 (SEQ ID NO:21), corresponding to amino acid sequence depicted in SEQ ID NO:75, or amino acid residues 24-456 of AA424839_P7 (SEQ ID NO:23), corresponding to amino acid sequence depicted in SEQ ID NO:76, or amino acid residues 24-105 of AA424839_1_P11 (SEQ ID NO:24), corresponding to amino acid sequence depicted in SEQ ID NO:296, or residues 50-160 of AA424839_1_P3 (SEQ ID NO:22), corresponding to amino acid sequence depicted in SEQ ID NO:301, or amino acid residues 38-349 of H68654_1_P2 (SEQ ID NO:35), corresponding to amino acid sequence depicted in SEQ ID NO:144, or residues 19-337 of H68654_1_P5 (SEQ ID NO:36), H68654_1_P7 (SEQ ID NO:37), H68654_1_P12 (SEQ ID NO:38), H68654_1_P13 (SEQ ID NO:39), or H68654_1_P14 (SEQ ID NO:40), corresponding to amino acid sequence depicted in SEQ ID NO:145, or residues 1-335 of the sequences H68654_1_P5 (SEQ ID NO:36), corresponding to amino acid sequence depicted in SEQ ID NO:300, or amino acid residues 29-147 of the sequence AI216611_P0 (SEQ ID NO:43) or AI216611_P1 (SEQ ID NO:44), or residues 1-145 of the sequence AI216611_P0 (SEQ ID NO:43), corresponding to amino acid sequence depicted in SEQ ID NO:298, corresponding to amino acid sequence depicted in SEQ ID NO:146, or amino acid residues 21-186 of H19011_1_P8 (SEQ ID NO:48), corresponding to amino acid sequence depicted in SEQ ID NO:147, or residues 21-169 of H19011_1_P9 (SEQ ID NO:50), corresponding to amino acid sequence depicted in SEQ ID NO:148, or residues 1-184 of the sequence H19011_1_P8 (SEQ ID NO:48), corresponding to amino acid sequence depicted in SEQ ID NO:299 (with non-silent SNPs as given in Table 94), or amino acid residues 21-36 of R31375_P0 (SEQ ID NO:70) or R31375_P31 (SEQ ID NO:73), corresponding to amino acid sequence depicted in SEQ ID NO:149, or residues 21-65 of R31375_P14 (SEQ ID NO:72), corresponding to amino acid sequence depicted in SEQ ID NO:150, or residues 21-25 of R31375_P33 (SEQ ID NO:74), corresponding to amino acid sequence depicted in SEQ ID NO:151, or residues 1-63 of the sequence R31375_P14 (SEQ ID NO:72), corresponding to amino acid sequence depicted in SEQ ID NO:297, or a variant or fragment or an epitope thereof.

In another embodiment the invention includes any of the foregoing antibodies or fragments, wherein the antigen binding site contains from about 3-7 contiguous or non-contiguous amino acids, more typically at least 5 contiguous or non-contiguous amino acids. These binding sites include conformational and non-conformational epitopes.

In another embodiment the invention includes any of the foregoing antibodies or fragments, wherein the antibody is a fully human antibody.

In another embodiment the invention includes any of the foregoing antibodies or fragments, wherein the antibody is a chimeric antibody.

In another embodiment the invention includes the foregoing antibodies or fragments wherein the antibody is a humanized or primatized antibody.

In another embodiment the invention includes any of the foregoing antibodies or fragments, wherein the fragment is selected from the group consisting of Fab, Fab', F(ab')2, F(ab'), F(ab), Fv or scFv fragment and minimal recognition unit.

In another embodiment the invention includes any of the foregoing antibodies or fragments, wherein the antibody or fragment is coupled to a detectable marker, or to an effector moiety.

In another embodiment the invention includes any of the foregoing antibodies or fragments, wherein the effector moiety is an enzyme, a toxin, a therapeutic agent, or a chemotherapeutic agent.

In another embodiment the invention includes any of the foregoing antibodies or fragments, wherein the detectable marker is a radioisotope, a metal chelator, an enzyme, a fluorescent compound, a bioluminescent compound or a chemiluminescent compound.

In another embodiment the invention includes a pharmaceutical composition that comprises any of the foregoing antibodies or a fragment thereof.

In another embodiment the invention includes a pharmaceutical composition that comprises the foregoing antibodies or a fragment thereof.

In another embodiment the invention includes a method of inducing or enhancing an immune response, comprising administering to a patient in need thereof any of the foregoing antibodies or fragments and detecting induction or enhancement of said immune response.

In another embodiment the invention includes a method for potentiating a secondary immune response to an antigen in a patient, which method comprises administering effective amounts any of the foregoing antibodies or fragments.

In another embodiment the invention includes the foregoing method, wherein the antigen is preferably a cancer antigen, a viral antigen or a bacterial antigen, and the patient has preferably received treatment with an anticancer vaccine or a viral vaccine.

In another embodiment the invention includes a method of treating a patient with a VSIG1, ILDR1, LOC253012, AI216611, C1ORF32, FXYD3 positive malignancy, comprising administering to the patient an effective amount of any of the foregoing antibodies or fragments.

In another embodiment the invention includes the foregoing method further comprising co-administering a chemotherapeutic agent.

In another embodiment the invention includes the foregoing method, wherein said malignancy is selected from a group consisting of hematological malignancies such as acute lymphocytic leukemia, chronic lymphocytic leukemia, acute myelogenous leukemia, chronic myelogenous leukemia, multiple myeloma, Hodgkin's lymphoma, Non-Hodgkin's lymphoma, and soft or solid tumors such as cancer of breast, prostate, lung, ovary, colon, spleen, kidney, bladder, head and neck, uterus, testicles, stomach, cervix, liver, bone, skin, pancreas, brain and wherein the cancer is non-metastatic, invasive or metastatic.

In another embodiment the invention includes the foregoing method, wherein said malignancy is selected from the group consisting of lung cancer, ovarian cancer, colon cancer, and wherein the lung cancer, the ovarian cancer or the colon cancer is non-metastatic, invasive or metastatic.

In another embodiment the invention includes an assay for detecting the presence of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof in a biological sample comprising contacting the sample with an antibody of any one of the foregoing, and detecting the binding of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof in the sample.

In another embodiment the invention includes a method for detecting a disease, diagnosing a disease, monitoring disease progression or treatment efficacy or relapse of a disease, or selecting a therapy for a disease, comprising detecting expression of a AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof.

In another embodiment the invention includes the foregoing method wherein detecting expression AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof is performed in vivo or in vitro.

In another embodiment the invention includes the foregoing method, wherein the disease is selected from lung cancer, ovarian cancer, or colon cancer, and wherein the lung cancer, the ovarian cancer or the colon cancer is non-metastatic, invasive or metastatic.

In another embodiment the invention includes the foregoing method, wherein the disease is multiple sclerosis; psoriasis; rheumatoid arthritis; Systemic lupus erythematosus; ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis or chondrocalcinosis.

In another embodiment the invention includes a method of inhibiting growth of cells that express a polypeptide selected from AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof in a subject, comprising: administering to said subject any of the foregoing antibodies or fragments.

In another embodiment the invention includes a method of treating or preventing cancer comprising the administration of a therapeutically effective amount of an antibody or binding fragment that specifically binds the AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof that possesses at least 80% sequence identity therewith.

In another embodiment the invention includes the foregoing method, wherein the cancer is selected from a group consisting of hematological malignancies such as acute lymphocytic leukemia, chronic lymphocytic leukemia, acute myelogenous leukemia, chronic myelogenous leukemia, multiple myeloma, Hodgkin's lymphoma, Non-Hodgkin's lymphoma, and soft or solid tumors such as cancer of breast, prostate, lung, ovary, colon, spleen, kidney, bladder, head and neck, uterus, testicles, stomach, cervix, liver, bone, skin, pancreas, brain and wherein the cancer is non-metastatic, invasive or metastatic.

In another embodiment the invention includes the foregoing method, wherein the cancer is selected from the group consisting of lung cancer, ovarian cancer, or colon cancer, and wherein the lung cancer, the ovarian cancer or the colon cancer is non-metastatic, invasive or metastatic.

In another embodiment the invention includes the foregoing method wherein the antibody is a human, humanized or chimeric antibody or antigen binding fragment.

In another embodiment the invention includes the foregoing method wherein the antibody or fragment is attached directly or indirectly to an effector moiety.

In another embodiment the invention includes the foregoing method, wherein the effector is selected from a drug, toxin, radionuclide, fluorophore and an enzyme.

In another embodiment the invention includes a method for treating or preventing an immune disorder, such as autoimmune or transplant related disease, comprising administering to a patient a therapeutically effective amount of an antibody that specifically binds to AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof that possesses at least 80% sequence identity therewith.

In another embodiment the invention includes the foregoing method, wherein the antibody has an antigen-binding region specific for the extracellular domain of any one of said VSIG1, ILDR1, LOC253012, AI216611, C1ORF32, FXYD3 polypeptides.

In another embodiment the invention includes the foregoing method, wherein the antibody or fragment modulates the B7/co-stimulatory system in a manner that inhibits positive stimulation of T cell activity that created an autoimmune effect.

In another embodiment the invention includes the foregoing method, wherein the treatment is combined with a moiety useful for treating autoimmune or transplant rejection conditions.

In another embodiment the invention includes the foregoing method, wherein the moiety is a cytokine antibody, cytokine receptor antibody, drug, or another immunomodulatory agent.

In another embodiment the invention includes the foregoing method, wherein the autoimmune diseases are selected from a group consisting of multiple sclerosis; psoriasis; rheumatoid arthritis; systemic lupus erythematosus; ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another embodiment the invention includes the foregoing method wherein the immune disorder is transplant rejection or graft versus host disease.

In another embodiment the invention includes a method of using an antibody or antigen binding fragment that specifically binds AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof for in vivo imaging of tumors or inflammatory sites characterized by the differential expression of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or a fragment or variant thereof.

In another embodiment the invention includes the foregoing method which is used in assessing cancer prognosis or a treatment protocol.

In another embodiment the invention includes a method for screening for a disease in a subject, comprising detecting in the subject or in a sample obtained from said subject a polypeptide having a sequence at least 85% homologous to the amino acid sequence as set forth in any one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or with a polypeptide having a sequence comprising the extracellular domain of any one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74).

In another embodiment the invention includes the foregoing method wherein screening for a disease comprises detecting the presence or severity of the disease, disorder or condition, or prognosis of the subject, or treatment selection for said subject, or treatment monitoring of said subject.

In another embodiment the invention includes the foregoing method, wherein the disease is a cancer, selected from the group consisting of lung cancer, ovarian cancer, colon cancer, and wherein the lung cancer, the ovarian cancer and the colon cancer is non-metastatic, invasive or metastatic.

In another embodiment the invention includes the foregoing method wherein the disease is autoimmune disease and is selected from multiple sclerosis; psoriasis; rheumatoid arthritis; systemic lupus erythematosus; ulcerative colitis; Crohn's disease; immune disorders associated with graft transplantation rejection; benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another embodiment the invention includes the foregoing method, wherein the detection is conducted by immunoassay.

In another embodiment the invention includes the foregoing method, wherein the immunoassay utilizes an antibody which specifically interacts with the polypeptide having a sequence at least 85% homologous to the amino acid sequence as set forth in any one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), or with a polypeptide having a sequence comprising the extracellular domain of any one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), and R31375_P33 (SEQ ID NO:74).

In another embodiment the invention includes an antibody specific to AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), and R31375_P33 (SEQ ID NO:74), or a fragment or variant thereof that elicits apoptosis or lysis of cancer cells that express said protein.

In another embodiment the invention includes any of the foregoing antibodies or fragments, wherein said apoptosis or lysis activity involves CDC or ADCC activity of the antibody.

In another embodiment the invention includes any of the foregoing antibodies or fragments, wherein the cancer cells are selected from a group consisting of hematological malignancies such as acute lymphocytic leukemia, chronic lymphocytic leukemia, acute myelogenous leukemia, chronic myelogenous leukemia, multiple myeloma, Hodgkin's lymphoma, Non-Hodgkin's lymphoma, and soft or solid tumors such as cancer of breast, prostate, lung, ovary, colon, spleen, kidney, bladder, head and neck, uterus, testicles, stomach, cervix, liver, bone, skin, pancreas, and brain.

In another embodiment the invention includes any of the foregoing antibodies or fragments, wherein the cancer cells are lung, ovarian or colon cancer cells.

In another embodiment the invention relates to any of the foregoing isolated soluble VSIG1, ILDR1, LOC253012, AI216611, C1ORF32, FXYD3 ectodomain polypeptides, wherein said polypeptide or a fragment or variant thereof is used as an anti-cancer vaccine for cancer immunotherapy.

In another embodiment the invention relates to any an isolated polypeptide comprising an amino acid sequence having at least 80%, 85%, 90%, 95, 96, 97, 98 or 99%, 100% homologous to the sequence as that set forth in any one of SEQ. ID NOs: 284-295, or a fragment thereof.

In another embodiment the invention relates to any an isolated polynucleotide, comprising an amplicon having a nucleic acid sequence selected from the group consisting of 187, 190, 193, 196, 199, 202, 205, 208, 211, 214, 217, 220, 223, 226, 229, 232, 235, 238, 241, 244, 247, 250, 253, or polynucleotides homologous thereto.

In another embodiment the invention relates to any a primer pair, comprising a pair of isolated oligonucleotides capable of amplifying the above mentioned amplicon.

The primer pair, comprising a pair of isolated oligonucleotides having a sequence selected from the group consisting of SEQ. ID NOs: 185-186, 188-189, 191-192, 194-195, 197-198, 200-201, 203-204, 206-207, 209-210, 212-213, 215-216, 218-219, 221-222, 224-225, 227-228, 230-231, 233-234, 236-237, 239-240, 242-243, 245-246, 248-249, and 251-252.

A method for screening for a disease, disorder or condition in a subject, comprising detecting in the subject or in a sample obtained from said subject a polynucleotide having a sequence at least 85% homologous to the nucleic acid sequence as set forth in any one of SEQ ID NOs:1-10, 17-20, 25-34, 41-42, 45-46, 51-69, 187, 190, 193, 196, 199, 202, 205, 208, 211, 214, 217, 220, 223, 226, 229, 232, 235, 238, 241, 244, 247, 250, and 253.

The method as above, wherein screening for a disease comprises detecting the presence or severity of the disease, disorder or condition, or prognosis of the subject, or treatment selection for said subject, or treatment monitoring.

The method as above, wherein the disease is a cancer, selected from the group consisting of lung cancer, colon cancer and ovarian cancer, and wherein the lung cancer, colon cancer and ovarian cancer is non-metastatic, invasive or metastatic.

The method as above, wherein the disease is autoimmune disease.

The method as above, wherein the detection is performed using an oligonucleotide pair capable of hybridizing to at least a portion of a nucleic acid sequence at least 85% homologous to the nucleic acid sequence set forth in SEQ. ID NO: 1-10, 17-20, 25-34, 41-42, 45-46, 51-69, 187, 190, 193, 196, 199, 202, 205, 208, 211, 214, 217, 220, 223, 226, 229, 232, 235, 238, 241, 244, 247, 250, and 253.

The method as above wherein the detection is performed using an oligonucleotide pair as set forth in any one of SEQ. ID NOs: 185-186, 188-189, 191-192, 194-195, 197-198, 200-201, 203-204, 206-207, 209-210, 212-213, 215-216, 218-219, 221-222, 224-225, 227-228, 230-231, 233-234, 236-237, 239-240, 242-243, 245-246, 248-249, and 251-252.

BRIEF DESCRIPTION OF THE FIGURES

FIGS. 3A-3E show alignment comparison of the AI581519_P4 (FIG. 3A), AI581519_P5 (FIG. 3B), AI581519_P7 (FIG. 3C), AI581519_P9 (FIG. 3D), and AI581519_P10 (FIG. 3E) proteins to the known VSIG1 proteins NP_872413 (SEQ ID NO: 11) and Q86XK7_HUMAN.

FIG. 6A shows expression of each sample relative to median of the ovary samples; FIG. 6B shows expression of each sample relative to median of the lung samples.

FIG. 12A shows expression of each sample relative to median of the lung samples; FIG. 12B shows expression of each sample relative to median of the ovary samples.

FIGS. 16A-16C show alignment comparison of the AA424839_P3 (FIG. 16A), AA424839_P7 (FIG. 16B), and AA424839_1_P11 (FIG. 16C), proteins to the known ILDR1 proteins Q86SU0_HUMAN and NP_787120 (SEQ ID NO: 21).

FIGS. 30A-30H show alignment comparison of the H68654_1_P7 (FIG. 30A and FIG. 30B), H68654_1_P12 (FIGS. 3C and 30D), H68654_1_P13 (FIG. 3E and FIG. 30F), and H68654_1_P14 (FIGS. 30G and 30H) proteins to the known LOC253012 proteins NP_937794 and Q6UXI0_HUMAN (SEQ ID NO: 36).

FIGS. 38A-38B show alignment comparison of the H19011_1_P8 (FIG. 38A) and H19011_1_P9 (FIG. 38B) proteins to the known C1ORF32 proteins Q71H61_HUMAN and NP_955383 (SEQ ID NO: 47).

FIG. 41A shows expression of each sample relative to median of the colon samples; FIG. 41B shows expression of each sample relative to median of the lung samples.

FIG. 45A shows expression of each sample relative to median of the colon samples; FIG. 45B shows expression of each sample relative to median of the lung samples.

FIGS. 49A-49E show alignment comparison of the R31375_P14 (FIG. 49A), R31375_P31 (FIGS. 49B and 49C) and R31375_P33 (FIGS. 49D and 49E), proteins to the known FXYD3 proteins NP_068710 (SEQ ID NO: 71), FXYD3_HUMAN (SEQ ID NO: 70), NP_005962 and Q6IB59_HUMAN (SEQ ID NO: 70).

FIG. 56A-56J presents the nucleotide sequences of the recombinant full length_EGFP ORFs: gene specific sequence correspond to the candidate's full length sequence is marked in bold, EGFP sequence is unbold Italic and known SNPs/silence mutation are underlined. FIG. 56A presents the full length_EGFP ORF nucleic acid sequence of FXYD3_T0_P0_EGFP DNA (996bp) (SEQ ID NO:77); FIG. 56B presents the full length_EGFP ORF nucleic acid sequence of FXYD3_T25_P14_EGFP DNA (1083bp) (SEQ ID NO:78); FIG. 56C presents the full length_EGFP ORF nucleic acid sequence of AI216611_T0_P0_EGFP DNA (1371bp) (SEQ ID NO:79); FIG. 56D presents the full length_EGFP ORF nucleic acid sequence of AI216611_T1_P1_EGFP DNA (1332bp) (SEQ ID NO:80); FIG. 56E presents the full length_EGFP ORF nucleic acid sequence of C1ORF32_T8_P8 EGFP DNA (1533bp) (SEQ ID NO:81); FIG. 56F presents the full length_EGFP ORF nucleic acid sequence of LOC253012_T4_P5_EGFP DNA (2085bp) (SEQ ID NO:82); FIG. 56G presents the full length_EGFP ORF nucleic acid sequence of ILDR1_T0_P3 EGFP DNA (2373bp) (SEQ ID NO:83); FIG. 56H presents the full length_EGFP ORF nucleic acid sequence of ILDR1_T2_P5_EGFP DNA (2241bp) (SEQ ID NO:84); FIG. 56I presents the full length_EGFP ORF nucleic acid sequence of VSIG1_T6_P5_EGFP DNA (2082bp) (SEQ ID NO:85); FIG. 56J presents the full length_EGFP ORF nucleic acid sequence of VSIG1_T5_P4 EGFP DNA (2004bp) (SEQ ID NO:86).

FIG. 57A-57J presents the sequences of the full length_EGFP fusion proteins of invention. Candidate's specific sequence corresponding to the full length sequence of the protein is marked in bold, EGFP sequence is unbold Italic and amino acids modified due to known SNPs are underlined. FIG. 57A presents the full length_EGFP ORF amino acid sequence of FXYD3_P0_EGFP protein (331aa) (SEQ ID NO:87); FIG. 57B presents the full length_EGFP ORF amino acid sequence of FXYD3_P14_EGFP protein (360aa) (SEQ ID NO:88); FIG. 57C presents the full length_EGFP ORF amino acid sequence of AI216611_P0_EGFP protein (456aa) (SEQ ID NO:89); FIG. 57D presents the full length_EGFP ORF amino acid sequence of AI216611_P1_EGFP protein (443aa) (SEQ ID NO:90); FIG. 57E presents the full length_EGFP ORF amino acid sequence of C1ORF32_P8 EGFP protein (510aa) (SEQ ID NO:91); FIG. 57F presents the full length_EGFP ORF amino acid sequence of LOC253012_P5_EGFP protein (694aa) (SEQ ID NO:92); FIG. 57G presents the full length_EGFP ORF amino acid sequence of ILDR1_P3 EGFP protein (790aa) (SEQ ID NO:93); FIG. 57H presents the full length_EGFP ORF amino acid sequence of ILDR1_P5_EGFP protein (746aa) (SEQ ID NO:94); FIG. 57I presents the full length_EGFP ORF amino acid sequence of VSIG1_P5_EGFP protein (693aa) (SEQ ID NO:95); FIG. 57J presents the full length- _EGFP ORF amino acid sequence of VSIG1_P4_EGFP protein (667aa) (SEQ ID NO:96).

FIG. 58A shows cellular localization of AI216611-EGFP_T0_P0 and AI216611-EGFP_T1_P1 proteins FIG. 58B shows cellular localization of FXYD3-EGFP_T0_P0 and FXYD3-EGFP_T25_P14 proteins. FIG. 58C shows cellular localization of C1ORF32-EGFP_T8_P8 protein. FIG. 58D shows cellular localization of LOC253012-EGFP_T4_P5 protein. FIG. 58E shows cellular localization of VSIG1-EGFP_T6_P5 and VSIG1-EGFP_T5_P4 proteins. FIG. 58F shows cellular localization of ILDR1-EGFP_T0_P3 and ILDR1-EGFP_T2_P5 proteins. All the images were obtained using the 40× objective of the confocal microscope.

FIGS. 59A-59F present the nucleotide sequences of the extracellular domains of the candidate proteins of the invention, fused to mouse Fc: ECD_mFc ORFs. Candidate protein's specific sequence corresponding to the ECD sequence is marked in bold, TEV cleavage site sequence is underlined, mFc sequence is unbold Italic and IL6sp sequence is bold Italic. FIG. 59A shows the FXYD3_T25_P14 ECD_mFc DNA sequence (924bp) (SEQ ID NO:97); FIG. 59B shows the AI216611_T0_P0 ECD_mFc DNA sequence (1170bp) (SEQ ID NO:98), FIG. 59C shows the C1ORF32_T8_P8_ECD_mFc DNA sequence (1287bp) (SEQ ID NO:99); FIG. 59D shows the LOC253012_T4_P5_ECD_mFc DNA sequence (1740bp) (SEQ ID NO:100), FIG. 59E shows the ILDR1_T0_P3_ECD_mFc DNA sequence (1167bp) (SEQ ID NO:101), and FIG. 59F shows the VSIG1_T6_P5_ECD_mFc DNA sequence (1641bp) (SEQ ID NO:102).

FIGS. 60A-60F present the amino acid sequence of the ECD_mFc fusion proteins. Candidate protein's specific sequence corresponding to the ECD sequence is marked in bold, TEV cleavage site sequence is underlined, mFc sequence is unbold Italic and IL6sp sequence is bold Italic. FIG. 60A shows the FXYD3_T25_P14_ECD_mFc amino acid sequence (307aa) (SEQ ID NO:103); FIG. 60B shows the AI216611_T0_P0_ECD_mFc amino acid sequence (389aa) (SEQ ID NO:104), FIG. 60C shows the C1ORF32_T8_P8_ECD_mFc amino acid sequence (428aa) (SEQ ID NO:105); FIG. 60D shows the LOC253012_T4_P5_ECD_mFc amino acid sequence (579aa) (SEQ ID NO:106), FIG. 60E shows the ILDR1_T0_P3_ECD_mFc amino acid sequence (388aa) (SEQ ID NO:107), and FIG. 60F shows the VSIG1_T6_P5_ECD_mFc amino acid sequence (546aa) (SEQ ID NO:108).

FIG. 62A shows the binding results for Fc-fused VSIG1 ECD; FIG. 62B shows the binding results for Fc-fused LOC253012; FIG. 62C shows the binding results for Fc-fused C1ORF32 ECD; and FIG. 62D shows the binding results for Fc-fused AI216611 ECD. FIG. 62E shows the binding results for Fc-fused FXYD3 ECD.

FIG. 64A shows the levels of BrdU incorporation. FIG. 64B shows the levels of IL-2 secretion.

FIGS. 65A-1, 65A-2 and 65B illustrate the binding of the Fc-fused ECDs of the VSIG1, ILDR1, LOC253012, AI216611, FXYD3 or C1ORF32 to lymphocytes.

FIGS. 66A-1, 66A-2 and 66B illustrate the binding of the Fc-fused ECDs of the ILDR1, C1ORF32 and AI216611 to CD4+ T cells.

DETAILED DESCRIPTION OF THE INVENTION

Figure 1:
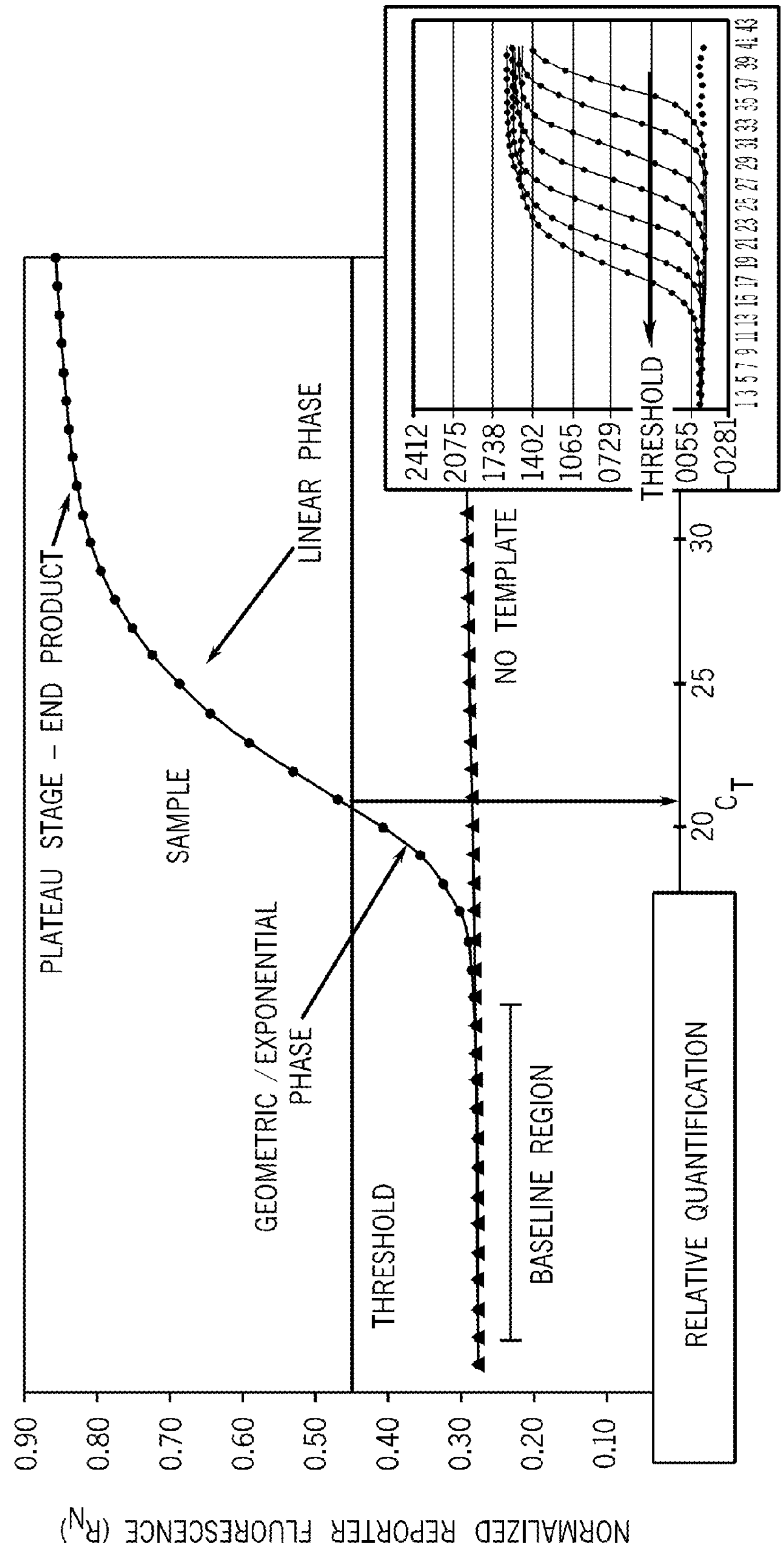
FIG. 1 shows a schematic summary of quantitative real-time PCR analysis.

The present invention relates to any one of the antigens referred to as VSIG1, ILDR1, LOC253012, AI216611, C1ORF32, FXYD3, and its corresponding nucleic acid sequence, and portions and variants thereof and conjugates containing and the use thereof as a therapeutic or diagnostic target. In particular the invention uses this antigen and discrete portions thereof as a drug target for therapeutic small molecules, peptides, antibodies, antisense RNAs, siRNAs, ribozymes, and the like. More particularly the invention relates to diagnostic and therapeutic polyclonal and monoclonal antibodies and fragments thereof that bind VSIG1, ILDR1, LOC253012, AI216611, C1ORF32, FXYD3 and portions and variants thereof, especially those that target the ectodomain or portions or variants thereof particularly human or chimeric monoclonal antibodies, that bind specifically to the antigen AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73), R31375_P33 (SEQ ID NO:74), and variants thereof including those that promote or inhibit activities elicited by VSIG1, ILDR1, LOC253012, AI216611, C1ORF32, FXYD3, including those relating to modulation of immune costimulation, e.g. B7 related costimulation.

In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical and diagnostic compositions containing the antibodies, immunoconjugates or bispecific molecules of the invention.

The invention also relates to in vitro and in vivo methods of using the antibodies and fragments, to detect VSIG1, ILDR1, LOC253012, AI216611, C1ORF32, FXYD3, as well as to treat diseases associated with expression of VSIG1, ILDR1, LOC253012, AI216611, C1ORF32, FXYD3, such as malignancies that differentially express VSIG1. The invention further relates to methods of using the antibodies and fragments, specific for VSIG1, ILDR1, LOC253012, AI216611, C1ORF32, FXYD3 to treat autoimmune disorders and transplant and graft versus host disease. Accordingly, the invention also provides methods of using the anti-VSIG1, anti-ILDR1, anti-LOC253012, anti-AI216611, anti-C1ORF32, anti-FXYD3 antibodies of the invention and other drugs that modulate VSIG1, ILDR1, LOC253012, AI216611, C1ORF32, FXYD3 to treat malignancies for example, in the treatment of lung cancer, ovarian cancer, colon cancer, non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, spleen, kidney, bladder, head and neck, uterus, testicles, stomach, cervix, liver, bone, skin, pancreas, brain and wherein the cancer may be non-metastatic, invasive or metastatic. The invention further provides methods of using the anti-VSIG1, anti-ILDR1, anti-LOC253012, anti-AI216611, anti-C1ORF32, anti-FXYD3 antibodies of the invention and other drugs that modulate VSIG1, ILDR1, LOC253012, AI216611, C1ORF32, FXYD3 to treat non-malignant disorders such as immune disorders including but not limited to autoimmune diseases, transplant rejection and graft versus host disease. Preferably these antibodies will possess ADCC or CDC activity against target cells such as cancer cells.

Also, the invention relates to the VSIG1, ILDR1, LOC253012, AI216611, C1ORF32, FXYD3 antigen and portions thereof including soluble polypeptide conjugates containing the ectodomain of VSIG1, ILDR1, LOC253012, AI216611, C1ORF32, FXYD3 and/or the corresponding DNAs or vectors or cells expressing same for use in immunotherapy. Further the invention provides vectors, cells containing and use thereof for the expression of the VSIG1, ILDR1, LOC253012, AI216611, C1ORF32, FXYD3 antigen, as well as discrete portions and variants thereof. Also, the invention provides non-antibody based VSIG1, ILDR1, LOC253012, AI216611, C1ORF32, FXYD3 modulatory agents such as peptides, antisense RNAs, siRNAs, carbohydrates, and other small molecules that specifically bind and/or modulate a VSIG1, ILDR1, LOC253012, AI216611, C1ORF32, FXYD3 related activity.

In order that the present invention may be more readily understood, certain terms are first defined. Additional definitions are set forth throughout the detailed description.

The terms VSIG1 refers to the protein encoded by any one of the AI581519_T0 (SEQ ID NO:1), AI581519_T1 (SEQ ID NO:2), AI581519_T2 (SEQ ID NO:3), AI581519_T3 (SEQ ID NO:4), AI581519_T4 (SEQ ID NO:5), AI581519_T5 (SEQ ID NO:6), AI581519_T6 (SEQ ID NO:7), AI581519_T8 (SEQ ID NO:8), AI581519_T10 (SEQ ID NO:9), AI581519_T11 (SEQ ID NO:10) transcripts reported herein, particularly to proteins as set forth in any one of AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), and variants thereof that are differentially expressed e.g., in cancers such as lung cancer and ovarian cancer, wherein the cancer may be non-metastatic, invasive or metastatic as well as non-malignant disorders such as immune disorders including but not limited to autoimmune diseases, transplant rejection and graft versus host disease.

The term ILDR1 refers to the to the protein encoded by any one of the AA424839_T0 (SEQ ID NO:17), AA424839_T2 (SEQ ID NO:18), AA424839_T4 (SEQ ID NO:19), AA424839_1_T7 (SEQ ID NO:20) transcripts reported herein, particularly to proteins as set forth in any one of AA424839_P3 (SEQ ID NO:22), AA424839_P5 (SEQ ID NO:21), AA424839_P7 (SEQ ID NO:23), AA424839_1_P11 (SEQ ID NO:24), and variants thereof that are differentially expressed e.g., in cancer such as colon cancer and ovarian cancer wherein the cancer may be non-metastatic, invasive or metastatic as well as non-malignant disorders such as immune disorders including but not limited to autoimmune diseases, transplant rejection and graft versus host disease.

The term LOC253012 refers to the protein encoded by any one of the H68654_1_T0 (SEQ ID NO:25), H68654_1_T4 (SEQ ID NO:26), H68654_1_T5 (SEQ ID NO:27), H68654_1_T8 (SEQ ID NO:28), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), H68654_1_T20 (SEQ ID NO:34) transcripts reported herein, particularly to proteins as set forth in any one of H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), and variants thereof that are differentially expressed e.g., in cancers such as lung cancer, especially small cell lung carcinoma, wherein the cancer may be non-metastatic, invasive or metastatic as well as non-malignant disorders such as immune disorders including but not limited to autoimmune diseases, transplant rejection and graft versus host disease.

The term AI216611 refers to the protein encoded by any one of the AI216611_T0 (SEQ ID NO:41), AI216611_T1 (SEQ ID NO:42) transcripts reported herein, particularly to proteins as set forth in any one of AI216611_P0 (SEQ ID NO:43), AI216611_P1 (SEQ ID NO:44), and variants thereof that are differentially expressed e.g., in cancers such as non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, and brain and wherein the cancer may be non-metastatic, invasive or metastatic as well as non-malignant disorders such as immune disorders including but not limited to autoimmune diseases, transplant rejection and graft versus host disease.

The terms C1ORF32 refers to the protein encoded by any one of the H19011_1_T8 (SEQ ID NO:45), H19011_1_T9 (SEQ ID NO:46) transcripts reported herein, particularly to proteins as set forth in any one of H19011_1_P8 (SEQ ID NO:48), H19011_1_P9 (SEQ ID NO:50), and variants thereof that are differentially expressed e.g., in cancers such as lung cancer, particularly lung small cell carcinoma, wherein the cancer may be non-metastatic, invasive or metastatic as well as non-malignant disorders such as immune disorders including but not limited to autoimmune diseases, transplant rejection and graft versus host disease.

The term FXYD3 refers to the protein encoded by any one of the R31375 T0 (SEQ ID NO:51); R31375_T1 (SEQ ID NO:52); R31375_T10 (SEQ ID NO:61); R31375_T11 (SEQ ID NO:62); R31375_T12 (SEQ ID NO:63); R31375_T13 (SEQ ID NO:64); R31375_T2 (SEQ ID NO:53); R31375_T3 (SEQ ID NO:54); R31375_T4 (SEQ ID NO:55); R31375_T5 (SEQ ID NO:56); R31375_T6 (SEQ ID NO:57); R31375_T7 (SEQ ID NO:58); R31375_T8 (SEQ ID NO:59); R31375_T9 (SEQ ID NO:60): R31375_T19 (SEQ ID NO:65); R31375_T25 (SEQ ID NO:66); R31375_T26 (SEQ ID NO:67); R31375_T29 (SEQ ID NO:68); R31375_T39 (SEQ ID NO:69) transcripts reported herein, particularly to proteins as set forth in any one of R31375_P0 (SEQ ID NO:70), R31375_P14 (SEQ ID NO:72), R31375_P31 (SEQ ID NO:73), R31375_P31 (SEQ ID NO:73), and variants thereof that are differentially expressed e.g., in cancers such as ovarian cancer as well as other non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic.

Preferably such VSIG1, ILDR1, LOC253012, AI216611, C1ORF32, FXYD3 variants will possess at least 80% sequence identity therewith, more preferably at least 90% sequence identity therewith and even more preferably at least 95% sequence identity therewith.

Any one of the VSIG1, ILDR1, LOC253012, AI216611, C1ORF32 proteins based on its domain structure is predicted to be an immune costimulatory protein, e.g., a B7 protein family member that is involved in B7 immune co-stimulation including for example T cell responses elicited against cancer cells and that elicit effects on immunity such as triggering of autoimmune effects.

The term the "soluble ectodomain (ECD)" or "ectodomain" of VSIG1 refers to the polypeptide sequences below or the corresponding nucleic acid sequences (which does not comprise the signal peptide and the TM of VSIG1 protein):

```
>AI581519_P3 (SEQ IDS NO: 11) residues 23 to 234
                                        (SEQ ID NO: 138)
QVTIPDGFVNVTVGSNVTLICIYTTTVASREQLSIQWSFFHKKEMEPISI

YFSQGGQAVAIGQFKDRITGSNDPGNASITISHMQPADSGIYICDVNNPP

DFLGQNQGILNVSVLVKPSKPLCSVQGRPETGHTISLSCLSALGTPSPVY

YWHKLEGRDIVPVKENFNPTTGILVIGNLTNFEQGYYQCTAINRLGNSSC

EIDLTSSHPEVG

>AI581519_P4 (SEQ IDS NO: 12) residues 23 to 270
                                        (SEQ ID NO: 139)
QVTIPDGFVNVTVGSNVTLICIYTTTVASREQLSIQWSFFHKKEMEPISH

SSCLSTEGMEEKAVGQCLKMTHVRDARGRCSWTSEIYFSQGGQAVAIGQF

KDRITGSNDPGNASITISHMQPADSGIYICDVNNPPDFLGQNQGILNVSV

LVKPSKPLCSVQGRPETGHTISLSCLSALGTPSPVYYWHKLEGRDIVPVK

ENFNPTTGILVIGNLTNFEQGYYQCTAINRLGNSSCEIDLTSSHPEVG

>AI581519_P5 (SEQ IDS NO: 13) residues 23 to 296
                                        (SEQ ID NO: 140)
QVTIPDGFVNVTVGSNVTLICIYTTTVASREQLSIQWSFFHKKEMEPISH

SSCLSTEGMEEKAVGQCLKMTHVRDARGRCSWTSESPWEEGKWPDVEAVK

GTLDGQQAELQIYFSQGGQAVAIGQFKDRITGSNDPGNASITISHMQPAD

SGIYICDVNNPPDFLGQNQGILNVSVLVKPSKPLCSVQGRPETGHTISLS

CLSALGTPSPVYYWHKLEGRDIVPVKENFNPTTGILVIGNLTNFEQGYYQ

CTAINRLGNSSCEIDLTSSHPEVG

>AI581519_P7 (SEQ IDS NO: 14) residues 23 To 193
                                        (SEQ ID NO: 141)
QVTIPDGFVNVTVGSNVTLICIYTTTVASREQLSIQWSFFHKKEMEPISI

YFSQGGQAVAIGQFKDRITGSNDPVKPSKPLCSVQGRPETGHTISLSCLS

ALGTPSPVYYWHKLEGRDIVPVKENFNPTTGILVIGNLTNFEQGYYQCTA

INRLGNSSCEIDLTSSHPEVG

>AI581519_P9 (SEQ IDS NO: 15) residues 23 to 203
                                        (SEQ ID NO: 142)
QVTIPDGFVNVTVGSNVTLICIYTTTVASREQLSIQWSFFHKKEMEPISI

YFSQGGQAVAIGQFKDRITGSNDPGNASITISHMQPADSGIYICDVNNPP

DFLGQNQGILNVSVLVKPSKPLCSVQGRPETGHTISLSCLSALGTPSPVY

YWHKLEGRDIVPVKENFTNHRDFGHWKSDKF

>AI581519_P10 (SEQ IDS NO: 16) residues 23 To 231
                                        (SEQ ID NO: 143)
QVTIPDGFVNVTVGSNVTLICIYTTTVASREQLSIQWSFFHKKEMEPISI

YFSQGGQAVAIGQFKDRITGSNDPGNASITISHMQPADSGIYICDVNNPP
```

-continued

DFLGQNQGILNVSVLVKPSKPLCSVQGRPETGHTISLSCLSALGTPSPVY

YWHKLEGRDIVPVKENFNPTTGILVIGNLTNFEQGYYQCTAINRLGNSSC

EIDLTSSRQ,

>AI581519_P5 (SEQ IDS NO: 13) residues 26 To 293 (SEQ ID NO: 302)

IPDGFVNVTVGSNVTLICIYTTTVASREQLSIQWSFFHKKEMEPISHSSC

LSTEGMEEKAVSQCLKMTHARDARGRCSVVTSESPWEEGKWPDVEAVKGT

LDGQQAELQIYFSQGGQAVAIGQFKDRITGSNDPGNASITISHMQPADSG

IYICDVNNPPDFLGQNQGILNVSVLVKPSKPLCSVQGRPETGHTISLSCL

SALGTPSPVYYWHKLEGRDIVPVKENFNPTTGILVIGNLTNFEQGYYQCT

AINRLGNSSCEIDLTSSHP, and variants thereof possessing at least 80% sequence identity, more preferably at least 90% sequence identity therewith and even more preferably at least 95, 96, 97, 98 or 99% sequence identity therewith.

The term the "soluble ectodomain (ECD)" or "ectodomain" of ILDR1 refers to the polypeptide sequences below or the corresponding nucleic acid sequences (which does not comprise the signal peptide and the TM of ILDR1 protein:

residues 24-105 of AA424839_1_P11 (SEQ ID NO: 24): SEQ ID NO: 296

ALSLGQDPSNDCNDNQREVRIVAQRRGQNEPVLGVDYRQRKITIQNRA

DLVINEVMWWDHGVYYCTIEAPGDTSGDPDKEVK (SEQ ID NO:

296);

residues 24-162 of AA424839_P3 (SEQ ID NO: 22) and AA424839_P5 (SEQ ID NO: 21): SEQ ID NO: 75

LLVTVQHTERYVTLFASIILKCDYTTSAQLQDVVVTWRFKSFCKDPIFDY

YSASYQAALSLGQDPSNDCNDNQREVRIVAQRRGQNEPVLGVDYRQRKIT

IQNRADLVINEVMVVVVDHGVYYCTIEAPGDTSGDPDKEVK:

residues 24-457 of AA424839_P7 (SEQ ID NO: 23): SEQ ID NO: 76

LLVTVQHTERYVTLFASIILKCDYTTSAQLQDVVVTWRFKSFCKDPIFDY

YSASYQAALSLGQDPSNDCNDNQREVRIVAQRRGQNEPVLGVDYRQRKIT

IQNPLARHRYMKQAQALGPQMMGKPLYWGADRSSQVSSYPMHPLLQRDLS

LPSSLPQMPMTQTTNQPPIANGVLEYLEKELRNLNLAQPLPPDLKGRFGH

PCSMLSSLGSEVVERRIIHLPPLIRDLSSSRRTSDSLHQQWLTPIPSRPW

DLREGRSHHHYPDFHQELQDRGPKSWALERRELDPSWSGRHRSSRLNGSP

IHWSDRDSLSDVPSSSEARWRPSHPPFRSRCQERPRRPSPRESTQRHGRR

RRHRSYSPPLPSGLSSWSSEEDKERQPQSWRAHRRGSHSPHWPEEKPPSY

RSLDITPGKNSRKKGSVERRSEKDSSHSGRSVVI;

residues 50-160 of AA424839_P3 (SEQ ID NO: 36): SEQ ID NO: 301

AQLQDVVVTWRFKSFCKDPIFDYYSASYQAALSLGQDPSNDCNDNQRE

VRIVAQRRGQNEPVLGVDYRQRKITIQNRADLVINEVMWWDHGVYYCT

IEAPGDTSGDPDKE, and variants thereof possessing at least 80% sequence identity, more preferably at least 90% sequence identity therewith and even more preferably at least 95, 96, 97, 98 or 99% sequence identity therewith.

The term the "soluble ectodomain (ECD)" or "ectodomain" of LOC253012 refers to the polypeptide sequences below or the corresponding nucleic acid sequences (which does not comprise the signal peptide and the TM of LOC253012 protein):

H68654_1_P2 (SEQ ID NO: 35) residues 38-349: (SEQ ID NO: 144)

SHTVHGVRGQALYLPVHYGFHTPASDIQIIVVLFERPHTMPKYLLGSVNK

SVVPDLEYQHKFTMMPPNASLLINPLQFPDEGNYIVKVNIQGNGTLSASQ

KIQVTVDDPVTKPVVQIHPPSGAVEYVGNMTLTCHVEGGTRLAYQWLKNG

RPVHTSSTYSFSPQNNTLHIAPVTKEDIGNYSCLVRNPVSEMESDIIMPI

IYYGPYGLQVNSDKGLKVGEVFTVDLGEAILFDCSADSHPPNTYSWIRRT

DNTTYIIKHGPRLEVASEKVAQKTMDYVCCAYNNITGRQDETHFTVIITS

VGLEKLAQKGKSL;

H68654_1_P5 (SEQ ID NO: 36), H68654_1_P7 (SEQ ID NO: 37), H68654_1_P12 (SEQ ID NO: 38), H68654_1_P13 (SEQ ID NO: 39), H68654_1_P14 (SEQ ID NO: 40) residues 19-337: (SEQ ID NO: 145)

GLKVTVPSHTVHGVRGQALYLPVHYGFHTPASDIQIIWLFERPHTMPKYL

LGSVNKSVVPDLEYQHKFTMMPPNASLLINPLQFPDEGNYIVKVNIQGNG

TLSASQKIQVTVDDPVTKPVVQIHPPSGAVEYVGNMTLTCHVEGGTRLAY

QWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTY

SWIRRTDNTTYIIKHGPRLEVASEKVAQKTMDYVCCAYNNITGRQDETHF

TVIITSVGLEKLAQKGKSL,

H68654_1_P5 (SEQ ID NO: 36) residues 1-335 (SEQ ID NO: 300):

MWLKVFTTFLSFATGACSGLKVTVPSHTVHGVRGQALYLPVHYGFHTPAS

DIQIIWLFERPHTMPKYLLGSVNKSVVPDLEYQHKFTMMPPNASLLINPL

QFPDEGNYIVKVNIQGNGTLSASQKIQVTVDDPVTKPVVQIHPPSGAVEY

VGNMTLTCHVEGGTRLAYQWLKNGRPVHTSSTYSFSPQNNTLHIAPVTKE

DIGNYSCLVRNPVSEMESDIIMPIIYYGPYGLQVNSDKGLKVGEVFTVDL

GEAILFDCSADSHPPNTYSWIRRTDNTTYIIKHGPRLEVASEKVAQKTMD

YVCCAYNNITGRQDETHFTVIITSVGLEKLAQKGK, and variants thereof possessing at least 80% sequence identity, more preferably at least 90% sequence identity therewith and even more preferably at least 95, 96, 97, 98 or 99% sequence identity therewith.

The term the "soluble ectodomain (ECD)" or "ectodomain" of AI216611 refers to the polypeptide sequences below or the corresponding nucleic acid sequences (which does not comprise the signal peptide and the TM of AI216611 protein):

>AI216611_PO (SEQ ID NO: 43) From 29 to 147 (SEQ ID NO: 146)

LQSQGVSLYIPQATINATVKEDILLSVEYSCHGVPTIEWTYSSNWGTQKI

VEWKPGTQANISQSHKDRVCTFDNGSIQLFSVGVRDSGYYVITVTERLGS

SQFGTIVLHVSEILYEDLH,

-continued

```
>AI216611_P0 (SEQ ID NO: 43) From 1 to 145
                                         (SEQ ID NO: 298)
MRPLPSGRRKTRGISLGLFALCLAAARCLQSQGVSLYIPQATINATVKED

ILLSVEYSCHGVPTIEWTYSSNWGTQKIVEWKPGTQANISQSHKDRVCTF

DNGSIQLFSVGVRDSGYYVITVTERLGSSQFGTIVLHVSEILYED,
```

and variants thereof possessing at least 80% sequence identity, more preferably at least 90% sequence identity therewith and even more preferably at least 95, 96, 97, 98 or 99% sequence identity therewith.

The term the "soluble ectodomain (ECD)" or "ectodomain" of C1ORF32 refers to the polypeptide sequences below or the corresponding nucleic acid sequences (which does not comprise the signal peptide and the TM of C1ORF32 protein):

```
>H19011_1_P8 (SEQ ID NO: 48) residues 21 to 186
                                         (SEQ ID NO: 147)
LQVTVPDKKKVAMLFQPTVLRCHFSTSSHQPAVVQWKFKSYCQDRMGESL

GMSSTRAQSLSKRNLEWDPYLDCLDSRRTVRVVASKQGSTVTLGDFYRGR

EITIVHDADLQIGKLMWGDSGLYYCIITTPDDLEGKNEGSLGLLVLGRTG

LLADLLPSFAVEIMPE

>H19011_1_P9 (SEQ ID NO: 50) residues 21 to 169
                                         (SEQ ID NO: 148)
LQVTVPDKKKVAMLFQPTVLRCHFSTSSHQPAVVQWKFKSYCQDRMGESL

GMSSTRAQSLSKRNLEWDPYLDCLDSRRTVRVVASKQGSTVTLGDFYRGR

EITIVHDADLQIGKLMWGDSGLYYCIITTPDDLEGKNEGSLGLLVLEWV,

>H19011_1_P8 (SEQ ID NO: 48) residues 1 to 184
                                         (SEQ ID NO: 299)
MDRVLLRWISLFWLTAMVEGLQVTVPDKKKVAMLFQPTVLRCHFSTSSHQ

PAVVQWKFKSYCQDRMGESLGMSSTRAQSLSKRNLEWDPYLDCLDSRRTV

RVVASKQGSTVTLGDFYRGREITIVHDADLQIGKLMWGDSGLYYCIITTP

DDLEGKNEDSVELLVLGRTGLLADLLPSFAVEIM,
```

and variants thereof possessing at least 80% sequence identity, more preferably at least 90% sequence identity therewith and even more preferably at least 95, 96, 97, 98 or 99% sequence identity therewith.

The term the "soluble ectodomain (ECD)" or "ectodomain" of FXYD3 refers to the polypeptide sequences below or the corresponding nucleic acid sequences (which does not comprise the signal peptide and the TM of FXYD3 protein):

```
>R31375_P0 (SEQ ID NO: 70); R31375_P31 (SEQ ID NO:
73) From 21 to 36
                                         (SEQ ID NO: 149)
NDLEDKNSPFYYDWHS

>R31375_P14 (SEQ ID NO: 72) From 21 to 65
                                         (SEQ ID NO: 150)
NDLEDKNSPFYYGAPYIFVKRMGGQMKRTQAGTEVPSTFLLDWHS

>R31375_P33 (SEQ ID NO: 74) From 21 to 25
                                         (SEQ ID NO: 151)
NDLED,

>R31375_P14 (SEQ ID NO: 72) From 1 to 63
                                         (SEQ ID NO: 297)
MQKVTLGLLVFLAGFPVLDANDLEDKNSPFYYGAPYIFVKRMGGQMKR

TQAGTEVPSTFLLDW,
```

and variants thereof possessing at least 80% sequence identity, more preferably at least 90% sequence identity therewith and even more preferably at least 95, 96, 97, 98 or 99% sequence identity therewith.

The term "immune response" refers to the action of, for example, lymphocytes, antigen presenting cells, phagocytic cells, granulocytes, and soluble macromolecules produced by the above cells or cells produced by the liver or spleen (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal, transduction pathway" refers to the biochemical relationship between a variety of signal transduction molecules that play a role in the transmission of a signal from one portion of a cell to another portion of a cell.

As used herein, the phrase "cell surface receptor" includes, for example, molecules and complexes of molecules capable of receiving a signal and the transmission of such a signal across the plasma membrane of a cell.

The term "antibody" as referred to herein includes whole polyclonal and monoclonal antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., VSIG1, ILDR1, LOC253012, AI216611, C1ORF32, FXYD3 proteins or VSIG1, ILDR1, LOC253012, AI216611, C1ORF32, or FXYD3). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V Light, V Heavy, Constant light (CL) and CH1 domains; (ii) a F(ab').2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds VSIG1, ILDR1, LOC253012, AI216611, C1ORF32, FXYD3 proteins or VSIG1, ILDR1, LOC253012, AI216611, C1ORF32, or FXYD3 is substantially free of antibodies that specifically bind antigens other than VSIG1, ILDR1, LOC253012, AI216611, C1ORF32, FXYD3 proteins or VSIG1, ILDR1, LOC253012, AI216611, C1ORF32, or FXYD3, respectively. An isolated antibody that specifically binds VSIG1, ILDR1, LOC253012, AI216611, C1ORF32, FXYD3 proteins or VSIG1, ILDR1, LOC253012, AI216611, C1ORF32, or FXYD3 may, however, have cross-reactivity to other antigens, such as VSIG1, ILDR1, LOC253012, AI216611, C1ORF32, FXYD3 proteins or VSIG1, ILDR1, LOC253012, AI216611, C1ORF32, or FXYD3 molecules from other species, respectively. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human VSIG1, ILDR1, LOC253012, AI216611, C1ORF32, FXYD3 proteins or VSIG1, ILDR1, LOC253012, AI216611, C1ORF32, or FXYD3 is intended to refer to an antibody that binds to human VSIG1, ILDR1, LOC253012, AI216611, C1ORF32, FXYD3 proteins or VSIG1, ILDR1, LOC253012, AI216611, C1ORF32, or FXYD3, respectively, preferably one with a KD of 5×10-8 M or less, more preferably 3×10-8 M or less, and even more preferably 1×10-9 M or less.

The term "K-assoc" or "Ka", as used herein, is intended to refer to the association rate of a particular antibody-antigen interaction, whereas the term "Kdiss" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface Plasmon resonance, preferably using a biosensor system such as a Biacore®. system.

As used herein, the term "high affinity" for an IgG antibody refers to an antibody having a KD of 10-8 M or less, more preferably 10-9 M or less and even more preferably 10-10 M or less for a target antigen. However, "high affinity" binding can vary for other antibody isotypes. For example, "high affinity" binding for an IgM isotype refers to an antibody having a KD of 10-7 M or less, more preferably 10-8 M or less.

As used herein, the term "subject" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc.

As used herein, the term "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein, the term "head" refers to a peptide sequence at the beginning of an amino acid sequence that is unique to a splice variant according to the present invention. Therefore, a splice variant having such a head may optionally be considered as a chimera, in that at least a first portion of the splice variant comprises the head, while at least a second portion is typically highly homologous (often 100% identical) to a portion of the corresponding known protein.

As used herein, the term "an edge portion" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a head and a "known protein" portion of a variant, or a join between a tail and a "known protein" portion of a variant, or a join between an insertion and a "known protein" portion of a variant.

In some embodiments, a bridge between a tail or a head or a unique insertion, and a "known protein" portion of a variant, comprises at least about 10 amino acids, or in some embodiments at least about 20 amino acids, or in some embodiments at least about 30 amino acids, or in some embodiments at least about 40 amino acids, in which at least one amino acid is from the tail/head/insertion and at least one amino acid is from the "known protein" portion of a variant. In some embodiments, the bridge may comprise any number of amino acids from about 10 to about 40 amino acids (for example, 10, 11, 12, 13 . . . 37, 38, 39, 40 amino acids in length, or any number in between).

It should be noted that a bridge cannot be extended beyond the length of the sequence in either direction, and it should be assumed that every bridge description is to be read in such manner that the bridge length does not extend beyond the sequence itself.

Furthermore, bridges are described with regard to a sliding window in certain contexts below. For example, certain descriptions of the bridges feature the following format: a bridge between two edges (in which a portion of the known protein is not present in the variant) may optionally be described as follows: a bridge portion of CONTIG-NAME_P1 (representing the name of the protein), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise XX (2 amino acids in the center of the bridge, one from each end of the edge), having a structure as follows (numbering according to the sequence of CONTIG-NAME_P1): a sequence starting from any of amino acid numbers 49−x to 49 (for example); and ending at any of amino acid numbers 50+((n−2)−x) (for example), in which x varies from 0 to n−2. In this example, it should also be read as including bridges in which n is any number of amino acids between 10-50 amino acids in length. Furthermore, the bridge polypeptide cannot extend beyond the sequence, so it should be read such that 49−x (for example) is not less than 1, nor 50+((n−2)−x) (for example) greater than the total sequence length.

Various aspects of the invention are described in further detail in the following subsections.

Nucleic Acids

A "nucleic acid fragment" or an "oligonucleotide" or a "polynucleotide" are used herein interchangeably to refer to a polymer of nucleic acid residues. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

Thus, the present invention encompasses nucleic acid sequences described hereinabove; fragments thereof, sequences hybridizable therewith, sequences homologous thereto [e.g., at least 90%, at least 95, 96, 97, 98 or 99% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention), which include sequence regions unique to the polynucleotides of the present invention.

In cases where the polynucleotide sequences of the present invention encode previously unidentified polypeptides, the present invention also encompasses novel polypeptides or portions thereof, which are encoded by the isolated polynucleotide and respective nucleic acid fragments thereof described hereinabove.

Thus, the present invention also encompasses polypeptides encoded by the polynucleotide sequences of the present invention. The present invention also encompasses homologues of these polypeptides, such homologues can be at least 90%, at least 95, 96, 97, 98 or 99% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

As mentioned hereinabove, biomolecular sequences of the present invention can be efficiently utilized as tissue or pathological markers and as putative drugs or drug targets for treating or preventing a disease.

Oligonucleotides designed for carrying out the methods of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect of the present invention are those having a length selected from a range of about 10 to about 200 bases preferably about 15 to about 150 bases, more preferably about 20 to about 100 bases, most preferably about 20 to about 50 bases.

The oligonucleotides of the present invention may comprise heterocyclic nucleosides consisting of purines and the pyrimidines bases, bonded in a 3' to 5' phosphodiester linkage.

Preferable oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclization does not severely interfere with peptide characteristics, cyclic forms of the peptide can also be utilized.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Expression Systems

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining elements, or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptides of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Recombinant Expression Vectors and Host Cells

Another aspect of the invention pertains to vectors, preferably expression vectors, containing a nucleic acid encoding a protein of the invention, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequences in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for production of variant proteins in prokaryotic or eukaryotic cells. For example, proteins of the invention can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89)—not accurate, pET11a-d have N terminal T7 tag.

One strategy to maximize recombinant protein expression in *E. coli* is to express the protein in a host bacterium with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

In another embodiment, the expression vector encoding for the protein of the invention is a yeast expression vector. Examples of vectors for expression in yeast *Saccharomyces cerevisiae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, polypeptides of the present invention can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for protein of the invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, protein of the invention can be produced in bacterial cells such as *E. coli*, insect cells, yeast, plant or mammalian cells (such as Chinese hamster ovary cells (CHO) or COS or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

For efficient production of the protein, it is preferable to place the nucleotide sequences encoding the protein of the invention under the control of expression control sequences optimized for expression in a desired host. For example, the sequences may include optimized transcriptional and/or translational regulatory sequences (such as altered Kozak sequences).

Protein Modifications

Fusion Proteins

According to the present invention, a fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331proline for serine may block the ability to activate complement, which may optionally be considered an undesired function (see M. Clark, "Chemical Immunol and Antibody Engineering", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Addition of Groups

If a protein according to the present invention is a linear molecule, it is possible to place various functional groups at various points on the linear molecule which are susceptible to or suitable for chemical modification. Functional groups can be added to the termini of linear forms of the protein of the invention. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lip ophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —$NH_2$, —$NHCH_3$, —$N(CH_3)_2$, —NH (ethyl), —N(ethyl)$_2$, —N(methyl) (ethyl), —NH (benzyl), —N(C1-C4 alkyl)(benzyl), —NH (phenyl), —N(C1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a protein of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Treatment

As mentioned hereinabove the VSIG1, ILDR1, LOC253012, AI216611, C1ORF32, FXYD3 proteins or VSIG1, ILDR1, LOC253012, AI216611, C1ORF32, FXYD3 proteins and polypeptides of the present invention or nucleic acid sequence or fragments thereof especially the ectodomain or secreted forms of VSIG1, ILDR1, LOC253012, AI216611, C1ORF32, FXYD3 proteins, as well as drugs which specifically bind to the VSIG1, ILDR1, LOC253012, AI216611, C1ORF32, FXYD3 proteins and/or splice variants, and/or drugs which agonize or antagonize the binding of other moieties to the VSIG1, ILDR1, LOC253012, AI216611, C1ORF32, FXYD3 proteins and/or splice variants, and/or drugs which modulate (agonize or antagonize) at least one VSIG1, ILDR1, LOC253012, AI216611, C1ORF32 or FXYD3 related biological activity (such drugs include by way of example antibodies, small molecules, peptides, ribozymes, antisense molecules, siRNA's and the like), can be used to treat cancer, including but not limited to non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic.

The VSIG1, ILDR1, LOC253012, AI216611, C1ORF32, FXYD3 proteins or VSIG1, ILDR1, LOC253012, AI216611, C1ORF32, FXYD3 proteins and polypeptides of the present invention or nucleic acid sequence or fragments thereof especially the ectodomain or secreted forms of VSIG1, ILDR1, LOC253012, AI216611, C1ORF32, FXYD3 proteins, as well as drugs which specifically bind to the VSIG1, ILDR1, LOC253012, AI216611, C1ORF32, FXYD3 proteins and/or splice variants, and/or drugs which agonize or antagonize the binding of other moieties to the VSIG1, ILDR1, LOC253012, AI216611, C1ORF32, FXYD3 proteins and/or splice variants, and/or drugs which modulate (agonize or antagonize) at least one VSIG1, ILDR1, LOC253012, AI216611, C1ORF32 or FXYD3 related biological activity (such drugs include by way of example antibodies, small molecules, peptides, ribozymes, antisense molecules, siRNA's and the like), can be further used to treat non-malignant disorders such as immune disorders including but not limited to autoimmune diseases, transplant rejection and graft versus host disease, and/or for blocking or promoting immune costimulation mediated by the VSIG1, ILDR1, LOC253012, AI216611, C1ORF32, FXYD3 polypeptide.

Thus, according to an additional aspect of the present invention there is provided a method of treating cancer, including but not limited to non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic as well as non-malignant disorders such as immune disorders including but not limited to autoimmune diseases, transplant rejection and graft versus host disease, and/or for blocking or promoting immune costimulation mediated by the VSIG1, ILDR1, LOC253012, AI216611, C1ORF32, or FXYD3 polypeptide in a subject.

The subject according to the present invention is a mammal, preferably a human which is diagnosed with one of the disease, disorder or conditions described hereinabove, or alternatively is predisposed to at least one type of cancer, including but not limited to non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain, as well as non-malignant disorders such as immune disorders including but not limited to autoimmune diseases, transplant rejection and graft versus host disease.

As used herein the term "treating" refers to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the polypeptides of the present invention in the subject.

Optionally, upregulation may be effected by administering to the subject at least one of the polypeptides of the present invention (e.g., recombinant or synthetic) or an active portion thereof, as described herein. However, since the bioavailability of large polypeptides may potentially be relatively small due to high degradation rate and low penetration rate, administration of polypeptides is preferably confined to small peptide fragments (e.g., about 100 amino acids). The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy). Thus, treatment of malignancies using the agents of the present invention may be combined with, for example, radiation therapy, antibody therapy and/or chemotherapy.

Alternatively or additionally, an upregulating method may optionally be effected by specifically upregulating the amount (optionally expression) in the subject of at least one of the polypeptides of the present invention or active portions thereof.

As is mentioned hereinabove and in the Examples section which follows, the biomolecular sequences of this aspect of the present invention may be used as valuable therapeutic tools in the treatment of diseases, disorders or conditions in which altered activity or expression of the wild-type gene product (known protein) is known to contribute to disease, disorder or condition onset or progression. For example, in case a disease is caused by overexpression of a membrane bound-receptor, a soluble variant thereof may be used as an antagonist which competes with the receptor for binding the ligand, to thereby terminate signaling from the receptor.

Anti-VSIG1, Anti-ILDR1, Anti-LOC253012, Anti-AI216611, Anti-C1ORF32, Anti-FXYD3 Antibodies The antibodies of the invention including those having the particular germline sequences, homologous antibodies, antibodies with conservative modifications, engineered and modified antibodies are characterized by particular functional features or properties of the antibodies. For example, the antibodies bind specifically to human VSIG1, ILDR1, LOC253012, AI216611, C1ORF32, or FXYD3. Preferably, an antibody of the invention binds to corresponding VSIG1, ILDR1, LOC253012, AI216611, C1ORF32, or FXYD3 with high affinity, for example with a KD of 10-8 M or less or 10-9 M or less or even 10-10 M or less. The anti-VSIG1, anti-ILDR1, anti-LOC253012, anti-AI216611, anti-C1ORF32, or anti-FXYD3 antibodies of the invention preferably exhibit one or more of the following characteristics:

(i) binds to corresponding human VSIG1, ILDR1, LOC253012, AI216611, C1ORF32, or FXYD3 with a KD of 5×10-8 M or less;

(ii) modulates (enhances or inhibits) B7 immune costimulation and related activities and functions such a T cell responses involved in antitumor immunity and autoimmunity. and/or (iii) binds to VSIG1, ILDR1, LOC253012, AI216611, C1ORF32, or FXYD3 antigen expressed by cancer cells including for example lung cancer, ovarian cancer, colon cancer, but does not substantially bind to normal cells In addition, preferably these antibodies and conjugates thereof will be effective in eliciting selective killing of such cancer cells and for modulating immune responses involved in autoimmunity and cancer.

More preferably, the antibody binds to corresponding human VSIG1, ILDR1, LOC253012, AI216611, C1ORF32, or FXYD3 antigen with a KD of 3×10-8 M or less, or with a KD of 1×10-9 M or less, or with a KD of 0.1×10-9 M or less, or with a KD Of 0.05×10-9 M or less or with a KD of between 1×10-9 and 1×10-11 M.

Standard assays to evaluate the binding ability of the antibodies toward VSIG1, ILDR1, LOC253012, AI216611, C1ORF32, or FXYD3 are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Upon production of anti-VSIG1, anti-ILDR1, anti-LOC253012, anti-AI216611, anti-C1ORF32, or anti-FXYD3 antibody sequences from antibodies can bind to VSIG1, ILDR1, LOC253012, AI216611, C1ORF32, or FXYD3 the VH and VL sequences can be "mixed and matched" to create other anti-VSIG1, ILDR1, LOC253012, AI216611, C1ORF32, or FXYD3 binding molecules of the invention. VSIG1, ILDR1, LOC253012, AI216611, C1ORF32, or FXYD3 binding of such "mixed and matched" antibodies can be tested using the binding assays described above. e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. For example, the VH and VL sequences of homologous antibodies are particularly amenable for mixing and matching.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, 96, 97, 98 or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to isolated anti-VSIG1, anti-ILDR1, anti-LOC253012, anti-AI216611, anti-C1ORF32, or anti-FXYD3 amino acid sequences of preferred anti-VSIG1, anti-ILDR1, anti-LOC253012, anti-AI216611, anti-C1ORF32, or anti-FXYD3 antibodies, respectively, wherein the antibodies retain the desired functional properties of the parent anti-VSIG1, anti-ILDR1, anti-LOC253012, anti-AI216611, anti-C1ORF32, or anti-FXYD3 antibodies.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on preferred anti-VSIG1, anti-ILDR1, anti-LOC253012, anti-AI216611, anti-C1ORF32, or anti-FXYD3 antibodies isolated and produced using methods herein, or conservative modifications thereof, and wherein the antibodies retain the desired functional properties of the anti-VSIG1, anti-ILDR1, anti-LOC253012, anti-AI216611, anti-C1ORF32, or anti-FXYD3 antibodies of the invention, respectively.

In various embodiments, the anti-VSIG1, anti-ILDR1, anti-LOC253012, anti-AI216611, anti-C1ORF32, or anti-FXYD3 antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

Antibodies that Bind to the Same Epitope as Anti-VSIG1, Anti-ILDR1, Anti-LOC253012, Anti-AI216611, Anti-C1ORF32, or Anti-FXYD3 Antibodies of the Invention In another embodiment, the invention provides antibodies that bind to preferred epitopes on human VSIG1, ILDR1, LOC253012, AI216611, C1ORF32, or FXYD3 which possess desired functional properties such as modulation of B7 co-stimulation and related functions. Other antibodies with desired epitope specificity may be selected and will have the ability to cross-compete for binding to VSIG1, ILDR1, LOC253012, AI216611, C1ORF32, or FXYD3 antigen with the desired antibodies.

Engineered and Modified Antibodies

An antibody of the invention further can be prepared using an antibody having one or more of the VH and/or VL sequences derived from an anti-VSIG1, anti-ILDR1, anti-LOC253012, anti-AI216611, anti-C1ORF32, or anti-FXYD3 antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T2545, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fc grammar, Fc gamma RII, Fc gammaRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve Fcgamma.RIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-VSIG1, anti-ILDR1, anti-LOC253012, anti-AI216611, anti-C1ORF32, or anti-FXYD3 antibodies having VH and VK sequences disclosed herein can be used to create new anti-VSIG1, anti-ILDR1, anti-LOC253012, anti-AI216611, anti-C1ORF32, or anti-FXYD3 antibodies, respectively, by modifying the VH and/or VL sequences, or the constant regions attached thereto. Thus, in another aspect of the invention, the structural features of an anti-VSIG1, anti-ILDR1, anti-LOC253012, anti-AI216611, anti-C1ORF32, or anti-FXYD3 antibody of the invention, are used to create structurally related anti-VSIG1, anti-ILDR1, anti-LOC253012, anti-AI216611, anti-C1ORF32, or anti-FXYD3 antibodies that retain at least one functional property of the antibodies of the invention, such as binding to human VSIG1, ILDR1, LOC253012, AI216611, C1ORF32, or FXYD3, respectively. For example, one or more CDR regions of one VSIG1, ILDR1, LOC253012, AI216611, C1ORF32, or FXYD3 antibody or mutations thereof, can be combined recombinantly with known framework regions and/or other CDRs to create additional, recombinantly-engineered, anti-VSIG1, anti-ILDR1, anti-LOC253012, anti-AI216611, anti-C1ORF32, or anti-FXYD3 antibodies of the invention, as discussed above. Other types of modifications include those described in the previous section. The starting material for the engineering method is one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence.

Preferably, the antibody encoded by the altered antibody sequences is one that retains one, some or all of the functional properties of the anti-VSIG1, anti-ILDR1, anti-LOC253012, anti-AI216611, anti-C1ORF32, or anti-FXYD3 antibodies, respectively, produced by methods and with sequences provided herein, which functional properties include binding to VSIG1, ILDR1, LOC253012, AI216611, C1ORF32, or FXYD3 antigen with a specific KD level or less and/or modulating B7 costimulation and/or selectively binding to desired target cells such as lung cancer, ovarian cancer, colon cancer, that express VSIG1, ILDR1, LOC253012, AI216611, C1ORF32, or FXYD3 antigen.

The functional properties of the altered antibodies can be assessed using standard assays available in the art and/or described herein.

In certain embodiments of the methods of engineering antibodies of the invention, mutations can be introduced randomly or selectively along all or part of an anti-VSIG1, anti-ILDR1, anti-LOC253012, anti-AI216611, ani-C1ORF32, or anti-FXYD3 antibody coding sequence and the resulting modified anti-VSIG1, anti-ILDR1, anti-LOC253012, anti-AI216611, ani-C1ORF32, or anti-FXYD3 antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production Of Anti-VSIG1, Anti-ILDR1, Anti-LOC253012, Anti-AI216611, Ani-C1ORF32, or Anti-FXYD3 Monoclonal Antibodies of the Invention Monoclonal antibodies (mAbs) of the present invention can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against VSIG1 can be generated using transgenic or transchromosomic mice carrying parts of the human immune system rather than the mouse system. These transgenic and transchromosomic mice include mice referred to herein as the HuMAb Mouse RTM and KM Mouse. RTM. respectively, and are collectively referred to herein as "human Ig mice." The HuMAb Mouse™. (Medarex. Inc.) contains human immunoglobulin gene miniloci that encode unrearranged human heavy (.mu. and .gamma.) and .kappa. light chain immunoglobulin sequences, together with targeted mutations that inactivate the endogenous .mu. and .kappa. chain loci (see e.g., Lonberg, et al. (1994) Nature 368(6474): 856-859). Accordingly, the mice exhibit reduced expression of mouse IgM or .kappa., and in response to immunization, the introduced human heavy and light chain transgenes undergo class switching and somatic mutation to generate high affinity human IgGkappa. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of the HuMab Mouse RTM., and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice TM.", are described in detail in PCT Publication WO 02/43478 to Ishida et al.

Still further, alternative transgenic animal systems expressing human immunoglobulin genes are available in the art and can be used to raise anti-VSIG1 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-VSIG1, anti-ILDR1, anti-LOC253012, anti-AI216611, ani-C1ORF32, or anti-FXYD3 antibodies of the invention. For example, mice carrying both a human heavy chain transchromosome and a human light chain transchromosome, referred to as "TC mice" can be used; such mice are described in Tomizuka et al. (2000) Proc. Natl. Acad Sci. USA 97:722-727. Furthermore, cows carrying human heavy and light chain transchromosomes have been described in the art (Kuroiwa et al. (2002) Nature Biotechnology 20:889-894) and can be used to raise anti-VSIG1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of VSIG1, ILDR1, LOC253012, AI216611, C1ORF32, or FXYD3 antigen and/or recombinant VSIG1, ILDR1, LOC253012, AI216611, C1ORF32, or FXY, or an VSIG1, ILDR1, LOC253012, AI216611, C1ORF32, or FXYD3 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 .mu.g) of VSIG1, ILDR1, LOC253012, AI216611, C1ORF32, or FXYD3 antigen can be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-VSIG1, anti-ILDR1, anti-LOC253012, anti-AI216611, anti-C1ORF32, or anti-FXYD3 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo 12). Alternatively or additionally, the KM Mouse. RTM. strain can be used.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×10-5 in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or .beta.-globin promoter. Still further, regulatory elements composed of sequences from different sources, such as the SR alpha. promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

For expression of the light and heavy chains, the expression vectors encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to VSIG1, ILDR1, LOC253012, AI216611, C1ORF32, or FXYD3 by, for example, standard ELISA. Briefly, microtiter plates are coated with purified VSIG1 at 0.25 .mu.g/ml in PBS, and then blocked with 5% bovine serum albumin in PBS. Dilutions of antibody (e.g., dilutions of plasma from VSIG1, ILDR1, LOC253012, AI216611, C1ORF32, or FXYD3-immunized mice) are added to each well and incubated for 1-2 hours at 37 degrees C. The plates are washed with PBS/Tween and then incubated with secondary reagent (e.g., for human antibodies, a goat-anti-human IgG Fc-specific polyclonal reagent) conjugated to alkaline phosphatase for 1 hour at 37 degrees C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with VSIG1, ILDR1, LOC253012, AI216611, C1ORF32, or FXYD3 immunogen. Hybridomas that bind with high avidity to VSIG1 are subcloned and further characterized. One clone from each hybridoma, which retains the reactivity of the parent cells (by ELISA), can be chosen for making a 5-10 vial cell bank stored at −140 degrees C., and for antibody purification.

To purify anti-VSIG1, anti-ILDR1, anti-LOC253012, anti-AI216611, anti-C1ORF32, or anti-FXYD3 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

To determine if the selected anti-VSIG1, anti-ILDR1, anti-LOC253012, anti-AI216611, anti-C1ORF32, or anti-FXYD3 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using VSIG1, ILDR1, LOC253012, AI216611, C1ORF32, or FXYD3 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 .mu.g/ml of anti-human immunoglobulin overnight at 4 degrees C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-VSIG1, anti-ILDR1, anti-LOC253012, anti-AI216611, anti-C1ORF32, or anti-FXYD3 human IgGs can be further tested for reactivity with VSIG1, ILDR1, LOC253012, AI216611, C1ORF32, or FXYD3 antigen, respectively, by Western blotting. Briefly, VSIG1, ILDR1, LOC253012, AI216611, C1ORF32, or FXYD3 antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Conjugates or Immunoconjugates

The present invention encompasses conjugates for use in immune therapy comprising the VSIG1, ILDR1, LOC253012, AI216611, C1ORF32, or FXYD3 antigen and soluble portions thereof including the ectodomain or portions or variants thereof. For example the invention encompasses conjugates wherein the ECD of the VSIG1, ILDR1, LOC253012, AI216611, C1ORF32, or FXYD3 antigen is attached to an immunoglobulin or fragment thereof. The invention contemplates the use thereof for promoting or inhibiting VSIG1, ILDR1, LOC253012, AI216611, C1ORF32, or FXYD3 antigen activities such as immune costimulation and the use thereof in treating transplant, autoimmune, and cancer indications described herein.

In another aspect, the present invention features immunoconjugates comprising an anti-VSIG1, anti-ILDR1, anti-LOC253012, anti-AI216611, anti-C1ORF32, or anti-FXYD3 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-VSIG1, anti-ILDR1, anti-LOC253012, anti-AI216611, anti-C1ORF32, or anti-FXYD3 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for VSIG1, ILDR1, LOC253012, AI216611, C1ORF32, or FXYD3 and a second binding specificity for a second target epitope. In a particular embodiment of the invention, the second target epitope is an Fc receptor, e.g., human Fc gamma RI (CD64) or a human Fc alpha receptor (CD89). Therefore, the invention includes bispecific molecules capable of binding both to Fc gamma. R, Fc alpha R or Fc epsilon R expressing effector cells (e.g., monocytes, macrophages or polymorphonuclear cells (PMNs)), and to target cells expressing VSIG1, ILDR1, LOC253012, AI216611, C1ORF32, or FXYD3, respectively. These bispecific molecules target VSIG1, ILDR1, LOC253012, AI216611, C1ORF32, or FXYD3 expressing cells to effector cell and trigger Fc receptor-mediated effector cell activities, such as phagocytosis of an VSIG1, ILDR1, LOC253012, AI216611, C1ORF32, or FXYD3 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-6f binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab').sub.2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcy receptor is provided by a monoclonal antibody, the binding of which is not blocked by human immunoglobulin G (IgG). As used herein, the term "IgG receptor" refers to any of the eight.gamma.-chain genes located on chromosome 1. These genes encode a total of twelve transmembrane or soluble receptor isoforms which are grouped into three Fc.gamma. receptor classes: Fc gamma R1 (CD64), Fc gamma RII (CD32), and Fc gamma.RIII (CD 16). In one preferred embodiment, the Fc gamma. receptor a human high affinity Fc.gamma RI. The human Fc gammaRI is a 72 kDa molecule, which shows high affinity for monomeric IgG (10 8-10-9 M.-1).

The production and characterization of certain preferred anti-Fc gamma. monoclonal antibodies are described by Fanger et al. in PCT Publication WO 88/00052 and in U.S. Pat. No. 4,954,617, the teachings of which are fully incorporated by reference herein. These antibodies bind to an epitope of Fc.gamma.R1, FcyRII or FcyRIII at a site which is distinct from the Fc.gamma. binding site of the receptor and, thus, their binding is not blocked substantially by physiological levels of IgG. Specific anti-Fc.gamma.RI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcy receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HAO22CLI and has the accession no. CRL 11177.

In still other preferred embodiments, the binding specificity for an Fc receptor is provided by an antibody that binds to a human IgA receptor, e.g., an Fc-alpha receptor (Fc alpha.RI(CD89)), the binding of which is preferably not blocked by human immunoglobulin A (IgA). The term "IgA receptor" is intended to include the gene product of one alpha.-gene (Fc alpha.RI) located on chromosome 19. This gene is known to encode several alternatively spliced transmembrane isoforms of 55 to 10 kDa Fc.alpha.RI (CD89) is constitutively expressed on monocytes/macrophages, eosinophilic and neutrophilic granulocytes, but not on non-effector cell populations. Fc alpha RI has medium affinity (Approximately 5×10-7 M-1) for both IgA1 and IgA2, which is increased upon exposure to cytokines such as G-CSF or GM-CSF (Morton, H. C. et al. (1996) Critical Reviews in Immunology 16:423-440). Four FcaRI-specific monoclonal antibodies, identified as A3, A59, A62 and A77, which bind Fc.alpha.RI outside the IgA ligand binding domain, have been described (Monteiro, R. C. et al. (1992) J. Immunol. 148:1764).

Fc. alpha. RI and Fc gamma. RI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-VSIG1, anti-ILDR1, anti-LOC253012, anti-AI216611, anti-C1ORF32, or anti-FXYD3 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyld-ithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF (ab')2 or ligandXFab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA)

(see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma. counter or a scintillation counter or by autoradiography.

PHARMACEUTICAL COMPOSITIONS

In another aspect, the present invention provides a composition, e.g., a pharmaceutical composition, containing one or a combination of monoclonal antibodies, or antigen-binding portions thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

As discussed supra, VSIG1, ILDR1, LOC253012, AI216611, C1ORF32, or FXYD3 the invention further embraces identifying other molecules such as small organic molecules, peptides, ribozymes, carbohydrates, glycoprotein, siRNAs, antisense RNAs and the like which specifically bind and/or modulate (enhance or inhibit) an activity elicited by the VSIG1, ILDR1, LOC253012, AI216611, C1ORF32, or FXYD3 antigen, respectively. These molecules may be identified by known screening methods such as binding assays. Typically these assays will be high throughput and will screen a large library of synthesized or native compounds in order to identify putative drug candidates that bind and/or modulate VSIG1, ILDR1, LOC253012, AI216611, C1ORF32, or FXYD3 related activities.

Specifically, the invention embraces the development of drugs containing the ectodomain of the VSIG1, ILDR1, LOC253012, AI216611, C1ORF32, or FXYD3 antigen or a fragment or variant thereof or a corresponding nucleic acid sequence encoding. These conjugates may contain a targeting or other moiety such as an immunoglobulin domain. These conjugates may be expressed in known vector systems or cells or vectors containing the corresponding nucleic acid sequences may be used for cancer treatment and in immune therapy such as in the treatment of autoimmunity, transplant, GVHD, cancer, and other immune disorders or conditions.

Thus, the present invention features a pharmaceutical composition comprising a therapeutically effective amount of a therapeutic agent according to the present invention. According to the present invention the therapeutic agent could be any one of VSIG1, ILDR1, LOC253012, AI216611, C1ORF32, or FXYD3 ectodomain, or a fragment or variant thereof, or a corresponding nucleic acid sequence encoding.

The pharmaceutical composition according to the present invention is further preferably used for the treatment of cancers including by way of example non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic.

The pharmaceutical composition according to the present invention is further used for the treatment of autoimmunity and preferably for treating an autoimmune disease selected from: Multiple sclerosis; Psoriasis; Rheumatoid arthritis; Systemic lupus erythematosus; Ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

The pharmaceutical composition according to the present invention is preferably used for the treatment of for rejection of any organ transplant and/or Graft versus host disease which might develop after bone marrow transplantation.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of agent according to the present invention that is effective to treat a disease or disorder in a mammal.

The therapeutic agents of the present invention can be provided to the subject alone, or as part of a pharmaceutical composition where they are mixed with a pharmaceutically acceptable carrier.

Pharmaceutical compositions of the invention also can be administered in combination therapy, i.e., combined with other agents. For example, the combination therapy can include an anti-VSIG1, anti-ILDR1, anti-LOC253012, anti-AI216611, anti-C1ORF32, or anti-FXYD3 antibody or VSIG1, ILDR1, LOC253012, AI216611, C1ORF32, or FXYD3 modulating agent according to the present invention such as a soluble polypeptide conjugate containing the ectodomain of the VSIG1, ILDR1, LOC253012, AI216611, C1ORF32, or FXYD3 antigen or a small molecule such as a peptide, ribozyme, siRNA, or other drug that binds VSIG1, ILDR1, LOC253012, AI216611, C1ORF32, or FXYD3 combined with at least one other therapeutic or immune modulatory agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound. The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Generally, out of one hundred percent, this amount will range from about 0.01 percent to about ninety-nine percent of active ingredient, preferably from about 0.1 percent to about 70 percent, most preferably from about I percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-VSIG1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 mug/ml and in some methods about 25-300. mu. g/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-VSIG1, anti-ILDR1, anti-LOC253012, anti-AI216611, anti-C1ORF32, or anti-FXYD3 antibody of the invention preferably results in a decrease in severity of disease symptoms, an increase in frequency and duration of disease symptom-free periods, an increase in lifepan, disease remission, or a prevention of impairment or disability due to the disease affliction. For example, for the treatment of VSIG1, ILDR1, LOC253012, AI216611, C1ORF32, or FXYD3 positive tumors, e.g., lung tumors, ovarian tumors, and colon tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or other VSIG1, ILDR1, LOC253012, AI216611, C1ORF32, or FXYD3 drug or molecule and their conjugates and combinations thereof that modulates a VSIG1, ILDR1, LOC253012, AI216611, C1ORF32, or FXYD3 antigen activity according to the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies or other VSIG1 related drugs of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Diagnostic Uses of VSIG1, ILDR1, LOC253012, AI216611, C1ORF32, or FXYD3 Antigen and Corresponding Polynucleotides According to some embodiments, the sample taken from a subject (patient) to perform the diagnostic assay according to the present invention is selected from the group consisting of a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cells or tissues, wherein the cell or tissue can be obtained from an organ selected from, but not limited to lung, colon, ovarian and/or breast tissue; stool or a tissue sample, or any combination thereof. In some embodiments, the term encompasses samples of in vivo cell culture constituents. Prior to be subjected to the diagnostic assay, the sample can optionally be diluted with a suitable eluant.

In some embodiments, the phrase "marker" in the context of the present invention refers to a nucleic acid fragment, a peptide, or a polypeptide, which is differentially present in a sample taken from patients (subjects) having one of the herein-described diseases or conditions, as compared to a comparable sample taken from subjects who do not have one the above-described diseases or conditions.

In some embodiments, the term "polypeptide" is to be understood to refer to a molecule comprising from at least 2 to several thousand or more amino acids. The term "polypeptide" is to be understood to include, inter alia, native peptides (either degradation products, synthetically synthesized peptides or recombinant peptides), peptidomimetics, such as peptoids and semipeptoids or peptide analogs, which may comprise, for example, any desirable modification, including, inter alia, modifications rendering the peptides more stable while in a body or more capable of penetrating into cells, or others as will be appreciated by one skilled in the art. Such modifications include, but are not limited to N terminus modification, C terminus modification, peptide bond modification, backbone modifications, residue modification, or others. Inclusion of such peptides within the polypeptides of this invention may produce a polypeptide sharing identity with the polypeptides described herein, for example, those provided in the sequence listing.

In some embodiments, the phrase "differentially present" refers to differences in the quantity or quality of a marker present in a sample taken from patients having one of the herein-described diseases or conditions as compared to a comparable sample taken from patients who do not have one of the herein-described diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of each individual marker below.

In some embodiments, the phrase "diagnostic" means identifying the presence or nature of a pathologic condition. Diagnostic methods differ in their sensitivity and specificity.

The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

In some embodiments, the phrase "qualitative" when in reference to differences in expression levels of a polynucleotide or polypeptide as described herein, refers to the presence versus absence of expression, or in some embodiments, the temporal regulation of expression, or in some embodiments, the timing of expression, or in some embodiments, any post-translational modifications to the expressed molecule, and others, as will be appreciated by one skilled in the art. In some embodiments, the phrase "quantitative" when in reference to differences in expression levels of a polynucleotide or polypeptide as described herein, refers to absolute differences in quantity of expression, as determined by any means, known in the art, or in other embodiments, relative differences, which may be statistically significant, or in some embodiments, when viewed as a whole or over a prolonged period of time, etc., indicate a trend in terms of differences in expression.

In some embodiments, the term "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

In some embodiments, the term "level" refers to expression levels of RNA and/or protein or to DNA copy number of a marker of the present invention.

Typically the level of the marker in a biological sample obtained from the subject is different (i.e., increased or decreased) from the level of the same marker in a similar sample obtained from a healthy individual (examples of biological samples are described herein).

Numerous well known tissue or fluid collection methods can be utilized to collect the biological sample from the subject in order to determine the level of DNA, RNA and/or polypeptide of the marker of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the marker can be determined and a diagnosis can thus be made.

Determining the level of the same marker in normal tissues of the same origin is preferably effected along-side to detect an elevated expression and/or amplification and/or a decreased expression, of the marker as opposed to the normal tissues.

In some embodiments, the term "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals).

In some embodiments, the term "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

In some embodiments, the term "detect" refers to identifying the presence, absence or amount of the object to be detected.

In some embodiments, the term "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

In another embodiment, this invention provides a method for detecting the polypeptides of this invention in a biological sample, comprising: contacting a biological sample with an antibody specifically recognizing a polypeptide according to the present invention and detecting said interaction; wherein the presence of an interaction correlates with the presence of a polypeptide in the biological sample.

In some embodiments of the present invention, the polypeptides described herein are non-limiting examples of markers for diagnosing a disease and/or an indicative condition. Each marker of the present invention can be used alone or in combination, for various uses, including but not limited to, prognosis, prediction, screening, early diagnosis, determination of progression, therapy selection and treatment monitoring of a disease and/or an indicative condition.

In a related object the detected diseases will include cancers such as non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic.

In another related object the detected diseases will include autoimmune and neoplastic disorders selected from the group consisting of Multiple sclerosis; Psoriasis; Rheumatoid arthritis; Systemic lupus erythematosus; Ulcerative colitis; Crohn's disease; immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

In another related object the detected diseases will include rejection of any organ transplant and/or Graft versus host disease.

Each polypeptide/polynucleotide of the present invention can be used alone or in combination, for various uses, including but not limited to, prognosis, prediction, screening, early diagnosis, determination of progression, therapy selection and treatment monitoring of disease and/or an indicative condition, as detailed above.

Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

According to further embodiments of the present invention markers of the present invention might optionally be used alone or in combination with known markers for lung cancer, including but not limited to CEA, CA15-3, Beta-2-microglobulin, CA19-9, TPA, and/or in combination with the known proteins for the variant marker as described herein.

According to further embodiments of the present invention markers of the present invention might optionally be used alone or in combination with known markers for ovarian cancer, including but not limited to CEA, CA125 (Mucin 16), CA72-4TAG, CA-50, CA 54-61, CA-195 and CA 19-9 in combination with CA-125, and/or in combination with the known proteins for the variant marker as described herein.

According to further embodiments of the present invention markers of the present invention might optionally be used alone or in combination with known markers for colon cancer, including but not limited to CEA, CA19-9, CA50, and/or in combination with the known proteins for the variant marker as described herein.

In some embodiments of the present invention, there are provided of methods, uses, devices and assays for the diagnosis of a disease or condition. Optionally a plurality of markers may be used with the present invention. The plurality of markers may optionally include a markers described herein, and/or one or more known markers. The plurality of markers is preferably then correlated with the disease or condition. For example, such correlating may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level.

Also alternatively, such correlating may optionally comprise determining a temporal change in at least one of the markers, and wherein the temporal change is used in the correlating step.

Also alternatively, such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Also alternatively, such correlating may optionally comprise determining whether a ratio of marker concentrations for two markers is outside a range and/or above or below a threshold. Optionally, if the ratio is above or below the threshold level and/or outside a range, the ratio correlates with the disease or condition.

Optionally, a combination of two or more these correlations may be used with a single panel and/or for correlating between a plurality of panels.

Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, etc., may be combined in a single assay or device. Markers may also be commonly used for multiple purposes by, for example, applying a different threshold or a different weighting factor to the marker for the different purposes.

In one embodiment, the panels comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those diseases that may feature one or more similar or identical symptoms.

In certain embodiments, one or more diagnostic or prognostic indicators are correlated to a condition or disease by merely the presence or absence of the indicators. In other embodiments, threshold levels of a diagnostic or prognostic indicators can be established, and the level of the indicators in a patient sample can simply be compared to the threshold levels. The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

According to embodiments of the present invention, VSIG1, ILDR1, LOC253012, AI216611, C1ORF32, or FXYD3 protein, polynucleotide or a fragment thereof, may be featured as a biomarker for detecting disease and/or an indicative condition, as detailed above.

According to still other embodiments, the present invention optionally and preferably encompasses any amino acid sequence or fragment thereof encoded by a nucleic acid sequence corresponding to VSIG1, ILDR1, LOC253012, AI216611, C1ORF32, or FXYD3 as described herein. Any oligopeptide or peptide relating to such an amino acid sequence or fragment thereof may optionally also (additionally or alternatively) be used as a biomarker.

In still other embodiments, the present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described below.

The present invention also relates to kits based upon such diagnostic methods or assays.

Nucleic Acid Technology (Nat) Based Assays:

Detection of a nucleic acid of interest in a biological sample may also optionally be effected by NAT-based assays, which involve nucleic acid amplification technology, such as PCR for example (or variations thereof such as real-time PCR for example). As used herein, a "primer" defines an oligonucleotide which is capable of annealing to (hybridizing with) a target sequence, thereby creating a double stranded region which can serve as an initiation point for DNA synthesis under suitable conditions. Amplification of a selected, or target, nucleic acid sequence may be carried out by a number of suitable methods known in the art.

Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Non-limiting examples of Nucleic Acid Technology-based assay is selected from the group consisting of a PCR, Real-Time PCR, LCR, Self-Sustained Synthetic Reaction, Q-Beta Replicase, Cycling probe reaction, Branched DNA, RFLP analysis, DGGE/TGGE, Single-Strand Conformation Polymorphism, Dideoxy fingerprinting, microarrays, Fluorescense In Situ Hybridization and Comparative Genomic Hybridization. The terminology "amplification pair" (or "primer pair") refers herein to a pair of oligonucleotides (oligos) of the present invention, which are selected to be used together in amplifying a selected nucleic acid sequence by one of a number of types of amplification processes, preferably a polymerase chain reaction. As commonly known in the art, the oligos are designed to bind to a complementary sequence under selected conditions. In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. It will be realized by a person skilled in the art that such methods could be adapted for the detection of differentially expressed proteins instead of differentially expressed nucleic acid sequences. The nucleic acid (i.e. DNA or RNA) for practicing the present invention may be obtained according to well known methods.

Oligonucleotide primers of the present invention may be of any suitable length, depending on the particular assay format and the particular needs and targeted genomes employed. Optionally, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

Immunoassays

In another embodiment of the present invention, an immunoassay can be used to qualitatively or quantitatively detect and analyze markers in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support.

After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

The immunoassay can be used to determine a test amount of a marker in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Radio-immunoassay (RIA): In one version, this method involves precipitation of the desired substrate and in the methods detailed herein below, with a specific antibody and radiolabeled antibody binding protein (e.g., protein A labeled with I125) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-Imaging Methods

These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Theranostics:

The term theranostics describes the use of diagnostic testing to diagnose the disease, choose the correct treatment regime according to the results of diagnostic testing and/or monitor the patient response to therapy according to the results of diagnostic testing. Theranostic tests can be used to select patients for treatments that are particularly likely to benefit them and unlikely to produce side-effects. They can also provide an early and objective indication of treatment efficacy in individual patients, so that (if necessary) the treatment can be altered with a minimum of delay. For example: DAKO and Genentech together created HercepTest and Herceptin (trastuzumab) for the treatment of breast cancer, the first theranostic test approved simultaneously with a new therapeutic drug. In addition to HercepTest (which is an immunohistochemical test), other theranostic tests are in development which use traditional clinical chemistry, immunoassay, cell-based technologies and nucleic acid tests. PPGx's recently launched TPMT (thiopurine S-methyltransferase) test, which is enabling doctors to identify patients at risk for potentially fatal adverse reactions to 6-mercaptopurine, an agent used in the treatment of leukemia. Also, Nova Molecular pioneered SNP genotyping of the apolipoprotein E gene to predict Alzheimer's disease patients' responses to cholinomimetic therapies and it is now widely used in clinical trials of new drugs for this indication. Thus, the field of theranostics represents the intersection of diagnostic testing information that predicts the response of a patient to a treatment with the selection of the appropriate treatment for that particular patient.

Surrogate Markers:

A surrogate marker is a marker, that is detectable in a laboratory and/or according to a physical sign or symptom on the patient, and that is used in therapeutic trials as a substitute for a clinically meaningful endpoint. The surrogate marker is a direct measure of how a patient feels, functions, or survives which is expected to predict the effect of the therapy. The need for surrogate markers mainly arises when such markers can be measured earlier, more conveniently, or more frequently than the endpoints of interest in terms of the effect of a treatment on a patient, which are referred to as the clinical endpoints. Ideally, a surrogate marker should be biologically plausible, predictive of disease progression and measurable by standardized assays (including but not limited to traditional clinical chemistry, immunoassay, cell-based technologies, nucleic acid tests and imaging modalities).

Surrogate endpoints were used first mainly in the cardiovascular area. For example, antihypertensive drugs have been approved based on their effectiveness in lowering blood pressure. Similarly, in the past, cholesterol-lowering agents have been approved based on their ability to decrease serum cholesterol, not on the direct evidence that they decrease mortality from atherosclerotic heart disease. The measurement of cholesterol levels is now an accepted surrogate marker of atherosclerosis. In addition, currently two commonly used surrogate markers in HIV studies are CD4+ T cell counts and quantitative plasma HIV RNA (viral load). In some embodiments of this invention, the polypeptide/polynucleotide expression pattern may serve as a surrogate marker for a particular disease, as will be appreciated by one skilled in the art.

Uses and Methods of the Invention

The VSIG1, ILDR1, LOC253012, AI216611, C1ORF32, or FXYD3 drugs according to the invention, especially antibodies, particularly the human antibodies, antibody compositions, and soluble conjugates containing the ectodomain of the VSIG1, ILDR1, LOC253012, AI216611, C1ORF32, or FXYD3 antigen or a fragment or variant thereof, or a corresponding nucleic acid sequence or vector or cell expressing same and methods of the present invention have numerous in vitro and in vivo diagnostic and therapeutic utilities involving the diagnosis and treatment of VSIG1, ILDR1, LOC253012, AI216611, C1ORF32, or FXYD3 antigen related disorders and/or disorders wherein modulation of immune co-stimulation e.g., involving B7-related immune costimulation involving VSIG1, ILDR1, LOC253012, AI216611, C1ORF32 or FXYD3 antigen is therapeutically desirable. As noted these conditions include in particular cancers that differentially express the VSIG1, ILDR1, LOC253012, AI216611, C1ORF32, or FXYD3 antigen such as lung cancer, ovarian cancer, colon cancer, including invasive and metastatic forms thereof, and/or autoimmune conditions wherein modulation of costimulation such as involving B7 is therapeutically desirable. The subject anti-VSIG1, anti-ILDR1, anti-LOC253012, anti-AI216611, anti-C1ORF32 or anti-FXYD3 antibodies may prevent B7 mediated negative stimulation of T cell activity against cancer cells and/or prevent positive stimulation of T cell activity. Such antibodies may be used in the treatment of conditions including cancers such non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic as well as non-malignant disorders such as immune disorders including but not limited to transplant rejection and graft versus host disease, and autoimmune disorders such as afore-mentioned.

For example, these molecules can be administered to cells in culture, in vitro or ex vivo, or to human subjects, e.g., in vivo, to treat, prevent and to diagnose a variety of disorders. Preferred subjects include human patients having disorders mediated by cells expressing the VSIG1, ILDR1, LOC253012, AI216611, C1ORF32, or FXYD3 antigen and cells that posses VSIG1, ILDR1, LOC253012, AI216611, C1ORF32 or FXYD3 activity. The methods are particularly suitable for treating human patients having a disorder associated with aberrant VSIG1, ILDR1, LOC253012, AI216611, C1ORF32 or FXYD3 antigen expression using antibodies that specifically bind AI581519_P3 (SEQ ID NO:11), AI581519_P4 (SEQ ID NO:12), AI581519_P5 (SEQ ID NO:13), AI581519_P7 (SEQ ID NO:14), AI581519_P9 (SEQ ID NO:15), AI581519_P10 (SEQ ID NO:16), AA424839_P3 (SEQ ID NO:22), AA424839_P5 (SEQ ID NO:21), AA424839_P7 (SEQ ID NO:23), or AA424839_1_P11 (SEQ ID NO:24), H68654_1_P2 (SEQ ID NO:35), H68654_1_P5 (SEQ ID NO:36), H68654_1_P7 (SEQ ID NO:37), H68654_1_P12 (SEQ ID NO:38), H68654_1_P13 (SEQ ID NO:39), H68654_1_P14 (SEQ ID NO:40), AI216611_P0 (SEQ ID NO:43), AI216611_P1 (SEQ ID NO:44), H19011_1_P8 (SEQ ID NO:48), H19011_1_P9 (SEQ ID NO:50), R31375_P0 (SEQ ID NO:70), R31375_P14 (SEQ ID NO:72), R31375_P31 (SEQ ID NO:73) or R31375_P33 (SEQ ID NO:74).

VSIG1, ILDR1, LOC253012, AI216611, C1ORF32, or FXYD3 drugs according to the invention, are administered together with another agent, the two can be administered in either order or simultaneously.

Given the specific binding of the antibodies of the invention for VSIG1, ILDR1, LOC253012, AI216611, C1ORF32 or FXYD3 the antibodies of the invention can be used to specifically detect VSIG1, ILDR1, LOC253012, AI216611, C1ORF32 or FXYD3 expression on the surface of cells and, moreover, can be used to purify VSIG1, ILDR1, LOC253012, AI216611, C1ORF32 or FXYD3 antigen via immunoaffinity purification.

Furthermore, given the expression of VSIG1, ILDR1, LOC253012, AI216611, C1ORF32 or FXYD3 on various tumor cells, the human antibodies, antibody compositions and methods of the present invention can be used to treat a subject with a tumorigenic disorder, e.g., a disorder characterized by the presence of tumor cells expressing VSIG1, ILDR1, LOC253012, AI216611, C1ORF32 or FXYD3 antigen such as lung cancer and ovarian cancer, as mentioned.

In one embodiment, the antibodies (e.g., human monoclonal antibodies, multispecific and bispecific molecules and compositions) of the invention can be used to detect levels of VSIG1, ILDR1, LOC253012, AI216611, C1ORF32 or FXYD3 or levels of cells which contain VSIG1, ILDR1, LOC253012, AI216611, C1ORF32 or FXYD3, respectively, on their membrane surface, which levels can then be linked to certain disease symptoms. Alternatively, the antibodies can be used to inhibit or block VSIG1, ILDR1, LOC253012, AI216611, C1ORF32 or FXYD3 function which, in turn, can be linked to the prevention or amelioration of certain disease symptoms, thereby implicating VSIG1, ILDR1, LOC253012, AI216611, C1ORF32 or FXYD3, respectively, as a mediator of the disease. This can be achieved by contacting a sample and a control sample with the anti-VSIG1, anti-ILDR1, anti-LOC253012, anti-AI216611, anti-C1ORF32 or anti-FXYD3 antibody under conditions that allow for the formation of a complex between the corresponding antibody and VSIG1, ILDR1, LOC253012, AI216611, C1ORF32 or FXYD3, respectively. Any complexes formed between the antibody and VSIG1, ILDR1, LOC253012, AI216611, C1ORF32 or FXYD3 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using low cytometric assays.

The antibodies (e.g., human antibodies, multispecific and bispecific molecules, immunoconjugates and compositions) of the invention have additional utility in therapy and diagnosis of VSIG1, ILDR1, LOC253012, AI216611, C1ORF32 or FXYD3-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing VSIG1, ILDR1, LOC253012, AI216611, C1ORF32 or FXYD3; to mediate phagocytosis or ADCC of a cell expressing VSIG1, ILDR1, LOC253012, AI216611, C1ORF32 or FXYD3 in the presence of human effector cells, or to block VSIG1, ILDR1, LOC253012, AI216611, C1ORF32 or FXYD3 ligand binding to VSIG1, ILDR1, LOC253012, AI216611, C1ORF32 or FXYD3, respectively.

In a particular embodiment, the antibodies (e.g., human antibodies, multispecific and bispecific molecules and compositions) are used in vivo to treat, prevent or diagnose a variety of VSIG1, ILDR1, LOC253012, AI216611, C1ORF32 or FXYD3-related diseases. Examples of VSIG1, ILDR1, LOC253012, AI216611, C1ORF32 or FXYD3-related diseases include, among others, cancer, such as lung cancer, ovarian cancer, colon cancer, other non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, spleen, kidney, bladder, head and neck, uterus, testicles, stomach, cervix, liver, bone, skin, pancreas, brain and wherein the cancer may be non-metastatic, invasive or metastatic. Additional examples of VSIG1, ILDR1, LOC253012, AI216611, C1ORF32 or FXYD3-related diseases include, among others, non-malignant disorders such as immune disorders including but not limited to autoimmune diseases, transplant rejection and graft versus host disease. Such disorders include by way of example autoimmune diseases selected from multiple sclerosis; psoriasis; rheumatoid arthritis; Systemic lupus erythematosus; Ulcerative colitis; Crohn's' disease, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-VSIG1, anti-ILDR1, anti-LOC253012, anti-AI216611, anti-C1ORF32 or anti-FXYD3 antibodies of the invention can be co-administered with one or other more therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-VSIG1, anti-ILDR1, anti-LOC253012, anti-AI216611, anti-C1ORF32 or anti-FXYD3 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of 10-8 to 10-9 but will vary depending on the therapeutic purpose. In general, the amount will be sufficient to obtain localization at the target cell, e.g., a tumor cell expressing VSIG1, ILDR1, LOC253012, AI216611, C1ORF32 or FXYD3 and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-VSIG1, anti-ILDR1, anti-LOC253012, anti-AI216611, anti-C1ORF32 or anti-FXYD3 antibodies linked to anti-Fc-gamma RI or anti-CD3 may be used in conjunction with IgG- or IgA-receptor specific binding agents.

Bispecific and multispecific molecules of the invention can also be used to modulate FcgammaR or FcgammaR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the VSIG1, ILDR1, LOC253012, AI216611, C1ORF32 or FXYD3 antigen or VSIG1, ILDR1, LOC253012, AI216611, C1ORF32 or FXYD3 conjugates or antibody compositions of the invention (e.g., human antibodies, bispecific or multispecific molecules, or immunoconjugates) and instructions for use. The kit can further contain one ore more additional reagents, such as an immunosuppressive reagent, a cytotoxic agent or a radiotoxic agent, or one or more additional human antibodies of the invention (e.g., a human antibody having a complementary activity which binds to an epitope in the VSIG1, ILDR1, LOC253012, AI216611, C1ORF32 or FXYD3 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcy or Fcy receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-.gamma. (IFN-.gamma.), and tumor necrosis factor (TNF).

The compositions (e.g., human antibodies, multispecific and bispecific molecules) of the invention can also be used to target cells expressing Fc gamma R or VSIG1, ILDR1, LOC253012, AI216611, C1ORF32 or FXYD3, for example for labeling such cells. For such use, the binding agent can be linked to a molecule that can be detected. Thus, the invention provides methods for localizing ex vivo or in vitro cells expressing Fc receptors, such as FcgammaR, or VSIG1, ILDR1, LOC253012, AI216611, C1ORF32 or FXYD3 antigen. The detectable label can be, e.g., a radioisotope, a fluorescent compound, an enzyme, or an enzyme co-factor.

In a particular embodiment, the invention provides methods for detecting the presence of VSIG1, ILDR1, LOC253012, AI216611, C1ORF32 or FXYD3 antigen in a sample, or measuring the amount of VSIG1, ILDR1, LOC253012, AI216611, C1ORF32 or FXYD3 antigen, respectively, comprising contacting the sample, and a control sample, with a human monoclonal antibody, or an antigen binding portion thereof, which specifically binds to VSIG1, ILDR1, LOC253012, AI216611, C1ORF32 or FXYD3, respectively, under conditions that allow for formation of a complex between the antibody or portion thereof and VSIG1, ILDR1, LOC253012, AI216611, C1ORF32 or FXYD3. The formation of a complex is then detected, wherein a difference complex formation between the sample compared to the control sample is indicative the presence of VSIG1, ILDR1, LOC253012, AI216611, C1ORF32 or FXYD3 antigen in the sample. As noted the invention in particular embraces assays for detecting VSIG1, ILDR1, LOC253012, AI216611, C1ORF32 or FXYD3 antigen in vitro and in vivo such as immunoassays, radioimmunassays, radioassays, radioimaging assays, ELISAs, Western blot, FACS, slot blot, immunohistochemical assays, and other assays well known to those skilled in the art.

In other embodiments, the invention provides methods for treating an VSIG1, ILDR1, LOC253012, AI216611, C1ORF32 or FXYD3 mediated disorder in a subject, e.g., cancer, such as non-solid and solid tumors, sarcomas, hematological malignancies including but not limited to acute lymphocytic leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate, lung, ovary, colon, spleen, kidney, bladder, head and neck, uterus, testicles, stomach, cervix, liver, bone, skin, pancreas, brain and wherein the cancer may be non-metastatic, invasive or metastatic, as well as non-malignant disorders such as immune disorders including but not limited to transplant rejection and graft versus host disease, or an autoimmune disease selected from those aforementioned and methods of treating any condition wherein modulation of immune costimulation that involves VSIG1, ILDR1, LOC253012, AI216611, C1ORF32 or FXYD3 is therapeutically desirable using anti-VSIG1, anti-ILDR1, anti-LOC253012, anti-AI216611, anti-C1ORF32 or anti-FXYD3 antibodies or soluble VSIG1, ILDR1, LOC253012, AI216611, C1ORF32 or FXYD3 antigen conjugates or other drugs that target and modulate (promote or inhibit) one or more VSIG1, ILDR1, LOC253012, AI216611, C1ORF32 or FXYD3 biological activities.

By administering the anti-VSIG1, anti-ILDR1, anti-LOC253012, anti-AI216611, anti-C1ORF32 or anti-FXYD3 antibody, soluble VSIG1, ILDR1, LOC253012, AI216611, C1ORF32 or FXYD3 antigen conjugate or other drug that targets the VSIG1, ILDR1, LOC253012, AI216611, C1ORF32 or FXYD3 antigen or a portion thereof to a subject, the ability of VSIG1, ILDR1, LOC253012, AI216611, C1ORF32 or FXYD3 antigen to induce such activities is inhibited or promoted and, thus, the associated disorder is treated. The soluble VSIG1, ILDR1, LOC253012, AI216611, C1ORF32 or FXYD3 antigen or antigen conjugate or anti-VSIG1, anti-ILDR1, anti-LOC253012, anti-AI216611, anti-C1ORF32 or anti-FXYD3 antibody or fragment containing composition or other drug that targets and modulates VSIG1, ILDR1, LOC253012, AI216611, C1ORF32 or FXYD3, can be administered alone or along with another therapeutic agent, such as a cytotoxic or a radiotoxic agent which acts in conjunction with or synergistically with the antibody composition to treat or prevent the VSIG1, ILDR1, LOC253012, AI216611, C1ORF32 or FXYD3 antigen mediated disease.

In yet another embodiment, immunoconjugates of the invention can be used to target compounds (e.g., therapeutic agents, labels, cytotoxins, radiotoxins immunosuppressants, etc.) to cells which have VSIG1, ILDR1, LOC253012, AI216611, C1ORF32 or FXYD3 cell surface receptors by linking such compounds to the antibody. Thus, the invention also provides methods for localizing ex vivo or in vivo cells expressing VSIG1, ILDR1, LOC253012, AI216611, C1ORF32 or FXYD3 (e.g., with a detectable label, such as a radioisotope, a fluorescent compound, an enzyme, or an enzyme co-factor). Alternatively, the immunoconjugates can be used to kill cells which have VSIG1, ILDR1, LOC253012, AI216611, C1ORF32 or FXYD3 cell surface receptors by targeting cytotoxins or radiotoxins to VSIG1, ILDR1, LOC253012, AI216611, C1ORF32 or FXYD3 antigen.

The present invention is further illustrated by the following sequence characterization of a DNA transcript encoding the VSIG1, ILDR1, LOC253012, AI216611, C1ORF32 or FXYD3 antigen, its domains and expression data in normal and cancerous tissues as well as prophetic examples describing the manufacture of fully human antibodies thereto. This information and examples is illustrative and should not be construed as further limiting. The contents of all figures and all references, patents and published patent applications cited throughout this application are expressly incorporated herein by reference.

EXAMPLES

Example 1

Methods Used to Analyze the Expression of the RNA Encoding the Proteins of the Invention The targets of the present invention were tested with regard to their expression in various cancerous and non-cancerous tissue samples and/or with regard to its expression in a wide panel of human samples which contains various types of immune cells, and hematological malignancies samples and cell lines, as well as several samples of normal tissues. The list of the blood specific RNA samples used for the qRT-PCR analysis is provided in Table 1 below. A description of the samples used in the normal tissue panel is provided in Table 2. A description of the samples used in the lung cancer testing panel is provided in Table 3 below. A description of the samples used in the ovary cancer testing panel is provided in Table 4 below. A description of the samples used in the colon cancer testing panel is provided in Table 5 below. The keys for the table 3, 4 and 5 are given in tables 3_1, 4_1, and 5_1, respectively. Tests were then performed as described in the "Materials and Experimental Procedures" section below.

TABLE 1

Samples in blood specific panel

| Blood panel sample | Description | Organ/Cell type | Tumor Type |
|---|---|---|---|
| 1_PBMC2 | PBMCs | blood-derived cells | |
| 2_PBMC3 | PBMCs | blood-derived cells | |
| 3_Bcell1 | B cells | blood-derived cells | |
| 4_Bcell2 | B cells | blood-derived cells | |
| 5_J_Bcell | B cells | blood-derived cells | |
| 6_K_Bcells_act | Bcells activated | blood-derived cells | |
| 7_Tcell1 | T cells | blood-derived cells | |
| 8_Tcell2 | T cells | blood-derived cells | |
| 9_M_CD8 | CD4+ T cells | blood-derived cells | |
| 10_G_CD4_unt | CD8+ T cells | blood-derived cells | |
| 11_H_CD4_Beads | CD4+ w Activation beads | blood-derived cells | |
| 12_I_CD4_Beads_IL12 | CD4 w act. Beads + IL12 | blood-derived cells | |
| 13_95_CD4+CD25− | CD4+CD25− | blood-derived cells | |
| 15_NK | NK cells | blood-derived cells | |
| 16_CD34+_1548 | CD34+(PCBM1548) | blood-derived cells | |
| 17_CD34+_1028 | CD34+(PCBM1028) | blood-derived cells | |
| 18_PMN | PMNs | blood-derived cells | |
| 19_A_Mono | Monocytes | blood-derived cells | |
| 20_B_Macro_imma | Macrophages immature | blood-derived cells | |
| 21_C_Macro_mat | Macrophages mature | blood-derived cells | |
| 22_D_DCs_immat | DCs immature | blood-derived cells | |
| 23_E_DCs_mat_LPS | DCs mature LPS | blood-derived cells | |
| 24_F_DCs_mat_CK | DCs mature CK | blood-derived cells | |
| 25_L_DCs + T | DCs + T cells | blood-derived cells | |
| 26_Lym1 | 13987A1 | Lymph Node | Lymphoma |
| 27_Lym2 | 43594B1 | Muscle | lymphoma |
| 28_Lym3 | 65493A1 | Testis | Lymphoma |
| 29_MalLym3 | 75894A1 | Brain | Lymphoma |
| 30_NonHod_SCLym | 83325A1 | Lymph Node | NHL Small Cell |
| 31_NonHod_FolLym | 76943A1(5 tubes) | Lymph Node | NHL Follicular |
| 32_Lym_Fol_GI | CN_4_ASRBNA35 | | NHL Follicular Grade I (Small Cell) |
| 33_Lym_Fol_GII | CN_1_113GHA8J | | NHL Follicular Grade II (mixed Small & Large Cell) |
| 34_Lym_Fol_GIII | CN_8_VXML6AXI | | NHL Follicular Grade III (Large Cell) |
| 35_MalLym1 | 76218B1 | Testis | NHL Large Cell |
| 36_MalLym2 | 76102A1 | Lymph Node | NHL Large Cell |
| 37_Lym_DifBCell1 | CN_2_4HDLNA2R | | NHL Diffuse Large B-Cell |
| 38_Lym_DifBCell2 | CN_3_4M4S7AAM | | NHL Diffuse Large B-Cell |
| 39_Lym_DifBCell3 | CN_5_HEODOAR2 | | NHL Diffuse Large B-Cell |
| 40_NonHod_Lym1 | 77332A1(5 tubes) | Colon | NHL Diffuse Large B-Cell |
| 41_MalLym4 | 76161A1 | Spleen | NHL Diffuse Large B-Cell |
| 42_Lym_MantleCell1 | CN_6_MAE47AOY | | NHL Mantle Cell |
| 43_Lym_MantleCell2 | CN_7_VJU9OAO9 | | NHL Mantle Cell |
| 44_NonHod_Lym2 | 95377A1(5 tubes) | Spleen | NHL |
| 45_THP_1 | THP-1 | monocytes | AML cell line |
| 46_KG_1 | KG-1 | myeloblast | AML cell line |
| 47_BDCM | BDCM | B and DC like | AML cell line |
| 48_CESS | CESS | lymphoblasts | AML cell line |

TABLE 1-continued

Samples in blood specific panel

| Blood panel sample | Description | Organ/Cell type | Tumor Type |
|---|---|---|---|
| 49_HL60 | HL60 | myeloblast | AML cell line |
| 50_K562 | K562 | lymphoblasts | CML cell line |
| 51_Jurkat | Jurkat | T lymphoblasts | T ALL cell line |
| 52_GA10 | GA10 | B lymphoblasts | Burkitts lymphoma cell line |
| 53_RAMOS | RAMOS | B lymphoblasts | Burkitts lymphoma cell line |
| 54_RAJI | RAJI | B lymphoblasts | Burkitts lymphoma cell line |
| 55_Daudi | Daudi | B lymphoblasts | Burkitts lymphoma cell line |
| 56_NL564 | -NL564 | B lymphoblasts | EBV transformed cell line |
| 57_NL553 | NL553 | B lymphoblasts | EBV transformed cell line |
| 58_SKW6.4 | SKW6.4 | B cells lymphoblasts | EBV transformed cell line |
| 59_NCI_H929 | NCI-H929 | B lymphoblasts | Multiple Myeloma cell line |
| 60_MC/CAR | MC/CAR | B lymphoblasts | Multiple Myeloma cell line |
| 61_U266 | U266 | B lymphoblasts | Multiple Myeloma cell line |
| 62_RPMI8226 | RPMI8226 | B lymphoblasts | Multiple Myeloma cell line |
| 63_IM_9 | IM-9 | B lymphoblasts | Multiple Myeloma cell line |
| 64_cereN | cerebellum normal | cerebellum normal | |
| 65_kidneyN1 | kidney normal | kidney normal | |
| 66_kidneyN2 | kidney normal | kidney normal | |
| 67_KidneyN3 | kidney normal | kidney normal | |
| 68_colonN1 | colon normal | colon normal | |
| 69_colonN2 | colon normal | colon normal | |
| 70_stomN | stomach normal | stomach normal | |
| 71_liverN | liver normal | liver normal | |
| 72_lungN1 | lung normal | lung normal | |
| 73_lungN2 | lung normal | lung normal | |
| 74_small intestineN | small intestine | small intestine | |
| 75_brainN | brain normal mix | brain normal mix | |
| 76_heartN | heart normal mix | heart normal mix | |

TABLE 2

Tissue samples in normal panel:

| sample name | Source | Sample id(GCI)/case id (Asterand) Lot no. | Tissue id (GCI)/Specimen id (Asternd) | Sample id (Asterand)/RNA id (GCI) |
|---|---|---|---|---|
| 1-(7)-Bc-Rectum | Biochain | A610297 | | |
| 2-(8)-Bc-Rectum | Biochain | A610298 | | |
| 3-GC-Colon | GCI | CDSUV | CDSUVNR3 | |
| 4-As-Colon | Asterand | 16364 | 31802 | 31802B1 |
| 5-As-Colon | Asterand | 22900 | 74446 | 74446B1 |
| 6-GC-Small bowel | GCI | V9L7D | V9L7DN6Z | |
| 7-GC-Small bowel | GCI | M3GVT | M3GVTN5R | |
| 8-GC-Small bowel | GCI | 196S2 | 196S2AJN | |
| 9-(9)-Am-Stomach | Ambion | 110P04A | | |
| 10-(10)-Bc-Stomach | Biochain | A501159 | | |
| 11-(11)-Bc-Esoph | Biochain | A603814 | | |

TABLE 2-continued

Tissue samples in normal panel:

| sample name | Source | Sample id(GCI)/case id (Asterand) Lot no. | Tissue id (GCI)/Specimen id (Asternd) | Sample id (Asterand)/RNA id (GCI) |
|---|---|---|---|---|
| 12-(12)-Bc-Esoph | Biochain | A603813 | | |
| 13-As-Panc | Asterand | 8918 | 9442 | 9442C1 |
| 14-As-Panc | Asterand | 10082 | 11134 | 11134B1 |
| 16-As-Liver | Asterand | 7916 | 7203 | 7203B1 |
| 17-(28)-Am-Bladder | Ambion | 071P02C | | |
| 18-(29)-Bc-Bladder | Biochain | A504088 | | |
| 19-(64)-Am-Kidney | Ambion | 111P0101B | | |
| 20-(65)-Cl-Kidney | Clontech | 1110970 | | |
| 21-(66)-Bc-Kidney | Biochain | A411080 | | |
| 22-GC-Kidney | GCI | N1EVZ | N1EVZN91 | |
| 23-GC-Kidney | GCI | BMI6W | BMI6WN9F | |
| 25-(43)-Bc-Adrenal | Biochain | A610374 | | |
| 26-(16)-Am-Lung | Ambion | 111P0103A | | |
| 28-As-Lung | Asterand | 9078 | 9275 | 9275B1 |
| 29-As-Lung | Asterand | 6692 | 6161 | 6161A1 |
| 30-As-Lung | Asterand | 7900 | 7180 | 7180F1 |
| 31-(75)-GC-Ovary | GCI | L629FRV1 | | |
| 32-(76)-GC-Ovary | GCI | DWHTZRQX | | |
| 33-(77)-GC-Ovary | GCI | FDPL9NJ6 | | |
| 34-(78)-GC-Ovary | GCI | GWXUZN5M | | |
| 36-GC-cervix | GCI | E2P2N | E2P2NAP4 | |
| 38-(26)-Bc-Uterus | Biochain | A504090 | | |
| 39-(30)-Am-Placen | Ambion | 021P33A | | |
| 40-(32)-Bc-Placen | Biochain | A411073 | | |
| 41-GC-Breast | GCI | DHLR1 | | |
| 42-GC-Breast | GCI | TG6J6 | | |
| 43-GC-Breast | GCI | E6UDD | E6UDDNCF | |
| 44-(38)-Am-Prostate | Ambion | 25955 | | |
| 45-Bc-Prostate | Biochain | A609258 | | |
| 46-As-Testis | Asterand | 13071 | 19567 | 19567B1 |
| 47-As-Testis | Asterand | 19671 | 42120 | 42120A1 |
| 49-GC-Artery | GCI | YGTVY | YGTVYAIN | |
| 50-TH-Blood-PBMC | Tel-Hashomer | 52497 | | |
| 51-TH-Blood-PBMC | Tel-Hashomer | 31055 | | |
| 52-TH-Blood-PBMC | Tel-Hashomer | 31058 | | |
| 53-(54)-Ic-Spleen | Ichilov | CG-267 | | |
| 54-(55)-Am-Spleen | Ambion | 111P0106B | 54-(55)-Am-Spleen | Ambion |
| 56-(58)-Am-Thymus | Ambion | 101P0101A | | |
| 57-(60)-Bc-Thyroid | Biochain | A610287 | | |
| 58-(62)-Ic-Thyroid | Ichilov | CG-119-2 | | |
| 59-Gc-Sali gland | GCI | NNSMV | NNSMVNJC | |
| 60-(67)-Ic-Cerebellum | Ichilov | CG-183-5 | | |
| 61-(68)-Ic-Cerebellum | Ichilov | CG-212-5 | | |
| 62-(69)-Bc-Brain | Biochain | A411322 | | |
| 63-(71)-Bc-Brain | Biochain | A411079 | | |
| 64-(72)-Ic-Brain | Ichilov | CG-151-1 | | |
| 65-(44)-Bc-Heart | Biochain | A411077 | | |
| 66-(46)-Ic-Heart | Ichilov | CG-227-1 | | |
| 67-(45)-Ic-Heart (Fibrotic) | Ichilov | CG-255-9 | | |
| 68-GC-Skel Mus | GCI | T8YZS | T8YZSN7O | |
| 69-GC-Skel Mus | GCI | Q3WKA | Q3WKANCJ | |
| 70-As-Skel Mus | Asterand | 8774 | 8235 | 8235G1 |
| 71-As-Skel Mus | Asterand | 8775 | 8244 | 8244A1 |
| 72-As-Skel Mus | Asterand | 10937 | 12648 | 12648C1 |
| 73-As-Skel Mus | Asterand | 6692 | 6166 | 6166A1 |

TABLE 3

| Lung cancer testing panel | | | | | | | | | | | | | |
|---|---|---|---|---|---|---|---|---|---|---|---|---|---|
| Tissue | Source/Delivery | sample name | sample id (GCI)/case id (Asterand)/lot no. (old samples) | TISSUE ID (GCI)/specimen ID (Asterand) | RNA ID (GCI)/Sample ID (Asterand) | Diag | Diag remarks | Specimen location | Gr | TNM | CS | Tum % | Gen |
| LC | GCI | 1-GC-BAC-SIA | 7Z9V4 | 7Z9V4AYM | | Aden | BC | | | | IA | 80 | F |
| LC | GCI | 2-GC-BAC-SIB | ZW2AQ | ZW2AQARP | | Aden | BC | | | | IB | 70 | F |
| LC | Bioch | 72-(44)-Bc-BAC | A501123 | | | AC | | | 2 | UN | | | F |
| LC | GCI | 4-GC-Adeno-SIA | 3MOPL | 3MOPLA79 | | Aden | | | | | IA | 60 | M |
| LC | GCI | 5-GC-Adeno-SIA | KOJXD | KOJXDAV4 | | Aden | | | | | IA | 90 | F |
| LC | GCI | 6-GC-Adeno-SIA | X2Q44 | X2Q44A79 | | Aden | | | | | IA | 85 | M |
| LC | GCI | 7-GC-Adeno-SIA | 6BACZ | 6BACZAP5 | | Aden | | | | | IA | 60 | F |
| LC | GCI | 8-GC-Adeno-SIA | BS9AF | BS9AFA3E | | Aden | | | | | IA | 55 | F |
| LC | GCI | 9-GC-Adeno-SIA | UCLOA | UCLOAA9L | | Aden | | | | | IA | 80 | F |
| LC | GCI | 10-GC-Adeno-SIA | BVYK3 | BVYK3A7Z | | Aden | | | | | IA | 60 | F |
| LC | GCI | 11-GC-Adeno-SIB | U4DM4 | U4DM4AFZ | | Aden | | | | | IB | 65 | F |
| LC | GCI | 12-GC-Adeno-SIB | OWX5Y | OWX5YA3S | | Aden | | | | | IB | 90 | M |
| LC | GCI | 13-GC-Adeno-SIIA | XYY96 | XYY96A6B | | Aden | | | | | IIA | 70 | F |
| LC | GCI | 14-GC-Adeno-SIIA | SO7B1 | SO7B1AIJ | | Aden | | | | | IIA | 70 | M |
| LC | GCI | 15-GC-Adeno-SIIIA | QANSY | QANSYACD | | Aden | | | | | IIIA | 65 | F |
| LC | Bioch | 16-(95)-BC-Adeno | A610063 | | | Aden | | | 1 | UN | | | F |
| LC | Bioch | 17-(89)-Bc-Adeno | A609077 | | | Aden | | | 2-3 | UN | | | M |
| LC | Bioch | 18-(76)-Bc-Adeno | A609218 | | | Aden | | | 3 | UN | | | M |
| LC | Bioch | 74-(2)-Bc-Adeno | A504118 | | | Aden | | | 1 | UN | | | M |
| LC | Bioch | 75-(77)-Bc-Adeno | A608301 | | | Aden | | | 2 | UN | | | M |
| LC | Bioch | 76-(75)-Bc-Adeno | A609217 | | | Aden | | | 2 | UN | | | M |
| LC | Bioch | 78-(13)-Bc-Adeno | A504116 | | | Aden | | | 2-3 | UN | | | M |
| LC | Ichilov | 81-(14)-Ic-Adeno | CG-111 | | | Aden | | | UN | UN | | | M |
| LC | Aster | 19-As-Sq-S0 | 9220 | 9418 | 9418A1 | SCC | | | 1 | TXN0M0 | Occult | 80 | M |
| LC | GCI | 20-GC-Sq-SIA | U2QHS | U2QHSA2N | | SCC | | | | | IA | 55 | F |
| LC | GCI | 21-GC-Sq-SIB | TRQR7 | TRQR7ACD | | SCC | | | | | IB | 75 | M |
| LC | Aster | 22-As-Sq-SIB | 17581 | 32603 | 32603B1 | SCC | | | 3 | T2N0M0 | IB | 90 | M |
| LC | Aster | 23-As-Sq-SIB | 18309 | 41454 | 41454B1 | SCC | | | 2 | T2N0MX | IB | 100 | M |

TABLE 3-continued

Lung cancer testing panel

| | | | | | | | | | | | | |
|---|---|---|---|---|---|---|---|---|---|---|---|---|
| LC | Aster | 24-As-Sq-SIB | 9217 | 9415 | 9415B1 | SCC | | 2 | T2N0M0 | IB | 90 | M |
| LC | GCI | 25-GC-Sq-SIIB | RXQ1P | RXQ1PAEA | | SCC | | | | IIB | 55 | F |
| LC | GCI | 26-GC-Sq-SIIB | KB5KH | KB5KHA6X | | SCC | | | | IIB | 65 | M |
| LC | GCI | 27-GC-Sq-SIIIA | LAYMB | LAYMBALF | | SCC | | | | IIIA | 65 | F |
| LC | Ichilov | 29-(25)-Ic-Sq | CG-204 | | | SCC | | UN | UN | | | M |
| LC | Bioch | 30-(19)-Bc-Sq | A408175 | | | SCC | | 1 | UN | | | M |
| LC | Bioch | 31-(78)-Bc-Sq | A607125 | | | SCC | | 2 | UN | | | M |
| LC | Bioch | 32-(16)-Bc-Sq | A409091 | | | SCC | | 2 | UN | | | F |
| LC | Bioch | 33-(80)-Bc-Sq | A609163 | | | SCC | | 2 | UN | | | M |
| LC | Bioch | 34-(18)-Bc-Sq | A503387 | | | SCC | | 2-3 | UN | | | M |
| LC | Bioch | 35-(81)-Bc-Sq | A609076 | | | SCC | | 3 | UN | | | M |
| LC | Bioch | 82-(21)-Bc-Sq | A503187 | | | SCC | | 2 | UN | | | M |
| LC | Bioch | 83-(17)-Bc-Sq | A503183 | | | SCC | | 2 | UN | | | M |
| LC | Bioch | 84-(79)-Bc-Sq | A609018 | | | SCC | | 3 | UN | | | M |
| LC | Bioch | 85-(22)-Bc-Sq | A503386 | | | SCC | | UN | UN | | | M |
| LC | Bioch | 86-(20)-Bc-Sq | A501121 | | | SCC | | UN | UN | | | M |
| LC | Bioch | 87-(88)-Bc-Sq | A609219 | | | SCC | | UN | UN | | | M |
| LC | Bioch | 88-(100)-Bc-Sq | A409017 | | | SCC | | UN | UN | | | M |
| LC | Ichilov | 89-(24)-Ic-Sq | CG-123 | | | SCC | | UN | UN | | | M |
| LC | GCI | 36-GC-LCC-SIA | AF8AL | AF8ALAAL | | LCC | | | | IA | 85 | M |
| LC | GCI | 37-GC-LCC-SIB | O62XU | O62XUA1X | | LCC | | | | IB | 75 | F |
| LC | GCI | 38-GC-LCC-SIB | OLOIM | OLOIMAS1 | | LCC | | | | IB | 70 | M |
| LC | GCI | 39-GC-LCC-SIIB | 1ZWSV | 1ZWSVAB9 | | LCC | | | | IIB | 50 | M |
| LC | GCI | 40-GC-LCC-SIIB | 2YHOD | 2YHODA1H | | LCC | NSCC . . . | | | IIB | 95 | M |
| LC | GCI | 41-GC-LCC-SIIB | 38B4D | 38B4DAQK | | LCC | | | | IIB | 90 | F |
| LC | Bioch | 90-(39)-Bc-LCC | A504114 | | | LCC | | UN | UN | | | F |
| LC | Bioch | 91-(87)-Bc-LCC | A609165 | | | LCC | | 3 | UN | | | F |
| LC | Bioch | 92-(38)-Bc-LCC | A504113 | | | LCC | | UN | UN | | | M |
| LC | Bioch | 93-(82)-Bc-LCC | A609170 | | | LCNC | | UN | UN | | | M |
| LC | GCI | 42-GC-SCC-SIB | QPJQL | QPJQLAF6 | | SMCC | NC | 3 | | IB | 65 | F |
| LC | Bioch | 43-(32)-Bc-SCC | A501391 | | | SMCC | | | UN | | | M |
| LC | Bioch | 44-(30)-Bc-SCC | A501389 | | | SMCC | | 3 | UN | | | M |
| LC | Bioch | 45-(83)-Bc-SCC | A609162 | | | SMCC | | UN | UN | | | F |
| LC | Bioch | 46-(86)-Bc-SCC | A608032 | | | SMCC | | 3 | UN | | | F |
| LC | Bioch | 47-(31)-Bc-SCC | A501390 | | | SMCC | | | UN | | | F |
| LC | Bioch | 48-(84)-Bc-SCC | A609167 | | | SMCC | | UN | UN | | | F |
| LC | Bioch | 49-(85)-Bc-SCC | A609169 | | | SMCC | | UN | UN | | | M |
| LC | Bioch | 50-(33)-Bc-SCC | A504115 | | | SMCC | | | UN | | | M |
| LN | Aster | 51-As-N-PS | 9078 | 9275 | 9275B1 | Norm-L | PS | | | | | M |

TABLE 3-continued

Lung cancer testing panel

| | | | | | | | | | |
|---|---|---|---|---|---|---|---|---|---|
| LN | Aster | 52-As-N-PM | 8757 | 8100 | 8100B1 | Norm-L | PM | (Right), Lobe Infe-rior | F |
| LN | Aster | 53-As-N-PM | 6692 | 6161 | 6161A1 | Norm-L | PM | | M |
| LN | Aster | 54-As-N-PM | 7900 | 7180 | 7180F1 | Norm-L | PM | | F |
| LN | Aster | 55-As-N-PM | 8771 | 8163 | 8163A1 | Norm-L | PM | (Left), Lobe Supe-rior | M |
| LN | Aster | 56-As-N-PM | 13094 | 19763 | 19763A1 | Norm-L | PM | | M |
| LN | Aster | 57-As-N-PM | 19174 | 40654 | 40654A2 | Norm-L | PM | | F |
| LN | Aster | 58-As-N-PM | 13128 | 19642 | 19642A1 | Norm-L | PM | | F |
| LN | Aster | 59-As-N-PM | 14374 | 20548 | 20548C1 | Norm-L | PM | (Right), Lobe Supe-rior | F |
| LN | Amb | 60-(99)-Am-NPM | 36856 | | | N-PM | PM | | M |
| LN | Amb | 61-(96)-Am-NPM | 36853 | | | N-PM | PM | | F |
| LN | Amb | 62-(97)-Am-NPM | 36854 | | | N-PM | PM | | M |
| LN | Amb | 63-(93)-Am-NPM | 111P0103A | | | N-PM | PM-ICH | | F |
| LN | Amb | 64-(98)-Am-NPM | 36855 | | | N-PM | PM | | F |
| LN | Bioch | 69-(91)-Bc-NPM | A607257 | | | N-P2-PM | PM | | P2 |
| LN | Bioch | 70-(90)-Bc-NPM | A608152 | | | N-P2PM | PM | | P2 |

| Tis-sue | Source/ Deliv-ery | sample name | age | Ethnic B | Smoking Status | # Cig. Per day | # of Y. Use of Tobacco | # Y. off Tobacco | Sm P Y? | Sm ppl | Dr Al | # Dr | Recov-ery Type | Cause of Death | Exc. Y. |
|---|---|---|---|---|---|---|---|---|---|---|---|---|---|---|---|
| LC | GCI | 1-GC-BAC-SIA | 63 | WCAU | Prev U. | 20 | 15 | 27 | N | . | Y | 0 | Surg | | 2001 |
| LC | GCI | 2-GC-BAC-SIB | 56 | WCAU | Prev U. | 15 | 28 | 10 | Y | 1 | Y | 6 | Surg | | 2002 |
| LC | Bioch | 72-(44)-Bc-BAC | 61 | | | | | | | | | | | | |
| LC | GCI | 4-GC-Adeno-SIA | 68 | WCAU | Nev U. | . | . | . | N | . | N | . | Surg | | 2001 |
| LC | GCI | 5-GC-Adeno-SIA | 64 | WCAU | Prev U. | 15 | 40 | 7 | Y | 1 | N | 0 | Surg | | 2003 |
| LC | GCI | 6-GC-Adeno-SIA | 58 | WCAU | Prev U. | 10 | 47 | 0 | Y | 2 | N | . | Surg | | 2004 |
| LC | GCI | 7-GC-Adeno-SIA | 65 | WCAU | Curr U. | 6 | 30 | . | Y | 1 | N | . | Surg | | 2004 |
| LC | GCI | 8-GC-Adeno-SIA | 59 | WCAU | Curr U. | 20 | 40 | . | N | . | N | . | Surg | | 2004 |
| LC | GCI | 9-GC-Adeno-SIA | 69 | WCAU | Curr U. | 30 | 52 | . | Y | 4 | N | . | Surg | | 2005 |
| LC | GCI | 10-GC-Adeno-SIA | 60 | WCAU | Curr U. | 40 | 40 | . | N | . | N | . | Surg | | 2002 |
| LC | GCI | 11-GC-Adeno-SIB | 68 | WCAU | Prev U. | 5 | 4 | 43 | N | . | N | . | Surg | | 2003 |
| LC | GCI | 12-GC-Adeno-SIB | 69 | WCAU | Curr U. | 10 | . | . | | . | N | . | Surg | | 2002 |
| LC | GCI | 13-GC-Adeno-SIIA | 62 | WCAU | Prev U. | 6 | 40 | 6 | N | . | Y | 0 | Surg | | 2004 |

TABLE 3-continued

| Lung cancer testing panel | | | | | | | | | | | | | | |
|---|---|---|---|---|---|---|---|---|---|---|---|---|---|---|
| LC | GCI | 14-GC-Adeno-SIIA | 56 | WCAU | Curr U. | 30 | 25 | . | Y | 1 | N | . | Surg | 2001 |
| LC | GCI | 15-GC-Adeno-SIIIA | 61 | WCAU | Curr U. | 30 | 36 | . | Y | 1 | N | . | Surg | 2004 |
| LC | Bioch | 16-(95)-BC-Adeno | 54 | | | | | | | | | | | |
| LC | Bioch | 17-(89)-Bc-Adeno | 62 | | | | | | | | | | | |
| LC | Bioch | 18-(76)-Bc-Adeno | 57 | | | | | | | | | | | |
| LC | Bioch | 74-(2)-Bc-Adeno | 64 | | | | | | | | | | | |
| LC | Bioch | 75-(77)-Bc-Adeno | 44 | | | | | | | | | | | |
| LC | Bioch | 76-(75)-Bc-Adeno | 65 | | | | | | | | | | | |
| LC | Bioch | 78-(13)-Bc-Adeno | 64 | | | | | | | | | | | |
| LC | Ichilov | 81-(14)-Ic-Adeno | 68 | | | | | | | | | | | |
| LC | Aster | 19-As-Sq-S0 | 67 | CAU | Curr U. | 11-20 | 31-40 | | | | O | | Surg | 2003 |
| LC | GCI | 20-GC-Sq-SIA | 68 | WCAU | Prev U. | 10 | 20 | 0 | N | . | N | . | Surg | 2004 |
| LC | GCI | 21-GC-Sq-SIB | 62 | WCAU | Prev U. | 20 | 50 | 0 | Y | 5 | N | . | Surg | 2005 |
| LC | Aster | 22-As-Sq-SIB | 73 | CAU | Prev U. | | | | | | O | | Surg | 2004 |
| LC | Aster | 23-As-Sq-SIB | 66 | CAU | Prev U. | 11-20 | 45 | | | | P | | Surg | 2005 |
| LC | Aster | 24-As-Sq-SIB | 65 | CAU | Curr U. | 6-10 | 41-50 | | | | O | | Surg | 2002 |
| LC | GCI | 25-GC-Sq-SIIB | 44 | WCAU | Prev U. | 20 | 20 | 0 | Y | 2 | N | . | Surg | 2004 |
| LC | GCI | 26-GC-Sq-SIIB | 68 | WCAU | Prev U. | 40 | 40 | 0 | Y | 2 | N | . | Surg | 2004 |
| LC | GCI | 27-GC-Sq-SIIIA | 58 | WCAU | Prev U. | 50 | 40 | 1 | Y | 2 | N | . | Surg | 2004 |
| LC | Ichilov | 29-(25)-Ic-Sq | 72 | | | | | | | | | | | |
| LC | Bioch | 30-(19)-Bc-Sq | 78 | | | | | | | | | | | |
| LC | Bioch | 31-(78)-Bc-Sq | 62 | | | | | | | | | | | |
| LC | Bioch | 32-(16)-Bc-Sq | 68 | | | | | | | | | | | |
| LC | Bioch | 33-(80)-Bc-Sq | 74 | | | | | | | | | | | |
| LC | Bioch | 34-(18)-Bc-Sq | 63 | | | | | | | | | | | |
| LC | Bioch | 35-(81)-Bc-Sq | 53 | | | | | | | | | | | |
| LC | Bioch | 82-(21)-Bc-Sq | 52 | | | | | | | | | | | |
| LC | Bioch | 83-(17)-Bc-Sq | 57 | | | | | | | | | | | |
| LC | Bioch | 84-(79)-Bc-Sq | 67 | | | | | | | | | | | |
| LC | Bioch | 85-(22)-Bc-Sq | 48 | | | | | | | | | | | |
| LC | Bioch | 86-(20)-Bc-Sq | 64 | | | | | | | | | | | |
| LC | Bioch | 87-(88)-Bc-Sq | 64 | | | | | | | | | | | |
| LC | Bioch | 88-(100)-Bc-Sq | 64 | | | | | | | | | | | |
| LC | Ichilov | 89-(24)-Ic-Sq | 76 | | | | | | | | | | | |
| LC | GCI | 36-GC-LCC-SIA | 45 | WCAU | Prev U. | 45 | 33 | 0 | Y | 2 | Y | 28 | Surg | 2004 |
| LC | GCI | 37-GC-LCC-SIB | 60 | WCAU | Prev U. | 30 | 45 | 0 | Y | 3 | N | . | Surg | 2004 |
| LC | GCI | 38-GC-LCC-SIB | 68 | WCAU | Prev U. | . | 55 | . | Y | . | N | . | Surg | 2001 |
| LC | GCI | 39-GC-LCC-SIIB | 51 | WCAU | Prev U. | 20 | 12 | 22 | Y | 1 | N | . | Surg | 2004 |

TABLE 3-continued

| Lung cancer testing panel | | | | | | | | | | | | | | | |
|---|---|---|---|---|---|---|---|---|---|---|---|---|---|---|---|
| LC | GCI | 40-GC-LCC-SIIB | 62 | WCAU | Prev U. | 40 | 40 | 0 | Y | 2 | Y | 12 | Surg | | 2004 |
| LC | GCI | 41-GC-LCC-SIIB | 70 | WCAU | Prev U. | 30 | 50 | . | Y | 2 | Y | 13 | Surg | | 2002 |
| LC | Bioch | 90-(39)-Bc-LCC | 35 | | | | | | | | | | | | |
| LC | Bioch | 91-(87)-Bc-LCC | 47 | | | | | | | | | | | | |
| LC | Bioch | 92-(38)-Bc-LCC | 58 | | | | | | | | | | | | |
| LC | Bioch | 93-(82)-Bc-LCC | 68 | | | | | | | | | | | | |
| LC | GCI | 42-GC-SCC-SIB | 62 | WCAU | Prev U. | 20 | 35 | 0.15 | Y | 2 | N | . | Surg | | 2003 |
| LC | Bioch | 43-(32)-Bc-SCC | 30 | | | | | | | | | | | | |
| LC | Bioch | 44-(30)-Bc-SCC | 34 | | | | | | | | | | | | |
| LC | Bioch | 45-(83)-Bc-SCC | 47 | | | | | | | | | | | | |
| LC | Bioch | 46-(86)-Bc-SCC | 52 | | | | | | | | | | | | |
| LC | Bioch | 47-(31)-Bc-SCC | 59 | | | | | | | | | | | | |
| LC | Bioch | 48-(84)-Bc-SCC | 59 | | | | | | | | | | | | |
| LC | Bioch | 49-(85)-Bc-SCC | 66 | | | | | | | | | | | | |
| LC | Bioch | 50-(33)-Bc-SCC | | | | | | | | | | | | | |
| LN | Aster | 51-As-N-PS | 22 | CAU | Nev U. | | | | | | NU | | Surg | | 2003 |
| LN | Aster | 52-As-N-PM | 26 | CAU | Nev U. | | | | | | O | | Aut | CA | 2003 |
| LN | Aster | 53-As-N-PM | 37 | CAU | Nev U. | | | | | | C | | Aut | MCE | 2002 |
| LN | Aster | 54-As-N-PM | 76 | CAU | Prev U. | | | | | | | | Aut | CPul A | 2002 |
| LN | Aster | 55-As-N-PM | 81 | CAU | Prev U. | 41 or more | 31-40 | | | | O | | Aut | CA | 2003 |
| LN | Aster | 56-As-N-PM | 0 | CAU | Prev U. | 21-40 | 41-50 | | | | P | | Aut | IC | |
| LN | Aster | 57-As-N-PM | 69 | CAU | Curr U. | 21-40 | 31-40 | | | | P | | Aut | CPul A | 2005 |
| LN | Aster | 58-As-N-PM | 75 | CAU | | | | | | | | | Aut | CPul A | 2004 |
| LN | Aster | 59-As-N-PM | 75 | CAU | | | | | | | | | Aut | Cer A | 2004 |
| LN | Amb | 60-(99)-Am-NPM | 31 | | | | | | | | | | | | |
| LN | Amb | 61-(96)-Am-NPM | 43 | | | | | | | | | | | | |
| LN | Amb | 62-(97)-Am-NPM | 46 | | | | | | | | | | | | |
| LN | Amb | 63-(93)-Am-NPM | 61 | | | | | | | | | | | | |
| LN | Amb | 64-(98)-Am-NPM | 72 | | | | | | | | | | | | |
| LN | Bioch | 69-(91)-Bc-NPM | 24, 29 | | | | | | | | | | | | |
| LN | Bioch | 70-(90)-Bc-NPM | 27, 28 | | | | | | | | | | | | |

TABLE 3_1

| Key | Full Name |
|---|---|
| # Cig. Per day | Number of Cigarettes per day |
| # Dr | Number of Drinks |
| # of Y. Use of Tobacco | Number of Years Using Tobacco |
| # Y. off Tobacco | Number of Years Off Tobacco |
| AC | Alveolus carcinoma |
| Aden | ADENOCARCINOMA |
| Amb | Ambion |
| Aster | Asterand |

TABLE 3_1-continued

| Key | Full Name |
|---|---|
| Aut | Autopsy |
| BC | BRONCHIOLOALVEOLAR CARCINOMA |
| Bioch | Biochain |
| C | Current Use |
| CA | Cardiac arrest |
| CAU | Caucasian |
| Cer A | Cerebrovascular accident |
| CPul A | Cardiopulmonary arrest |

TABLE 3_1-continued

| Key | Full Name |
|---|---|
| CS | Cancer Stage |
| Curr U. | Current Use |
| Diag | Diagnosis |
| Dr Al | Drink Alcohol? |
| Exc Y. | Excision Year |
| Gen | Gender |
| Gr | Grade |
| Height | HT |
| IC | Ischemic cardiomyopathy |
| LC | Lung Cancer |
| LCC | LARGE CELL CARCINOMA |
| LCNC | Large Cell Neuroendocrine Carcinoma |
| LN | Lung Normal |
| MCE | Massive cerebral edema |
| N | No |
| NC | NEUROENDOCRINE CARCINOMA |
| Nev. U. | Never Used |
| Norm-L | Normal Lung |
| N-P2-PM | Normal (Pool 2)-PM |
| N-PM | Normal-PM |

TABLE 3_1-continued

| Key | Full Name |
|---|---|
| NSCC... | NON-SMALL CELL CARCINOMA WITH SARCOMUTOUS TRANSFORMTAIO |
| NU | Never Used |
| O | Occasional Use |
| P | Previous Use |
| P2 | Pool 2 |
| Prev U. | Previous Use |
| SCC | Squamous Cell Carcinoma |
| Sm P Y? | Have people at home smoked in past 15 yr |
| Sm ppl | If yes, how many? |
| SMCC | SMALL CELL CARCINOMA |
| SMOKE_GROWN G_UP | Did people smoke at home while growing up |
| Surg | Surgical |
| Tum % | Tumor Percentage |
| WCAU | White Caucasian |
| Y | Yes |

TABLE 4

Tissue samples in ovary panel

| Tissue | Source/ Delivery | sample name | sample__id (GCI)/ case id (Asterand)/ lot no. (old samples) | RNA ID (GCI)/ Sample ID (Asterand) | Diag | C Stage | Tumor % | age | Ethnic BG | CA 125 PRE | Meno-pausal Status | Mens Age |
|---|---|---|---|---|---|---|---|---|---|---|---|---|
| OVC | Asterand | 1-As-Ser SI | 23074 | 71900A2 | SA | I | 80 | 49 | CAU | | Pre-M | |
| OVC | Asterand | 2-As-Ser SI | 22653 | 70270A1 | SA | I | 90 | 69 | WCAU | | Post-M | |
| OVC | Asterand | 3-As-Ser SIB | 18700 | 40771B1 | SA | IB | 100 | 62 | WCAU | | Post-M | |
| OVC | GOG | 79-(32)-GO-Ser SIB | 93-09-4901 | | SPC | 1B | | 67 | | | | |
| OVC | Asterand | 4-As-Ser SIB | 17646 | 32667B1 | SA | IB | 100 | 68 | W | | Post-M | |
| OVC | Asterand | 5- As-Ser SIC | 15644 | 22996A1 | SA | IC | 100 | 48 | CAU | | M | |
| OVC | Asterand | 6-As-Ser SIIA | 18701 | 40773C1 | SA | IIA | 100 | 59 | CAU | | Post-M | |
| OVC | GCI | 7-GC-Ser SIIB | 2O37O | | SA | IIB | 75 | 43 | WCAU | . | Pre-M | 12 |
| OVC | GCI | 8-GC-Ser SIIB | 7B3DP | | SA | IIB | 70 | 70 | WCAU | . | Post-M | 14 |
| OVC | GOG | 80-(30)-GO-Ser SIIIA | 2001-08-G011 | | PSC | 3A | | 72 | | | | |
| OVC | GOG | 81-(70)-GO-Ser SIIIB | 95-08-G069 | | PSA | 3B | | 50 | | | | |
| OVC | GOG | 82-(5)-GO-Ser SIIIC | 99-12-G432 | | A | 3C | | 46 | | >500 | | |
| OVC | Asterand | 9-As-Ser SIIIC | 13268 | 19832A1 | SA | IIIC | 90 | 48 | C | | Post-M | |
| OVC | GOG | 83-(29)-GO-Ser SIIIC | 2001-12-G035 | | SA | 3C | | 50 | | 260 | | |
| OVC | GCI | 10-GC-Ser SIIIC | 3NTIS | | SA | IIIC | 70 | 53 | WCAU | 70 | Post-M | 12 |
| OVC | GCI | 11-GC-Ser SIIIC | CEJUS | | SA | IIIC | 70 | 53 | WCAU | 4814 | Pre-M | . |
| OVC | GCI | 12-GC-Ser SIIIC | 5NCLK | | SA | IIIC | 70 | 54 | WCAU | 209 | Post-M | 13 |
| OVC | ABS | 84-(25)-AB-Ser SIIIC | N0021 | | PSA | 3C | | 55 | CAU | | | |

TABLE 4-continued

Tissue samples in ovary panel

| | | | | | | | | | | | |
|---|---|---|---|---|---|---|---|---|---|---|---|
| OVC | GCI | 13-GC-Ser SIIIC | 1HI5H | SA | IIIC | 90 | 61 | WCAU | 34 | Post-M | 12 |
| OVC | GCI | 14-GC-Ser SIIIC | 7RMHZ | SA | IIIC | 80 | 63 | WCAU | . | Post-M | 12 |
| OVC | GCI | 15-GC-Ser SIIIC | 4WAAB | SA | IIIC | 90 | 63 | WCAU | . | Post-M | 11 |
| OVC | GCI | 16-GC-Ser SIIIC | 79Z67 | SA | IIIC | 85 | 67 | WCAU | . | Post-M | 12 |
| OVC | GOG | 85-(13)-GO-Ser SIIIC | 94-05-7603 | APP | 3C | | 67 | | | | |
| OVC | GCI | 17-GC-Ser SIIIC | DDSNL | SA | IIIC | 70 | 68 | WCAU | . | Post-M | 11 |
| OVC | GCI | 18-GC-Ser SIV | DH8PH | SA | IV | 95 | 70 | WCAU | . | Post-M | 13 |
| OVC | BioChain | 86-(33)-BC-Ser | A503175 | SPC | | | 41 | Asian | | | |
| OVC | BioChain | 87-(14)-Bc-Ser | A501111 | A | | | 41 | Asian | | | |
| OVC | Biochain | 88-(12)-Bc-Ser | A406023 | A | | | 45 | Asian | | | |
| OVC | Biochain | 89-(11)-Bc-Ser | A407068 | A | | | 49 | Asian | | | |
| OVC | ABS | 90-(4)-AB-Ser | ILS-7286 | PC | UN | | 50 | Asian | | | |
| OVC | ABS | 91-(6)-AB-Ser | A0106 | A | UN | | 51 | Asian | | | |
| OVC | ABS | 92-(3)-AB-Ser | ILS-1431 | PA | UN | | 52 | Asian | | | |
| OVC | BioChain | 93-(31)-Bc-Ser | A503176 | SPC | | | 52 | Asian | | | |
| OVC | ABS | 94-(2)-AB-Ser | ILS-1408 | PA | UN | | 53 | Asian | | | |
| OVC | ABS | 95-(7)-AB-Ser | IND-00375 | A | | | 59 | Asian | | | |
| OVC | BioChain | 96-(8)-Bc-Ser | A501113 | A | | | 60 | Asian | | | |
| OVC | Biochain | 97-(10)-Bc-Ser | A407069 | A | | | 60 | Asian | | | |
| OVC | ABS | 98-(1)-AB-Ser | ILS-1406 | PA | UN | | 73 | Asian | | | |
| OVC | GCI | 19-GC-Endo SIA | E2WKF | EA | IA | 70 | 30 | WCAU | . | Pre-M | 12 |
| OVC | GCI | 20-GC-Endo SIA | 5895C | EA | IA | 95 | 39 | WCAU | . | Pre-M | 14 |
| OVC | GCI | 21-GC-Endo SIA | 533DX | EA | IA | 95 | 50 | WCAU | 190 | Pre-M | 11 |
| OVC | GCI | 22-GC-Endo SIA | HZ2EY | EA | IA | 90 | 55 | WCAU | 1078 | Pre-M | 13 |
| OVC | GCI | 23-GC-Endo SIA | RWOIV | EA | IA | 65 | 47 | WCAU | 1695 | Pre-M | 14 |
| OVC | GCI | 24-GC-Endo SIIA | 1U52X | EA | IIA | 95 | 61 | WCAU | 275 | | . |
| OVC | GCI | 25-GC-Endo SIIB | A17WS | EA | IIB | 70 | 67 | WCAU | 78 | Post-M | 14 |
| OVC | GCI | 26-GC-Endo SIIIC | 1VT3I | EA | IIIC | 90 | 50 | WCAU | . | Pre-M | 12 |
| OVC | GCI | 27-GC-Endo SIIIC | PZQXH | EA | IIIC | 80 | 52 | WCAU | . | Pre-M | 11 |
| OVC | GCI | 28-GC-Endo SIV | I8VHZ | EA | IV | 90 | 68 | WCAU | . | Post-M | . |
| OVC | GOG | 99-(41)-GO-Ser Mix SII | 98-03-G803 | Mixed . . . | 2 | | 38 | | >35 | | |
| OVC | GOG | 100-(40)-GO-Ser Mix SIIIC | 95-11-G006 | PS & EC | 3C | | 49 | | | | |
| OVC | GOG | 101-(37)-GO-Ser Mix SIIIC | 2002-05-G513 | MS & EA | 3C | | 56 | | | | |
| OVC | GOG | 102-(38)-GO-Ser Mix SIIIC | 2002-05-G509 | MS & EAM | 3C | | 64 | | | | |
| OVC | GOG | 103-(34)-GO-Ser Mix SIIIC | 95-04-2002 | PEA | 3C | | 68 | | | | |

TABLE 4-continued

Tissue samples in ovary panel

| | | | | | | | | | | | | |
|---|---|---|---|---|---|---|---|---|---|---|---|---|
| OVC | GOG | 29-(21)-GO-Muc SIA | 95-10-G020 | | MC | IA | | 44 | | | >100 | |
| OVC | GCI | 30-GC-Muc SIC | IMDA1 | | MA | IC | 70 | 41 | WCAU | 50 | Pre-M | 12 |
| OVC | Asterand | 31-As-Muc SIC | 12742 | 18920A1 | MA | IC | 70 | 61 | C | | Post-M | |
| OVC | ABS | 32-(22)-AB-Muc SIC | A0139 | | MC | IC | | 72 | Asian | | | |
| OVC | GCI | 33-GC-Muc SIIA | NJM4U | | MA | IIA | 80 | 51 | WCAU | | | |
| OVC | ABS | 34-(20)-AB-Muc SIIIA | USA-00273 | | PMC | IIIA | | 45 | C | | | |
| OVC | GCI | 35-GC-Muc SIIIA | RAFCW | | MA | IIIA | 75 | 55 | WCAU | 95 | Post-M | 13 |
| OVC | Asterand | 36-As-Muc SIIIC | 23177 | 72888A1 | MA | IIIC | 60 | 52 | C | | Pre-M | |
| OVC | Asterand | 37-As-Muc SIIIC | 16103 | 29374B1 | MA | IIIC | 100 | 62 | W | | Post-M | |
| OVC | BioChain | 104-(19)-Bc-Muc | A504085 | | MA | | | 34 | Asian | | | |
| OVC | BioChain | 105-(18)-Bc-Muc | A504083 | | MA | | | 45 | Asian | | | |
| OVC | BioChain | 106-(17)-Bc-Muc | A504084 | | MA | | | 51 | Asian | | | |
| OVC | BioChain | 107-(15)-Bc-Car | A407065 | | C | | | 27 | Asian | | | |
| OVC | Clontech | 108-(16)-Cl-Car | 1090387 | | CNOS | | | 58 | Asian | | | |
| OVC | GOG | 109-(44)-GO-Clear cell SIA | 2001-07-G084 | | CCA | 1A | | 73 | | | | |
| OVC | GOG | 110-(43)-GO-Clear cell SIIIA | 2001-10-G002 | | CCA | 3A | | 74 | | slightly elevated | | |
| OVC_BT | GCI | 38-GC-Muc Border SIA | SC656 | | MBT | IA | 75 | 40 | WCAU | 138 | Pre-M | 13 |
| OVC_BT | GCI | 39-GC-Muc Border SIA | 3D5FO | | MBT | IA | 85 | 51 | WCAU | 19 | ? | 15 |
| OVC_BT | GCI | 40-GC-Muc Border SIA | 7JP3F | | MBT | IA | 75 | 56 | WCAU | 125 | Post-M | 14 |
| OVC_BT | ABS | 111-(23)-AB-Border | VNM-00187 | | MC Low M | | | 45 | Asian | | | |
| OVC_BT | GOG | 112-(42)-GO-Border SIA | 98-08-G001 | | EA of BM | 1A | | 46 | | | | |
| OVC_B | GOG | 41-(62)-Go-Ben Muc | 99-10-G442 | | BMC | | | 32 | | 6 | | |
| OVC_B | GCI | 43-GC-Ben Muc | QLIKY | | BMC | | 100 | 42 | WCAU | | | |
| OVC_B | Asterand | 44-As-Ben Muc | 16870 | 30534A1 | BMC | | 100 | 45 | W | | Pre-M | |
| OVC_B | GOG | 45-(56)-GO-Ben Muc | 99-01-G407 | | BMC | | | 46 | | | | |
| OVC_B | GCI | 46-GC-Ben Muc | 943EC | | BMC | | 75 | 54 | WCAU | | | |
| OVC_B | GCI | 47-GC-Ben Muc | JO8W7 | | BMC | | 50 | 56 | WCAU | | | |
| OVC_B | Asterand | 48-As-Ben Ser | 17016 | 30645B1 | BSC | IA | 100 | 38 | C | | Pre-M | |
| OVC_B | GOG | 49-(64)-GO-Ben Ser | 99-06-G039 | | BSC | | | 57 | | | | |
| OVC_B | GCI | 50-GC-Ben Ser | DQQ2F | | BSCF | | 95 | 68 | WCAU | | | |
| OVC_B | Asterand | 51-As-Ben Ser | 8786 | 8275A1 | BSC | | 100 | 80 | CAU | | Post-M | |
| OVC_NBM | Asterand | 52-As-NBM | 15690 | 23054A1 | NO-BM | | | 52 | CAU | | Pre-M | |
| OVC_NBM | Asterand | 53-As-NBM | 16843 | 30488A1 | NO-BM | | | 57 | W | | Post-M | |

TABLE 4-continued

Tissue samples in ovary panel

| | | | | | | | | | |
|---|---|---|---|---|---|---|---|---|---|
| OVC_NBM | Asterand | 54-As-NBM | 16850 | 30496B1 | NO-BM | | 65 | W | Post-M |
| OVC_NBM | Asterand | 55-As-NBM | 16848 | 30499C1 | NO-BM | | 66 | CAU | Post-M |
| OVC_N | GCI | 56-GC-NPS | WPU1U | | NO-PS | 0 | 32 | WC | |
| OVC_N | GCI | 57-GC-NPS | Y9VHI | | NO-PS | 0 | 35 | WCAU | |
| OVC_N | GCI | 58-GC-NPS | 76VM9 | | NO-PS | 0 | 41 | WCAU | |
| OVC_N | GCI | 59-GC-NPS | DWHTZ | | NO-PS | 0 | 42 | WCAU | |
| OVC_N | GCI | 60-GC-NPS | SJ2R2 | | NO-PS | 0 | 43 | WCAU | |
| OVC_N | GCI | 61-GC-NPS | 9RQMN | | NO-PS | 0 | 45 | WCAU | |
| OVC_N | GCI | 62-GC-NPS | TOAE5 | | NO-PS | 0 | 45 | WCAU | |
| OVC_N | GCI | 63-GC-NPS | TW9PM | | NO-PS | 0 | 46 | WCAU | |
| OVC_N | GCI | 64-GC-NPS | 2VND2 | | NO-PS | 0 | 46 | WCAU | |
| OVC_N | GCI | 65-GC-NPS | L629F | | NO-PS | 0 | 47 | WCAU | |
| OVC_N | GCI | 66-GC-NPS | XLB23 | | NO-PS | 0 | 47 | WCAU | |
| OVC_N | GCI | 67-GC-NPS | IDUVY | | NO-PS | 0 | 47 | WCAU | |
| OVC_N | GCI | 68-GC-NPS | ZCXAD | | NO-PS | 0 | 48 | WCAU | |
| OVC_N | GCI | 69-GC-NPS | PEQ6C | | NO-PS | 0 | 49 | WCAU | |
| OVC_N | GCI | 70-GC-NPS | DD73B | | NO-PS | 0 | 49 | WCAU | |
| OVC_N | GCI | 71-GC-NPS | E2UF7 | | NO-PS | 0 | 53 | WCAU | |
| OVC_N | GCI | 72-GC-NPS | GWXUZ | | NO-PS | 0 | 53 | WCAU | |
| OVC_N | GCI | 73-GC-NPS | 4YG5P | | NO-PS | 0 | 55 | WCAU | |
| OVC_N | GCI | 74-GC-NPS | FDPL9 | | NO-PS | 0 | 56 | WCAU | |
| OVC_N | BioChain | 75-(45)-Bc-NPM | A503274 | | NO-PM | | 41 | Asian | |
| OVC_N | BioChain | 76-(46)-Bc-NPM | A504086 | | NO-PM | | 41 | Asian | |
| OVC_N | Ichilov | 77-(71)-Ic-NPM | CG-188-7 | | NO-PM | | 49 | | |
| OVC_N | BioChain | 78-(48)-Bc-NPM | A504087 | | NO-PM | | 51 | Asian | |

| Tissue | Source/Delivery | sample name | Preg Times | Preg Toterm | Age at first child | OC | Oral Con Length | Oral Con Unit | Tubal ligation | Recovery Type |
|---|---|---|---|---|---|---|---|---|---|---|
| OVC | Asterand | 1-As-Ser SI | 2 | 1 | | | | | | Surg |
| OVC | Asterand | 2-As-Ser SI | 1 | 1 | | | | | | Surg |
| OVC | Asterand | 3-As-Ser SIB | 3 | 3 | | | | | | Surg |
| OVC | GOG | 79-(32)-GO-Ser SIB | | | | | | | | |
| OVC | Asterand | 4-As-Ser SIB | 9 | 2 | | | | | | Surg |
| OVC | Asterand | 5- As-Ser SIC | 4 | 2 | | | | | | Surg |
| OVC | Asterand | 6-As-Ser SIIA | 1 | 1 | | | | | | Surg |
| OVC | GCI | 7-GC-Ser SIIB | 0 | 0 | 0 | NO | . | | NO | Surg |
| OVC | GCI | 8-GC-Ser SIIB | 5 | 3 | 20 | YES | 6 | months | NO | Surg |
| OVC | GOG | 80-(30)-GO-Ser SIIIA | | | | | | | | |

TABLE 4-continued

Tissue samples in ovary panel

| | | | | | | | | | | |
|---|---|---|---|---|---|---|---|---|---|---|
| OVC | GOG | 81-(70)-GO-Ser SIIIB | | | | | | | | |
| OVC | GOG | 82-(5)-GO-Ser SIIIC | | | | | | | | |
| OVC | Asterand | 9-As-Ser SIIIC | | | | | | | | Surg |
| OVC | GOG | 83-(29)-GO-Ser SIIIC | | | | | | | | |
| OVC | GCI | 10-GC-Ser SIIIC | 1 | 1 | 26 | YES | 3 | months | NO | Surg |
| OVC | GCI | 11-GC-Ser SIIIC | 2 | 2 | 30 | NO | . | | NO | Surg |
| OVC | GCI | 12-GC-Ser SIIIC | 2 | 2 | 21 | YES | 1 | years | NO | Surg |
| OVC | ABS | 84-(25)-AB-Ser SIIIC | | | | | | | | |
| OVC | GCI | 13-GC-Ser SIIIC | 6 | 3 | 22 | NO | . | | NO | Surg |
| OVC | GCI | 14-GC-Ser SIIIC | 2 | 2 | 20 | YES | 10 | years | NO | Surg |
| OVC | GCI | 15-GC-Ser SIIIC | 2 | 1 | 29 | YES | 4 | years | NO | Surg |
| OVC | GCI | 16-GC-Ser SIIIC | 6 | 5 | 24 | YES | 2 | years | YES | Surg |
| OVC | GOG | 85-(13)-GO-Ser SIIIC | | | | | | | | |
| OVC | GCI | 17-GC-Ser SIIIC | 4 | 4 | 19 | NO | . | | NO | Surg |
| OVC | GCI | 18-GC-Ser SIV | 4 | 3 | 20 | NO | . | | NO | Surg |
| OVC | BioChain | 86-(33)-BC-Ser | | | | | | | | |
| OVC | BioChain | 87-(14)-Bc-Ser | | | | | | | | |
| OVC | Biochain | 88-(12)-Bc-Ser | | | | | | | | |
| OVC | Biochain | 89-(11)-Bc-Ser | | | | | | | | |
| OVC | ABS | 90-(4)-AB-Ser | | | | | | | | |
| OVC | ABS | 91-(6)-AB-Ser | | | | | | | | |
| OVC | ABS | 92-(3)-AB-Ser | | | | | | | | |
| OVC | BioChain | 93-(31)-Bc-Ser | | | | | | | | |
| OVC | ABS | 94-(2)-AB-Ser | | | | | | | | |
| OVC | ABS | 95-(7)-AB-Ser | | | | | | | | |
| OVC | BioChain | 96-(8)-Bc-Ser | | | | | | | | |
| OVC | Biochain | 97-(10)-Bc-Ser | | | | | | | | |
| OVC | ABS | 98-(1)-AB-Ser | | | | | | | | |
| OVC | GCI | 19-GC-Endo SIA | 6 | 5 | 17 | YES | 6 | years | NO | Surg |
| OVC | GCI | 20-GC-Endo SIA | 2 | 2 | 20 | NO | . | | NO | Surg |
| OVC | GCI | 21-GC-Endo SIA | 0 | . | . | YES | 2 | years | NO | Surg |
| OVC | GCI | 22-GC-Endo SIA | 0 | . | . | NO | . | | NO | Surg |
| OVC | GCI | 23-GC-Endo SIA | 0 | . | . | NO | . | | NO | Surg |
| OVC | GCI | 24-GC-Endo SIIA | . | . | . | | . | | | Surg |
| OVC | GCI | 25-GC-Endo SIIB | 0 | . | . | NO | . | | NO | Surg |
| OVC | GCI | 26-GC-Endo SIIIC | 2 | 2 | 24 | YES | 1 | years | NO | Surg |

TABLE 4-continued

Tissue samples in ovary panel

| | | | | | | | | | | |
|---|---|---|---|---|---|---|---|---|---|---|
| OVC | GCI | 27-GC-Endo SIIIC | 0 | . | . | YES | 5 | years | NO | Surg |
| OVC | GCI | 28-GC-Endo SIV | 2 | 2 | 27 | NO | . | | NO | Surg |
| OVC | GOG | 99-(41)-GO-Ser Mix SII | | | | | | | | |
| OVC | GOG | 100-(40)-GO-Ser Mix SIIIC | | | | | | | | |
| OVC | GOG | 101-(37)-GO-Ser Mix SIIIC | | | | | | | | |
| OVC | GOG | 102-(38)-GO-Ser Mix SIIIC | | | | | | | | |
| OVC | GOG | 103-(34)-GO-Ser Mix SIIIC | | | | | | | | |
| OVC | GOG | 29-(21)-GO-Muc SIA | | | | | | | | |
| OVC | GCI | 30-GC-Muc SIC | 2 | 1 | 24 | NO | . | | | Surg |
| OVC | Asterand | 31-As-Muc SIC | 3 | 3 | | | | | | Surg |
| OVC | ABS | 32-(22)-AB-Muc SIC | | | | | | | | |
| OVC | GCI | 33-GC-Muc SIIA | | | | | | | | Surg |
| OVC | ABS | 34-(20)-AB-Muc SIIIA | | | | | | | | |
| OVC | GCI | 35-GC-Muc SIIIA | 4 | 3 | 22 | NO | . | | NO | Surg |
| OVC | Asterand | 36-As-Muc SIIIC | | | | | | | | Surg |
| OVC | Asterand | 37-As-Muc SIIIC | 1 | 1 | | | | | | Surg |
| OVC | BioChain | 104-(19)-Bc-Muc | | | | | | | | |
| OVC | BioChain | 105-(18)-Bc-Muc | | | | | | | | |
| OVC | BioChain | 106-(17)-Bc-Muc | | | | | | | | |
| OVC | BioChain | 107-(15)-Bc-Car | | | | | | | | |
| OVC | Clontech | 108-(16)-Cl-Car | | | | | | | | |
| OVC | GOG | 109-(44)-GO-Clear cell SIA | | | | | | | | |
| OVC | GOG | 110-(43)-GO-Clear cell SIIIA | | | | | | | | |
| OVC_BT | GCI | 38-GC-Muc Border SIA | 2 | 2 | 23 | NO | . | | YES | Surg |
| OVC_BT | GCI | 39-GC-Muc Border SIA | 0 | . | . | NO | . | | NO | Surg |
| OVC_BT | GCI | 40-GC-Muc Border SIA | 3 | 3 | 19 | YES | 5 | years | NO | Surg |
| OVC_BT | ABS | 111-(23)-AB-Border | | | | | | | | |
| OVC_BT | GOG | 112-(42)-GO-Border SIA | | | | | | | | |
| OVC_B | GOG | 41-(62)-Go-Ben Muc | | | | | | | | |
| OVC_B | GCI | 43-GC-Ben Muc | | | | | | | | Surg |
| OVC_B | Asterand | 44-As-Ben Muc | 2 | 2 | | | | | | Surg |

TABLE 4-continued

Tissue samples in ovary panel

| | | | | | |
|---|---|---|---|---|---|
| OVC_B | GOG | 45-(56)-GO-Ben Muc | | | |
| OVC_B | GCI | 46-GC-Ben Muc | | | Surg |
| OVC_B | GCI | 47-GC-Ben Muc | | | Surg |
| OVC_B | Asterand | 48-As-Ben Ser | 2 | 2 | Surg |
| OVC_B | GOG | 49-(64)-GO-Ben Ser | | | |
| OVC_B | GCI | 50-GC-Ben Ser | | | Surg |
| OVC_B | Asterand | 51-As-Ben Ser | 10 | 9 | Surg |
| OVC_NBM | Asterand | 52-As-NBM | 10 | 3 | Surg |
| OVC_NBM | Asterand | 53-As-NBM | 4 | 2 | Surg |
| OVC_NBM | Asterand | 54-As-NBM | 2 | 2 | Surg |
| OVC_NBM | Asterand | 55-As-NBM | 9 | 2 | Surg |
| OVC_N | GCI | 56-GC-NPS | | | Surg |
| OVC_N | GCI | 57-GC-NPS | | | Surg |
| OVC_N | GCI | 58-GC-NPS | | | Surg |
| OVC_N | GCI | 59-GC-NPS | | | Surg |
| OVC_N | GCI | 60-GC-NPS | | | Surg |
| OVC_N | GCI | 61-GC-NPS | | | Surg |
| OVC_N | GCI | 62-GC-NPS | | | Surg |
| OVC_N | GCI | 63-GC-NPS | | | Surg |
| OVC_N | GCI | 64-GC-NPS | | | Surg |
| OVC_N | GCI | 65-GC-NPS | | | Surg |
| OVC_N | GCI | 66-GC-NPS | | | Surg |
| OVC_N | GCI | 67-GC-NPS | | | Surg |
| OVC_N | GCI | 68-GC-NPS | | | Surg |
| OVC_N | GCI | 69-GC-NPS | | | Surg |
| OVC_N | GCI | 70-GC-NPS | | | Surg |
| OVC_N | GCI | 71-GC-NPS | | | Surg |
| OVC_N | GCI | 72-GC-NPS | | | Surg |
| OVC_N | GCI | 73-GC-NPS | | | Surg |
| OVC_N | GCI | 74-GC-NPS | | | Surg |
| OVC_N | BioChain | 75-(45)-Bc-NPM | | | |
| OVC_N | BioChain | 76-(46)-Bc-NPM | | | |
| OVC_N | Ichilov | 77-(71)-Ic-NPM | | | |
| OVC_N | BioChain | 78-(48)-Bc-NPM | | | |

TABLE 4_1

| Key | Full Name |
|---|---|
| A | Adenocarcinoma |
| APP | Adenocarcinoma from primary peritioneal |
| BMC | BENIGN MUCINOUS CYSTADENOMA |
| BSC | BENIGN SEROUS CYSTADENOMA |
| BSCF | BENIGN SEROUS CYSTADENOFIBROMA |
| C | Carcinoma |
| C Stage | Cancer stage |
| CAU | Caucasian |
| CCA | Clear cell adenocarcinoma |
| CNOS | Carcinoma NOS |
| EA | ENDOMETROID ADENOCARCINOMA |
| EA of BM | Endometroid adenocarcinoma of borderline malignancy |
| M | Menopausal |
| MA | MUCINOUS ADENOCARCINOMA |
| MBT | MUCINOUS BORDERLINE TUMOR |
| MC | Mucinous cystadenocarcinoma |
| MC Low M | Mucinous cystadenocarcinoma with low malignant |
| Mens. Age | Mestrual Age |
| Mixed . . . | Mixed epithelial cystadenocarcinoma with mucinous, endometroid, squamous and papillary serous |
| MS & EA | Mixed serous and endometrioid adenocarcinoma |
| MS & EAM | Mixed serous and endometrioid adenocarcinoma of mullerian |

TABLE 4_1-continued

| Key | Full Name |
|---|---|
| NO-BM | NORMAL OVARY-BM |
| NO-PM | NORMAL OVARY-PM |
| NO-PS | NORMAL OVARY-PS |
| OC | Oral Contraceptive |
| OVC | Ovary Cancer |
| OVC_B | Ovary Benign |
| OVC_BT | Ovary Borderline Tumor |
| OVC_N | Ovary Normal |
| OVC_N BM | Ovary normal-benign matched |
| PA | Papillary adenocarcinoma |
| PC | Papillary cystadenocarcinoma |
| PEA | Papillary endometriod adenocarcinoma |
| PMC | Papillary mucinous cystadenocarcinoma |
| Post-M | Post-menopausal |
| Pre-M | Pre-menopausal |
| PS & EC | Papillary serous and endometrioid cystadenocarcinoma |
| PSA | Papillary serous adenocarcinoma |
| PSC | Papillary serous carcinoma |
| SA | SEROUS ADENOCARCINOMA |
| SPC | Serous papillary cystadenocarcinoma |
| W | White |
| WCAU | WHITE/CAUCASIAN |

TABLE 5

Colon cancer testing panel

| Tissue | Source/Delivery | sample name | sample_id (GCI)/case id (Asterand)/lot no. (old samples | TISSUE ID (GCI)/specimen ID (Asterand) | Sample ID (Asterand) | Diag | Diag remarks | Specimen location | Gr | TNM | CS | CS2 |
|---|---|---|---|---|---|---|---|---|---|---|---|---|
| CC | Asterand | 1-As-AdenS0 | 18036 | 31312 | 31312B1 | Aden | | Cec | 3 | TXN0M0 | 0 | |
| CC | GCI | 2-GC-AdenoSI | 4QDH8 | 4QDH8ADT | | Aden | | Dis C | | | I | Duke A |
| CC | Ichilov | 3-(7)-Ic-AdenoSI | CG-235 | | | AI | | Rectum | UN | | I | Duke A |
| CC | GCI | 4-GC-AdenoSI | NTAI8 | NTAI8AOU | | Aden | | Cec | | | I | Duke B1 |
| CC | GCI | 5-GC-AdenoSI | ARA7P | ARA7PAQA | | Aden | | Ret, Low Ant | | | I | Duke B1 |
| CC | Ichilov | 6-(20)-Ic-AdenoSIIA | CG-249 | | | UA | | | 3 | | IIA | Duke B2 |
| CC | GCI | 7-GC-AdenoSIIA | AFTS6 | AFTS6AP6 | | Aden | | | | | IIA | Duke B2 |
| CC | GCI | 8-GC-AdenoSIIA | 5CYDK | 5CYDKACS | | Aden | | | | | IIA | Duke B2 |
| CC | GCI | 9-GC-AdenoSIIA | XKSLS | XKSLSAF7 | | Aden | | | | | IIA | Duke B2 |
| CC | GCI | 10-GC-AdenoSIIA | B4RU8 | B4RU8A8Q | | Aden | | | | | IIA | Duke B2 |
| CC | GCI | 11-GC-AdenoSIIA | HB8EY | HB8EYA8I | | Aden | | | | | IIA | Duke B2 |
| CC | Ichilov | 12-(22)-AdenoSII | CG-229C | | | Aden | | | 2 | | II | Duke B |
| CC | GCI | 13-GC-AdenoSIIA | X8C7X | X8C7XATL | | Aden | | | | | IIA | Duke B2 |
| CC | GCI | 14-GC-AdenoSIIA | HCP6K | HCP6KA8Z | | Aden | | | | | IIA | Duke B2. |
| CC | GCI | 15-GC-AdenoSIIA | ZX4X7 | ZX4X7AXA | | Aden | | | | | IIA | Duke B2 |
| CC | Asterand | 16-As-AdenoSIIA | 17915 | 31176 | 31176A1 | Aden | | | 2-3 | T3N0M0 | IIA | Duke B2 |

TABLE 5-continued

| Colon cancer testing panel | | | | | | | | | | | |
|---|---|---|---|---|---|---|---|---|---|---|---|
| CC | Ichilov | 17-(1)-Ic-AdenoSIIA | CG-335 | | | Aden | Cec | 2 | | IIA | Duke B2 |
| CC | Asterand | 19-As-AdenoSIIA | 12772 | 18885 | 18885A1 | Aden | rectum | 2 | T3NXM0 | IIA | Duke B2 |
| CC | GCI | 20-GC-AdenoSIIA | JFYXP | JFYXPAMP | | Aden | | | | IIA | Duke B2 |
| CC | GCI | 21-GC-AdenoSIIA | OJXW9 | OJXW9ASR | | Aden | | | | IIA | Duke B2 |
| CC | Ichilov | 22-(28)-Ic-AdenoSIIA | CG-284 | | | Aden | sigma | 2 | | IIA | Duke B2 |
| CC | Ichilov | 23-(10)-Ic-AdenoSIIA | CG-311 | | | Aden | Sig Col | 1-2 | | eIIA | Duke B2 |
| CC | Ichilov | 24-(14)-Ic-AdenoSIII | CG-222(2) | | | WP Aden | Rectum | | | III | Duke C |
| CC | Ichilov | 25-(23)-Ic-AdenoSIII | CG-282 | | | MA | sigma | UN | | III | Duke C |
| CC | GCI | 26-GC-AdenoSIII | OTPI7 | OTPI7AWY | | Aden | | | | III | Duke C2 |
| CC | GCI | 27-GC-AdenoSIII | IG9NK | IG9NKAD3 | | MA | | | | III | Duke C2 |
| CC | GCI | 28-GC-AdenoSIII | 53OM7 | 53OM7AGL | | Aden | | | | III | Duke C2 |
| CC | GCI | 29-GC-AdenoSIII | BLUW6 | BLUW6A6Y | | Aden | | | | III | Duke C2 |
| CC | GCI | 30-GC-AdenoSIII | VZ6QA | VZ6QAAFA | | Aden | RECTUM | | | III | Duke C2 |
| CC | Ichilov | 31-(6)-Ic-AdenoSIII | CG-303(3) | | | Aden | | 1-2 | | III | Duke C2. |
| CC | Ichilov | 32-(2)-Ic-AdenoSIII | CG-307 | | | Aden | Cecum | 2 | | III | Duke C2. |
| CC | Ichilov | 33-(11)-Ic-AdenoSIII | CG-337 | | | Aden | | 1-2 | | III | Duke C2. |
| CC | Asterand | 34-As-AdenoSIIIC | 18462 | 40971 | 40971A1 | TA | Sig Col | 2 | TXN2M0 | IIIC | |
| CC | Ichilov | 35-(13)-Ic-AdenoSIV | CG-290 | | | Aden | Rect Col | 2 | | IV | Duke D. |
| CC | GCI | 36-GC-AdenoSIV | 7D7QV | 7D7QVAE6 | | Aden | | | | IV | Duke D |
| CC | GCI | 37-GC-AdenoSIV | 38U4V | 38U4VAA4 | | Aden | | | | IV | Duke D |
| CC | Ichilov | 38-(9)-Ic-AdenoSIV | CG-297 | | | Aden | Rectum | 2 | | IV | Duke D. |
| CC | Ichilov | 71-(16)-Ic-Adeno | CG-278C | | | Aden | | 2 | | | UN |
| CC | Ichilov | 72-(4)-Ic-Adeno | CG-276 | | | Carc | | 3 | | | UN |
| CC | Ichilov | 73-(17)-Ic-Adeno | CG-163 | | | Aden | Rectum | 2 | | | UN |
| CC | Ichilov | 74-(5)-Ic-Adeno | CG-308 | | | Aden | Col Sig | 2 | | | UN |
| CC | Ichilov | 75-(72)-Ic-Adeno | CG-309 | | | Aden | | 3 | | | UN |
| CC | Ichilov | 76-(18)-Ic-Adeno | CG-22C | | | Aden | | UN | | | UN |
| CC | Ichilov | 78-(21)-Ic-Adeno | CG-18C | | | Aden | | UN | | | UN |
| CC | Ichilov | 79-(24)-Ic-Adeno | CG-12 | | | Aden | | UN | | | UN |

TABLE 5-continued

Colon cancer testing panel

| | | | | | | | | | | |
|---|---|---|---|---|---|---|---|---|---|---|
| CC | Ichilov | 80-(25)-Ic-Adeno | CG-2 | | | Aden | | | UN | UN |
| CC | biochain | 82-(61)-Bc-Adeno | A606258 | | | Aden, Ulcer | | | 2 | UN |
| CC | biochain | 83-(57)-Bc-Adeno | A609150 | | | Aden | | | 3 | UN |
| CC | biochain | 84-(56)-Bc-Adeno | A609148 | | | Aden | | | 2 | UN |
| CC | biochain | 85-(53)-Bc-Adeno | A609161 | | | Aden | | | 3 | UN |
| CC | biochain | 86-(54)-Bc-Adeno | A609142 | | | Aden | | | 3 | UN |
| CC | biochain | 87-(59)-Bc-Adeno | A609059 | | | Aden, Ulcer | | | 1 | UN |
| CC | biochain | 88-(60)-Bc-Adeno | A609058 | | | Aden, Ulcer | | | 2 | UN |
| CC | biochain | 89-(55)-Bc-Adeno | A609144 | | | Aden | | | 3 | UN |
| CC | biochain | 90-(58)-Bc-Adeno | A609152 | | | Aden | | | 1 | UN |
| CB | GCI | 40-GC-Ben | IG3OY | IG3OYN7S | | TS Aden | | RT Col | | |
| CB | GCI | 41-GC-Ben | GKIEY | GKIEYAV4 | | TS Aden HGD | | Prox T Col | | |
| CN | GCI | 42-GC-NPS | AGVTG | AGVTCNK7 | | NG | DIV | | | |
| CN | Asterand | 43-As-NPS | 8956 | 9153 | 9153B1 | NG | | | | |
| CN | GCI | 44-GC-NPS | IG3OY | IG3OYN7S | | NG | | RT Col | | |
| CN | GCI | 45-GC-NPS | K9OYX | K9OYXN4F | | NG | Divs w/ FDIV | LT Col | | |
| CN | Asterand | 46-As-NPS | 23024 | 74445 | 74445B1 | NG | Chr Divs | | | |
| CN | Asterand | 47-As-NPS | 23049 | 71410 | 71410B2 | NG | Chr Divs | | | |
| CN | GCI | 48-GC-NPS | G7JJX | G7JJXAX7 | | NG | Divs w/ DIV . . . | Sig Col | | |
| CN | Asterand | 49-As-NPS | 22900 | 74446 | 74446B1 | NG | AD w/AF | | | |
| CN | GCI | 50-GC-NPS | XVPZ2 | XVPZ2NDD | | NC | Div | | | |
| CN | GCI | 51-GC-NPS | CDSUV | CDSUVNR3 | | NC | CU | | | |
| CN | GCI | 52-GC-NPS | GP5KH | GP5KHAOC | | NC | Div | | | |
| CN | GCI | 53-GC-NPS | YUZNR | YUZNRNDN | | NC | Divs | Sig Col | | |
| CN | GCI | 54-GC-NPS | 28QN6 | 28QN6NI1 | | NC | TS Aden | RT Col | | |
| CN | GCI | 55-GC-NPS | GV6N8 | GV6N8NG9 | | NC | Divs, PA | | | |
| CN | GCI | 56-GC-NPS | ZJ17R | ZJ17RNIH | | NC | Tub Aden | RT Col | | |
| CN | GCI | 57-GC-NPS | 2EEBJ | 2EEBJN2Q | | NC | Div/ Chr Infl | | | |
| CN | GCI | 58-GC-NPS | 68IX5 | 68IX5N1H | | NC | Chr Div | LT Col | | |
| CN | GCI | 59-GC-NPS | 9GEGL | 9GEGLN1V | | NC | Ext Divs | Sig Col | | |
| CN | GCI | 60-GC-NPS | PKU8O | PKU8OAJ3 | | NG | Divs, Chr Div . . . | Sig Col | | |
| CN | Asterand | 61-As-NPS | 22903 | 74452 | 74452B1 | NG | MU w/ MI | | | |

TABLE 5-continued

Colon cancer testing panel

| | | | | | | | |
|---|---|---|---|---|---|---|---|
| CN | Asterand | 62-As-NPS | 16364 | 31802 | 31802B1 | NG | UC |
| CN | biochain | 63-(65)-Bc-NPM | A607115 | | | N-PM | PM |
| CN | Ambion | 64-(71)-Am-NPM | 071P10B | | | N-PM | PM |
| CN | biochain | 65-(66)-Bc-NPM | A609262 | | | N-PM | PM |
| CN | biochain | 66-(63)-Bc-NPM | A609260 | | | N-PM | PM |
| CN | biochain | 67-(62)-Bc-NPM | A608273 | | | N-PM | PM |
| CN | biochain | 68-(64)-Bc-NPM | A609261 | | | N-PM | PM |
| CN | biochain | 69-(41)-Bc-NPM | A501156 | | | N-PM | PM |
| CN | biochain | 70-(67)-Bc-NPM | A406029 + A411078 | | | N-PMP10 | PM |

| Tissue | Source/Delivery | sample name | Tumor % | Gender | age | Ethnic B | Alcohol Status | Dr. per day | Alc. Dur. | Recovery Type | Exc. Y. |
|---|---|---|---|---|---|---|---|---|---|---|---|
| CC | Asterand | 1-As-AdenS0 | 80 | F | 43 | CAU | NU | | | Auto | 2004 |
| CC | GCI | 2-GC-AdenoSI | 85 | F | 44 | WCAU | Y | 4 | | Surg | |
| CC | Ichilov | 3-(7)-Ic-AdenoSI | | F | 66 | | | | | | |
| CC | GCI | 4-GC-AdenoSI | 80 | M | 53 | WCAU | Y | | | Surg | |
| CC | GCI | 5-GC-AdenoSI | 70 | F | 70 | WCAU | Y | 0 | | Surg | |
| CC | Ichilov | 6-(20)-Ic-AdenoSIIA | | M | 36 | | | | | | |
| CC | GCI | 7-GC-AdenoSIIA | 75 | M | 39 | WCAU | N | 0 | | Surg | |
| CC | GCI | 8-GC-AdenoSIIA | 65 | M | 44 | WCAU | N | | | Surg | |
| CC | GCI | 9-GC-AdenoSIIA | 65 | M | 48 | WCAU | Y | 10 | | Surg | |
| CC | GCI | 10-GC-AdenoSIIA | 65 | F | 50 | WCAU | N | | | Surg | |
| CC | GCI | 11-GC-AdenoSIIA | 65 | M | 53 | WCAU | N | | | Surg | |
| CC | Ichilov | 12-(22)-AdenoSII | | F | 55 | | | | | | |
| CC | GCI | 13-GC-AdenoSIIA | 90 | M | 56 | WCAU | N | | | Surg | |
| CC | GCI | 14-GC-AdenoSIIA | 80 | M | 58 | WCAU | Y | 4 | | Surg | |
| CC | GCI | 15-GC-AdenoSIIA | 90 | M | 60 | WCAU | Y | 5 | | Surg | |
| CC | Asterand | 16-As-AdenoSIIA | 60 | F | 64 | CAU | occ | 1 drink/Week | 21-30 years | Auto | 2004 |
| CC | Ichilov | 17-(1)-Ic-AdenoSIIA | | F | 66 | | | | | | |
| CC | Asterand | 19-As-AdenoSIIA | 60 | F | 67 | CAU | NU | | | Surg | 2004 |
| CC | GCI | 20-GC-AdenoSIIA | 60 | F | 68 | WCAU | Y | | | Surg | |
| CC | GCI | 21-GC-AdenoSIIA | 90 | F | 69 | WCAU | N | | | Surg | |
| CC | Ichilov | 22-(28)-Ic-AdenoSIIA | | F | 72 | | | | | | |
| CC | Ichilov | 23-(10)-Ic-AdenoSIIA | | M | 88 | | | | | | |
| CC | Ichilov | 24-(14)-Ic-AdenoSIII | | F | 49 | | | | | | |

TABLE 5-continued

Colon cancer testing panel

| | | | | | | | | | | |
|---|---|---|---|---|---|---|---|---|---|---|
| CC | Ichilov | 25-(23)-Ic-AdenoSIII | | M | 51 | | | | | |
| CC | GCI | 26-GC-AdenoSIII | 70 | F | 54 | WCAU | N | | Surg | |
| CC | GCI | 27-GC-AdenoSIII | 90 | F | 54 | WCAU | N | | Surg | |
| CC | GCI | 28-GC-AdenoSIII | 75 | F | 61 | WCAU | N | | Surg | |
| CC | GCI | 29-GC-AdenoSIII | 85 | F | 64 | WCAU | N | | Surg | |
| CC | GCI | 30-GC-AdenoSIII | 60 | M | 67 | WCAU | Y | 14 | Surg | |
| CC | Ichilov | 31-(6)-Ic-AdenoSIII | | F | 77 | | | | | |
| CC | Ichilov | 32-(2)-Ic-AdenoSIII | | F | 89 | | | | | |
| CC | Ichilov | 33-(11)-Ic-AdenoSIII | | NA | NA | | | | | |
| CC | Asterand | 34-As-AdenoSIIIC | 76 | F | 68 | CAU | NU | | Surg | 2005 |
| CC | Ichilov | 35-(13)-Ic-AdenoSIV | | M | 47 | | | | | |
| CC | GCI | 36-GC-AdenoSIV | 80 | F | 52 | WCAU | Y | 3 | Surg | |
| CC | GCI | 37-GC-AdenoSIV | 85 | F | 53 | WCAU | | | Surg | |
| CC | Ichilov | 38-(9)-Ic-AdenoSIV | | M | 62 | | | | | |
| CC | Ichilov | 71-(16)-Ic-Adeno | 50 | F | 60 | | | | | |
| CC | Ichilov | 72-(4)-Ic-Adeno | 75 | M | 64 | | | | | |
| CC | Ichilov | 73-(17)-Ic-Adeno | | M | 73 | | | | | |
| CC | Ichilov | 74-(5)-Ic-Adeno | | F | 80 | | | | | |
| CC | Ichilov | 75-(72)-Ic-Adeno | | F | 88 | | | | | |
| CC | Ichilov | 76-(18)-Ic-Adeno | | NA | NA | | | | | |
| CC | Ichilov | 78-(21)-Ic-Adeno | | NA | NA | | | | | |
| CC | Ichilov | 79-(24)-Ic-Adeno | | NA | NA | | | | | |
| CC | Ichilov | 80-(25)-Ic-Adeno | | NA | NA | | | | | |
| CC | biochain | 82-(61)-Bc-Adeno | | M | 41 | | | | | |
| CC | biochain | 83-(57)-Bc-Adeno | | F | 45 | | | | | |
| CC | biochain | 84-(56)-Bc-Adeno | 40 | F | 48 | | | | | |
| CC | biochain | 85-(53)-Bc-Adeno | | F | 53 | | | | | |
| CC | biochain | 86-(54)-Bc-Adeno | | M | 53 | | | | | |

TABLE 5-continued

Colon cancer testing panel

| | | | | | | | | | | |
|---|---|---|---|---|---|---|---|---|---|---|
| CC | biochain | 87-(59)-Bc-Adeno | | M | 58 | | | | | |
| CC | biochain | 88-(60)-Bc-Adeno | | M | 67 | | | | | |
| CC | biochain | 89-(55)-Bc-Adeno | | M | 68 | | | | | |
| CC | biochain | 90-(58)-Bc-Adeno | | M | 73 | | | | | |
| CB | GCI | 40-GC-Ben | | F | 48 | WCAU | Y | 1 | Surg | |
| CB | GCI | 41-GC-Ben | | F | 75 | WCAU | N | | Surg | |
| CN | GCI | 42-GC-NPS | 0 | M | 45 | WCAU | N | | Surg | |
| CN | Asterand | 43-As-NPS | 0 | F | 46 | CAU | NU | | Surg | 2002 |
| CN | GCI | 44-GC-NPS | 0 | F | 48 | WCAU | Y | 1 | Surg | |
| CN | GCI | 45-GC-NPS | 0 | F | 50 | WCAU | N | | Surg | |
| CN | Asterand | 46-As-NPS | 0 | F | 52 | CAU | Occ | | Surg | 2005 |
| CN | Asterand | 47-As-NPS | 0 | F | 52 | CAU | occ | | Surg | 2005 |
| CN | GCI | 48-GC-NPS | 0 | M | 52 | WCAU | N | | Surg | |
| CN | Asterand | 49-As-NPS | 0 | M | 54 | CAU | CurU | | Surg | 2005 |
| CN | GCI | 50-GC-NPS | 0 | F | 55 | WCAU | N | | Surg | |
| CN | GCI | 51-GC-NPS | 0 | M | 55 | WCAU | N | | Surg | |
| CN | GCI | 52-GC-NPS | 0 | F | 57 | WCAU | Y | 6 | Surg | |
| CN | GCI | 53-GC-NPS | 0 | F | 57 | WCAU | Y | 1 | Surg | |
| CN | GCI | 54-GC-NPS | 0 | M | 59 | WCAU | Y | 42 | Surg | |
| CN | GCI | 55-GC-NPS | 0 | F | 61 | WCAU | Y | 3 | Surg | |
| CN | GCI | 56-GC-NPS | 0 | M | 61 | WCAU | Y | | Surg | |
| CN | GCI | 57-GC-NPS | 0 | F | 66 | WCAU | Y | 4 | Surg | |
| CN | GCI | 58-GC-NPS | 0 | F | 66 | WCAU | N | | Surg | |
| CN | GCI | 59-GC-NPS | 0 | M | 68 | WCAU | N | | Surg | |
| CN | GCI | 60-GC-NPS | 0 | F | 69 | WCAU | N | | Surg | |
| CN | Asterand | 61-As-NPS | 0 | M | 71 | CAU | Occ | | Surg | 2005 |
| CN | Asterand | 62-As-NPS | 0 | F | 74 | WCAU | Occ | | Surg | 2004 |
| CN | biochain | 63-(65)-Bc-NPM | | M | 24 | | | | | |
| CN | Ambion | 64-(71)-Am-NPM | | F | 34 | | | | | |
| CN | biochain | 65-(66)-Bc-NPM | | M | 58 | | | | | |
| CN | biochain | 66-(63)-Bc-NPM | | M | 61 | | | | | |
| CN | biochain | 67-(62)-Bc-NPM | | M | 66 | | | | | |
| CN | biochain | 68-(64)-Bc-NPM | | F | 68 | | | | | |
| CN | biochain | 69-(41)-Bc-NPM | | M | 78 | | | | | |
| CN | biochain | 70-(67)-Bc-NPM | | F&M | M (26-78) & F (53-77). | | | | | |

TABLE 5_1

| Key | Full Name |
|---|---|
| CC | Colon Cancer |
| CB | Colon Benign |
| CN | Colon Normal |
| WT | Weight |
| HT | Height |
| Aden | Adenocarcinoma |
| AI | Adenocarcinoma intramucosal |
| UA | Ulcerated adenocarcinoma |
| WP Aden | Well polypoid adeocarcinoma |
| MA | Mucinus adenocarcinoma |
| TA | Tubular adenocarcinoma |
| Carc | Carcinoma |
| TS Aden | TUBULOVILLOUS ADENOMA |
| TS Aden HGD | TUBULOVILLOUS ADENOMA with HIGH GRADE DYSPLASIA |
| NC | Normal Colon |
| N-PM | Normal PM |
| N-PM P10 | Normal PM (Pool 10) |
| Diag | Diagnosis |
| Div | DIVERTICULITIS |
| Divs w/ F DIV | Diverticulosis with Focal DIVERTICULITIS |
| Chr Divs | Chronic diverticulosis |
| Divs w/ DIV . . . | DIVERTICULOSIS WITH DIVERTICULITIS AND FOCAL ABSCESS FORMATION; NO MALIG-NANCY |
| AD w/ AF | Acute diverticulosis with abscess formation |
| CU | CECAL ULCERATION |
| Divs, PA | DIVERTICULOSIS AND PERICOLIC ABSCESS |
| Tub Aden | TUBULAR ADENOMA |
| Div/Chr Infl | DIVERTICULOSIS/CHRONIC INFLAMMATION |
| Chr Div | CHRONIC DIVERTICULITIS |
| Ext Divs | EXTENSIVE DIVERTICULOSIS |
| Divs, Chr Div . . . | DIVERTICULOSIS AND CHRONIC DIVERTICULITIS, SEROSAL FIBROSIS AND CHRONIC SEROSITIS |
| MU w/ MI | Mucosal ulceration with mural inflammation |
| UC | Ulcerative colitis |
| Cec | cecum |
| Dis C | DISTAL COLON |
| Ret, Low Ant | RETROSIGMOID, LOW ANTERIOR |
| Rect Col | Rectosigmoidal colon |
| Sig col | Sigmod colon |
| Col Sig | Colon Sigma |
| RT Col | RIGHT COLON |
| Prox T Col | PROXIMAL TRANSVERSE COLON |
| LT Col | Left Colon |
| Gr | Grade |
| CS | Cancer Stage |
| Ethnic B | Ethnic background |
| NU | Never Used |
| Occ | Occasion |
| Cur U | Current use |
| Dr. per day | Drinks per day |
| Alc. Dur. | Alcohol Duration |
| Auto. | Autopsy |
| Surg. | Surgical |
| Exc. Y. | Excision Year |

Materials and Experimental Procedures Used to Obtain Expression Data RNA Preparation—

RNA was obtained from ABS (Wilmington, Del. 19801, USA, http://www.absbioreagents.com), BioChain Inst. Inc. (Hayward, Calif. 94545 USA www.biochain.com), GOG for ovary samples—Pediatic Cooperative Human Tissue Network, Gynecologic Oncology Group Tissue Bank, Children Hospital of Columbus (Columbus Ohio 43205 USA), Clontech (Franklin Lakes, N.J. USA 07417, www.clontech.com), Ambion (Austin, Tex. 78744 USA, http://www.ambion.com), Asternad (Detroit, Mich. 48202-3420, USA, www.asterand.com), and from Genomics Collaborative Inc. a Division of Seracare (Cambridge, Mass. 02139, USA, www.genomicsinc.com). Alternatively, RNA was generated from blood cells, cell lines or tissue samples using TRI-Reagent (Molecular Research Center), according to Manufacturer's instructions. Tissue and RNA samples were obtained from patients or from postmortem. Most total RNA samples were treated with DNaseI (Ambion).

RT PCR—Purified RNA (2-10 μg) was mixed with 300-1500 ng Random Hexamer primers (Invitrogen) and 500 μM dNTP in a total volume of 31.2 to 156 μl. The mixture was incubated for 5 mM at 65° C. and then quickly chilled on ice. Thereafter, 10-50 μl of 5× SuperscriptII first strand buffer (Invitrogen), 4.8 to 24 μl 0.1M DTT and 80-400 units RNasin (Promega) were added, and the mixture was incubated for 10 mM at 25° C., followed by further incubation at 42° C. for 2 mM. Then, 2-10 μl (400-2000 units) of SuperscriptII (Invitrogen) was added and the reaction (final volume of 50-2500 was incubated for 50 mM at 42° C. and then inactivated at 70° C. for 15 min. The resulting cDNA was diluted 1:20 in TE buffer (10 mM Tris pH=8, 1 mM EDTA pH=8).

Real-Time RT-PCR analysis carried out as described below—cDNA (5 μl), prepared as described above, was used as a template in Real-Time PCR reactions (final volume of 20 μl) using the SYBR Green I assay (PE Applied Biosystem) with specific primers and UNG Enzyme (Eurogentech or ABI or Roche). The amplification was effected as follows: 50° C. for 2 min, 95° C. for 10 min, and then 40 cycles of 95° C. for 15 sec, followed by 60° C. for 1 min, following by dissociation step. Detection was performed by using the PE Applied Biosystem SDS 7000. The cycle in which the reactions achieved a threshold level of fluorescence (Ct=Threshold Cycle, described in detail below) was registered and was used to calculate the relative transcript quantity in the RT reactions. The relative quantity was calculated using the equation Q=efficiency^-Ct. The efficiency of the PCR reaction was calculated from a standard curve, created by using different dilutions of several reverse transcription (RT) reactions. To minimize inherent differences in the RT reaction, the resulting relative quantities were normalized using a normalization factor calculated in the following way:

The expression of several housekeeping (HSKP) genes was checked on every panel. The relative quantity (Q) of each housekeeping gene in each sample, calculated as described above, was divided by the median quantity of this gene in all panel samples to obtain the "relative Q rel to MED". Then, for each sample the median of the "relative Q rel to MED" of the selected housekeeping genes was calculated and served as normalization factor of this sample for further calculations. Schematic summary of quantitative real-time PCR analysis is presented in FIG. 1. As shown, the x-axis shows the cycle number. The CT=Threshold Cycle point, which is the cycle that the amplification curve crosses the fluorescence threshold that was set in the experiment. This point is a calculated cycle number in which PCR products signal is above the background level (passive dye ROX) and still in the Geometric/Exponential phase (as shown, once the level of fluorescence crosses the measurement threshold, it has a geometrically increasing phase, during which measurements are most accurate, followed by a linear phase and a plateau phase; for quantitative measurements, the latter two phases do not provide accurate measurements). The y-axis shows the normalized reporter fluorescence. It should be noted that this type of analysis provides relative quantification.

For each RT sample, the expression of the specific amplicon was normalized to the normalization factor calculated from the expression of different house keeping genes as described in section above.

These house keeping genes are different for each panel. For colon panel—HPRT1 (GenBank Accession No.

NM_000194 (SEQ ID NO: 118); amplicon—HPRT1-amplicon (SEQ ID NO:181)), PBGD (GenBank Accession No. BC019323 (SEQ ID NO: 117); amplicon—PBGD-amplicon (SEQ ID NO:178)), and G6PD (GenBank Accession No. NM_000402 (SEQ ID NO: 119); G6PD amplicon (SEQ ID NO: 184)). For lung panel—HPRT1 (GenBank Accession No. NM_000194 (SEQ ID NO: 118); amplicon—HPRT1-amplicon (SEQ ID NO:181)), PBGD (GenBank Accession No. BC019323 (SEQ ID NO: 117); amplicon—PBGD-amplicon (SEQ ID NO:178)), SDHA (GenBank Accession No. NM_004168 (SEQ ID NO: 116); amplicon—SDHA-amplicon (SEQ ID NO:175)) and Ubiquitin (GenBank Accession No. BC000449 (SEQ ID NO: 115); amplicon—Ubiquitin-amplicon (SEQ ID NO: 172)). For ovary panel—SDHA (GenBank Accession No. NM_004168 (SEQ ID NO: 116); amplicon—SDHA-amplicon (SEQ ID NO:175)), HPRT1 (GenBank Accession No. NM_000194 (SEQ ID NO: 118); amplicon—HPRT1-amplicon (SEQ ID NO:181)) and G6PD (GenBank Accession No. NM_000402 (SEQ ID NO: 119); G6PD amplicon (SEQ ID NO: 184)). For normal panel—SDHA (GenBank Accession No. NM_004168 (SEQ ID NO: 116); amplicon—SDHA-amplicon (SEQ ID NO:175)), Ubiquitin (GenBank Accession No. BC000449 (SEQ ID NO: 115); amplicon—Ubiquitin-amplicon (SEQ ID NO: 172)), and TATA box (GenBank Accession No. NM_003194 (SEQ ID NO: 114); TATA amplicon (SEQ ID NO: 169)). For blood panel—HSB1L_HUMAN (Accession No. Q9Y450)(SEQ ID NO: 109), DHSA_HUMAN (SEQ ID NO: 110) (Accession No P31040), SFRS4_HUMAN (SEQ ID NO: 111) (Accession No Q08170) and SLC25A3 (Accession No Q7Z7N7) (SEQ ID NO: 112).

The sequences of the housekeeping genes measured in all the examples of blood panel were as follows:

```
HSB1L_HUMAN (SEQ ID NO: 109) (Accession No.
Q9Y450)
T05337_seg30-34F1-Forward primer (SEQ ID NO: 152):
GCTCCAGGCCATAAGGACTTC

T05337_seg30-34R1 (SEQ ID NO: 153)-Reverse
primer:
CAGCTTCAAACTCTCCCCTGC

Amplicon (SEQ ID NO: 154):
GCTCCAGGCCATAAGGACTTCATTCCAAATATGATTACAGGAGCAGCCCA

GGCGGATGTAGCTGTTTTAGTTGTAGATGCCAGCAGGGGAGAGTTTGAAG

CTG

DHSA_HUMAN (SEQ ID NO: 110) (Accession No P31040)
M78124_seg45-48F1 (SEQ ID NO: 155)-Forward
primer:
TTCCTTGCCAGGACCTAGAG

M78124_seg45-48R1-Reverse primer (SEQ ID NO: 156):
CATAAACCTTTCGCCTTGAC

Amplicon (SEQ ID NO: 157):
TTCCTTGCCAGGACCTAGAGTTTGTTCAGTTCCACCCCACAGGCATATAT

GGTGCTGGTTGTCTCATTACGGAAGGATGTCGTGGAGAGGGAGGCATTCT

CATTAACAGTCAAGGCGAAAGGTTTATG

SFRS4_HUMAN (SEQ ID NO: 111) (Accession No Q08170)
HUMSRP75Aseg30-33F1 (SEQ ID NO: 158)- Forward
primer:
AATTTGTCAAGTCGGTGCAGC

HUMSRP75Aseg30-33R1 (SEQ ID NO: 159)- Reverse
primer:
TCACCCCTTCATTTTTGCGT
```

-continued

```
Amplicon (SEQ ID NO: 160):
AATTTGTCAAGTCGGTGCAGCTGGCAAGACCTAAAGGATTATATGCGTCA

GGCAGGAGAAGTGACTTATGCAGATGCTCACAAGGGACGCAAAAATGAAG

GGGTGA

SLC25A3 (Accession No Q7Z7N7) (SEQ ID NO: 112)
SSMPCPseg24-25-29F1- Forward primer (SEQ ID NO:
161):
CCCAAAATGTATAAGGAAGAAGGC

SSMPCPseg24-25-29R1- Reverse primer (SEQ ID NO:
162):
TTCAAAGCAGGCGAACTTCA

Amplicon (SEQ ID NO: 163):
CAGCCAGGTTATGCCAACACTTTGAGGGATGCAGCTCCCAAAATGTATAA

GGAAGAAGGCCTAAAAGCATTCTACAAGGGGGTTGCTCCTCTCTGGATGA

GACAGATACCATACACCATGATGAAGTTCGCCTGCTTTGA
```

The sequences of the housekeeping genes measured in all the examples on normal tissue samples panel were as follows:

```
TATA box (GenBank Accession No. NM_003194 (SEQ ID
NO: 114)),
TATA box Forward primer (SEQ ID NO: 167):
CGGTTTGCTGCGGTAATCAT

TATA box Reverse primer (SEQ ID NO: 168):
TTTCTTGCTGCCAGTCTGGAC

TATA box -amplicon (SEQ ID NO: 169):
CGGTTTGCTGCGGTAATCATGAGGATAAGAGAGCCACGAACCACGGCACT

GATTTTCAGTTCTGGGAAAATGGTGTGCACAGGAGCCAAGAGTGAAGAAC

AGTCCAGACTGGCAGCAAGAAA

Ubiquitin (GenBank Accession No. BC000449 (SEQ ID
NO: 115))
Ubiquitn Forward primer (SEQ ID NO: 170):
ATTTGGGTCGCGGTTCTTG

Ubiquitin Reverse primer (SEQ ID NO: 171):
TGCCTTGACATTCTCGATGGT

Ubiquitin-amplicon (SEQ ID NO: 172)
ATTTGGGTCGCGGTTCTTGTTTGTGGATCGCTGTGATCGTCACTTGACA

ATGCAGATCTTCGTGAAGACTCTGACTGGTAAGACCATCACCCTCGAGG

TTGAGCCCAGTGACACCATCGAGAATGTCAAGGCA

SDHA (GenBank Accession No. NM_004168 (SEQ ID NO:
116))
SDHA Forward primer (SEQ ID NO: 173):
TGGGAACAAGAGGGCATCTG

SDHA Reverse primer (SEQ ID NO: 174):
CCACCACTGCATCAAATTCATG

SDHA-amplicon (SEQ ID NO: 175):
TGGGAACAAGAGGGCATCTGCTAAAGTTTCAGATTCCATTTCTGCTCAGT

ATCCAGTAGTGGATCATGAATTTGATGCAGTGGTGG
```

The sequences for primers and amplicons of the housekeeping genes measured in all the cancer examples are listed below. For colon panel—HPRT1, PBGD and G6PD were used. For lung panel—PBGD, HPRT1, Ubiquitin and SDHA were used. For ovary panel—HPRT1, SDHA and G6PD were used.

SDHA (GenBank Accession No. NM_004168 (SEQ ID NO: 116):

```
SDHA Forward primer (SEQ ID NO: 173):
TGGGAACAAGAGGGCATCTG

SDHA Reverse primer (SEQ ID NO: 174):
CCACCACTGCATCAAATTCATG

SDHA-amplicon (SEQ ID NO: 175):
TGGGAACAAGAGGGCATCTGCTAAAGTTTCAGATTCCATTTCTGCTCAGT

ATCCAGTAGTGGATCATGAATTTGATGCAGTGGTGG

PBGD (GenBank Accession No. BC019323 (SEQ ID NO:
117)),
PBGD Forward primer (SEQ ID NO: 176):
TGAGAGTGATTCGCGTGGG

PBGD Reverse primer (SEQ ID NO: 177):
CCAGGGTACGAGGCTTTCAAT

PBGD-amplicon (SEQ ID NO: 178):
TGAGAGTGATTCGCGTGGGTACCCGCAAGAGCCAGCTTGCTCGCATACAG

ACGGACAGTGTGGTGGCAACATTGAAAGCCTCGTACCCTGG

HPRT1 (GenBank Accession No. NM_000194 (SEQ ID NO:
118)),
HPRT1 Forward primer (SEQ ID NO: 179):
TGACACTGGCAAAACAATGCA

HPRT1 Reverse primer (SEQ ID NO: 180):
GGTCCTTTTCACCAGCAAGCT

HPRT1-amplicon (SEQ ID NO: 181):
TGACACTGGCAAAACAATGCAGACTTTGCTTTCCTTGGTCAGGCAGTATA

ATCCAAAGATGGTCAAGGTCGCAAGCTTGCTGGTGAAAAGGACC

G6PD (GenBank Accession No. NM_000402 (SEQ ID NO:
119))
G6PD Forward primer (SEQ ID NO: 182):
gaggccgtcaccaagaacat

G6PD Reverse primer (SEQ ID NO: 183):
ggacagccggtcagagctc

G6PD-amplicon (SEQ ID NO: 184):
gaggccgtcaccaagaacattcacgagtcctgcatgagccagataggctg

gaaccgcatcatcgtggagaagcccttcgggagggacctgcagagctctg

accggctgtcc

Ubiquitin (GenBank Accession No. BC000449 (SEQ ID
NO: 115))
Ubiquitin Forward primer (SEQ ID NO: 170):
ATTTGGGTCGCGGTTCTTG

Ubiquitin Reverse primer (SEQ ID NO: 171):
TGCCTTGACATTCTCGATGGT

Ubiquitin Amplicon (SEQ ID NO: 172):
ATTTGGGTCGCGGTTCTTGTTTGTGGATCGCTGTGATCGTCACTTGACAA

TGCAGATCTTCGTGAAGACTCTGACTGGTAAGACCATCACCCTCGAGG

TTGAGCCCAGTGACACCATCGAGAATGTCAAGGCA
```

Another methodology used to predict the expression pattern of the proteins of the invention was MED discovery engine:

MED is a platform for collection of public gene-expression data, normalization, annotation and performance of various queries. Expression data from the most widely used Affymetrix microarrays is downloaded from the Gene Expression Omnibus (GEO—www.ncbi.nlm.nih.gov/GEO). Data is multiplicatively normalized by setting the 95 percentile to a constant value (normalized expression=1200), and noise is filtered by setting the lower 30% to 0. Experiments are annotated, first automatically, and then manually, to identify tissue and condition, and chips are grouped according to this annotation, and cross verification of this grouping by comparing the overall expression pattern of the genes of each chip to the overall average expression pattern of the genes in this group. Each probeset in each group is assigned an expression value which is the median of the expressions of that probeset in all chips included in the group. The vector of expression of all probesets within a certain group is the virtual chip of that group, and the collection of all such virtual chips is a virtual panel. The panel (or sub-panels) can be queried to identify probesets with a required behavior (e.g. specific expression in a sub-set of tissues, or differential expression between disease and healthy tissues). These probesets are linked to LEADS contigs and to RefSeqs (http://www.ncbi.nlm.nih.gov/RefSeq/) by probe-level mapping, for further analysis.

The Affymetrix platforms that are downloaded are HG-U95A and the HG-U133 family (A, B, A2.0 and PLUS 2.0). Than three virtual panels were created: U95 and U133 Plus 2.0, based on the corresponding platforms, and U133 which uses the set of common probesets for HG-U133A, HG-U133A2.0 and HG-U133 PLUS 2.0+.

The results of the MED discovery engine are presented in scatter plots. The scatter plot is a compact representation of a given panel (collection of groups). The y-axis is the (normalized) expression and the x-axis describes the groups in the panel. For each group, the median expression is represented by a solid marker., and the expression values of the different chips in the group are represented by small dashes ("-"). The groups are ordered and marked as follows—"Other" groups (e.g. benign, non-cancer diseases, etc.) with a triangle, Treated cells with a square, Normal with a circle, Matched with a cross, and Cancer with a diamond. The number of chips in each group is also written adjacent to it's name.

Example 2

Description for Cluster AI581519

The present invention relates to VSIG1 polypeptides, novel splice variants and diagnostics and therapeutics based thereon.

According to the present invention, Cluster AI581519 (internal ID 72756422) features 10 transcripts and 2 segments of interest, the names for which are given in Tables 6 and 7, respectively. The selected protein variants are given in table 8.

TABLE 6

| Transcripts of interest Transcript Name | |
|---|---|
| AI58519_T0 | (SEQ ID NO: 1) |
| AI58519_T1 | (SEQ ID NO: 2) |
| AI58519_T2 | (SEQ ID NO: 3) |
| AI58519_T3 | (SEQ ID NO: 4) |
| AI58519_T4 | (SEQ ID NO: 5) |
| AI58519_T5 | (SEQ ID NO: 6) |
| AI58519_T6 | (SEQ ID NO: 7) |
| AI58519_T8 | (SEQ ID NO: 8) |
| AI58519_T10 | (SEQ ID NO: 9) |
| AI58519_T11 | (SEQ ID NO: 10) |

TABLE 7

| Segments of interest<br>Segment Name |
|---|
| AI581519_N7 (SEQ ID NO: 120) |
| AI581519_N9 (SEQ ID NO: 121) |

TABLE 8

| Proteins of interest | |
|---|---|
| Protein Name | Corresponding Transcripts |
| AI581519_P3 (SEQ ID NO: 11) | AI581519_T0 (SEQ ID NO: 1); AI581519_T1 (SEQ ID NO: 2); AI581519_T2 (SEQ ID NO: 3); AI581519_T3 (SEQ ID NO: 4); AI581519_T4 (SEQ ID NO: 5) |
| AI581519_P4 (SEQ ID NO: 12) | AI581519_T5 (SEQ ID NO: 6) |
| AI581519_P5 (SEQ ID NO: 13) | AI581519_T6 (SEQ ID NO: 7) |
| AI581519_P7 (SEQ ID NO: 14) | AI581519_T8 (SEQ ID NO: 8) |
| AI581519_P9 (SEQ ID NO: 15) | AI581519_T10 (SEQ ID NO: 9) |
| AI581519_P10 (SEQ ID NO: 16) | AI581519_T11 (SEQ ID NO: 10) |

These sequences are variants of the known protein V-set and immunoglobulin domain containing 1 (RefSeq accession identifier NP_872413, synonyms: RP5-889N15.1, 1700062D20Rik, GPA34, MGC44287, dJ889N15.1), referred to herein as the previously known protein.

VSIG1 is a V-set and immunoglobulin domain containing 1 protein also known as glycoprotein A34 (GPA34). This gene was originally identified as a transcript encoding a protein with similarity to the glycoprotein A33 (GPA33), a colon cancer antigen (Scanlan et al. Cancer Immunotherapy 6:2 2006), that has 32% identity to GPA33. The authors showed that A34 mRNA and protein expression is highly tissue-restricted, as it is expressed predominantly in stomach and testis. A34 mRNA and protein expression was also detected in gastric cancers, esophageal carcinomas, and ovarian cancers. In their studies they did not detect A34 in lung, breast or colon carcinomas (Scanlan et al. 2006, Cancer Immunity 6: 2).

A known wild type VSIG1 nucleic acid sequence has been reported in various patent and non-patent literarture references. For example, the sequence of AI581519_P3 (SEQ ID NO:11) is disclosed in WO2004037999, refered there as glycoprotein A34 (GPA34). This PCT application contains the sequence for AI581519_P3 (SEQ ID NO:11) which encodes the A34 antigen disclosed herein. The corresponding antigen A34 is indicated to be expressed in some tested stomach cancers (29%), esophageal (63%) and to be expressed to a much lesser number extent (9%) on tested ovarian cancers. The authors suggest that this antigen may be used for therapy and may be a suitable target for antibody based cancer therapies.

WO9926972 discloses that this antigenic protein may also exhibit immune stimulating or immune suppressing activit such as for the treatment of various immune deficiencies and disorders (including severe combined immunodeficiency (SCID)), e. g., in regulating (up or down) growth and proliferation of T and/or B lymphocytes, as well as effecting the cytolytic activity of NK cells and other cell populations.

In addition this same protein sequence, as depicted in AI581519_P3 (SEQ ID NO:11) herein, is mentioned in WO9960020 and US2002193567 wherein it is identified as Human secreted protein #62.

A sequence homologous to VSIG1 variant as depicted in AI581519_P4 (SEQ ID NO:12) herein, (containing 2 mismatches corresponding to known SNPs) is disclosed in WO2003027228 application, which purportedly discloses an extensive list of different alleged differentially expressed sequences.

Further, a sequence closely related to AI581519_P5 (SEQ ID NO:13), (containing 2 mismatches corresponding to known SNPs) is disclosed in PCT application WO2004100774, which also teaches many other purported differentially expressed sequences.

Still further, a sequence closely related to AI581519_P7 (SEQ ID NO:14), (containing 1 mismatch corresponding to known SNP) is disclosed in PCT application WO2004048550 which similarly contains an extensive listing of alleged differentially expressed sequences.

According to the present invention, VSIG1 is predicted to be a novel B7 member, based on the presence of an IgV and an IgC2 domain. A large portion of proteins having one domain of each Ig subtype are co-stimulatory molecules. Like other known B7 members, VSIG1 is also a type I membrane protein. In the present invention several alternative spliced variants of VSIG1 were identified, as described below, containing a unique region within the ectodomain. The new variants of VSIG1 were demonstrated in the present invention to be overexpressed in lung adenocarcinoma and ovarian cancer.

Figure 2:
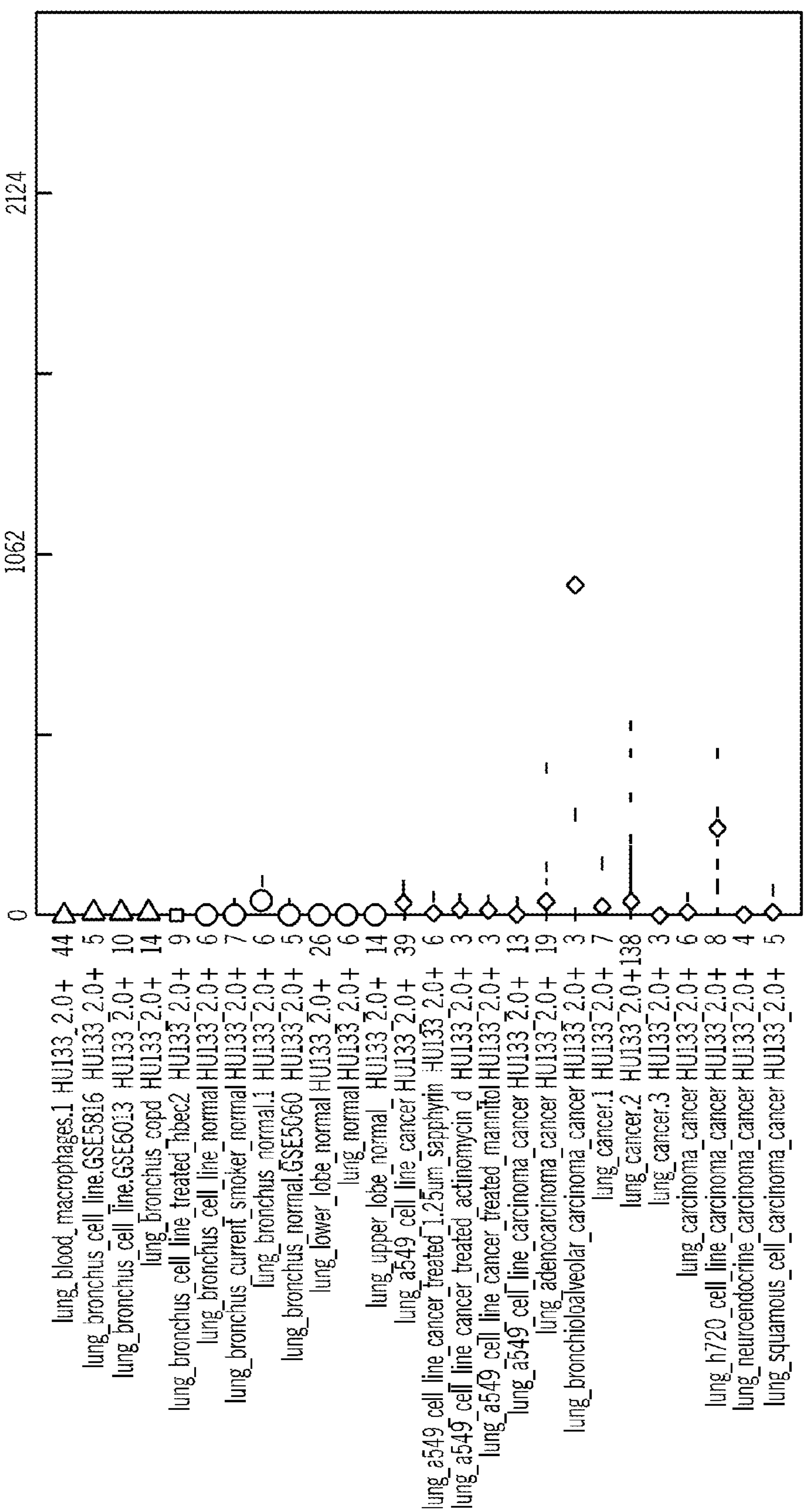
FIG. 2 shows a scatter plot, demonstrating the expression of AI581519 transcripts, that encode the VSIG1 proteins, on a virtual panel of all tissues and conditions using MED discovery engine, demonstrating overexpression of AI581519 transcripts in lung cancer compared to normal lung samples.

MED discovery engine described in Example 1 herein, was used to assess the expression of VSIG1 transcripts. Expression data for Affymetrix probe sets 234370 at representing the VSIG1 gene data is shown in FIG. 2. As evident from the scatter plot, presented in FIG. 2, the expression of VSIG1 transcripts detectable with the above probe sets was higher in lung cancer compared to normal lung samples.

As noted above, cluster AI581519 features 10 transcripts, which were listed in Table 6 above. These transcripts encode for proteins which are variants of protein V-set and immunoglobulin domain containing 1. A description of each variant protein according to the present invention is now provided.

Variant protein AI581519_P3 (SEQ ID NO:11) according to the present invention has an amino acid sequence encoded by transcripts AI581519_T0 (SEQ ID NO:1), AI581519_T1 (SEQ ID NO:2), AI581519_T2 (SEQ ID NO:3), AI581519_T3 (SEQ ID NO:4) and AI581519_T4 (SEQ ID NO:5).

The localization of the variant protein was determined according to results from a number of different software programs and analyses, including analyses from SignalP and other specialized programs. The variant protein is believed to be located as follows with regard to the cell: membrane.

Variant protein AI581519_P3 (SEQ ID NO:11) also has the following non-silent SNPs (Single Nucleotide Polymorphisms) as listed in Table 9, (given according to their positions on the amino acid sequence, with the alternative amino acids listed).

TABLE 9

| Amino acid mutations | |
|---|---|
| SNP positions on amino acid sequence | Alternative amino acids |
| 23 | Q -> R |
| 35 | V -> |
| 51 | S -> F |
| 90 | I -> V |

TABLE 9-continued

| Amino acid mutations | |
|---|---|
| SNP positions on amino acid sequence | Alternative amino acids |
| 127 | Q -> |
| 146 | S -> R |
| 176 | K -> |
| 176 | K -> E |
| 181 | D -> G |
| 181 | D -> V |
| 189 | F -> L |
| 195 | I -> T |
| 196 | L -> |
| 202 | T -> |
| 280 | T -> |
| 288 | S -> G |
| 322 | P -> |
| 344 | L -> P |

The variant protein has the following domains, as determined by using InterPro. The domains are described in Table 10:

TABLE 10

| InterPro domains | | |
|---|---|---|
| Domain description | Analysis type | Positions on protein |
| Immunoglobulin C2 type | HMMSmart | 34-123, 152-218 |
| Immunoglobulin-like | Profile Scan | 36-120, 140-227 |
| Immunoglobulin-like | HMMPfam | 36-118, 154-213 |
| Immunoglobulin subtype | HMMSmart | 28-137, 146-229 |
| Myelin P0 protein | FPrintScan | 35-59, 110-139 |
| Immunoglobulin V-set | HMMPfam | 21-137 |
| Immunoglobulin V-type | HMMSmart | 38-118 |

Variant protein AI581519_P3 (SEQ ID NO:11) is encoded by the following transcripts: AI581519_T0 (SEQ ID NO:1), AI581519_T1 (SEQ ID NO:2), AI581519_T2 (SEQ ID NO:3), AI581519_T3 (SEQ ID NO:4) and AI581519_T4 (SEQ ID NO:5).

The coding portion of transcript AI581519_T0 (SEQ ID NO:1) starts at position 171 and ends at position 1331. The transcript also has the following SNPs as listed in Table 11 (given according to their position on the nucleotide sequence, with the alternative nucleic acid listed (SEQ ID NO:11)).

TABLE 11

| Nucleic acid SNPs | |
|---|---|
| Polymorphism | SNP positions on nucleotide sequence |
| A -> G | 238, 438, 696, 712, 1031, 1032, 2314, 2471 |
| T -> | 275, 757 |
| C -> T | 322, 452 |
| C -> A | 449, 608 |
| C -> | 549 |
| C -> G | 608 |
| A -> | 696, 776, 1010, 1136 |
| A -> T | 712 |
| T -> C | 735, 754, 1201 |
| G -> A | 1679, 1800, 1867 |
| T -> A | 2260 |

The coding portion of transcript AI581519_T1 (SEQ ID NO:2) starts at position 171 and ends at position 1331. The transcript also has the following SNPs as listed in Table 12 (given according to their position on the nucleotide sequence, with the alternative nucleic acid listed).

TABLE 12

| Nucleic acid SNPs | |
|---|---|
| Polymorphism | SNP positions on nucleotide sequence |
| A -> G | 238, 438, 696, 712, 1031, 1032, 2314, 2471 |
| T -> | 275, 757 |
| C -> T | 322, 452 |
| C -> A | 449, 608 |
| C -> | 549 |
| C -> G | 608 |
| A -> | 696, 776, 1010, 1136 |
| A -> T | 712 |
| T -> C | 735, 754, 1201 |
| G -> A | 1679, 1800, 1867 |
| T -> A | 2260 |

The coding portion of transcript AI581519_T2 (SEQ ID NO:3) starts at position 171 and ends at position 1331. The transcript also has the following SNPs as listed in Table 13 (given according to their position on the nucleotide sequence, with the alternative nucleic acid listed).

TABLE 13

| Nucleic acid SNPs | |
|---|---|
| Polymorphism | SNP positions on nucleotide sequence |
| A -> G | 238, 438, 696, 712, 1031, 1032, 1782 |
| T -> | 275, 757 |
| C -> T | 322, 452 |
| C -> A | 449, 608 |
| C -> | 549 |
| C -> G | 608 |
| A -> | 696, 776, 1010, 1136 |
| A -> T | 712 |
| T -> C | 735, 754, 1201 |
| G -> A | 1679 |

The coding portion of transcript AI581519_T3 (SEQ ID NO:4) starts at position 171 and ends at position 1331. The transcript also has the following SNPs as listed in Table 14 (given according to their position on the nucleotide sequence, with the alternative nucleic acid listed).

TABLE 14

| Nucleic acid SNPs | |
|---|---|
| Polymorphism | SNP positions on nucleotide sequence |
| A -> G | 238, 438, 696, 712, 1031, 1032, 1702 |
| T -> | 275, 757 |
| C -> T | 322, 452 |
| C -> A | 449, 608 |
| C -> | 549 |
| C -> G | 608 |
| A -> | 696, 776, 1010, 1136 |
| A -> T | 712 |
| T -> C | 735, 754, 1201 |
| G -> A | 1679 |

The coding portion of transcript AI581519_T4 (SEQ ID NO:5) starts at position 171 and ends at position 1331. The transcript also has the following SNPs as listed in Table 15 (given according to their position on the nucleotide sequence, with the alternative nucleic acid listed).

TABLE 15

| Nucleic acid SNPs | |
|---|---|
| Polymorphism | SNP positions on nucleotide sequence |
| A -> G | 238, 438, 696, 712, 1031, 1032 |
| T -> | 275, 757 |
| C -> T | 322, 452 |
| C -> A | 449, 608 |
| C -> | 549 |
| C -> G | 608 |
| A -> | 696, 776, 1010, 1136 |
| A -> T | 712 |
| T -> C | 735, 754, 1201 |

Variant protein AI581519_P4 (SEQ ID NO:12) according to the present invention has an amino acid sequence encoded by transcript AI581519_T5 (SEQ ID NO:6). Alignments to previously published protein sequences are shown in FIG. 3A. A brief description of the relationship of the variant protein according to the present invention to each such aligned protein is as follows:

2. Comparison report between AI581519_P4 (SEQ ID NO:12) and known proteins NP_872413 (SEQ ID NO: 11) and Q86XK7_HUMAN (FIG. 3A):

A. An isolated chimeric polypeptide encoding for AI581519_P4 (SEQ ID NO:12), comprising a first amino acid sequence being at least 90% homologous to

```
MVFAFWKVFLILSCLAGQVSVVQVTIPDGFVNVTVGSNVTLICIYTTTVA

SREQLSIQWSFFHKKEMEPIS
```

corresponding to amino acids 1-71 of known proteins NP_872413 and Q86XK7_HUMAN (SEQ ID NO: 11), which also corresponds to amino acids 1-71 of AI581519_P4 (SEQ ID NO:12), a second amino acid sequence being at least 70%, optionally at least 80%, preferably at least 85%, more preferably at least 90% and most preferably at least 95, 96, 97, 98 or 99% homologous to a polypeptide having the sequence HSSCLSTEGMEEKAVGQCLKMTHVRDARGRCSWTSE (SEQ ID NO: 284) corresponding to amino acids 72-107 of AI581519_P4 (SEQ ID NO:12), and a third amino acid sequence being at least 90% homologous to

```
IYFSQGGQAVAIGQFKDRITGSNDPGNASITISHMQPADSGIYICDVNNP

PDFLGQNQGILNVSVLVKPSKPLCSVQGRPETGHTISLSCLSALGTPSPV

YYWHKLEGRDIVPVKENFNPTTGILVIGNLTNFEQGYYQCTAINRLGNSS

CEIDLTSSHPEVGIIVGALIGSLVGAAIIISVVCFARNKAKAKAKERNSK

TIAELEPMTKINPRGESEAMPREDATQLEVTLPSSIHETGPDTIQEPDYE

PKPTQEPAPEPAPGSEPMAVPDLDIELELEPETQSELEPEPEPEPESEPG

VVVEPLSEDEKGVVKA
```

corresponding to amino acids 72-387 of known proteins NP_872413 and Q86XK7_HUMAN (SEQ ID NO: 11), which also corresponds to amino acids 108-423 of AI581519_P4 (SEQ ID NO:12), wherein said first amino acid sequence, second amino acid sequence and third amino acid sequence are contiguous and in a sequential order.

C. An isolated polypeptide encoding for an edge portion of AI581519_P4 (SEQ ID NO:12), comprising an amino acid sequence being at least 70%, optionally at least about 80%, preferably at least about 85%, more preferably at least about 90% and most preferably at least about 95, 96, 97, 98 or 99% homologous to the sequence HSSCLSTEGMEEKAVGQCLKMTHVRDARGRCSWTSE (SEQ ID NO: 284) of AI581519_P4 (SEQ ID NO:12).

The localization of the variant protein was determined according to results from a number of different software programs and analyses, including analyses from SignalP and other specialized programs. The variant protein is believed to be located as follows with regard to the cell: membrane.

Variant protein AI581519_P4 (SEQ ID NO:12) also has the following non-silent SNPs (Single Nucleotide Polymorphisms) as listed in Table 16, (given according to their positions on the amino acid sequence, with the alternative amino acids listed (SEQ ID NO:12)).

TABLE 16

| Amino acid mutations | |
|---|---|
| SNP positions on amino acid sequence | Alternative amino acids |
| 23 | Q -> R |
| 35 | V -> |
| 51 | S -> F |
| 87 | G -> S |
| 95 | V -> A |
| 126 | I -> V |
| 163 | Q -> |
| 182 | S -> R |
| 212 | K -> |
| 212 | K -> E |
| 217 | D -> G |
| 217 | D -> V |
| 225 | F -> L |
| 231 | I -> T |
| 232 | L -> |
| 238 | T -> |
| 316 | T -> |
| 324 | S -> G |
| 358 | P -> |
| 380 | L -> P |

The variant protein has the following domains, as determined by using InterPro. The domains are described in Table 17:

TABLE 17

| InterPro domains | | |
|---|---|---|
| Domain description | Analysis type | Positions on protein |
| Immunoglobulin C2 type | HMMSmart | 34-159, 188-254 |
| Immunoglobulin subtype | HMMSmart | 28-173, 182-265 |
| Immunoglobulin-like | Profile Scan | 36-156, 176-263 |
| Immunoglobulin V-set | HMMPfam | 21-173 |
| Immunoglobulin V-type | HMMSmart | 38-154 |

Variant protein AI581519_P4 (SEQ ID NO:12) is encoded by the AI581519_T5 (SEQ ID NO:6), for which the coding portion starts at position 171 and ends at position 1439. The transcript also has the following SNPs as listed in Table 18 (given according to their position on the nucleotide sequence, with the alternative nucleic acid listed).

TABLE 18

| Nucleic acid SNPs | |
|---|---|
| Polymorphism | SNP positions on nucleotide sequence |
| A -> G | 238, 546, 804, 820, 1139, 1140, 2422, 2579 |
| T -> | 275, 865 |
| C -> T | 322, 560 |
| G -> A | 429, 1787, 1908, 1975 |
| T -> C | 454, 843, 862, 1309 |
| C -> A | 557, 716 |
| C -> | 657 |
| C -> G | 716 |
| A -> | 804, 884, 1118, 1244 |
| A -> T | 820 |
| T -> A | 2368 |

Variant protein AI581519_P5 (SEQ ID NO:13) according to the present invention has an amino acid sequence encoded by transcript AI581519_T6 (SEQ ID NO:7). Alignments to previously published protein sequences are shown in FIG. 3B. A brief description of the relationship of the variant protein according to the present invention to each such aligned protein is as follows:

2. Comparison report between AI581519_P5 (SEQ ID NO:13) and known proteins NP_872413 and Q86XK7_HUMAN (SEQ ID NO: 11) (FIG. 3B):

A. An isolated chimeric polypeptide encoding for AI581519_P5 (SEQ ID NO:13), comprising a first amino acid sequence being at least 90% homologous to

```
MVFAFWKVFLILSCLAGQVSVVQVTIPDGFVNVTVGSNVTLICIYTTTVA

SREQLSIQWSFFHKKEMEPIS
```

corresponding to amino acids 1-71 of known proteins NP_872413 and Q86XK7_HUMAN (SEQ ID NO: 11), which also corresponds to amino acids 1-71 of AI581519_P5 (SEQ ID NO:13), a second amino acid sequence being at least 70%, optionally at least 80%, preferably at least 85%, more preferably at least 90% and most preferably at least 95, 96, 97, 98 or 99% homologous to a polypeptide having the sequence

```
                                     (SEQ ID NO: 285)
HSSCLSTEGMEEKAVGQCLKMTHVRDARGRCSWTSESPWEEGKWPDVEAV

KGTLDGQQAELQ
```

corresponding to amino acids 72-133 of AI581519_P5 (SEQ ID NO:13), and a third amino acid sequence being at least 90% homologous to

```
IYFSQGGQAVAIGQFKDRITGSNDPGNASITISHMQPADSGIYICDVNNP

PDFLGQNQGILNVSVLVKPSKPLCSVQGRPETGHTISLSCLSALGTPSPV

YYWHKLEGRDIVPVKENFNPTTGILVIGNLTNFEQGYYQCTAINRLGNSS

CEIDLTSSHPEVGIIVGALIGSLVGAAIIISVVCFARNKAKAKAKERNSK

TIAELEPMTKINPRGESEAMPREDATQLEVTLPSSIHETGPDTIQEPDYE

PKPTQEPAPEPAPGSEPMAVPDLDIELELEPETQSELEPEPEPEPESEPG

VVVEPLSEDEKGVVKA
```

corresponding to amino acids 72-387 of known proteins NP_872413 and Q86XK7_HUMAN (SEQ ID NO: 11), which also corresponds to amino acids 134-449 of AI581519_P5 (SEQ ID NO:13), wherein said first amino acid sequence, second amino acid sequence and third amino acid sequence are contiguous and in a sequential order.

C. An isolated polypeptide encoding for an edge portion of AI581519_P5 (SEQ ID NO:13), comprising an amino acid sequence being at least 70%, optionally at least about 80%, preferably at least about 85%, more preferably at least about 90% and most preferably at least about 95, 96, 97, 98 or 99% homologous to the sequence

```
                                     (SEQ ID NO: 285)
HSSCLSTEGMEEKAVGQCLKMTHVRDARGRCSWTSESPWEEGKWPDVEAV

KGTLDGQQAELQ
```

of AI581519_P5 (SEQ ID NO:13).

The localization of the variant protein was determined according to results from a number of different software programs and analyses, including analyses from SignalP and other specialized programs. The variant protein is believed to be located as follows with regard to the cell: membrane.

Variant protein AI581519_P5 (SEQ ID NO:13) also has the following non-silent SNPs (Single Nucleotide Polymorphisms) as listed in Table 19, (given according to their positions on the amino acid sequence, with the alternative amino acids listed (SEQ ID NO:13)).

TABLE 19

| Amino acid mutations | |
|---|---|
| SNP positions on amino acid sequence | Alternative amino acids |
| 23 | Q -> R |
| 35 | V -> |
| 51 | S -> F |
| 87 | G -> S |
| 95 | V -> A |
| 152 | I -> V |
| 189 | Q -> |
| 208 | S -> R |
| 238 | K -> |
| 238 | K -> E |
| 243 | D -> G |
| 243 | D -> V |
| 251 | F -> L |
| 257 | I -> T |
| 258 | L -> |
| 264 | T -> |
| 342 | T -> |
| 350 | S -> G |
| 384 | P -> |
| 406 | L -> P |

The variant protein has the following domains, as determined by using InterPro. The domains are described in Table 20:

TABLE 20

| InterPro domains | | |
|---|---|---|
| Domain description | Analysis type | Positions on protein |
| Immunoglobulin subtype | HMMSmart | 28-199, 208-291 |
| Immunoglobulin C2 type | HMMSmart | 34-185, 214-280 |
| Immunoglobulin V-set | HMMPfam | 21-199 |
| Immunoglobulin-like | Profile Scan | 202-289 |

Variant protein AI581519_P5 (SEQ ID NO:13) is encoded by the following transcript AI581519_T6 (SEQ ID NO:7), for which the coding portion starts at position 171 and ends at position 1517. The transcript also has the following SNPs as listed in Table 21 (given according to their position on the nucleotide sequence, with the alternative nucleic acid listed).

TABLE 21

| Nucleic acid SNPs | |
|---|---|
| Polymorphism | SNP positions on nucleotide sequence |
| A -> G | 238, 624, 882, 898, 1217, 1218, 2500, 2657 |
| T -> | 275, 943 |
| C -> T | 322, 638 |
| G -> A | 429, 1865, 1986, 2053 |
| T -> C | 454, 921, 940, 1387 |
| C -> A | 635, 794 |
| C -> | 735 |
| C -> G | 794 |
| A -> | 882, 962, 1196, 1322 |
| A -> T | 898 |
| T -> A | 2446 |

Variant protein AI581519_P7 (SEQ ID NO:14) according to the present invention is encoded by transcript AI581519_T8 (SEQ ID NO:8). Alignments to one or more previously published protein sequences are shown in FIG. 3C. A brief description of the relationship of the variant protein according to the present invention to each such aligned protein is as follows:

2. Comparison report between AI581519_P7 (SEQ ID NO:14) and known proteins NP_872413 and Q86XK7_HUMAN (SEQ ID NO: 11) (FIG. 3C):

A. An isolated chimeric polypeptide encoding for AI581519_P7 (SEQ ID NO:14), comprising a first amino acid sequence being at least 90% homologous to

MVFAFWKVFLILSCLAGQVSVVQVTIPDGFVNVTVGSNVTLICIYTTTVA

SREQLSIQWSFFHKKEMEPISIYFSQGGQAVAIGQFKDRITGSNDP corresponding to amino acids 1-96 of known proteins NP_872413 and Q86XK7_HUMAN (SEQ ID NO: 11), which also corresponds to amino acids 1-96 of AI581519_P7 (SEQ ID NO:14), and a second amino acid sequence being at least 90% homologous to

VKPSKPLCSVQGRPETGHTISLSCLSALGTPSPVYYWHKLEGRDIVPVKE

NFNPTTGILVIGNLTNFEQGYYQCTAINRLGNSSCEIDLTSSHPEVGIIV

GALIGSLVGAAIIISVVCFARNKAKAKAKERNSKTIAELEPMTKINPRGE

SEAMPREDATQLEVTLPSSIHETGPDTIQEPDYEPKPTQEPAPEPAPGSE

PMAVPDLDIELELEPETQSELEPEPEPEPESEPGVVVEPLSEDEKGVVKA corresponding to amino acids 138-387 of known proteins NP_872413 and Q86XK7_HUMAN (SEQ ID NO: 11), which also corresponds to amino acids 97-446 of AI581519_P7 (SEQ ID NO:14), wherein said first amino acid sequence and second amino acid sequence are contiguous and in a sequential order.

C. An isolated chimeric polypeptide encoding for an edge portion of AI581519_P7 (SEQ ID NO:14), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise PV, having a structure as follows: a sequence starting from any of amino acid numbers 96−x to 96; and ending at any of amino acid numbers 97+((n−2)−x), in which x varies from 0 to n−2.

The localization of the variant protein was determined according to results from a number of different software programs and analyses, including analyses from SignalP and other specialized programs. The variant protein is believed to be located as follows with regard to the cell: membrane.

Variant protein AI581519_P7 (SEQ ID NO:14) also has the following non-silent SNPs (Single Nucleotide Polymorphisms) as listed in Table 22, (given according to their positions on the amino acid sequence, with the alternative amino acids listed (SEQ ID NO:14)).

TABLE 22

| Amino acid mutations | |
|---|---|
| SNP positions on amino acid sequence | Alternative amino acids |
| 23 | Q -> R |
| 35 | V -> |
| 51 | S -> F |
| 90 | I -> V |
| 105 | S -> R |
| 135 | K -> |
| 135 | K -> E |
| 140 | D -> G |
| 140 | D -> V |
| 148 | F -> L |
| 154 | I -> T |
| 155 | L -> |
| 161 | T -> |
| 239 | T -> |
| 247 | S -> G |
| 281 | P -> |
| 303 | L -> P |

The variant protein has the following domains, as determined by using InterPro. The domains are described in Table 23:

TABLE 23

| InterPro domains | | |
|---|---|---|
| Domain description | Analysis type | Positions on protein |
| Immunoglobulin-like | Profile Scan | 99-186 |
| Immunoglobulin C2 type | HMMSmart | 111-177 |
| Immunoglobulin subtype | HMMSmart | 28-188 |

Variant protein AI581519_P7 (SEQ ID NO:14) is encoded by the transcript AI581519_T8 (SEQ ID NO:8), for which the coding portion starts at position 171 and ends at position 1208. The transcript also has the following SNPs as listed in Table 24 (given according to their position on the nucleotide sequence, with the alternative nucleic acid listed).

TABLE 24

| Nucleic acid SNPs | |
|---|---|
| Polymorphism | SNP positions on nucleotide sequence |
| A -> G | 238, 438, 573, 589, 908, 909, 2191, 2348 |

TABLE 24-continued

| Nucleic acid SNPs | |
|---|---|
| Polymorphism | SNP positions on nucleotide sequence |
| T -> | 275, 634 |
| C -> T | 322, 452 |
| C -> A | 449, 485 |
| C -> G | 485 |
| A -> | 573, 653, 887, 1013 |
| A -> T | 589 |
| T -> C | 612, 631, 1078 |
| G -> A | 1556, 1677, 1744 |
| T -> A | 2137 |

Variant protein AI581519_P9 (SEQ ID NO:15) according to the present invention has an amino acid sequence encoded by transcript AI581519_T10 (SEQ ID NO:9). Alignments to one or more previously published protein sequences are shown in FIG. 3D. A brief description of the relationship of the variant protein according to the present invention to each such aligned protein is as follows:

2. Comparison report between AI581519_P9 (SEQ ID NO:15) and known proteins NP_872413 and Q86XK7_HUMAN (SEQ ID NO: 11) (FIG. 3D):

A. An isolated chimeric polypeptide encoding for AI581519_P9 (SEQ ID NO:15), comprising a first amino acid sequence being at least 90% homologous to

MVFAFWKVFLILSCLAGQVSVVQVTIPDGFVNVTVGSNVTLICIYTTTVA

SREQLSIQWSFFHKKEMEPISIYFSQGGQAVAIGQFKDRITGSNDPGNAS

ITISHMQPADSGIYICDVNNPPDFLGQNQGILNVSVLVKPSKPLCSVQGR

PETGHTISLSCLSALGTPSPVYYWHKLEGRDIVPVKENF corresponding to amino acids 1-189 of known proteins NP_872413 and Q86XK7_HUMAN (SEQ ID NO: 11), which also corresponds to amino acids 1-189 of AI581519_P9 (SEQ ID NO:15), and a second amino acid sequence being at least 70%, optionally at least 80%, preferably at least 85%, more preferably at least 90% and most preferably at least 95, 96, 97, 98 or 99% homologous to a polypeptide having the sequence TNHRDFGHWKSDKF (SEQ ID NO: 286) corresponding to amino acids 190-203 of AI581519_P9 (SEQ ID NO:15), wherein said first amino acid sequence and second amino acid sequence are contiguous and in a sequential order.

C. An isolated polypeptide encoding for an edge portion of AI581519_P9 (SEQ ID NO:15), comprising an amino acid sequence being at least 70%, optionally at least about 80%, preferably at least about 85%, more preferably at least about 90% and most preferably at least about 95, 96, 97, 98 or 99% homologous to the sequence TNHRDFGHWKSDKF (SEQ ID NO: 286) of AI581519_P9 (SEQ ID NO:15).

The localization of the variant protein was determined according to results from a number of different software programs and analyses, including analyses from SignalP and other specialized programs. The variant protein is believed to be located as follows with regard to the cell: membrane.

Variant protein AI581519_P9 (SEQ ID NO:15) also has the following non-silent SNPs (Single Nucleotide Polymorphisms) as listed in Table 25, (given according to their positions on the amino acid sequence, with the alternative amino acids listed (SEQ ID NO:15)).

TABLE 25

| Amino acid mutations | |
|---|---|
| SNP positions on amino acid sequence | Alternative amino acids |
| 23 | Q -> R |
| 35 | V -> |
| 51 | S -> F |
| 90 | I -> V |
| 127 | Q -> |
| 146 | S -> R |
| 176 | K -> |
| 176 | K -> E |
| 181 | D -> G |
| 181 | D -> V |
| 189 | F -> L |
| 195 | F -> |
| 202 | K -> |

The variant protein has the following domains, as determined by using InterPro. The domains are described in Table 26:

TABLE 26

| InterPro domains | | |
|---|---|---|
| Domain description | Analysis type | Positions on protein |
| Immunoglobulin-like | HMMPfam | 36-118 |
| Myelin P0 protein | FPrintScan | 35-59, 110-139 |
| Immunoglobulin-like | Profile Scan | 36-120 |
| Immunoglobulin subtype | HMMSmart | 28-137 |
| Immunoglobulin V-set | HMMPfam | 21-137 |
| Immunoglobulin V-type | HMMSmart | 38-118 |

Variant protein AI581519_P9 (SEQ ID NO:15) is encoded by the transcript AI581519_T10 (SEQ ID NO:9), for which the coding portion starts at position 171 and ends at position 779. The transcript also has the following SNPs as listed in Table 27 (given according to their position on the nucleotide sequence, with the alternative nucleic acid listed).

TABLE 27

| Nucleic acid SNPs | |
|---|---|
| Polymorphism | SNP positions on nucleotide sequence |
| A -> G | 238, 438, 696, 712, 1029, 1030, 2312, 2469 |
| T -> | 275, 755 |
| C -> T | 322, 452 |
| C -> A | 449, 608 |
| C -> | 549 |
| C -> G | 608 |
| A -> | 696, 774, 1008, 1134 |
| A -> T | 712 |
| T -> C | 735, 752, 1199 |
| G -> A | 1677, 1798, 1865 |
| T -> A | 2258 |

Variant protein AI581519_P10 (SEQ ID NO:16) according to the present invention has an amino acid sequence as encoded by transcript AI581519_T11 (SEQ ID NO:10). Alignments to previously published protein sequences are shown in FIG. 3E. A brief description of the relationship of the variant protein according to the present invention to each such aligned protein is as follows:

2. Comparison report between AI581519_P10 (SEQ ID NO:16) and known proteins NP_872413 and Q86XK7_HUMAN (SEQ ID NO: 11) (FIG. 3E):

A. An isolated chimeric polypeptide encoding for AI581519_P10 (SEQ ID NO:16), comprising a first amino acid sequence being at least 90% homologous to

MVFAFWKVFLILSCLAGQVSVVQVTIPDGFVNVTVGSNVTLICIYTTTVA

SREQLSIQWSFFHKKEMEPISIYFSQGGQAVAIGQFKDRITGSNDPGNAS

ITISHMQPADSGIYICDVNNPPDFLGQNQGILNVSVLVKPSKPLCSVQGR

PETGHTISLSCLSALGTPSPVYYWHKLEGRDIVPVKENFNPTTGILVIGN

LTNFEQGYYQCTAINRLGNSSCEIDLTSS corresponding to amino acids 1-229 of known proteins NP_872413 and Q86XK7_HUMAN (SEQ ID NO: 11), which also corresponds to amino acids 1-229 of AI581519_P10 (SEQ ID NO:16), and a second amino acid sequence RQ (SEQ ID NO: 287) corresponding to amino acids 230-231 of AI581519_P10 (SEQ ID NO:16), wherein said first amino acid sequence, second amino acid sequence and third amino acid sequence are contiguous and in a sequential order.

The localization of the variant protein was determined according to results from a number of different software programs and analyses, including analyses from SignalP and other specialized programs. The variant protein is believed to be located as follows with regard to the cell: membrane.

Variant protein AI581519_P10 (SEQ ID NO:16) also has the following non-silent SNPs (Single Nucleotide Polymorphisms) as listed in Table 28, (given according to their positions on the amino acid sequence, with the alternative amino acids listed (SEQ ID NO:16)).

TABLE 28

| Amino acid mutations | |
|---|---|
| SNP positions on amino acid sequence | Alternative amino acids |
| 23 | Q -> R |
| 35 | V -> |
| 51 | S -> F |
| 90 | I -> V |
| 127 | Q -> |
| 146 | S -> R |
| 176 | K -> |
| 176 | K -> E |
| 181 | D -> G |
| 181 | D -> V |
| 189 | F -> L |
| 195 | I -> T |
| 196 | L -> |
| 202 | T -> |

The variant protein has the following domains, as determined by using InterPro. The domains are described in Table 29:

TABLE 29

| InterPro domains | | |
|---|---|---|
| Domain description | Analysis type | Positions on protein |
| Immunoglobulin C2 type | HMMSmart | 34-123, 152-218 |
| Immunoglobulin subtype | HMMSmart | 28-137, 146-229 |
| Immunoglobulin-like | HMMPfam | 36-118, 154-113 |
| Myelin P0 protein | FPrintScan | 35-59, 110-139 |
| Immunoglobulin V-type | HMMSmart | 38-118 |
| Immunoglobulin V-set | HMMPfam | 21-137 |
| Immunoglobulin-like | Profile Scan | 36-120, 140-227 |

Variant protein AI581519_P10 (SEQ ID NO:16) is encoded by the transcript AI581519_T11 (SEQ ID NO:10), for which the coding portion starts at position 171 and ends at position 863. The transcript also has the following SNPs as listed in Table 30 (given according to their position on the nucleotide sequence, with the alternative nucleic acid listed).

TABLE 30

| Nucleic acid SNPs | |
|---|---|
| Polymorphism | SNP positions on nucleotide sequence |
| A -> G | 238, 438, 696, 712, 889, 890, 2172, 2329 |
| T -> | 275, 757 |
| C -> T | 322, 452 |
| C -> A | 449, 608 |
| C -> | 549 |
| C -> G | 608 |
| A -> | 696, 776, 868, 994 |
| A -> T | 712 |
| T -> C | 735, 754, 1059 |
| G -> A | 1537, 1658, 1725 |
| T -> A | 2118 |

According to an optional embodiment of the present invention, short segments related to the above cluster are also provided. These segments are up to about 120bp in length, and so are included in a separate description.

Segment cluster AI581519_N7 (SEQ ID NO:120) according to the present invention is supported by 6 libraries. The number of libraries was determined as previously described. This segment can be found in the following transcripts: AI581519_T5 (SEQ ID NO:6) and AI581519_T6 (SEQ ID NO:7). Table 31 below describes the starting and ending position of this segment on each transcript.

TABLE 31

| Segment location on transcripts | | |
|---|---|---|
| Transcript name | Segment starting position | Segment ending position |
| AI581519_T5 (SEQ ID NO: 6) | 384 | 491 |
| AI581519_T6 (SEQ ID NO: 7) | 384 | 491 |

Segment cluster AI581519_N9 (SEQ ID NO:121) according to the present invention is supported by 1 libraries. The number of libraries was determined as previously described. This segment can be found in the following transcripts: AI581519_T6 (SEQ ID NO:7). Table 32 below describes the starting and ending position of this segment on each transcript.

TABLE 32

| Segment location on transcripts | | |
|---|---|---|
| Transcript name | Segment starting position | Segment ending position |
| AI581519_T6 (SEQ ID NO: 7) | 492 | 569 |

Expression of V-set and immunoglobulin domain containing 1 (VSIG1) AI581519 transcripts which are detectable by amplicon as depicted in sequence name AI581519_seg7 (SEQ ID NO:190) in normal and cancerous Ovary tissues, in normal and cancerous lung tissues and in different normal tissues Expression of V-set and immunoglobulin domain containing 1 (VSIG1) transcripts detectable by or according to seg7—AI581519_seg7 (SEQ ID NO:190) amplicon and primers AI581519_seg7F1 (SEQ ID NO: 188) and AI581519_seg7R1 (SEQ ID NO: 189) was measured by real time PCR on ovary panel, lung panel and normal panel. The samples used are detailed in Table 4, Table 3 and Table 2 above, respectively.

Ovary panel—Non-detected samples (samples no. 80, 83, 100 and 109, Table 4) were assigned Ct value of 41 and were calculated accordingly. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 52-78, Table 4 above), to obtain a value of fold up-regulation for each sample relative to median of the normal samples.

Figure 4:
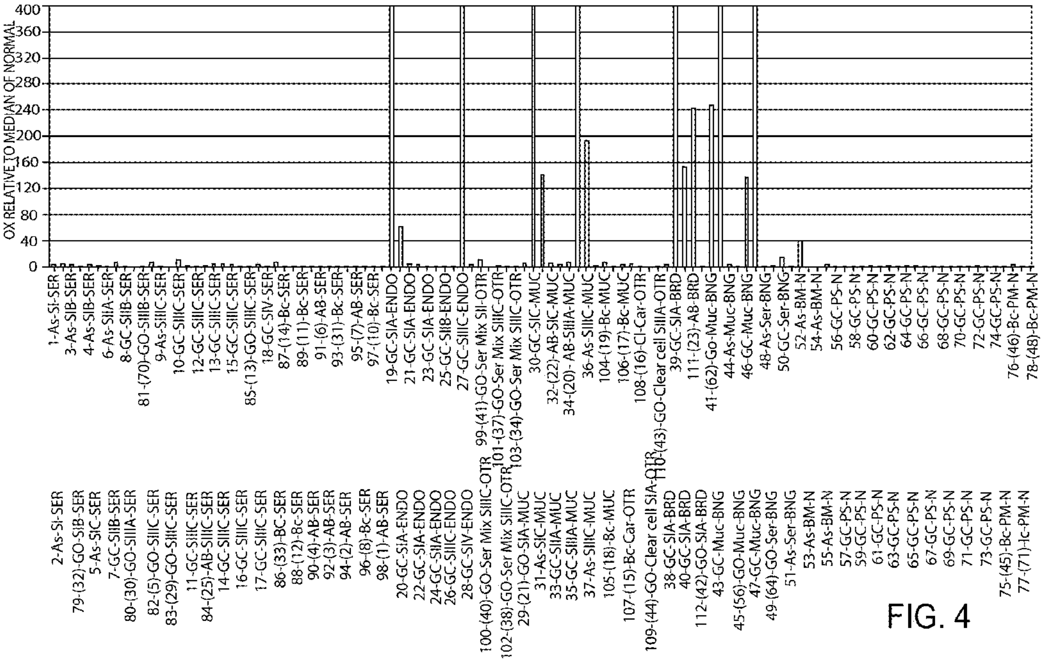
FIG. 4 presents a histogram showing expression of V-set and immunoglobulin domain containing 1 (VSIG1) AI581519 transcripts which are detectable by amplicon as depicted in sequence name AI581519_seg7 (SEQ ID NO: 190) in normal and cancerous Ovary tissues.

FIG. 4 is a histogram showing over expression of the above-indicated V-set and immunoglobulin domain containing 1 (VSIG1) transcripts in cancerous Ovary samples relative to the normal samples.

As is evident from FIG. 4, the expression of V-set and immunoglobulin domain containing 1 (VSIG1) transcripts detectable by the above amplicon in mucinous carcinoma and endometroid samples was significantly higher than in the non-cancerous samples (sample numbers 52-78, Table 4 above). Notably an over-expression of at least 40 fold was found in 4 out of 12 mucinous carcinoma samples and in 3 out of 10 endometroid samples.

Statistical analysis was applied to verify the significance of these results, as described below. Threshold of 40 fold over expression was found to differentiate between mucinous carcinoma and endometroid and normal samples with P value of 6.02e-003 and 1.54e-002, respectively as checked by exact Fisher test. The above values demonstrate statistical significance of the results.

Lung panel—For each RT sample, the expression of the above amplicon was normalized to the normalization factor calculated from the expression of several house keeping genes as described in Example 1. The normalized quantity of each RT sample was then divided by the median of the quantities of the normal samples (sample numbers 51-64 and 69-70 Table 3 above), to obtain a value of fold up-regulation for each sample relative to median of the normal samples.

Figure 5:
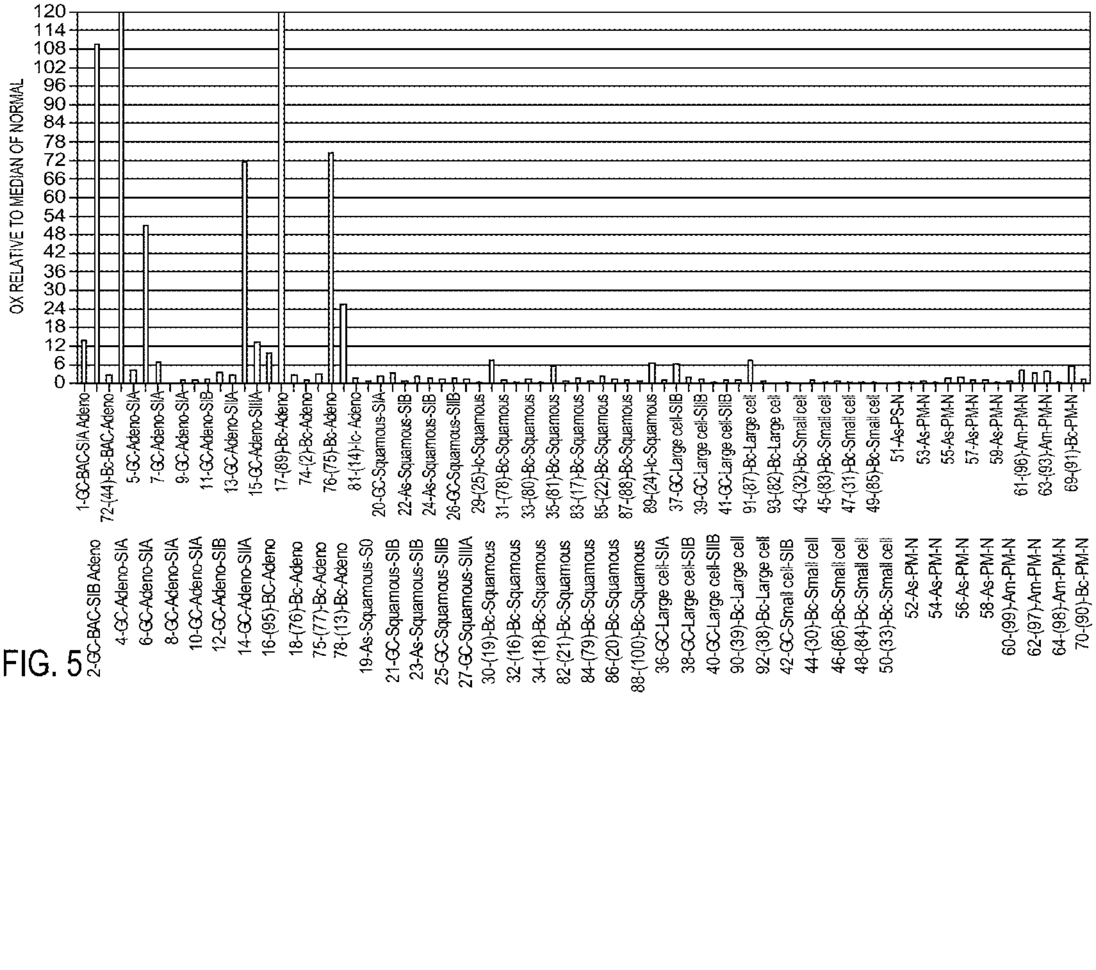
FIG. 5 presents a histogram showing expression of V-set and immunoglobulin domain containing 1 (VSIG1) AI581519 transcripts which are detectable by amplicon as depicted in sequence name AI581519_seg7 (SEQ ID NO: 190) in normal and cancerous lung tissues.

FIG. 5 is a histogram showing over expression of the above-indicated V-set and immunoglobulin domain containing 1 (VSIG1) transcripts in cancerous Lung samples relative to the normal samples.

As is evident from FIG. 5, the expression of V-set and immunoglobulin domain containing 1 (VSIG1) transcripts detectable by the above amplicon in adenocarcinoma samples was significantly higher than in the non-cancerous samples (sample numbers 51-64 and 69-70, Table 3 above). Notably an over-expression of at least 6 fold was found in 11 out of 23 adenocarcinoma samples.

Statistical analysis was applied to verify the significance of these results, as described below. The P value for the difference in the expression levels of V-set and immunoglobulin domain containing 1 (VSIG1) transcripts detectable by the above amplicon in Lung adenocarcinoma samples versus the normal tissue samples was determined by T test as 9.36e-003. Threshold of 6 fold over expression was found to differentiate between adenocarcinoma and normal samples with P value of 8.07e-004 as checked by exact Fisher test.

The above values demonstrate statistical significance of the results.

Figure 6A:
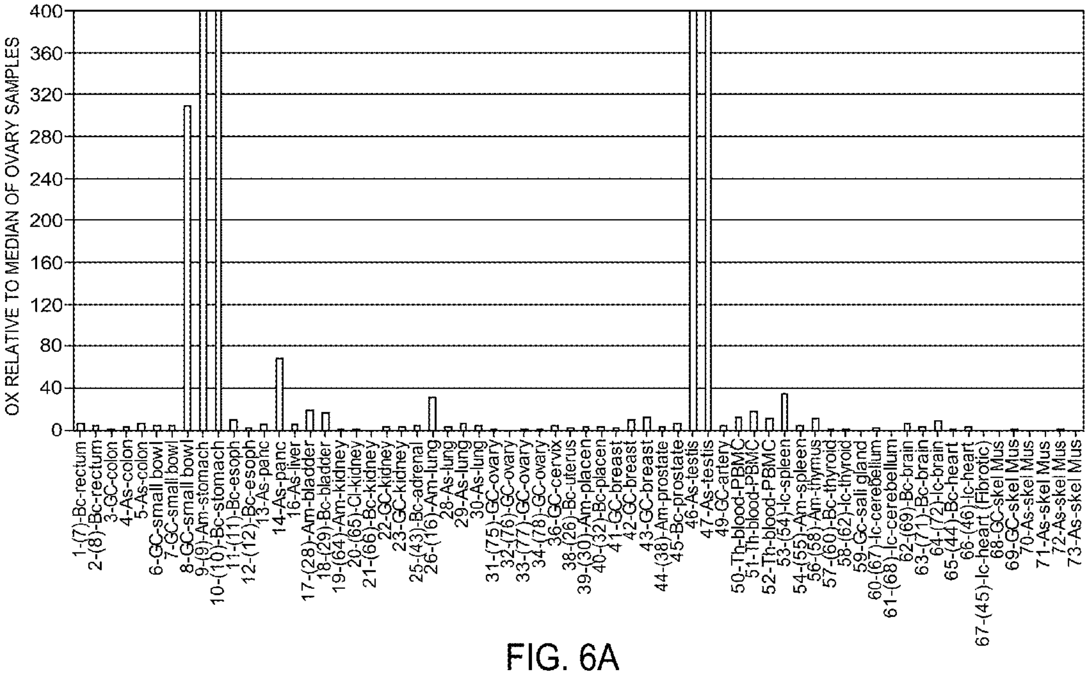
FIGS. 6A-6B present histograms showing expression of V-set and immunoglobulin domain containing 1 (VSIG1) AI581519 transcripts which are detectable by amplicon as depicted in sequence name AI581519_seg7 (SEQ ID NO: 190) in various normal tissues.
Figure 6B:
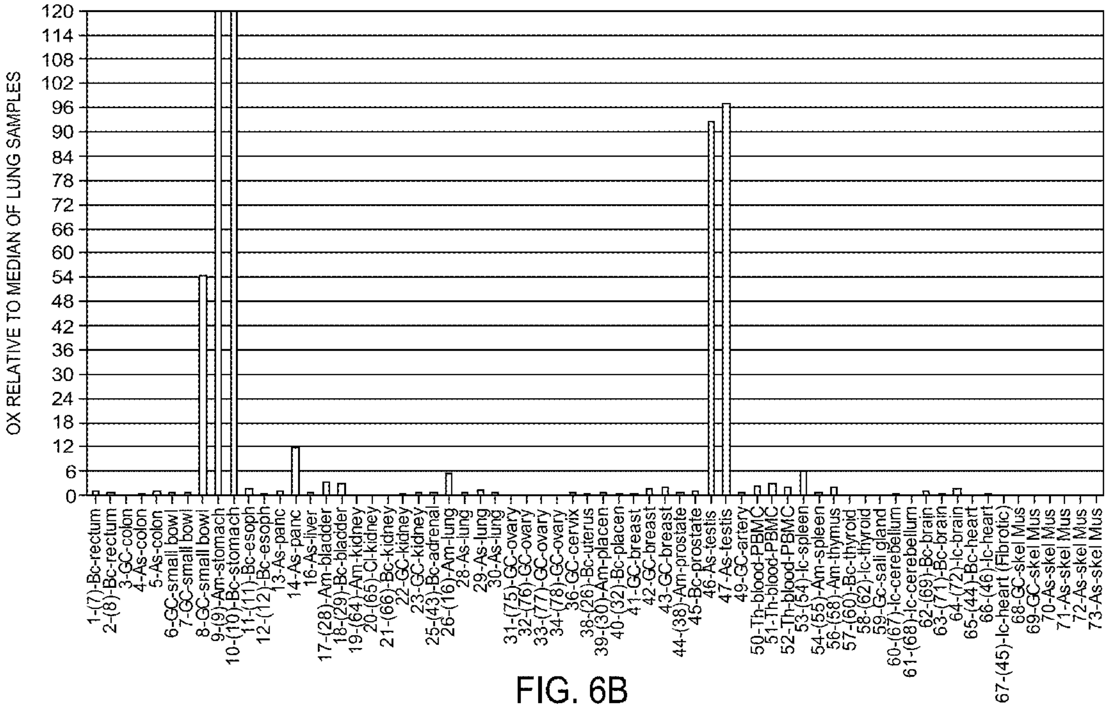

Normal panel—For each RT sample, the expression of the above amplicon was normalized to the normalization factor calculated from the expression of several house keeping genes as described in Example 1. The normalized quantity of each RT sample was then divided by the median of the quantities of the ovary samples (sample numbers 31, 32, 33 and 34, Table 2 above), to obtain a value of relative expression of each sample relative to median of the ovary samples, as shown in FIG. 6A. The normalized quantity of each RT sample was also divided by the median of the quantities of the ovary samples (sample numbers 31-34, Table 2 above), to obtain a value of relative expression of each sample relative to median of the lung samples (sample numbers 26, 28, 29 and 30, Table 2 above), as shown in FIG. 6B.

Primer pairs are also optionally and preferably encompassed within the present invention; for example, for the above experiment, the following primer pair was used as a non-limiting illustrative example only of a suitable primer pair: AI581519_seg7F1 (SEQ ID NO: 188) forward primer; and AI581519_seg7R1 (SEQ ID NO: 189) reverse primer.

The present invention also preferably encompasses any amplicon obtained through the use of any suitable primer pair; for example, for the above experiment, the following amplicon was obtained as a non-limiting illustrative example only of a suitable amplicon: AI581519_seg7 (SEQ ID NO:190).

```
Forward Primer >AI581519_seg7F1
(SEQ ID NO: 188):
CACAGCTCGTGCCTCAGTACTG

Reverse Primer >AI581519_seg7R1
(SEQ ID NO: 189):
AGCTACATCTTCCCCGAGCG

Amplicon >AI581519_seg7
                                   (SEQ ID NO: 190)
CACAGCTCGTGCCTCAGTACTGAGGGTATGGAGGAAAAG
GCAGTCGGTCAGTGTCTAAAAATGACGCACGTAAGAGAC
GCTCGGGGAAGATGTAGCT
```

Expression of V-set and immunoglobulin domain containing 1(VSIG1) AI581519 transcripts which are detectable by amplicon as depicted in sequence name AI581519_seg7-9 (SEQ ID NO: 187) in normal and cancerous ovary tissues and in normal and cancerous lung tissues Expression of V-set and immunoglobulin domain containing 1(VSIG1) transcripts detectable by or according to seg7-9—AI581519_seg7-9 (SEQ ID NO: 187) amplicon and primers AI581519_seg7-9F1 (SEQ ID NO: 185) and AI581519_seg7-9R1 (SEQ ID NO: 186) was measured by real time PCR on ovary panel and lung panel. The samples used are detailed in Table 4 and Table 3 above, respectively.

Ovary panel—Non-detected sample (sample no. 40 Table 4) was assigned Ct value of 41 and was calculated accordingly. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 52-78, Table 4 above), to obtain a value of fold up-regulation for each sample relative to median of the normal samples.

Figure 7:
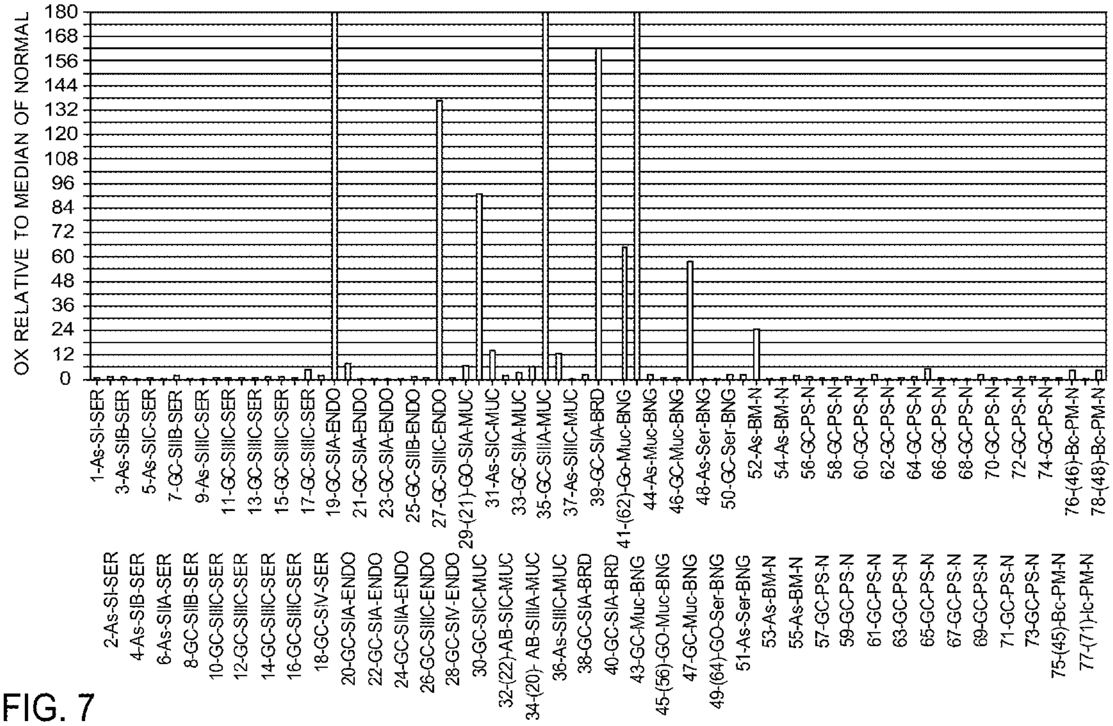
FIG. 7 presents a histogram showing expression of V-set and immunoglobulin domain containing 1(VSIG1) AI581519 transcripts which are detectable by amplicon as depicted in sequence name AI581519_seg7-9 (SEQ ID NO: 187) in normal and cancerous Ovary tissues.

FIG. 7 is a histogram showing over expression of the above-indicated V-set and immunoglobulin domain containing 1(VSIG1) transcripts in cancerous Ovary samples relative to the normal samples.

As is evident from FIG. 7, the expression of V-set and immunoglobulin domain containing 1(VSIG1) transcripts detectable by the above amplicon in mucinous carcinoma samples was significantly higher than in the non-cancerous samples (sample numbers 52-78, Table 4 above) and was higher in a few adenocarcinoma samples than in the non-cancerous samples. Notably an over-expression of at least 6 fold was found in 6 out of 9 mucinous carcinoma samples and in 9 out of 37 endometroid samples.

Statistical analysis was applied to verify the significance of these results, as described below. Threshold of 6 fold over expression was found to differentiate between mucinous carcinoma and normal samples with P value of 2.75e-004 as checked by exact Fisher test. Threshold of 6 fold over expression was found to differentiate between adenocarcinoma and normal samples with P value of 2.44e-002 as checked by exact Fisher test.

The above values demonstrate statistical significance of the results.

Lung panel—For each RT sample, the expression of the above amplicon was normalized to the normalization factor calculated from the expression of several house keeping genes as described in Example 1. The normalized quantity of each RT sample was then divided by the median of the quantities of the normal samples (sample numbers 51-64 and 69-70, Table 3 above), to obtain a value of fold up-regulation for each sample relative to median of the normal samples.

Figure 8:
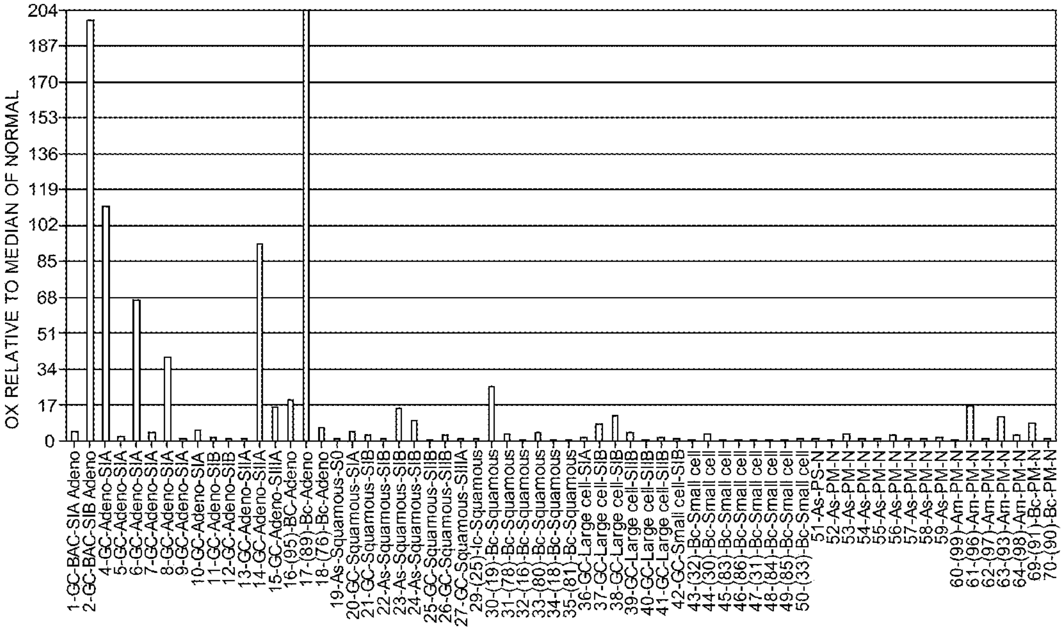
FIG. 8 presents a histogram showing expression of V-set and immunoglobulin domain containing 1(VSIG1) AI581519 transcripts which are detectable by amplicon as depicted in sequence name AI581519_seg7-9 (SEQ ID NO: 187) in normal and cancerous lung tissues.

FIG. 8 is a histogram showing over expression of the above-indicated V-set and immunoglobulin domain containing 1(VSIG1) transcripts in cancerous Lung samples relative to the normal samples.

As is evident from FIG. 8, the expression of V-set and immunoglobulin domain containing 1(VSIG1) transcripts detectable by the above amplicon in adenocarcinoma samples was significantly higher than in the non-cancerous samples (sample numbers 51-64 and 69-70, Table 3 above) and was higher in a few non-small cell carcinoma samples than in the non-cancerous samples. Notably an over-expression of at least 17 fold was found in 8 out of 18 adenocarcinoma samples.

Statistical analysis was applied to verify the significance of these results, as described below. The P value for the difference in the expression levels of V-set and immunoglobulin domain containing 1(VSIG1) transcripts detectable by the above amplicon in Lung adenocarcinoma samples versus the normal tissue samples was determined by T test as 1.17e-002.

Threshold of 17 fold over expression was found to differentiate between adenocarcinoma and normal samples with P value of 2.41e-003 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: AI581519_seg7-9F1 (SEQ ID NO: 185) forward primer; and AI581519_seg7-9R1 (SEQ ID NO: 186) reverse primer.

The present invention also preferably encompasses any amplicon obtained through the use of any suitable primer pair; for example, for the above experiment, the following amplicon was obtained as a non-limiting illustrative example only of a suitable amplicon: AI581519_seg7-9 (SEQ ID NO: 187).

```
Forward Primer >AI581519_seg7-9F1
(SEQ ID NO: 185):
AATGACGCACGTAAGAGACGC

Reverse Primer >AI581519_seg7-9R1
(SEQ ID NO: 186):
GAGTGCCCTTCACAGCCTCA

Amplicon >AI581519_seg7-9
                                  (SEQ ID NO: 187)
AATGACGCACGTAAGAGACGCTCGGGGAAGATGTAGC
TGGACCTCTGAGTCTCCTTGGGAGGAGGGGAAGTGGC
CAGATGTTGAGGCTGTGAAGGGCACTC
```

Expression of V-set and immunoglobulin domain containing 1(VSIG1) AI581519 transcripts which are detectable by amplicon as depicted in sequence name AI581519seg7-9 (SEQ ID NO: 196) in the blood-specific panel.

Expression of VSIG1 transcripts detectable by or according to seg7-9-AI581519seg7-9F3R3 (SEQ ID NO:196) amplicon and primers AI581519seg7-9F3 (SEQ ID NO:194) and AI581519seg7-9R3 (SEQ ID NO:195) was measured by real time PCR on blood panel. The samples used are detailed in Table 1 above. Non-detected samples (samples no. 28, 33, 83, 85, 90 and 63, Table 1) were assigned Ct value of 41 and were calculated accordingly. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 64, 69-72 and 74-76, Table 1 above), to obtain a value of relative expression of each sample relative to median of the normal samples.

Figure 9:
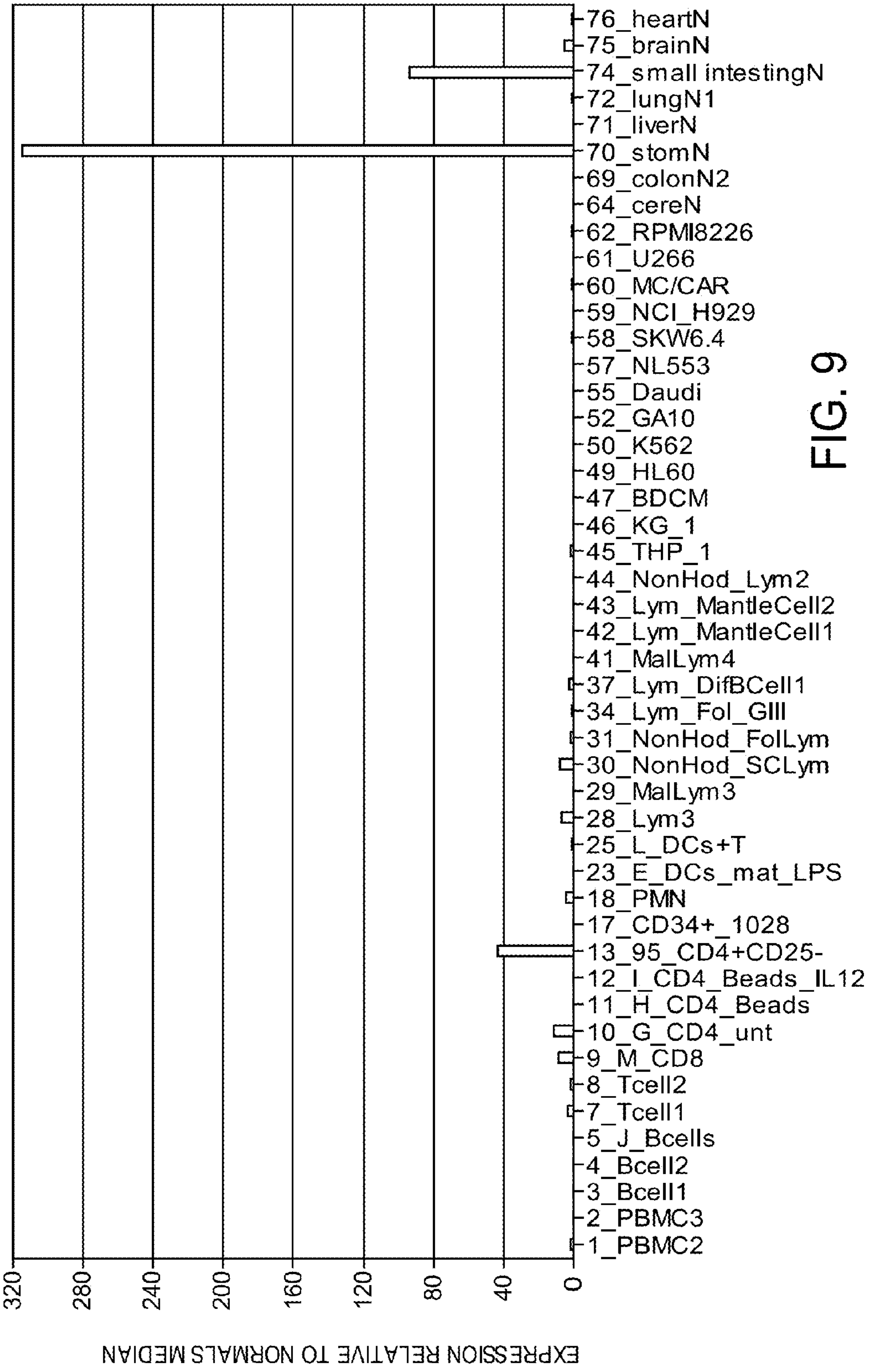
FIG. 9 presents a histogram showing expression of V-set and immunoglobulin domain containing 1(VSIG1) AI581519 transcripts which are detectable by amplicon as depicted in sequence name AI581519seg7-9 (SEQ ID NO: 196) in blood-specific panel.

The results of this analysis are depicted in the histogram in FIG. 9. Expression of the above-indicated VSIG1 transcript is high in CD8, CD4 untreated and CD4+CD25− samples but even higher in normal small intestine and normal stomach samples.

Primer pairs are also optionally and preferably encompassed within the present invention; for example, for the above experiment, the following primer pair was used as a non-limiting illustrative example only of a suitable primer pair: seg7-9F3 forward primer (SEQ ID NO:194); and seg7-9R3 reverse primer (SEQ ID NO:195).

The present invention also preferably encompasses any amplicon obtained through the use of any suitable primer pair; for example, for the above experiment, the following amplicon was obtained as a non-limiting illustrative example only of a suitable amplicon: seg7-9F3R3 (SEQ ID NO:196).

```
Forward Primer > AI581519seg7-9F3
                                    (SEQ ID NO: 194)
ATGACGCACGTAAGAGACGCTCG

Reverse Primer > AI581519seg7-9R3
                                    (SEQ ID NO: 195)
GGAGTTCAGCCTGCTGTCCATCAAG

Amplicon > AI581519seg7-9F3R3
                                    (SEQ ID NO: 196)
ATGACGCACGTAAGAGACGCTCGGGGAAGATGTAGCTGGA

CCTCTGAGTCTCCTTGGGAGGAGGGGAAGTGGCCAGATGT

TGAGGCTGTGAAGGGCACTCTTGATGGACAGCAGGCTGAA

CTCC
```

Expression of V-set and immunoglobulin domain containing 1(VSIG1) AI581519 transcripts which are detectable by amplicon as depicted in sequence name AI581519_junc7-11F2R2 (SEQ ID NO:193) in normal and cancerous lung tissues, normal and cancerous ovary tissues, different normal tissues and blood-specific panel.

Expression of VSIG1 transcripts detectable by or according to junc7-11F2R2-AI581519_junc7-11F2R2 (SEQ ID NO:193) amplicon and primers AI581519_junc7-11F2 (SEQ ID NO:191) and AI581519_junc7-11R2 (SEQ ID NO:192) was measured by real time PCR on lung panel, ovary panel, normal panel and blood panel. The samples used are detailed in Table 3, Table 4, Table 2 and Table 1 above, respectively. For each RT sample, the expression of the above amplicon was normalized to the normalization factor calculated from the expression of several house keeping genes as described in Example 1.

For lung panel—Non-detected sample (sample no. 49, Table 3) was assigned Ct value of 41 and was calculated accordingly. The normalized quantity of each RT sample was then divided by the median of the quantities of the normal samples (samples numbers 51-64, 69 and 70, Table 3 above), to obtain a value of fold up-regulation for each sample relative to median of the normal samples.

Figure 10:
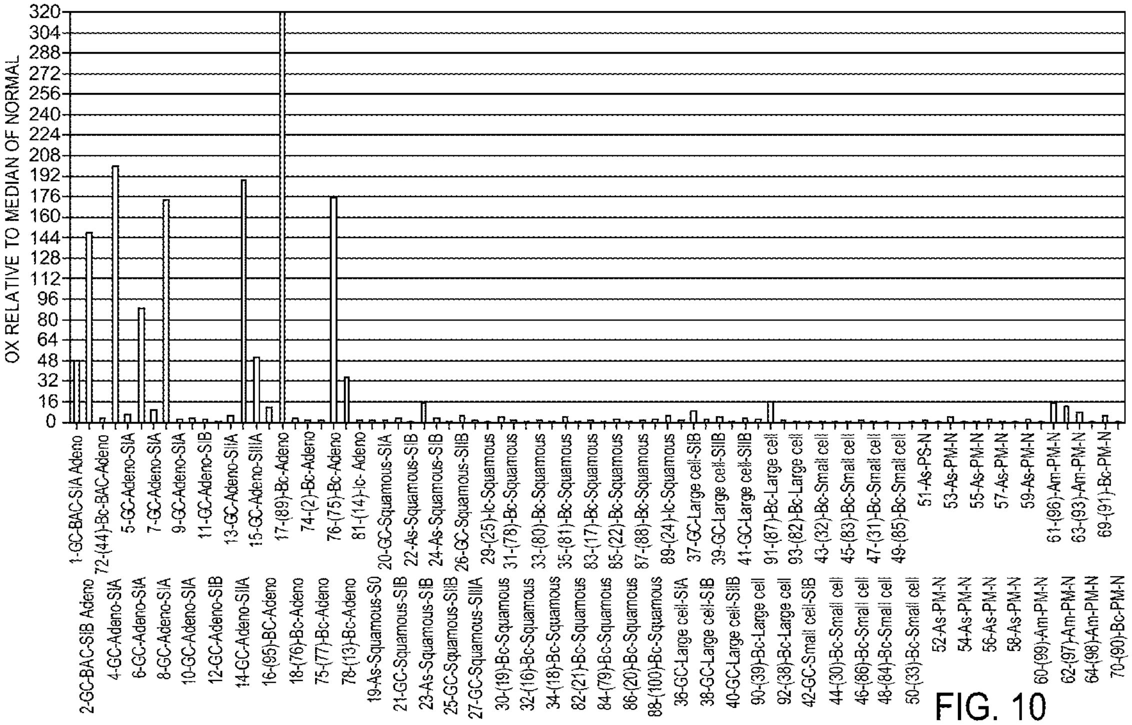
FIG. 10 presents a histogram showing expression of V-set and immunoglobulin domain containing 1(VSIG1) AI581519 transcripts which are detectable by amplicon as depicted in sequence name AI581519_junc7-11F2R2 (SEQ ID NO: 193) in normal and cancerous lung tissues.

FIG. 10 is a histogram showing over expression of the above-indicated VSIG1 transcripts in cancerous Lung samples relative to the normal samples.

As is evident from FIG. 10, the expression of VSIG1 transcripts detectable by the above amplicon in adenocarcinoma samples was significantly higher than in the non-cancerous samples (sample numbers 51-64, 69 and 70, Table 3 above). Notably an over-expression of at least 16 fold was found in 10 out of 23 adenocarcinoma samples.

Statistical analysis was applied to verify the significance of these results, as described below. The P value for the difference in the expression levels of VSIG1 transcripts detectable by the above amplicon in lung adenocarcinoma samples versus the normal tissue samples was determined by T test as 5.13e-003.

Threshold of 16 fold over expression was found to differentiate between adenocarcinoma and normal samples with P value of 1.80e-003 as checked by exact Fisher test.

The above values demonstrate statistical significance of the results.

For ovary panel—Non-detected samples (samples no. 16, 23, 57, 60-62, 67, 68, 71-74, 77 and 78, Table 4) were assigned Ct value of 41 and were calculated accordingly. The normalized quantity of each RT sample was then divided by the median of the quantities of the normal samples (sample numbers 52, 53, 55 and 57-67, Table 4 above), to obtain a value of fold up-regulation for each sample relative to median of the normal samples.

Figure 11:
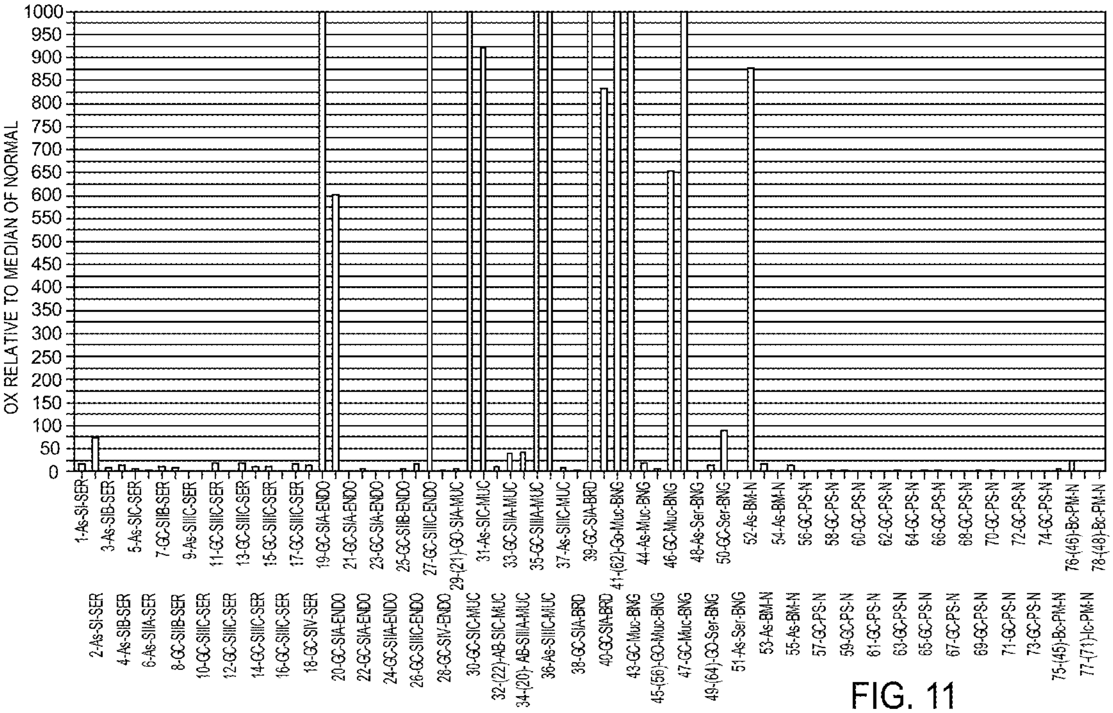
FIG. 11 presents a histogram showing expression of V-set and immunoglobulin domain containing 1(VSIG1) AI581519 transcripts which are detectable by amplicon as depicted in sequence name AI581519_junc7-11F2R2 (SEQ ID NO: 193) in normal and cancerous ovarian tissues.

FIG. 11 is a histogram showing over expression of the above-indicated VSIG1 transcripts in cancerous Ovary samples relative to the normal samples.

As is evident from FIG. 11, the expression of VSIG1 transcripts detectable by the above amplicon in mucinous carcinoma samples was significantly higher than in the non-cancerous samples (sample numbers 52, 53, 55 and 57-67, Table 4 above) and was higher in a few adenocarcinoma samples than in the non-cancerous samples. Notably an over-expression of at least 25 fold was found in 6 out of 9 mucinous carcinoma samples and in 10 out of 37 adenocarcinoma samples.

Statistical analysis was applied to verify the significance of these results, as described below. Threshold of 25 fold over expression was found to differentiate between mucinous carcinoma samples and adenocarcinoma and normal samples with P value of 3.95e-004 and 1.88e-002, respectively, as checked by exact Fisher test. The above values demonstrate statistical significance of the results.

Figure 12A:
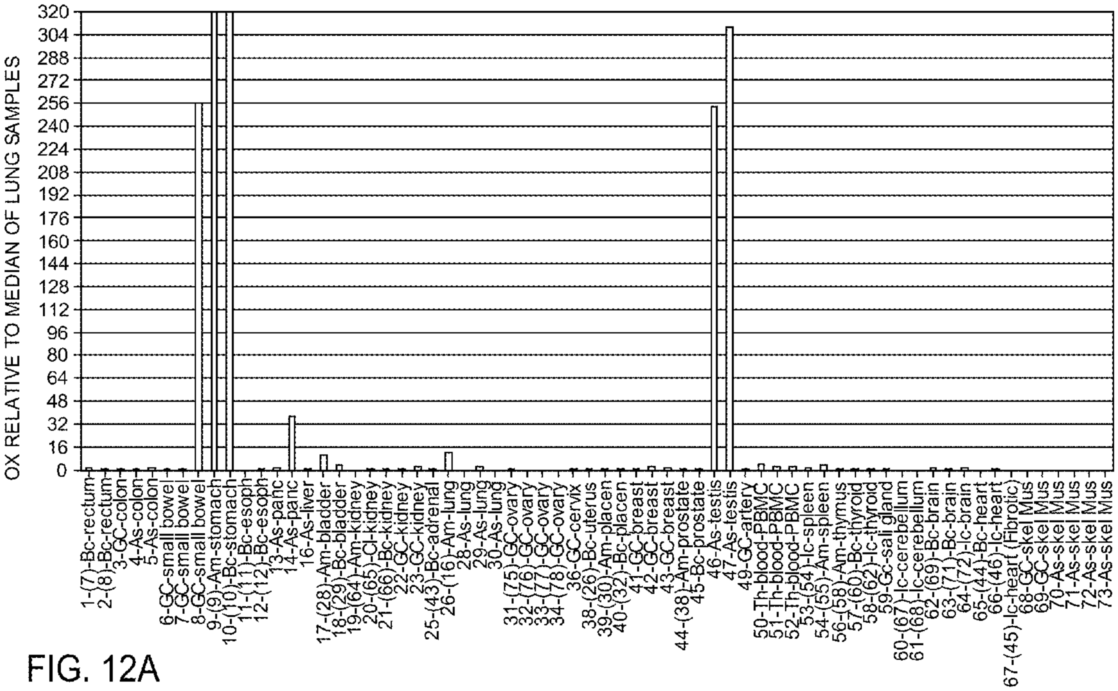
FIGS. 12A-12B present histograms showing expression of V-set and immunoglobulin domain containing 1(VSIG1) AI581519 transcripts which are detectable by amplicon as depicted in sequence name AI581519_junc7-11F2R2 (SEQ ID NO: 193) in various normal tissues.
Figure 12B:
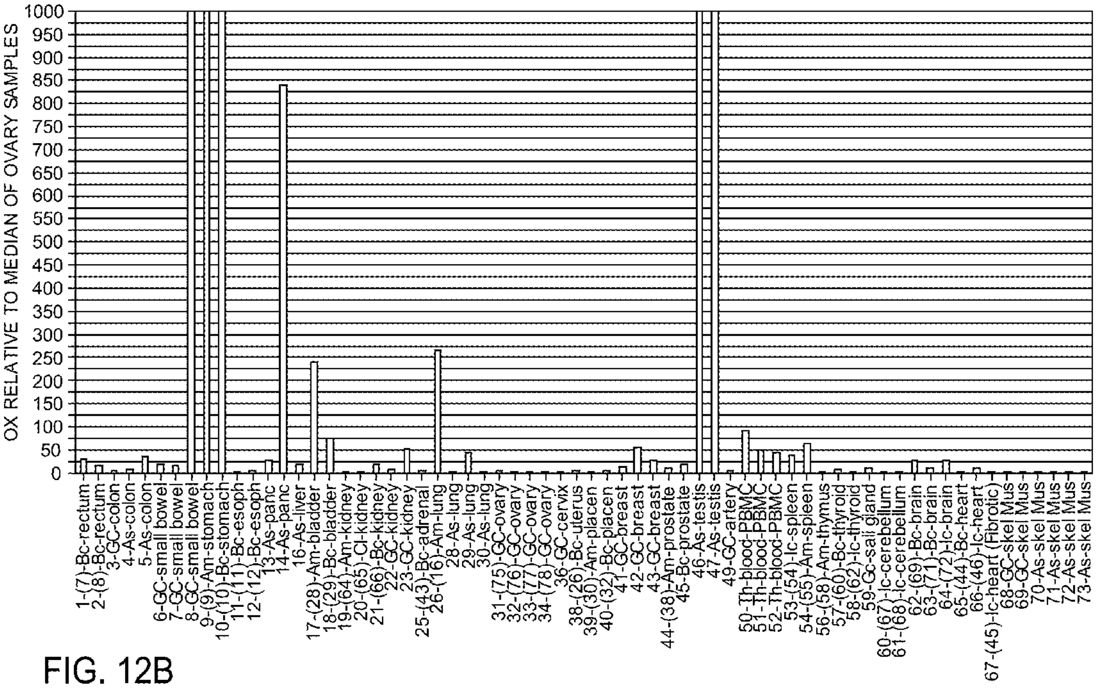

For normal panel—Non-detected samples (samples no. 11-20, 28, 30, 32-34, 36, 38-40, 49 and 56, Table 2) were assigned Ct value of 41 and were calculated accordingly. The normalized quantity of each RT sample was then divided by the median of the quantities of the lung samples (sample numbers 26, and 28-30, Table 2 above), to obtain a value of relative expression of each sample relative to median of the lung samples, as shown in FIG. 12A. The normalized quantity of each RT sample was then divided by the median of the quantities of the ovary samples (sample numbers 31-34, Table 2 above), to obtain a value of relative expression of each sample relative to median of the ovary samples, as shown in FIG. 12B.

For blood panel—Non-detected samples (samples no. 6, 15-19, 22-24, 27, 29, 40, 41, 46-50, 52-58, 60-64, 71 and 76, Table 1) were assigned Ct value of 41 and were calculated accordingly. The normalized quantity of each RT sample was then divided by the median of the quantities of the kidney normal samples (sample numbers 65-67, Table 1 above), to obtain a value of relative expression of each sample relative to median of the normal samples.

Figure 13:
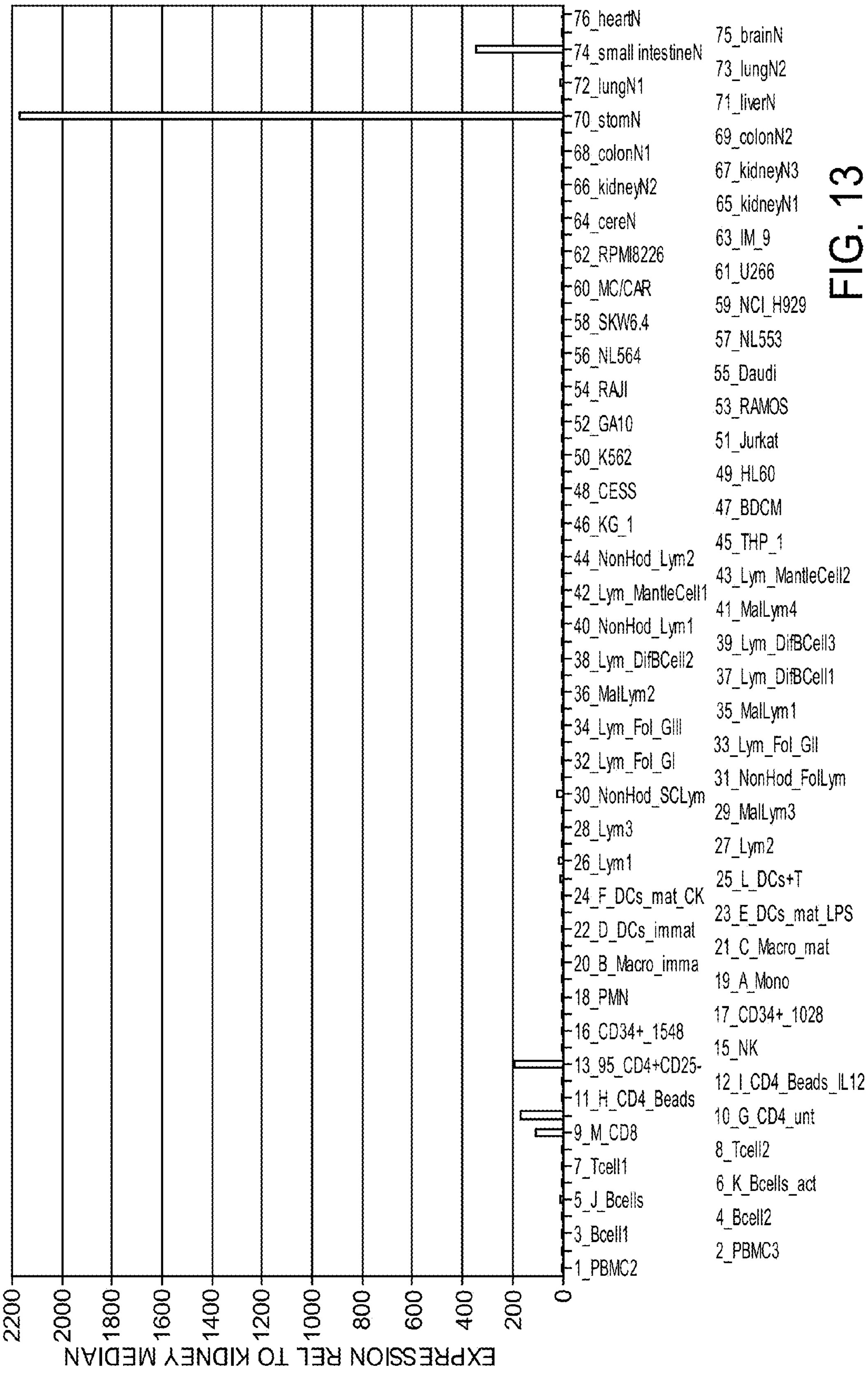
FIG. 13 presents a histogram showing expression of V-set and immunoglobulin domain containing 1(VSIG1) AI581519 transcripts which are detectable by amplicon as depicted in sequence name AI581519_junc7-11F2R2 (SEQ ID NO: 193) in blood-specific panel.

The results of this analysis are depicted in the histogram in FIG. 13. Expression of the above-indicated VSIG1 transcript is very high in CD8, CD4 untreated and CD4+CD25− samples, is high in several lymphomas but also very high in normal small intestine and normal stomach samples.

Primer pairs are also optionally and preferably encompassed within the present invention; for example, for the above experiment, the following primer pair was used as a non-limiting illustrative example only of a suitable primer pair: AI581519_junc7-11F2 (SEQ ID NO:191) forward primer; and AI581519_junc7-11R2 (SEQ ID NO:192) reverse primer.

The present invention also preferably encompasses any amplicon obtained through the use of any suitable primer pair; for example, for the above experiment, the following amplicon was obtained as a non-limiting illustrative example only of a suitable amplicon: AI581519_junc7-11F2R2 (SEQ ID NO:193).

```
Forward Primer >AI581519_junc7-11F2
                                    (SEQ ID NO: 191)
GAAGATGTAGCTGGACCTCTGAGATTTA
```

-continued

```
Reverse Primer >AI581519_junc7-11R2
                                    (SEQ ID NO: 192)
GTTGGACCCTGTAATTCGATCTTT

Amplicon >AI581519_junc7_11F2R2
                                    (SEQ ID NO: 193)
GAAGATGTAGCTGGACCTCTGAGATTTACTTTTCTCAAG
GTGGACAAGCTGTAGCCATCGGGCAATTTAAAGATCGAA
TTACAGGGTCCAAC
```

Example 3

Description for Cluster AA424839

The present invention relates to ILDR1 polypeptides, novel splice variants and diagnostics and therapeutics based thereon.

According to the present invention, Cluster AA424839 (internal ID 71418261) features 4 transcripts and 1 segment of interest, the names for which are given in Tables 33 and 34, respectively. The selected protein variants are given in table 35.

TABLE 33

| Transcripts of interest<br>Transcript Name |
|---|
| AA424839_T0 (SEQ ID NO: 17) |
| AA424839_T2 (SEQ ID NO: 18) |
| AA424839_T4 (SEQ ID NO: 19) |
| AA424839_1_T7 (SEQ ID NO: 20) |

TABLE 34

| Segments of interest<br>Segment Name |
|---|
| AA424839_N18 (SEQ ID NO: 122) |

TABLE 35

| Proteins of interest | |
|---|---|
| Protein Name | Corresponding Transcripts |
| AA424839_P3 (SEQ ID NO: 22) | AA424839_T0 (SEQ ID NO: 17) |
| AA424839_P5 (SEQ ID NO: 21) | AA424839_T2 (SEQ ID NO: 18) |
| AA424839_P7 (SEQ ID NO: 23) | AA424839_T4 (SEQ ID NO: 19) |
| AA424839_1_P11 (SEQ ID NO: 24) | AA424839_1_T7 (SEQ ID NO: 20) |

These sequences are variants of the known protein immunoglobulin-like domain containing receptor 1 (RefSeq accession identifier NP_787120 (SEQ ID NO: 21), also known as ILDR1alpha, ILDR1beta, MGC50831), referred to herein as the previously known protein.

ILDR1, denoted immunoglobulin-like domain containing receptor 1 (SEQ ID NO:21), was described by Hauge et al. (2004) BBRC 323: 970-978, that demonstrated differential expression of the transcripts encoding this protein in indolent follicular lymphoma (FL) and matched transformed diffuse large B cell lymphoma (DLBCL). The gene was identified using a cDNA substraction strategy on patient-matched biopsies of FL and DLBCL. The protein was shown to contain a signal peptide and transmembrane domain, and an Ig domain in the extracellular portion, and it was found to be membrane bound protein, having 31% identity to lipolysis-stimulated remnant receptor (LSR).

According to the present invention, ILDR1 protein and ILDR1 splice variants were predicted to be novel B7/CD28 members. According to the present invention, ILDR1 and ILDR1 splice variants were demonstrated to be overexpressed in ovarian cancer.

Figure 14:
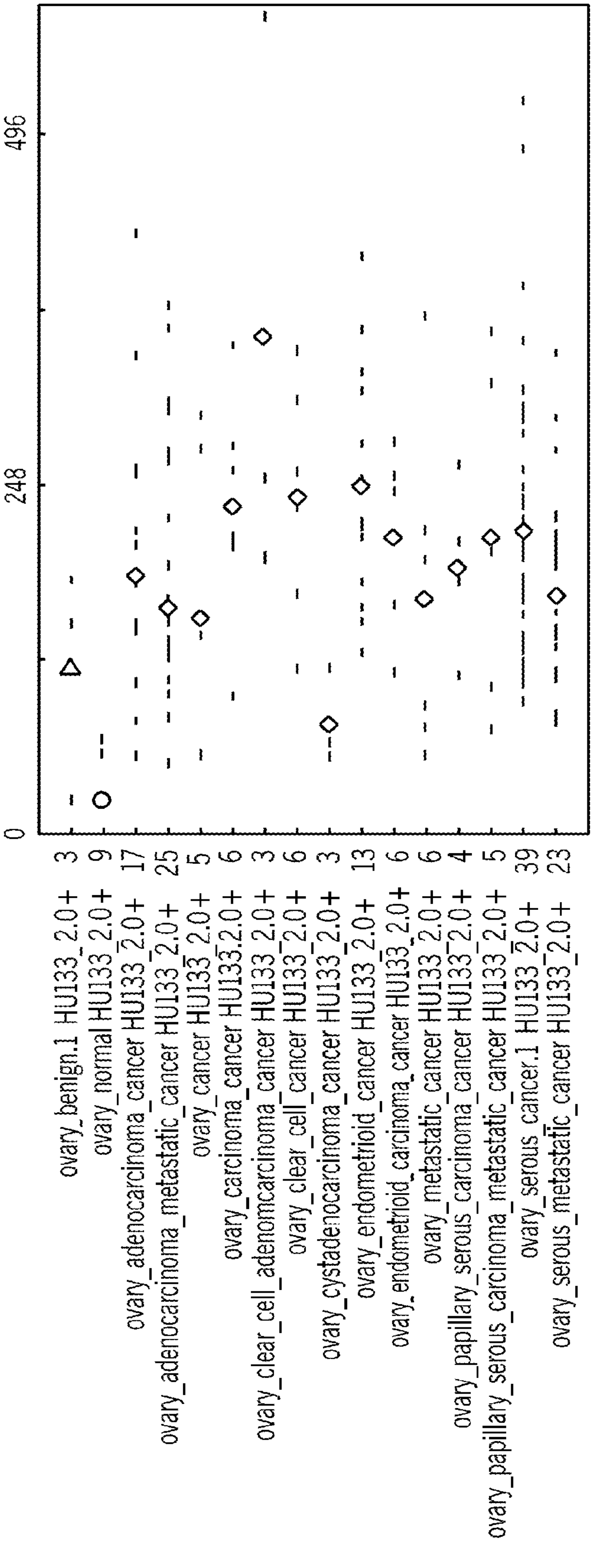
FIG. 14 shows a scatter plot, demonstrating the expression of AA424839 transcripts, that encode the ILDR1 proteins, on a virtual panel of all tissues and conditions using MED discovery engine, demonstrating overexpression of AA424839 transcripts in ovarian cancer compared to normal ovary samples.
Figure 15:
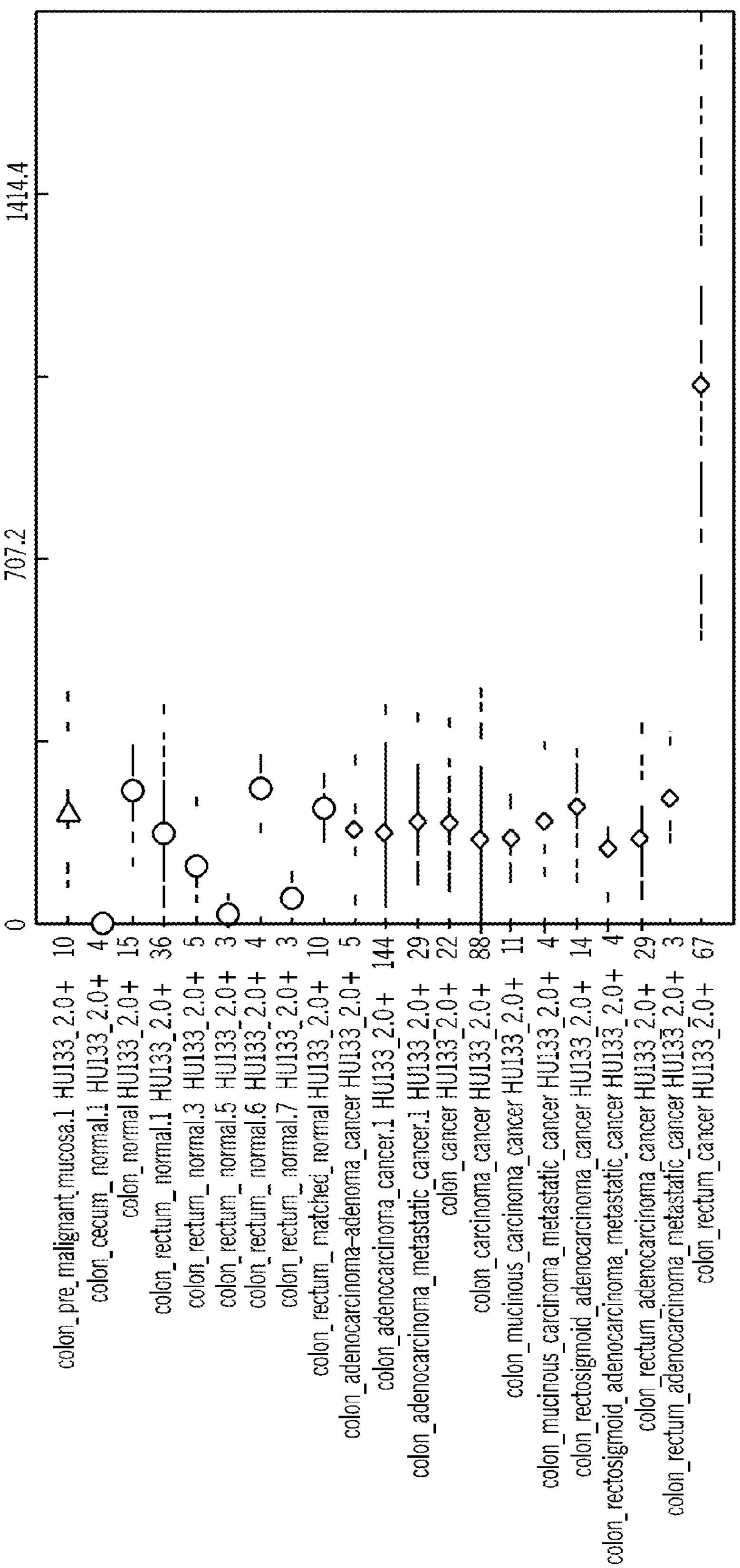
FIG. 15 shows a scatter plot, demonstrating the expression of AA424839 transcripts, that encode the ILDR1 proteins, on a virtual panel of all tissues and conditions using MED discovery engine, demonstrating overexpression of AA424839 transcripts in colon cancer compared to normal colon samples.

MED discovery engine described in Example 1 herein, was used to assess the expression of ILDR1 transcripts. Expression data for Affymetrix probe set 235583_at representing the ILDR1 gene data is shown in FIGS. 14 and 15. As evident from the scatter plot, presented in FIG. 14, the expression of ILDR1 transcripts detectable with the above probe sets was higher in ovarian cancer compared to normal ovary samples. As evident from the scatter plot, presented in FIG. 15, the expression of ILDR1 transcripts detectable with the above probe sets was higher in colon cancer compared to normal colon samples.

As noted above, cluster AA424839 features 4 transcripts, which were listed in Table 33 above. These transcripts encode for proteins which are variants of protein immunoglobulin-like domain containing receptor 1 (SEQ ID NO:21). A description of each protein according to the present invention is now provided.

Variant protein AA424839_P3 (SEQ ID NO:22) according to the present invention has an amino acid sequence as encoded by transcript AA424839_T0 (SEQ ID NO:17). Alignments to previously published protein sequences are shown in FIG. 16A. A brief description of the relationship of the variant protein according to the present invention to each such aligned protein is as follows:

1. Comparison report between AA424839_P3 (SEQ ID NO:22) and known proteins Q86SU0_HUMAN (SEQ ID NO: 21) and NP_787120 (SEQ ID NO: 21) (FIG. 16A):

A. An isolated chimeric polypeptide encoding for AA424839_P3 (SEQ ID NO:22), comprising a first amino acid sequence being at least 90% homologous to

```
MAWPKLPAPWLLLCTWLPAGCLSLLVTVQHTERYVTLFASIILKCDYTTS
AQLQDVVVTWRFKSFCKDPIFDYYSASYQAALSLGQDPSNDCNDNQREVR
IVAQRRGQNEPVLGVDYRQRKITIQNRADLVINEVMWWDHGVYYCTIEAP
GDTSGDPDKEVKLIVLHWLTVIFIILGALLLLLLIGVCWCQCCPQYCCCY
IRCPCCPAHCCCPEE
```

corresponding to amino acids 1-215 of known proteins Q865U0_HUMAN (SEQ ID NO: 21) and NP_787120 (SEQ ID NO: 21), which also corresponds to amino acids 1-215 of AA424839_P3 (SEQ ID NO:22), a second amino acid sequence being at least 70%, optionally at least 80%, preferably at least 85%, more preferably at least 90% and most preferably at least 95, 96, 97, 98 or 99% homologous to a polypeptide having the sequence

```
                                    (SEQ ID NO: 288)
ALARHRYMKQAQALGPQMMGKPLYWGADRSSQVSSYPMHPLLQR
```

corresponding to amino acids 216-259 of AA424839_P3 (SEQ ID NO:22), and a third amino acid sequence being at least 90% homologous to

```
DLSLPSSLPQMPMTQTTNQPPIANGVLEYLEKELRNLNLAQPLPPDLKGR
FGHPCSMLSSLGSEVVERRIIHLPPLIRDLSSSRRTSDSLHQQWLTPIPS
RPWDLREGRSHHHYPDFHQELQDRGPKSWALERRELDPSWSGRHRSSRLN
```

-continued

GSPIHWSDRDSLSDVPSSSEARWRPSHPPFRSRCQERPRRPSPRESTQRH

GRRRRHRSYSPPLPSGLSSWSSEEDKERQPQSWRAHRRGSHSPHWPEEKP

PSYRSLDITPGKNSRKKGSVERRSEKDSSHSGRSVVI corresponding to amino acids 216-502 of known proteins Q865U0_HUMAN (SEQ ID NO: 21) and NP_787120 (SEQ ID NO: 21), which also corresponds to amino acids 260-546 of AA424839_P3 (SEQ ID NO:22), wherein said first amino acid sequence, second amino acid sequence and third amino acid sequence are contiguous and in a sequential order.

B. An isolated polypeptide encoding for an edge portion of AA424839_P3 (SEQ ID NO:22), comprising an amino acid sequence being at least 70%, optionally at least about 80%, preferably at least about 85%, more preferably at least about 90% and most preferably at least about 95, 96, 97, 98 or 99% homologous to the (SEQ ID NO: 288)
ALARHRYMKQAQALGPQMMGKPLYWGADRSSQVSSYPMHPLLQR of AA424839_P3 (SEQ ID NO:22).

The localization of the variant protein was determined according to results from a number of different software programs and analyses, including analyses from SignalP and other specialized programs. The variant protein is believed to be located as follows with regard to the cell: membrane.

Variant protein AA424839_P3 (SEQ ID NO:22) also has the following non-silent SNPs (Single Nucleotide Polymorphisms) as listed in Table 36, (given according to their positions on the amino acid sequence, with the alternative amino acids listed (SEQ ID NO:22)).

TABLE 36

| Amino acid mutations | |
|---|---|
| SNP positions on amino acid sequence | Alternative amino acids |
| 165 | V -> F |
| 165 | V -> L |
| 264 | P -> R |
| 388 | W -> L |
| 388 | W -> S |
| 436 | H -> N |
| 500 | H -> L |
| 500 | H -> P |
| 516 | D -> Y |

The variant protein has the following domains, as determined by using InterPro. The domains are described in Table 37.

TABLE 37

| InterPro domains | | |
|---|---|---|
| Domain description | Analysis type | Positions on protein |
| Phospholipase A2 | ScanReg Exp | 205-212 |
| Immunoglobulin subtype | HMMSmart | 30-166 |

Variant protein AA424839_P3 (SEQ ID NO:22) is encoded by the transcript AA424839_T0 (SEQ ID NO:17), for which the coding portion starts at position 204 and ends at position 1841. The transcript also has the following SNPs as listed in Table 38 (given according to their position on the nucleotide sequence, with the alternative nucleic acid listed).

TABLE 38

| Nucleic acid SNPs | |
|---|---|
| Polymorphism | SNP positions on nucleotide sequence |
| G -> T | 696, 1366, 1748, 1749 |
| G -> C | 696, 995, 1366 |
| C -> G | 994, 1529, 2305 |
| A -> T | 1442, 1702 |
| A -> C | 1442, 1702 |
| G -> A | 1502 |
| C -> A | 1509, 1529 |

Protein AA424839_P5 (SEQ ID NO:21) according to the present invention has an amino acid sequence as encoded by transcript AA424839_T2 (SEQ ID NO:18).

The localization of the protein was determined according to results from a number of different software programs and analyses, including analyses from SignalP and other specialized programs. The protein is believed to be located as follows with regard to the cell: membrane.

Protein AA424839_P5 (SEQ ID NO:21) also has the following non-silent SNPs (Single Nucleotide Polymorphisms) as listed in Table 39, (given according to their positions on the amino acid sequence, with the alternative amino acids listed (SEQ ID NO:21)).

TABLE 39

| Amino acid mutations | |
|---|---|
| SNP positions on amino acid sequence | Alternative amino acids |
| 165 | V -> F |
| 165 | V -> L |
| 220 | P -> R |
| 344 | W -> L |
| 344 | W -> S |
| 392 | H -> N |
| 456 | H -> L |
| 456 | H -> P |
| 472 | D -> Y |

The protein has the following domains, as determined by using InterPro. The domains are described in Table 40:

TABLE 40

| InterPro domains | | |
|---|---|---|
| Domain description | Analysis type | Positions on protein |
| Phospholipase A2 | ScanReg Exp | 205-212 |
| Immunoglobulin subtype | HMMSmart | 30-166 |

Protein AA424839_P5 (SEQ ID NO:21) is encoded by the transcript AA424839_T2 (SEQ ID NO:18), for which the coding portion starts at position 204 and ends at position 1709. The transcript also has the following SNPs as listed in Table 41 (given according to their position on the nucleotide sequence, with the alternative nucleic acid listed).

TABLE 41

| Nucleic acid SNPs | |
|---|---|
| Polymorphism | SNP positions on nucleotide sequence |
| G -> T | 696, 1234, 1616, 1617 |
| G -> C | 696, 863, 1234 |
| C -> G | 862, 1397, 2173 |
| A -> T | 1310, 1570 |
| A -> C | 1310, 1570 |
| G -> A | 1370 |
| C -> A | 1377, 1397 |

The genomic structure of protein AA424839_P5 (SEQ ID NO:21) (number of exons relevant to the extra-cellular region of the protein, the length of these exons, the frame of the codon in which the introns are inserted and the location of the protein features and domains in the gene structure) is characteristic to the ligands of the B7/co-stimulatory protein family, as given in table 42

TABLE 42

| genomic structure and protein features | | | |
|---|---|---|---|
| Exon number | Exon Length | Amino-Acids | Protein feature on exon |
| 1 | 58 | 1-19 | Signal Peptide |
| 2 | 171 | 20-76 | Ig Domain |
| 3 | 150 | 77-126 | Ig Domain |
| 4 | 120 | 127-166 | Ig Domain/Trans-membrane region |
| 5 | 147 | 167-215 | Trans-membrane region |
| 6 | 821 | 216-489 | |
| 7 | 39 | 490-502 | |

Variant protein AA424839_P7 (SEQ ID NO:23) according to the present invention has an amino acid sequence as encoded by transcript AA424839_T4 (SEQ ID NO:19). Alignments to one or more previously published protein sequences are shown in FIG. 16B. A brief description of the relationship of the variant protein according to the present invention to each such aligned protein is as follows:

1. Comparison report between AA424839_P7 (SEQ ID NO:23) and known proteins Q865U0_HUMAN and NP_787120 (SEQ ID NO: 21) (FIG. 16B):

A. An isolated chimeric polypeptide encoding for AA424839_P7 (SEQ ID NO:23), comprising a first amino acid sequence being at least 90% homologous to

```
MAWPKLPAPWLLLCTWLPAGCLSLLVTVQHTERYVTLFASIILKCDYTTS

AQLQDVVVTWRFKSFCKDPIFDYYSASYQAALSLGQDPSNDCNDNQREVR

IVAQRRGQNEPVLGVDYRQRKITIQN
```

corresponding to amino acids 1-126 of known proteins Q865U0_HUMAN and NP_787120 (SEQ ID NO: 21), which also corresponds to amino acids 1-126 of AA424839_P7 (SEQ ID NO:23), a second amino acid sequence being at least 70%, optionally at least 80%, preferably at least 85%, more preferably at least 90% and most preferably at least 95, 96, 97, 98 or 99%, homologous to a polypeptide having the sequence PLARHRYMKQAQALGPQMMGKPLYWGADRSSQVSSYPMHPLLQR corresponding to amino acids 127-170 of AA424839_P7 (SEQ ID NO:23), and a third amino acid sequence being at least 90% homologous to

```
DLSLPSSLPQMPMTQTTNQPPIANGVLEYLEKELRNLNLAQPLPPDLKGR

FGHPCSMLSSLGSEVVERRIIHLPPLIRDLSSSRRTSDSLHQQWLTPIPS

RPWDLREGRSHHHYPDFHQELQDRGPKSWALERRELDPSWSGRHRSSRLN

GSPIHWSDRDSLSDVPSSSEARWRPSHPPFRSRCQERPRRPSPRESTQRH

GRRRRHRSYSPPLPSGLSSWSSEEDKERQPQSWRAHRRGSHSPHWPEEKP

PSYRSLDITPGKNSRKKGSVERRSEKDSSHSGRSVVI
```

corresponding to amino acids 216-502 of known proteins Q865U0_HUMAN and NP_787120 (SEQ ID NO: 21), which also corresponds to amino acids 171-457 of AA424839_P7 (SEQ ID NO:23), wherein said first amino acid sequence, second amino acid sequence and third amino acid sequence are contiguous and in a sequential order.

The localization of the variant protein was determined according to results from a number of different software programs and analyses, including analyses from SignalP and other specialized programs. The variant protein is believed to be located as follows with regard to the cell: secreted.

Variant protein AA424839_P7 (SEQ ID NO:23) also has the following non-silent SNPs (Single Nucleotide Polymorphisms) as listed in Table 43, (given according to their positions on the amino acid sequence, with the alternative amino acids listed).

TABLE 43

| Amino acid mutations | |
|---|---|
| SNP positions on amino acid sequence | Alternative amino acids |
| 175 | P -> R |
| 299 | W -> L |
| 299 | W -> S |
| 347 | H -> N |
| 411 | H -> L |
| 411 | H -> P |
| 427 | D -> Y |

Variant protein AA424839_P7 (SEQ ID NO:23) is encoded by the transcript AA424839_T4 (SEQ ID NO:19), for which the coding portion starts at position 204 and ends at position 1574. The transcript also has the following SNPs as listed in Table 44 (given according to their position on the nucleotide sequence, with the alternative nucleic acid listed).

TABLE 44

| Nucleic acid SNPs | |
|---|---|
| Polymorphism | SNP positions on nucleotide sequence |
| C -> G | 727, 1262, 2038 |
| G -> C | 728, 1099 |
| G -> T | 1099, 1481, 1482 |
| A -> T | 1175, 1435 |
| A -> C | 1175, 1435 |
| G -> A | 1235 |
| C -> A | 1242, 1262 |

Variant protein AA424839_1_P11 (SEQ ID NO:24) according to the present invention has an amino acid sequence as encoded by transcript AA424839_1_T7 (SEQ ID NO:20). Alignments to one or more previously published protein sequences are given in FIG. 16C.

The localization of the variant protein was determined according to results from a number of different software programs and analyses, including analyses from SignalP and other specialized programs. The variant protein is believed to be located as follows with regard to the cell: membrane.

Variant protein AA424839_1_P11 (SEQ ID NO:24) also has the following non-silent SNPs (Single Nucleotide Polymorphisms) as listed in Table 45, (given according to their positions on the amino acid sequence, with the alternative amino acids listed (SEQ ID NO:24)).

TABLE 45

| Amino acid mutations | |
|---|---|
| SNP positions on amino acid sequence | Alternative amino acids |
| 108 | V -> F |
| 108 | V -> L |
| 207 | P -> R |
| 331 | W -> L |
| 331 | W -> S |
| 379 | H -> N |
| 443 | H -> L |
| 443 | H -> P |
| 459 | D -> Y |

The variant protein has the following domains, as determined by using InterPro. The domains are described in Table 46:

TABLE 46

| InterPro domains | | |
|---|---|---|
| Domain description | Analysis type | Positions on protein |
| Phospholipase A2 | ScanReg Exp | 148-155 |
| Immunoglobulin subtype | HMMSmart | 30-109 |

Variant protein AA424839_1_P11 (SEQ ID NO:24) is encoded by the transcript AA424839_1_T7 (SEQ ID NO:20), for which the coding portion starts at position 204 and ends at position 1670. The transcript also has the following SNPs as listed in Table 47 (given according to their position on the nucleotide sequence, with the alternative nucleic acid listed).

TABLE 47

| Nucleic acid SNPs | |
|---|---|
| Polymorphism | SNP positions on nucleotide sequence |
| G -> T | 525, 1195, 1577, 1578 |
| G -> C | 525, 824, 1195 |
| C -> G | 823, 1358, 2134 |
| A -> T | 1271, 1531 |
| A -> C | 1271, 1531 |
| G -> A | 1331 |
| C -> A | 1338, 1358 |

Segment cluster AA424839_N18 (SEQ ID NO:122) according to the present invention is supported by 10 libraries. The number of libraries was determined as previously described. This segment can be found in the following transcripts: AA424839_T0 (SEQ ID NO:17), AA424839_T2 (SEQ ID NO:18), AA424839_T4 (SEQ ID NO:19) and AA424839_1_T7 (SEQ ID NO:20). Table 48 below describes the starting and ending position of this segment on each transcript.

TABLE 48

| Segment location on transcripts | | |
|---|---|---|
| Transcript name | Segment starting position | Segment ending position |
| AA424839_T0 (SEQ ID NO: 17) | 1173 | 1802 |
| AA424839_T2 (SEQ ID NO: 18) | 1041 | 1670 |
| AA424839_T4 (SEQ ID NO: 19) | 906 | 1535 |
| AA424839_1_T7 (SEQ ID NO: 20) | 1002 | 1631 |

Expression of immunoglobulin-like domain containing receptor 1 (ILDR1) AA424839 transcripts which are detectable by amplicon as depicted in sequence name AA424839_seg18wt (SEQ ID NO:199) in normal and cancerous Ovary tissues and in different normal tissues Expression of immunoglobulin-like domain containing receptor 1 (ILDR1) transcripts detectable by or according to seg18wt—AA424839_seg18wt (SEQ ID NO:199) amplicon and primers AA424839_seg18wtF1 (SEQ ID NO:197) and AA424839_seg18wtR1 (SEQ ID NO:198) was measured by real time PCR on ovary panel and normal panel. The samples used are detailed in Table 4 and Tabel 2 above, respectively. For each RT sample, the expression of the above amplicon was normalized to the normalization factor calculated from the expression of several house keeping genes as described in Example 1.

Ovary panel—The normalized quantity of each RT sample was then divided by the median of the quantities of the normal samples (sample numbers 52-78, Table 4 above), to obtain a value of fold up-regulation for each sample relative to median of the normal samples.

Figure 17:
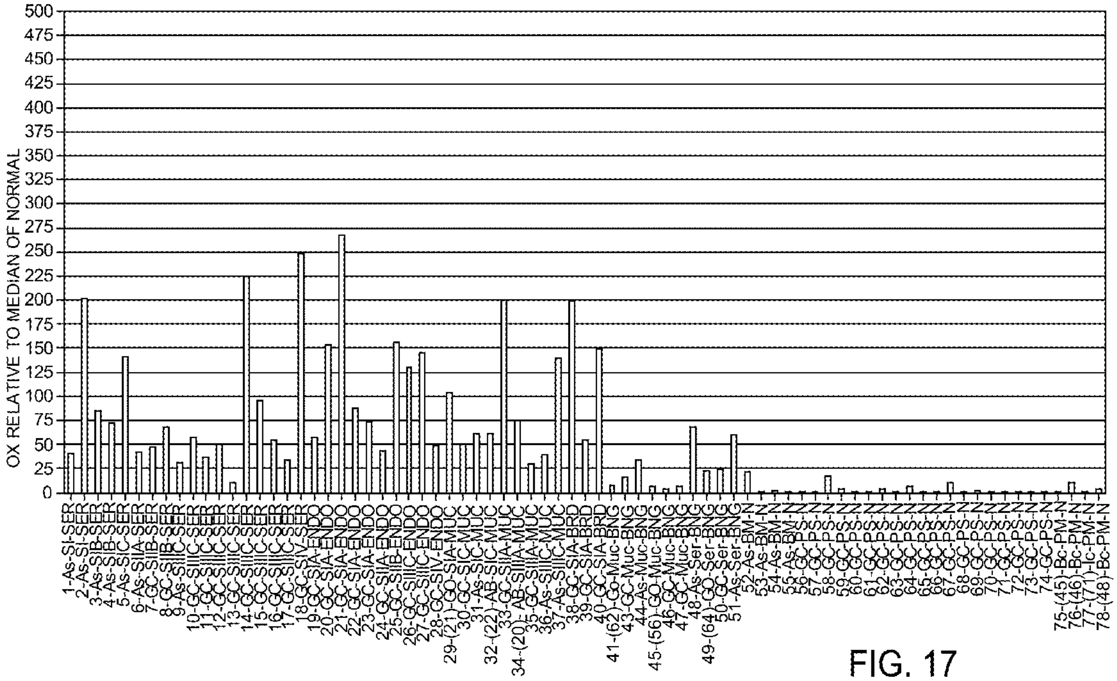
FIG. 17 presents a histogram showing expression of immunoglobulin-like domain containing receptor 1 (ILDR1) AA424839 transcripts which are detectable by amplicon as depicted in sequence name AA424839_seg18wt (SEQ ID NO: 199) in normal and cancerous ovary tissues.

FIG. 17 is a histogram showing over expression of the above-indicated immunoglobulin-like domain containing receptor 1 (ILDR1) transcripts in cancerous Ovary samples relative to the normal samples.

As is evident from FIG. 17, the expression of immunoglobulin-like domain containing receptor 1 (ILDR1) transcripts detectable by the above amplicon in serous carcinoma, mucinous carcinoma and adenocarcinoma samples was significantly higher than in the non-cancerous samples (sample numbers 52-78, Table 4 above). Notably an over-expression of at least 25 fold was found in 36 out of 37 adenocarcinoma samples, specifically in 17 out of 18 serous carcinoma samples, in 9 out of 9 mucinous carcinoma samples and in 10 out of 10 endometroid samples.

Statistical analysis was applied to verify the significance of these results, as described below. The P value for the difference in the expression levels of immunoglobulin-like domain containing receptor 1 (ILDR1) transcripts detectable by the above amplicon in Ovary adenocarcinoma samples, serous carcinoma samples mucinous carcinoma and endometriod versus the normal tissue samples was determined by T test as 3.85e-010, 6.21e-005, 1.10e-003 and 2.94e-004 respectively.

Threshold of 25 fold over expression was found to differentiate between adenocarcinoma, serous carcinoma, mucinous carcinoma, endometriod and normal samples with P value of 3.31e-017, 1.63e-011, 1.06e-008 and 2.87e-009, respectively, as checked by exact Fisher test.

The above values demonstrate statistical significance of the results.

Figure 18:
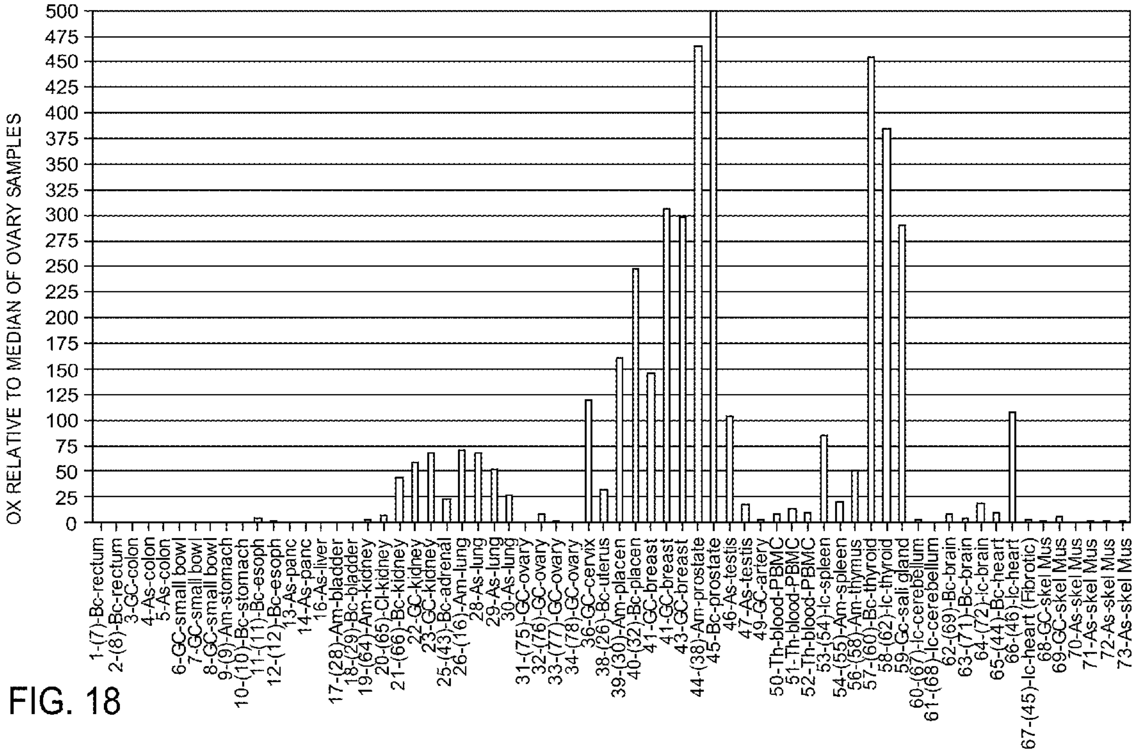
FIG. 18 presents a histogram showing expression of immunoglobulin-like domain containing receptor 1 (ILDR1) AA424839 transcripts which are detectable by amplicon as depicted in sequence name AA424839_seg18wt (SEQ ID NO: 199) in various normal tissues.

Normal panel—The normalized quantity of each RT sample was then divided by the median of the quantities of the ovary samples (sample numbers 31, 32, 33 and 34, Table 2 above), to obtain a value of relative expression of each sample relative to median of the ovary samples, as shown in FIG. 18.

Primer pairs are also optionally and preferably encompassed within the present invention; for example, for the above experiment, the following primer pair was used as a non-limiting illustrative example only of a suitable primer pair: AA424839_seg18wtF1 (SEQ ID NO:197) forward primer; and AA424839_seg18wtR1 (SEQ ID NO:198) reverse primer.

The present invention also preferably encompasses any amplicon obtained through the use of any suitable primer pair; for example, for the above experiment, the following amplicon was obtained as a non-limiting illustrative example only of a suitable amplicon: AA424839_seg18wt (SEQ ID NO:199).

```
Forward Primer >AA424839_seg18wtF1
                                        (SEQ ID NO: 197)
AGCCACCACCATTACCCTGA

Reverse Primer >AA424839_seg18wtR1
                                        (SEQ ID NO: 198)
TGCCTTCCACTCCACGATG

Amplicon >AA424839_seg18wt
                                        (SEQ ID NO: 199)
AGCCACCACCATTACCCTGATTTCCACCAGGAGCTCCA
GGACCGGGGGCCAAAGTCTTGGGCATTGGAAAGAAGGG
AGTTGGACCCATCGTGGAGTGGAAGGCA
```

Expression of immunoglobulin-like domain containing receptor 1 (ILDR1) AA424839 transcripts which are detectable by amplicon as depicted in sequence name AA424839_seg14-16 (SEQ ID NO: 202) in normal and cancerous ovary tissues or different normal tissues Expression of ILDR1 transcripts detectable by or according to seg14-16-AA424839_seg14-16 (SEQ ID NO: 202) amplicon and primers AA424839_seg14-16F1 (SEQ ID NO:200) and AA424839_seg14-16R1 (SEQ ID NO:201) was measured by real time PCR on ovary panel or normal panel. The samples used are detailed in Table 4 and in table 2 above, respectively. For each RT sample, the expression of the above amplicon was normalized to the normalization factor calculated from the expression of several house keeping genes as described in Example 1.

For ovary panel—the normalized quantity of each RT sample was then divided by the median of the quantities of the normal samples (sample numbers 52-55, 58, 59, 63-69 and 71-78, Table 4 above), to obtain a value of fold up-regulation for each sample relative to median of the normal samples.

Figure 19:
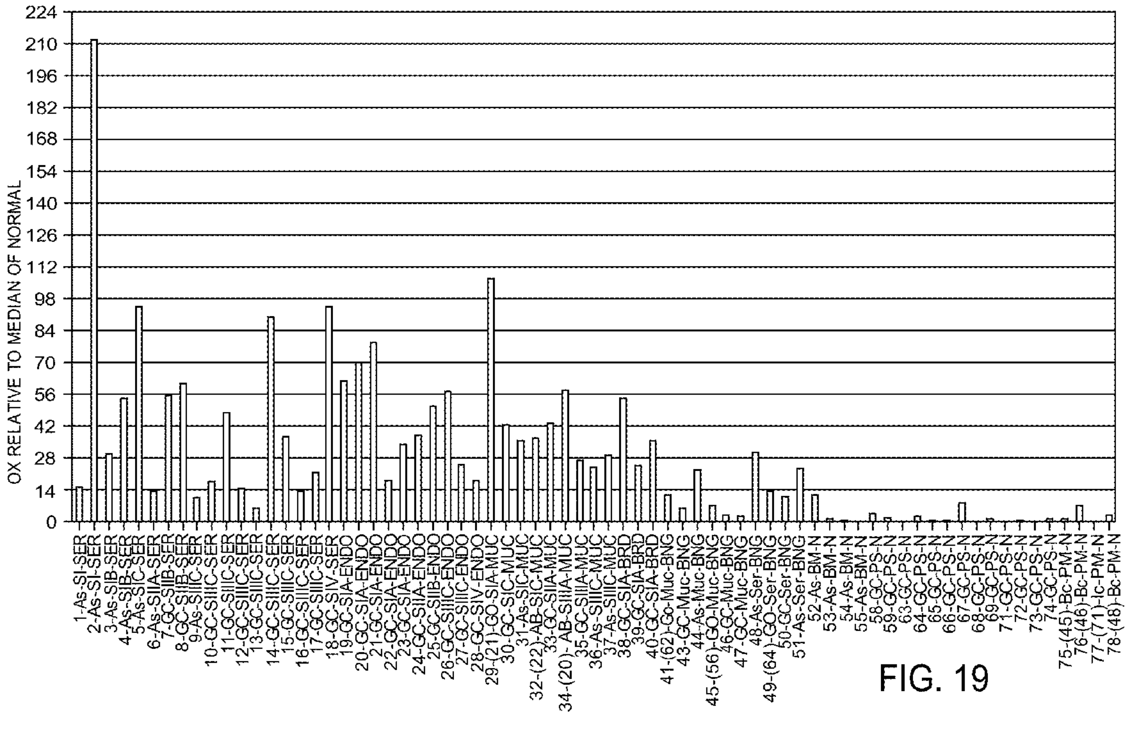
FIG. 19 presents a histogram showing expression of immunoglobulin-like domain containing receptor 1 (ILDR1) AA424839 transcripts which are detectable by amplicon as depicted in sequence name AA424839_seg14-16 (SEQ ID NO: 202) in normal and cancerous ovary tissues.

FIG. 19 is a histogram showing over expression of the above-indicated ILDR1 transcripts in cancerous Ovary samples relative to the normal samples.

As is evident from FIG. 19, the expression of ILDR1 transcripts detectable by the above amplicon in serous carcinoma, mucinous carcinoma and adenocarcinoma samples was significantly higher than in the non-cancerous samples (sample numbers 52-55, 58, 59, 63-69 and 71-78, Table 4 above). Notably an over-expression of at least 14 fold was found in 33 out of 37 adenocarcinoma samples: 14 out of 18 serous carcinoma samples, in 9 out of 9 mucinous carcinoma samples and in 10 out of 10 adenocarcinoma samples.

Statistical analysis was applied to verify the significance of these results, as described below.

The P value for the difference in the expression levels of ILDR1 transcripts detectable by the above amplicon in ovary adenocarcinoma samples, ovary serous carcinoma samples, ovary mucinous carcinoma samples and ovary endometroid samples versus the normal tissue samples was determined by T test as 1.00e-008, 4.79e-004, 4.97e-004 and 6.93e-005, respectively.

Threshold of 14 fold over expression was found to differentiate between adenocarcinoma, serous carcinoma, mucinous carcinoma, endometriod and normal samples with P value of 3.78e-012, 2.03e-007, 6.99e-008 and 2.25e-008, respectively, as checked by exact Fisher test.

The above values demonstrate statistical significance of the results.

For normal panel—The normalized quantity of each RT sample was then divided by the median of the quantities of the ovary samples (sample numbers 31-34, Table 2 above), to obtain a value of relative expression of each sample relative to median of the ovary samples.

Primer pairs are also optionally and preferably encompassed within the present invention; for example, for the above experiment, the following primer pair was used as a non-limiting illustrative example only of a suitable primer pair: AA424839_seg14-16F1 (SEQ ID NO:200) forward primer; and AA424839_seg14-16R1 (SEQ ID NO:201) reverse primer.

Figure 20:
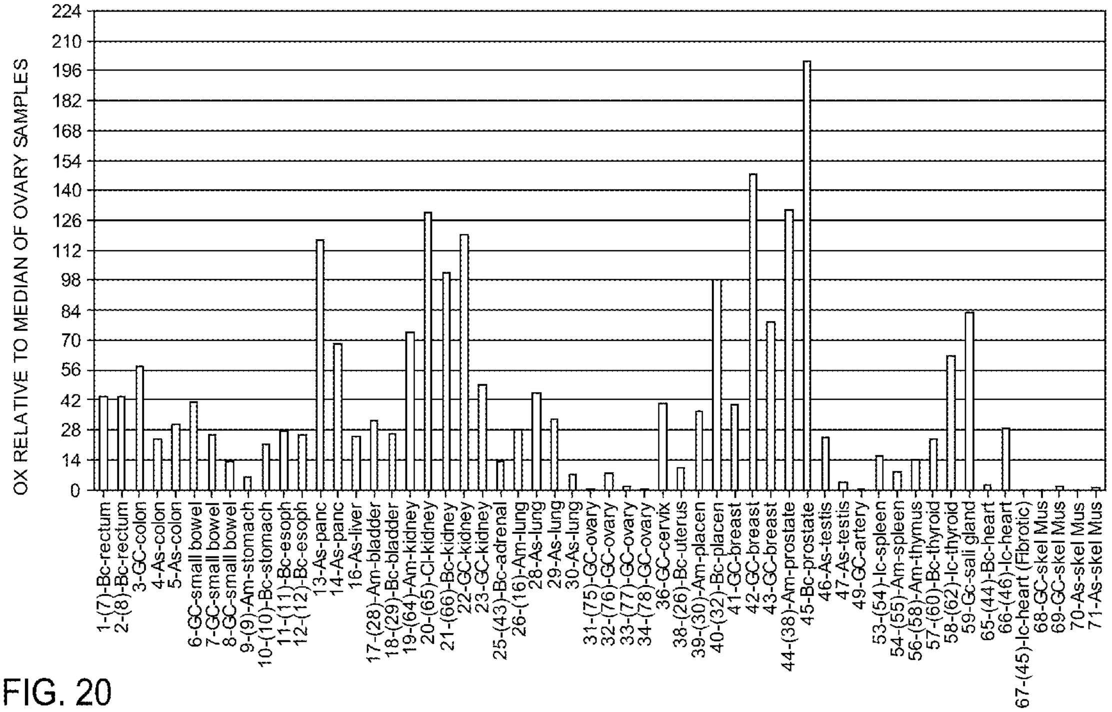
FIG. 20 presents a histogram showing expression of immunoglobulin-like domain containing receptor 1 (ILDR1) AA424839 transcripts which are detectable by amplicon as depicted in sequence name AA424839_seg14-16 (SEQ ID NO: 202) in various normal tissues.

The results demonstrating the expression of ILDR1 AA424839 transcripts which are detectable by amplicon as depicted in sequence name AA424839_seg14-16 (SEQ ID NO: 202) in different normal tissues are presented in FIG. 20.

The present invention also preferably encompasses any amplicon obtained through the use of any suitable primer pair; for example, for the above experiment, the following amplicon was obtained as a non-limiting illustrative example only of a suitable amplicon: AA424839_seg14-16F1R1 (SEQ ID NO:202).

```
Forward Primer >AA424839_seg14-16F1
                                        (SEQ ID NO: 200)
GCCACCGCTACATGAAGCA

Reverse Primer >AA424839_seg14-16R1
                                        (SEQ ID NO: 201)
CTGGACGGCAGGGACAAAT

Amplicon >AA424839_seg14-16F1R1
                                        (SEQ ID NO: 202)
GCCACCGCTACATGAAGCAGGCCCAGGCCCTAGGTCCT

CAGATGATGGGAAAACCCCTGTACTGGGGGGCGGACAG

GAGCTCCCAGGTTTCATCTTATCCAATGCACCCGCTGC

TGCAGCGAGATTTGTCCCTGCCGTCCAG
```

Expression of immunoglobulin-like domain containing receptor 1 (ILDR1) AA424839 transcripts which are detectable by amplicon as depicted in sequence name AA424839_seg11-14F3R3 (SEQ ID NO:205) in the blood-specific panel.

Expression of ILDR1 transcripts detectable by or according to seg11-14-AA424839seg11-14F3R3 (SEQ ID NO: 205) amplicon and primers AA424839seg11-14F3 (SEQ ID NO: 203) and AA424839seg11-14R3 (SEQ ID NO: 204) was measured by real time PCR on blood panel. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the kidney normal samples (sample numbers 65-67, Table 1 above), to obtain a value of relative expression of each sample relative to median of the kidney normal samples.

Figure 21:
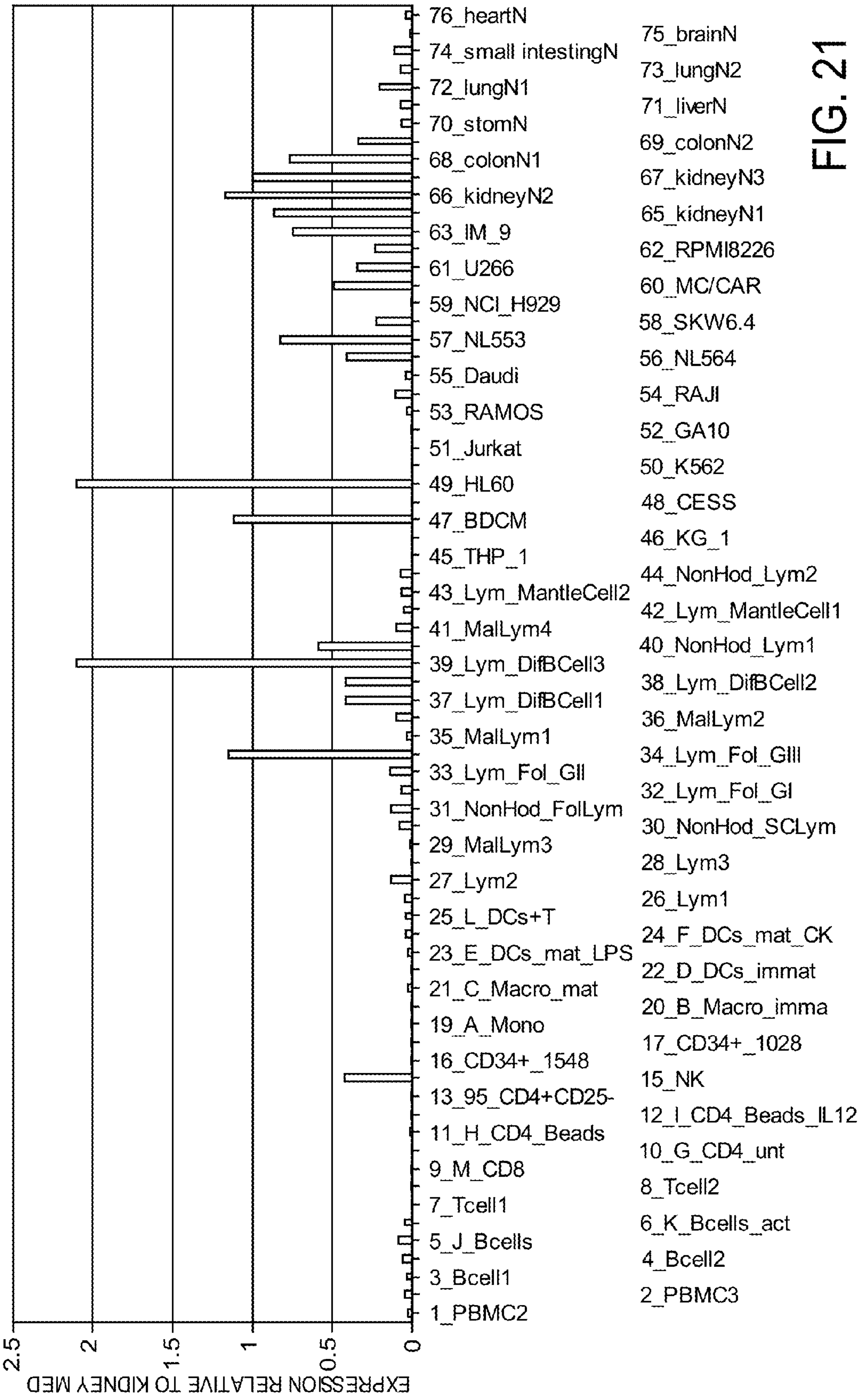
FIG. 21 presents a histogram showing expression of immunoglobulin-like domain containing receptor 1 (ILDR1) AA424839 transcripts which are detectable by amplicon as depicted in sequence name AA424839seg11-14F3R3 (SEQ ID NO: 205) in blood-specific panel.

The results of this analysis are depicted in the histogram in FIG. 21. Expression of the above-indicated ILDR1 transcript was seen in several lymphomas and cell lines, however the expression was as high as in kidney normal samples.

Primer pairs are also optionally and preferably encompassed within the present invention; for example, for the above experiment, the following primer pair was used as a non-limiting illustrative example only of a suitable primer pair: seg11-14F3 forward primer; and seg11-14R3 reverse primer.

The present invention also preferably encompasses any amplicon obtained through the use of any suitable primer pair; for example, for the above experiment, the following amplicon was obtained as a non-limiting illustrative example only of a suitable amplicon: seg11-14F3R3.

```
Forward Primer > AA424839_seg11-14F3
                                    (SEQ ID NO: 203)
TCCTCCTCCTGCTGCTGATTG

Reverse Primer > AA424839_seg11-14R3
                                    (SEQ ID NO: 204)
TGGGCCTGCTTCATGTAGCG

Amplicon > AA424839_seg11-14F3R3
                                    (SEQ ID NO: 205)
TCCTCCTCCTGCTGCTGATTGGAGTGTGCTGGTGCCAG

TGCTGTCCTCAGTATTGCTGCTGCTATATCCGCTGTCC

CTGCTGTCCTGCCCACTGCTGCTGTCCTGAGGAAGCCC

TGGCCCGCCACCGCTACATGAAGCAGGCCCA
```

Example 4

Description for Cluster AI216611

The present invention relates in particular to a putative B7/CD28 member referred to as AI216611 and diagnostics and therapeutics based thereon. According to the present invention, Cluster AI216611 (internal ID 70605934) features 2 transcripts and 3 segments of interest, the names for which are given in Tables 49 and 50, respectively. The selected proteins are given in table 51.

TABLE 49

| Transcripts of interest<br>Transcript Name |
|---|
| AI216611_T0 (SEQ ID NO: 41) |
| AI216611_T1 (SEQ ID NO: 42) |

TABLE 50

| Segments of interest<br>Segment Name |
|---|
| AI216611_N2 (SEQ ID NO: 126) |
| AI216611_N4 (SEQ ID NO: 127) |
| AI216611_N6 (SEQ ID NO: 128) |

TABLE 51

| Proteins of interest | |
|---|---|
| Protein Name | Corresponding Transcripts |
| AI216611_P0 (SEQ ID NO: 43) | AI216611_T0 (SEQ ID NO: 41) |
| AI216611_P1 (SEQ ID NO: 44) | AI216611_T1 (SEQ ID NO: 42) |

AI216611 is an uncharacterized gene having no full length mRNA deposited in Genbank. The protein corresponding to AI216611_P0 appears in Celera's annotation of the human genome, based on computational analysis and translation of the genome (DNA sequence accession CH471065) (Venter, J. C et al., 2001 Science 291, 1304-1351). The protein corresponding to AI216611_P0 is also listed among other sequences disclosed in WO2003025148. However, this application does not characterize its function or more particularly teach that it is a B7/CD28 costimulatory protein.

The protein corresponding to AI216611_P1 sequence is a novel protein, that is only partially similar (186 out of 199 amino acids are the same) to a polypeptide reported in WO205108415, assigned to Biogen-Idec, which purports that this polypeptide is a transmembrane protein that may be targeted in the treatment of hyperproliferative disorders. WO205108415 does not report a function of this polypeptide. More specifically, there is no indication that it is a B7/CD28 costimulatory protein.

According to the present invention, AI216611 is predicted to be a novel B7/CD28 family member based on the presence of an IgV domain, a characteristic structural feature of the B7/CD28 family members. In addition, AI216611 is similar to the known CD28 family members in its exons' sizes and the position of the IgV and transmembrane domains within these exons. Like all known B7/CD28 members, AI216611 is also a type I membrane protein. According to the present invention, two alternatively spliced transcripts of AI216611 are provided, each one containing a unique region within the intracellular region. The expression of AI216611 and its variants was demonstrated in the present invention to be downregulated in colon cancer, further supporting an immune costimulatory role.

As noted above, contig AI216611 features 2 transcripts, which were listed in Table 49 above. A description of each protein according to the present invention is now provided.

Protein AI216611_P0 (SEQ ID NO:43) according to the present invention has an amino acid sequence as encoded by transcript AI216611_T0 (SEQ ID NO:41).

The localization of the protein was determined according to results from a number of different software programs and analyses, including analyses from SignalP and other specialized programs. The variant protein is believed to be located as follows with regard to the cell: membrane.

Protein AI216611_P0 (SEQ ID NO:43) also has the following non-silent SNPs (Single Nucleotide Polymorphisms) as listed in Table 52, (given according to their positions on the amino acid sequence, with the alternative amino acids listed (SEQ ID NO:43)).

TABLE 52

| Amino acid mutations | |
|---|---|
| SNP positions on amino acid sequence | Alternative amino acids |
| 27 | R -> L |
| 27 | R -> P |

TABLE 52-continued

| Amino acid mutations | |
|---|---|
| SNP positions on amino acid sequence | Alternative amino acids |
| 76 | Q -> R |
| 129 | S -> R |

The protein has the following domains, as determined by using InterPro. The domains are described in Table 53:

TABLE 53

| InterPro domains | | |
|---|---|---|
| Domain description | Analysis type | Positions on protein |
| Immunoglobulin V-set domain | HMMPfam | 33-129 |
| Immunoglobulin subtype | HMMSmart | 40-129 |

Protein AI216611_P0 (SEQ ID NO:43) is encoded by the transcript AI216611_T0 (SEQ ID NO:41), for which the coding portion starts at position 1 and ends at position 600. The transcript also has the following SNPs as listed in Table 54 (given according to their position on the nucleotide sequence, with the alternative nucleic acid listed).

TABLE 54

| Nucleic acid SNPs | |
|---|---|
| Polymorphism | SNP positions on nucleotide sequence |
| G -> T | 80, 991 |
| G -> C | 80, 991 |
| C -> T | 387, 990 |
| C -> G | 387, 1205 |
| T -> C | 906, 1063, 1090 |
| A -> G | 227, 1109 |
| T -> A | 1409, 1448 |
| G -> A | 1447 |
| T -> G | 1448 |

The genomic structure of protein AI216611_P0 (SEQ ID NO:43) (number of exons relevant to the extra-cellular region of the protein, the length of these exons, the frame of the codon in which the introns are inserted and the location of the protein features and domains in the gene structure) is characteristic to the receptors of the B7/co-stimulatory protein family, as given in table 55

TABLE 55

| genomic structure and protein features | | | |
|---|---|---|---|
| Exon number | Exon Length | Amino-Acids | Protein feature on exon |
| 1 | 91 | 1-30 | Signal Peptide |
| 2 | 327 | 31-139 | Ig-like domain |
| 3 | 141 | 140-186 | Trans-membrane region |
| 4 | 41 | 187-200 | |

Protein AI216611_P1 (SEQ ID NO:44) according to the present invention has an amino acid sequence as encoded by transcript AI216611_T1 (SEQ ID NO:42).

The localization of the protein was determined according to results from a number of different software programs and analyses, including analyses from SignalP and other specialized programs. The variant protein is believed to be located as follows with regard to the cell: membrane.

Protein AI216611_P1 (SEQ ID NO:44) also has the following non-silent SNPs (Single Nucleotide Polymorphisms) as listed in Table 56, (given according to their positions on the amino acid sequence, with the alternative amino acids listed (SEQ ID NO:44)).

TABLE 56

| Amino acid mutations | |
|---|---|
| SNP positions on amino acid sequence | Alternative amino acids |
| 27 | R -> L |
| 27 | R -> P |
| 76 | Q -> R |
| 129 | S -> R |

The protein has the following domains, as determined by using InterPro. The domains are described in Table 57:

TABLE 57

| InterPro domains | | |
|---|---|---|
| Domain description | Analysis type | Positions on protein |
| Immunoglobulin V-set domain | HMMPfam | 33-129 |
| Immunoglobulin subtype | HMMSmart | 40-129 |

Protein AI216611_P1 (SEQ ID NO:44) is encoded by the transcript AI216611_T1 (SEQ ID NO:42), for which the coding portion starts at position 1 and ends at position 597. The transcript also has the following SNPs as listed in Table 58 (given according to their position on the nucleotide sequence, with the alternative nucleic acid listed).

TABLE 58

| Nucleic acid SNPs | |
|---|---|
| Polymorphism | SNP positions on nucleotide sequence |
| G -> T | 80, 1121 |
| G -> C | 80, 1121 |
| C -> T | 387, 1120 |
| C -> G | 387, 1335 |
| T -> C | 1036, 1193, 1220 |
| A -> G | 227, 1239 |
| T -> A | 1549, 1578 |
| G -> A | 1577 |
| T -> G | 1578 |

As noted above, cluster AI216611 features 3 segments, which were listed in Table 50 above. These segments are portions of nucleic acid sequences which are described herein separately because they are of particular interest. A description of each segment according to the present invention is now provided.

Segment cluster AI216611_N2 (SEQ ID NO:126) according to the present invention is supported by 4 libraries. The number of libraries was determined as previously described. This segment can be found in the following transcripts: AI216611_T0 (SEQ ID NO:41) and AI216611_T1 (SEQ ID NO:42). Table 59 below describes the starting and ending position of this segment on each transcript.

TABLE 59

| Segment location on transcripts | | |
| --- | --- | --- |
| Transcript name | Segment starting position | Segment ending position |
| AI216611_T0 (SEQ ID NO: 41) | 92 | 418 |
| AI216611_T1 (SEQ ID NO: 42) | 92 | 418 |

Segment cluster AI216611_N4 (SEQ ID NO:127) according to the present invention is supported by 4 libraries. The number of libraries was determined as previously described. This segment can be found in the following transcripts: AI216611_T0 (SEQ ID NO:41) and AI216611_T1 (SEQ ID NO:42). Table 60 below describes the starting and ending position of this segment on each transcript.

TABLE 60

| Segment location on transcripts | | |
| --- | --- | --- |
| Transcript name | Segment starting position | Segment ending position |
| AI216611_T0 (SEQ ID NO: 41) | 419 | 559 |
| AI216611_T1 (SEQ ID NO: 42) | 419 | 559 |

Segment cluster AI216611_N6 (SEQ ID NO:128) according to the present invention is supported by 2 libraries. The number of libraries was determined as previously described. This segment can be found in the following transcripts: AI216611_T0 (SEQ ID NO:41) and AI216611_T1 (SEQ ID NO:42). Table 61 below describes the starting and ending position of this segment on each transcript.

TABLE 61

| Segment location on transcripts | | |
| --- | --- | --- |
| Transcript name | Segment starting position | Segment ending position |
| AI216611_T0 (SEQ ID NO: 41) | 560 | 885 |
| AI216611_T1 (SEQ ID NO: 42) | 690 | 1015 |

Expression of AI216611 transcripts which are detectable by amplicon as depicted in sequence name AI216611_junc4-6F2R2 (SEQ ID NO: 208) in normal and cancerous Colon tissues and in different normal tissues Expression of AI216611 transcripts detectable by or according to junc4-6-AI216611_junc4-6F2R2 (SEQ ID NO: 208) amplicon and primers AI216611_junc4-6F2 (SEQ ID NO: 206) and AI216611_junc4-6R2 (SEQ ID NO: 207) was measured by real time PCR on colon panel and normal panel. The samples used are detailed in Table 5 and Table 2 above, respectively. For each RT sample, the expression of the above amplicon was normalized to the normalization factor calculated from the expression of several house keeping genes as described in Example 1.

Colon panel—The normalized quantity of each RT sample was then divided by the median of the quantities of the normal samples (sample numbers 42-70, Table 5 above). Then the reciprocal of this ratio was calculated, to obtain a value of fold down-regulation for each sample relative to median of the normal samples.

Figure 22:
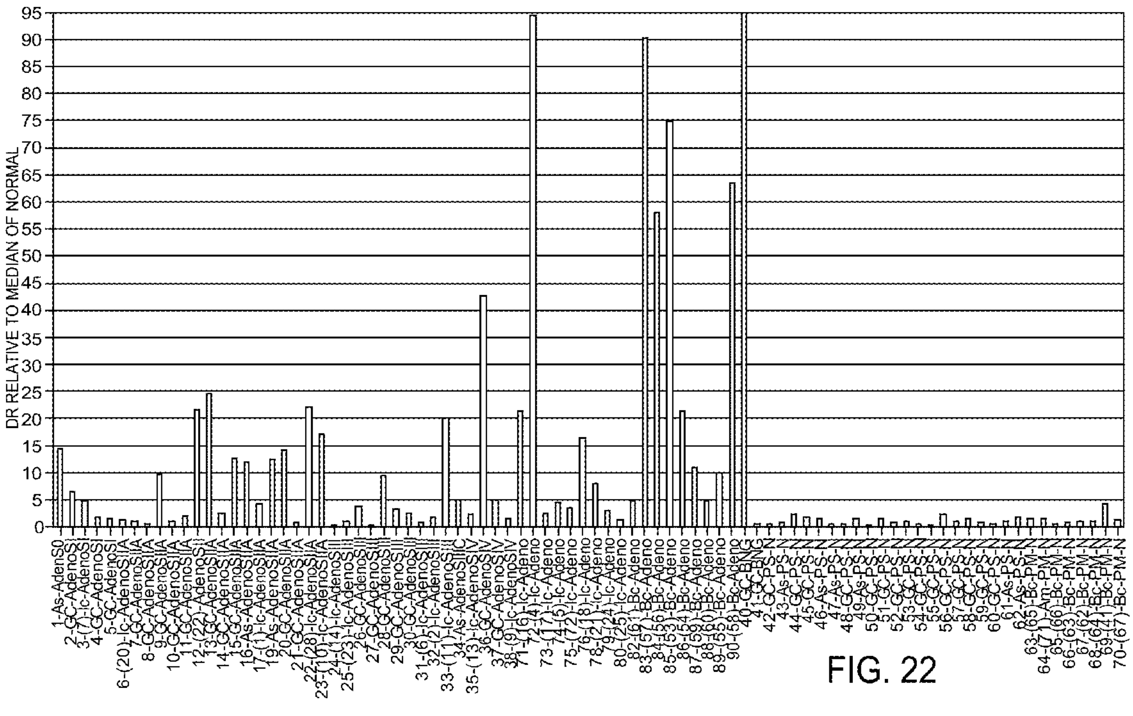
FIG. 22 presents a histogram showing expression of AI216611 transcripts which are detectable by amplicon as depicted in sequence name AI216611_junc4-6F2R2 (SEQ ID NO: 208) in normal and cancerous colon tissues.

FIG. 22 is a histogram showing down regulation of the above-indicated AI216611 transcripts in cancerous Colon samples relative to the normal samples.

As is evident from FIG. 22, the expression of AI216611 transcripts detectable by the above amplicon in cancer samples was significantly lower than in the non-cancerous samples (sample numbers 42-70, Table 5 above). Notably down regulation of at least 5 fold was found in 27 out of 55 adenocarcinoma samples.

Statistical analysis was applied to verify the significance of these results, as described below. The P value for the difference in the expression levels of AI216611 transcripts detectable by the above amplicon in Colon cancer samples versus the normal tissue samples was determined by T test as 2.39e-005.

Threshold of 5 fold down regulation was found to differentiate between cancer and normal samples with P value of 5.09e-007 as checked by exact Fisher test.

The above values demonstrate statistical significance of the results.

Figure 23:
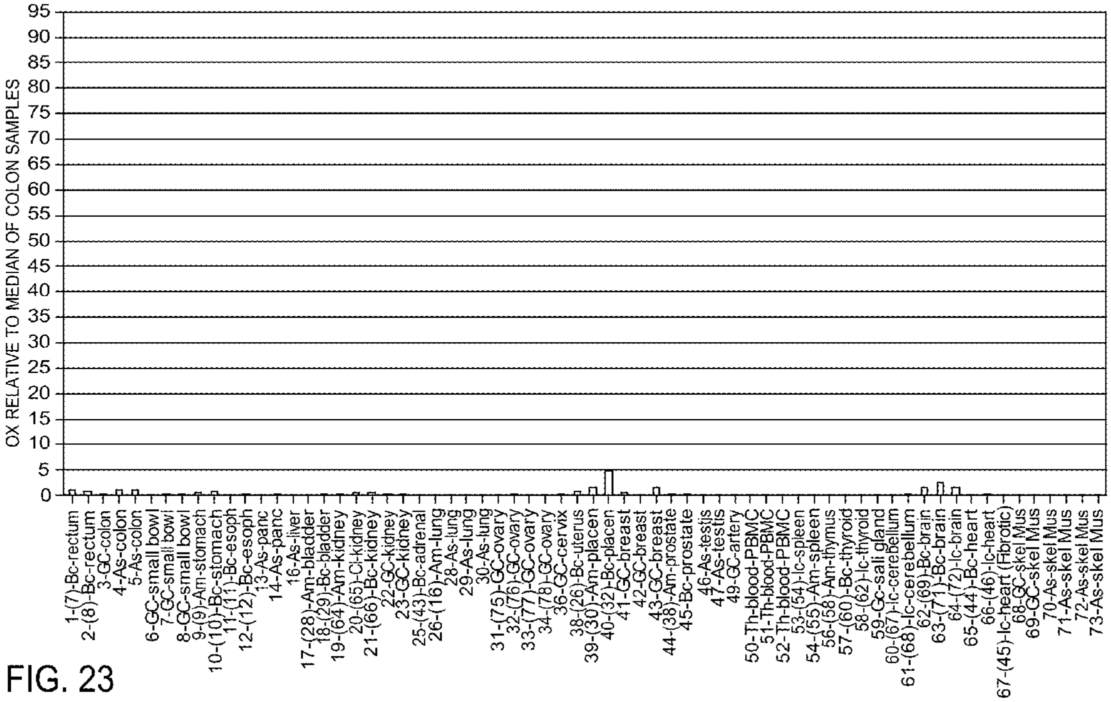
FIG. 23 presents a histogram showing expression of AI216611 transcripts which are detectable by amplicon as depicted in sequence name AI216611_junc4-6F2R2 (SEQ ID NO: 208) in various normal tissues.

Normal panel—Non-detected samples (samples no. 50, 52, 54 and 56, Table 2) were assigned Ct value of 41 and were calculated accordingly. For each RT sample, the expression of the above amplicon was normalized to the normalization factor calculated from the expression of several house keeping genes as described in Example 1. The normalized quantity of each RT sample was then divided by the median of the quantities of the colon samples (sample numbers 3, 4 and 5, Table 2 above), to obtain a value of relative expression of each sample relative to median of the colon samples, as shown in FIG. 23.

Primer pairs are also optionally and preferably encompassed within the present invention; for example, for the above experiment, the following primer pair was used as a non-limiting illustrative example only of a suitable primer pair: AI216611_junc4-6F2 (SEQ ID NO: 206) forward primer; and AI216611_junc4-6R2 (SEQ ID NO: 207) reverse primer.

The present invention also preferably encompasses any amplicon obtained through the use of any suitable primer pair; for example, for the above experiment, the following amplicon was obtained as a non-limiting illustrative example only of a suitable amplicon: AI216611_junc4-6F2R2 (SEQ ID NO: 208).

```
Forward Primer >AI216611_junc4-6F2
(SEQ ID NO: 206):
CCGCAGTATTAATCAGCCTCATG

Reverse Primer >AI216611_junc4-6R2
(SEQ ID NO: 207):
AATCTCCTCAGTTGTGCTTTCTTTG

Amplicon >AI216611_junc4-6F2R2
                              (SEQ ID NO: 208)
CCGCAGTATTAATCAGCCTCATGTGGGTTTGTAAT
AAGTGTGCATATAAATTTCAGAGGAAGAGAAGACA
CAAACTCAAAGAAAGCACAACTGAGGAGATT
```

Expression of AI216611 transcripts which are detectable by amplicon as depicted in sequence name AI216611_seg2WT (SEQ ID NO: 211) in normal and cancerous Colon tissues and in different normal tissues Expression of AI216611 transcripts detectable by or according to seg2WT-AI216611_seg2WT (SEQ ID NO: 211) amplicon and primers AI216611_seg2WTF1 (SEQ ID NO: 209) and AI216611_seg2WTR1 (SEQ ID NO: 210) was measured by real time PCR on colon panel and normal panel. The samples used are detailed in Table 5 and Table 2 above, respectively.

Colon panel—Non-detected sample (sample no. 33, Table 5) was assigned Ct value of 41 and was calculated accordingly. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 42-70, Table 5 above). Then the reciprocal of this ratio was calculated, to obtain a value of fold down-regulation for each sample relative to median of the normal samples.

Figure 24:
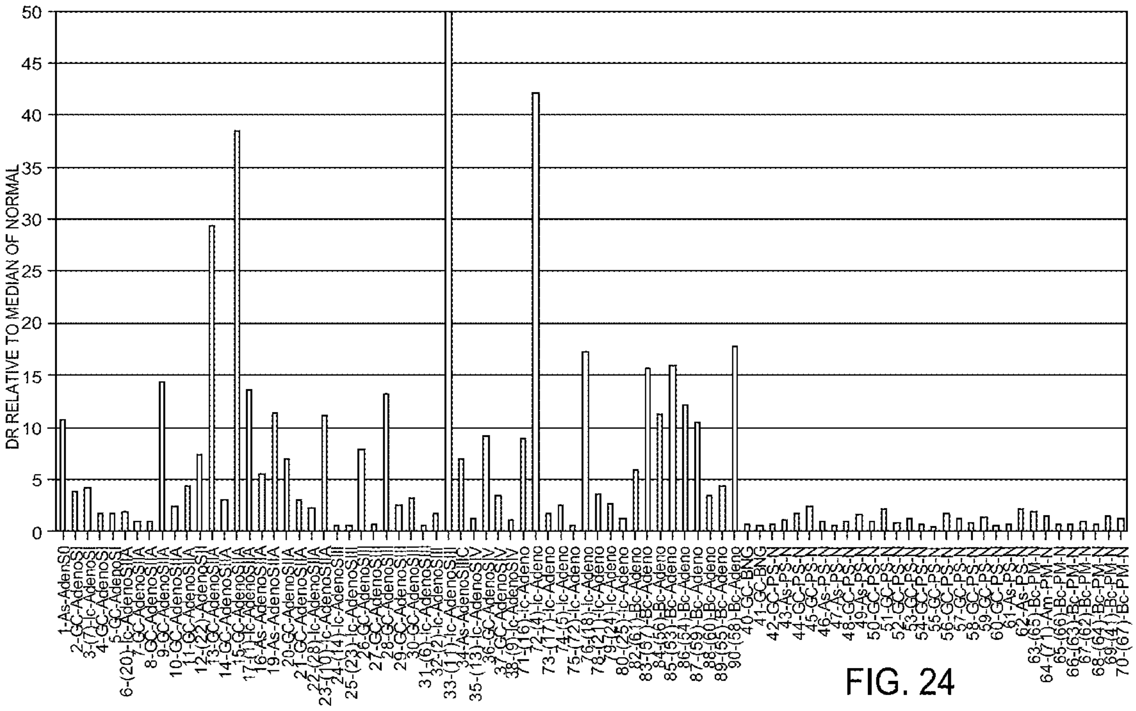
FIG. 24 presents a histogram showing expression of AI216611 transcripts which are detectable by amplicon as depicted in sequence name AI216611_seg2WT (SEQ ID NO: 211) in normal and cancerous colon tissues.

FIG. 24 is a histogram showing down regulation of the above-indicated AI216611 transcripts in cancerous Colon samples relative to the normal samples.

As is evident from FIG. 24, the expression of AI216611 transcripts detectable by the above amplicon in cancer samples was significantly lower than in the non-cancerous samples (sample numbers 42-70, Table 5 above). Notably down regulation of at least 5 fold was found in 25 out of 55 adenocarcinoma samples.

Statistical analysis was applied to verify the significance of these results, as described below. Threshold of 5 fold down regulation was found to differentiate between cancer and normal samples with P value of 2.00e-006 as checked by exact Fisher test.

The above values demonstrate statistical significance of the results.

Figure 25:
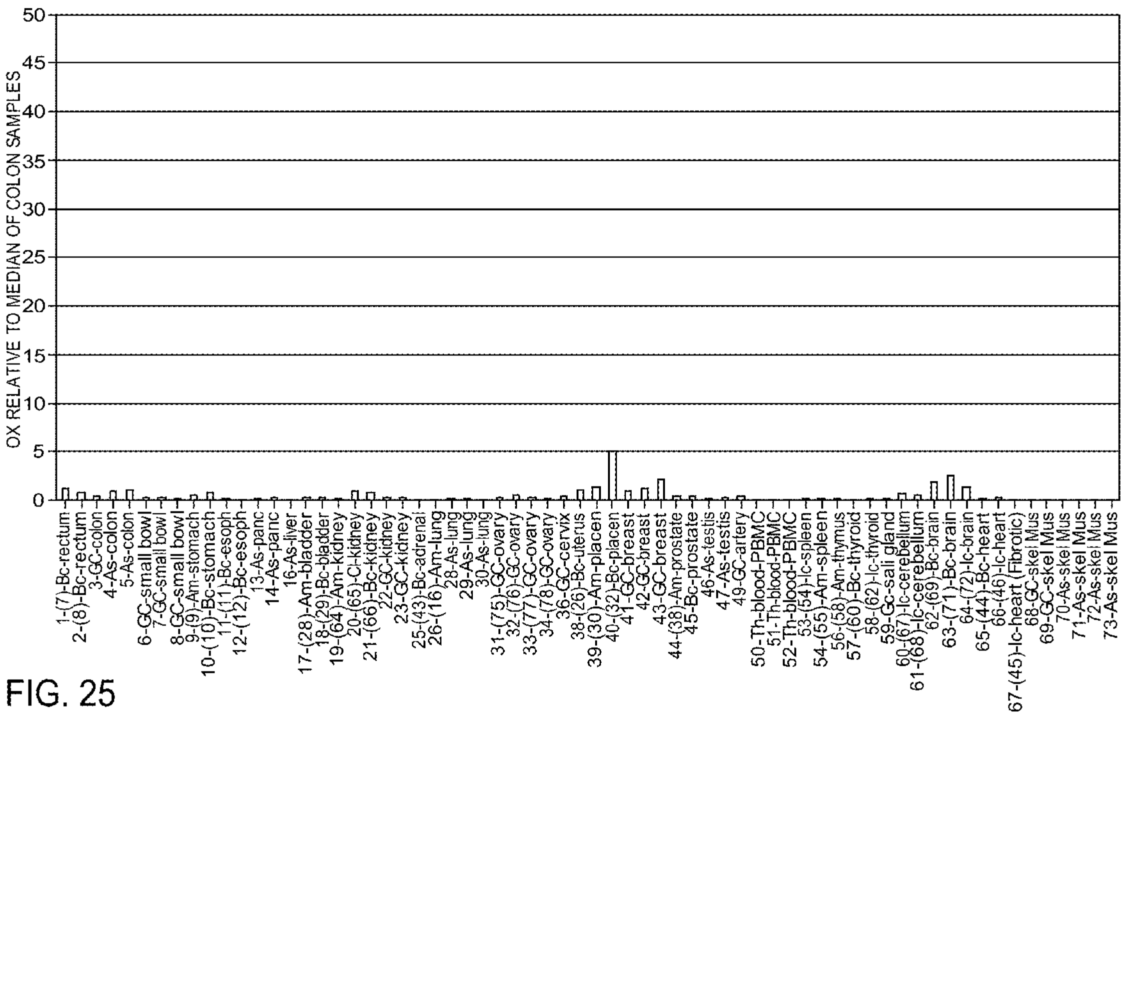
FIG. 25 presents a histogram showing expression of AI216611 transcripts which are detectable by amplicon as depicted in sequence name AI216611_seg2WT (SEQ ID NO: 211) in various normal tissues.

Normal panel—For each RT sample, the expression of the above amplicon was normalized to the normalization factor calculated from the expression of these house keeping genes as described in Example 1, herein. The normalized quantity of each RT sample was then divided by the median of the quantities of the colon samples (sample numbers 3, 4 and 5, Table 5 above), to obtain a value of relative expression of each sample relative to median of the colon samples, as shown in FIG. 25.

Primer pairs are also optionally and preferably encompassed within the present invention; for example, for the above experiment, the following primer pair was used as a non-limiting illustrative example only of a suitable primer pair: AI216611_seg2WTF1 (SEQ ID NO: 209) forward primer; and AI216611_seg2WTR1 (SEQ ID NO: 210) reverse primer.

The present invention also preferably encompasses any amplicon obtained through the use of any suitable primer pair; for example, for the above experiment, the following amplicon was obtained as a non-limiting illustrative example only of a suitable amplicon: AI216611_seg2WT (SEQ ID NO: 211).

```
Forward Primer >AI216611_seg2WTF1
                                   (SEQ ID NO: 209)
GAACGCAGAAGATCGTGGAGT

Reverse Primer >AI216611_seg2WTR1
                                   (SEQ ID NO: 210)
CTGAAGAGCTGGATGGAGCC

Amplicon >AI216611_seg2WT
                                   (SEQ ID NO: 211)
GAACGCAGAAGATCGTGGAGTGGAAACCAGGGACTCA
GGCCAACATCTCTCAAAGCCACAAGGACAGAGTCTGC
ACCTTTGACAACGGCTCCATCCAGCTCTTCAG
```

Expression of AI216611 transcripts which are detectable by amplicon as depicted in sequence name AI216611junc4-6 (SEQ ID NO: 214) in the blood-specific panel.

Expression of AI216611 transcripts detectable by or according to junc4-6-junc4-6F4R4 (SEQ ID NO: 214) amplicon and primers junc4-6F4 (SEQ ID NO: 212) and junc4-6R4 (SEQ ID NO: 213) was measured by real time PCR on blood panel. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the kidney normal samples (sample numbers 65-67, Table 1 above), to obtain a value of relative expression of each sample relative to median of the kidney normal samples.

Figure 26:
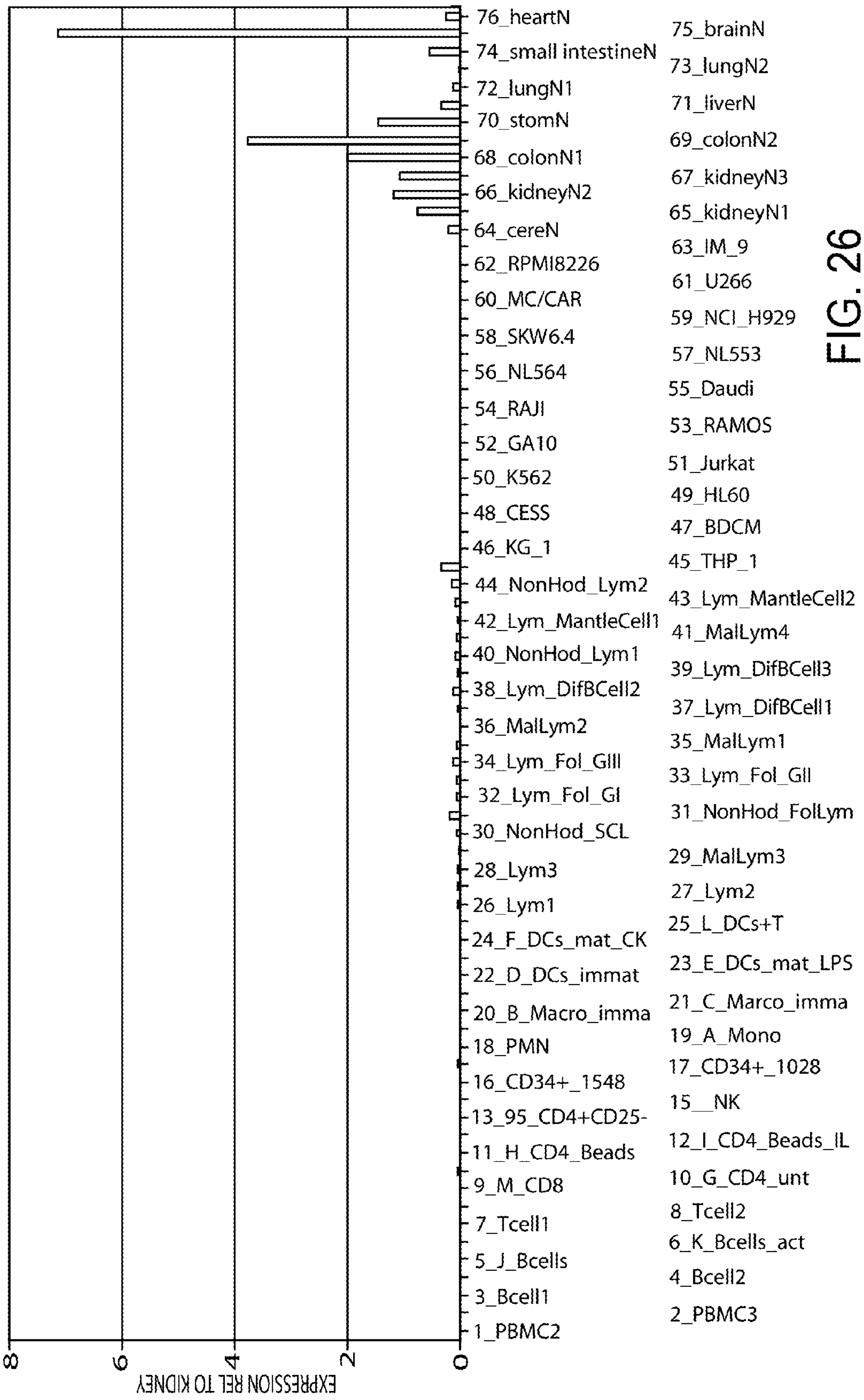
FIG. 26 presents a histogram showing expression of AI216611 transcripts which are detectable by amplicon as depicted in sequence name AI216611_junc4-6 (SEQ ID NO: 214) in blood-specific pane.

The results of this analysis are depicted in the histogram in FIG. 26. Expression of the above-indicated AI216611 transcript was much high in normal samples checked relative to the different blood specific samples in the panel.

Primer pairs are also optionally and preferably encompassed within the present invention; for example, for the above experiment, the following primer pair was used as a non-limiting illustrative example only of a suitable primer pair: junc4-6F4 (SEQ ID NO: 212) forward primer; and junc4-6R4 reverse primer (SEQ ID NO: 213).

The present invention also preferably encompasses any amplicon obtained through the use of any suitable primer pair; for example, for the above experiment, the following amplicon was obtained as a non-limiting illustrative example only of a suitable amplicon: junc4-6F4R4 (SEQ ID NO: 214).

```
Forward Primer AI216611junc4-6F4
(SEQ ID NO: 212):
CTGCACTTTGTCGCTGTCATC

Reverse Primer AI216611junc4-6R4
(SEQ ID NO: 213):
CAATCTCCTCAGTTGTGCTTTCTTTG

Amplicon AI216611junc4-6F4R4
(SEQ ID NO: 214):
CTGCACTTTGTCGCTGTCATCCTTGCTTTTCTCGCTG

CTGTGGCCGCAGTATTAATCAGCCTCATGTGGGTTTG

TAATAAGTGTGCATATAAATTTCAGAGGAAGAGAAGA

CACAAACTCAAAGAAAGCACAACTGAGGAGATTG
```

Expression of AI216611 transcripts which are detectable by amplicon as depicted in sequence name AI216611junc2-4seg5 (SEQ ID NO: 217) in the blood-specific panel.

Expression of AI216611 transcripts detectable by or according to junc2-4seg5-junc2-4seg5F3R4 amplicon (SEQ ID NO: 217) and primers junc2-4seg5F3 (SEQ ID NO: 215) and junc2-4seg5R4 (SEQ ID NO: 216) was measured by real time PCR on blood panel. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the kidney normal samples (sample numbers 65-67, Table 1 above), to obtain a value of relative expression of each sample relative to median of the kidney normal samples.

Figure 27:
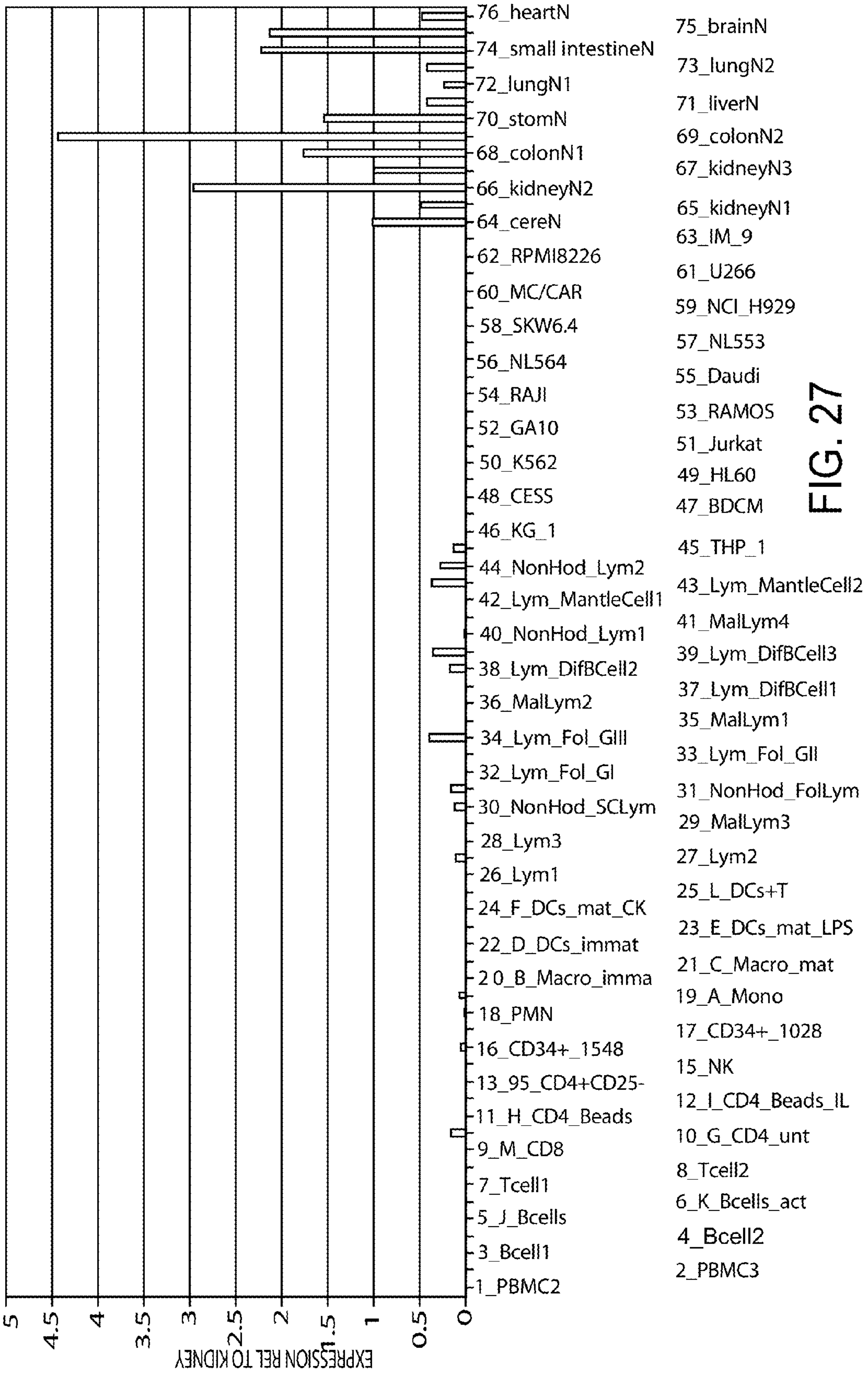
FIG. 27 presents a histogram showing expression of AI216611 transcripts which are detectable by amplicon as depicted in sequence name AI216611_junc2-4seg5F2R2 (SEQ ID NO: 220) in blood-specific pane.

The results of this analysis are depicted in the histogram in FIG. 27. Expression of the above-indicated AI216611 transcript was much high in normal samples checked relative to the different blood specific samples in the panel.

Primer pairs are also optionally and preferably encompassed within the present invention; for example, for the above experiment, the following primer pair was used as a non-limiting illustrative example only of a suitable primer pair: junc2-4seg5F3 (SEQ ID NO: 215) forward primer; and junc2-4seg5R4 (SEQ ID NO: 216) reverse primer.

The present invention also preferably encompasses any amplicon obtained through the use of any suitable primer pair; for example, for the above experiment, the following amplicon was obtained as a non-limiting illustrative example only of a suitable amplicon: junc2-4seg5F3R4 (SEQ ID NO: 217).

```
Forward Primer AI216611 junc2-4seg5F3
(SEQ ID NO: 215):
TGCTGCACGTCTCTGAGATCC

Reverse Primer AI216611 junc2-4seg5R4
(SEQ ID NO: 216):
CACCTCTGGCCTCAAAACCACTC

Amplicon > AI216611 junc2-4seg5F3R4
                                  (SEQ ID NO: 217)
TGCTGCACGTCTCTGAGATCCTCTATGAAGACCTGCAC

TTTGTCGCTGTCATCCTTGCTTTTCTCGCTGCTGTGGC

CGCAGTATTAATCAGCCTCATGTGGGTTTGTAATAAGT

GTGCATATAAATTTCAGAGGAAGAGAAGACACAAACTC

AAAGGTAACCCCCTGGGCCTTGTGATAATCCATGAGTG

GTTTTGAGGCCAGAGGTG
```

Expression of AI216611 transcripts which are detectable by amplicon as depicted in sequence name AI216611_junc2-4seg5F2R2 (SEQ ID NO: 220) in normal and cancerous Colon tissues Expression of AI216611 transcripts detectable by or according to junc2-4seg5F2R2—AI216611_junc2-4seg5F2R2 (SEQ ID NO: 220) amplicon and primers AI216611_junc2-4seg5F2 (SEQ ID NO: 218) and AI216611_junc2-4seg5R2 (SEQ ID NO: 219) was measured by real time PCR on colon panel. The samples used are detailed in Table 5 above. Non-detected samples (samples no. 28, 33, 83, 85, 90 and 63, Table 5) were assigned Ct value of 41 and were calculated accordingly. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 42-62 and 64-70, Table 5 above). Then the reciprocal of this ratio was calculated, to obtain a value of fold down-regulation for each sample relative to median of the normal samples.

Figure 28:
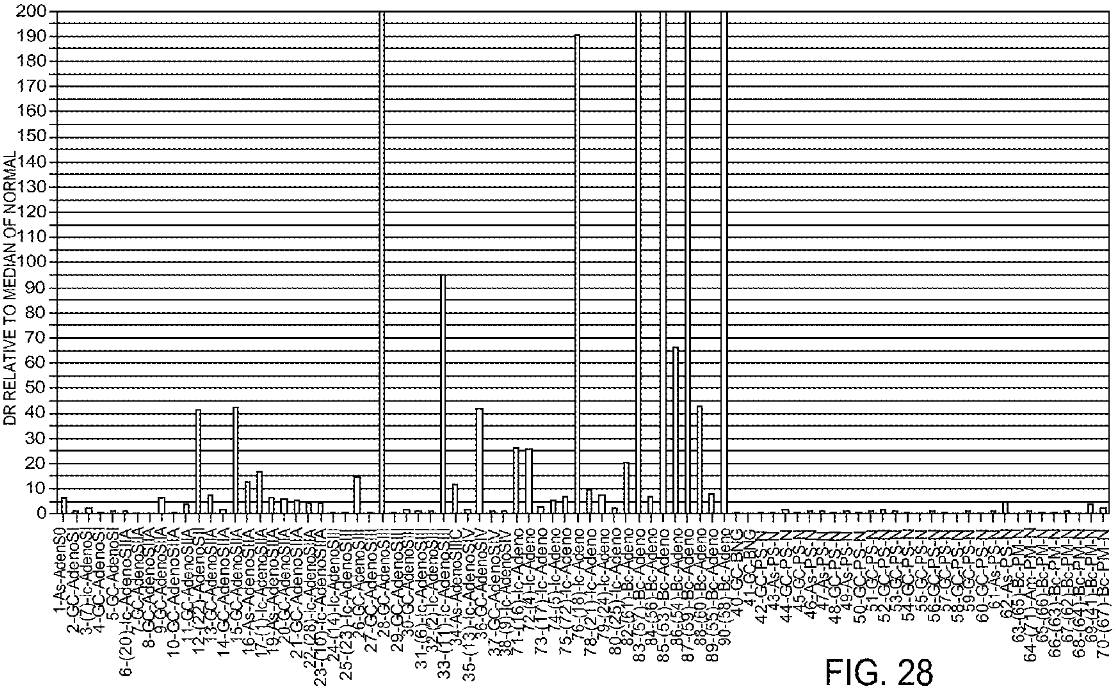
FIG. 28 presents a histogram showing expression of AI216611 transcripts which are detectable by amplicon as depicted in sequence name AI216611_junc2-4seg5F2R2 (SEQ ID NO: 220) in normal and cancerous colon tissues.

FIG. 28 is a histogram showing down regulation of the above-indicated AI216611 transcripts in cancerous Colon samples relative to the normal samples.

As is evident from FIG. 28, the expression of AI216611 transcripts detectable by the above amplicon in cancer samples was significantly lower than in the non-cancerous samples (sample numbers 42-62 and 64-70, Table 5 above). Notably down regulation of at least 5 fold was found in 31 out of 55 adenocarcinoma samples.

Statistical analysis was applied to verify the significance of these results, as described below. The P value for the difference in the expression levels of AI216611 transcripts detectable by the above amplicon in Colon cancer samples versus the normal tissue samples was determined by T test as 5.29e-003.

Threshold of 5 fold down regulation was found to differentiate between cancer and normal samples with P value of 4.18e-008 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: AI216611_junc2-4seg5F2 (SEQ ID NO: 218) forward primer; and AI216611_junc2-4seg5R2 (SEQ ID NO: 219) reverse primer.

The present invention also preferably encompasses any amplicon obtained through the use of any suitable primer pair; for example, for the above experiment, the following amplicon was obtained as a non-limiting illustrative example only of a suitable amplicon: AI216611_junc2-4seg5F2R2 (SEQ ID NO: 220).

```
Forward Primer >AI216611_junc2-4seg5F2
                                  (SEQ ID NO: 218)
GCTGCACGTCTCTGAGATCCT

Reverse Primer >AI216611_junc2-4seg5R2
                                  (SEQ ID NO: 219)
CACCTCTGGCCTCAAAACCA

Amplicon >AI216611_junc2-4seg5F2R2
                                  (SEQ ID NO: 220)
GCTGCACGTCTCTGAGATCCTCTATGAAGACCTGCACTT

TGTCGCTGTCATCCTTGCTTTTCTCGCTGCTGTGGCCGC

AGTATTAATCAGCCTCATGTGGGTTTGTAATAAGTGTGC

ATATAAATTTCAGAGGAAGAGAAGACACAAACTCAAAGG

TAACCCCCTGGGCCTTGTGATAATCCATGAGTGGTTTTG

AGGCCAGAGGTG
```

Example 5

Description for Cluster H68654_1

The present invention relates to LOC253012 polypeptides, novel splice variants and diagnostics and therapeutics based thereon.

According to the present invention, Cluster H68654_1 (internal ID 76432882) features 10 transcripts and 3 segments of interest, the names for which are given in Tables 62 and 63, respectively. The selected protein variants are given in table 64.

TABLE 62

| Transcripts of interest<br>Transcript Name |
|---|
| H68654_1_T0 (SEQ ID NO: 25) |
| H68654_1_T4 (SEQ ID NO: 26) |
| H68654_1_T5 (SEQ ID NO: 27) |
| H68654_1_T8 (SEQ ID NO: 28) |
| H68654_1_T15 (SEQ ID NO: 29) |
| H68654_1_T16 (SEQ ID NO: 30) |
| H68654_1_T17 (SEQ ID NO: 31) |
| H68654_1_T18 (SEQ ID NO: 32) |
| H68654_1_T19 (SEQ ID NO: 33) |
| H68654_1_T20 (SEQ ID NO: 34) |

TABLE 63

| Segments of interest Segment Name |
|---|
| H68654_1_N3 (SEQ ID NO: 123) |
| H68654_1_N7 (SEQ ID NO: 124) |
| H68654_1_N12 (SEQ ID NO: 125) |

TABLE 64

| Proteins of interest | |
|---|---|
| Protein Name | Corresponding Transcripts |
| H68654_1_P2 (SEQ ID NO: 35) | H68654_1_T0 (SEQ ID NO: 25); H68654_1_T5 (SEQ ID NO: 27) |
| H68654_1_P5 (SEQ ID NO: 36) | H68654_1_T4 (SEQ ID NO: 26) |
| H68654_1_P7 (SEQ ID NO: 37) | H68654_1_T8 (SEQ ID NO: 28) |
| H68654_1_P12 (SEQ ID NO: 38) | H68654_1_T15 (SEQ ID NO: 29); H68654_1_T16 (SEQ ID NO: 30); H68654_1_T18 (SEQ ID NO: 32) |
| H68654_1_P13 (SEQ ID NO: 39) | H68654_1_T17 (SEQ ID NO: 31); H68654_1_T19 (SEQ ID NO: 33) |
| H68654_1_P14 (SEQ ID NO: 40) | H68654_1_T20 (SEQ ID NO: 34) |

These sequences are variants of the known protein hypothetical protein LOC253012 isoform 1 (RefSeq accession identifier NP_001034461 (SEQ ID NO: 35), NP_937794 (SEQ ID NO: 36)), referred to herein as the previously known protein.

The known LOC253012 is a hypothetical protein that was computationally discovered during the secreted protein discovery initiative project (SPDI), a large-scale effort to identify novel human secreted and transmembrane proteins (Clark et al 2003, Genome Res. 13: 2265-2270). Its closest paralog that is experimentally validated is the hepatocyte cell adhesion molecule (Refseq accession NP_689935) (evalue e-21).

LOC253012 antigen has been reported in European patent application Number EP162070, assigned to Genentech Inc. purports that LOC253012 (PRO346), corresponding to H68654_1_P2 (SEQ ID NO:35), is differentially expressed in a lung tumor samples. This patent specification alleges that the corresponding polypeptide can be used for developing antibodies against the disclosed PRO antigens, including PRO346. The patent application further suggests that antibodies to a genus of polypeptides reported therein that includes PRO346 may be used for treating and diagnosing cancer and specifically for diagnosing and treating lung cancer. The Genentech patent application does not teach, however, that LOC253012 (PRO346) is differentially expressed in small cell lung carcinoma. Also, there is no specific teaching in Genentech Inc. patent application that the anti-PRO346 antibodies can be used for treating small cell lung carcinomas and/or for modulating co-stimulation of the APC/T cell activity. Also, there is no teaching in the Genentech Inc. patent application that the PRO346 is an immune costimulatory protein or more specifically a B7 family member. There is no teaching in the Genentech Inc. patent application of the use of antibodies against the PRO346 antigen for modulating immune co-stimulation or particularly the B7 co-stimulatory pathway.

According to the present invention, LOC253012 was predicted to be a novel immune costimulatory protein and in particular a B7 co-stimulatory protein. The prediction was based on the presence of both an IgV domain and IgC2, a characteristic structural feature of the B7-family members. Like other B7 members, LOC253012 is also a type I membrane protein. LOC253012 and its variants were demonstrated in the present invention to be overexpressed in lung cancer.

Figure 29:
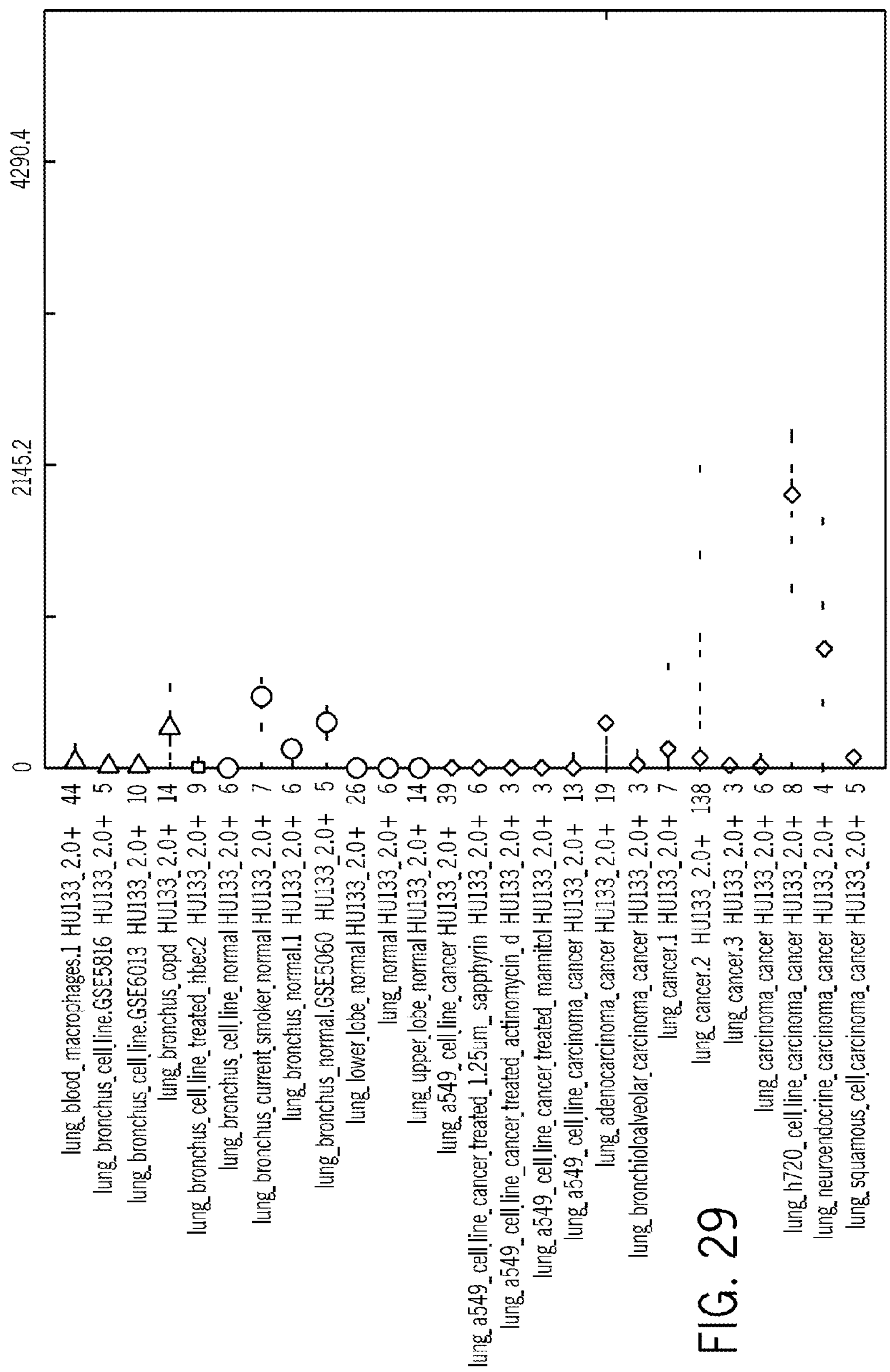
FIG. 29 shows a scatter plot, demonstrating the expression of H68654 transcripts, that encode the LOC253012 proteins, on a virtual panel of all tissues and conditions using MED discovery engine, demonstrating overexpression of H68654 transcripts in lung cancer compared to normal lung samples.

MED discovery engine described in Example 1 herein, was used to assess the expression of LOC253012 transcripts. Expression data for Affymetrix probe set 242601 at representing the LOC253012 gene data is shown in FIG. 29. As evident from the scatter plot, presented in FIG. 29, the expression of LOC253012 transcripts detectable with the above probe sets was higher in lung cancer compared to normal lung samples.

As noted above, cluster H68654 features 10 transcripts, which were listed in Table 62 above. These transcripts encode for proteins which are variants of protein hypothetical protein LOC253012 isoform 1 (SEQ ID NO:35). A description of each variant protein according to the present invention is now provided.

Variant protein H68654_1_P2 (SEQ ID NO:35) according to the present invention has an amino acid sequence as encoded by transcripts H68654_1_T0 (SEQ ID NO:25) and H68654_1_T5 (SEQ ID NO:27).

The localization of the variant protein was determined according to results from a number of different software programs and analyses, including analyses from SignalP and other specialized programs. The variant protein is believed to be located as follows with regard to the cell: membrane.

Variant protein H68654_1_P2 (SEQ ID NO:35) also has the following non-silent SNPs (Single Nucleotide Polymorphisms) as listed in Table 65, (given according to their positions on the amino acid sequence, with the alternative amino acids listed).

TABLE 65

| Amino acid mutations | |
|---|---|
| SNP positions on amino acid sequence | Alternative amino acids |
| 33 | K -> R |
| 86 | K -> N |
| 204 | L -> P |

The variant protein has the following domains, as determined by using InterPro. The domains are described in Table 66:

TABLE 66

| InterPro domains | | |
|---|---|---|
| Domain description | Analysis type | Positions on protein |
| Immunoglobulin subtype | HMMSmart | 38-141, 155-235, 255-333 |
| Immunoglobulin-like | Profile Scan | 149-233, 235-331 |
| Immunoglobulin-like | HMMPfam | 163-221 |
| Immunoglobulin V-set | HMMPfam | 31-143 |
| Immunoglobulin C2 type | HMMSmart | 164-226 |

The coding portion of transcript H68654_1_T0 (SEQ ID NO:25) starts at position 79 and ends at position 1464. The transcript also has the following SNPs as listed in Table 67 (given according to their position on the nucleotide sequence, with the alternative nucleic acid listed).

TABLE 67

| Nucleic acid SNPs | |
|---|---|
| Polymorphism | SNP positions on nucleotide sequence |
| A -> G | 176, 1545 |
| G -> A | 336, 1754 |
| G -> C | 336 |
| T -> C | 564, 689 |
| A -> T | 1545 |
| G -> T | 1684 |
| T -> A | 1755 |
| T -> G | 1755 |

The coding portion of transcript H68654_1_T5 (SEQ ID NO:27) starts at position 79 and ends at position 1464. The transcript also has the following SNPs as listed in Table 68 (given according to their position on the nucleotide sequence, with the alternative nucleic acid listed).

TABLE 68

| Nucleic acid SNPs | |
|---|---|
| Polymorphism | SNP positions on nucleotide sequence |
| A -> G | 176, 1545 |
| G -> A | 336, 1754 |
| G -> C | 336 |
| T -> C | 564, 689 |
| A -> T | 1545 |
| G -> T | 1684 |
| T -> A | 1755 |
| T -> G | 1755 |

The genomic structure of protein H68654_1_P2 (SEQ ID NO: 35) (number of exons relevant to the extra-cellular region of the protein, the length of these exons, the frame of the codon in which the introns are inserted and the location of the protein features and domains in the gene structure) is characteristic to the ligands of the B7/co-stimulatory protein family, as given in table 69.

TABLE 69

| genomic structure and protein features | | | |
|---|---|---|---|
| Exon number | Exon Length | Amino-Acids | Protein feature on exon |
| 1 | 79 | 1-26 | Signal Peptide |
| 2 | 351 | 27-143 | IgV domain |
| 3 | 285 | 144-238 | IgC2 domain |
| 4 | 297 | 239-337 | Ig-like domain |
| 5 | 126 | 338-379 | Trans-membrane region |
| 6 | 25 | 380-387 | |
| 7 | 38 | 388-400 | |
| 8 | 74 | 401-425 | |
| 9 | 110 | 426-462 | |
| 10 | 1 | 462-462 | |

Variant protein H68654_1_P5 (SEQ ID NO:36) according to the present invention has an amino acid sequence encoded by transcripts H68654_1_T4 (SEQ ID NO:26).

The localization of the variant protein was determined according to results from a number of different software programs and analyses, including analyses from SignalP and other specialized programs. The variant protein is believed to be located as follows with regard to the cell: membrane.

Variant protein H68654_1_P5 (SEQ ID NO:36) also has the following non-silent SNPs (Single Nucleotide Polymorphisms) as listed in Table 70, (given according to their positions on the amino acid sequence, with the alternative amino acids listed (SEQ ID NO:36)).

TABLE 70

| Amino acid mutations | |
|---|---|
| SNP positions on amino acid sequence | Alternative amino acids |
| 21 | K -> R |
| 74 | K -> N |
| 192 | L -> P |

The variant protein has the following domains, as determined by using InterPro. The domains are described in Table 71:

TABLE 71

| InterPro domains | | |
|---|---|---|
| Domain description | Analysis type | Positions on protein |
| Immunoglobulin C2 type | HMMSmart | 152-214 |
| Immunoglobulin subtype | HMMSmart | 26-129, 143-223, 243-321 |
| Immunoglobulin-like | HMMPfam | 151-209 |
| Immunoglobulin V-set | HMMPfam | 19-131 |
| Immunoglobulin-like | Profile Scan | 137-221, 223-319 |

Variant protein H68654_1_P5 (SEQ ID NO:36) is encoded by the transcript H68654_1_T4 (SEQ ID NO:26), for which the coding portion starts at position 102 and ends at position 1451. The transcript also has the following SNPs as listed in Table 72 (given according to their position on the nucleotide sequence, with the alternative nucleic acid listed).

TABLE 72

| Nucleic acid SNPs | |
|---|---|
| Polymorphism | SNP positions on nucleotide sequence |
| A -> G | 163, 1532 |
| G -> A | 323, 1741 |
| G -> C | 323 |
| T -> C | 551, 676 |
| A -> T | 1532 |
| G -> T | 1671 |
| T -> A | 1742 |
| T -> G | 1742 |

Variant protein H68654_1_P7 (SEQ ID NO:37) according to the present invention has an amino acid sequence encoded by transcript H68654_1_T8 (SEQ ID NO:28). Alignment of H68654_1_P7 (SEQ ID NO:37) to one or more previously published protein sequences are shown in FIGS. 30A and 30B. A brief description of the relationship of the variant protein according to the present invention to each such aligned protein is as follows:

1. Comparison report between H68654_1_P7 (SEQ ID NO:37) and known proteins NP_937794 and Q6UXI0_HUMAN (SEQ ID NO: 36) (FIG. 30A):

A. An isolated chimeric polypeptide encoding for H68654_1_P7 (SEQ ID NO:37), comprising a first amino acid sequence being at least 90% homologous to

MWLKVFTTFLSFATGACSGLKVTVPSHTVHGVRGQALYLPVHYGFHTPAS

DIQIIWLFERPHTMPKYLLGSVNKSVVPDLEYQHKFTMMPPNASLLINPL

QFPDEGNYIVKVNIQGNGTLSASQKIQVTVDDPVTKPVVQIHPPSGAVEY

VGNMTLTCHVEGGTRLAYQWLKNGRPVHTSSTYSFSPQNNTLHIAPVTKE

DIGNYSCLVRNPVSEMESDIIMPIIYYGPYGLQVNSDKGLKVGEVFTVDL

GEAILFDCSADSHPPNTYSWIRRTDNTTYIIKHGPRLEVASEKVAQKTMD

YVCCAYNNITGRQDETHFTVIITSVGLEKLAQKGKSLSPLASITGISLFL

IISMCLLFLWKKYQPYK corresponding to amino acids 1-367 of known proteins NP_937794 and Q6UXI0_HUMAN (SEQ ID NO: 36), which also corresponds to amino acids 1-367 of H68654_1_P7 (SEQ ID NO:37), and a second amino acid sequence being at least 70%, optionally at least 80%, preferably at least 85%, more preferably at least 90% and most preferably at least 95, 96, 97, 98 or 99% homologous to a polypeptide having the sequence (SEQ ID NO: 290)
GQKQNTGKLKHFQAMKMLWMTSEYMNLLLFQMFLVFPGSQAGLFQPLIVYR

GKICTVQCMKLFSTSLPSSKTIQSELSWAKQYIRVKF corresponding to amino acids 368-455 of H68654_1_P7 (SEQ ID NO:37), wherein said first amino acid sequence and second amino acid sequence are contiguous and in a sequential order.

B. An isolated polypeptide encoding for an edge portion of H68654_1_P7 (SEQ ID NO:37), comprising an amino acid sequence being at least 70%, optionally at least about 80%, preferably at least about 85%, more preferably at least about 90% and most preferably at least about 95, 96, 97, 98 or 99% homologous to the sequence (SEQ ID NO: 290)
GQKQNTGKLKHFQAMKMLWMTSEYMNLLLFQMFLVFPGSQAGLFQPLIVYR

GKICTVQCMKLFSTSLPSSKTIQSELSWAKQYIRVKF of H68654_1_P7 (SEQ ID NO:37).

2. Comparison report between H68654_1_P7 (SEQ ID NO:37) and known proteins NP_001034461 (SEQ ID NO: 35) FIG. 30B):

A. An isolated chimeric polypeptide encoding for H68654_1_P7 (SEQ ID NO:37), comprising a first amino acid sequence being at least 70%, optionally at least 80%, preferably at least 85%, more preferably at least 90% and most preferably at least 95, 96, 97, 98 or 99%, homologous to a polypeptide having the sequence MWLKVFTTFLSFAT (SEQ ID NO: 289) corresponding to amino acids 1-14 of H68654_1_P7 (SEQ ID NO:37), a second amino acid sequence being at least 90% homologous to

GACSGLKVTVPSHTVHGVRGQALYLPVHYGFHTPASDIQIIWLFERPHTMP

KYLLGSVNKSVVPDLEYQHKFTMMPPNASLLINPLQFPDEGNYIVKVNIQG

NGTLSASQKIQVTVDDPVTKPVVQIHPPSGAVEYVGNMTLTCHVEGGTRLA

YQWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTYS

-continued

WIRRTDNTTYIIKHGPRLEVASEKVAQKTMDYVCCAYNNITGRQDETHFTV

IITSVGLEKLAQKGKSLSPLASITGISLFLIISMCLLFLWKKYQPYK corresponding to amino acids 27-379 of known proteins NP_001034461 (SEQ ID NO: 35), which also corresponds to amino acids 15-367 of H68654_1_P7 (SEQ ID NO:37), and a third amino acid sequence being at least 70%, optionally at least 80%, preferably at least 85%, more preferably at least 90% and most preferably at least 95, 96, 97, 98 or 99% homologous to a polypeptide having the sequence (SEQ ID NO: 290)
GQKQNTGKLKHFQAMKMLWMTSEYMNLLLFQMFLVFPGSQAGLFQPLIVYR

GKICTVQCMKLFSTSLPSSKTIQSELSWAKQYIRVKF corresponding to amino acids 368-455 of H68654_1_P7 (SEQ ID NO:37), wherein said first amino acid sequence, second amino acid sequence and third amino acid sequence are contiguous and in a sequential order.

B. An isolated polypeptide encoding for a head of H68654_1_P7 (SEQ ID NO:37), comprising a polypeptide being at least 70%, optionally at least about 80%, preferably at least about 85%, more preferably at least about 90% and most preferably at least about 95, 96, 97, 98 or 99% homologous to the sequence MWLKVFTTFLSFAT (SEQ ID NO: 289) of H68654_1_P7 (SEQ ID NO:37).

C. An isolated polypeptide encoding for an edge portion of H68654_1_P7 (SEQ ID NO:37), comprising an amino acid sequence being at least 70%, optionally at least about 80%, preferably at least about 85%, more preferably at least about 90% and most preferably at least about 95, 96, 97, 98 or 99% homologous to the sequence (SEQ ID NO: 290)
GQKQNTGKLKHFQAMKMLWMTSEYMNLLLFQMFLVFPGSQAGLFQPLIVYR

GKICTVQCMKLFSTSLPSSKTIQSELSWAKQYIRVKF of H68654_1_P7 (SEQ ID NO:37).

The localization of the variant protein was determined according to results from a number of different software programs and analyses, including analyses from SignalP and other specialized programs. The variant protein is believed to be located as follows with regard to the cell: membrane.

Variant protein H68654_1_P7 (SEQ ID NO:37) also has the following non-silent SNPs (Single Nucleotide Polymorphisms) as listed in Table 73, (given according to their positions on the amino acid sequence, with the alternative amino acids listed (SEQ ID NO:37)).

TABLE 73

| Amino acid mutations | |
|---|---|
| SNP positions on amino acid sequence | Alternative amino acids |
| 21 | K -> R |
| 74 | K -> N |
| 192 | L -> P |

The variant protein has the following domains, as determined by using InterPro. The domains are described in Table 74:

TABLE 74

| InterPro domains | | |
|---|---|---|
| Domain description | Analysis type | Positions on protein |
| Immunoglobulin subtype | HMMSmart | 26-129, 143-223, 243-321 |
| Immunoglobulin C2 type | HMMSmart | 152-214 |
| Immunoglobulin-like | Profile Scan | 137-221, 223-319 |
| Immunoglobulin V-set | HMMPfam | 19-131 |
| Immunoglobulin-like | HMMPfam | 151-209 |

Variant protein H68654_1_P7 (SEQ ID NO:37) is encoded by the transcript H68654_1_T8 (SEQ ID NO:28), for which the coding portion starts at position 102 and ends at position 1466. The transcript also has the following SNPs as listed in Table 75 (given according to their position on the nucleotide sequence, with the alternative nucleic acid listed).

TABLE 75

| Nucleic acid SNPs | |
|---|---|
| Polymorphism | SNP positions on nucleotide sequence |
| A -> G | 163, 1507 |
| G -> A | 323, 1716 |
| G -> C | 323 |
| T -> C | 551, 676 |
| A -> T | 1507 |
| G -> T | 1646 |
| T -> A | 1717 |
| T -> G | 1717 |

Variant protein H68654_1_P12 (SEQ ID NO:38) according to the present invention has an amino acid sequence as encoded by transcripts H68654_1_T15 (SEQ ID NO:29), H68654_1_T16 (SEQ ID NO:30) and H68654_1_T18 (SEQ ID NO:32). Alignment of H68654_1_P12 (SEQ ID NO:38) to previously published protein sequences are shown in FIGS. 30C and 30D. A brief description of the relationship of the variant protein according to the present invention to each such aligned protein is as follows:

1. Comparison report between H68654_1_P12 (SEQ ID NO:38) and known proteins NP_937794 and Q6UXI0_HUMAN (SEQ ID NO: 36) (FIG. 30C):

A. An isolated chimeric polypeptide encoding for H68654_1_P12 (SEQ ID NO:38), comprising a first amino acid sequence being at least 90% homologous to

MWLKVFTTFLSFATGACSGLKVTVPSHTVHGVRGQALYLPVHYGFHTPASD

IQIIWLFERPHTMPKYLLGSVNKSVVPDLEYQHKFTMMPPNASLLINPLQF

PDEGNYIVKVNIQGNGTLSASQKIQVTVDDPVTKPVVQIHPPSGAVEYVGN

MTLTCHVEGGTRLAYQWLKNGRPVHTSSTYSFSPQNNTLHIAPVTKEDIGN

YSCLVRNPVSEMESDIIMPIIYYGPYGLQVNSDKGLKVGEVFTVDLGEAIL

FDCSADSHPPNTYSWIRRTDNTTYIIKHGPRLEVASEKVAQKTMDYVCCAY

NNITGRQDETHFTVIITSVGLEKLAQKGKSLSPLASITGISLFLIISMCLL

FLWKKYQPYKVIKQKLEGRPETEYRKAQTFSGHEDALDDFGIYEFVAFPDV

SGVSR corresponding to amino acids 1-413 of known proteins NP_937794 and Q6UXI0_HUMAN (SEQ ID NO: 36), which also corresponds to amino acids 1-413 of H68654_1_P12 (SEQ ID NO:38), and a second amino acid sequence being at least 70%, optionally at least 80%, preferably at least 85%, more preferably at least 90% and most preferably at least 95, 96, 97, 98 or 99% homologous to a polypeptide having the sequence VGFPSG (SEQ ID NO: 291) corresponding to amino acids 414-419 of H68654_1_P12 (SEQ ID NO:38), wherein said first amino acid sequence and second amino acid sequence are contiguous and in a sequential order.

B. An isolated polypeptide encoding for an edge portion of H68654_1_P12 (SEQ ID NO:38), comprising an amino acid sequence being at least 70%, optionally at least about 80%, preferably at least about 85%, more preferably at least about 90% and most preferably at least about 95, 96, 97, 98 or 99% homologous to the sequence VGFPSG (SEQ ID NO: 291) of H68654_1_P12 (SEQ ID NO:38).

2. Comparison report between H68654_1_P12 (SEQ ID NO:38) and known proteins NP_001034461 (SEQ ID NO: 35) (FIG. 30D):

A. An isolated chimeric polypeptide encoding for H68654_1_P12 (SEQ ID NO:38), comprising a first amino acid sequence being at least 70%, optionally at least 80%, preferably at least 85%, more preferably at least 90% and most preferably at least 95, 96, 97, 98 or 99%, homologous to a polypeptide having the sequence MWLKVFTTFLSFAT (SEQ ID NO: 289) corresponding to amino acids 1-14 of H68654_1_P12 (SEQ ID NO:38), a second amino acid sequence being at least 90% homologous to

GACSGLKVTVPSHTVHGVRGQALYLPVHYGFHTPASDIQIIWLFERPHTMP

KYLLGSVNKSVVPDLEYQHKFTMMPPNASLLINPLQFPDEGNYIVKVNIQG

NGTLSASQKIQVTVDDPVTKPVVQIHPPSGAVEYVGNMTLTCHVEGGTRLA

YQWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTYS

WIRRTDNTTYIIKHGPRLEVASEKVAQKTMDYVCCAYNNITGRQDETHFTV

IITSVGLEKLAQKGKSLSPLASITGISLFLIISMCLLFLWKKYQPYKVIKQ

KLEGRPETEYRKAQTFSGHEDALDDFGIYEFVAFPDVSGVSR corresponding to amino acids 27-425 of known proteins NP_001034461 (SEQ ID NO: 35), which also corresponds to amino acids 15-413 of H68654_1_P12 (SEQ ID NO:38), and a third amino acid sequence being at least 70%, optionally at least 80%, preferably at least 85%, more preferably at least 90% and most preferably at least 95, 96, 97, 98 or 99% homologous to a polypeptide having the sequence VGFPSG (SEQ ID NO: 291) corresponding to amino acids 414-419 of H68654_1_P12 (SEQ ID NO:38), wherein said first amino acid sequence, second amino acid sequence and third amino acid sequence are contiguous and in a sequential order.

B. An isolated polypeptide encoding for a head of H68654_1_P12 (SEQ ID NO:38), comprising a polypeptide being at least 70%, optionally at least about 80%, preferably at least about 85%, more preferably at least about 90% and most preferably at least about 95, 96, 97, 98 or 99% homologous to the sequence MWLKVFTTFLSFAT (SEQ ID NO: 289) of H68654_1_P12 (SEQ ID NO:38).

C. An isolated polypeptide encoding for an edge portion of H68654_1_P12 (SEQ ID NO:38), comprising an amino acid sequence being at least 70%, optionally at least about 80%, preferably at least about 85%, more preferably at least about 90% and most preferably at least about 95, 96, 97, 98 or 99% homologous to the sequence VGFPSG (SEQ ID NO: 291) of H68654_1_P12 (SEQ ID NO:38).

The localization of the variant protein was determined according to results from a number of different software programs and analyses, including analyses from SignalP and other specialized programs. The variant protein is believed to be located as follows with regard to the cell: membrane.

Variant protein H68654_1_P12 (SEQ ID NO:38) also has the following non-silent SNPs (Single Nucleotide Polymorphisms) as listed in Table 76, (given according to their positions on the amino acid sequence, with the alternative amino acids listed (SEQ ID NO:38)).

TABLE 76

| Amino acid mutations | |
|---|---|
| SNP positions on amino acid sequence | Alternative amino acids |
| 21 | K - > R |
| 74 | K -> N |
| 192 | L -> P |

The variant protein has the following domains, as determined by using InterPro. The domains are described in Table 77.

TABLE 77

| InterPro domains | | |
|---|---|---|
| Domain description | Analysis type | Positions on protein |
| Immunoglobulin subtype | HMMSmart | 26-129, 143-223, 243-321 |
| Immunoglobulin-like | HMMPfam | 151-209 |
| Immunoglobulin C2 type | HMMSmart | 152-214 |
| Immunoglobulin V-set | HMMPfam | 19-131 |
| Immunoglobulin-like | Profile Scan | 137-221, 223-319 |

The coding portion of transcript H68654_1_T15 (SEQ ID NO:29) starts at position 102 and ends at position 1358. The transcript also has the following SNPs as listed in Table 78 (given according to their position on the nucleotide sequence, with the alternative nucleic acid listed).

TABLE 78

| Nucleic acid SNPs | |
|---|---|
| Polymorphism | SNP positions on nucleotide sequence |
| A -> G | 163, 1586 |
| G -> A | 323, 1795 |
| G -> C | 323 |
| T -> C | 551, 676 |
| A -> T | 1586 |
| G -> T | 1725 |
| T -> A | 1796 |
| T -> G | 1796 |

The coding portion of transcript H68654_1_ starts at position 102 and ends at position 1358. The transcript also has the following SNPs as listed in Table 79 (given according to their position on the nucleotide sequence, with the alternative nucleic acid listed).

TABLE 79

| Nucleic acid SNPs | |
|---|---|
| Polymorphism | SNP positions on nucleotide sequence |
| A -> G | 163, 1588 |
| G -> A | 323, 1797 |
| G -> C | 323 |
| T -> C | 551, 676 |
| A -> T | 1588 |
| G -> T | 1727 |
| T -> A | 1798 |
| T -> G | 1798 |

The coding portion of transcript H68654_1_T18 (SEQ ID NO:32) starts at position 102 and ends at position 1358. The transcript also has the following SNPs as listed in Table 80 (given according to their position on the nucleotide sequence, with the alternative nucleic acid listed).

TABLE 80

| Nucleic acid SNPs | |
|---|---|
| Polymorphism | SNP positions on nucleotide sequence |
| A -> G | 163 |
| G -> A | 323, 2117 |
| G -> C | 323 |
| T -> C | 551, 676 |
| T -> A | 1603 |
| T -> G | 1603 |

Variant protein H68654_1_P13 (SEQ ID NO:39) according to the present invention has an amino acid sequence as encoded by transcripts H68654_1_T17 (SEQ ID NO:31) and H68654_1_T19 (SEQ ID NO:33). Alignments to one or more previously published protein sequences are shown in FIGS. 30E and 30F. A brief description of the relationship of the variant protein according to the present invention to each such aligned protein is as follows:

1. Comparison report between H68654_1_P13 (SEQ ID NO:39) and known proteins NP_937794 and Q6UXI0_HUMAN (SEQ ID NO: 36) (FIG. 30E):

A. An isolated chimeric polypeptide encoding for H68654_1_P13 (SEQ ID NO:39), comprising a amino acid sequence being at least 90% homologous to

```
MWLKVFTTFLSFATGACSGLKVTVPSHTVHGVRGQALYLPVHYGFHTPASD

IQIIWLFERPHTMPKYLLGSVNKSVVPDLEYQHKFTMMPPNASLLINPLQF

PDEGNYIVKVNIQGNGTLSASQKIQVTVDDPVTKPVVQIHPPSGAVEYVGN

MTLTCHVEGGTRLAYQWLKNGRPVHTSSTYSFSPQNNTLHIAPVTKEDIGN

YSCLVRNPVSEMESDIIMPIIYYGPYGLQVNSDKGLKVGEVFTVDLGEAIL

FDCSADSHPPNTYSWIRRTDNTTYIIKHGPRLEVASEKVAQKTMDYVCCAY

NNITGRQDETHFTVIITSVGLEKLAQKGKSLSPLASITGISLFLIISMCLL

FLWKKYQPYKVIKQKLEGR
```

corresponding to amino acids 1-376 of known proteins NP_937794 and Q6UXI0_HUMAN (SEQ ID NO: 36), which also corresponds to amino acids 1-376 of H68654_1_P13 (SEQ ID NO:39), wherein said and first amino acid sequence are contiguous and in a sequential order.

2. Comparison report between H68654_1_P13 (SEQ ID NO:39) and known proteins NP_001034461 (SEQ ID NO: 35) (FIG. 30F):

A. An isolated chimeric polypeptide encoding for H68654_1_P13 (SEQ ID NO:39), comprising a first amino acid sequence being at least 70%, optionally at least 80%, preferably at least 85%, more preferably at least 90% and most preferably at least 95, 96, 97, 98 or 99%, homologous to a polypeptide having the sequence MWLKVFTTFLSFAT (SEQ ID NO: 289) corresponding to amino acids 1-14 of H68654_1_P13 (SEQ ID NO:39), and a second amino acid sequence being at least 90% homologous to

```
GACSGLKVTVPSHTVHGVRGQALYLPVHYGFHTPASDIQIIWLFERPHTMP

KYLLGSVNKSVVPDLEYQHKFTMMPPNASLLINPLQFPDEGNYIVKVNIQG

NGTLSASQKIQVTVDDPVTKPVVQIHPPSGAVEYVGNMTLTCHVEGGTRLA

YQWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTYS

WIRRTDNTTYIIKHGPRLEVASEKVAQKTMDYVCCAYNNITGRQDETHFTV

IITSVGLEKLAQKGKSLSPLASITGISLFLIISMCLLFLWKKYQPYKVIKQ

KLEGR
```

corresponding to amino acids 27-388 of known proteins NP_001034461 (SEQ ID NO: 35), which also corresponds to amino acids 15-376 of H68654_1_P13 (SEQ ID NO:39), wherein said first amino acid sequence and second amino acid sequence are contiguous and in a sequential order.

B. An isolated polypeptide encoding for a head of H68654_1_P13 (SEQ ID NO:39), comprising a polypeptide being at least 70%, optionally at least about 80%, preferably at least about 85%, more preferably at least about 90% and most preferably at least about 95, 96, 97, 98 or 99% homologous to the sequence MWLKVFTTFLSFAT (SEQ ID NO: 289) of H68654_1_P13 (SEQ ID NO:39).

The localization of the variant protein was determined according to results from a number of different software programs and analyses, including analyses from SignalP and other specialized programs. The variant protein is believed to be located as follows with regard to the cell: membrane.

Variant protein H68654_1_P13 (SEQ ID NO:39) also has the following non-silent SNPs (Single Nucleotide Polymorphisms) as listed in Table 81, (given according to their positions on the amino acid sequence, with the alternative amino acids listed (SEQ ID NO:39)).

TABLE 81

| Amino acid mutations | |
|---|---|
| SNP positions on amino acid sequence | Alternative amino acids |
| 21 | K -> R |
| 74 | K -> N |
| 192 | L -> P |

The variant protein has the following domains, as determined by using InterPro. The domains are described in Table 82:

TABLE 82

| InterPro domains | | |
|---|---|---|
| Domain description | Analysis type | Positions on protein |
| Immunoglobulin subtype | HMMSmart | 26-129, 143-223, 243-321 |
| Immunoglobulin-like | Profile Scan | 137-221, 223-319 |
| Immunoglobulin C2 type | HMMSmart | 152-214 |
| Immunoglobulin V-set | HMMPfam | 19-131 |
| Immunoglobulin-like | HMMPfam | 151-209 |

The coding portion of transcript H68654_1_T17 (SEQ ID NO:31) starts at position 102 and ends at position 1229. The transcript also has the following SNPs as listed in Table 83 (given according to their position on the nucleotide sequence, with the alternative nucleic acid listed).

TABLE 83

| Nucleic acid SNPs | |
|---|---|
| Polymorphism | SNP positions on nucleotide sequence |
| A -> G | 163, 1626 |
| G -> A | 323, 1835 |
| G -> C | 323 |
| T -> C | 551, 676 |
| A -> T | 1626 |
| G -> T | 1765 |
| T -> A | 1836 |
| T -> G | 1836 |

The coding portion of transcript H68654_1_T19 (SEQ ID NO:33) starts at position 102 and ends at position 1229. The transcript also has the following SNPs as listed in Table 84 (given according to their position on the nucleotide sequence, with the alternative nucleic acid listed).

TABLE 84

| Nucleic acid SNPs | |
|---|---|
| Polymorphism | SNP positions on nucleotide sequence |
| A -> G | 163 |
| G -> A | 323, 2211 |
| G -> C | 323 |
| T -> C | 551, 676 |
| T -> A | 1697 |
| T -> G | 1697 |

Variant protein H68654_1_P14 (SEQ ID NO:40) according to the present invention has an amino acid sequence as encoded by transcript H68654_1_T20 (SEQ ID NO:34). Alignments to previously published protein sequences are shown in FIGS. 30G and 30H. A brief description of the relationship of the variant protein according to the present invention to each such aligned protein is as follows:

1. Comparison report between H68654_1_P14 (SEQ ID NO:40) and known proteins NP_937794 and Q6UXI0_HUMAN (SEQ ID NO: 36) (FIG. 30G):

A. An isolated chimeric polypeptide encoding for H68654_1_P14 (SEQ ID NO:40), comprising a first amino acid sequence being at least 90% homologous to MWLKVFTTFLSFATGACSGLKVTVPSHTVHGVRGQALYLPVHYGFHTPASDIQII WLFERPHTMPKYLLGS- VNKSVVPDLEYQHKFTMMPPNASLLINPLQFPDEG-NYI VKVNIQGNGTLSASQKIQVTVDDPVTKPVVQIH-PPSGAVEYVGNMTLTCHVEG GTRLAYQWLKNGR-PVHTSSTYSFSPQNNTLHIAPVTKEDIGNYSCLVRN-PVSEM ESDIIMPIIYYGPYGLQVNSDKGLKVGEVFT-VDLGEAILFDCSADSHPPNTYSWIR RTDNTTYIIKHG-PRLEVASEKVAQKTMDYVCCAYNNITGRQDETHFT-VIITSVGL EKLAQKGKSLSPLASITGISLFLIISMCLLFLWKKY-QPYKVIKQKLEGRPETEYRKA QTFSG corresponding to amino acids 1-389 of known proteins NP_937794 and Q6UXI0_HUMAN (SEQ ID NO: 36), which also corresponds to amino acids 1-389 of H68654_1_P14 (SEQ ID NO:40), and a second amino acid sequence being at least 70%, optionally at least 80%, preferably at least 85%, more preferably at least 90% and most preferably at least 95, 96, 97, 98 or 99% homologous to a polypeptide having the sequence FMLAAPSQREEEKKIWQGPGLLLCPHCN-PHYHQY (SEQ ID NO: 292) corresponding to amino acids 390-423 of H68654_1_P14 (SEQ ID NO:40), wherein said first amino acid sequence and second amino acid sequence are contiguous and in a sequential order.

B. An isolated polypeptide encoding for an edge portion of H68654_1_P14 (SEQ ID NO:40), comprising an amino acid sequence being at least 70%, optionally at least about 80%, preferably at least about 85%, more preferably at least about 90% and most preferably at least about 95, 96, 97, 98 or 99% homologous to the sequence FMLAAPSQREEEK-KIWQGPGLLLCPHCNPHYHQY (SEQ ID NO: 292) of H68654_1_P14 (SEQ ID NO:40).

2. Comparison report between H68654_1_P14 (SEQ ID NO:40) and known proteins NP_001034461 (SEQ ID NO: 35) (FIG. 30H):

A. An isolated chimeric polypeptide encoding for H68654_1_P14 (SEQ ID NO:40), comprising a first amino acid sequence being at least 70%, optionally at least 80%, preferably at least 85%, more preferably at least 90% and most preferably at least 95, 96, 97, 98 or 99%, homologous to a polypeptide having the sequence MWLKVFTTFLSFAT (SEQ ID NO: 289) corresponding to amino acids 1-14 of H68654_1_P14 (SEQ ID NO:40), a second amino acid sequence being at least 90% homologous to

```
GACSGLKVTVPSHTVHGVRGQALYLPVHYGFHTPASDIQIIWLFERPHTMP

KYLLGSVNKSVVPDLEYQHKFTMMPPNASLLINPLQFPDEGNYIVKVNIQG

NGTLSASQKIQVTVDDPVTKPVVQIHPPSGAVEYVGNMTLTCHVEGGTRLA

YQWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTYS

WIRRTDNTTYIIKHGPRLEVASEKVAQKTMDYVCCAYNNITGRQDETHFTV

IITSVGLEKLAQKGKSLSPLASITGISLFLIISMCLLFLWKKYQPYKVIKQ

KLEGRPETEYRKAQTFSG
```

corresponding to amino acids 27-401 of known proteins NP_001034461 (SEQ ID NO: 35), which also corresponds to amino acids 15-389 of H68654_1_P14 (SEQ ID NO:40), and a third amino acid sequence being at least 70%, optionally at least 80%, preferably at least 85%, more preferably at least 90% and most preferably at least 95, 96, 97, 98 or 99% homologous to a polypeptide having the sequence FMLAAPSQREEEKKIWQGPGLLLCPHCNPHYHQY (SEQ ID NO: 292) corresponding to amino acids 390-423 of H68654_1_P14 (SEQ ID NO:40), wherein said first amino acid sequence, second amino acid sequence and third amino acid sequence are contiguous and in a sequential order.

B. An isolated polypeptide encoding for a head of H68654_1_P14 (SEQ ID NO:40), comprising a polypeptide being at least 70%, optionally at least about 80%, preferably at least about 85%, more preferably at least about 90% and most preferably at least about 95, 96, 97, 98 or 99% homologous to the sequence MWLKVFTTFLSFAT (SEQ ID NO: 289) of H68654_1_P14 (SEQ ID NO:40).

C. An isolated polypeptide encoding for an edge portion of H68654_1_P14 (SEQ ID NO:40), comprising an amino acid sequence being at least 70%, optionally at least about 80%, preferably at least about 85%, more preferably at least about 90% and most preferably at least about 95, 96, 97, 98 or 99% homologous to the sequence FMLAAPSQREEEK-KIWQGPGLLLCPHCNPHYHQY (SEQ ID NO: 292) of H68654_1_P14 (SEQ ID NO:40).

The localization of the variant protein was determined according to results from a number of different software programs and analyses, including analyses from SignalP and other specialized programs. The variant protein is believed to be located as follows with regard to the cell: membrane.

Variant protein H68654_1_P14 (SEQ ID NO:40) also has the following non-silent SNPs (Single Nucleotide Polymorphisms) as listed in Table 85, (given according to their positions on the amino acid sequence, with the alternative amino acids listed (SEQ ID NO:40)).

TABLE 85

| Amino acid mutations | |
|---|---|
| SNP positions on amino acid sequence | Alternative amino acids |
| 21 | K -> R |
| 74 | K -> N |
| 192 | L -> P |

The variant protein has the following domains, as determined by using InterPro. The domains are described in Table 86:

TABLE 86

| InterPro domains | | |
|---|---|---|
| Domain description | Analysis type | Positions on protein |
| Immunoglobulin C2 type | HMMSmart | 152-214 |
| Immunoglobulin subtype | HMMSmart | 26-129, 143-223, 243-321 |
| Immunoglobulin-like | Profile Scan | 137-221, 223-319 |
| Immunoglobulin V-set | HMMPfam | 19-131 |
| Immunoglobulin-like | HMMPfam | 151-209 |

Variant protein H68654_1_P14 (SEQ ID NO:40) is encoded by the transcript H68654_1_T20 (SEQ ID NO:34), for which the coding portion starts at position 102 and ends at position 1370. The transcript also has the following SNPs as listed in Table 87 (given according to their position on the nucleotide sequence, with the alternative nucleic acid listed).

TABLE 87

| Nucleic acid SNPs | |
|---|---|
| Polymorphism | SNP positions on nucleotide sequence |
| A -> G | 163 |
| G -> A | 323 |
| G -> C | 323 |
| T -> C | 551, 676 |
| C -> A | 1491 |
| C -> G | 1491 |

As noted above, cluster H68654 features 3 segments, which were listed in Table 63. These segments are portions of nucleic acid sequences which are described herein separately because they are of particular interest. A description of each segment according to the present invention is now provided.

Segment cluster H68654_1_N3 (SEQ ID NO:123) according to the present invention is supported by 24 libraries. The number of libraries was determined as previously described. This segment can be found in the following transcripts: H68654_1_T0 (SEQ ID NO:25), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), H68654_1_T20 (SEQ ID NO:34), H68654_1_T4 (SEQ ID NO:26), H68654_1_T5 (SEQ ID NO:27) and H68654_1_T8 (SEQ ID NO:28). Table 88 below describes the starting and ending position of this segment on each transcript.

TABLE 88

| Segment location on transcripts | | |
|---|---|---|
| Transcript name | Segment starting position | Segment ending position |
| H68654_1_T0 (SEQ ID NO: 25) | 158 | 508 |
| H68654_1_T15 (SEQ ID NO: 29) | 145 | 495 |
| H68654_1_T16 (SEQ ID NO: 30) | 145 | 495 |
| H68654_1_T17 (SEQ ID NO: 31) | 145 | 495 |
| H68654_1_T18 (SEQ ID NO: 32) | 145 | 495 |
| H68654_1_T19 (SEQ ID NO: 33) | 145 | 495 |
| H68654_1_T20 (SEQ ID NO: 34) | 145 | 495 |
| H68654_1_T4 (SEQ ID NO: 26) | 145 | 495 |
| H68654_1_T5 (SEQ ID NO: 27) | 158 | 508 |
| H68654_1_T8 (SEQ ID NO: 28) | 145 | 495 |

Segment cluster H68654_1_N7 (SEQ ID NO:124) according to the present invention is supported by 20 libraries. The number of libraries was determined as previously described. This segment can be found in the following transcripts: H68654_1_T0 (SEQ ID NO:25), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), H68654_1_T20 (SEQ ID NO:34), H68654_1_T4 (SEQ ID NO:26), H68654_1_T5 (SEQ ID NO:27) and H68654_1_T8 (SEQ ID NO:28). Table 89 below describes the starting and ending position of this segment on each transcript.

TABLE 89

| Segment location on transcripts | | |
|---|---|---|
| Transcript name | Segment starting position | Segment ending position |
| H68654_1_T0 (SEQ ID NO: 25) | 794 | 1090 |
| H68654_1_T15 (SEQ ID NO: 29) | 781 | 1077 |
| H68654_1_T16 (SEQ ID NO: 30) | 781 | 1077 |
| H68654_1_T17 (SEQ ID NO: 31) | 781 | 1077 |
| H68654_1_T18 (SEQ ID NO: 32) | 781 | 1077 |
| H68654_1_T19 (SEQ ID NO: 33) | 781 | 1077 |
| H68654_1_T20 (SEQ ID NO: 34) | 781 | 1077 |
| H68654_1_T4 (SEQ ID NO: 26) | 781 | 1077 |
| H68654_1_T5 (SEQ ID NO: 27) | 794 | 1090 |
| H68654_1_T8 (SEQ ID NO: 28) | 781 | 1077 |

Segment cluster H68654_1_N12 (SEQ ID NO:125) according to the present invention is supported by 18 libraries. The number of libraries was determined as previously described. This segment can be found in the following transcripts: H68654_1_T0 (SEQ ID NO:25), H68654_1_T15 (SEQ ID NO:29), H68654_1_T16 (SEQ ID NO:30), H68654_1_T17 (SEQ ID NO:31), H68654_1_T18 (SEQ ID NO:32), H68654_1_T19 (SEQ ID NO:33), H68654_1_T20 (SEQ ID NO:34), H68654_1_T4 (SEQ ID NO:26), H68654_1_T5 (SEQ ID NO:27) and H68654_1_T8 (SEQ ID NO:28). Table 90 below describes the starting and ending position of this segment on each transcript.

TABLE 90

| Segment location on transcripts | | |
|---|---|---|
| Transcript name | Segment starting position | Segment ending position |
| H68654_1_T0 (SEQ ID NO: 25) | 1091 | 1216 |
| H68654_1_T15 (SEQ ID NO: 29) | 1078 | 1203 |
| H68654_1_T16 (SEQ ID NO: 30) | 1078 | 1203 |
| H68654_1_T17 (SEQ ID NO: 31) | 1078 | 1203 |
| H68654_1_T18 (SEQ ID NO: 32) | 1078 | 1203 |
| H68654_1_T19 (SEQ ID NO: 33) | 1078 | 1203 |
| H68654_1_T20 (SEQ ID NO: 34) | 1078 | 1203 |
| H68654_1_T4 (SEQ ID NO: 26) | 1078 | 1203 |
| H68654_1_T5 (SEQ ID NO: 27) | 1091 | 1216 |
| H68654_1_T8 (SEQ ID NO: 28) | 1078 | 1203 |

Expression of hypothetical protein LOC253012 H68654 transcripts which are detectable by amplicon as depicted in sequence name H68654_seg3WTF2R2 (SEQ ID NO: 226) in normal and cancerous Lung tissues and in different normal tissues Expression of hypothetical protein LOC253012 transcripts detectable by or according to seg3F2R2-H68654_seg3WTF2R2 (SEQ ID NO: 226) amplicon and primers H68654_seg3WTF2 (SEQ ID NO: 224) and H68654_seg3WTR2 (SEQ ID NO: 225) was measured by real time PCR on lung panel and normal panel. The samples used are detailed in Table 3 and Table 2 above, respectively. For each RT sample, the expression of the above amplicon was normalized to the normalization factor calculated from the expression of several house keeping genes as described in Example 1.

Lung panel—The normalized quantity of each RT sample was then divided by the median of the quantities of the normal samples (sample numbers 51-64 and 69-70, Table 3 above), to obtain a value of fold up-regulation for each sample relative to median of the normal samples.

Figure 31:
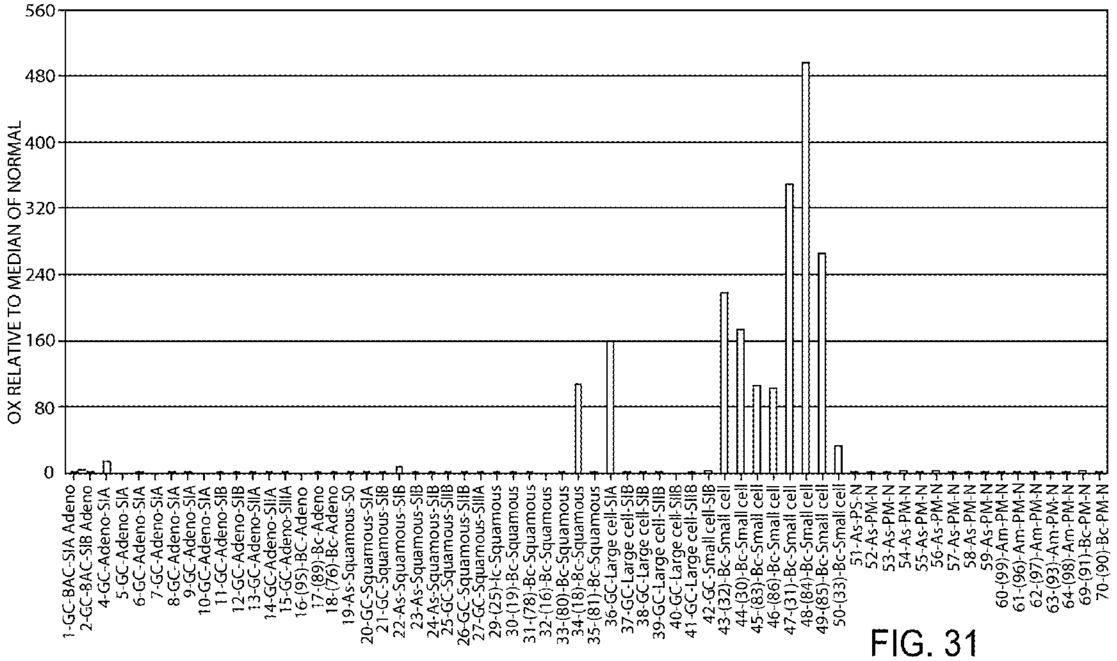
FIG. 31 presents a histogram showing expression of hypothetical protein LOC253012 H68654 transcripts which are detectable by amplicon as depicted in sequence name H68654_seg3WTF2R2 (SEQ ID NO: 226) in normal and cancerous Lung tissues.

FIG. 31 is a histogram showing over expression of the above-indicated hypothetical protein LOC253012 transcripts in cancerous Lung samples relative to the normal samples.

As is evident from FIG. 31, the expression of hypothetical protein LOC253012 transcripts detectable by the above amplicon in small cell carcinoma samples was significantly higher than in the non-cancerous samples (sample numbers 51-64 and 69-70, Table 3 above). Notably an over-expression of at least 80 fold was found in 7 out of 9 small cell carcinoma samples.

Statistical analysis was applied to verify the significance of these results, as described below.

The P value for the difference in the expression levels of hypothetical protein LOC253012 transcripts detectable by the above amplicon in Lung small cell carcinoma samples versus the normal tissue samples was determined by T test as 3.24e-003.

Threshold of 80 fold over expression was found to differentiate between small cell carcinoma and normal samples with P value of 7.49e-005 as checked by exact Fisher test.

The above values demonstrate statistical significance of the results.

Figure 32:
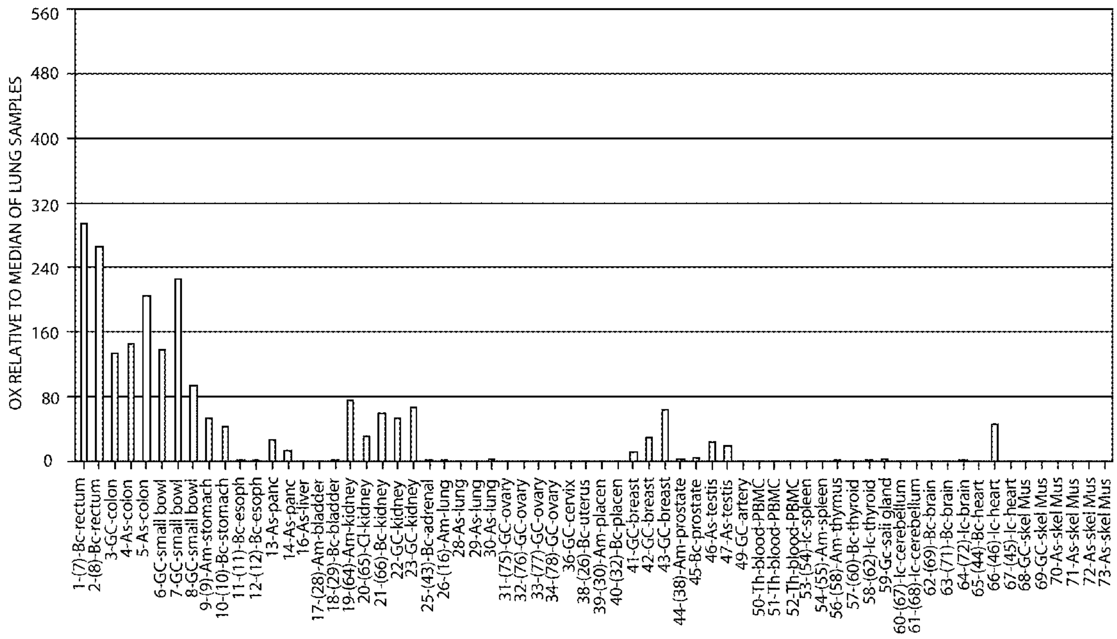
FIG. 32 presents a histogram showing expression of hypothetical protein LOC253012 H68654 transcripts which are detectable by amplicon as depicted in sequence name H68654_seg3WTF2R2 (SEQ ID NO: 226) in various normal and tissues.

Normal panel—The normalized quantity of each RT sample was then divided by the median of the quantities of the lung samples (sample numbers 26, 28, 29 and 30, Table 2 above), to obtain a value of relative expression of each sample relative to median of the lung samples, as shown in FIG. 32.

Primer pairs are also optionally and preferably encompassed within the present invention; for example, for the above experiment, the following primer pair was used as a non-limiting illustrative example only of a suitable primer pair: H68654_seg3WTF2 (SEQ ID NO: 224) forward primer; and H68654_seg3WTR2 (SEQ ID NO: 225) reverse primer.

The present invention also preferably encompasses any amplicon obtained through the use of any suitable primer pair; for example, for the above experiment, the following amplicon was obtained as a non-limiting illustrative example only of a suitable amplicon: H68654_seg3WTF2R2 (SEQ ID NO: 226).

```
Forward Primer >H68654_seg3WTF2
(SEQ ID NO: 224):
ATCACACACTGTCCATGGCGT

Reverse Primer >H68654_seg3WTR2
(SEQ ID NO: 225):
GTCTCTCAAATAGCCATATGATCTGG

Amplicon >H68654_seg3WTF2R2
                              (SEQ ID NO: 226)
ATCACACACTGTCCATGGCGTCAGAGGTCAGGCCCTC
TACCTACCCGTCCACTATGGCTTCCACACTCCAGCAT
CAGACATCCAGATCATATGGCTATTTGAGAGAC
```

Expression of hypothetical protein LOC253012 H68654 transcripts which are detectable by amplicon as depicted in sequence name H68654_seg7-12WT (SEQ ID NO: 223) in normal and cancerous Lung tissues and in different normal tissues Expression of hypothetical protein LOC253012 transcripts detectable by or according to seg7-12-H68654_seg7-12WT (SEQ ID NO: 223) amplicon and primers H68654_seg7-12WTF1 (SEQ ID NO: 221) and H68654_seg7-12WTR1 (SEQ ID NO: 222) was measured by real time PCR on lung panel and normal panel. The samples used are detailed in Table 3 and Table 2 above, respectively. For each RT sample, the expression of the above amplicon was normalized to the normalization factor calculated from the expression of several house keeping genes as described in Example 1.

Lung panel—Non-detected samples (samples no. 30, 41, 78 and 92, Table 3) were assigned Ct value of 41 and were calculated accordingly. The normalized quantity of each RT sample was then divided by the median of the quantities of the normal samples (sample numbers 51-64 and 69-70, Table 3 above), to obtain a value of fold up-regulation for each sample relative to median of the normal samples.

Figure 33:
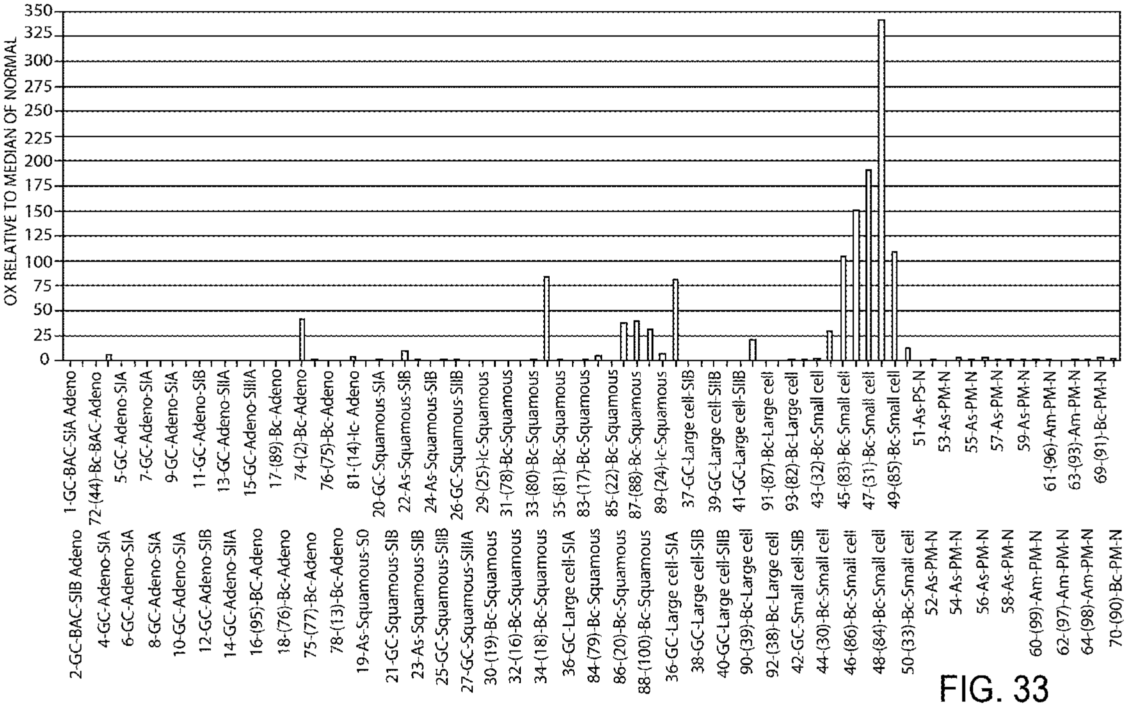
FIG. 33 presents a histogram showing expression of hypothetical protein LOC253012 H68654 transcripts which are detectable by amplicon as depicted in sequence name H68654_seg7-12WT (SEQ ID NO: 223) in normal and cancerous Lung tissues.

FIG. 33 is a histogram showing over expression of the above-indicated hypothetical protein LOC253012 transcripts in cancerous Lung samples relative to the normal samples.

As is evident from FIG. 33, the expression of hypothetical protein LOC253012 transcripts detectable by the above amplicon in small cell carcinoma samples was significantly higher than in the non-cancerous samples (sample numbers 51-64 and 69-70, Table 3 above) and was higher in a few squamous cell carcinoma samples. Notably an over-expression of at least 25 fold was found in 6 out of 9 small cell carcinoma samples and in 4 out of 24 squamous cell carcinoma samples.

Statistical analysis was applied to verify the significance of these results, as described below. The P value for the difference in the expression levels of hypothetical protein LOC253012 transcripts detectable by the above amplicon in Lung small cell carcinoma samples and Lung squamous cell carcinoma samples versus the normal tissue samples was determined by T test as 1.24e-002 and 2.97e-002, respectively.

Threshold of 25 fold over expression was found to differentiate between small cell carcinoma and normal samples with P value of 4.74e-004 as checked by exact Fisher test.

The above values demonstrate statistical significance of the results.

Figure 34:
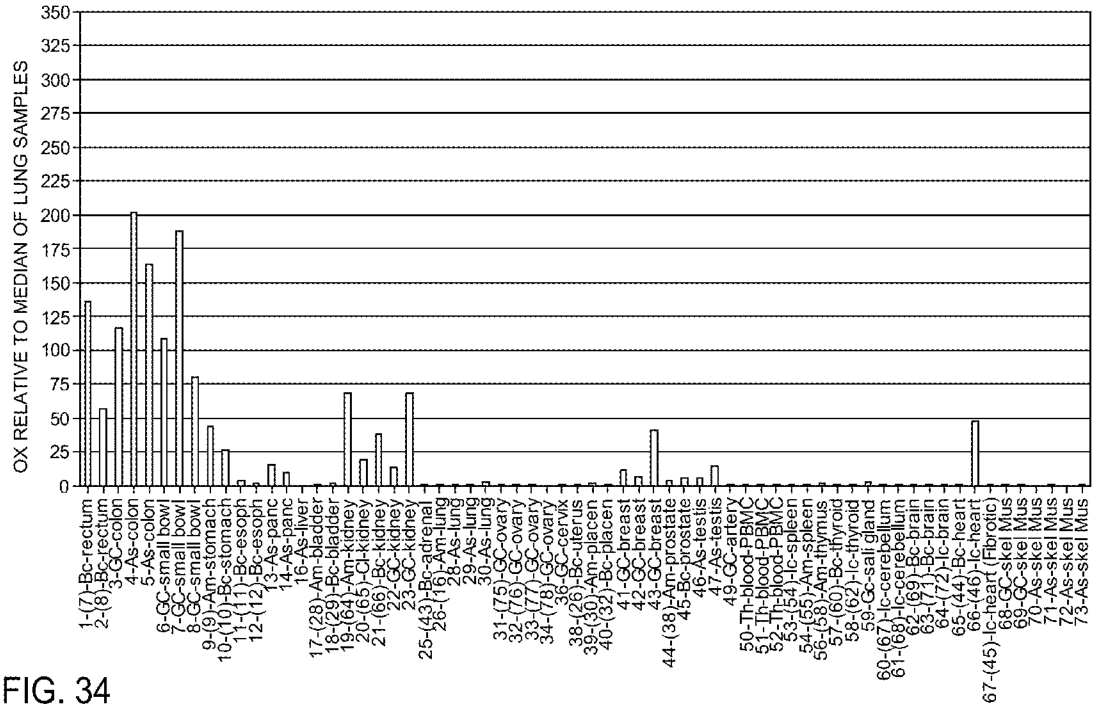
FIG. 34 presents a histogram showing expression of hypothetical protein LOC253012 H68654 transcripts which are detectable by amplicon as depicted in sequence name H68654_seg7-12WT (SEQ ID NO: 223) in various normal and tissues.

Normal panel—Non-detected sample (sample no. 16) was assigned Ct value of 41 and was calculated accordingly. The normalized quantity of each RT sample was then divided by the median of the quantities of the lung samples (sample numbers 26, 28, 29 and 30, Table 2 above), to obtain a value of relative expression of each sample relative to median of the lung samples, as shown in FIG. 34.

Primer pairs are also optionally and preferably encompassed within the present invention; for example, for the above experiment, the following primer pair was used as a non-limiting illustrative example only of a suitable primer pair: H68654_seg7-12WTF1 (SEQ ID NO: 221) forward primer; and H68654_seg7-12WTR1 (SEQ ID NO: 222) reverse primer.

The present invention also preferably encompasses any amplicon obtained through the use of any suitable primer pair; for example, for the above experiment, the following amplicon was obtained as a non-limiting illustrative example only of a suitable amplicon: H68654_seg7-12WT (SEQ ID NO: 223).

```
Forward Primer >H68654_seg7-12WTF1 (SEQ ID NO:
221):
ATGGGCCTCGCTTAGAAGTTG

Reverse Primer >H68654_seg7-12WTR1 (SEQ ID NO:
222):
TTCTGTGCAAGCTTCTCCAGTC

Amplicon >H68654_seg7-12WT (SEQ ID NO: 223):
ATGGGCCTCGCTTAGAAGTTGCATCTGAGAAAGTAGCCCAGAAGACAATG

GACTATGTGTGCTGTGCTTACAACAACATAACCGGCAGGCAAGATGAAAC

TCATTTCACAGTTATCATCACTTCCGTAGGACTGGAGAAGCTTGCACAGA

A
```

Expression of LOC253012 H68654 transcripts which are detectable by amplicon as depicted in sequence name H68654_seg3WTF2R2 (SEQ ID NO: 226) in the blood-specific panel.

Expression of LOC253012 transcripts detectable by or according to seg3-H68654seg3F2R2 (SEQ ID NO: 226) amplicon and primers H68654seg3F2 (SEQ ID NO: 224) and H68654seg3R2 (SEQ ID NO: 225) was measured by real time PCR on blood panel. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the kidney normal samples (sample numbers 65-67, Table 1 above), to obtain a value of relative expression of each sample relative to median of the kidney normal samples.

Figure 35A:
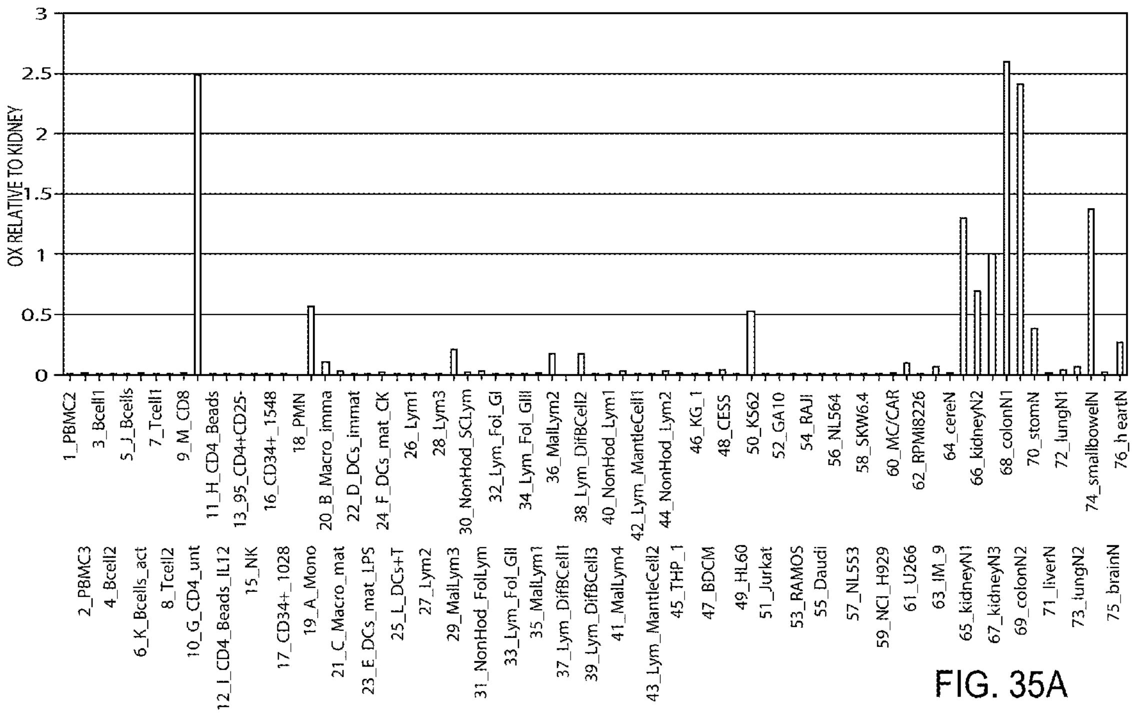
FIG. 35A presents a histogram showing expression of hypothetical protein LOC253012 H68654 transcripts which are detectable by amplicon as depicted in sequence name H68654seg3F2R2 (SEQ ID NO: 226) in blood-specific panel.

The results of this analysis are depicted in the histogram in FIG. 35A. Expression of the above-indicated LOC253012 transcript is high in the kidney normal, colon normal and small intestine normal asin few of the different blood samples checked.

Primer pairs are also optionally and preferably encompassed within the present invention; for example, for the above experiment, the following primer pair was used as a non-limiting illustrative example only of a suitable primer pair: H68654_seg3WTF2 forward primer; and H68654_seg3WTR2 reverse primer.

The present invention also preferably encompasses any amplicon obtained through the use of any suitable primer pair; for example, for the above experiment, the following amplicon was obtained as a non-limiting illustrative example only of a suitable amplicon: H68654_seg3WTF2R2.

```
Forward Primer >H68654_seg3WTF2:
                                    (SEQ ID NO: 224)
ATCACACACTGTCCATGGCGT

Reverse Primer >H68654_seg3WTR2:
                                    (SEQ ID NO: 225)
GTCTCTCAAATAGCCATATGATCTGG

Amplicon >H68654_seg3WTF2R2
                                    (SEQ ID NO: 226)
ATCACACACTGTCCATGGCGTCAGAGGTCAGGCCCTCTACCTACCCGTCC

ACTATGGCTTCCACACTCCAGCATCAGACATCCAGATCATATGGCTATTT

GAGAGAC
```

Expression of LOC253012 H68654 transcripts which are detectable by amplicon as depicted in sequence name H68654seg7-12 (SEQ ID NO: 223) in the blood-specific panel.

Expression of LOC253012 transcripts detectable by or according to seg7-12-H68654seg7-12WTF1R1 (SEQ ID NO: 223) amplicon and primers H68654seg7-12WTF1 (SEQ ID NO: 221) and H68654seg7-12WTR1 (SEQ ID NO: 222) was measured by real time PCR on blood panel. The samples used are detailed in Table 1 above. For each RT sample, the expression of the above amplicon was normalized to the normalization factor calculated from the expression of several house keeping genes as described in Example 1. The normalized quantity of each RT sample was then divided by the median of the quantities of the kidney normal samples (sample numbers 65-67, Table 1 above), to obtain a value of relative expression of each sample relative to median of the kidney normal samples.

Figure 35B:
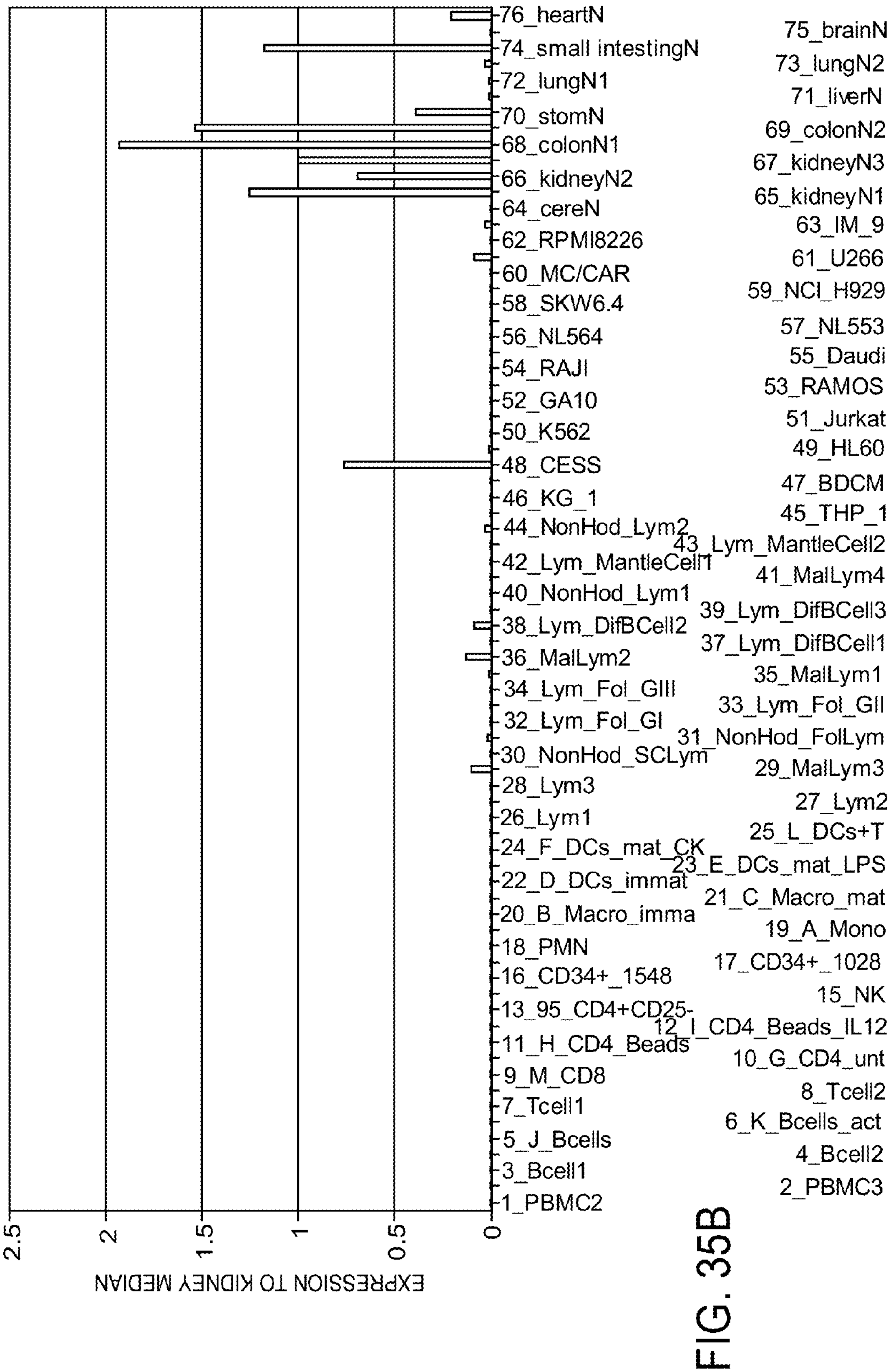
FIG. 35B presents a histogram showing expression of hypothetical protein LOC253012 H68654 transcripts which are detectable by amplicon as depicted in sequence name H68654seg7-12F1R1 (SEQ ID NO: 223) in blood-specific panel.

The results of this analysis are depicted in the histogram in FIG. 35B. Expression of the above-indicated LOC253012 transcript is higher in the kidney normal, colon normal and small intestine normal relative to the different blood samples checked.

Primer pairs are also optionally and preferably encompassed within the present invention; for example, for the above experiment, the following primer pair was used as a non-limiting illustrative example only of a suitable primer pair: seg7-12WTF1 forward primer (SEQ ID NO: 221); and seg7-12WTR1 reverse primer (SEQ ID NO: 222).

The present invention also preferably encompasses any amplicon obtained through the use of any suitable primer pair; for example, for the above experiment, the following amplicon was obtained as a non-limiting illustrative example only of a suitable amplicon: seg7-12WTF1R1 (SEQ ID NO: 223).

```
Forward Primer >H68654_seg7-12WTF1
                                    (SEQ ID NO: 221)
ATGGGCCTCGCTTAGAAGTTG

Reverse Primer >H68654_seg7-12WTR1
                                    (SEQ ID NO: 222)
TTCTGTGCAAGCTTCTCCAGTC

Amplicon >H68654_seg7-12WT
                                    (SEQ ID NO: 223)
ATGGGCCTCGCTTAGAAGTTGCATCTGAGAAAGTAGCCCAGAAGACAATG

GACTATGTGTGCTGTGCTTACAACAACATAACCGGCAGGCAAGATGAAAC

TCATTTCACAGTTATCATCACTTCCGTAGGACTGGAGAAGCTTGCACAGA

A
```

Expression of hypothetical protein LOC253012 H68654 transcripts which are detectable by amplicon as depicted in sequence name H68654_seg0-3 (SEQ ID NO: 229) in normal and cancerous Lung tissues Expression of LOC253012 transcripts detectable by or according to seg0-3-H68654_seg0-3 (SEQ ID NO: 229) amplicon and primers H68654_seg0-3F1 (SEQ ID NO: 227) and H68654_seg0-3R1 (SEQ ID NO: 228) was measured by real time PCR on lung panel. The samples used are detailed in Table 3 above. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 51-54, 56-64, 69 and 70, Table 3 above), to obtain a value of fold up-regulation for each sample relative to median of the normal samples.

Figure 36:
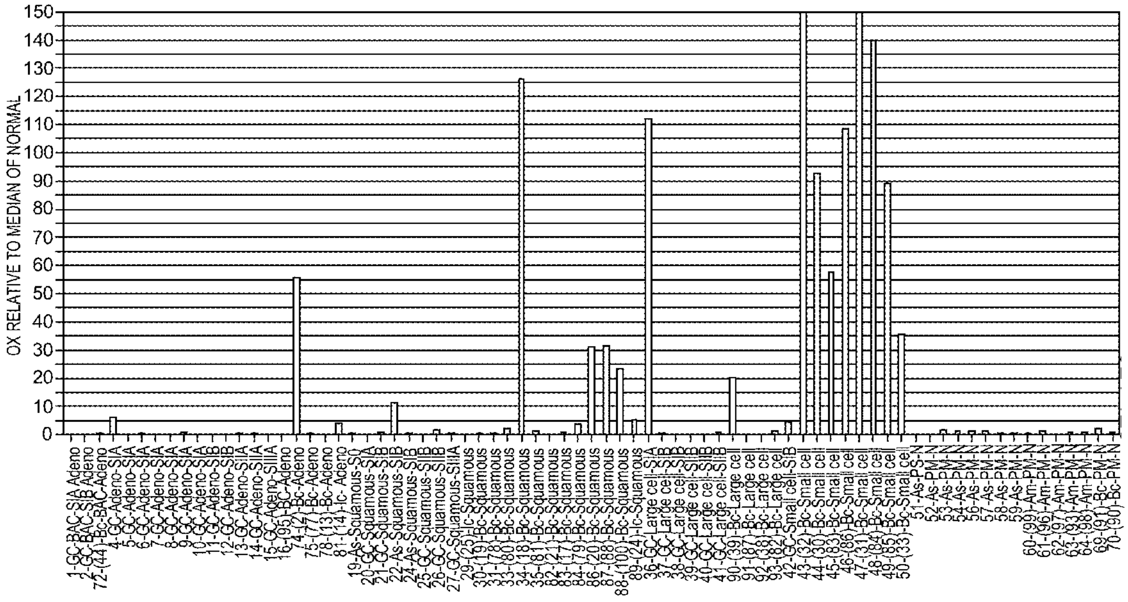
FIG. 36 presents a histogram showing expression of hypothetical protein LOC253012 H68654 transcripts which are detectable by amplicon as depicted in sequence name H68654_seg0-3 (SEQ ID NO: 229) in normal and cancerous Lung tissues.

FIG. 36 is a histogram showing over expression of the above-indicated LOC253012 transcripts in cancerous Lung samples relative to the normal samples.

As is evident from FIG. 36, the expression of LOC253012 transcripts detectable by the above amplicon in squamous cell carcinoma and small cell carcinoma samples was significantly higher than in the non-cancerous samples (sample numbers 51-54, 56-64, 69 and 70, Table 3 above). Notably an over-expression of at least 5 fold was found in 6 out of 21 squamous cell carcinoma samples and in 8 out of 9 small cell carcinoma samples.

Statistical analysis was applied to verify the significance of these results, as described below. The P value for the difference in the expression levels of LOC253012 transcripts detectable by the above amplicon in lung squamous cell carcinoma samples and lung small cell carcinoma samples versus the normal tissue samples was determined by T test as 4.96e-002 and 1.05e-003, respectively.

Threshold of 5 fold over expression was found to differentiate between squamous cell carcinoma and small cell carcinoma and normal samples with P value of 2.79e-002 and 1.22e-005, respectively, as checked by exact Fisher test. The above values demonstrate statistical significance of the results.

Primer pairs are also optionally and preferably encompassed within the present invention; for example, for the above experiment, the following primer pair was used as a non-limiting illustrative example only of a suitable primer pair: H68654_seg0-3F1 (SEQ ID NO: 227) forward primer; and H68654_seg0-3R1 (SEQ ID NO: 228) reverse primer.

The present invention also preferably encompasses any amplicon obtained through the use of any suitable primer pair; for example, for the above experiment, the following amplicon was obtained as a non-limiting illustrative example only of a suitable amplicon: H68654_seg0-3F1R1 (SEQ ID NO: 229).

```
Forward Primer >H68654_seg0-3F1
                                        (SEQ ID NO: 227)
GCTTTCATGGAGCCCTTCG

Reverse Primer >H68654_seg0-3R1
                                        (SEQ ID NO: 228)
GCCTGACCTCTGACGCCA

Amplicon >H68654_seg0-3F1R1
                                        (SEQ ID NO: 229)
GCTTTCATGGAGCCCTTCGGTGACACACTTGGGGTCTTTCAGTGCAAAAT

ATACCTCCTTCTCTTCGGTGCTTGCTCGGGGCTGAAGGTGACAGTGCCAT

CACACACTGTCCATGGCGTCAGAGGTCAGGC
```

Expression of hypothetical protein LOC253012 H68654 transcripts which are detectable by amplicon as depicted in sequence name H68654_seg2-3 (SEQ ID NO: 232) in normal and cancerous Lung tissues Expression of LOC253012 transcripts detectable by or according to seg2-3-H68654_seg2-3 (SEQ ID NO: 232) amplicon and primers H68654_seg2-3F1 (SEQ ID NO: 230) and H68654_seg2-3R1 (SEQ ID NO: 231) was measured by real time PCR on lung panel. The samples used are detailed in Table 3 above. For each RT sample, the expression of the above amplicon was normalized to the normalization factor calculated from the expression of several house keeping genes as described in Example 1. The normalized quantity of each RT sample was then divided by the median of the quantities of the normal samples (sample numbers 51, 52, 54-64, 69 and 70, Table 3 above), to obtain a value of fold up-regulation for each sample relative to median of the normal samples.

Figure 37:
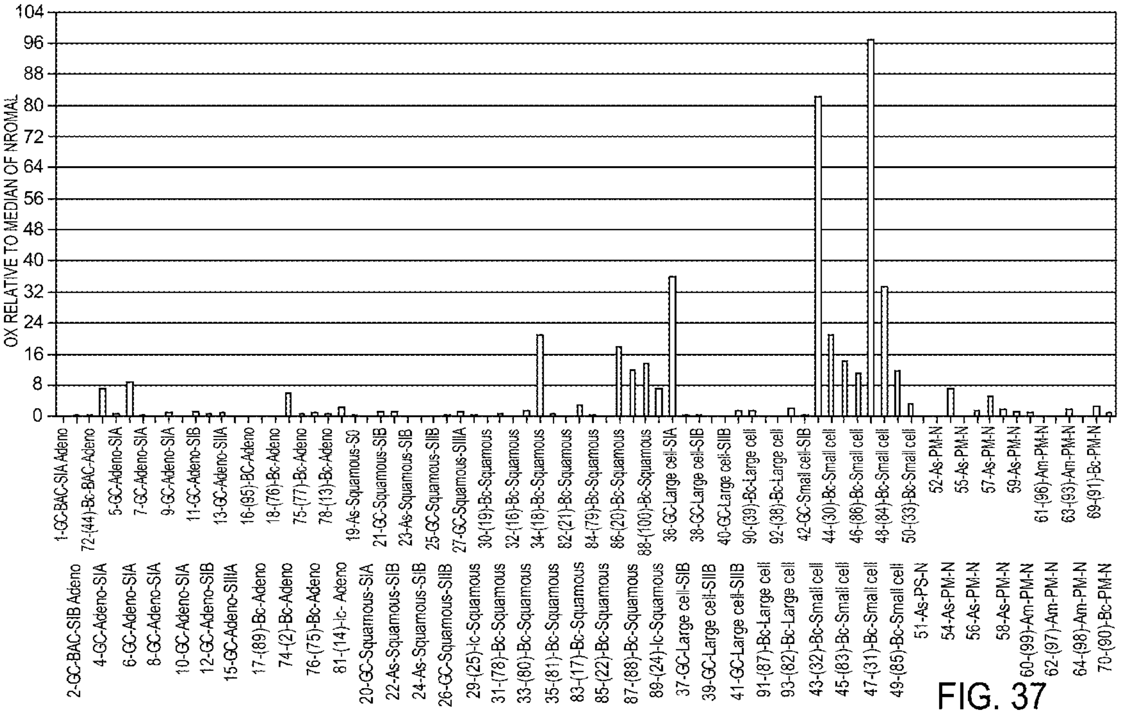
FIG. 37 presents a histogram showing expression of hypothetical protein LOC253012 H68654 transcripts which are detectable by amplicon as depicted in sequence name H68654_seg2-3 (SEQ ID NO: 232) in normal and cancerous Lung tissues.

FIG. 37 is a histogram showing over expression of the above-indicated LOC253012 transcripts in cancerous Lung samples relative to the normal samples.

As is evident from FIG. 37, the expression of LOC253012 transcripts detectable by the above amplicon in small cell carcinoma samples was significantly higher than in the non-cancerous samples (sample numbers 51, 52, 54-64, 69 and 70, Table 3 above) Notably an over-expression of at least 8 fold was found in 7 out of 9 small cell carcinoma samples.

Statistical analysis was applied to verify the significance of these results, as described below. The P value for the difference in the expression levels of LOC253012 transcripts detectable by the above amplicon in Lung small cell carcinoma samples versus the normal tissue samples was determined by T test as 1.93e-002.

Threshold of 8 fold over expression was found to differentiate between small cell carcinoma and normal samples with P value of 1.04e-004 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: H68654_seg2-3F1 (SEQ ID NO: 230) forward primer; and H68654_seg2-3R1 (SEQ ID NO: 231) reverse primer.

The present invention also preferably encompasses any amplicon obtained through the use of any suitable primer pair; for example, for the above experiment, the following amplicon was obtained as a non-limiting illustrative example only of a suitable amplicon: H68654_seg2-3F1R1 (SEQ ID NO: 232).

```
Forward Primer >H68654_seg2-3F1
                                        (SEQ ID NO: 230)
CTCTGCATTTGCCCCTTTAGA

Reverse Primer >H68654_seg2-3R1
                                        (SEQ ID NO: 231)
GATGGCACTGTCACCTTCAGC

Amplicon >H68654_seg2-3F1R1
                                        (SEQ ID NO: 232)
CTCTGCATTTGCCCCTTTAGATTGTGAAATGTGGCTCAAGGTCTTCACAA

CTTTCCTTTCCTTTGCAACAGGTGCTTGCTCGGGGCTGAAGGTGACAGTG

CCATC
```

Example 6

Description for Cluster H19011_1

The present invention relates to C1ORF32 polypeptides, novel splice variants and diagnostics and therapeutics based thereon.

Cluster H19011_1 (internal ID 76432827) features 2 transcripts and 5 segments of interest, the names for which are given in Tables 91 and 92, respectively. The selected protein variants are given in table 93.

TABLE 91

| Transcripts of interest<br>Transcript Name |
|---|
| H19011_1_T8 (SEQ ID NO: 45) |
| H19011_1_T9 (SEQ ID NO: 46) |

TABLE 92

| Segments of interest<br>Segment Name |
|---|
| H19011_1_N13 (SEQ ID NO: 129) |
| H19011_1_N8 (SEQ ID NO: 130) |
| H19011_1_N10 (SEQ ID NO: 131) |
| H19011_1_N11 (SEQ ID NO: 132) |
| H19011_1_N12 (SEQ ID NO: 133) |

TABLE 93

| Proteins of interest | |
|---|---|
| Protein Name | Corresponding Transcripts |
| H19011_1_P8 (SEQ ID NO: 48) | H19011_1_T8 (SEQ ID NO: 45) |
| H19011_1_P9 (SEQ ID NO: 50) | H19011_1_T9 (SEQ ID NO: 46) |

These sequences are variants of the known protein hypothetical protein LOC387597 (RefSeq accession identifier NP_955383 (SEQ ID NO: 47), synonims: C1ORF32, NP_955383; LISCH-like; RP4-782G3.2; dJ782G3.1), referred to herein as the previously known protein.

C1ORF32 is a hypothetical protein that was computationally discovered during the annotation of chromosome 1 (Gregory S G et al. 2006, Nature 441 (7091) 315-321). Its closest annotated homolog belongs to the LISCH7 family, a subfamily of the immunoglobulin super family. One of the annotated members of this family is the lipolysis-stimulated lipoprotein receptor which has a probable role in the clearance of triglyceride-rich lipoprotein from blood (Swissprot annotation of accession Q86×29).

According to the present invention, C1ORF32 was predicted to be a novel B7/CD28 member based on the presence of an IgV domain, in addition of its being a type I membrane protein, like other known B7 members. Also, two alternatively spliced variants of the present invention (H19011_1_P8 (SEQ ID NO:48) and H19011_1_P9 (SEQ ID NO:50)), which share only the first 5 exons with the wild type C1ORF32, are similar to the known B7 family members in their exons' sizes and the position of the IgV and transmembrane domains within these exons. In addition, C1ORF32 was shown in the present invention to be overexpressed in small cell lung cancer.

As noted above, cluster H19011 features 2 transcripts, which were listed in Table 91 above. These transcripts encode for proteins which are variants of protein hypothetical protein LOC387597 (SEQ ID NO:47). A description of each variant protein according to the present invention is now provided.

Variant protein H19011_1_P8 (SEQ ID NO:48) according to the present invention has an amino acid sequence as encoded by transcript H19011_1_T8 (SEQ ID NO:45). Alignments to one or more previously published protein sequences are shown in FIG. 38A. A brief description of the relationship of the variant protein according to the present invention to each such aligned protein is as follows:

Comparison report between H19011_1_P8 (SEQ ID NO:48) and known proteins Q71H61_HUMAN and NP_955383 (SEQ ID NO: 47) (FIG. 38A):

A. An isolated chimeric polypeptide encoding for H19011_1_P8 (SEQ ID NO:48), comprising a first amino acid sequence being at least 90% homologous to

MDRVLLRWISLFWLTAMVEGLQVTVPDKKKVAMLFQPTVLRCHFSTSSHQP

AVVQWKFKSYCQDRMGESLGMSSTRAQSLSKRNLEWDPYLDCLDSRRTVRV

VASKQGSTVTLGDFYRGREITIVHDADLQIGKLMWGDSGLYYCIITTPDDL

EGKNE corresponding to amino acids 1-158 of known proteins Q71H61_HUMAN and NP_955383 (SEQ ID NO: 47), which also corresponds to amino acids 1-158 of H19011_1_P8 (SEQ ID NO:48), a bridging amino acid G corresponding to amino acid 159 of H19011_1_P8 (SEQ ID NO:48), a second amino acid sequence being at least 90% homologous to S corresponding to amino acids 160-160 of known proteins Q71H61_HUMAN and NP_955383 (SEQ ID NO: 47), which also corresponds to amino acids 160-160 of H19011_1_P8 (SEQ ID NO:48), bridging amino acids LG corresponding to amino acid 161-162 of H19011_1_P8 (SEQ ID NO:48), a third amino acid sequence being at least 90% homologous to

LLVLGRTGLLADLLPSFAVEIMPEWVFVGLVLLGVFLFFVLVGICWCQCCP

HSCCCYVRCPCCPDSC corresponding to amino acids 163-229 of known proteins Q71H61_HUMAN and NP_955383 (SEQ ID NO: 47), which also corresponds to amino acids 163-229 of H19011_1_P8 (SEQ ID NO:48), a bridging amino acid W corresponding to amino acid 230 of H19011_1_P8 (SEQ ID NO:48), a fourth amino acid sequence being at least 90% homologous to CPQA corresponding to amino acids 231-234 of known proteins Q71H61_HUMAN and NP_955383 (SEQ ID NO: 47), which also corresponds to amino acids 231-234 of H19011_1_P8 (SEQ ID NO:48), and a fifth amino acid sequence being at least 70%, optionally at least 80%, preferably at least 85%, more preferably at least 90% and most preferably at least 95, 96, 97, 98 or 99% homologous to a polypeptide having the sequence CEYSDRWGDRAIERNVYLST (SEQ ID NO: 293) corresponding to amino acids 235-254 of H19011_1_P8 (SEQ ID NO:48), wherein said first amino acid sequence, bridging amino acid, second amino acid sequence, bridging amino acid, third amino acid sequence, bridging amino acid, fourth amino acid sequence and fifth amino acid sequence are contiguous and in a sequential order.

B. An isolated polypeptide encoding for an edge portion of H19011_1_P8 (SEQ ID NO:48), comprising an amino acid sequence being at least 70%, optionally at least about 80%, preferably at least about 85%, more preferably at least about 90% and most preferably at least about 95, 96, 97, 98 or 99% homologous to the sequence CEYSDRWGDRAIERNVYLST (SEQ ID NO: 293) of H19011_1_P8 (SEQ ID NO:48).

The localization of the variant protein was determined according to results from a number of different software programs and analyses, including analyses from SignalP and other specialized programs. The variant protein is believed to be located as follows with regard to the cell: membrane.

Variant protein H19011_1_P8 (SEQ ID NO:48) also has the following non-silent SNPs (Single Nucleotide Polymorphisms) as listed in Table 94, (given according to their positions on the amino acid sequence, with the alternative amino acids listed (SEQ ID NO:48)). An example of such a deduced sequence, with alternative amino-acids, that was produced (using part of the SNPs below), is given under the name H19011_1_P8_V1 (SEQ ID NO:49).

TABLE 94

| Amino acid mutations | |
|---|---|
| SNP positions on amino acid sequence | Alternative amino acids |
| 159 | G -> D |
| 161 | L -> V |
| 162 | G -> E |
| 202 | V -> D |
| 202 | V -> G |
| 230 | W -> C |

The variant protein has the following domains, as determined by using InterPro. The domains are described in Table 95:

TABLE 95

| InterPro domains | | |
|---|---|---|
| Domain description | Analysis type | Positions on protein |
| LISCH7 | HMMPfam | 186-234 |
| IG | SMART | 27-166 |

Variant protein H19011_1_P8 (SEQ ID NO:48) is encoded by the transcript H19011_1_T8 (SEQ ID NO:45), for which the coding portion starts at position 181 and ends at position 942. The transcript also has the following SNPs as listed in Table 96 (given according to their position on the nucleotide sequence, with the alternative nucleic acid listed).

TABLE 96

| Nucleic acid SNPs | |
|---|---|
| Polymorphism | SNP positions on nucleotide sequence |
| G -> A | 656 |
| C -> G | 661 |
| G -> A | 665 |
| T -> A | 785 |
| T -> G | 785 |
| G -> C | 870 |

The genomic structure of protein H19011_1_P8 (SEQ ID NO:48) (number of exons relevant to the extra-cellular region of the protein, the length of these exons, the frame of the codon in which the introns are inserted and the location of the protein features and domains in the gene structure) is characteristic to the ligands of the B7/co-stimulatory protein family, as given in table 97

TABLE 97

| genomic structure and protein features | | | |
|---|---|---|---|
| Exon number | Exon Length | Amino-Acids | Protein feature on exon |
| 1 | 46 | 1-15 | Signal Peptide |
| 2 | 333 | 16-126 | IgV domain |
| 3 | 120 | 127-166 | IgC2 domain |
| 4 | 57 | 167-185 | |
| 5 | 206 | 186-254 | Trans-membrane region |

Variant protein H19011_1_P9 (SEQ ID NO:50) according to the present invention has an amino acid sequence as encoded by transcript H19011_1_T9 (SEQ ID NO:46). Alignments to one or more previously published protein sequences are shown in FIG. 38B. A brief description of the relationship of the variant protein according to the present invention to each such aligned protein is as follows:

Comparison report between H19011_1_P9 (SEQ ID NO:50) and known proteins Q71H61_HUMAN and NP_955383 (SEQ ID NO: 47) (FIG. 38B):

A. An isolated chimeric polypeptide encoding for H19011_1_P9 (SEQ ID NO:50), comprising a first amino acid sequence being at least 90% homologous to

```
MDRVLLRWISLFWLTAMVEGLQVTVPDKKKVAMLFQPTVLRCHFSTSSHQP
AVVQWKFKSYCQDRMGESLGMSSTRAQSLSKRNLEWDPYLDCLDSRRTVRV
VASKQGSTVTLGDFYRGREITIVHDADLQIGKLMWGDSGLYYCIITTPDDL
EGKNE
```

corresponding to amino acids 1-158 of known proteins Q71H61_HUMAN and NP_955383 (SEQ ID NO: 47), which also corresponds to amino acids 1-158 of H19011_1_P9 (SEQ ID NO:50), a bridging amino acid G corresponding to amino acid 159 of H19011_1_P9 (SEQ ID NO:50), a second amino acid sequence being at least 90% homologous to S corresponding to amino acids 160-160 of known proteins Q71H61_HUMAN and NP_955383 (SEQ ID NO: 47), which also corresponds to amino acids 160-160 of H19011_1_P9 (SEQ ID NO:50), bridging amino acids LG corresponding to amino acid 161-162 of H19011_1_P9 (SEQ ID NO:50), a third amino acid sequence being at least 90% homologous to LLVL corresponding to amino acids 163-166 of known proteins Q71H61_HUMAN and NP_955383 (SEQ ID NO: 47), which also corresponds to amino acids 163-166 of H19011_1_P9 (SEQ ID NO:50), a fourth amino acid sequence being at least 90% homologous to EWVFVGLVLLGVFLFFVLVGICWCQCCPHSC-CCYVRCPCCPDSC corresponding to amino acids 186-229 of known proteins Q71H61_HUMAN and NP_955383 (SEQ ID NO: 47), which also corresponds to amino acids 167-210 of H19011_1_P9 (SEQ ID NO:50), a bridging amino acid W corresponding to amino acid 211 of H19011_1_P9 (SEQ ID NO:50), a fifth amino acid sequence being at least 90% homologous to CPQA corresponding to amino acids 231-234 of known proteins Q71H61_HUMAN and NP_955383 (SEQ ID NO: 47), which also corresponds to amino acids 212-215 of H19011_1_P9 (SEQ ID NO:50), and a sixth amino acid sequence being at least 70%, optionally at least 80%, preferably at least 85%, more preferably at least 90% and most preferably at least 95, 96, 97, 98 or 99% homologous to a polypeptide having the sequence CEYSDRWGDRAIERNVYLST (SEQ ID NO: 293) corresponding to amino acids 216-235 of H19011_1_P9 (SEQ ID NO:50), wherein said first amino acid sequence, bridging amino acid, second amino acid sequence, bridging amino acid, third amino acid sequence, fourth amino acid sequence, bridging amino acid, fifth amino acid sequence and sixth amino acid sequence are contiguous and in a sequential order.

B. An isolated chimeric polypeptide encoding for an edge portion of H19011_1_P9 (SEQ ID NO:50), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise LE, having a structure as follows: a sequence starting from any of amino acid numbers 166−x to 166; and ending at any of amino acid numbers 167+((n−2)−x), in which x varies from 0 to n−2.

C. An isolated polypeptide encoding for an edge portion of H19011_1_P9 (SEQ ID NO:50), comprising an amino acid sequence being at least 70%, optionally at least about 80%, preferably at least about 85%, more preferably at least about 90% and most preferably at least about 95, 96, 97, 98 or 99% homologous to the sequence CEYSDRWGDRAIERNVYLST (SEQ ID NO: 293) of H19011_1_P9 (SEQ ID NO:50).

The localization of the variant protein was determined according to results from a number of different software programs and analyses, including analyses from SignalP and other specialized programs. The variant protein is believed to be located as follows with regard to the cell: membrane.

Variant protein H19011_1_P9 (SEQ ID NO:50) also has the following non-silent SNPs (Single Nucleotide Polymorphisms) as listed in Table 98, (given according to their positions on the amino acid sequence, with the alternative amino acids listed (SEQ ID NO:50)).

TABLE 98

| Amino acid mutations | |
|---|---|
| SNP positions on amino acid sequence | Alternative amino acids |
| 159 | G -> D |
| 161 | L -> V |
| 162 | G -> E |
| 183 | V -> D |
| 183 | V -> G |
| 211 | W -> C |

Variant protein H19011_1_P9 (SEQ ID NO:50) is encoded by the transcript H19011_1_T9 (SEQ ID NO:46), for which the coding portion starts at position 181 and ends at position 885. The transcript also has the following SNPs as listed in Table 99 (given according to their position on the nucleotide sequence, with the alternative nucleic acid listed).

TABLE 99

| Nucleic acid SNPs | |
|---|---|
| Polymorphism | SNP positions on nucleotide sequence |
| G -> A | 656 |
| C -> G | 661 |
| G -> A | 665 |
| T -> A | 728 |

TABLE 99-continued

| Nucleic acid SNPs | |
|---|---|
| Polymorphism | SNP positions on nucleotide sequence |
| T -> G | 728 |
| G -> C | 813 |

As noted above, cluster H19011 features 5 segments, which were listed in Table 92 above. These segments are portions of nucleic acid sequences which are described herein separately because they are of particular interest. A description of each segment according to the present invention is now provided.

Segment cluster H19011_1_N13 (SEQ ID NO:129) according to the present invention is supported by 3 libraries. The number of libraries was determined as previously described. This segment can be found in the following transcripts: H19011_1_T8 (SEQ ID NO:45) and H19011_1_T9 (SEQ ID NO:46). Table 100 below describes the starting and ending position of this segment on each transcript.

TABLE 100

| Segment location on transcripts | | |
|---|---|---|
| Transcript name | Segment starting position | Segment ending position |
| H19011_1_T8 (SEQ ID NO: 45) | 884 | 1407 |
| H19011_1_T9 (SEQ ID NO: 46) | 827 | 1350 |

According to an optional embodiment of the present invention, short segments related to the above cluster are also provided. These segments are up to about 120 bp in length, and so are included in a separate description.

Segment cluster H19011_1_N8 (SEQ ID NO:130) according to the present invention is supported by 4 libraries. The number of libraries was determined as previously described. This segment can be found in the following transcripts: H19011_1_T8 (SEQ ID NO:45). Table 101 below describes the starting and ending position of this segment on each transcript.

TABLE 101

| Segment location on transcripts | | |
|---|---|---|
| Transcript name | Segment starting position | Segment ending position |
| H19011_1_T8 (SEQ ID NO: 45) | 680 | 736 |

Segment cluster H19011_1_N10 (SEQ ID NO:131) according to the present invention is supported by 5 libraries. The number of libraries was determined as previously described. This segment can be found in the following transcripts: H19011_1_T8 (SEQ ID NO:45) and H19011_1_T9 (SEQ ID NO:46). Table 102 below describes the starting and ending position of this segment on each transcript.

TABLE 102

| Segment location on transcripts | | |
|---|---|---|
| Transcript name | Segment starting position | Segment ending position |
| H19011_1_T8 (SEQ ID NO: 45) | 737 | 797 |
| H19011_1_T9 (SEQ ID NO: 46) | 680 | 740 |

Segment cluster H19011_1_N11 (SEQ ID NO:132) according to the present invention is supported by 3 libraries. The number of libraries was determined as previously described. This segment can be found in the following transcripts: H19011_1_T8 (SEQ ID NO:45) and H19011_1_T9 (SEQ ID NO:46). Table 103 below describes the starting and ending position of this segment on each transcript.

TABLE 103

| Segment location on transcripts | | |
|---|---|---|
| Transcript name | Segment starting position | Segment ending position |
| H19011_1_T8 (SEQ ID NO: 45) | 798 | 863 |
| H19011_1_T9 (SEQ ID NO: 46) | 741 | 806 |

Segment cluster H19011_1_N12 (SEQ ID NO:133) according to the present invention is supported by 5 libraries. The number of libraries was determined as previously described. This segment can be found in the following transcripts: H19011_1_T8 (SEQ ID NO:45) and H19011_1_T9 (SEQ ID NO:46). Table 104 below describes the starting and ending position of this segment on each transcript.

TABLE 104

| Segment location on transcripts | | |
|---|---|---|
| Transcript name | Segment starting position | Segment ending position |
| H19011_1_T8 (SEQ ID NO: 45) | 864 | 883 |
| H19011_1_T9 (SEQ ID NO: 46) | 807 | 826 |

Expression of C1ORF32, chromosome 1 open reading frame 32, H19011 transcripts which are detectable by amplicon as depicted in sequence name H19011_seg13F2R2 (SEQ ID NO: 235) in normal and cancerous Colon tissues, in normal and cancerous Lung tissues and in different normal tissues Expression of C1ORF32, chromosome 1 open reading frame 32, transcripts detectable by or according to seg13-H19011_seg13F2R2 (SEQ ID NO: 235) amplicon and primers H19011_seg13F2 (SEQ ID NO: 233) and H19011_seg13R2 (SEQ ID NO: 234) was measured by real time PCR on colon panel, lung panel and normal panel. The samples used are detailed in Table 5, Table 3 and Table 2 above, respectively. For each RT sample, the expression of the above amplicon was normalized to the normalization factor calculated from the expression of several house keeping genes as described in Example 1.

Colon panel—The normalized quantity of each RT sample was then divided by the median of the quantities of the normal samples (sample numbers 42-70, Table 5 above). Then the reciprocal of this ratio was calculated, to obtain a value of fold down-regulation for each sample relative to median of the normal samples.

Figure 39:
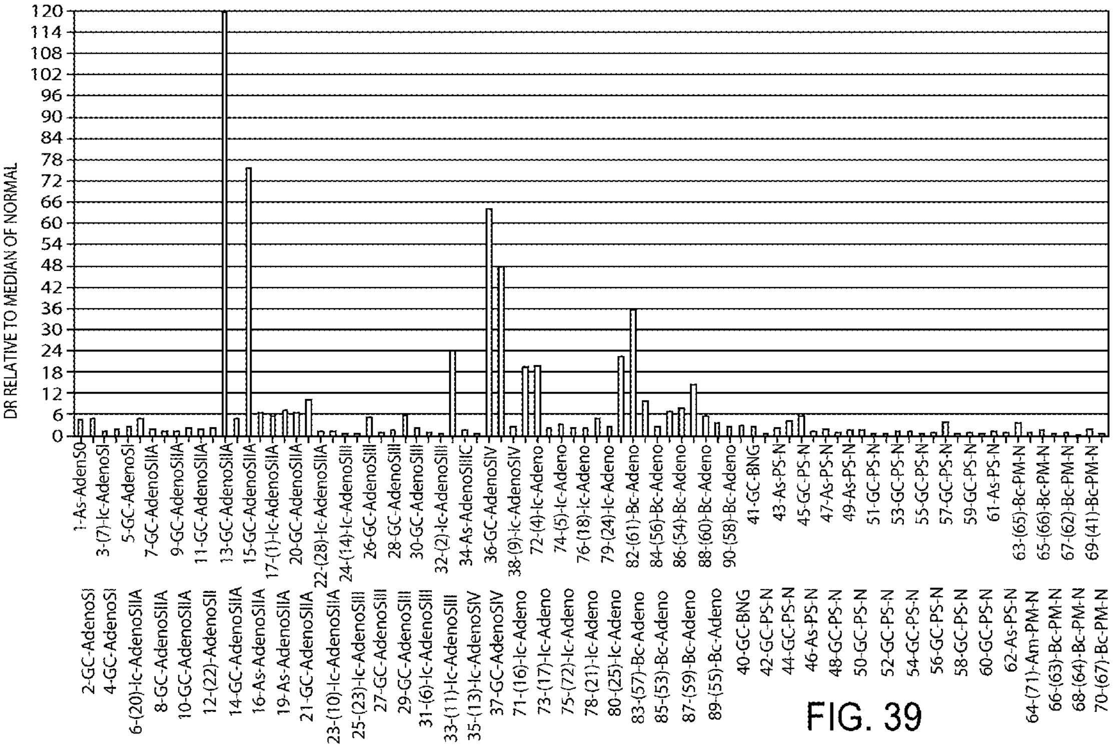
FIG. 39 presents a histogram showing expression of C1ORF32, chromosome 1 open reading frame 32, H19011 transcripts which are detectable by amplicon as depicted in sequence name H19011_seg13F2R2 (SEQ ID NO: 235) in normal and cancerous Colon tissues.

FIG. 39 is a histogram showing down regulation of the above-indicated C1ORF32 transcripts in cancerous Colon samples relative to the normal samples.

As is evident from FIG. 39, the expression of C1ORF32 transcripts detectable by the above amplicon in cancer samples was significantly lower than in the non-cancerous samples (sample numbers 42-70, Table 5 above). Notably down regulation of at least 6 fold was found in 17 out of 55 adenocarcinoma samples.

Statistical analysis was applied to verify the significance of these results, as described below. The P value for the difference in the expression levels of C1ORF32 transcripts detectable by the above amplicon in Colon cancer samples versus the normal tissue samples was determined by T test as 9.36e-004.

Threshold of 6 fold down regulation was found to differentiate between cancer and normal samples with P value of 2.67e-004 as checked by exact Fisher test.

The above values demonstrate statistical significance of the results.

Lung panel—The normalized quantity of each RT sample was then divided by the median of the quantities of the normal samples (sample numbers 51-64 and 69-70, Table 3 above), to obtain a value of fold up-regulation for each sample relative to median of the normal samples.

Figure 40:
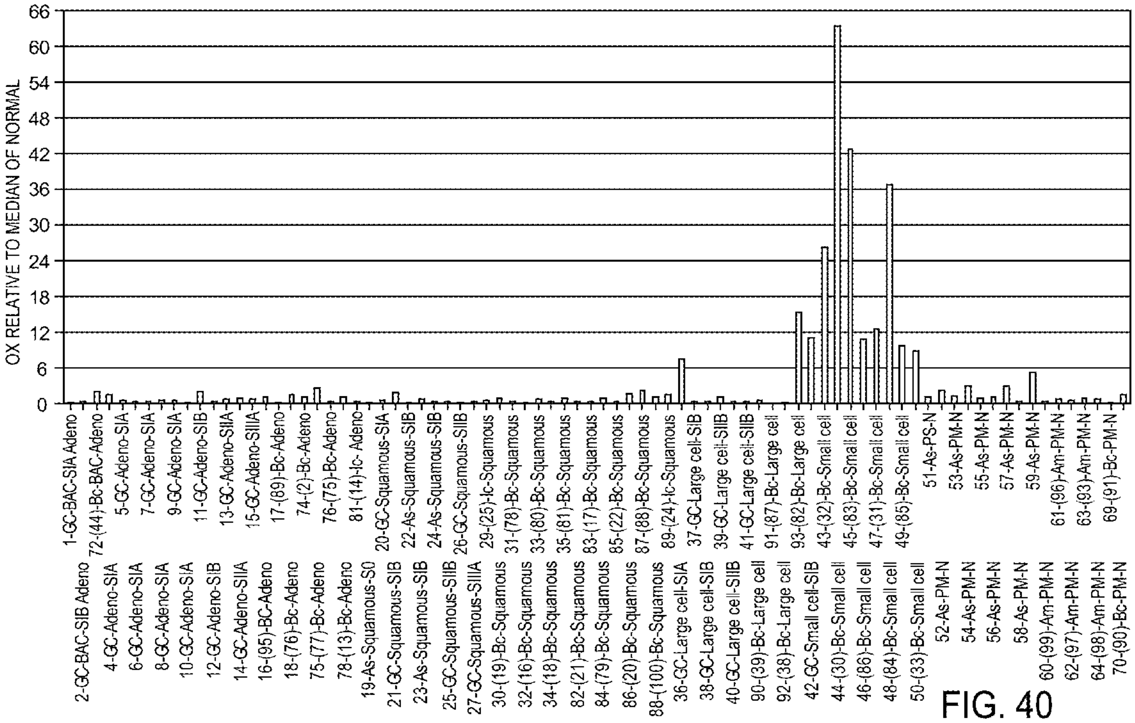
FIG. 40 presents a histogram showing expression of C1ORF32, chromosome 1 open reading frame 32, H19011 transcripts which are detectable by amplicon as depicted in sequence name H19011_seg13F2R2 (SEQ ID NO: 235) in normal and cancerous lung tissues.

FIG. 40 is a histogram showing over expression of the above-indicated C1ORF32 transcripts in cancerous Lung samples relative to the normal samples.

As is evident from FIG. 40, the expression of C1ORF32 transcripts detectable by the above amplicon in small cell carcinoma samples was significantly higher than in the non-cancerous samples (sample numbers 51-64 and 69-70, Table 3 above). Notably an over-expression of at least 6 fold was found in 9 out of 9 small cell carcinoma samples.

Statistical analysis was applied to verify the significance of these results, as described below.

The P value for the difference in the expression levels of C1ORF32 transcripts detectable by the above amplicon in Lung small cell carcinoma samples versus the normal tissue samples was determined by T test as 3.43e-003.

Threshold of 6 fold over expression was found to differentiate between small cell carcinoma and normal samples with P value of 4.89e-007 as checked by exact Fisher test.

The above values demonstrate statistical significance of the results.

Figure 41A:
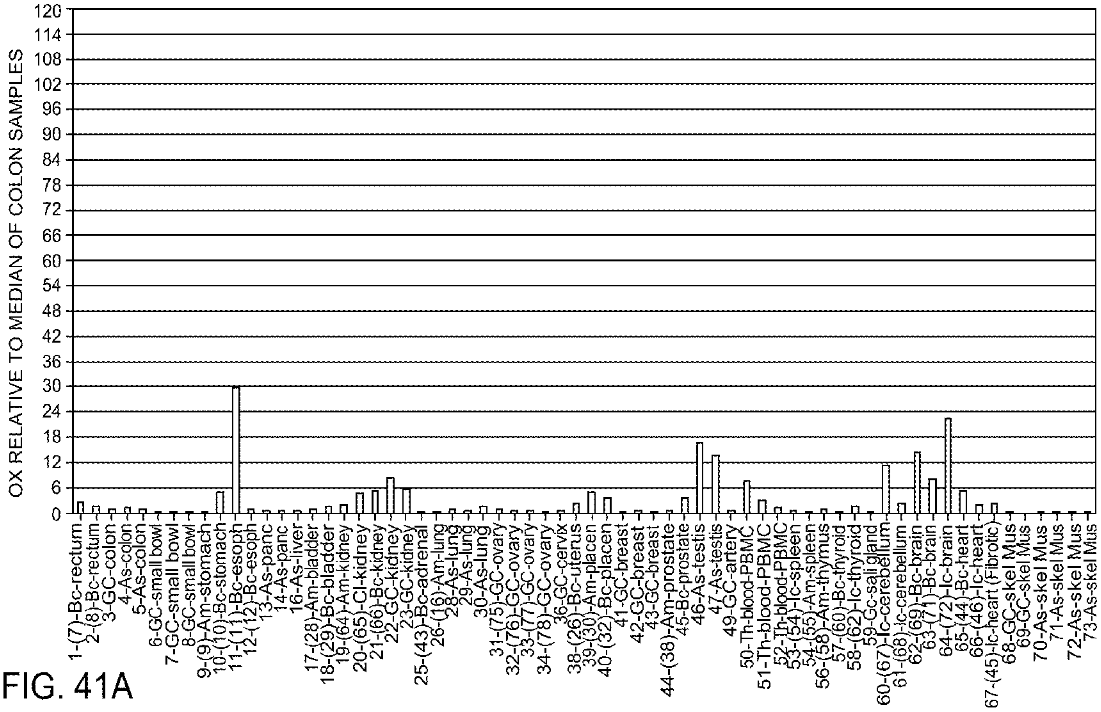
FIGS. 41A-41B present a histogram showing expression of C1ORF32, chromosome 1 open reading frame 32, H19011 transcripts which are detectable by amplicon as depicted in sequence name H19011_seg13F2R2 (SEQ ID NO: 235) in various normal tissues.
Figure 41B:
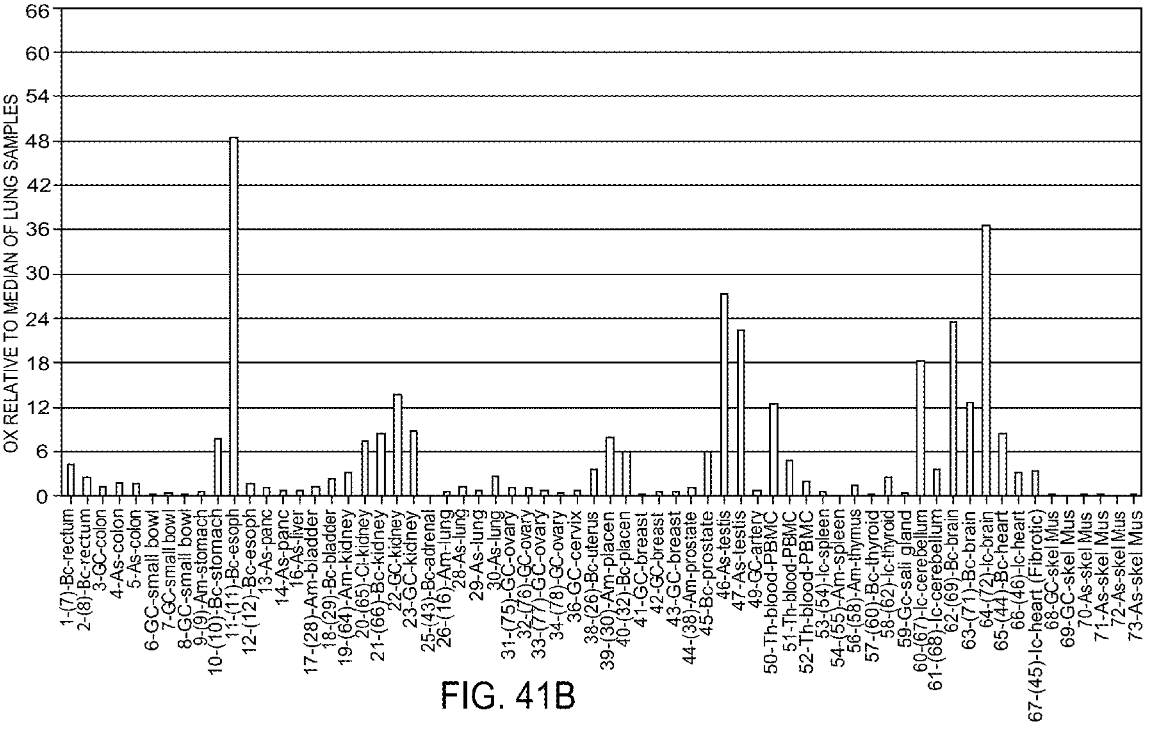

Normal panel—The normalized quantity of each RT sample was then divided by the median of the quantities of the colon samples (sample numbers 3, 4 and 5, Table 2 above), to obtain a value of relative expression of each sample relative to median of the colon samples, as shown in FIG. 41A. The normalized quantity of each RT sample was then divided by the median of the quantities of the lung samples (sample numbers 26, 28, 29 and 30, Table 2 above), to obtain a value of relative expression of each sample relative to median of the lung samples, as shown in FIG. 41B.

Primer pairs are also optionally and preferably encompassed within the present invention; for example, for the above experiment, the following primer pair was used as a non-limiting illustrative example only of a suitable primer pair: H19011_seg13F2 (SEQ ID NO: 233) forward primer; and H19011_seg13R2 (SEQ ID NO: 234) reverse primer.

The present invention also preferably encompasses any amplicon obtained through the use of any suitable primer pair; for example, for the above experiment, the following amplicon was obtained as a non-limiting illustrative example only of a suitable amplicon: H19011_seg13F2R2 (SEQ ID NO: 235).

```
Forward Primer >H19011_seg13F2 (SEQ ID NO: 233):
GTGAGTACAGTGACCGCTGGG

Reverse Primer >H19011_seg13R2 (SEQ ID NO: 234):
GGAGAAGAGTCTGGAATGACCAA

Amplicon >H19011_seg13F2R2 (SEQ ID NO: 235)
GTGAGTACAGTGACCGCTGGGGAGACAGAGCGATCGAGAGAAATGTCTAC

CTCTCTACCTGACAGCTGTGTGCGCTGGGTTCCTCCTCCACCTCCTGTCC

TGCCACCCCCAAGATTGGTCATTCCAGACTCTTCTCC
```

Expression of C1ORF32, chromosome 1 open reading frame 32, H19011 transcripts which are detectable by amplicon as depicted in sequence name H19011_seg8-13F1R1 (SEQ ID NO: 238) in normal and cancerous Lung tissues Expression of C1ORF32, chromosome 1 open reading frame 32, transcripts detectable by or according to seg8-13F1R1-H19011_seg8-13F1R1 (SEQ ID NO: 238) amplicon and primers H19011_seg8-13F1 (SEQ ID NO: 236) and H19011_seg8-13R1 (SEQ ID NO: 237) was measured by real time PCR on lung panel. The samples used are detailed in Table 3 above. Samples that showed no detection of the amplicon (samples no. 1, 2, 4-10, 12-27, 29-35, 37-41, 51-64 and 69-70, Table 3) were assigned Ct value of 41 and were calculated accordingly. These samples showed a primer-dimer product with a characteristic dissociation curve and a significantly lower TM (this artefactual product was identified by its appearance in the negative control without RT sample). For each RT sample, the expression of the above amplicon was normalized to the normalization factor calculated from the expression of several house keeping genes as described in Example 1. The normalized quantity of each RT sample was then divided by the median of the quantities of the normal samples (sample numbers 51-64 and 69-70, Table 3 above), to obtain a value of fold up-regulation for each sample relative to median of the normal samples.

Figure 42:
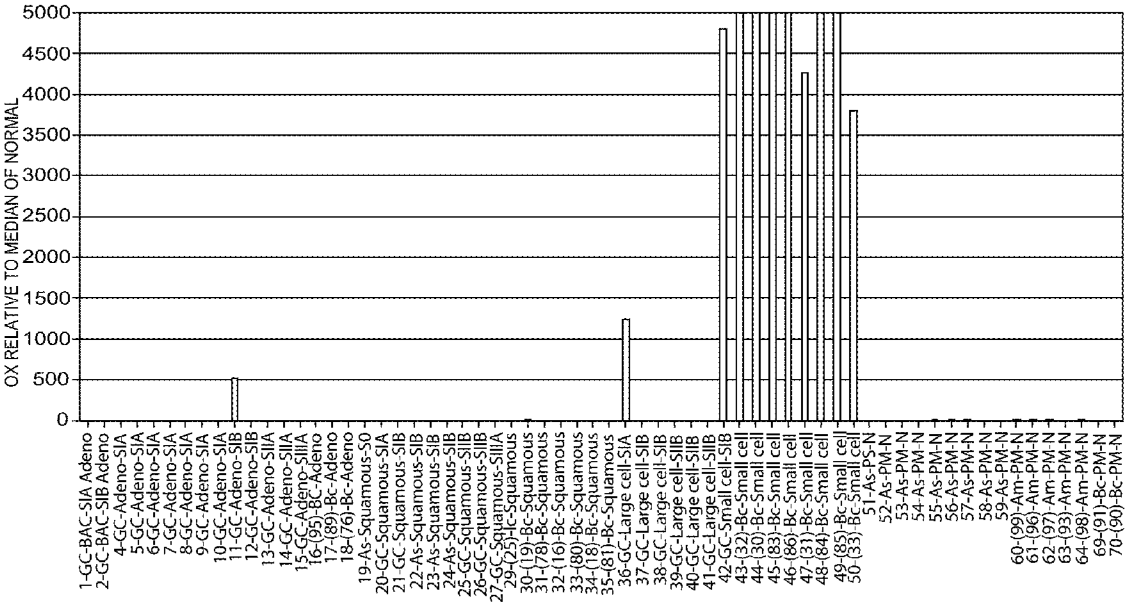
FIG. 42 presents a histogram showing expression of C1ORF32, chromosome 1 open reading frame 32, H19011 transcripts which are detectable by amplicon as depicted in sequence name H19011_seg8-13F1R1 (SEQ ID NO: 238) in normal and cancerous lung tissues.

FIG. 42 is a histogram showing over expression of the above-indicated C1ORF32 transcripts in cancerous Lung samples relative to the normal samples.

As is evident from FIG. 42, the expression of C1ORF32 transcripts detectable by the above amplicon in small cell carcinoma samples was significantly higher than in the non-cancerous samples (sample numbers 51-64 and 69-70, Table 3 above). Notably an over-expression of at least 500 fold was found in 9 out of 9 small cell carcinoma samples.

Statistical analysis was applied to verify the significance of these results, as described below. The P value for the difference in the expression levels of C1ORF32 transcripts detectable by the above amplicon in Lung small cell carcinoma samples versus the normal tissue samples was determined by T test as 6.70e-003.

Threshold of 500 fold over expression was found to differentiate between small cell carcinoma and normal samples with P value of 4.89e-007 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: H19011_seg8-13F1 (SEQ ID NO: 236) forward primer; and H19011_seg8-13R1 (SEQ ID NO: 237) reverse primer.

The present invention also preferably encompasses any amplicon obtained through the use of any suitable primer pair; for example, for the above experiment, the following amplicon was obtained as a non-limiting illustrative example only of a suitable amplicon: H19011_seg8-13F1R1 (SEQ ID NO: 238).

```
Forward Primer >H19011_seg8-13F1 (SEQ ID NO: 236):
GCCCAGTTTTGCTGTGGAGA

Reverse Primer >H19011_seg8-13R1 (SEQ ID NO: 237):
GGTAGACATTTCTCTCGATCGCTC

Amplicon >H19011_seg8-13F1R1
                                        (SEQ ID NO: 238)
GCCCAGTTTTGCTGTGGAGATTATGCCAGAGTGGGTGTTTGTTGGCCTGG

TGCTCCTGGGCGTCTTCCTCTTCTTCGTCCTGGTGGGGATCTGCTGGTGC

CAGTGCTGCCCTCACAGCTGCTGCTGCTATGTCCGCTGCCCATGCTGCCC

AGATTCCTGCTGGTGCCCTCAAGCCTGTGAGTACAGTGACCGCTGGGGAG

ACAGAGCGATCGAGAGAAATGTCTACC
```

Expression of C1ORF32, chromosome 1 open reading frame 32, H19011 transcripts which are detectable by amplicon as depicted in sequence name H19011_junc8-10seg13 (SEQ ID NO: 241) in normal and cancerous lung tissues, in normal and cancerous colon tissues, in different normal tissues and in the blood-specific panel.

Expression of C1ORF32 transcripts detectable by or according to junc8-10seg13-H19011_junc8-10seg13 (SEQ ID NO: 241) amplicon and primers H19011_junc8-10seg13F1 (SEQ ID NO: 239) and H19011_junc8-10seg13R1 (SEQ ID NO: 240) was measured by real time PCR lung panel, colon panel, normal panel and blood panel. The samples used are detailed in Table 3, Table 5, Table 2 and Table 1 above, respectively. For each RT sample, the expression of the above amplicon was normalized to the normalization factor calculated from the expression of several house keeping genes as described in Example 1.

For lung panel—Non-detected sample (sample no. 69, Table 3) was assigned Ct value of 41 and was calculated accordingly. The normalized quantity of each RT sample was then divided by the median of the quantities of the normal samples (sample numbers 51, 53, 54, 56, 57, 59, 61, 62, 64 and 70, Table 3 above), to obtain a value of fold up-regulation for each sample relative to median of the normal samples.

Figure 43:
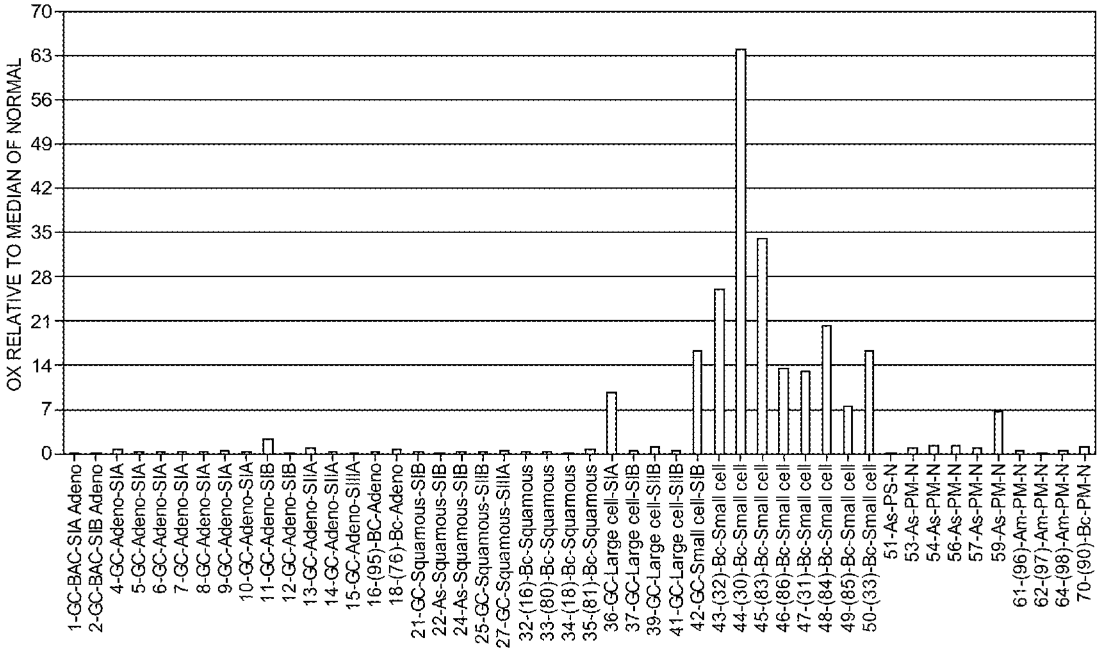
FIG. 43 presents a histogram showing expression of C1ORF32, chromosome 1 open reading frame 32, H19011 transcripts which are detectable by amplicon as depicted in sequence name H19011_junc8-10seg13 (SEQ ID NO: 241) in normal and cancerous lung tissues.

FIG. 43 is a histogram showing over expression of the above-indicated C1ORF32 transcripts in cancerous Lung samples relative to the normal samples.

As is evident from FIG. 43, the expression of C1ORF32 transcripts detectable by the above amplicon in small cell carcinoma samples was significantly higher than in the non-cancerous samples (sample numbers 51, 53, 54, 56, 57, 59, 61, 62, 64 and 70, Table 3 above). Notably an over-expression of at least 7 fold was found in 9 out of 9 small cell carcinoma samples.

Statistical analysis was applied to verify the significance of these results, as described below.

The P value for the difference in the expression levels of C1ORF32 transcripts detectable by the above amplicon in Lung small cell carcinoma samples versus the normal tissue samples was determined by T test as 2.34e-003.

Threshold of 7 fold over expression was found to differentiate between small cell carcinoma and normal samples with P value of 1.08e-005 as checked by exact Fisher test.

The above values demonstrate statistical significance of the results.

For colon panel—Non-detected sample (sample no. 79, Table 5) was assigned Ct value of 41 and was calculated accordingly. The normalized quantity of each RT sample was then divided by the median of the quantities of the normal samples (sample numbers 42-62 and 65-70, Table 5 above). Then the reciprocal of this ratio was calculated, to obtain a value of fold down-regulation for each sample relative to median of the normal samples.

Figure 44:
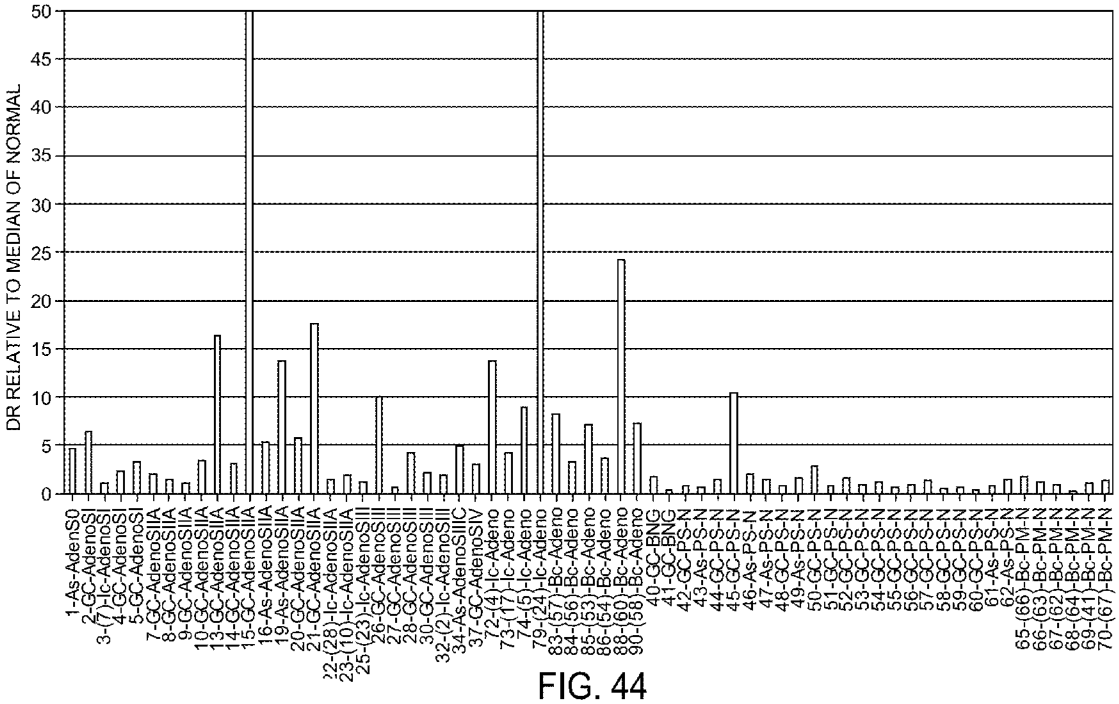
FIG. 44 presents a histogram showing expression of C1ORF32, chromosome 1 open reading frame 32, H19011 transcripts which are detectable by amplicon as depicted in sequence name H19011_junc8-10seg13 (SEQ ID NO: 241) in normal and cancerous colon tissues.

FIG. 44 is a histogram showing down regulation of the above-indicated C1ORF32 transcripts in cancerous colon samples relative to the normal samples.

As is evident from FIG. 44, the expression of C1ORF32 transcripts detectable by the above amplicon in cancer samples was significantly lower than in the non-cancerous samples (sample numbers 42-62 and 65-70, Table 5 above). Notably down regulation of at least 5 fold was found in 15 out of 36 adenocarcinoma samples.

Statistical analysis was applied to verify the significance of these results, as described below. Threshold of 5 fold down regulation was found to differentiate between cancer and normal samples with P value of 4.29e-004 as checked by exact Fisher test.

The above values demonstrate statistical significance of the results.

Figure 45A:
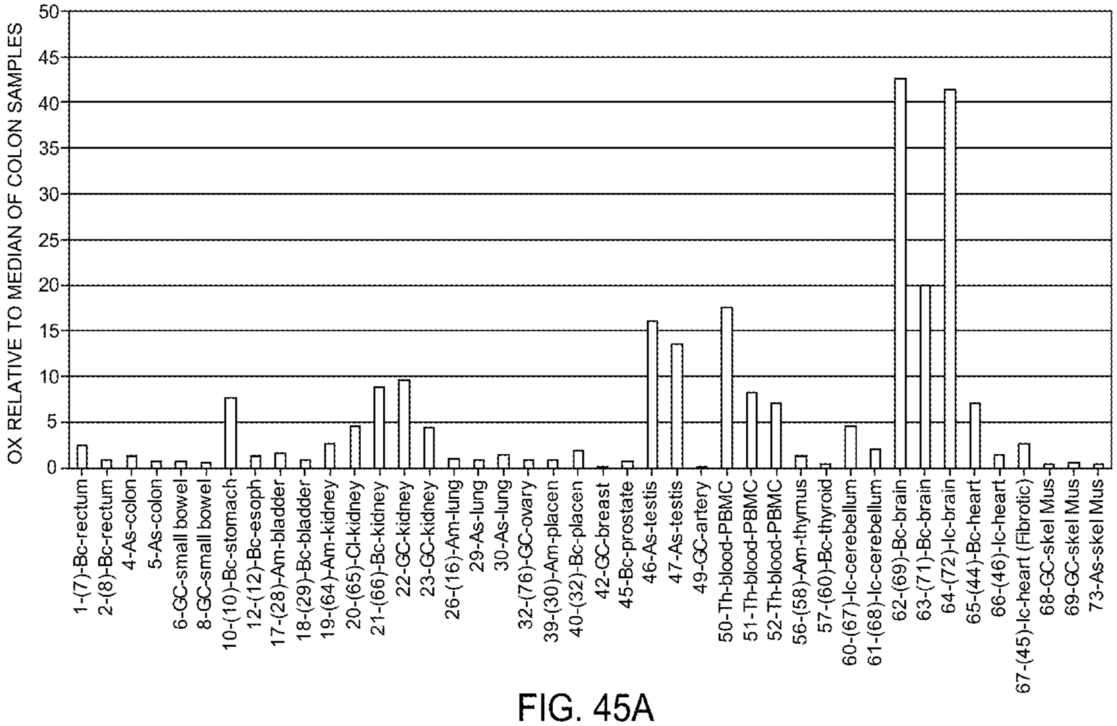
FIGS. 45A-45B presents a histogram showing expression of C1ORF32, chromosome 1 open reading frame 32, H19011 transcripts which are detectable by amplicon as depicted in sequence name H19011_junc8-10seg13 (SEQ ID NO: 241) in various normal tissues.
Figure 45B:
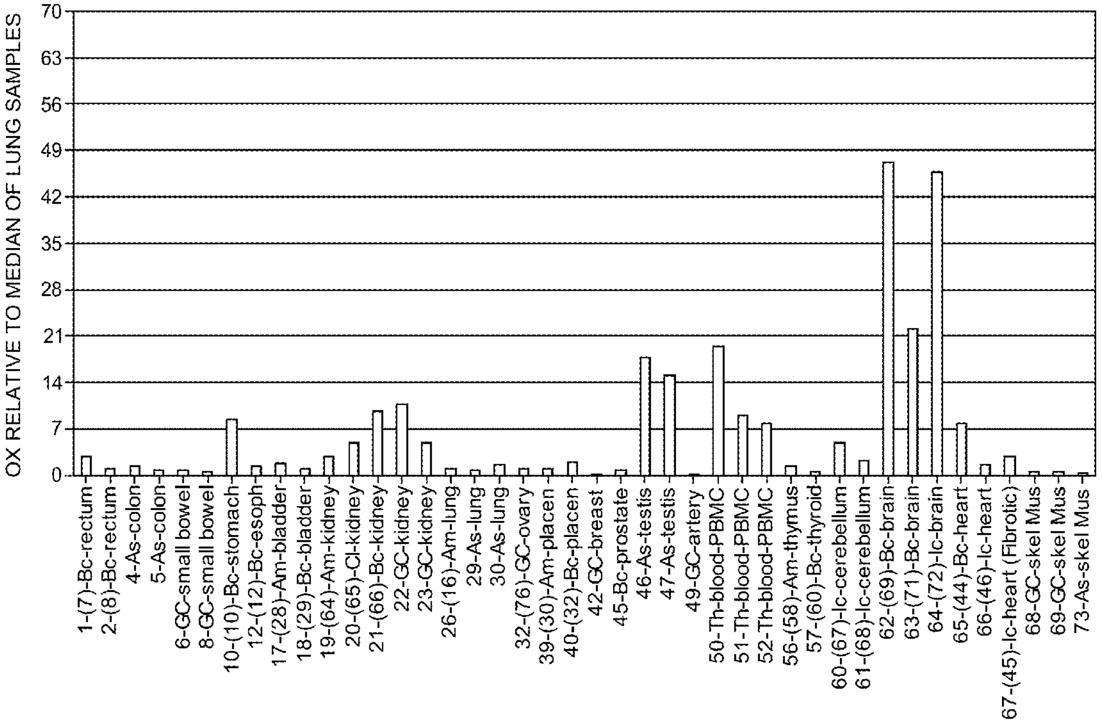

For normal panel—Non-detected samples (samples no. 42 and 49, Table 2) were assigned Ct value of 41 and were calculated accordingly. The normalized quantity of each RT sample was then divided by the median of the quantities of the colon samples (sample numbers 4 and 5, Table 2 above), to obtain a value of relative expression of each sample relative to median of the colon samples, as shown in FIG. 45A. The normalized quantity of each RT sample was then divided by the median of the quantities of the lung samples (sample numbers 26, 29 and 30, Table 2 above), to obtain a value of relative expression of each sample relative to median of the lung samples, as shown in FIG. 45B.

For blood panel—The normalized quantity of each RT sample was then divided by the median of the quantities of the kidney normal samples (sample numbers 65-67, Table 1 above), to obtain a value of relative expression of each sample relative to median of the kidney normal samples.

Figure 46:
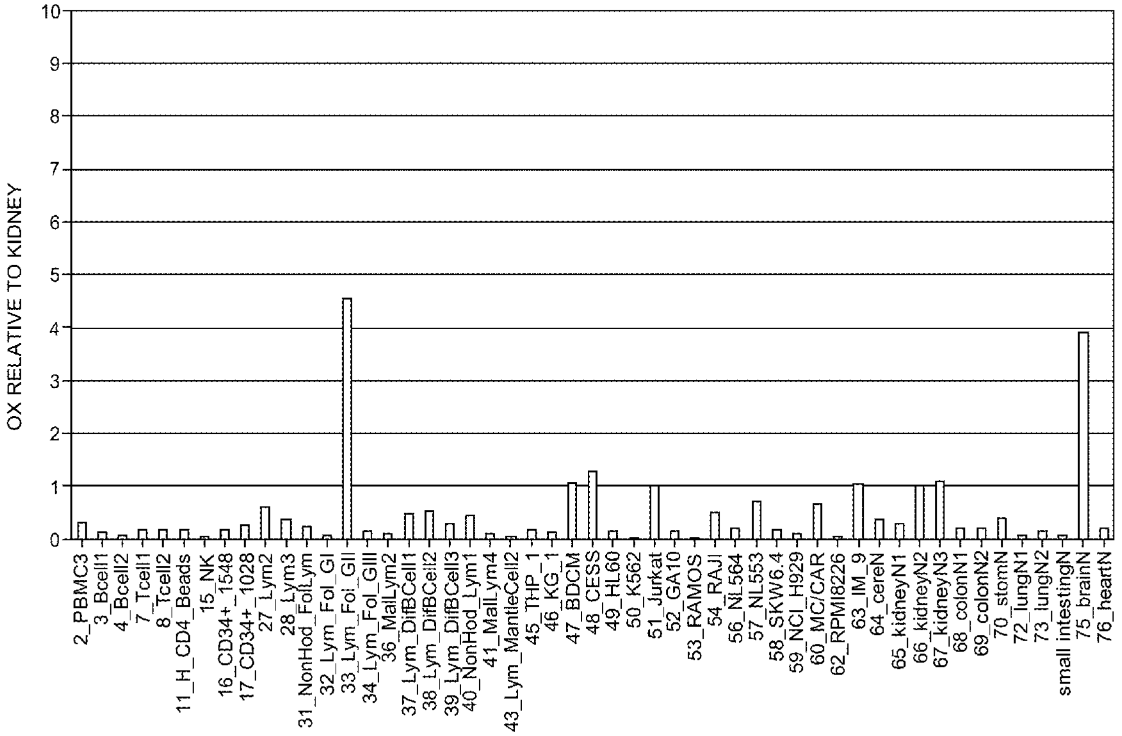
FIG. 46 presents a histogram showing expression of C1ORF32, chromosome 1 open reading frame 32, H19011 transcripts which are detectable by amplicon as depicted in sequence name H19011_junc8-10seg13 (SEQ ID NO: 241) in blood-specific panel.

The results of this analysis are depicted in the histogram in FIG. 46. Expression of the above-indicated C1ORF32 transcript is high in one lymphoma sample (sample no. 33, Table 1) but in normal brain sample too.

Primer pairs are also optionally and preferably encompassed within the present invention; for example, for the above experiment, the following primer pair was used as a non-limiting illustrative example only of a suitable primer pair: H19011_junc8-10seg13F1 (SEQ ID NO: 239) forward primer; and H19011_junc8-10seg13R1 (SEQ ID NO: 240) reverse primer.

The present invention also preferably encompasses any amplicon obtained through the use of any suitable primer pair; for example, for the above experiment, the following amplicon was obtained as a non-limiting illustrative example only of a suitable amplicon: H19011_junc8-10seg13F1R1 (SEQ ID NO: 241).

```
Forward Primer >H19011_junc8-10seg13F1
                                        (SEQ ID NO: 239)
TGTGGAGATTATGCCAGAGTGG

Reverse Primer >H19011 junc8-10seg13R1
                                        (SEQ ID NO: 240)
GACATTTCTCTCGATCGCTCTGT

Amplicon >H19011 junc8-10seg13F1R1
                                        (SEQ ID NO: 241)
TGTGGAGATTATGCCAGAGTGGGTGTTTGTTGGCCTGGTGCTCCTGGGCG

TCTTCCTCTTCTTCGTCCTGGTGGGGATCTGCTGGTGCCAGTGCTGCCCT

CACAGCTGCTGCTGCTATGTCCGCTGCCCATGCTGCCCAGATTCCTGCTG

GTGCCCTCAAGCCTGTGAGTACAGTGACCGCTGGGGAGACAGAGCGATCG

AGAGAAATGTC
```

Expression of C1ORF32, chromosome 1 open reading frame 32, H19011 transcripts which are detectable by amplicon as depicted in sequence name H19011_junc6-10 (SEQ ID NO: 244) in normal and cancerous lung tissues and in normal and cancerous Colon tissues Expression of C1ORF32 transcripts detectable by or according to junc6-10-H19011_junc6-10F1R1 (SEQ ID NO: 244) amplicon and primers H19011_junc6-10F1 (SEQ ID NO: 242) and H19011_junc6-10R1 (SEQ ID NO: 243) was measured by real time PCR on lung panel and colon panel. The samples used are detailed in Table 3 and Table 5 above, respectively. For each RT sample, the expression of the above amplicon was normalized to the normalization factor calculated from the expression of several house keeping genes as described in Example 1.

Lung panel—The normalized quantity of each RT sample was then divided by the median of the quantities of the normal samples (sample numbers 51-64, 69 and 70, Table 3 above). Then the reciprocal of this ratio was calculated, to obtain a value of fold down-regulation for each sample relative to median of the normal samples.

Figure 47:
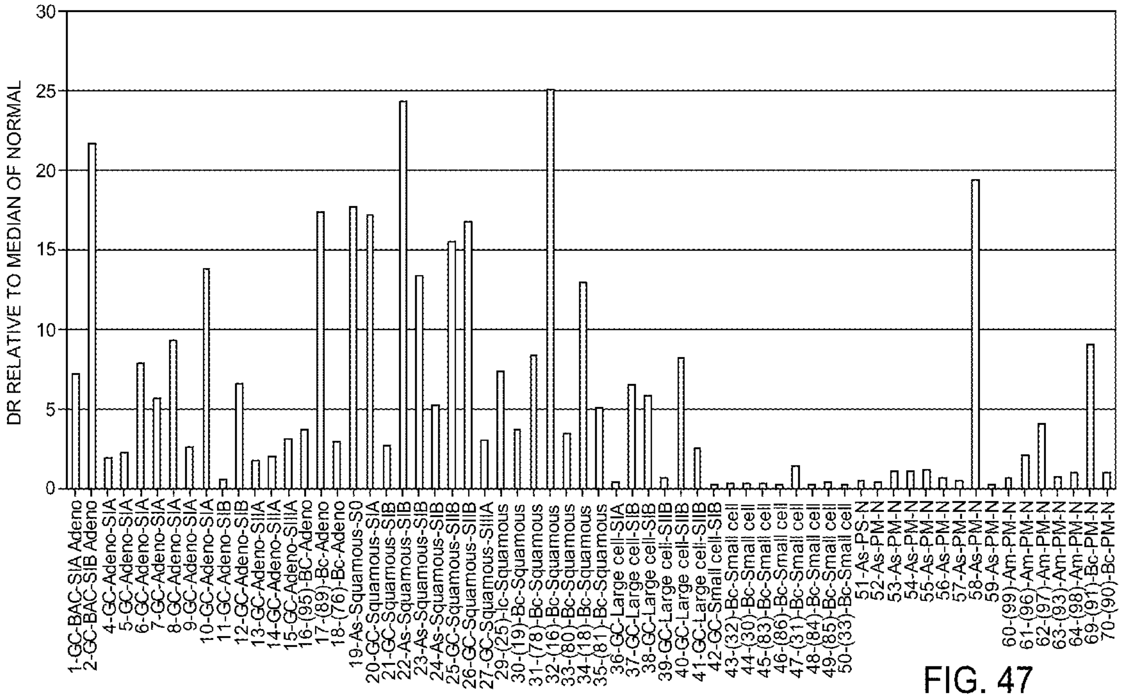
FIG. 47 presents a histogram showing expression of C1ORF32, chromosome 1 open reading frame 32, H19011 transcripts which are detectable by amplicon as depicted in sequence name H19011_junc6-10F1R1 (SEQ ID NO: 244) in normal and cancerous lung tissues.

FIG. 47 is a histogram showing down regulation of the above-indicated C1ORF32 transcripts in cancerous Lung samples relative to the normal samples.

As is evident from FIG. 47, the expression of C1ORF32 transcripts detectable by the above amplicon in non-small cell carcinoma samples, adenocarcinoma and squamous cell carcinoma was significantly lower than in the non-cancerous samples (sample numbers 51-64, 69 and 70, Table 3 above). Notably down regulation of at least 5 fold was found in 23 out of 39 non-small cell carcinoma samples especially in 8 out of 17 adenocarcinoma samples and in 12 out of 16 squamous cell carcinoma samples.

Statistical analysis was applied to verify the significance of these results, as described below. The P value for the difference in the expression levels of C1ORF32 transcripts detectable by the above amplicon lung non-small cell carcinoma, lung adenocarcinoma and lung squamous cell carcinoma samples, versus the normal tissue samples was determined by T test as 1.18e-003, 2.87e-002 and 3.55e-004, respectively.

Threshold of 5 fold down regulation was found to differentiate between lung non-small cell carcinoma, lung adenocarcinoma and lung squamous cell carcinoma samples and normal samples with P value of 1.59e-003, 3.54e-002 and 4.78e-004, respectively, as checked by exact Fisher test.

The above values demonstrate statistical significance of the results.

Colon panel—The normalized quantity of each RT sample was then divided by the median of the quantities of the normal samples (sample numbers 42-70, Table 5 above). Then the reciprocal of this ratio was calculated, to obtain a value of fold down-regulation for each sample relative to median of the normal samples.

Figure 48:
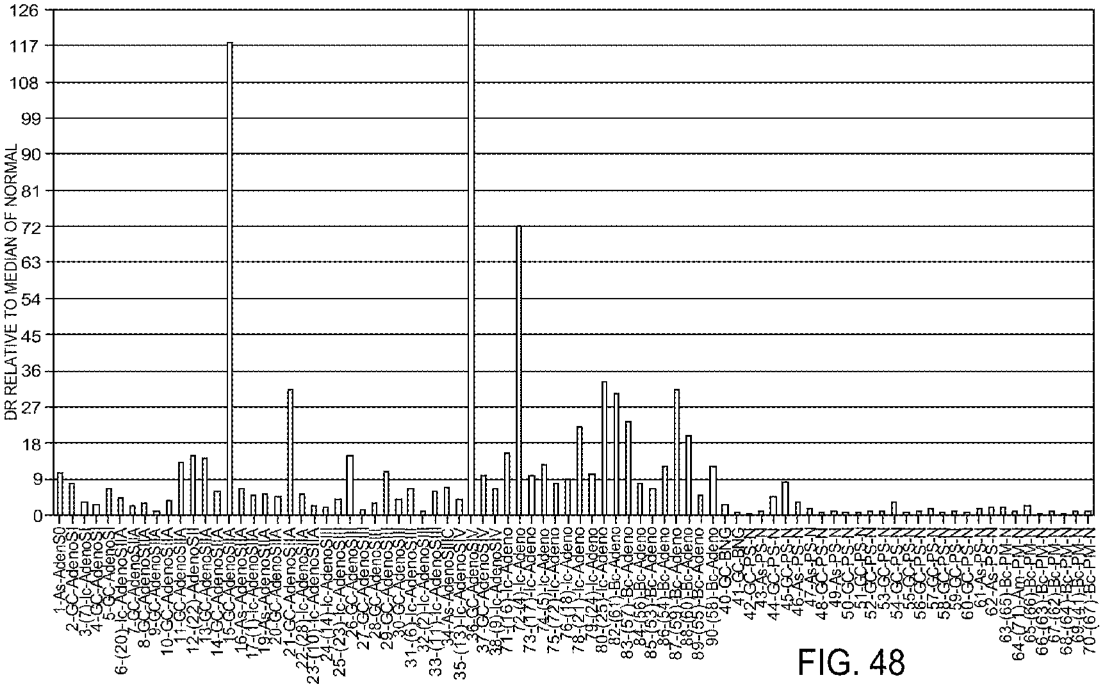
FIG. 48 presents a histogram showing expression of C1ORF32, chromosome 1 open reading frame 32, H19011 transcripts which are detectable by amplicon as depicted in sequence name H19011_junc6-10F1R1 (SEQ ID NO: 244) in normal and cancerous colon tissues.

FIG. 48 is a histogram showing down regulation of the above-indicated C1ORF32 transcripts in cancerous Colon samples relative to the normal samples.

As is evident from FIG. 48, the expression of C1ORF32 transcripts detectable by the above amplicon in cancer samples was significantly lower than in the non-cancerous samples (sample numbers 42-70, Table 5 above). Notably down regulation of at least 9 fold was found in 23 out of 55 adenocarcinoma samples.

Statistical analysis was applied to verify the significance of these results, as described below.

Threshold of 9 fold down regulation was found to differentiate between cancer and normal samples with P value of 7.39e-006 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: H19011_junc6-10F1 (SEQ ID NO: 242) forward primer; and H19011_junc6-10R1 (SEQ ID NO: 243) reverse primer.

The present invention also preferably encompasses any amplicon obtained through the use of any suitable primer pair; for example, for the above experiment, the following amplicon was obtained as a non-limiting illustrative example only of a suitable amplicon: H19011_junc6-10F1R1 (SEQ ID NO: 244).

```
Forward Primer >H19011_junc6-10F1
                                     (SEQ ID NO: 242)
ACTCTATTACTGTATTATCACCACCCCAG

Reverse Primer >H19011 junc6-10R1
                                     (SEQ ID NO: 243)
CCAACAAACACCCACTCCAAC

Amplicon >H19011 junc6-10F1R1
                                     (SEQ ID NO: 244)
ACTCTATTACTGTATTATCACCACCCCAGATGACCTGGAGGGGAAAAA

TGAGGGCTCACTGGGACTGCTGGTGTTGGAGTGGGTGTTTGTTGG
```

Example 7

Description for Cluster R31375

The present invention relates to a specific antigen FXYD3 and related diagnostic and therapeutics based thereon.

According to the present invention, Cluster R31375 (internal ID 72360301) features 19 transcripts and 4 segments of interest, the names for which are given in Tables 105 and 106, respectively. The selected protein variants are given in table 107.

TABLE 105

| Transcripts of interest<br>Transcript Name |
|---|
| R31375_T0 (SEQ ID NO: 51) |
| R31375_T1 (SEQ ID NO: 52) |
| R31375_T2 (SEQ ID NO: 53) |
| R31375_T3 (SEQ ID NO: 54) |
| R31375_T4 (SEQ ID NO: 55) |
| R31375_T5 (SEQ ID NO: 56) |
| R31375_T6 (SEQ ID NO: 57) |
| R31375_T7 (SEQ ID NO: 58) |
| R31375_T8 (SEQ ID NO: 59) |
| R31375_T9 (SEQ ID NO: 60) |
| R31375_T10 (SEQ ID NO: 61) |
| R31375_T11 (SEQ ID NO: 62) |
| R31375_T12 (SEQ ID NO: 63) |
| R31375_T13 (SEQ ID NO: 64) |
| R31375_T19 (SEQ ID NO: 65) |
| R31375_T25 (SEQ ID NO: 66) |
| R31375_T26 (SEQ ID NO: 67) |
| R31375_T29 (SEQ ID NO: 68) |
| R31375_T39 (SEQ ID NO: 69) |

TABLE 106

| Segments of interest<br>Segment Name |
|---|
| R31375_N30 (SEQ ID NO: 134) |
| R31375_N33 (SEQ ID NO: 135) |
| R31375_N34 (SEQ ID NO: 136) |
| R31375_N37 (SEQ ID NO: 137) |

TABLE 107

| Proteins of interest | |
|---|---|
| Protein Name | Corresponding Transcripts |
| R31375_P0 (SEQ ID NO: 70) | R31375_T0 (SEQ ID NO: 51); R31375_T1 (SEQ ID NO: 52); R31375_T10 (SEQ ID NO: 61); R31375_T11 (SEQ ID NO: 62); R31375_T12 (SEQ ID NO: 63); R31375_T13 (SEQ ID NO: 64); R31375_T2 (SEQ ID NO: 53); R31375_T3 (SEQ ID NO: 54); R31375_T4 (SEQ ID NO: 55); R31375_T5 (SEQ ID NO: 56); R31375_T6 (SEQ ID NO: 57); R31375_T7 (SEQ ID NO: 58); R31375_T8 (SEQ ID NO: 59); R31375_T9 (SEQ ID NO: 60) |
| R31375_P14 (SEQ ID NO: 72) | R31375_T19 (SEQ ID NO: 65); R31375_T25 (SEQ ID NO: 66); R31375_T26 (SEQ ID NO: 67) |
| R31375_P31 (SEQ ID NO: 73) | R31375_T29 (SEQ ID NO: 68) |
| R31375_P33 (SEQ ID NO: 74) | R31375_T39 (SEQ ID NO: 69) |

These sequences are variants of the known protein FXYD domain-containing ion transport regulator 3 precursor (SwissProt accession identifier FXYD3_HUMAN (SEQ ID NO: 70); known also according to the synonyms Chloride conductance inducer protein Mat-8; Mammary tumor 8 kDa protein; Phospholemman-like), referred to herein as the previously known protein.

FXYD3 was previously identified within a set of genes induced by the neu or Ha-Ras oncogenes in murine breast tumors, and was named Mat-8 (Mammary tumor, 8 kDa) (Morrison et al 1995). In normal tissues, FXYD3 is mainly expressed in the uterus, stomach, colon and skin (Morrison et al 1995). Its expression was found elevated in human primary breast tumors, as well as prostate carcinoma and pancreatic ductal adenocarcinoma (Grzmil et al 2004, Kayed et al 2006). Specific inhibition of its expression by siRNA in prostate cancer cell lines indicates a role in cellular proliferation (Grzmil et al 2004).

FXYD3 belongs to the FXYD family proteins. The seven known members of this family are all small membrane proteins that contain a common signature of 6 amino acids comprising the FXYD motif. Most FXYD proteins, including human FXYD3, are type I membrane proteins, containing a transmembrane domain and a cleavable signal peptide. However, the signal peptide of mouse FXYD3 is not cleaved and the signal peptide may act as a second transmembrane domain (Crambert et al 2005, Geering 2006). FXYD3, like other members of the FXYD family, interacts with Na/K-ATPase and modulates its activity in a tissue-specific manner (Crambert et al 2005, Arimochi et al 2007, Geering 2006).

Two splice variant isoforms of FXYD3 have been previously described (Bibert et al 2006). These differ in a 26 amino acids in frame insertion after the transmembrane domain, and are differentially expressed during cell differentiation. Furthermore, both isoforms are able to stably associate with Na/K-ATPase and play different functional roles in the regulation of the activities of this ATPase (Bibert et al 2006).

In addition, WO 2003101283 may be relevant to the present invention. This PCT application purports to disclose that R31375_P0 (SEQ ID NO:70) (wild-type FXYD3 nucleic acid coding sequence reported herein) is a differentially expressed nucleic acid which encodes a protein sequences that allegedly may be used as a diagnostic marker for human lung cancer.

Further, WO2003000012 purports to disclose a human breast cancer related protein referred to as protein #12 that seems to correspond to the R31375-P0 (wild-type) disclosed herein. Also, U.S. Pat. No. 7,189,507 discloses a gene referred to as MAT8 in a long table of gene sequences that seems to correspond to R31375_P0 (SEQ ID NO:70). The table seems to suggest that this gene may be expressed in ovarian cancer.

Protein FXYD domain-containing ion transport regulator 3 precursor (SEQ ID NO:70) is known or believed to have the following functions: Induces a hyperpolarization-activated chloride current when expressed in *Xenopus* oocytes. May be a modulator capable of activating endogenous oocyte channels. Known polymorphisms for this sequence are as shown in Table 108.

TABLE 108

Amino acid mutations for Known Protein

| SNP positions on amino acid sequence | Comment |
|---|---|
| 36-37 | Missing |
| 58 | S → SEWRSSGEQAGRGWGSPPLTTQLSPTG |

Protein FXYD domain-containing ion transport regulator 3 precursor (SEQ ID NO:70) localization is believed to be Membrane; single-pass type I membrane protein (Potential).

The following GO Annotations apply to the previously known protein. The following annotations were found: chloride transport, which are annotations related to Biological Process; chloride channel activity, which are annotations related to Molecular Function; and integral to plasma membrane, which are annotations related to Cellular Component.

The GO assignment relies on information from one or more of the SwissProt/TremBl Protein knowledgebase, available from <http://www.expasy.ch/sprot/>; or Locuslink, available from <http://www.ncbi.nlm.nih.gov/projects/LocusLink/>.

According to the present invention, novel FXYD3 splice variants were identified as membrane bound proteins that are predicted to be over expressed in cancers. FXYD3 is a type I membrane bound protein (Bibert et. al 2006) and according to the present invention 3 novel splice variants of this protein are provided. The novel splice variant refered herein as R31375_P14 (SEQ ID NO:72) has an additional in-frame exon in its extracellular region. The addition of this exon increases the length of the extracellular region by 298 amino acids, which comprises a significant addition to rather short extracellular domain of 18 amino acids of the wild type protein. The novel splice variant refered herein as R31375_P31 (SEQ ID NO:73) has an additional in-frame exon in the juxtamembrane domain of FXYD3, which adds 26 new amino acids to the intracellular region. The novel splice variant refered herein as R31375_P33 (SEQ ID NO:74) skips the 3rd coding exon of the wild type FXYD3 and, like R31375_P31 (SEQ ID NO:73), has the additional in-frame exon in the juxtamembrane domain. This causes the deletion of 8 amino acids in the ectodomain.

According to the present invention FXYD3 and R31375_P14 (SEQ ID NO:72) were shown to be overexpressed in ovarian cancer.

As noted above, cluster R31375 features 19 transcripts, which were listed in Table 105 above. These transcripts encode for proteins which are variants of protein FXYD domain-containing ion transport regulator 3 precursor (SEQ ID NO:70). A description of each variant protein according to the present invention is now provided.

Variant protein R31375_P0 (SEQ ID NO:70) according to the present invention has an amino acid sequence encoded by transcripts R31375 T0 (SEQ ID NO:51), R31375_T1 (SEQ ID NO:52), R31375_T10 (SEQ ID NO:61), R31375_T11 (SEQ ID NO:62), R31375_T12 (SEQ ID NO:63), R31375_T13 (SEQ ID NO:64), R31375_T2 (SEQ ID NO:53), R31375_T3 (SEQ ID NO:54), R31375_T4 (SEQ ID NO:55), R31375_T5 (SEQ ID NO:56), R31375_T6 (SEQ ID NO:57), R31375_T7 (SEQ ID NO:58), R31375_T8 (SEQ ID NO:59) and R31375_T9 (SEQ ID NO:60).

The localization of the variant protein was determined according to results from a number of different software programs and analyses, including analyses from SignalP and other specialized programs. The variant protein is believed to be located as follows with regard to the cell: membrane.

Variant protein R31375_P0 (SEQ ID NO:70) also has the following non-silent SNPs (Single Nucleotide Polymorphisms) as listed in Table 109, (given according to their positions on the amino acid sequence, with the alternative amino acids listed (SEQ ID NO:70)).

TABLE 109

| Amino acid mutations | |
|---|---|
| SNP positions on amino acid sequence | Alternative amino acids |
| 3 | K -> R |
| 19 | D -> A |
| 19 | D -> V |
| 50 | A -> P |
| 75 | E -> |

The coding portion of transcript R31375_T0 (SEQ ID NO:51) starts at position 491 and ends at position 751. The transcript also has the following SNPs as listed in Table 110 (given according to their position on the nucleotide sequence, with the alternative nucleic acid listed).

TABLE 110

| Nucleic acid SNPs | |
|---|---|
| Polymorphism | SNP positions on nucleotide sequence |
| C -> A | 469 |
| A -> G | 498, 900, 1571 |
| A -> T | 546 |
| A -> C | 546 |
| T -> A | 607, 926 |
| T -> G | 607 |
| G -> C | 638 |
| G -> | 713 |
| C -> T | 792 |
| G -> A | 901, 1572 |

The coding portion of transcript R31375_T1 (SEQ ID NO:52) starts at position 795 and ends at position 1055. The transcript also has the following SNPs as listed in Table 111 (given according to their position on the nucleotide sequence, with the alternative nucleic acid listed).

TABLE 111

| Nucleic acid SNPs | |
|---|---|
| Polymorphism | SNP positions on nucleotide sequence |
| G -> A | 513, 1205, 1876 |
| C -> A | 773 |
| A -> G | 802, 1204, 1875 |
| A -> T | 850 |
| A -> C | 850 |
| T -> A | 911, 1230 |
| T -> G | 911 |
| G -> C | 942 |
| G -> | 1017 |
| C -> T | 1096 |

The coding portion of transcript R31375_T10 (SEQ ID NO:61) starts at position 1826 and ends at position 2086. The transcript also has the following SNPs as listed in Table 112 (given according to their position on the nucleotide sequence, with the alternative nucleic acid listed).

TABLE 112

| Nucleic acid SNPs | |
|---|---|
| Polymorphism | SNP positions on nucleotide sequence |
| C -> A | 469 |
| A -> G | 639, 984, 1504, 1833, 2235, 2906 |
| A -> C | 860, 1183, 1447, 1504, 1881 |
| C -> | 1063 |
| A -> T | 1183, 1447, 1881 |
| T -> A | 1942, 2261 |
| T -> G | 1942 |
| G -> C | 1973 |
| G -> | 2048 |
| C -> T | 2127 |
| G -> A | 2236, 2907 |

The coding portion of transcript R31375_T11 (SEQ ID NO:62) starts at position 613 and ends at position 873. The transcript also has the following SNPs as listed in Table 113 (given according to their position on the nucleotide sequence, with the alternative nucleic acid listed).

TABLE 113

| Nucleic acid SNPs | |
|---|---|
| Polymorphism | SNP positions on nucleotide sequence |
| C -> A | 469 |
| A -> G | 620, 1022, 1693 |
| A -> T | 668 |
| A -> C | 668 |
| T -> A | 729, 1048 |
| T -> G | 729 |
| G -> C | 760 |
| G -> | 835 |
| C -> T | 914 |
| G -> A | 1023, 1694 |

The coding portion of transcript R31375_T12 (SEQ ID NO:63) starts at position 711 and ends at position 971. The transcript also has the following SNPs as listed in Table 114 (given according to their position on the nucleotide sequence, with the alternative nucleic acid listed).

TABLE 114

| Nucleic acid SNPs | |
|---|---|
| Polymorphism | SNP positions on nucleotide sequence |
| C -> A | 469 |
| G -> | 545, 933 |
| G -> C | 545, 858 |
| C -> | 549 |
| A -> G | 718, 1120, 1791 |
| A -> T | 766 |
| A -> C | 766 |
| T -> A | 827, 1146 |
| T -> G | 827 |
| C -> T | 1012 |
| G -> A | 1121, 1792 |

The coding portion of transcript R31375_T13 (SEQ ID NO:64) starts at position 1015 and ends at position 1275.

The transcript also has the following SNPs as listed in Table 115 (given according to their position on the nucleotide sequence, with the alternative nucleic acid listed).

TABLE 115

| Nucleic acid SNPs | |
|---|---|
| Polymorphism | SNP positions on nucleotide sequence |
| G -> A | 513, 1425, 2096 |
| C -> A | 773 |
| G -> | 849, 1237 |
| G -> C | 849, 1162 |
| C -> | 853 |
| A -> G | 1022, 1424, 2095 |
| A -> T | 1070 |
| A -> C | 1070 |
| T -> A | 1131, 1450 |
| T -> G | 1131 |
| C -> T | 1316 |

The coding portion of transcript R31375_T2 (SEQ ID NO:53) starts at position 678 and ends at position 938. The transcript also has the following SNPs as listed in Table 116 (given according to their position on the nucleotide sequence, with the alternative nucleic acid listed).

TABLE 116

| Nucleic acid SNPs | |
|---|---|
| Polymorphism | SNP positions on nucleotide sequence |
| G -> A | 513, 1088, 1759 |
| C -> A | 656 |
| A -> G | 685, 1087, 1758 |
| A -> T | 733 |
| A -> C | 733 |
| T -> A | 794, 1113 |
| T -> G | 794 |
| G -> C | 825 |
| G -> | 900 |
| C -> T | 979 |

The coding portion of transcript R31375_T3 (SEQ ID NO:54) starts at position 572 and ends at position 832. The transcript also has the following SNPs as listed in Table 117 (given according to their position on the nucleotide sequence, with the alternative nucleic acid listed).

TABLE 117

| Nucleic acid SNPs | |
|---|---|
| Polymorphism | SNP positions on nucleotide sequence |
| C -> A | 550 |
| A -> G | 579, 981, 1652 |
| A -> T | 627 |
| A -> C | 627 |
| T -> A | 688, 1007 |
| T -> G | 688 |
| G -> C | 719 |
| G -> | 794 |
| C -> T | 873 |
| G -> A | 982, 1653 |

The coding portion of transcript R31375_T4 (SEQ ID NO:55) starts at position 575 and ends at position 835. The transcript also has the following SNPs as listed in Table 118 (given according to their position on the nucleotide sequence, with the alternative nucleic acid listed).

TABLE 118

| Nucleic acid SNPs | |
|---|---|
| Polymorphism | SNP positions on nucleotide sequence |
| C -> A | 469 |
| A -> G | 582, 984, 1655 |
| A -> T | 630 |
| A -> C | 630 |
| T -> A | 691, 1010 |
| T -> G | 691 |
| G -> C | 722 |
| G -> | 797 |
| C -> T | 876 |
| G -> A | 985, 1656 |

The coding portion of transcript R31375_T5 (SEQ ID NO:56) starts at position 656 and ends at position 916. The transcript also has the following SNPs as listed in Table 119 (given according to their position on the nucleotide sequence, with the alternative nucleic acid listedn).

TABLE 119

| Nucleic acid SNPs | |
|---|---|
| Polymorphism | SNP positions on nucleotide sequence |
| C -> A | 550 |
| A -> G | 663, 1065, 1736 |
| A -> T | 711 |
| A -> C | 711 |
| T -> A | 772, 1091 |
| T -> G | 772 |
| G -> C | 803 |
| G -> | 878 |
| C -> T | 957 |
| G -> A | 1066, 1737 |

The coding portion of transcript R31375_T6 (SEQ ID NO:57) starts at position 697 and ends at position 957. The transcript also has the following SNPs as listed in Table 120 (given according to their position on the nucleotide sequence, with the alternative nucleic acid listed).

TABLE 120

| Nucleic acid SNPs | |
|---|---|
| Polymorphism | SNP positions on nucleotide sequence |
| C -> A | 469 |
| A -> G | 704, 1106, 1777 |
| A -> T | 752 |
| A -> C | 752 |
| T -> A | 813, 1132 |
| T -> G | 813 |
| G -> C | 844 |
| G -> | 919 |
| C -> T | 998 |
| G -> A | 1107, 1778 |

The coding portion of transcript R31375_T7 (SEQ ID NO:58) starts at position 2475 and ends at position 2735. The transcript also has the following SNPs as listed in Table 121 (given according to their position on the nucleotide sequence, with the alternative nucleic acid listed).

TABLE 121

| Nucleic acid SNPs | |
|---|---|
| Polymorphism | SNP positions on nucleotide sequence |
| C -> A | 469 |
| A -> G | 639, 984, 1504, 2482, 2884, 3555 |
| A -> C | 860, 1183, 1447, 1504, 2530 |
| C -> | 1063 |
| A -> T | 1183, 1447, 2530 |
| C -> T | 1999, 2022, 2776 |
| -> G | 2279 |
| -> A | 2280 |
| G -> T | 2285 |
| G -> C | 2285, 2622 |
| T -> A | 2591, 2910 |
| T -> G | 2591 |
| G -> | 2697 |
| G -> A | 2885, 3556 |

The coding portion of transcript R31375_T8 (SEQ ID NO:59) starts at position 1329 and ends at position 1589. The transcript also has the following SNPs as listed in Table 122 (given according to their position on the nucleotide sequence, with the alternative nucleic acid listed).

TABLE 122

| Nucleic acid SNPs | |
|---|---|
| Polymorphism | SNP positions on nucleotide sequence |
| C -> A | 469 |
| A -> G | 639, 984, 1336, 1738, 2409 |
| A -> C | 860, 1183, 1384 |
| C -> | 1063 |
| A -> T | 1183, 1384 |
| T -> A | 1445, 1764 |
| T -> G | 1445 |
| G -> C | 1476 |
| G -> | 1551 |
| C -> T | 1630 |
| G -> A | 1739, 2410 |

The coding portion of transcript R31375_T9 (SEQ ID NO:60) starts at position 2586 and ends at position 2846. The transcript also has the following SNPs as listed in Table 123 (given according to their position on the nucleotide sequence, with the alternative nucleic acid listed).

TABLE 123

| Nucleic acid SNPs | |
|---|---|
| Polymorphism | SNP positions on nucleotide sequence |
| C -> A | 469, 2531, 2549 |
| A -> G | 639, 984, 1504, 2593, 2995, 3666 |
| A -> C | 860, 1183, 1447, 1504, 2641 |
| C -> | 1063 |
| A -> T | 1183, 1447, 2641 |
| C -> T | 1999, 2022, 2887 |
| -> G | 2279 |
| -> A | 2280 |
| G -> T | 2285 |
| G -> C | 2285, 2733 |
| C -> G | 2531, 2549 |
| G -> A | 2550, 2996, 3667 |
| T -> A | 2702, 3021 |

TABLE 123-continued

| Nucleic acid SNPs | |
|---|---|
| Polymorphism | SNP positions on nucleotide sequence |
| T -> G | 2702 |
| G -> | 2808 |

Variant protein R31375_P14 (SEQ ID NO:72) according to the present invention has an amino acid sequence as encoded by transcripts R31375_T19 (SEQ ID NO:65), R31375_T25 (SEQ ID NO:66) and R31375_T26 (SEQ ID NO:67). Alignments to one or more previously published protein sequences are shown in FIG. 49A. A brief description of the relationship of the variant protein according to the present invention to each such aligned protein is as follows:

1. Comparison report between R31375_P14 (SEQ ID NO:72) and known proteins FXYD3_HUMAN, NP_005962 and Q6IB59 HUMAN (SEQ ID NO: 70) (FIG. 49A):

A. An isolated chimeric polypeptide encoding for R31375_P14 (SEQ ID NO:72), comprising a first amino acid sequence being at least 90% homologous to MQKVTLGLLVFLAGFPVLDANDLEDKNSPFYY corresponding to amino acids 1-32 of known proteins FXYD3_HUMAN, NP_005962 and Q6IB59 HUMAN (SEQ ID NO: 70), which also corresponds to amino acids 1-32 of R31375_P14 (SEQ ID NO:72), a second amino acid sequence being at least 70%, optionally at least 80%, preferably at least 85%, more preferably at least 90% and most preferably at least 95, 96, 97, 98 or 99% homologous to a polypeptide having the sequence GAPYIFVKRMGGQMKRTQAGTEVPSTFLL (SEQ ID NO: 294) corresponding to amino acids 33-61 of R31375_P14 (SEQ ID NO:72), and a third amino acid sequence being at least 90% homologous to

```
DWHSLQVGGLICAGVLCAMGIIIVMSAKCKCKFGQKSGHHPGETPPLITPG
SAQS
```

corresponding to amino acids 33-87 of known proteins FXYD3_HUMAN, NP_005962 and Q6IB59 HUMAN (SEQ ID NO: 70), which also corresponds to amino acids 62-116 of R31375_P14 (SEQ ID NO:72), wherein said first amino acid sequence, second amino acid sequence and third amino acid sequence are contiguous and in a sequential order.

B. An isolated polypeptide encoding for an edge portion of R31375_P14 (SEQ ID NO:72), comprising an amino acid sequence being at least 70%, optionally at least about 80%, preferably at least about 85%, more preferably at least about 90% and most preferably at least about 95, 96, 97, 98 or 99% homologous to the sequence GAPYIFVKRMGGQMKRTQAGTEVPSTFLL (SEQ ID NO: 294) of R31375_P14 (SEQ ID NO:72).

The localization of the variant protein was determined according to results from a number of different software programs and analyses, including analyses from SignalP and other specialized programs. The variant protein is believed to be located as follows with regard to the cell: membrane.

Variant protein R31375_P14 (SEQ ID NO:72) also has the following non-silent SNPs (Single Nucleotide Polymorphisms) as listed in Table 124, (given according to their positions on the amino acid sequence, with the alternative amino acids listed (SEQ ID NO:72)).

TABLE 124

| Amino acid mutations | |
|---|---|
| SNP positions on amino acid sequence | Alternative amino acids |
| 3 | K -> R |
| 19 | D -> A |
| 19 | D -> V |
| 46 | M -> I |
| 47 | K -> E |
| 79 | A -> P |
| 104 | E -> |

The coding portion of transcript R31375_T19 (SEQ ID NO:65) starts at position 491 and ends at position 838. The transcript also has the following SNPs as listed in Table 125 (given according to their position on the nucleotide sequence, with the alternative nucleic acid listed).

TABLE 125

| Nucleic acid SNPs | |
|---|---|
| Polymorphism | SNP positions on nucleotide sequence |
| C -> A | 469 |
| A -> G | 498, 629, 987, 1658 |
| A -> T | 546 |
| A -> C | 546 |
| G -> A | 628, 988, 1659 |
| T -> A | 694, 1013 |
| T -> G | 694 |
| G -> C | 725 |
| G -> | 800 |
| C -> T | 879 |

The coding portion of transcript R31375_T25 (SEQ ID NO:66) starts at position 575 and ends at position 922. The transcript also has the following SNPs as listed in Table 126 (given according to their position on the nucleotide sequence, with the alternative nucleic acid listed).

TABLE 126

| Nucleic acid SNPs | |
|---|---|
| Polymorphism | SNP positions on nucleotide sequence |
| C -> A | 469 |
| A -> G | 582, 713, 1071, 1742 |
| A -> T | 630 |
| A -> C | 630 |
| G -> A | 712, 1072, 1743 |
| T -> A | 778, 1097 |
| T -> G | 778 |
| G -> C | 809 |
| G -> | 884 |
| C -> T | 963 |

The coding portion of transcript R31375_T26 (SEQ ID NO:67) starts at position 1443 and ends at position 1790. The transcript also has the following SNPs as listed in Table 127 (given according to their position on the nucleotide sequence, with the alternative nucleic acid listed).

TABLE 127

| Nucleic acid SNPs | |
|---|---|
| Polymorphism | SNP positions on nucleotide sequence |
| C -> A | 469 |
| A -> G | 639, 984, 1450, 1581, 1939, 2610 |
| A -> C | 860, 1183, 1498 |
| C -> | 1063 |
| A -> T | 1183, 1498 |
| G -> A | 1580, 1940, 2611 |
| T -> A | 1646, 1965 |
| T -> G | 1646 |
| G -> C | 1677 |
| G -> | 1752 |
| C -> T | 1831 |

Variant protein R31375_P31 (SEQ ID NO:73) according to the present invention has an amino acid sequence as encoded by transcript R31375_T29 (SEQ ID NO:68). Alignments to one or more previously published protein sequences are given in FIGS. 49B and 49C. A brief description of the relationship of the variant protein according to the present invention to each such aligned protein is as follows:

1. Comparison report between R31375_P31 (SEQ ID NO:73) and known proteins FXYD3_HUMAN, NP_005962 and Q6IB59_HUMAN (SEQ ID NO: 70) (FIG. 49B):

A. An isolated chimeric polypeptide encoding for R31375_P31 (SEQ ID NO:73), comprising a first amino acid sequence being at least 90% homologous to MQKVTLGLLVFLAGFPVLDANDLEDKNSPFYYDWHSLQVGGLICAGVLCAMGI IIVMS corresponding to amino acids 1-58 of known proteins FXYD3_HUMAN, NP_005962 and Q6IB59_HUMAN (SEQ ID NO: 70), which also corresponds to amino acids 1-58 of R31375_P31 (SEQ ID NO:73), a second amino acid sequence being at least 70%, optionally at least 80%, preferably at least 85%, more preferably at least 90% and most preferably at least 95, 96, 97, 98 or 99% homologous to a polypeptide having the sequence EWRSSGEQAGRGWGSPPLTTQLSPTG (SEQ ID NO: 295) corresponding to amino acids 59-84 of R31375_P31 (SEQ ID NO:73), and a third amino acid sequence being at least 90% homologous to AKCKCKFGQKSG corresponding to amino acids 59-70 of known proteins FXYD3_HUMAN, NP_005962 and Q6IB59_HUMAN (SEQ ID NO: 70), which also corresponds to amino acids 85-96 of R31375_P31 (SEQ ID NO:73), wherein said first amino acid sequence, second amino acid sequence and third amino acid sequence are contiguous and in a sequential order.

B. An isolated polypeptide encoding for an edge portion of R31375_P31 (SEQ ID NO:73), comprising an amino acid sequence being at least 70%, optionally at least about 80%, preferably at least about 85%, more preferably at least about 90% and most preferably at least about 95, 96, 97, 98 or 99% homologous to the sequence EWRSSGEQAGRGWGSPPLTTQLSPTG (SEQ ID NO: 295) of R31375_P31 (SEQ ID NO:73).

2. Comparison report between R31375_P31 (SEQ ID NO:73) and known proteins NP_068710 (SEQ ID NO: 71) (FIG. 49C):

A. An isolated chimeric polypeptide encoding for R31375_P31 (SEQ ID NO:73), comprising a amino acid sequence being at least 90% homologous to

MQKVTLGLLVFLAGFPVLDANDLEDKNSPFYYDWHSLQVGGLICAGVLCAM

GIIIVMSEWRSSGEQAGRGWGSPPLTTQLSPTGAKCKCKFGQKSG corresponding to amino acids 1-96 of known proteins NP_068710 (SEQ ID NO: 71), which also corresponds to amino acids 1-96 of R31375_P31 (SEQ ID NO:73), wherein said and first amino acid sequence are contiguous and in a sequential order.

The localization of the variant protein was determined according to results from a number of different software programs and analyses, including analyses from SignalP and other specialized programs. The variant protein is believed to be located as follows with regard to the cell: membrane.

Variant protein R31375_P31 (SEQ ID NO:73) also has the following non-silent SNPs (Single Nucleotide Polymorphisms) as listed in Table 128, (given according to their positions on the amino acid sequence, with the alternative amino acids listed (SEQ ID NO:73)).

TABLE 128

| Amino acid mutations | |
|---|---|
| SNP positions on amino acid sequence | Alternative amino acids |
| 3 | K -> R |
| 19 | D -> A |
| 19 | D -> V |
| 50 | A -> P |

Variant protein R31375_P31 (SEQ ID NO:73) is encoded by the transcript R31375_T29 (SEQ ID NO:68), for which the coding portion starts at position 491 and ends at position 778. The transcript also has the following SNPs as listed in Table 129 (given according to their position on the nucleotide sequence, with the alternative nucleic acid listed).

TABLE 129

| Nucleic acid SNPs | |
|---|---|
| Polymorphism | SNP positions on nucleotide sequence |
| C -> A | 469 |
| A -> G | 498, 1294, 1965 |
| A -> T | 546 |
| A -> C | 546 |
| T -> A | 607, 1320 |
| T -> G | 607 |
| G -> C | 638 |
| G -> | 1107 |
| C -> T | 1186 |
| G -> A | 1295, 1966 |

Variant protein R31375_P33 (SEQ ID NO:74) according to the present invention has an amino acid sequence as encoded by transcript R31375_T39 (SEQ ID NO:69). Alignments to one or more previously published protein sequences are given in FIGS. 49D and 49E. A brief description of the relationship of the variant protein according to the present invention to each such aligned protein is as follows:

1. Comparison report between R31375_P33 (SEQ ID NO:74) and known proteins FXYD3_HUMAN, NP_005962 and Q6IB59_HUMAN (SEQ ID NO: 70) (FIG. 49D):

A. An isolated chimeric polypeptide encoding for R31375_P33 (SEQ ID NO:74), comprising a first amino acid sequence being at least 90% homologous to MQKVTLGLLVFLAGFPVLDANDLE corresponding to amino acids 1-24 of known proteins FXYD3_HUMAN, NP_005962 and Q6IB59_HUMAN (SEQ ID NO: 70), which also corresponds to amino acids 1-24 of R31375_P33 (SEQ ID NO:74), a second amino acid sequence being at least 90% homologous to DWHSLQVGGLICAGVLCAMGIIIVMS corresponding to amino acids 33-58 of known proteins FXYD3_HUMAN, NP_005962 and Q6IB59_HUMAN (SEQ ID NO: 70), which also corresponds to amino acids 25-50 of R31375_P33 (SEQ ID NO:74), a third amino acid sequence being at least 70%, optionally at least 80%, preferably at least 85%, more preferably at least 90% and most preferably at least 95, 96, 97, 98 or 99% homologous to a polypeptide having the sequence EWRSSGEQAGRGWGSPPLTTQLSPTG (SEQ ID NO: 295) corresponding to amino acids 51-76 of R31375_P33 (SEQ ID NO:74), and a fourth amino acid sequence being at least 90% homologous to AKCKCKFGQKSG corresponding to amino acids 59-70 of known proteins FXYD3_HUMAN, NP_005962 and Q6IB59_HUMAN (SEQ ID NO: 70), which also corresponds to amino acids 77-88 of R31375_P33 (SEQ ID NO:74), wherein said first amino acid sequence, second amino acid sequence, third amino acid sequence and fourth amino acid sequence are contiguous and in a sequential order.

B. An isolated chimeric polypeptide encoding for an edge portion of R31375_P33 (SEQ ID NO:74), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise ED, having a structure as follows: a sequence starting from any of amino acid numbers 24−x to 24; and ending at any of amino acid numbers 25+((n−2)−x), in which x varies from 0 to n−2.

C. An isolated polypeptide encoding for an edge portion of R31375_P33 (SEQ ID NO:74), comprising an amino acid sequence being at least 70%, optionally at least about 80%, preferably at least about 85%, more preferably at least about 90% and most preferably at least about 95, 96, 97, 98 or 99% homologous to the sequence EWRSSGEQAGRGWGSPPLTTQLSPTG (SEQ ID NO: 295) of R31375_P33 (SEQ ID NO:74).

2. Comparison report between R31375_P33 (SEQ ID NO:74) and known proteins NP_068710 (SEQ ID NO: 71) (FIG. 49E):

A. An isolated chimeric polypeptide encoding for R31375_P33 (SEQ ID NO:74), comprising a first amino acid sequence being at least 90% homologous to MQKVTLGLLVFLAGFPVLDANDLE corresponding to amino acids 1-24 of known proteins NP_068710 (SEQ ID NO: 71), which also corresponds to amino acids 1-24 of R31375_P33 (SEQ ID NO:74), and a second amino acid sequence being at least 90% homologous to

DWHSLQVGGLICAGVLCAMGIIIVMSEWRSSGEQAGRGWGSPPLTTQLSPT

GAKCKCKFGQKSG corresponding to amino acids 33-96 of known proteins NP_068710 (SEQ ID NO: 71), which also corresponds to amino acids 25-88 of R31375_P33 (SEQ ID NO:74), wherein said first amino acid sequence and second amino acid sequence are contiguous and in a sequential order.

B. An isolated chimeric polypeptide encoding for an edge portion of R31375_P33 (SEQ ID NO:74), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise ED, having a structure as follows: a sequence starting from any of amino acid numbers 24−x to 24; and ending at any of amino acid numbers 25+((n−2)−x), in which x varies from 0 to n−2.

The localization of the variant protein was determined according to results from a number of different software programs and analyses, including analyses from SignalP and other specialized programs. The variant protein is believed to be located as follows with regard to the cell: secreted.

Variant protein R31375_P33 (SEQ ID NO:74) also has the following non-silent SNPs (Single Nucleotide Polymorphisms) as listed in Table 130, (given according to their positions on the amino acid sequence, with the alternative amino acids listed (SEQ ID NO:74)).

TABLE 130

| Amino acid mutations | |
|---|---|
| SNP positions on amino acid sequence | Alternative amino acids |
| 3 | K -> R |
| 19 | D -> A |
| 19 | D -> V |
| 42 | A -> P |

The coding portion of transcript R31375_T39 (SEQ ID NO:69) starts at position 491 and ends at position 754. The transcript also has the following SNPs as listed in Table 131 (given according to their position on the nucleotide sequence, with the alternative nucleic acid listed).

TABLE 131

| Nucleic acid SNPs | |
|---|---|
| Polymorphism | SNP positions on nucleotide sequence |
| C -> A | 469 |
| A -> G | 498, 1270, 1941 |
| A -> T | 546 |
| A -> C | 546 |
| T -> A | 583, 1296 |
| T -> G | 583 |
| G -> C | 614 |
| G -> | 1083 |
| C -> T | 1162 |
| G -> A | 1271, 1942 |

According to an optional embodiment of the present invention, short segments related to the above cluster are also provided. These segments are up to about 120bp in length, and so are included in a separate description.

Segment cluster R31375_N30 (SEQ ID NO:134) according to the present invention is supported by 7 libraries. The number of libraries was determined as previously described. This segment can be found in the following transcripts: R31375_T19 (SEQ ID NO:65), R31375_T25 (SEQ ID NO:66) and R31375_T26 (SEQ ID NO:67). Table 132 below describes the starting and ending position of this segment on each transcript.

TABLE 132

| Segment location on transcripts | | |
|---|---|---|
| Transcript name | Segment starting position | Segment ending position |
| R31375_T19 (SEQ ID NO: 65) | 588 | 674 |
| R31375_T25 (SEQ ID NO: 66) | 672 | 758 |
| R31375_T26 (SEQ ID NO: 67) | 1540 | 1626 |

Segment cluster R31375_N33 (SEQ ID NO:135) according to the present invention is supported by 278 libraries. The number of libraries was determined as previously described. This segment can be found in the following transcripts: R31375_T0 (SEQ ID NO:51), R31375_T1 (SEQ ID NO:52), R31375_T10 (SEQ ID NO:61), R31375_T11 (SEQ ID NO:62), R31375_T12 (SEQ ID NO:63), R31375_T13 (SEQ ID NO:64), R31375_T19 (SEQ ID NO:65), R31375_T2 (SEQ ID NO:53), R31375_T25 (SEQ ID NO:66), R31375_T26 (SEQ ID NO:67), R31375_T29 (SEQ ID NO:68), R31375_T3 (SEQ ID NO:54), R31375_T39 (SEQ ID NO:69), R31375_T4 (SEQ ID NO:55), R31375_T5 (SEQ ID NO:56), R31375_T6 (SEQ ID NO:57), R31375_T7 (SEQ ID NO:58), R31375_T8 (SEQ ID NO:59) and R31375_T9 (SEQ ID NO:60). Table 133 below describes the starting and ending position of this segment on each transcript.

TABLE 133

| Segment location on transcripts | | |
|---|---|---|
| Transcript name | Segment starting position | Segment ending position |
| R31375_T0 (SEQ ID NO: 51) | 588 | 631 |
| R31375_T1 (SEQ ID NO: 52) | 892 | 935 |
| R31375_T10 (SEQ ID NO: 61) | 1923 | 1966 |
| R31375_T11 (SEQ ID NO: 62) | 710 | 753 |
| R31375_T12 (SEQ ID NO: 63) | 808 | 851 |
| R31375_T13 (SEQ ID NO: 64) | 1112 | 1155 |
| R31375_T19 (SEQ ID NO: 65) | 675 | 718 |
| R31375_T2 (SEQ ID NO: 53) | 775 | 818 |
| R31375_T25 (SEQ ID NO: 66) | 759 | 802 |
| R31375_T26 (SEQ ID NO: 67) | 1627 | 1670 |
| R31375_T29 (SEQ ID NO: 68) | 588 | 631 |
| R31375_T3 (SEQ ID NO: 54) | 669 | 712 |
| R31375_T39 (SEQ ID NO: 69) | 564 | 607 |
| R31375_T4 (SEQ ID NO: 55) | 672 | 715 |
| R31375_T5 (SEQ ID NO: 56) | 753 | 796 |
| R31375_T6 (SEQ ID NO: 57) | 794 | 837 |
| R31375_T7 (SEQ ID NO: 58) | 2572 | 2615 |
| R31375_T8 (SEQ ID NO: 59) | 1426 | 1469 |
| R31375_T9 (SEQ ID NO: 60) | 2683 | 2726 |

Segment cluster R31375_N34 (SEQ ID NO:136) according to the present invention is supported by 275 libraries. The number of libraries was determined as previously described. This segment can be found in the following transcripts: R31375_T0 (SEQ ID NO:51), R31375_T1 (SEQ ID NO:52), R31375_T10 (SEQ ID NO:61), R31375_T11 (SEQ ID NO:62), R31375_T12 (SEQ ID NO:63), R31375_T13 (SEQ ID NO:64), R31375_T19 (SEQ ID NO:65), R31375_T2 (SEQ ID NO:53), R31375_T25 (SEQ ID NO:66), R31375_T26 (SEQ ID NO:67), R31375_T29 (SEQ ID NO:68), R31375_T3 (SEQ ID NO:54), R31375_T39 (SEQ ID NO:69), R31375_T4 (SEQ ID NO:55), R31375_T5 (SEQ ID NO:56), R31375_T6 (SEQ ID NO:57), R31375_T7 (SEQ ID NO:58), R31375_T8 (SEQ ID NO:59) and R31375_T9 (SEQ ID NO:60). Table 134 below describes the starting and ending position of this segment on each transcript.

TABLE 134

| Segment location on transcripts | | |
|---|---|---|
| Transcript name | Segment starting position | Segment ending position |
| R31375_T0 (SEQ ID NO: 51) | 632 | 662 |
| R31375_T1 (SEQ ID NO: 52) | 936 | 966 |
| R31375_T10 (SEQ ID NO: 61) | 1967 | 1997 |
| R31375_T11 (SEQ ID NO: 62) | 754 | 784 |
| R31375_T12 (SEQ ID NO: 63) | 852 | 882 |
| R31375_T13 (SEQ ID NO: 64) | 1156 | 1186 |
| R31375_T19 (SEQ ID NO: 65) | 719 | 749 |
| R31375_T2 (SEQ ID NO: 53) | 819 | 849 |
| R31375_T25 (SEQ ID NO: 66) | 803 | 833 |
| R31375_T26 (SEQ ID NO: 67) | 1671 | 1701 |
| R31375_T29 (SEQ ID NO: 68) | 632 | 662 |
| R31375_T3 (SEQ ID NO: 54) | 713 | 743 |
| R31375_T39 (SEQ ID NO: 69) | 608 | 638 |
| R31375_T4 (SEQ ID NO: 55) | 716 | 746 |
| R31375_T5 (SEQ ID NO: 56) | 797 | 827 |
| R31375_T6 (SEQ ID NO: 57) | 838 | 868 |
| R31375_T7 (SEQ ID NO: 58) | 2616 | 2646 |
| R31375_T8 (SEQ ID NO: 59) | 1470 | 1500 |
| R31375_T9 (SEQ ID NO: 60) | 2727 | 2757 |

Segment cluster R31375_N37 (SEQ ID NO:137) according to the present invention is supported by 254 libraries. The number of libraries was determined as previously described. This segment can be found in the following transcripts: R31375_T0 (SEQ ID NO:51), R31375_T1 (SEQ ID NO:52), R31375_T10 (SEQ ID NO:61), R31375_T11 (SEQ ID NO:62), R31375_T12 (SEQ ID NO:63), R31375_T13 (SEQ ID NO:64), R31375_T19 (SEQ ID NO:65), R31375_T2 (SEQ ID NO:53), R31375_T25 (SEQ ID NO:66), R31375_T26 (SEQ ID NO:67), R31375_T29 (SEQ ID NO:68), R31375_T3 (SEQ ID NO:54), R31375_T39 (SEQ ID NO:69), R31375_T4 (SEQ ID NO:55), R31375_T5 (SEQ ID NO:56), R31375_T6 (SEQ ID NO:57), R31375_T7 (SEQ ID NO:58), R31375_T8 (SEQ ID NO:59) and R31375_T9 (SEQ ID NO:60). Table 135 below describes the starting and ending position of this segment on each transcript.

TABLE 135

| Segment location on transcripts | | |
|---|---|---|
| Transcript name | Segment starting position | Segment ending position |
| R31375_T0 (SEQ ID NO: 51) | 663 | 699 |
| R31375_T1 (SEQ ID NO: 52) | 967 | 1003 |
| R31375_T10 (SEQ ID NO: 61) | 1998 | 2034 |
| R31375_T11 (SEQ ID NO: 62) | 785 | 821 |
| R31375_T12 (SEQ ID NO: 63) | 883 | 919 |
| R31375_T13 (SEQ ID NO: 64) | 1187 | 1223 |
| R31375_T19 (SEQ ID NO: 65) | 750 | 786 |
| R31375_T2 (SEQ ID NO: 53) | 850 | 886 |
| R31375_T25 (SEQ ID NO: 66) | 834 | 870 |
| R31375_T26 (SEQ ID NO: 67) | 1702 | 1738 |
| R31375_T29 (SEQ ID NO: 68) | 741 | 777 |
| R31375_T3 (SEQ ID NO: 54) | 744 | 780 |
| R31375_T39 (SEQ ID NO: 69) | 717 | 753 |
| R31375_T4 (SEQ ID NO: 55) | 747 | 783 |
| R31375_T5 (SEQ ID NO: 56) | 828 | 864 |
| R31375_T6 (SEQ ID NO: 57) | 869 | 905 |
| R31375_T7 (SEQ ID NO: 58) | 2647 | 2683 |
| R31375_T8 (SEQ ID NO: 59) | 1501 | 1537 |
| R31375_T9 (SEQ ID NO: 60) | 2758 | 2794 |

Expression of FXYD3 domain containing ion transport regulator 3 R31375 transcripts which are detectable by amplicon as depicted in sequence name R31375_junc30-33 (SEQ ID NO: 247) in normal and cancerous Ovary tissues and in different normal tissues Expression of FXYD3 domain containing ion transport regulator 3 transcripts detectable by or according to junc30-33-R31375_junc30-33 (SEQ ID NO: 247) amplicon and primers R31375_junc30-33F1 (SEQ ID NO: 245) and R31375_junc30-33R1 (SEQ ID NO: 246) was measured by real time PCR on ovary panel and normal panel. The samples used are detailed in Table 4 and Table 2 above, respectively. For each RT sample, the expression of the above amplicon was normalized to the normalization factor calculated from the expression of several house keeping genes as described in Example 1.

Ovary panel—Non-detected samples (samples no. 33 and 53, Table 4,) were assigned Ct value of 41 and were calculated accordingly. The normalized quantity of each RT sample was then divided by the median of the quantities of the normal samples (sample numbers 52-78, Table 4 above), to obtain a value of fold up-regulation for each sample relative to median of the normal samples.

Figure 50:
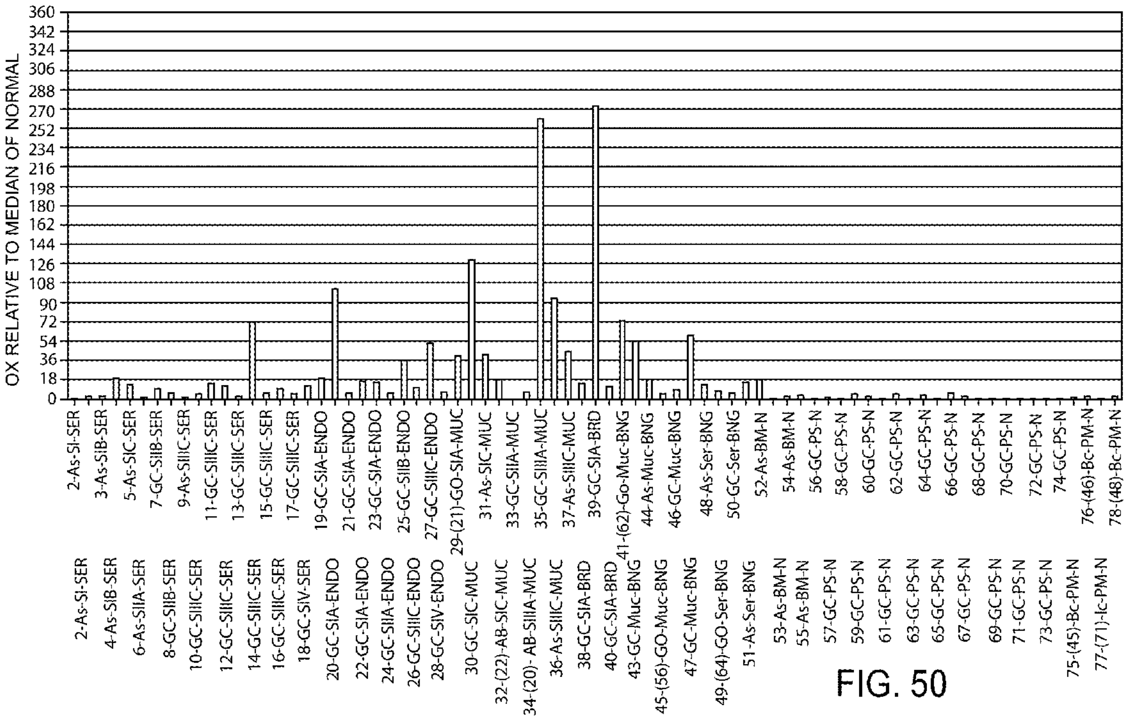
FIG. 50 presents a histogram showing expression of FXYD3 domain containing ion transport regulator 3 R31375 transcripts which are detectable by amplicon as depicted in sequence name R31375_junc30-33 (SEQ ID NO: 247) in normal and cancerous ovary tissues.

FIG. 50 is a histogram showing over expression of the above-indicated FXYD3 domain containing ion transport regulator 3 transcripts in cancerous Ovary samples relative to the normal samples.

As is evident from FIG. 50, the expression of FXYD3 domain containing ion transport regulator 3 transcripts detectable by the above amplicon in adenocarcinoma samples specifically mucinous carcinoma and endometroid samples was significantly higher than in the non-cancerous samples (sample numbers 52-78, Table 4 above). Notably an over-expression of at least 18 fold was found in 13 out of 37 adenocarcinoma samples, specifically 7 out of 9 mucinous carcinoma samples and in 4 out of 10 endometroid samples.

Statistical analysis was applied to verify the significance of these results, as described below. The P value for the difference in the expression levels of FXYD3 domain containing ion transport regulator 3 transcripts detectable by the above amplicon in Ovary adenocarcinoma samples, mucinous carcinoma samples and endometroid samples versus the normal tissue samples was determined by T test as 9.75e-004, 1.92e-002 and 1.55e-002, respectively.

Threshold of 18 fold over expression was found to differentiate between adenocarcinoma mucinous carcinoma samples and endometroid samples and normal samples with P value of 2.71e-004, 4.31e-006 and 3.18e-003, respectively, as checked by exact Fisher test.

The above values demonstrate statistical significance of the results.

Figure 51:
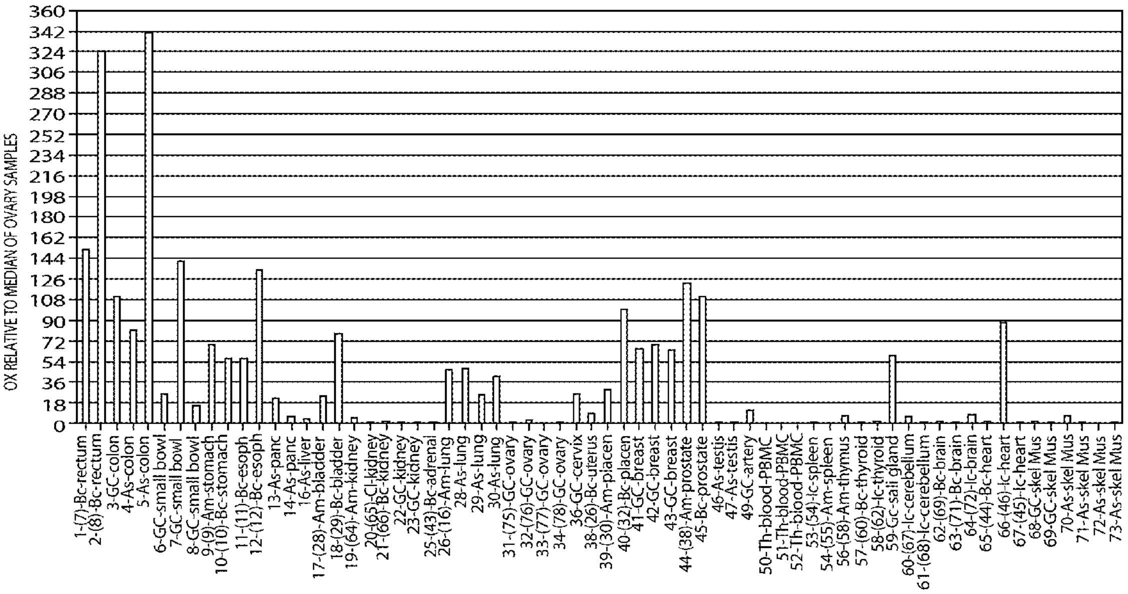
FIG. 51 presents a histogram showing expression of FXYD3 domain containing ion transport regulator 3 R31375 transcripts which are detectable by amplicon as depicted in sequence name R31375_junc30-33 (SEQ ID NO: 247) in various normal tissues.

Normal panel—Non-detected samples (samples no. 50 and 54, Table 2) were assigned Ct value of 41 and were calculated accordingly. The normalized quantity of each RT sample was then divided by the median of the quantities of the ovary samples (sample numbers 31-34, Table 2 above), to obtain a value of relative expression of each sample relative to median of the ovary samples, as shown in FIG. 51.

Primer pairs are also optionally and preferably encompassed within the present invention; for example, for the above experiment, the following primer pair was used as a non-limiting illustrative example only of a suitable primer pair: R31375_junc30-33F1 (SEQ ID NO: 245) forward primer; and R31375_junc30-33R1 (SEQ ID NO: 246) reverse primer.

The present invention also preferably encompasses any amplicon obtained through the use of any suitable primer pair; for example, for the above experiment, the following amplicon was obtained as a non-limiting illustrative example only of a suitable amplicon: R31375_junc30-33 (SEQ ID NO: 247).

```
Forward Primer >R31375 junc30-33F1 (SEQ ID NO:
245):
GTGCTCCATATATATTTGTCAAGAGAATG

Reverse Primer >R31375_junc30-33R1 (SEQ ID NO:
246):
GGAGGCTGTGCCAGTCTAGG

Amplicon >R31375 junc30-33 (SEQ ID NO: 247):
GTGCTCCATATATATTTGTCAAGAGAATGGGGGGACAGATGAAGAGGACA

CAGGCTGGCACTGAGGTCCCCTCCACTTTCCTCCTAGACTGGCACAGCCT

CC
```

Expression of FXYD3 domain containing ion transport regulator 3 R31375 transcripts which are detectable by amplicon as depicted in sequence name R31375_seg33junc34-37 (SEQ ID NO: 250) in normal and cancerous Ovary tissues and in different normal tissues Expression of FXYD3 domain containing ion transport regulator 3 transcripts detectable by or according to seg33junc34-37-R31375_seg33junc34-37 (SEQ ID NO: 250) amplicon and primers R31375_seg33junc34-37F1 (SEQ ID NO: 248) and R31375_seg33junc34-37R1 (SEQ ID NO: 249) was measured by real time PCR on ovary panel and normal panel. The samples used are detailed in Table 4 and Table 2 above, respectively. For each RT sample, the expression of the above amplicon was normalized to the normalization factor calculated from the expression of several house keeping genes as described in Example 1.

Ovary panel—Non-detected samples (samples no. 52, 61 and 70, Table 4) were assigned Ct value of 41 and were calculated accordingly. The normalized quantity of each RT sample was then divided by the median of the quantities of the normal samples (sample numbers 52-78, Table 4 above), to obtain a value of fold up-regulation for each sample relative to median of the normal samples.

Figure 52:
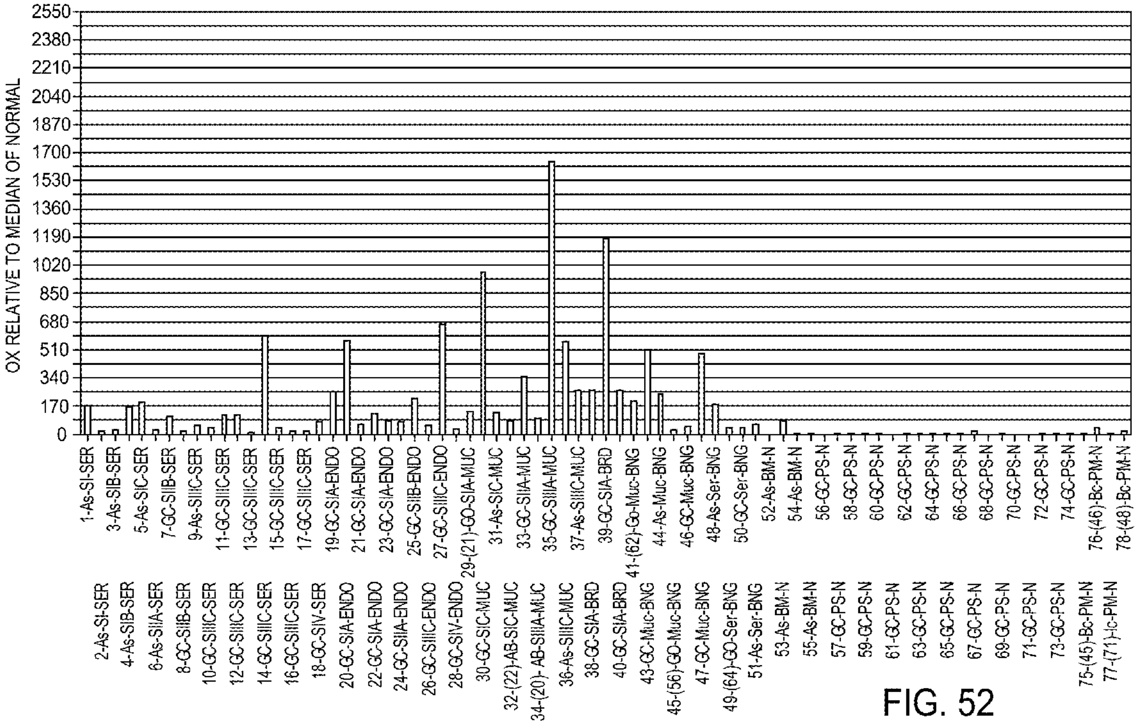
FIG. 52 presents a histogram showing expression of FXYD3 domain containing ion transport regulator 3 R31375 transcripts which are detectable by amplicon as depicted in sequence name R31375_seg33junc34-37 (SEQ ID NO: 250) in normal and cancerous ovary tissues.

FIG. 52 is a histogram showing over expression of the above-indicated FXYD3 domain containing ion transport regulator 3 transcripts in cancerous Ovary samples relative to the normal samples.

As is evident from FIG. 52, the expression of FXYD3 domain containing ion transport regulator 3 transcripts detectable by the above amplicon in adenocarcinoma samples—serous carcinoma, mucinous carcinoma and endometroid was significantly higher than in the non-cancerous samples (sample numbers 52-78, Table 4 above). Notably an over-expression of at least 85 fold was found in 20 out of 37 adenocarcinoma samples, specifically in 7 out of 18 serous carcinoma samples, in 8 out of 9 mucinous carcinoma samples and in 5 out of 10 endometroid samples.

Statistical analysis was applied to verify the significance of these results, as described below. The P value for the difference in the expression levels of FXYD3 domain containing ion transport regulator 3 transcripts detectable by the above amplicon in Ovary adenocarcinoma samples, serous carcinoma samples, mucinous carcinoma samples and endometriod samples versus the normal tissue samples was determined by T test as 1.61e-004, 5.40e-003, 1.49e-002 and 9.08e-003, respectively.

Threshold of 85 fold over expression was found to differentiate between adenocarcinoma, serous carcinoma, mucinous carcinoma and endometriod and normal samples with P value of 8.11e-007, 7.01e-004, 2.97e-007 and 5.78e-004, respectively, as checked by exact Fisher test.

The above values demonstrate statistical significance of the results.

Figure 53:
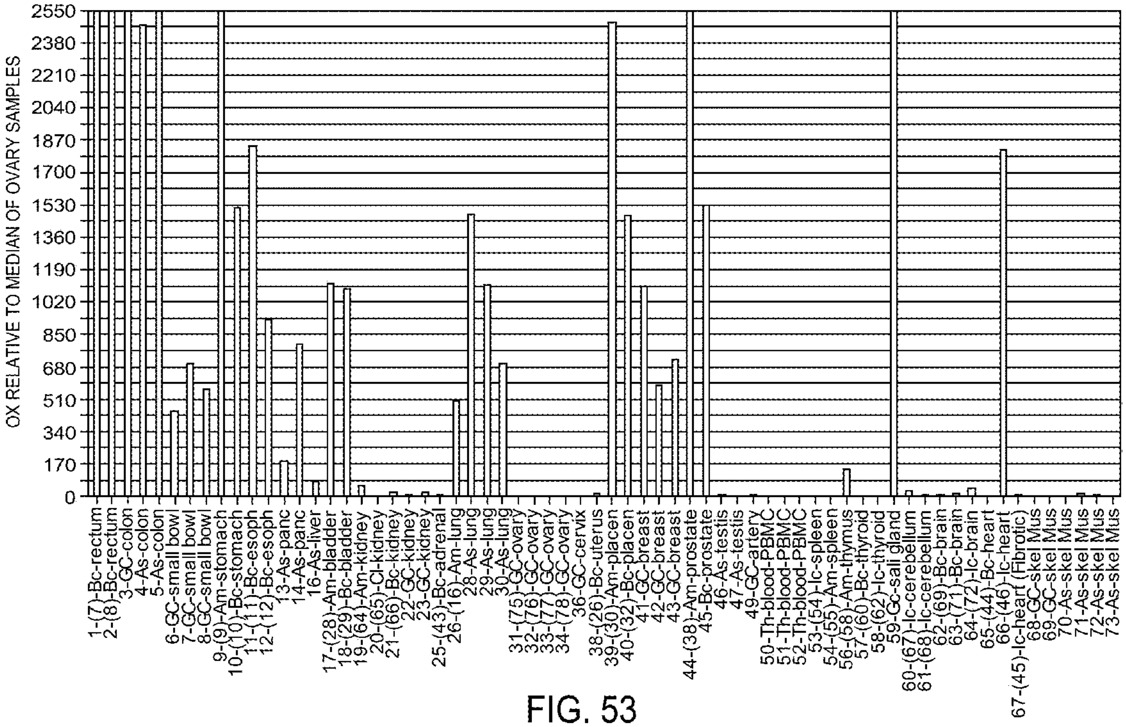
FIG. 53 presents a histogram showing expression of FXYD3 domain containing ion transport regulator 3 R31375 transcripts which are detectable by amplicon as depicted in sequence name R31375_seg33junc34-37 (SEQ ID NO: 250) in various normal tissues.

Normal panel—The normalized quantity of each RT sample was then divided by the median of the quantities of the ovary samples (sample numbers 31-34, Table 2 above), to obtain a value of relative expression of each sample relative to median of the ovary samples, as shown in FIG. 53.

Primer pairs are also optionally and preferably encompassed within the present invention; for example, for the above experiment, the following primer pair was used as a non-limiting illustrative example only of a suitable primer pair: R31375_seg33junc34-37F1 (SEQ ID NO: 248) forward primer; and R31375_seg33junc34-37R1 (SEQ ID NO: 249) reverse primer.

The present invention also preferably encompasses any amplicon obtained through the use of any suitable primer pair; for example, for the above experiment, the following amplicon was obtained as a non-limiting illustrative example only of a suitable amplicon: R31375_seg33junc34-37 (SEQ ID NO: 250).

```
Forward Primer >R31375_seg33junc34-37F1
                                    (SEQ ID NO: 248)
ACTGGCACAGCCTCCAGG

Reverse Primer >R31375_seg33junc34-37R1
                                    (SEQ ID NO: 249)
CATTTGCATTTTGCACTCATG

Amplicon >R31375_seg33junc34-37
                                    (SEQ ID NO: 250)
ACTGGCACAGCCTCCAGGTTGGCGGGCTCATCTGCGCTGGGGTTCTGT

GCGCCATGGGCATCATCATCGTCATGAGTGCAAAATGCAAATG
```

Expression of FXYD3 domain containing ion transport regulator 3 R31375 transcripts which are detectable by amplicon as depicted in sequence name R31375_junc20-22seg30F6R6 (SEQ ID NO: 253) in normal and cancerous ovary tissues and in different normal tissues.

Expression of FXYD3 domain containing ion transport regulator 3 transcripts detectable by or according to junc20-22seg30-R31375_junc20-22seg30F6R6 (SEQ ID NO: 253) amplicon and primers R31375_junc20-22seg30F6 (SEQ ID NO: 251) and R31375_junc20-22seg30R6 (SEQ ID NO: 252) was measured by real time PCR on ovary panel and normal panel. The samples used are detailed in Table 4 and Table 2 above, respectively. For each RT sample, the expression of the above amplicon was normalized to the normalization factor calculated from the expression of several house keeping genes as described in Example 1.

For ovary panel—Non-detected samples (samples no. 2, 6, 9, 12, 15, 19, 21, 24, 32, 34, 38, 45, 53, 56-59, 62, 63, 65-67 and 72-78, Table 4) were assigned Ct value of 41 and were calculated accordingly. The normalized quantity of each RT sample was then divided by the median of the quantities of the normal samples (sample numbers 52, 53, 56-59, 62, 63, 65-67 and 72-78, Table 4 above), to obtain a value of fold up-regulation for each sample relative to median of the normal samples.

Figure 54:
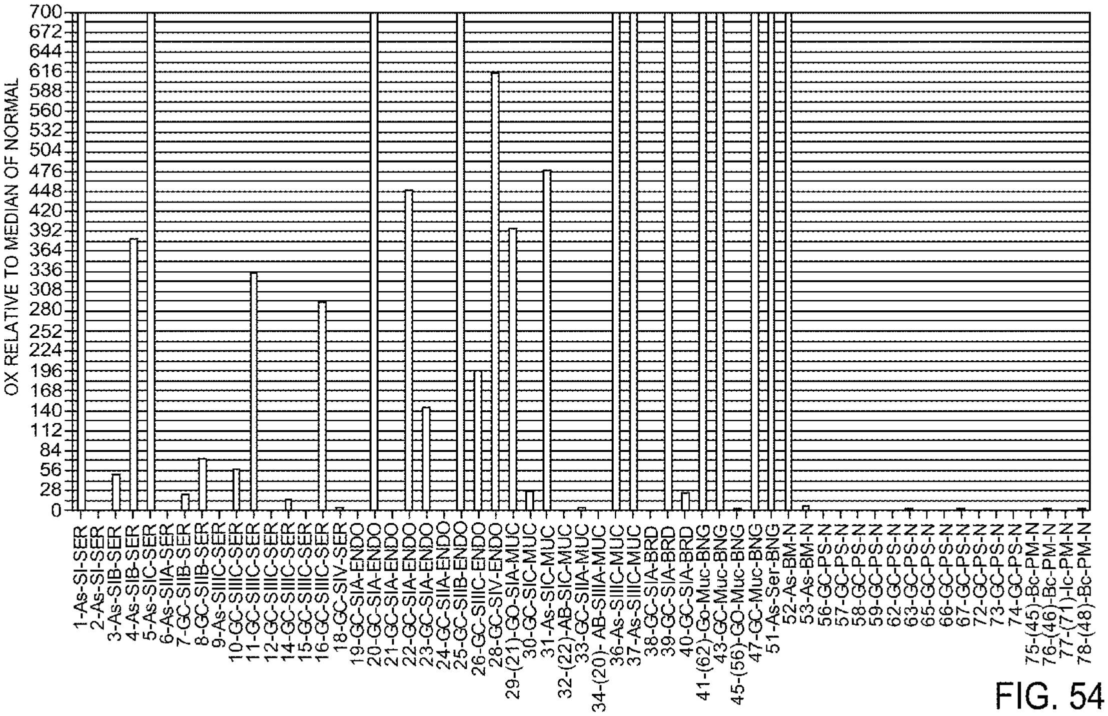
FIG. 54 presents a histogram showing expression of FXYD3 domain containing ion transport regulator 3 R31375 transcripts which are detectable by amplicon as depicted in sequence name R31375_junc20-22seg30F6R6 (SEQ ID NO: 253) in normal and cancerous ovary tissues.

FIG. 54 is a histogram showing over expression of the above-indicated FXYD3 transcripts in cancerous Ovary samples relative to the normal samples.

As is evident from FIG. 54, the expression of FXYD3 transcripts detectable by the above amplicon in adenocarcinoma samples, serous carcinoma samples, mucinous carcinoma samples and endometroid samples was significantly higher than in the non-cancerous samples (sample numbers 52, 53, 56-59, 62, 63, 65-67 and 72-78, Table 4 above). Notably an over-expression of at least 14 fold was found in 21 out of 33 adenocarcinoma samples, 10 out of 16 serous carcinoma samples, in 5 out of 8 mucinous carcinoma samples and in 6 out of 9 endometroid samples.

Statistical analysis was applied to verify the significance of these results, as described below. The P value for the difference in the expression levels of FXYD3 transcripts detectable by the above amplicon in ovary adenocarcinoma samples versus the normal tissue samples was determined by T test as 3.78e-003.

Threshold of 14 fold over expression was found to differentiate between adenocarcinoma, serous carcinoma, mucinous carcinoma and endometriod and normal samples with P value of 4.21e-005, 5.17e-004, 4.46e-003 and 1.73e-003, respectively, as checked by exact Fisher test.

The above values demonstrate statistical significance of the results.

Figure 55:
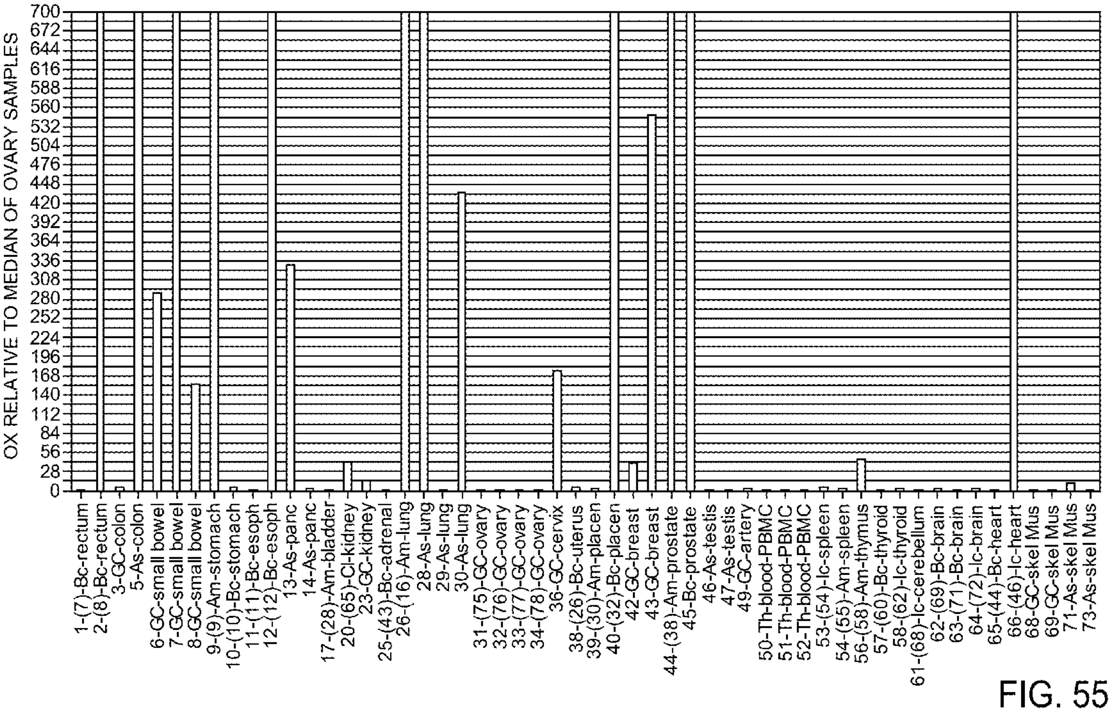
FIG. 55 presents a histogram showing expression of FXYD3 domain containing ion transport regulator 3 R31375 transcripts which are detectable by amplicon as depicted in sequence name R31375_junc20-22seg30F6R6 (SEQ ID NO: 253) in various normal tissues.

For normal panel—Non-detected samples (samples no. 1, 10, 11, 14, 17, 25, 29, 31-34, 38, 39, 46, 47, 49-54, 57, 58, 61-65, 68, 69 and 73, Table 2) were assigned Ct value of 41 and were calculated accordingly. The normalized quantity of each RT sample was then divided by the median of the quantities of the ovary samples (sample numbers 31-34, Table 2 above), to obtain a value of relative expression of each sample relative to median of the ovary samples, as shown in FIG. 55.

Primer pairs are also optionally and preferably encompassed within the present invention; for example, for the above experiment, the following primer pair was used as a non-limiting illustrative example only of a suitable primer pair: R31375_junc20-22seg30F6 (SEQ ID NO: 251) forward primer; and R31375_junc20-22seg30R6 (SEQ ID NO: 252) reverse primer.

The present invention also preferably encompasses any amplicon obtained through the use of any suitable primer pair; for example, for the above experiment, the following amplicon was obtained as a non-limiting illustrative example only of a suitable amplicon: R31375_junc20-22seg30F6R6 (SEQ ID NO: 253).

```
Forward Primer >R31375 junc20-22seg30F6
                                        (SEQ ID NO: 251)
TTGTGTTCCTGGCAGGCTTT

Reverse Primer >R31375_junc20-22seg30R6
                                        (SEQ ID NO: 252)
TCATCTGTCCCCCCATTCTC

Amplicon >R31375_junc20-22seg30F6R6
                                        (SEQ ID NO: 253)
TTGTGTTCCTGGCAGGCTTTCCTGTCCTGGACGCCAATGACCTAGAAGAT

AAAAACAGTCCTTTCTACTATGGTGCTCCATATATATTTGTCAAGAGAAT

GGGGGGACAGATGA
```

Example 8

Cloning of Full Length Transcripts Encoding VSIG1, ILDR1, LOC253012, AI216611, C1ORF32, FXYD3 Fused to EGFP Cloning of Full Length transcripts encoding VSIG1, ILDR1, LOC253012, AI216611, C1ORF32, FXYD3 fused to EGFP was done as described below.

First, EGFP expression vector was constructed and then the VSIG1, ILDR1, LOC253012, AI216611, C1ORF32 or FXYD3 open reading frames (ORFs) were cloned. EGFP was subcloned into pIRESpuro3 (Clontech catalog number: 631619) as follows: EGFP-N1 vector (Clontech cataloge number: 6085-1) was digested with NheI and NotI to excise the EGFP gene. The EGFP insert was then ligated into pIRESpuro3 (Clontech cataloge number: 631619), which was previously digested with the same enzymes, in order to obtain the EGFP-pIRESpuro3 vector.

Cloning of the VSIG1, ILDR1, LOC253012, AI216611, C1ORF32, FXYD3 open reading frames (ORFs) was done using the following steps:

1. A reverse transcription reaction was carried out as follows: 10 μg of purified RNA was mixed with 150 ng Random Hexamer primers (Invitrogen, Carlsbad, Calif., USA, catalog number: 48190-011) and 500 μM dNTPs in a total volume of 156 μl. The mixture was incubated for 5 min at 65□C and then quickly chilled on ice. Thereafter, 50 μl of 5× SuperscriptII first strand buffer (Invitrogen, catalog number: 18064-014, part number: Y00146), 24 μl 0.1M DTT and 400 units RNasin (Promega, Milwaukee, Wis., U.S.A., catalog number: N2511) were added, and the mixture was incubated for 10 min at 25□C, followed by further incubation at 42□C for 2 min. Then, 10 μl (2000 units) of SuperscriptII (Invitrogen, catalog number: 18064-014) was added and the reaction (final volume of 250 μl) was incubated for 50 min at 42□C and then inactivated at 70□C for 15 min. The resulting cDNA was diluted 1:20 in TE buffer (10 mM Tris, 1 mM EDTA pH 8).

2. PCR was done using Platinum PFX™ (Invitrogen., Carlsbad, Calif., USA, catalog number: 1178-021) under the following conditions: 5 μl Platinum PFX 10× buffer; 5 μl—cDNA from the above; 2 μl-10 mM dNTPs (2.5 mM of each nucleotide); 0.5 μl—Platinum PFX enzyme; 37 μl—H2O; and 1.5 μl—of each primer (15 μM) in a total reaction volume of 50 μl; with a reaction program of 5 minutes in 95° C.; 35 cycles of: 30 seconds at 94° C., 30 seconds at 55° C., 50 seconds at 68° C.; then 10 minutes at 68° C. Primers which were used include gene specific sequences corresponding to the desired coordinates of the protein and restriction enzyme sites and Kozak sequence, as listed in table 136, below. Bold letters in Table 136 represent the specific gene sequence while the restriction site extensions utilized for cloning purposes are in Italic and kozak sequences are underlined.

Table 136 demonstartes the cloning steps of ORF targets. For example, FXYD3_T25_P14 and VSIG1_T6_P5 were cloned by PCR amplification of two overlapping fragments of the full length at step 1, followed by additional PCR at step 2 using both PCR fragments from step 1 as a template for generating the full length. VSIG1_T5_P4 was cloned using both PCR fragments generated at step 1 for digestion and direct ligation, AI216611_T1_P1 was cloned by performing nested PCR on the PCR product generated from step 1. 5 μl of products No. 1, 4, 5, 8, 9, 10, 11, 12, 15, 16 and 17 (Table 136), were loaded onto a 1% agarose gel stained with ethidium bromide, electrophoresed in 1×TBE solution at 100V, and visualized with UV light. After verification of expected size band, remaining PCR product was processed for DNA purification using Qiaquick PCR purification kit (Qiagen™, Valencia, Calif., U.S.A., catalog number 28106). The extracted PCR products were digested with the appropriate restriction enzymes (New England Biolabs, Beverly, Mass., U.S.A.), as listed in table 136. After digestion, DNAs were loaded onto a 1% agarose gel as described above. The expected band size was excised and extracted from the gel using QiaQuick™ Gel Extraction kit (Qiagen, catalog number: 28707).

The digested targets' ORF DNAs were ligated to EGFP_pIRESpuro3 vector using the LigaFast™ Rapid DNA Ligation System (Promega, catalog number: M8221.). The resulting DNAs were transformed into competent *E. Coli* bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C.

The following day, a number of colonies from each transformation that grew on the selective plates were taken for further analysis by streak-plating on another selective plate and by PCR using GoTaq ReadyMix (Promega, catalog number: M7122.). Screening positive clones was performed by PCR using pIRESpuro3 vector specific primer and gene specific primer (data not shown). After completion of all PCR cycles, half of the reaction was analyzed using 1% agarose gel as described above. After verification of expected size band, 2 positive colonies from each ligation reactions were grown in 5 ml Terrific Broth supplemented with 100 μg/ml ampicillin, with shaking overnight at 37° C. Plasmid DNA was isolated from bacterial cultures using Qiaprep™ Spin Miniprep Kit (Qiagen, catalog number: 27106). Accurate cloning was verified by sequencing the inserts (Weizmann Institute, Rehovot, Israel). Upon verification of an error-free colony (i.e. no mutations within the ORF), recombinant plasmids were processed for further analysises.

The DNA sequences of the resulting VSIG1, ILDR1, LOC253012, AI216611, C1ORF32 or FXYD3 full length fused to EGFP are shown in FIGS. 56A-J. In FIGS. 56A-J gene specific sequence correspond to the target's full length sequence is marked in bold faced, EGFP sequence is unbold Italic and known SNPs/silence mutations are underlined. FIG. 56A presents the DNA sequence of FXYD3 T0_P0_EGFP (996bp)(SEQ ID NO:77); FIG. 56B presents the DNA sequence of FXYD3_T25_P14_EGFP (1083bp) (SEQ ID NO:78); FIG. 56C presents the DNA sequence of AI216611_T0_P0_EGFP (1371bp) (SEQ ID NO:79); FIG. 56D presents the DNA sequence of AI216611_T1_P1_EGFP (1332bp) (SEQ ID NO:80); FIG. 56E presents the DNA sequence of C1ORF32_T8_P8 EGFP (1533bp) (SEQ ID NO:81); FIG. 56F presents the DNA sequence of LOC253012_T4_P5_EGFP (2085bp) (SEQ ID NO:82); FIG. 56G presents the DNA sequence of ILDR1_T0_P3 EGFP DNA sequence (2373bp) (SEQ ID NO:83); FIG. 56H presents the DNA sequence of ILDR1_T2_P5_EGFP (2241bp) (SEQ ID NO:84); FIG. 56I presents the DNA sequence of VSIG1_T6_P5_EGFP (2082bp) (SEQ ID NO:85); FIG. 56J presents the DNA sequence of VSIG1_T5_P4_EGFP DNA (2004bp) (SEQ ID NO:86).

The amino acid sequences of the resulting VSIG1, ILDR1, LOC253012, AI216611, C1ORF32 or FXYD3 full length fused to EGFP are shown in FIG. 57A-J; gene specific sequence correspond to the full length sequence of the protein is marked in bold faced, EGFP sequence is unbold Italic and amino acids modified due to known SNPs are underlined. FIG. 57A presents the amino acid sequence of FXYD3_P0_EGFP protein (331aa) (SEQ ID NO:87); FIG. 57B presents the amino acid sequence of FXYD3_P14_EGFP protein (360aa) (SEQ ID NO:88); FIG. 57C presents the amino acid sequence of AI216611_P0_EGFP protein (456aa) (SEQ ID NO:89); FIG. 57D presents the amino acid sequence of AI216611_P1_EGFP protein (443aa) (SEQ ID NO:90); FIG. 57E presents the amino acid sequence of C1ORF32_P8 EGFP protein (510aa) (SEQ ID NO:91); FIG. 57F presents the amino acid sequence of LOC253012_P5_EGFP protein (694aa) (SEQ ID NO:92); FIG. 57G presents the amino acid sequence of ILDR1_P3 EGFP protein (790aa) (SEQ ID NO:93); FIG. 57H presents the amino acid sequence of ILDR1_P5_EGFP protein (746aa) (SEQ ID NO:94); FIG. 57I presents the amino acid sequence of VSIG1_P5_EGFP protein (693aa) (SEQ ID NO:95); FIG. 57J presents the amino acid sequence of VSIG1_P4_EGFP protein (667aa) (SEQ ID NO:96).

TABLE 136 full length cloning details

| CGEN ID | Target name | Full length (aa) | PCR product No | DNA template | Primer ID | Primer sequence | Primer orientation | Restriction site |
|---|---|---|---|---|---|---|---|---|
| CGEN 789 | FXYD3_T0_P0 | 87 | 1 | ovary 30, 39, 59 cDNA (Table 4) | 100-813 (SEQ ID NO: 254) | CTA*GCTAGCCACC* **ATGCAGAAGGTGA CCCTG** | For | NheI |
| | | | | | 100-814 (SEQ ID NO: 255) | CGCG*ACCGGT*CCG **CTTTGGGCTGAGC CTGG** | Rev | AgeI |
| | FXYD3_T25_P14 | 116 | 2 | lung 1, 19, 20, 37, 42 cDNA (Table 3) | 100-813 (SEQ ID NO: 254) | CTA*GCTAGCCACC* **ATGCAGAAGGTGA CCCTG** | For | NheI |
| | | | | | 100-843 (SEQ ID NO: 256) | CCTGTGTCCTCTT CATCTGTC | Rev | |
| | | | 3 | lung 1, 19, 20, 37, 42 cDNA (Table 3) | 100-842 (SEQ ID NO: 257) | GACAGATGAAGAG GACACAGG | For | |
| | | | | | 100-814 (SEQ ID NO: 255) | CGCG*ACCGGT*CCG **CTTTGGGCTGAGC CTGG** | Rev | AgeI |
| | | | 4 | PCR products No 2 + 3 above | 100-813 (SEQ ID NO: 254) | CTA*GCTAGCCACC* **ATGCAGAAGGTGA CCCTG** | For | NheI |
| | | | | | 100-814 (SEQ ID NO: 255) | CGCG*ACCGGT*CCG **CTTTGGGCTGAGC CTGG** | Rev | AgeI |

TABLE 136-continued full length cloning details

| CGEN ID | Target name | Full length (aa) | PCR product No | DNA template | Primer ID | Primer sequence | Primer orientation | Restriction site |
|---|---|---|---|---|---|---|---|---|
| CGEN 721 | AI216611_T0_P0 | 200 | 5 | lung 49 cDNA (Table 3) | 100-740 (SEQ ID NO: 258) | CTAGCTAGCCACC**ATGAGGCCTCTGCCCAGCG** | For | NheI |
| | | | | | 100-741 (SEQ ID NO: 259) | CGCGAATTC**GACACTCAACATCTTCCAGCTC** | Rev | EcoRI |
| | AI216611_T1_P1 | 199 | 6 | lung 4 cDNA (Table 3) | 100-738 (SEQ ID NO: 260) | AAGGCTGCATAGGAGCTG | For | |
| | | | | | 100-919 (SEQ ID NO: 261) | CAATGAGTTGGAAATCAAGCCAC | Rev | |
| | | | 7 | PCR product No 6 above | 100-740 (SEQ ID NO: 258) | CTAGCTAGCCACC**ATGAGGCCTCTGCCCAGCG** | For | NheI |
| | | | | | 100-919 (SEQ ID NO: 261) | CAATGAGTTGGAAATCAAGCCAC | Rev | |
| | | | 8 | PCR product No 7 above | 100-740 (SEQ ID NO: 258) | CTAGCTAGCCACC**ATGAGGCCTCTGCCCAGCG** | For | NheI |
| | | | | | 100-836 (SEQ ID NO: 262) | CGCGACCGGTCC**AAACCACTCATGGATTATCACAAGGCCCAGGGGGTTACCTTTGAGTTTGTGTCTTCTC** | Rev | AgeI |
| CGEN 754 | C1ORF32_T8_P8 | 254 | 9 | lung 44, 45, 48 cDNA (Table 3) | 100-746 (SEQ ID NO: 263) | CTAGCTAGCCACC**ATGGATAGGGTCTTGCTGAG** | For | NheI |
| | | | | | 100-694 (SEQ ID NO: 264) | CGCGAATTCGGGT**AGAGAGGTAGACATTTC** | Rev | EcoRI |
| CGEN 702 | LOC253012_T4_P5 | 450 | 10 | IMAGE clone BD139906.1 | 100-765 (SEQ ID NO: 265) | GCGCTTCGAAGCCACC**ATGTGGCTCAAGGTCTTCAC** | For | BstBI |
| | | | | | 100-766 (SEQ ID NO: 266) | CGCGACCGGTCC**CTCTGGATGGTCTTGCTGCTG** | Rev | AgeI |
| CGEN 770 | ILDR1_T0_P3 | 546 | 11 | ovary 19, 20, 27 cDNA (Table 4) | 100-780 (SEQ ID NO: 267) | CTAGCTAGCCACC**ATGGCATGGCCCAAACTGCC** | For | NheI NheI |
| | | | | | 100-781 (SEQ ID NO: 268) | CGCGACCGGTCC**AATGACCACACTCCTTCCACTA** | Rev | AgeI |
| | ILDRI_T2_P5 | 502 | 12 | ovary 19, 20, 27 cDNA (Table 4) | 100-780 (SEQ ID NO: 267) | CTAGCTAGCCACC**ATGGCATGGCCCAAACTGCC** | For | NheI |
| | | | | | 100-781 (SEQ ID NO: 268) | CGCGACCGGTCC**AATGACCACACTCCTTCCACTA** | Rev | AgeI |
| CGEN 768 | VSIG1_T6_P5 | 449 | 13 | lung 17 cDNA (Table 3) | 100-783 (SEQ ID NO: 269) | CTAGCTAGCCACC**ATGGTGTTCGCATTTTGGAAG** | For | NheI |
| | | | | | 100-838 (SEQ ID NO: 270) | CTGGAGTTCAGCCTGCTGTCCATCAAGAG | Rev | |
| | | | 14 | lung 17 cDNA (Table 3) | 100-837 (SEQ ID NO: 271) | CTCTTGATGGACAGCAGGCTGAACTCCAG C | For | |
| | | | | | 100-782 (SEQ ID NO: 272) | CGCGACCGGTCC**TGCCTTAACCACTCCCTTTTC** | Rev | AgeI |

TABLE 136-continued full length cloning details

| CGEN ID | Target name | Full length (aa) | PCR product No | DNA template | Primer ID | Primer sequence | Primer orientation | Restriction site |
|---|---|---|---|---|---|---|---|---|
| | | | 15 | PCR produts No 13 + 14 above | 100-783 (SEQ ID NO: 269) | CTAGCTAGCCACCATGGTGTTCGCATTTTGGAAG | For | NheI |
| | | | | | 100-782 (SEQ ID NO: 272) | CGCGACCGGTCCTGCCTTAACCACTCCCTTTTC | Rev | AgeI |
| | VSIG1_T5_P4 | 423 | 16 | lung 4 cDNA (Table 3) | 100-783 (SEQ ID NO: 269) | CTAGCTAGCCACCATGGTGTTCGCATTTTGGAAG | For | NheI |
| | | | | | 100-785 (SEQ ID NO: 273) | CCTCAGTACTGAGGCACGAGCTGTG | Rev | ScaI |
| | | | 17 | lung 4 cDNA (Table 3) | 100-784 (SEQ ID NO: 274) | CCTCAGTACTGAGGGTATGG | For | ScaI |
| | | | | | 100-782 (SEQ ID NO: 272) | CGCGACCGGTCCTGCCTTAACCACTCCCTTTTC | Rev | AgeI |

Example 9

Determining Cell Localization of VSIG1, ILDR1, LOC253012, AI216611, C1ORF32 and FXYD3

In order to determine the cellular localization of the protein targets, they were cloned as EGFP (Enhanced Green Fluorescent Protein) fusion proteins. Proteins localization was observed upon transient transfection (Chen et al., Molecular vision 2002; 8; 372-388) using the confocal microscope. The cells were observed for the presence of fluorescent products 48 hours following transfection.

Determining cell localization of VSIG1, ILDR1, LOC253012, AI216611, C1ORF32 and FXYD3 was done by transient transfection of the recombinant ORF-EGFP constructs which were described above.

The VSIG1, ILDR1, LOC253012, AI216611, C1ORF32 and FXYD3-EGFP pIRESpuro3 constructs were subsequently transiently transfected into HEK-293T cells as follows:

HEK-293T (ATCC, CRL-11268) cells were plated on sterile glass coverslips, 13 mm diameter (Marienfeld, catalog number: 01 115 30), which were placed in a 6 well plate, using 2 ml pre-warmed DMEM [Dulbecco's modified Eagle's Media, Biological Industries (Beit Ha'Emek, Israel), cataloge number: 01-055-1A]+10% FBS (Fetal Bovin Serum)+4 mM L-Glutamine. 500,000 cells per well were transfected with 2 μg of the DNA construct using 6 μl FuGENE 6 reagent (Roche, catalog number: 11-814-443-001) diluted into 94 ul DMEM. The mixture was incubated at room temperature for 15 minutes. The complex mixture was added dropwise to the cells and swirled. Cells were placed in incubator maintained at 37° C. with 5% CO2 content.

48 hours post transient transfection the cells were further processed for analysis in confocal microscopy. The cover slips were washed 3 times in phosphate buffered saline (PBS) and fixed for 15 minutes with 3.7% or 1% paraformaldehyde (PFA) (Sigma, catalog number: P-6148). After 2 washes in PBS, the fixed coverslips were glued to a slide using mounting solution (Sigma, catalog number: G0918) and cells were observed for the presence of fluorescent product using confocal microscope. The results are presented in FIG. 58A-F.

Figure 58A:
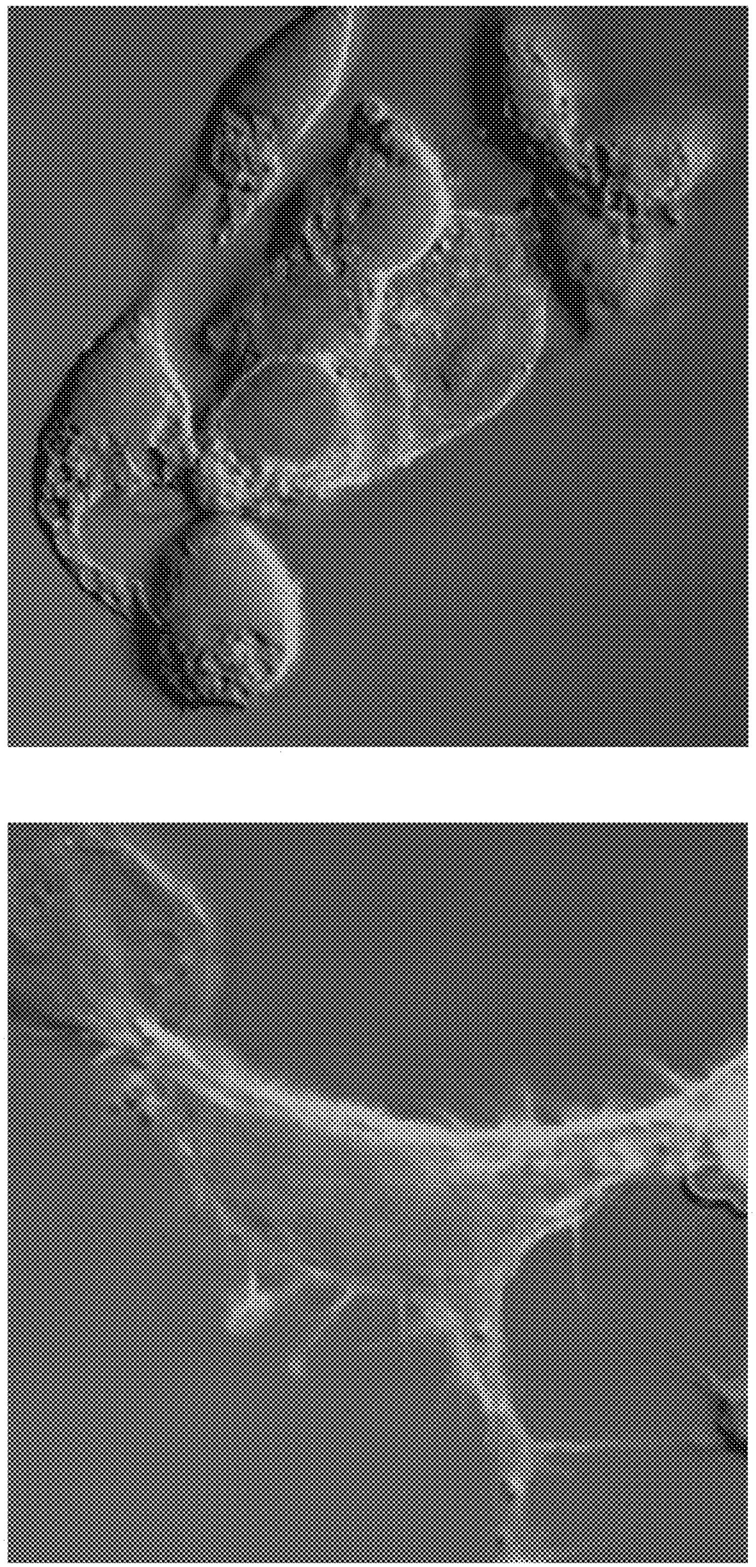
FIGS. 58A-58F demonstrate the localization of the proteins of invention to cell membrane.

FIG. 58A demonstrates that the AI216611_P0_EGFP (SEQ ID NO:89) and AI216611_P1_EGFP (SEQ ID NO:90) fused proteins localizes to cell membrane upon expression in HEK 293T cells. The image was obtained using the 40× objective of the confocal microscope.

Figure 58B:
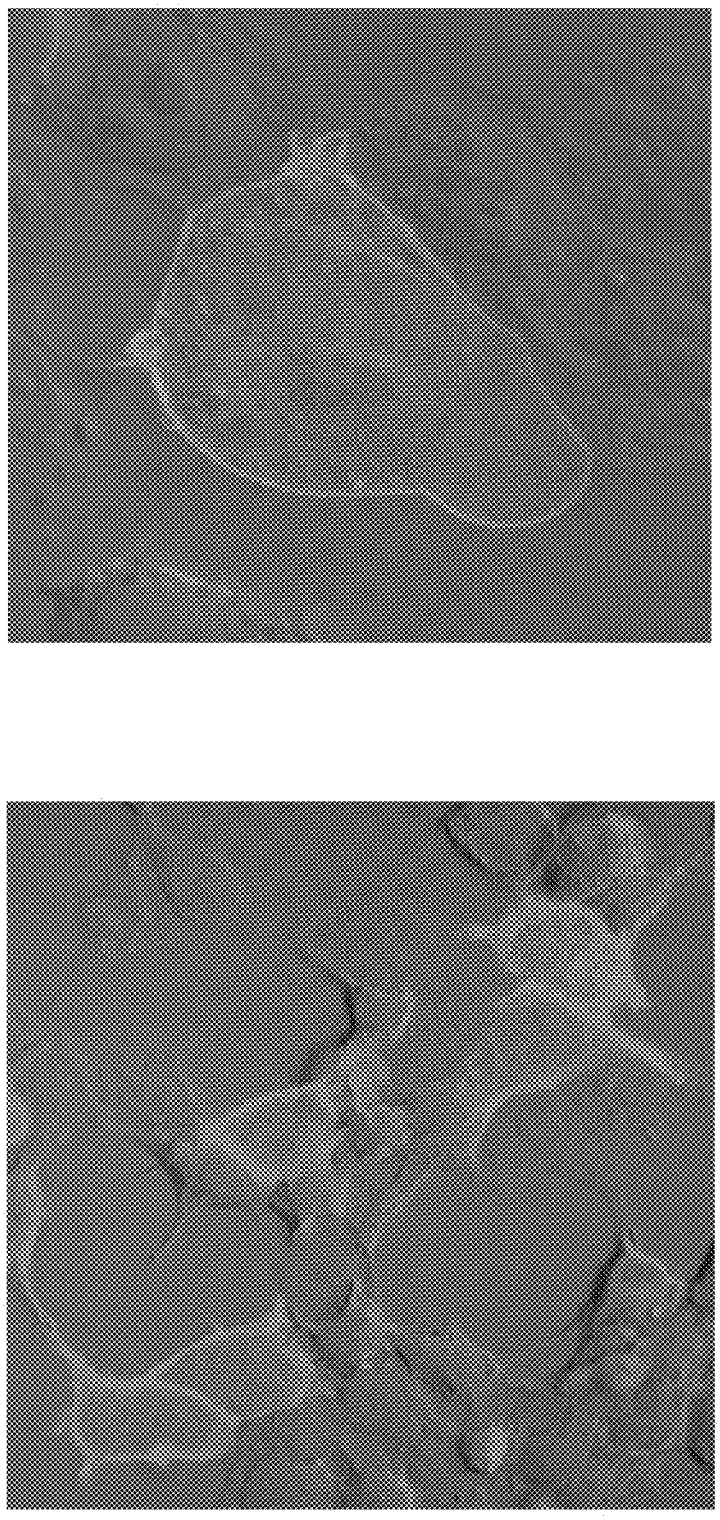

FIG. 58B demonstrates that the FXYD3_P0_EGFP (SEQ ID NO:87) and FXYD3_P14_EGFP (SEQ ID NO:88) fused proteins localizes to cell membrane upon expression in HEK 293T cells. The image was obtained using the 40× objective of the confocal microscope.

Figure 58C:
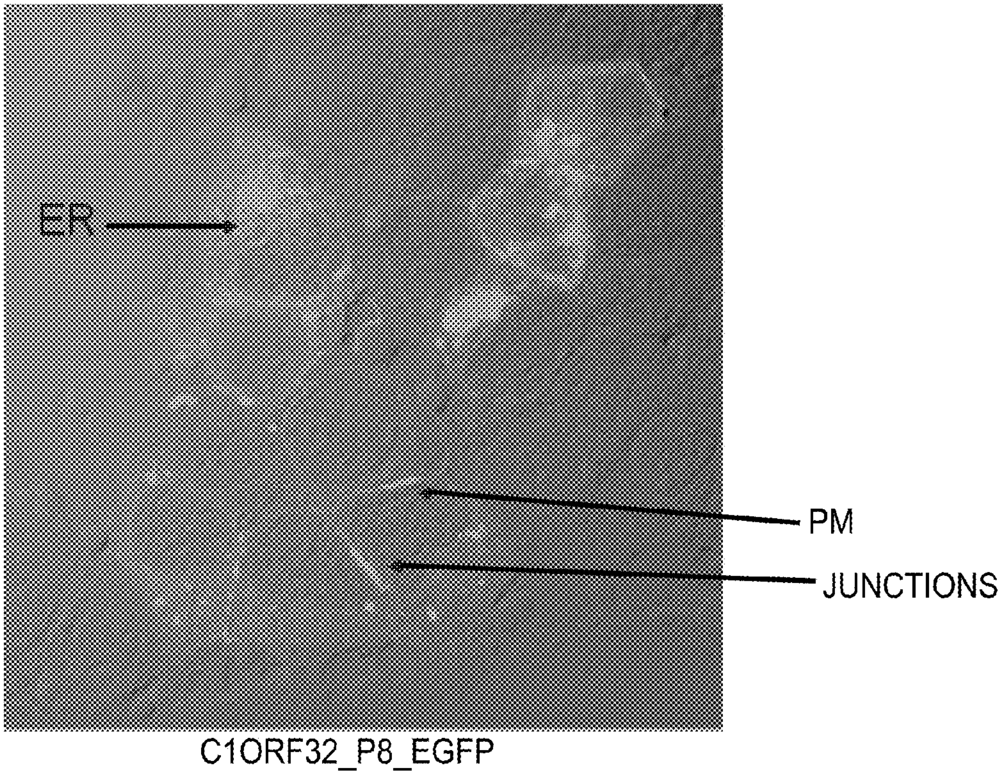

FIG. 58C demonstrates that the C1ORF32_P8 EGFP (SEQ ID NO:91) fused protein localizes to cell membrane; endoplasmatic reticulum (ER) membrane and to cell junctions upon expression in HEK 293T cells. The image was obtained using the 40× objective of the confocal microscope.

Figure 58D:
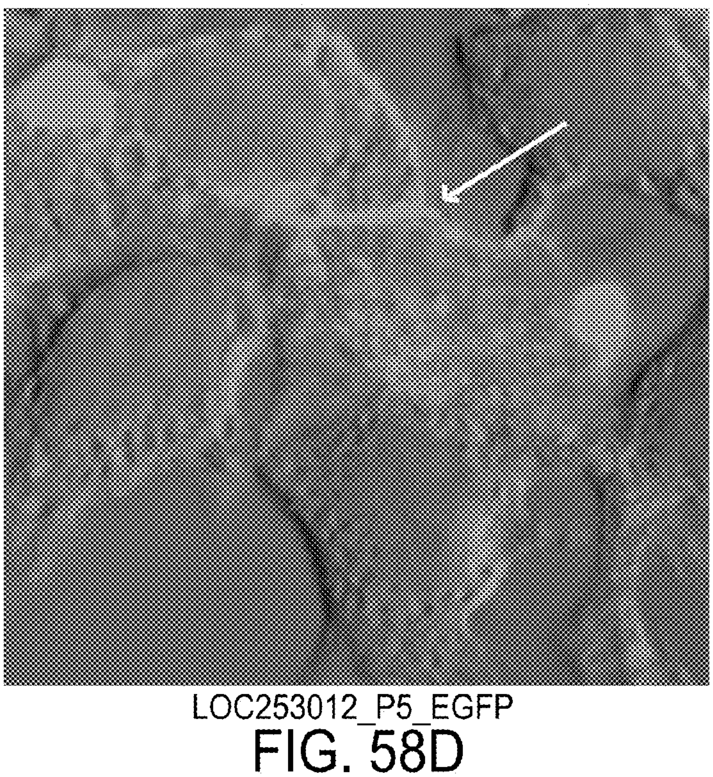

FIG. 58D demonstrates that the LOC253012_P5_EGFP (SEQ ID NO:92) fused protein localizes to cell membrane and endoplasmatic reticulum (ER) membrane upon expression in HEK 293T cells. The image was obtained using the 40× objective of the confocal microscope.

Figure 58E:
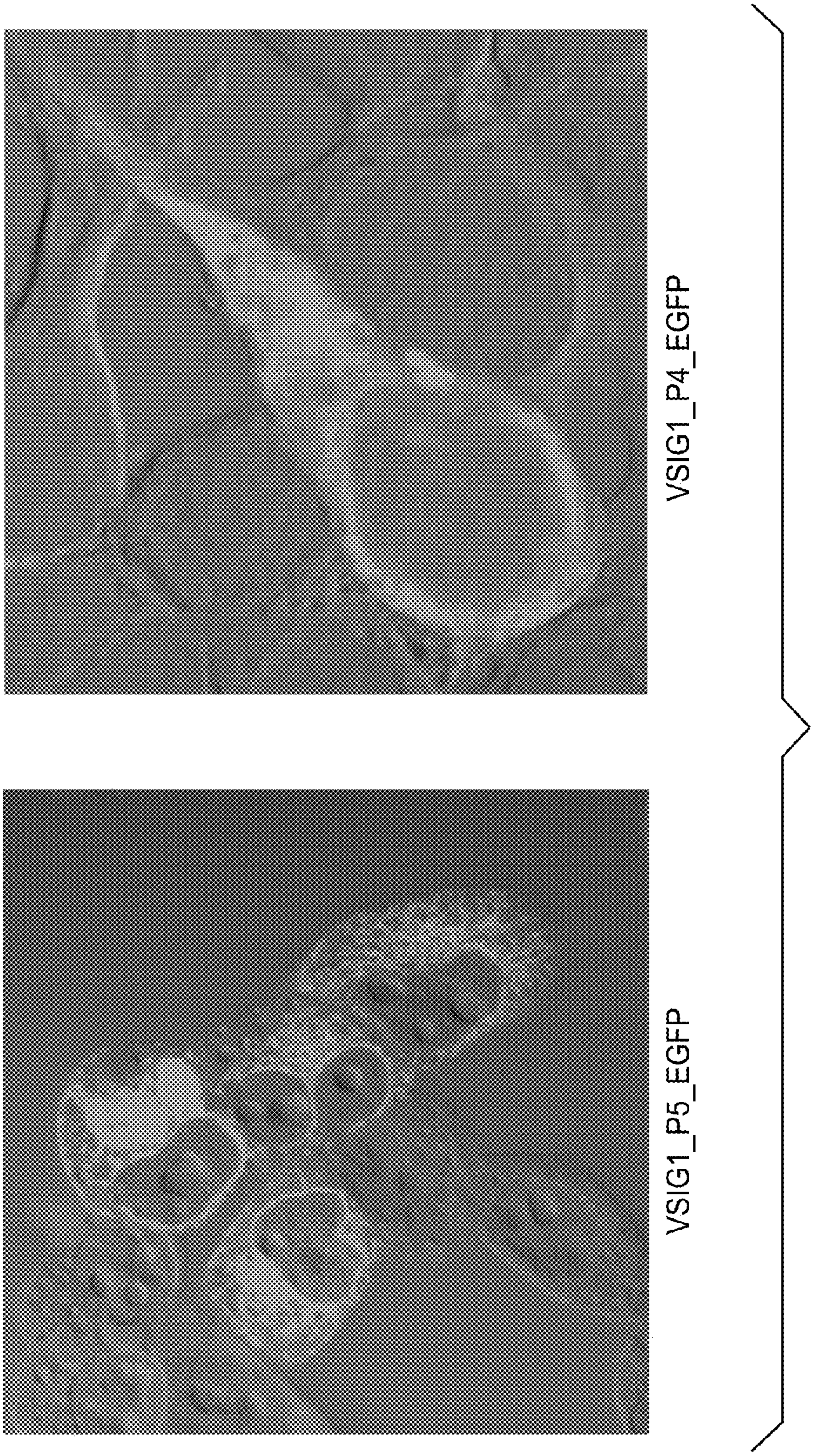

FIG. 58E demonstrates that the VSIG1_P5_EGFP (SEQ ID NO:95) and VSIG1-P4_EGFP (SEQ ID NO:96) fused proteins localizes to nuclear cell membrane and endoplasmatic reticulum membrane upon expression in HEK 293T cells. The image was obtained using the 40× objective of the confocal microscope.

Figure 58F:
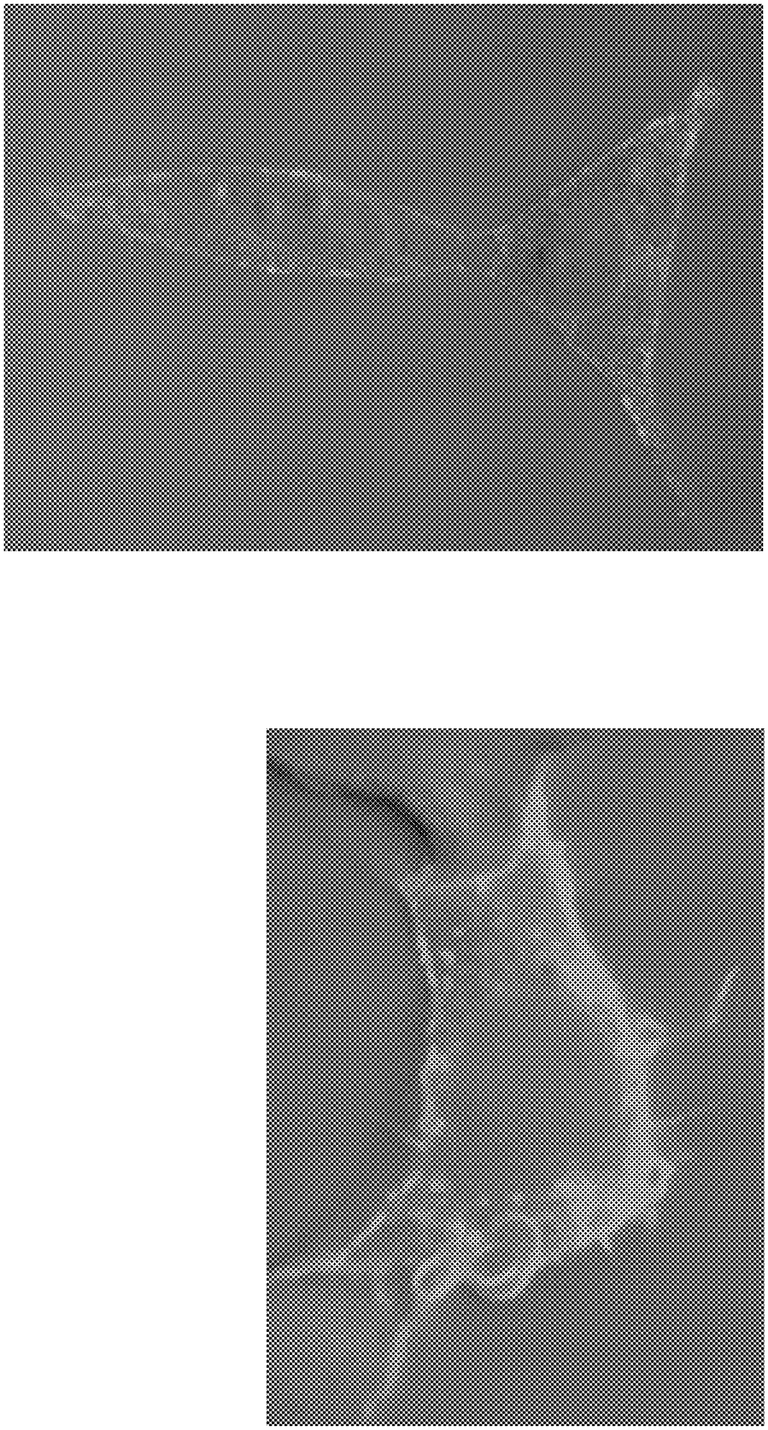

FIG. 58F demonstrates that the ILDR1_P3 EGFP (SEQ ID NO:93) and ILDR1_P5_EGFP (SEQ ID NO:94) fused proteins localizes to cell membrane and endoplasmatic reticulum membrane upon expression in HEK 293T cells. The image was obtained using the 40× objective of the confocal microscope.

Example 10

Cloning and Expression of VSIG1, ILDR1, LOC253012, AI216611, C1ORF32 and FXYD3 Extra Cellular Domain (ECD) Fused to Mouse Fc The purpose of this analysis was to clone the VSIG1, ILDR1, LOC253012, AI216611, C1ORF32 and FXYD3

ECDs fused via its corresponding C' terminus to mouse Fc (mFc), and to express the fused ECDs in HEK293T cells (ATCC-CRL-11268), in order to be further used for antibody production as well as for functional assessment of VSIG1, ILDR1, LOC253012, AI216611, C1ORF32 and FXYD3 ECDs.

The coordinates of the cloned ECD are described in table 137:

TABLE 137

| CG EN ID | protein name | Transcript No. | Protein No. | Full length (aa) | Recombinant ECD Coordinates (aa) | SEQ ID |
|---|---|---|---|---|---|---|
| CG EN789 | FXYD3 | T25 (SEQ ID NO: 66) | P14 (SEQ ID NO:72) | 116 | 1-63 | SEQ ID No.-297 |
| CG EN721 | AI216611 | T0 (SEQ ID NO: 41) | P0 (SEQ ID NO: 43) | 200 | 1-145 | SEQ ID No.-298 |
| CG EN754 | C1ORF32 | T8 (SEQ ID NO: 45) | P8 (SEQ ID NO: 48) | 254 | 1-184 | SEQ ID No.-299 |
| CG EN702 | LOC253012 | T4 (SEQ ID NO: 26) | P5 (SEQ ID NO: 36) | 450 | 1-335 | SEQ ID No.-300 |
| CG EN770 | ILDR1 | T0 (SEQ ID NO: 17) | P3 (SEQ ID NO: 22) | 546 | 51-160 | SEQ ID No.-301 |
| CG EN768 | VSIG1 | T6 (SEQ ID NO: 7) | P5 (SEQ ID NO: 13) | 449 | 26-293 | SEQ ID No.-302 |

The cloning of the fusion proteins (ECD_mFc) was done in two steps:

1. Cloning of ECD to pIRESpuro3.
2. Subcloning of the mouse Fc IgG2a in frame to the C' terminus of the ECD previously cloned into pIRESpuro3, from step1.

The cloning of ECD to pIRESpuro3 was carried out as follows:

Cloning of the ECD for each one of the VSIG1, ILDR1, LOC253012, AI216611, C1ORF32 and FXYD3 was done by PCR delimit partial amino acids sequence of its ECD as described in table 137, using its full length sequence as a template, and primers as listed in table 138.

TABLE 138

ECD cloning details

| CGEN ID | candidate name | primer ID | primer sequence | Primer orientation | restriction site |
|---|---|---|---|---|---|
| CGEN789 | FXYD3 | 100-813 SEQ ID NO: 254 | CTA*GCTAGC*CACC**ATGCAGAAGGTGACCCTG** | For | NheI |
| | | 100-852 SEQ ID NO: 275 | CGC*GGATCC***CCAGTCTAGGAGGAAAGTGG** | Rev | BamHI |
| CGEN721 | AI216611 | 100-740 SEQ ID NO: 258 | CTA*GCTAGC*CACC**ATGAGGCCTCTGCCCAGCG** | For | NheI |
| | | 100-850 SEQ ID NO: 276 | CGC*GGATCC***GTCTTCATAGAGGATCTCAG** | Rev | BamHI BamHI |
| CGEN754 | C1ORF32 | 100-746 SEQ ID NO: 263 | CTA*GCTAGC*CACC**ATGGATAGGGTCTTGCTGAG** | For | NheI |
| | | 100-851 SEQ ID NO: 277 | CGC*GGATCC***CATAATCTCCACAGCAAAAC** | Rev | BamHI |
| CGEN702 | LOC253012 | 100-789 SEQ ID NO: 278 | AA*CCGGT*GCCACC**ATGTGGCTCAAGGTCTTCAC** | For | AgeI |
| | | 100-854 SEQ ID NO: 279 | CGC*GGATCC***TTTTCCTTTCTGTGCAAGCT** | Rev | BamHI |
| CGEN770 | ILDRI | 100-873 SEQ ID NO: 280 | GCG*TTCGAA***GCCCAGCTCCAGGACGTGGTG** | For | BstBI |
| | | 100-853 SEQ ID NO: 281 | CGC*GGATCC***TTCCTTATCGGGGTCTCCTG** | Rev | BamHI |

TABLE 138-continued

| ECD cloning details | | | | | |
|---|---|---|---|---|---|
| CGEN ID | candidate name | primer ID | primer sequence | Primer orientation | restriction site |
| CGEN768 | VSIG1 | 100-867 SEQ ID NO: 282 | GCGC*TTCGAA***ATCCCAGACGGTTTCGTG** | For | BstBI |
| | | 100-855 SEQ ID NO: 283 | CGC*GGATCC***TGGATGTGAAGAAGTGAGAT** | Rev | BamHI |

In Table 138, above the bold letters represent the gene specific sequence while the restriction site extensiuons utilized for cloning purposes are Italic and Kozak sequence is underlined.

The PCR products were purified and digested with the appropriate restriction enzymes as describe in table 138. PCR products for FXYD3, AI216611, C1ORF32 and LOC253012 were ligated into pIRESpuro3, while PCR products for VSIG1 and ILDR1 were ligated into IL6sp pIRESpuro3 in order to increase their secretion. The ligation mixture was transformed into DH5a competent cells. Positive transformants were screened and verified by DNA sequencing.

Cloning of ECD-mFc pIRESpuro3

Mouse Fc (IgG2a) (Accession-CAA49868 aa 237-469) protein sequence followed by TEV cleavage site sequence was codon optimized to boost protein expression in mammalian system. The optimized sequence was synthesized by GeneArt (Germany) with flanking BamHI restriction site at the N' terminus and NotI restriction site at the C' terminus. The DNA fragment was digested with BamHI/NotI and ligated in frame into ECD_pIRESpuro3 constructs previously digested with the same enzymes to give ECD_mFc pIRESpuro3. The ligation mixture was transformed into DH5a competent cells. Positive transformants were screened and verified by DNA sequencing.

The nucleotide sequences of the resulting ECD_mFc ORFs are shown in FIG. 59A-F: gene specific sequence correspond to the ECD sequence is marked in bold faced, TEV cleavage site sequence is underlined, mFc sequence is unbold Italic and IL6sp sequence is bold Italic. FIG. 59A shows the FXYD3_T25_P14_ECD_mFc DNA sequence (924bp) (SEQ ID NO:97); FIG. 59B shows the AI216611_T0_P0_ECD_mFc DNA sequence (1170bp) (SEQ ID NO:98), FIG. 59C shows the C1ORF32_T8_P8_ECD_mFc DNA sequence (1287bp) (SEQ ID NO:99); FIG. 59D shows the LOC253012_T4_P5_ECD_mFc DNA sequence (1740bp) (SEQ ID NO:100), FIG. 59E shows the ILDR1_T0_P3_ECD_mFc DNA sequence (1167bp) (SEQ ID NO:101), and FIG. 59F shows the VSIG1_T6_P5_ECD_mFc DNA sequence (1641bp) (SEQ ID NO:102).

The sequence of the resulting ECD_mFc fusion proteins are shown in FIG. 60A-60F; gene specific sequence correspond to the ECD sequence is marked in bold faced, TEV cleavage site sequence is underlined, mFc sequence is unbold Italic and IL6sp sequence is bold Italic. FIG. 60A shows the FXYD3_T25_P14_ECD_mFc amino acid sequence (307aa) (SEQ ID NO:103); FIG. 60B shows the AI216611_T0_P0_ECD_mFc amino acid sequence (389aa) (SEQ ID NO:104), FIG. 60C shows the C1ORF32_T8_P8_ECD_mFc amino acid sequence (428aa) (SEQ ID NO:105); FIG. 60D shows the LOC253012_T4_P5_ECD_mFc amino acid sequence (579aa) (SEQ ID NO:106), FIG. 60E shows the ILDR1_T0_P3_ECD_mFc amino acid sequence (388aa) (SEQ ID NO:107), and FIG. 60F shows the VSIG1_T6_P5_ECD_mFc amino acid sequence (546aa) (SEQ ID NO:108).

To generate ECD-mFc expressing cells, HEK-293T cells were transfected with the above described constructs corresponding to VSIG1, ILDR1, LOC253012, AI216611, C1ORF32 and FXYD3 extra cellular domain fused to mouse Fc. Stable pools were generated as follows 48 hrs post transfection, the cells were trypsinized and transferred to T75 flask containing selection medium (DMEM 10% FCS and 5 μg/ml puromycin) for obtaining stable pool. Media was changed every 3 to 4 days until colonies formation.

To verify the identity of cells, genomic PCR was performed, indicating the correct sequences integrated into the cell genome (data not shown).

Cell-deprived medium was collected and purified by Protein A-Sepharose beads (Amersham catalog number 17-5280-04) as follows: 1 ml of cell-deprived medium was incubated with 50 μl Protein A sepharose beads for 45 minutes at room temperature. At the end of incubation time proteins were eluted from the beads pellet with 50 μl sample buffer containing 100 mM Citrate Phosphate pH 3.5 and 10 mM DTT. The samples were boiled for 3 minutes and 25 μl were loaded on 12% NuPAGE Bis Tris gel (Invitrogen, catalog number NPO342). The proteins were transferred to a nitrocellulose membrane and blocked with 10% low fat milk in PBST (PBS supplemented with 0.05% tween-20). The membrane was then blotted for 1 hour with Goat anti mouse IgG Fc fragment HRP (Jackson, catalog number 115-035-206.) (1:40,000 in blocking solution) at room temperature. Following incubation with ECL solution (Amersham Biosciences, Catalog No. RPN2209), the membrane was exposed to film.

Figure 61:
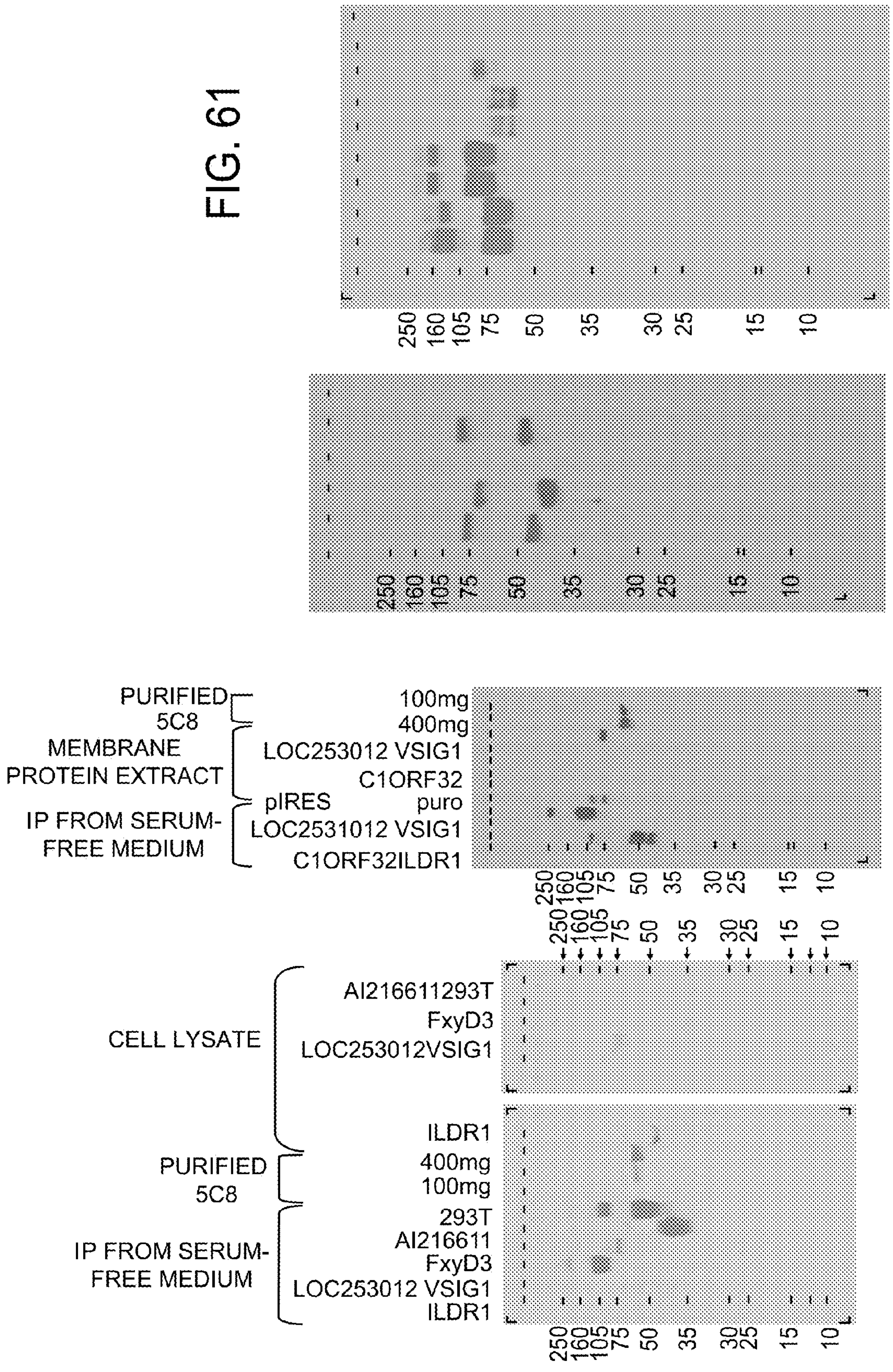
FIG. 61 shows the results of a western blot analysis of the expressed FXYD3_ECD_mFc (SEQ ID NO:103), AI216611 ECD_mFc (SEQ ID NO:104), C1ORF32_ECD_mFc (SEQ ID NO:105), LOC253012_ECD_mFc (SEQ ID NO:106), ILDR1_ECD_mFc (SEQ ID NO:107), VSIG1_ECD_mFc (SEQ ID NO:108). The lanes are as follows: lane 1 Molecular weight markers (Amersham, full range ranbow, catalog number RPN800); lane 2—LOC253012_ECD_mFc; lane 3-FXYD3_ECD_mFc; lane 4—AI216611 ECD_mFc; lane 5—C1ORF32_ECD_mFc; lane 6—ILDR1_ECD_mFc; lane 7—VSIG1_ECD_mFc.

FIG. 61 shows the results of a western blot on expressed FXYD3_ECD_mFc (SEQ ID NO:103), AI216611 ECD_mFc (SEQ ID NO:104), C1ORF32_ECD_mFc (SEQ ID NO:105), LOC253012_ECD_mFc (SEQ ID NO:106), ILDR1_ECD_mFc (SEQ ID NO:107), VSIG1_ECD_mFc (SEQ ID NO:108) according to the present invention.

The lanes are as follows: lane 1 Molecular weight markers (Amersham, full range ranbow, catalog number RPN800); lane 2-LOC253012_ECD_mFc (SEQ ID NO:106); lane 3-FXYD3_ECD_mFc (SEQ ID NO:103); lane 4-AI216611 ECD_mFc (SEQ ID NO:104); lane 5-C1ORF32_ECD_mFc (SEQ ID NO:105); lane 6-ILDR1_ECD_mFc (SEQ ID NO:107); lane 7-VSIG1_ECD_mFc (SEQ ID NO:108).

Example 11

Protein Production of VSIG1, ILDR1, LOC253012, AI216611, C1ORF32 and FXYD3 Extra Cellular Domain (ECD) Fused T0 Mouse Fc To produce VSIG1, ILDR1, LOC253012, AI216611, C1ORF32 and FXYD3_ECD fused to mouse Fc, pool of transfected HEK293T cells stably transfected with the corresponding constructs described herein above, were used. The transfected cells, usually maintained in 10% serum supplemented medium, were transferred into serum free medium (EX-CELL293, SAFC) supplemented with 4 mM glutamine and selection antibiotics (5 ug/ml puromycin), and grown in suspension in shake flasks at 37° C., with agitation. The culture volume was increased by sequential dilutions until a production phase of 3-4 days carried out in 2 L spinners flasks. Medium from the spinners was harvested, cleared from cells by centrifugation, filtered through a 0.22 μm filter and kept at −20° C.

The VSIG1, ILDR1, LOC253012, AI216611, C1ORF32 and FXYD3 ECD fused to mouse Fc were purified using nProtein A-affinity chromatography as described below.

Harvests were concentrated approximately 10 fold using PALL ultrafiltration system on two 10 kD cassettes. The concentrate was then adjusted to pH 7.5, by the addition of 5M NaOH and filtrated through 0.2 μm Stericup filter.

Purification process was carried out using AKTA Explorer (GE Healthcare). 2 ml of nProtein A Sepharose™, Fast Flow resin (cat#17-5280-02) were washed on Poly-prep chromatograohy column under vacumn with 10 column volumes (CV) of 70% ethanol, 10 CV WFI (Sterile Water for Irrigation (TEVA)) followed by 10CV buffer A. 2 ml resin were transffered into two 500 ml tubes (1 ml each) and the concentrated harvest was added. The tube was icubated overnight at 4° C. on a roller to allow binding of the protein. Bound resin was then transffered and packed under constant flow into XK16 coulmn (GE Healthcare, cat#18-8773-01). The column was washed with 20CV buffer A (100 Mm Tris pH 7.4) and elution was carried out in one step using 100% buffer B (Citrate/Phosphate pH 3.0). The fractions were titrated with 12.5% (v/v) buffer C (2M Tris pH 8.5) to adjust the pH to ~7.5 and pooled.

The final buffer was exchanged to DPBS (Dulbecco's Phosphate bufferes saline pH 7.4, /o Ca, w/o Mg) pH 7.4 w/o Ca, w/o Mg using a 53 ml HiPrep™ (GE Healthcare, cat#17-5087-01) desalting column. The protein was filtered through 0.22 μm filter, aliqouted under sterile conditions, and stored at −800 C.

The final protein concentration was determined by BCA total protein assay and protein was analyzed by coomassie stained reducing SDS/PAGE (data not shown). Endotoxin level was determined by colorimetric LAL assay (Limulus Amebocyte Lysate, QCL-1000, Cambrex). The identities of the specific proteins were verified by MS (at the Smoler Proteomics Center, Technion, Haifa, data not shown).

The resulted protein analyses are summerized in table 139.

TABLE 139

| Protein | Concentration (mg/ml) | Purity (%) | Endotoxins (EU/mg) |
|---|---|---|---|
| C1ORF32-P8-ECD-mFc (SEQ ID NO: 105) | 0.9 | >90 | 1.04 |
| IL6-VSIG1 P5 ECD aa26-end mFc (SEQ ID NO: 108) | 0.94 | >95 | 0.95 |
| FXYD3-T25P14-ECD-mFc (SEQ ID NO: 103) | 1.1 | >80 | 0.14 |
| AI216611-T0P0-mFc (SEQ ID NO: 104) | 1.6 | >94 | 0.72 |
| IL6 ILDR1 ECD aa50-160 mFc (SEQ ID NO: 107) | 1 | 85 | <0.2 |
| LOC253012-P5-ECD-mFc (SEQ ID NO: 106) | 1 | >95 | 1.45 |

Example 12

Binding of the ECDs Fc-Fused Proteins of the Invention to Activated T Cells

In order to examine of the ability of the VSIG1, ILDR1, LOC253012, AI216611, C1ORF32 and FXYD3 Fc-fused ECDs described above to bind a putative counter-receptor on T cells, these Fc-fused ECDs were tested on resting or activated T cells. Purified T cells were activated with ConA (Sigma Aldrich, Cat # C5275), followed by incubation with the VSIG1, ILDR1, LOC253012, AI216611, C1ORF32 or FXYD3 Fc-fused ECDs and analyzed by flow cytometry.

T cells were purified from whole blood by negative selection using RosetteSep™ Human T Cell Enrichment Cocktail (StemCell Technologies, CAT #15061). This resulted in a population of T (CD3+) cells with a purity of ~90%. Purified T cells (1×105) were cultured for 48 hours in 100 ul of complete RPMI 1640 medium containing 10% FBS, either without any activation or activated with ConA (Concovalin A, 10 ug/ml, Sigma Aldrich, Cat # C5275). Cultures were harvested and stained with the ECDs Fc-fused proteins for 1 hour at 4° C. (VSIG1, ILDR1, LOC253012, AI216611, FXYD3 or C1ORF32 ECDs fused to mouse IgG2 Fc). The bound proteins were detected with FITC-conjugated F(ab)2 goat anti-mouse Fc for half an hour at 4° C. (Jackson ImmunoResearch Laboratories. CAT #115-096-071). Samples were analyzed using a FACSCalibur (BD Immunocytometry Systems) and CellQuest software.

Figure 62A:
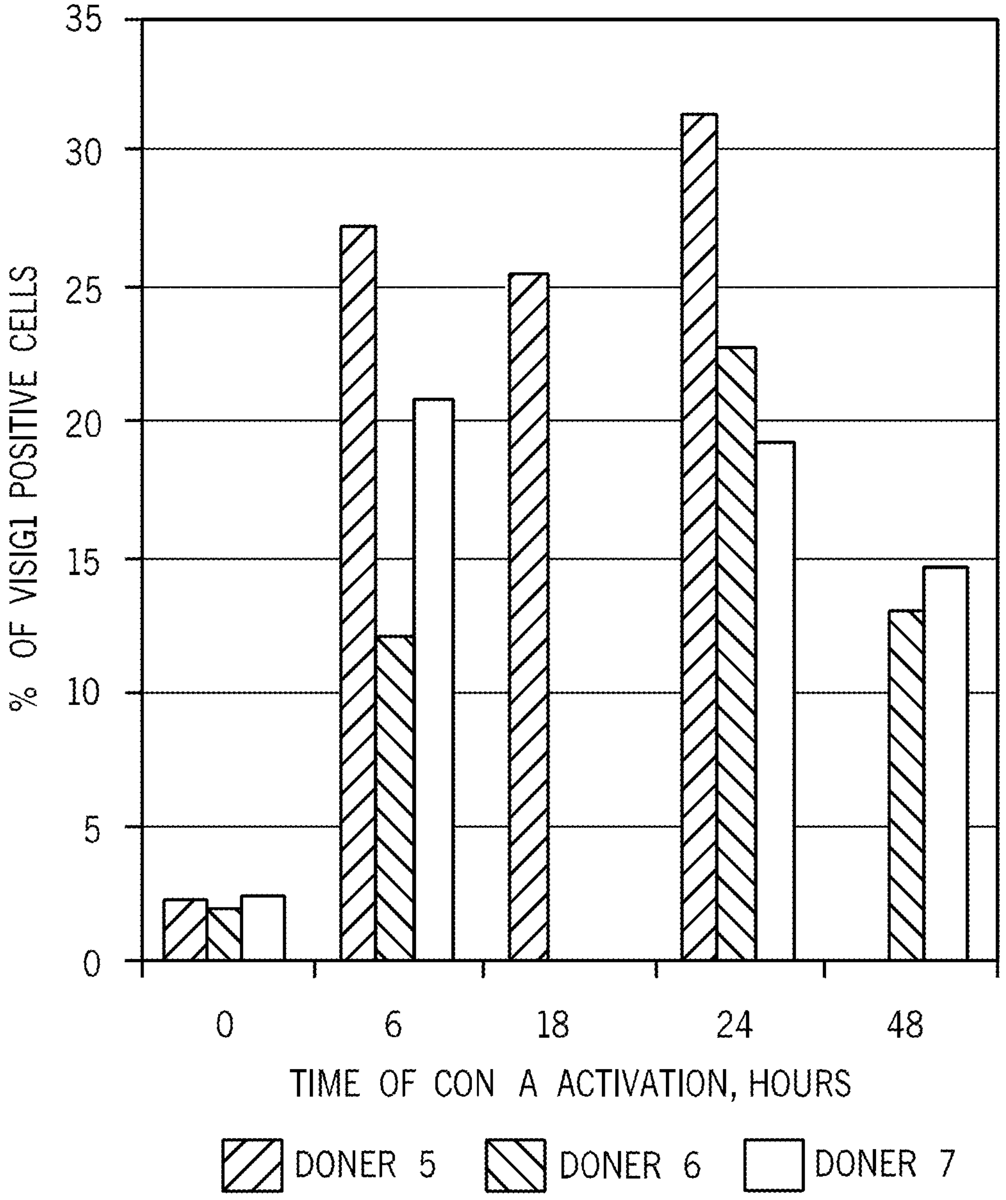
FIGS. 62A-62E present the binding of the Fc-fused B7-like proteins ECDs to resting T cells or T cells activated with Con A for different periods of time.
Figure 62B:
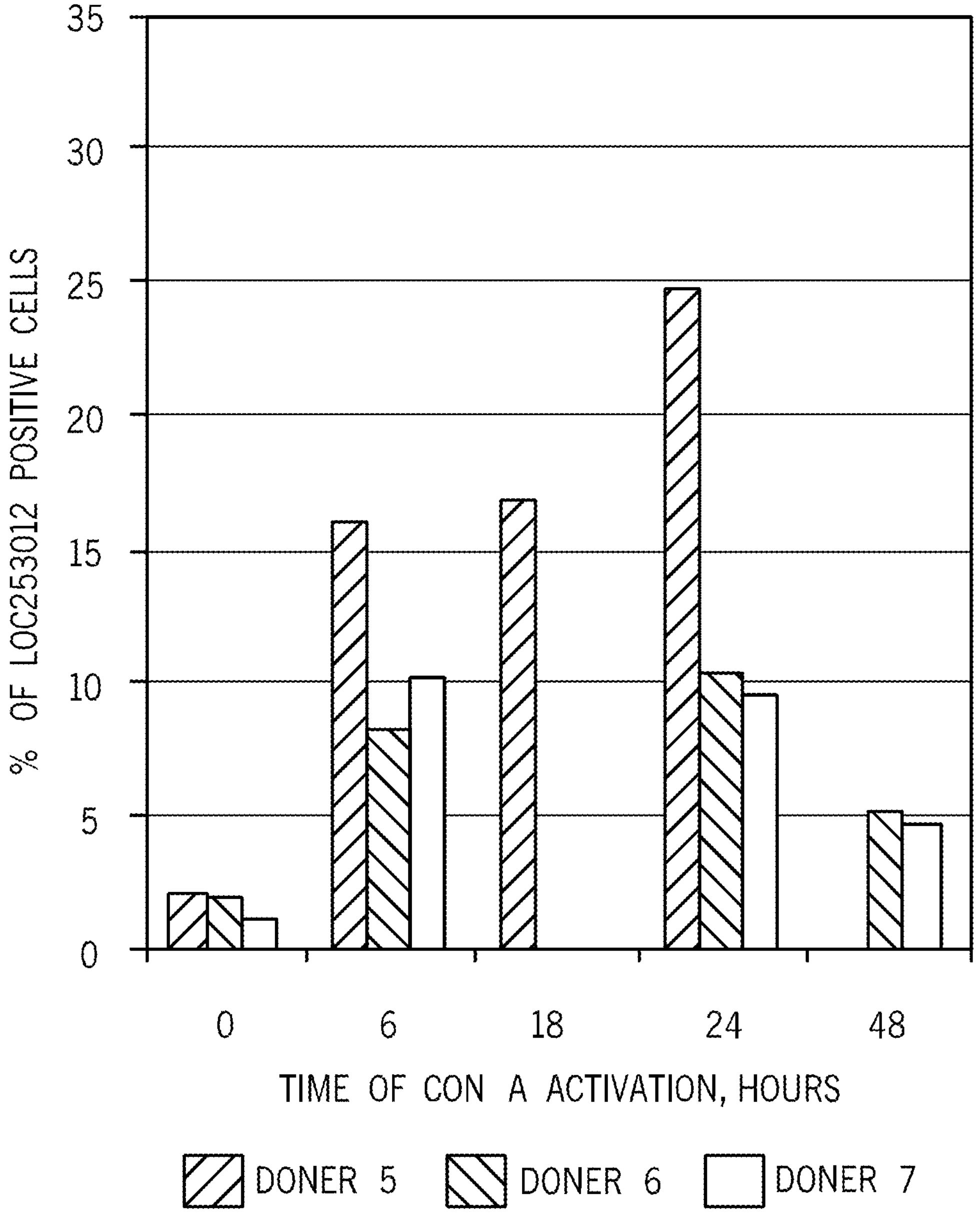
Figure 62C:
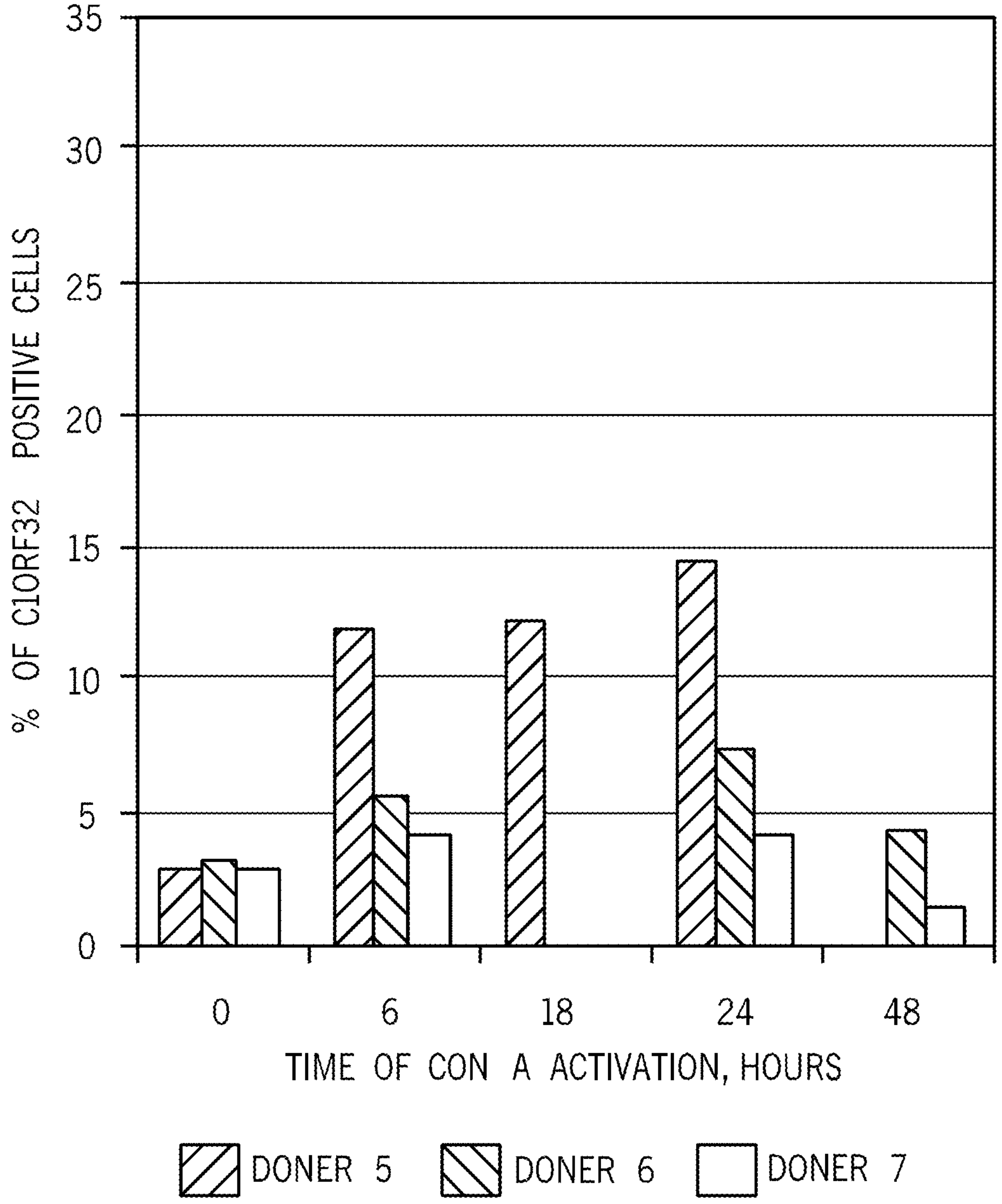
Figure 62D:
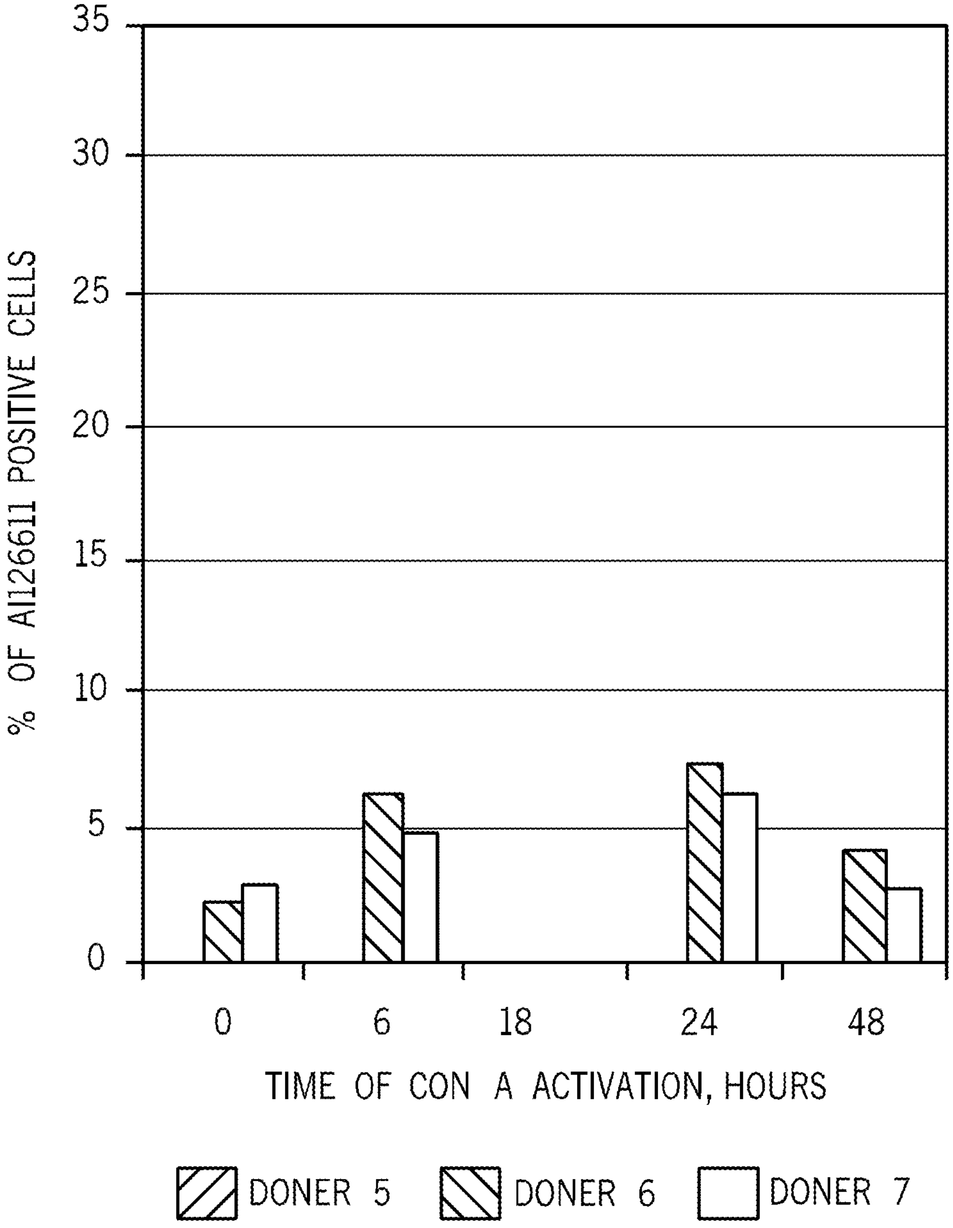
Figure 62E:
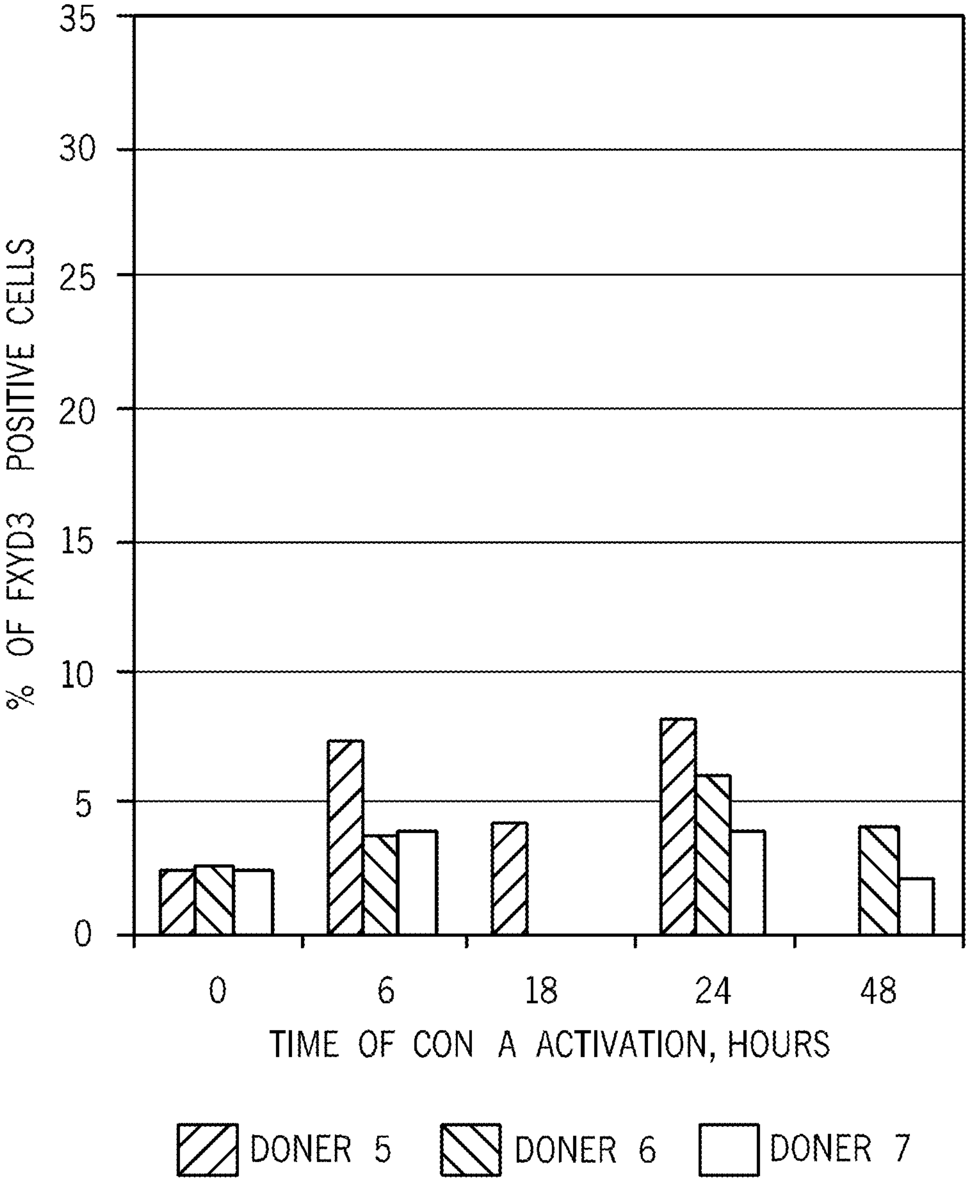
Figure 63:
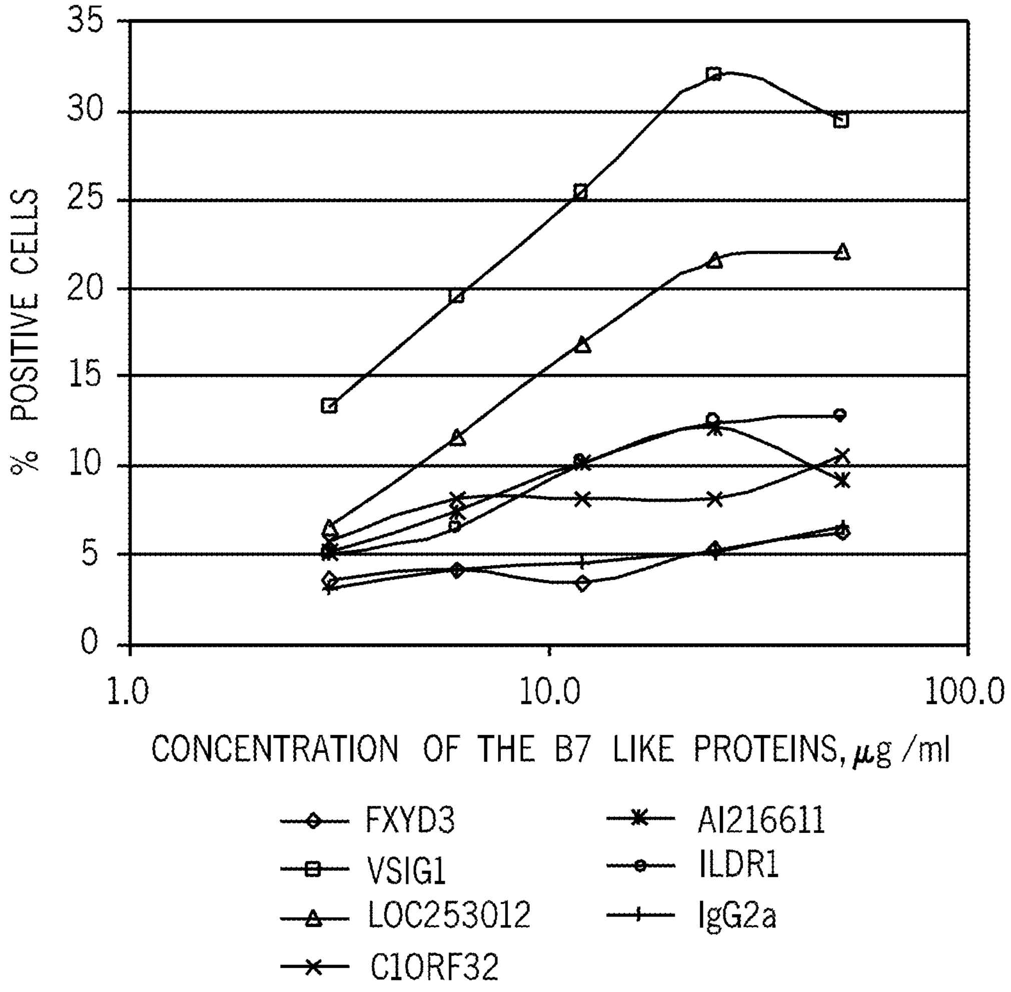
FIG. 63 presents the dose response of the binding of Fc-fused B7-like proteins ECDs to activated T cells. Purified T cells were cultured for 48 hours. Con A was added for the last 24 hours. Cells were then harvested and stained with increasing concentrations (3, 6, 12, 25 and 50 μg/ml) of Fc-fused VSIG1, LOC253012, C1ORF32, AI216611, ILDR1 or FXYD3 ECDs. As negative controls, mouse IgG2a was used at the same concentrations.

FIGS. 62A-D present the binding of the ECDs Fc-fused proteins (VSIG1 (SEQ ID NO:108), LOC253012 (SEQ ID NO:106), AI216611 (SEQ ID NO:104) or C1ORF32 (SEQ ID NO:105)) to resting T cells or T cells activated with Con A for different periods of time. Primary human T cells from three different donors were cultured for a total of 48 hours in the absence of stimulus (0 hrs) or in the presence of Con A, which was added to a final concentration of 10 μg/ml for the last 6, 18, 24 or 48 hours of culture (T cells from donor 5 were cultured with Con A for 0, 6, 18 and 24 hrs, while donors 6 & 7 were cultured for 0, 6, 24 and 48 hrs). Cells were then harvested and incubated with 10 μg/ml of the indicated ECDs Fc-fused proteins. FIG. 62A shows the binding results for Fc-fused VSIG1 ECD; FIG. 62B shows the binding results for Fc-fused LOC253012; FIG. 62C shows the binding results for Fc-fused C1ORF32 ECD; FIG. 62D shows the binding results for Fc-fused AI216611 ECD and FIG. 62E shows the binding results for Fc-fused FXYD3 ECD. The percentage of positive cells was determined as the difference between the positive cells with the indicated protein and the positive cells obtained with FITC-conjugated F(ab)2 goat anti-mouse Fc. FIG. 63 presents the dose response of the binding of B7-like proteins to activated T cells. Purified T cells were cultured for 48 hours. Con A was added for the last 24 hours. Cells were then harvested and stained with increasing concentrations (3, 6, 12, 25 and 50 μg/ml) of Fc-fused VSIG1, LOC253012, C1ORF32, AI216611 or ILDR1 ECDs. As a negative controls, mouse IgG2a was used at the same concentrations.

The results presented in FIGS. 62A-D and 63 demonstrate binding of all the ECDs Fc-fused proteins tested (VSIG1, ILDR1, LOC253012, AI216611 or C1ORF32 ECDs fused to mouse IgG2 Fc, SEQ ID NO:108, 107, 106, 104, or 105, respectively), at binding levels above those of the negative controls: mouse IgG2a (R&D Systems, CAT # MAB003) as isotype control. A substantial binding was detected for Fc-fused VSIG1 ECD and for LOC253012 ECD-Fc to T cells stimulated with ConA. Fc-fused ECDs of C1ORF32 and AI216611 showed a weaker binding to these cells, as can be seen from FIGS. 62A-D and 63. Each protein was found to bind a certain percentage of activated T cells. The rating of binding levels was as follows VSIG1>LOC253012>ILDR1=AI216611>C1ORF32. None of the proteins bound resting T cells (i.e O hrs of ConA in FIGS. 62A-D).

Effect of the ECDs Fc-Fused Proteins of the Invention on T Cells Activation.

In order to test potential costimulatory or/and coinhibitory activity of the soluble proteins of the invention, VSIG1, ILDR1, LOC253012, AI216611, FXYD3 or C1ORF32 ECDs fused to mouse IgG2 Fc, SEQ ID NO:108, 107, 106, 104, or 105, respectively, on T cells proliferation and IL-2 secretion, human T cells were cultured in the presence of anti-CD3 ((clone OKT3, eBioscience, CAT #16-0037-85) and the B7-like proteins of the invention, described above. Recombinant human B7-1 protein (R&D Systems, CAT #140-B1) was used as a positive control for costimulatory activity. Recombinant mouse B7-H4 protein (R&D Systems, CAT #4206-B7) was used as positive control for coinhibitory activity.

Flat-bottom 96-well plates were first coated at 4° C. overnight with 3 μg/ml of anti-CD3 mAb (clone OKT3) and subsequently coated with the indicated concentrations of human B7-1 (R&D, 3 μg/ml), mouse B7-H4 (R&D, 10 μg/ml) or the ECDs Fc-fused proteins of the invention, VSIG1, ILDR1, LOC253012, AI216611, FXYD3 or C1ORF32 ECDs fused to mouse IgG2 Fc, for 4 h at 37° C. Human T cells were purified from whole blood as described above, and were cultured in the pre-coated 96-well plates (1×105 cells/well) in 250 μl of complete RPMI 1640 medium containing 10% FBS for 48 hrs. Coated plates were washed with PBS three times before seeding of the cells. T cell proliferation was determined by BrdU incorporation by Cell proliferation ELISA, BrdU (colorimetric) (Roche). Cells were labeled with BrdU labeling reagent at a final concentration of 100 μM for the last 18 hours. The plates were then centrifuged (at 300 g, for 10 min,), and supernatants were aspirated and stored at −20° C. for subsequent IL-2 determination using a Human IL-2 ELISA (Diaclone, CAT #850.010 096). BrdU incorporation was measured according to instructions of the manufacturer of the Cell proliferation ELISA, BrdU (colorimetric) (Roche, CAT #11-647-229).

Figure 64A:
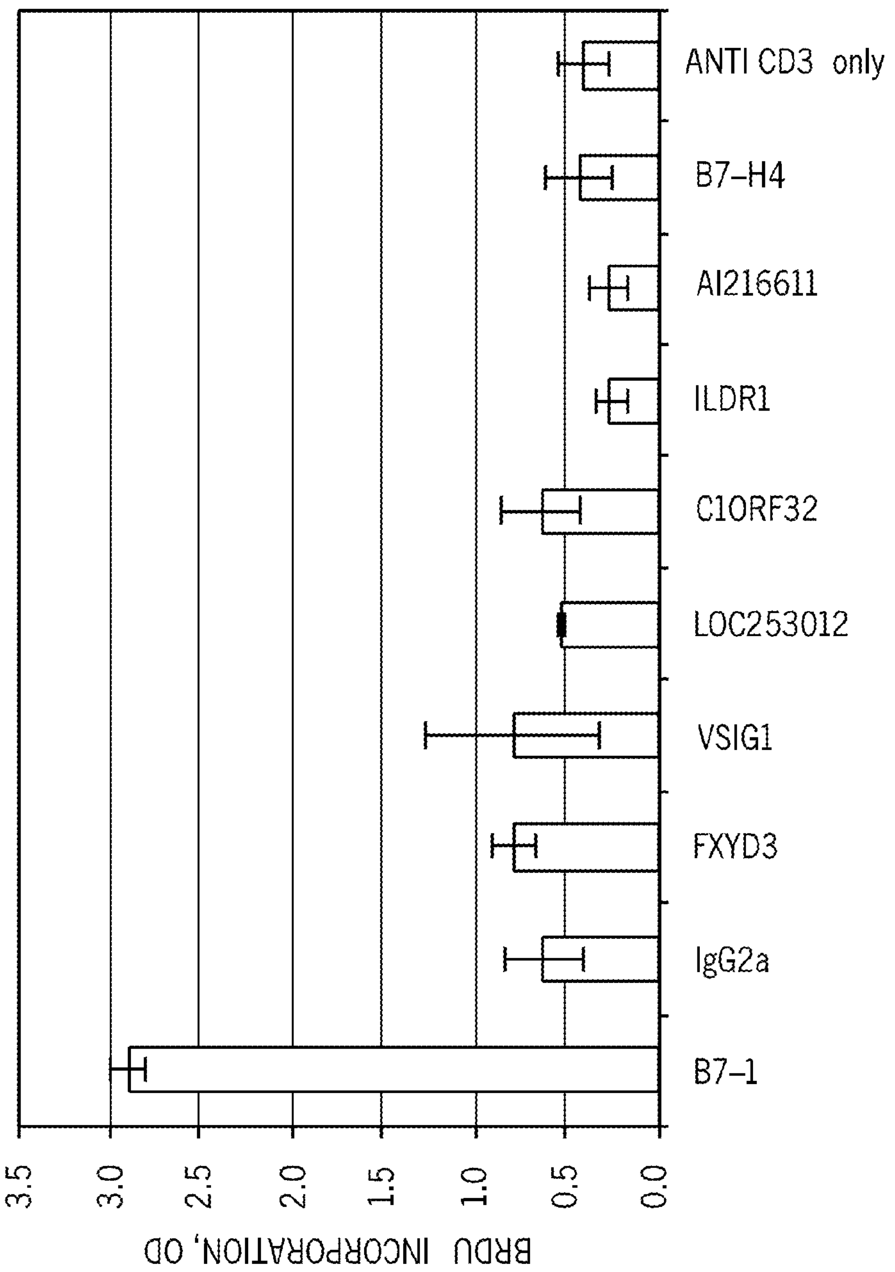
FIGS. 64A-64B present the effect of the ECD-Fc fused proteins on T cells proliferation or IL-2 secretion, upon activation with anti-CD3 Ab.
Figure 64B:
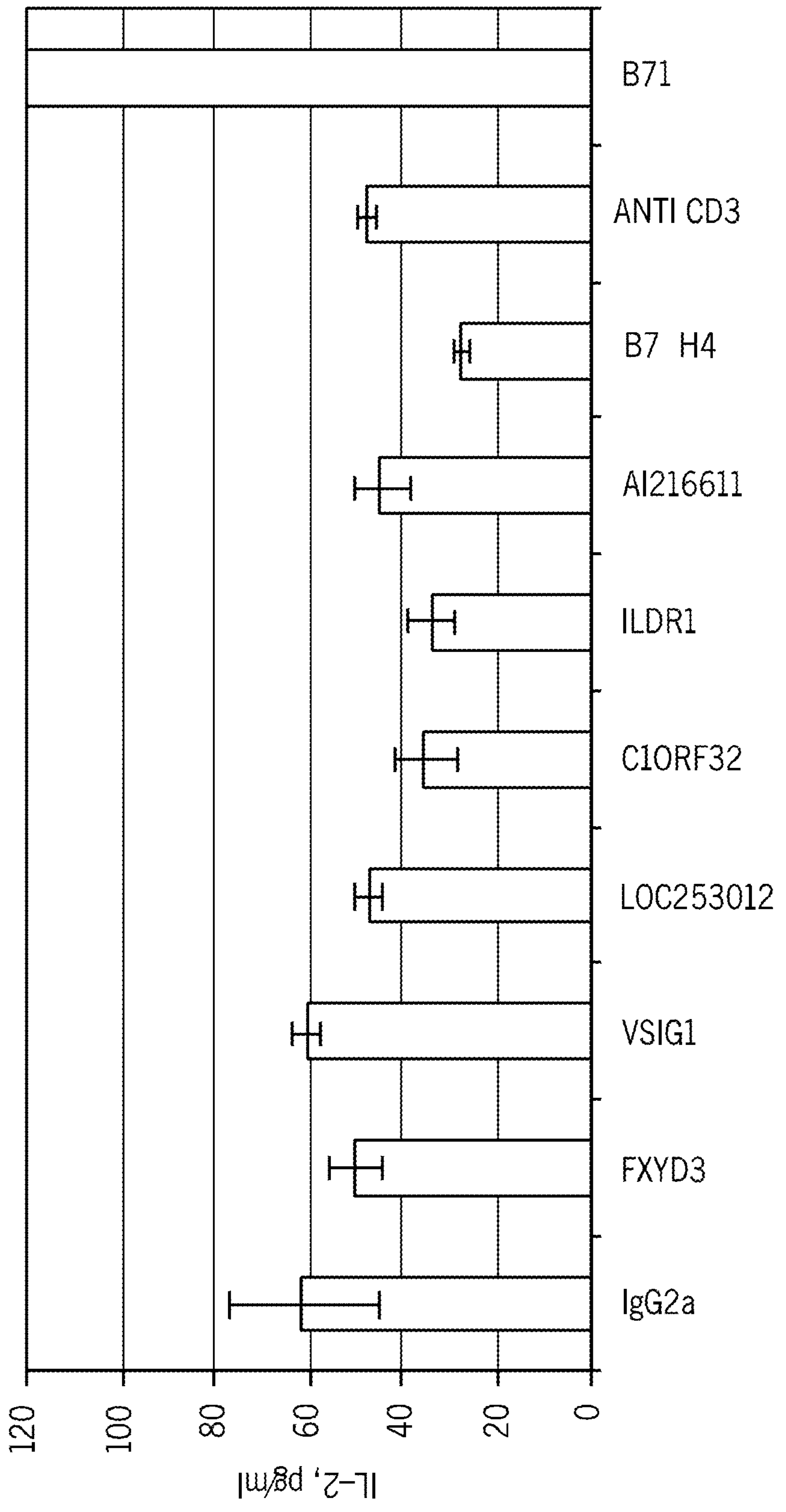

FIGS. 64A-B presents the effect of the ECDs Fc-fused proteins of the invention on T cell proliferation or IL-2 secretion, upon activation with anti-CD3 Ab. FIG. 64A shows the levels of BrdU incorporation. FIG. 64B shows the levels of IL-2 secretion.

The results, presented in FIG. 64A-B, indicate that none of the ECD-Fc fused proteins VSIG1, ILDR1, LOC253012, AI216611, FXYD3 or C1ORF32 ECDs fused to mouse IgG2 Fc, showed costimulatory activity. The positive control, B7-1, showed a strong costimulatory activity, as expected. Fc-fused ILDR1_ECD and Fc-fused AI216611 ECD appear to have coinhibitory activity, since they inhibited cell proliferation similarly to B7-H4, in comparison to that obtained in the presence of the negative control: mouse IgG2a (FIG. 64A). However, no significant effect was observed on IL-2 secretion of any of the ECD-Fc fused proteins, VSIG1, ILDR1, LOC253012, AI216611, FXYD3 or C1ORF32 Fc-fused ECDs (FIG. 64B).

Example 13

Binding of the ECDs Fc-Fused Proteins of the Invention to Lymphocytes and to and to CD4 Positive Cells In order to further examine of the ability of the VSIG1, ILDR1, LOC253012, AI216611, FXYD3 and C1ORF32 Fc-fused ECDs to bind a putative counter-receptor on T cells, these Fc-fused ECDs were tested first on lymphocyes. PBMCs were prepared from human peripheral blood, in FACS buffer at 1×10e7/ml. Fc blocker (hIgG (16D10), lot#080706, 1.3 mg/ml) at 30 ug/ml was added and cells were incubated with the blocker on ice for 30 min. Fusion proteins were added at 1 ug/10e6 per stain on ice for 30 min. 2nd Ab was added at 1 ug/100 ul/stain for 25-30 min (G@mIgG-Fc-FITC: Jackson Immunol Lab, 1 mg/ml, code#115-096-071, lot#71453, 1.0 mg/ml, used at 1 ug/stain). Cells were washed with the buffer at each step outlined above. The binding was analyzed by flow cytometry.

Figures 1, 2, 65A:
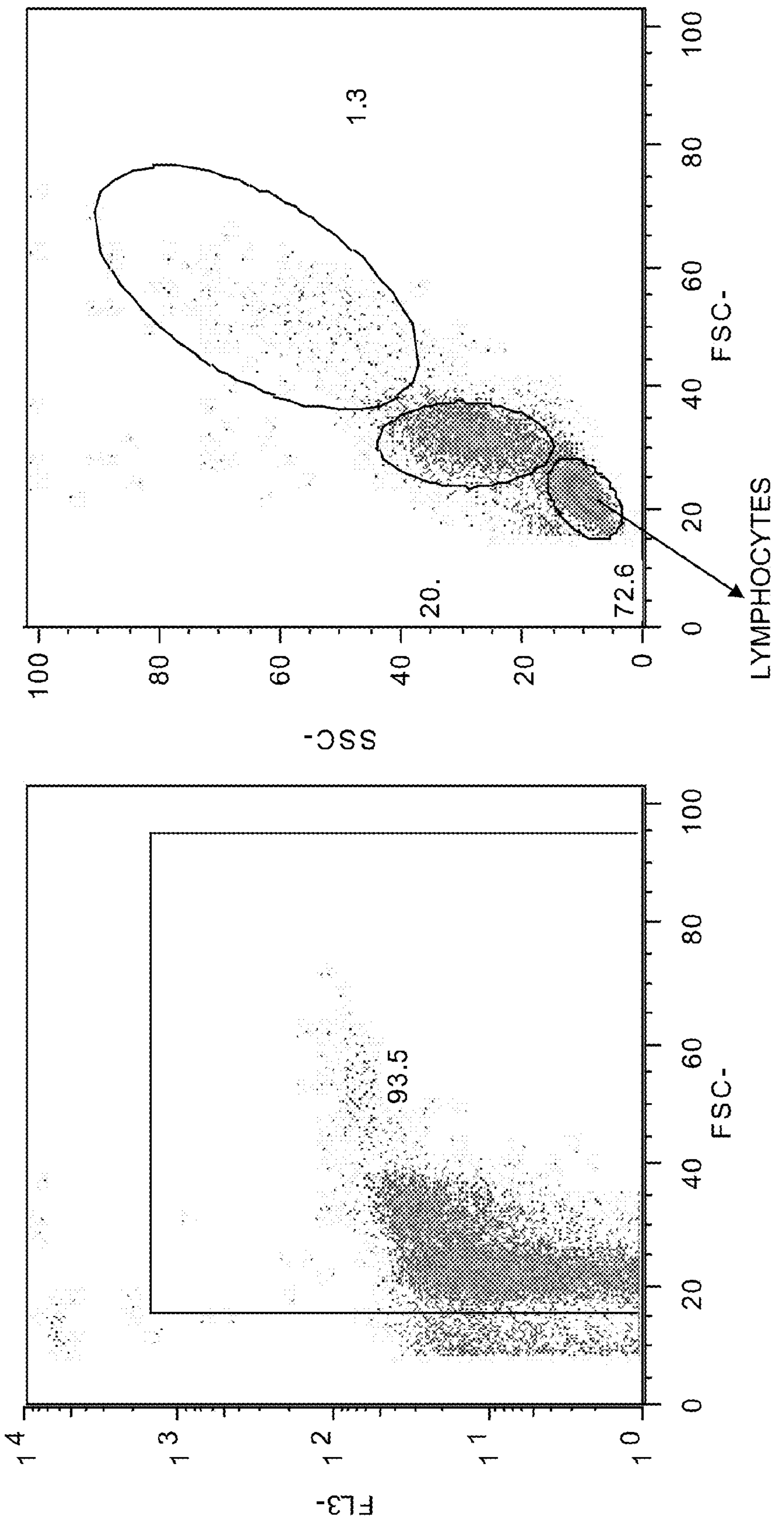
Figure 65B:
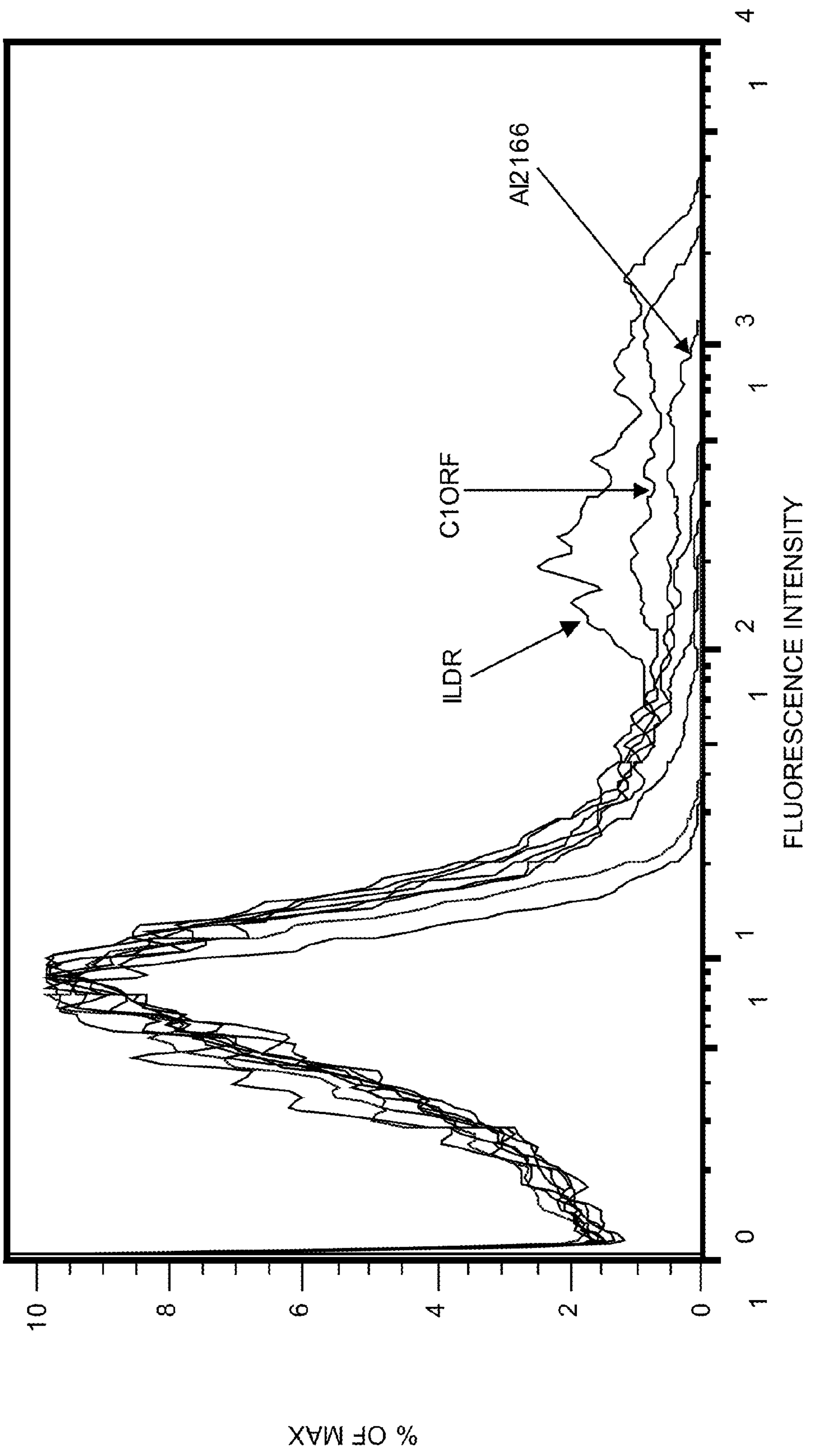

FIG. 65 illustrates the binding of the ECDs Fc-fused of the VSIG1, ILDR1, LOC253012, AI216611, FXYD3 or C1ORF32 to lymphocytes. As can be seen from FIG. 65, C1ORF32, AI216611 and ILDR1 bind to a counterpart expressed on lymphocytes.

Next, binding of the VSIG1, ILDR1, LOC253012, AI216611, FXYD3 and C1ORF32 Fc-fused ECDs to CD4+ cells. Fc blocker (hIgG (16D10), lot#080706, 1.3 mg/ml) at 30 ug/ml was added and cells were incubated with the blocker on ice for 30 mM. Fusion proteins were added at 1 ug/10e6 per stain on ice for 30 min. Add 2nd Ab at 1 ug/100 ul/stain for 25-30 min (G@mIgG-Fc-FITC: Jackson Immunol Lab, 1 mg/ml, code#115-096-071, lot#71453, 1.0 mg/ml, used at 1 ug/stain). @CD4 (m@hCD4-APC: BD, cat3555349, lot#44331) was added 20 ul of each per stain, on ice for 30 min.

Cells were washed with the buffer at each step outlined above. The binding was analyzed by flow cytometry.

Figure 66A:
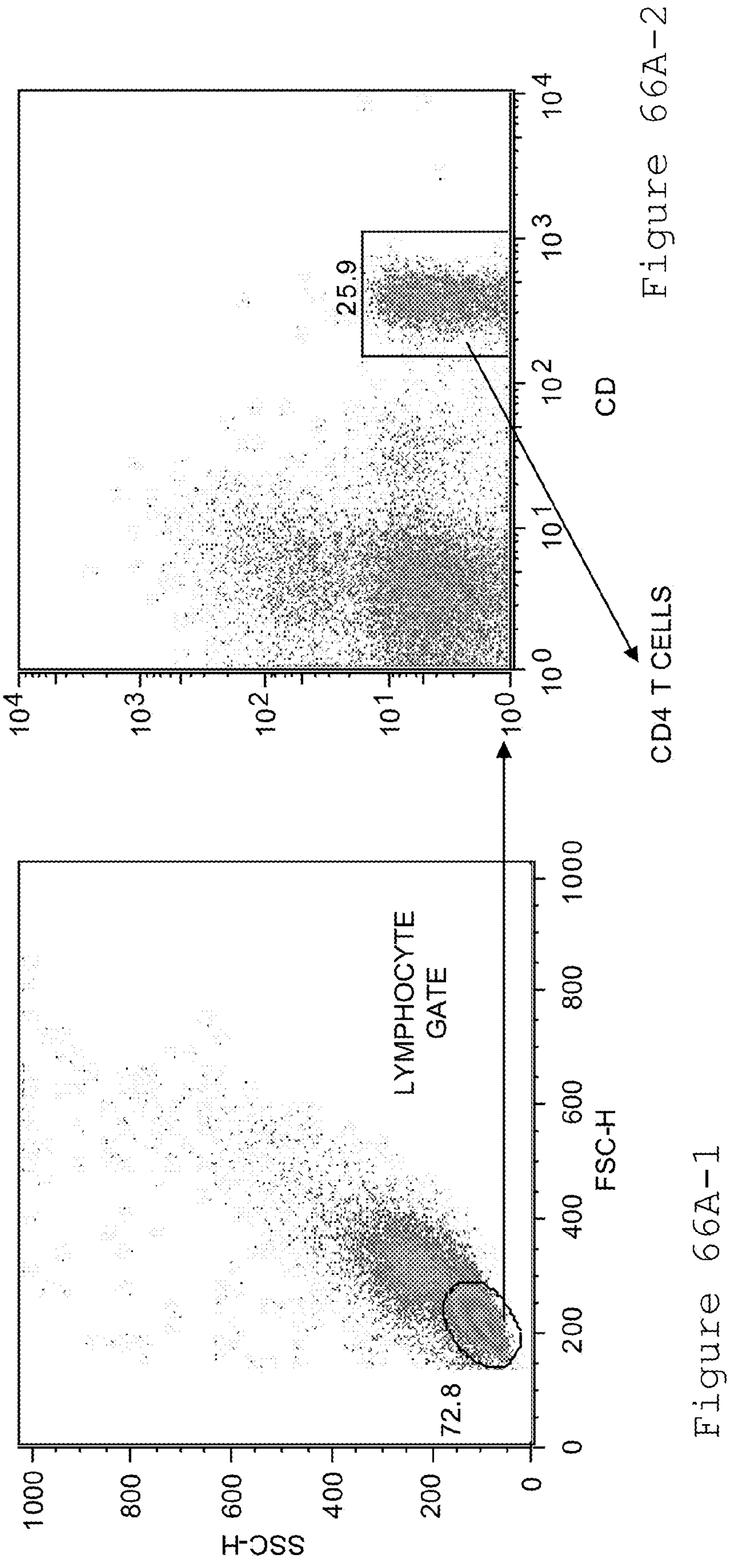
Figure 66B:
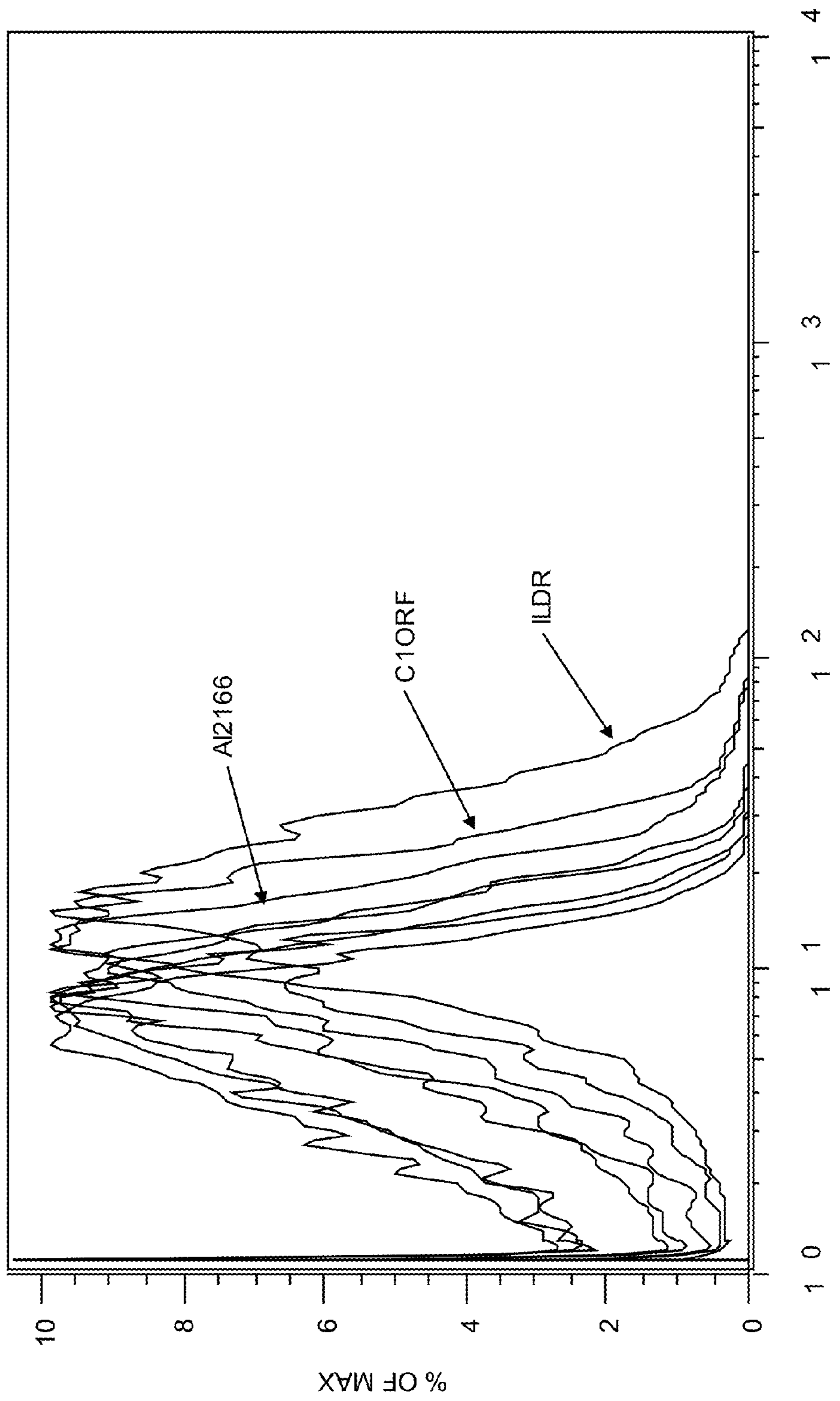

FIG. 66 illustrates the binding of the ECDs Fc-fused of ILDR1, C1ORF32 and AI216611 to CD4+ cells.

Example 14

Effect of the ECDs Fc-Fused Proteins of the Invention on T Cell Activation

In order to test potential costimulatory or/and coinhibitory activity of the B7-like proteins of the invention, the affect of the VSIG1, ILDR1, LOC253012, AI216611 or C1ORF32 ECDs fused to mouse IgG2 Fc on T cells proliferation was tested. T cells were purified from whole blood by positive selection using CD3 microbeads (microbeads conjugated to monoclonal anti-human CD3 antibodies (isotype: mouse IgG2a) (MACS Whole Blood CD3 Microbeads #130-090-874). Dynabeads are coated with CD3+/−B7 with M-450

Figure 67A:
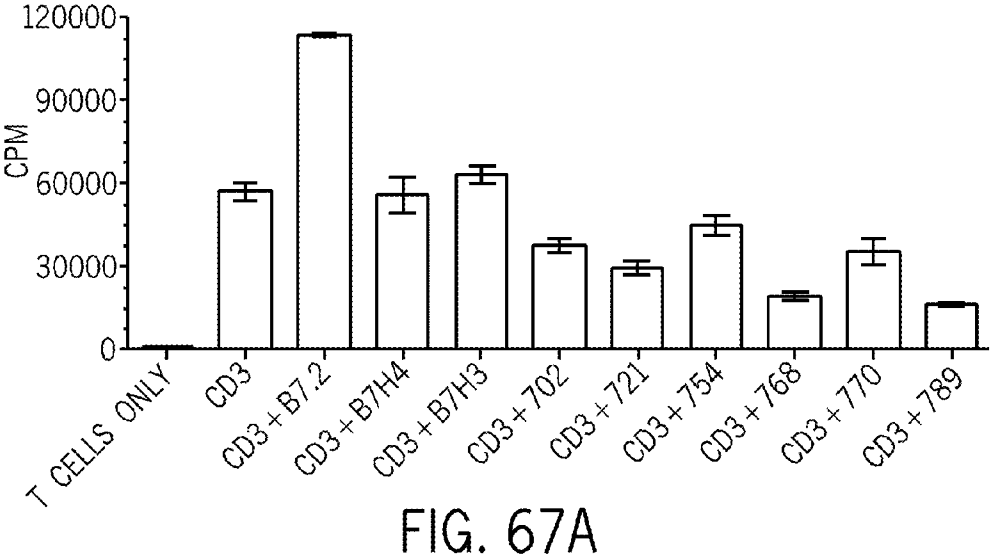
FIGS. 67A, B and C present 3 different experiments of 3 different donors
Figure 67B:
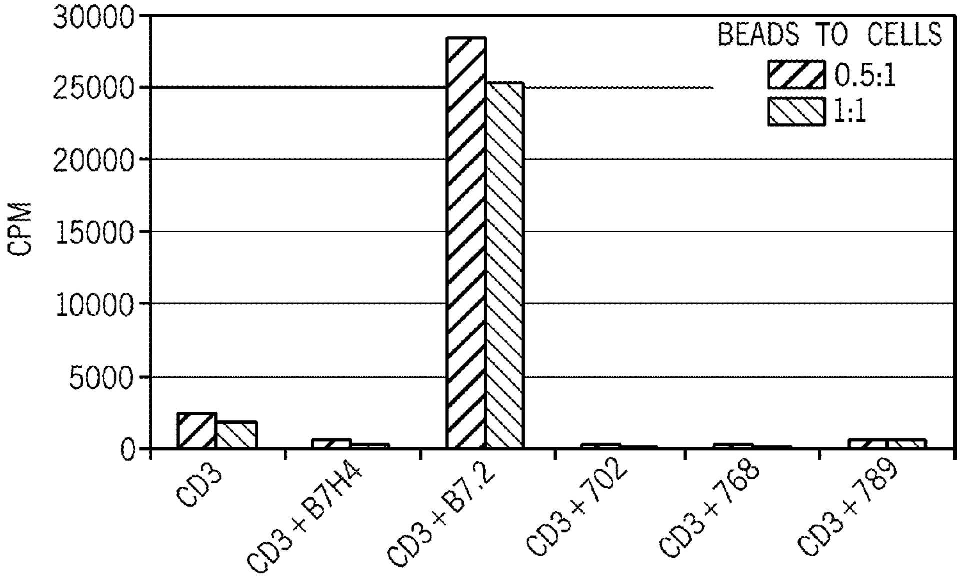
FIG. 67 shows the effect of B7-like proteins on T cell activation. "CD3" means CD3 only without the presence of a costimulatory molecule; "CD3+B7.2" means CD3+a known B7 stimulatory control, B7.2; "CD3+B7H4" means CD3 and B7H4 a known B7 inhibitory control; "CD3+B7H3" means CD3 and B7H3 a known B7 stimulatory protein; "CD3+702" means CD3+LOC253012-ECD-Fc fused (SEQ ID NO:106); "CD3+721" means CD3+AI216611-ECD-Fc fused (SEQ ID NO:104); "CD3+754" means CD3+C1ORF32-ECD-Fc fused (SEQ ID NO:105); "CD3+768" means CD3+VSIG1-ECD-Fc fused (SEQ ID NO:108) "CD3+770" means CD3+ILDR1-ECD-Fc fused (SEQ ID NO:107); "CD3+789" means CD3+FXYD3-ECD-Fc fused (SEQ ID NO:103).
Figure 67C:
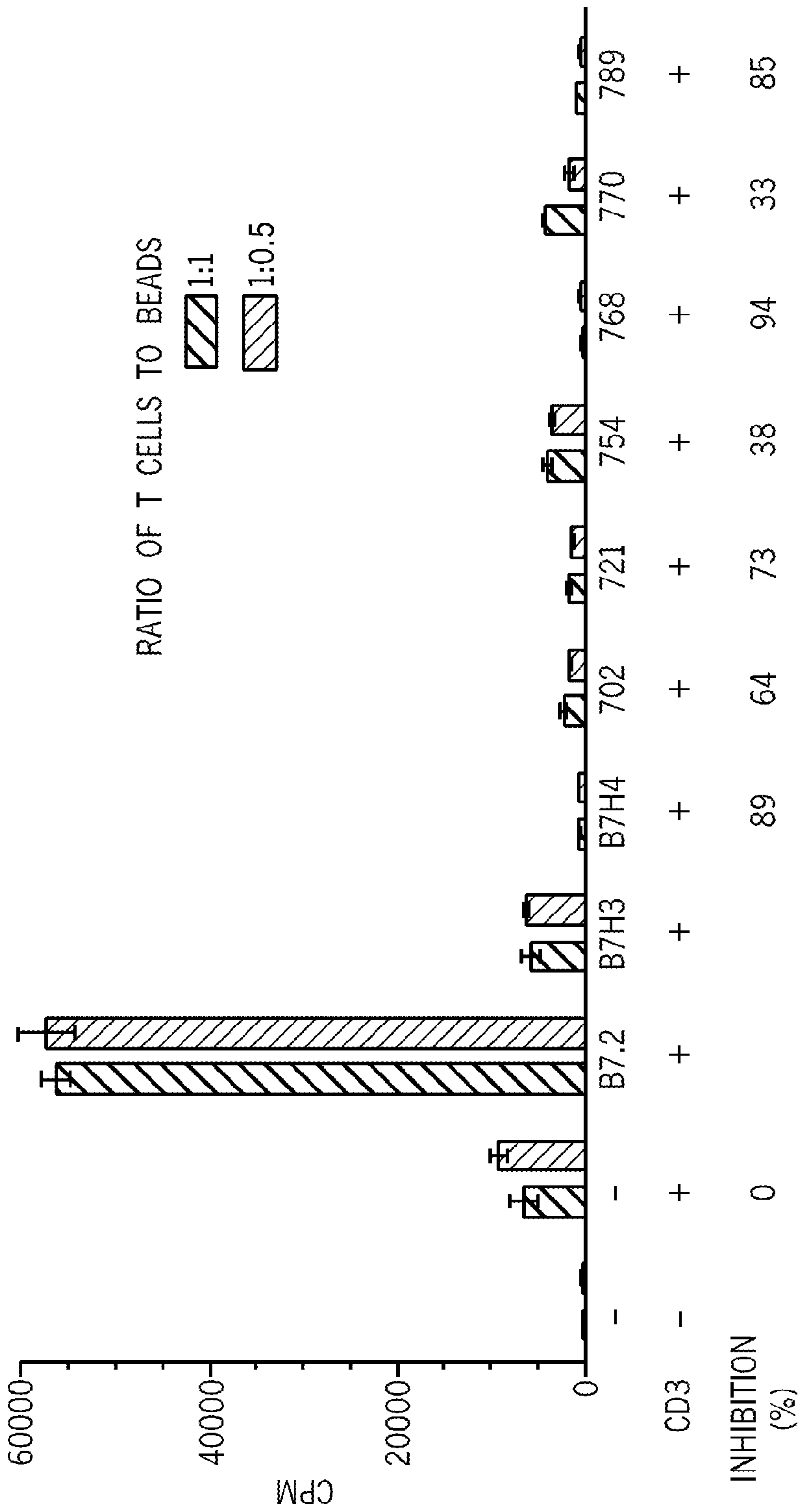

Epoxy Dynabeads (Invitrogen cat. No. 140.11). For activation of CD3 T cells, purified CD3 T cells are stimulated with the CD3+CD28 coated beads at 1:1 or 1:05 ratio for various time points as needed. The cells were seeded at 2×10e5 per well in presence or absence of CD3+CD28 (2 ug/ml each)-coated beads and the cell proliferation was measured after 72 hours by tritium-thymidine incorporation. The results are shown in FIG. 67. "CD3" in FIG. 67 mean CD3 only without the presence of a costimulatory or coinhibitory molecule; "CD3+B7.2" means CD3+a known B7 stimulatory control, B7.2; "CD3+B7H4" means CD3 and B7H4 a known B7 inhibitory control; "CD3+B7H3" means CD3 and B7H3 a known B7 stimulatory protein; "CD3+702" means CD3+LOC253012-ECD-Fc fused (SEQ ID NO:106); "CD3+721" means CD3+AI216611-ECD-Fc fused (SEQ ID NO:104); "CD3+754" means CD3+C1ORF32-ECD-Fc fused (SEQ ID NO:105); "CD3+768" means CD3+VSIG1-ECD-Fc fused (SEQ ID NO:108) "CD3+770" means CD3+ILDR1-ECD-Fc fused (SEQ ID NO:107); "CD3+789" means CD3+FXYD3-ECD-Fc fused (SEQ ID NO:103).

As can be seen in FIG. 67, LOC253012-ECD-Fc, AI216611-ECD-Fc, VSIG1-ECD-Fc and FXYD3-ECD-Fc had an inhibitory effect on T cells compared to CD3 alone in 3 different experiments (FIGS. 67 A, B, and C).

Example 15

Interaction of the ECDs-Fc Fused Proteins of the Invention with Resting B Cells, Activated B Cells, and B Cell Derived Lymphoma Cell Lines Following demonstration of binding of the proteins of the invention to lymphocytes (Example 12 and 13, herein), the ability of the soluble proteins of the invention to bind to B cells was examined.

PBMCs were prepared from human peripheral blood, in FACS buffer at 1×10e7/ml. Fc blocker (hIgG (16D10), lot#080706, 1.3 mg/ml) at 30 µg/ml was added and cells were incubated with the blocker on ice for 30 min. Fusion proteins of invention ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) were added at 1 µg/10e6 per stain on ice for 30 minutes. 2nd Ab was added at 1 µg/100 ul/stain for 25-30 min (G@mIgG-Fc-FITC: Jackson Immunol Lab, 1 mg/ml, code#115-096-071, lot#71453, 1.0 mg/ml, used at 1 ug/stain). Cells were washed with the buffer at each step outlined above. The binding was analyzed by flow cytometry. After that cells were stained with mouse @human IgM-PE (BD Bioscience, CA, USA, cat#555783) which is specific for B cells. The stained cells analyzed by flow cytometry. The @human IgM positive cells were gated to analyze the binding of the fusion proteins of invention to the B cells.

Figures 1, 2, 68A:
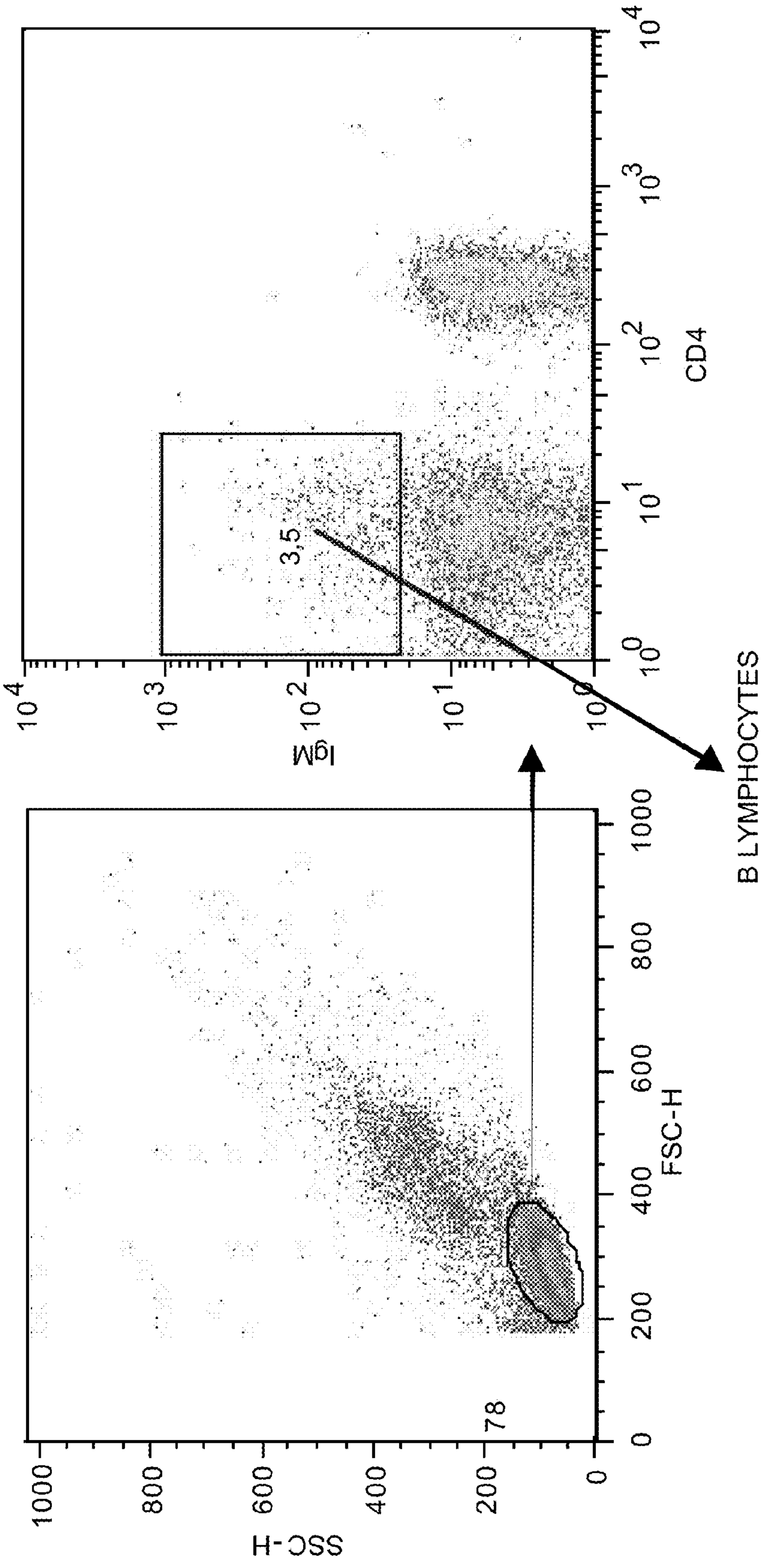
FIG. 68A presents FACS results of binding of ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) to resting B cells
Figures 3, 68A:
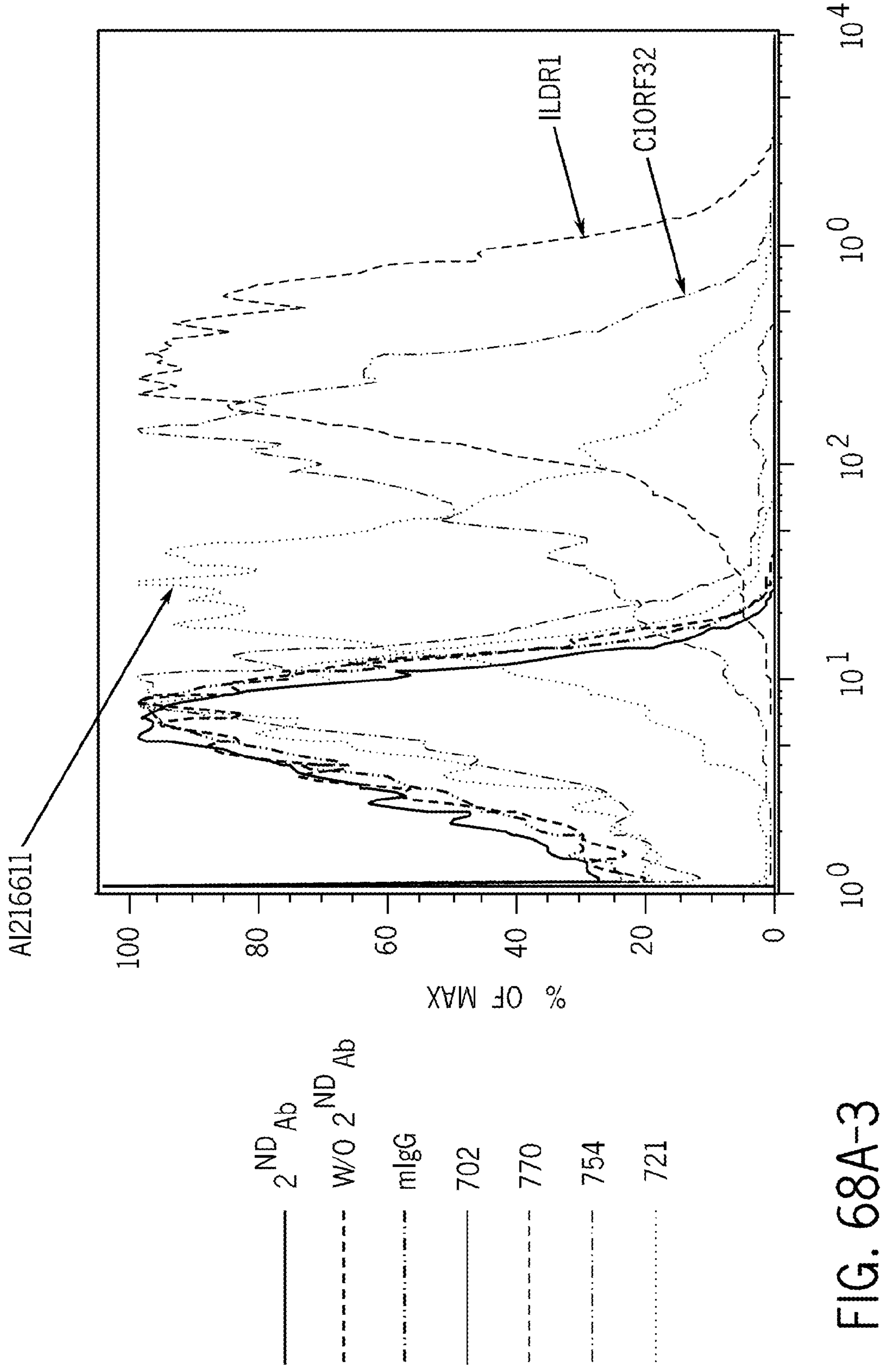
Figures 4, 68A:
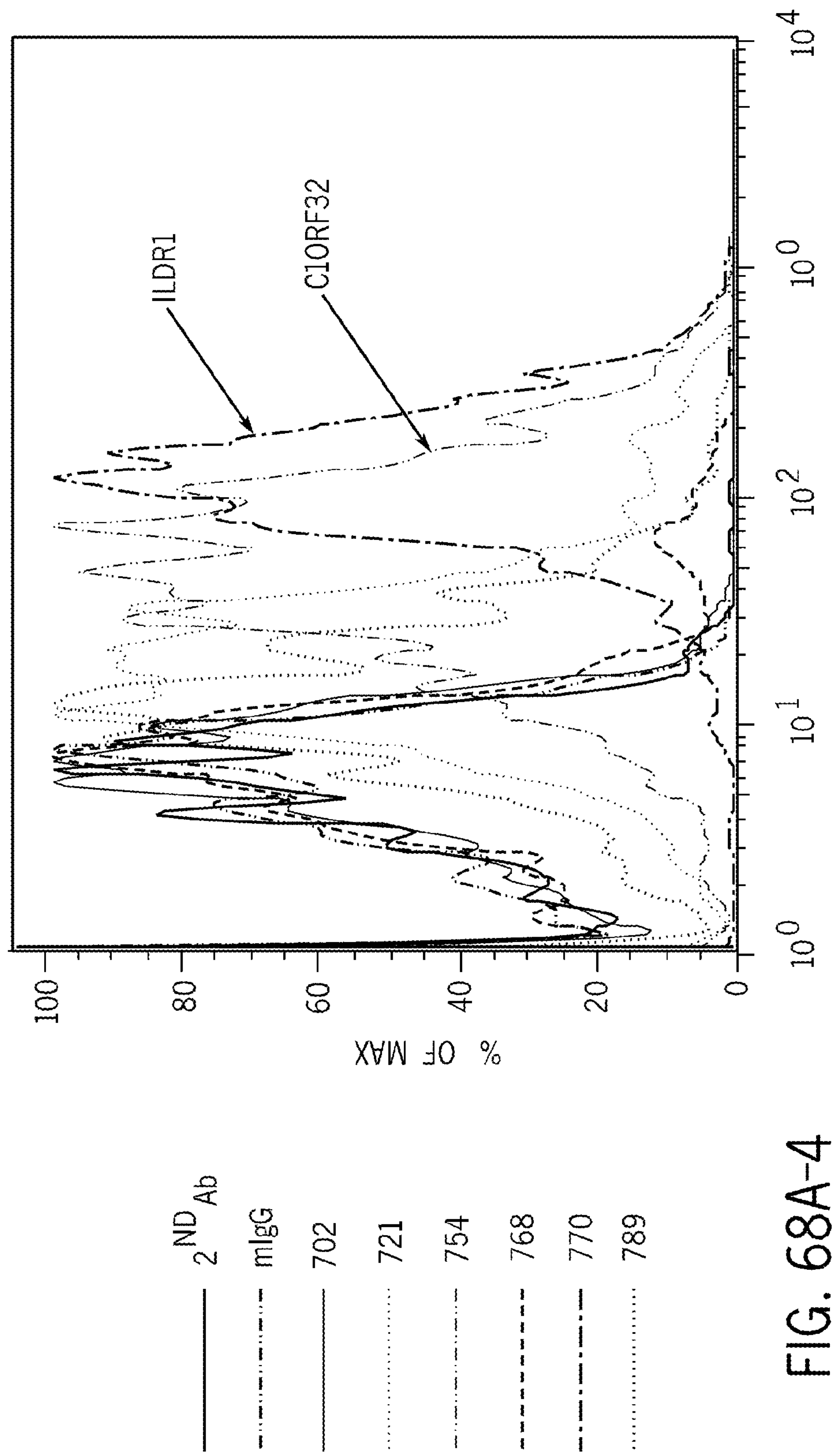
Figures 5, 68A:
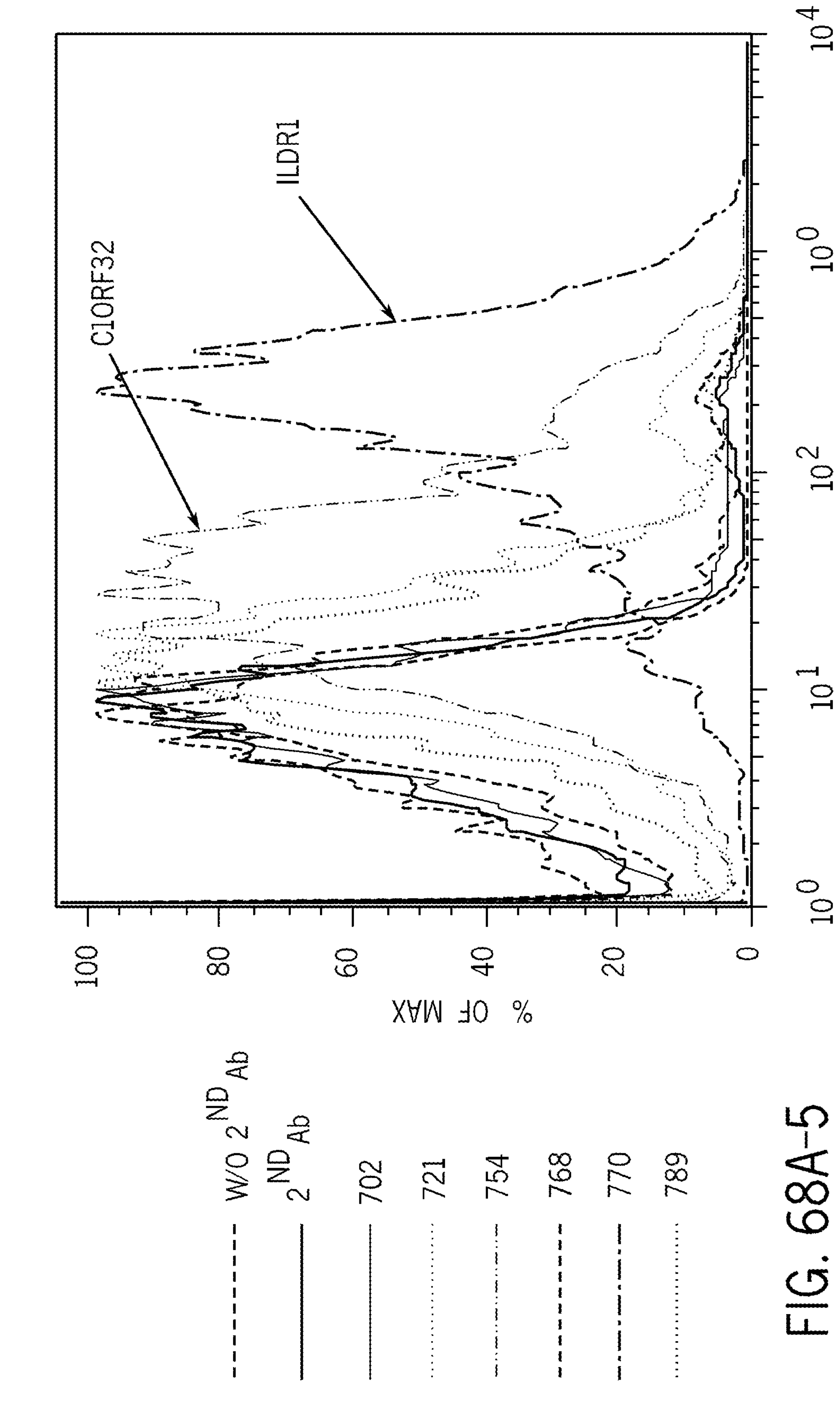

As shown in FIG. 68A, ILDR1-ECD-Fc and C1ORF32-ECD-Fc bound to B cells of all 3 donors tested. AI216611-ECD-Fc exhibited binding to B cells in 1 donor only.

In order to determine the existence of the counterpart on activated B cells, PBMCs were activated with LPS for 72 hours with LPS. Thereafter, binding with the ECDs Fc-fused proteins of the invention ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) was done as described above, and cells were stained with mouse @human CD86-Cy5PE (BD Bioscience, CA, USA, S, cat#555659) and mouse @human CD19-PE (BD Bioscience, CA, USA) antibodies. The activated B cells were defined as double positive CD19+/CD86+ population of cells.

Figures 2, 68B:
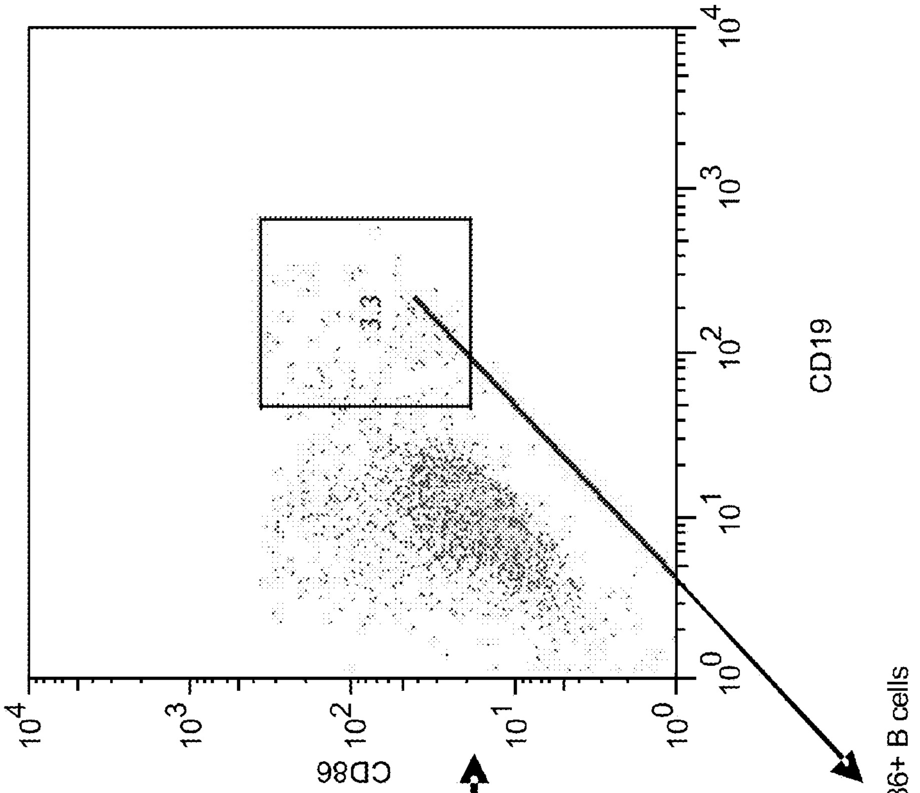
FIG. 68B presents FACS results of binding of binding of ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) to activated B cells.
Figures 1, 68B:
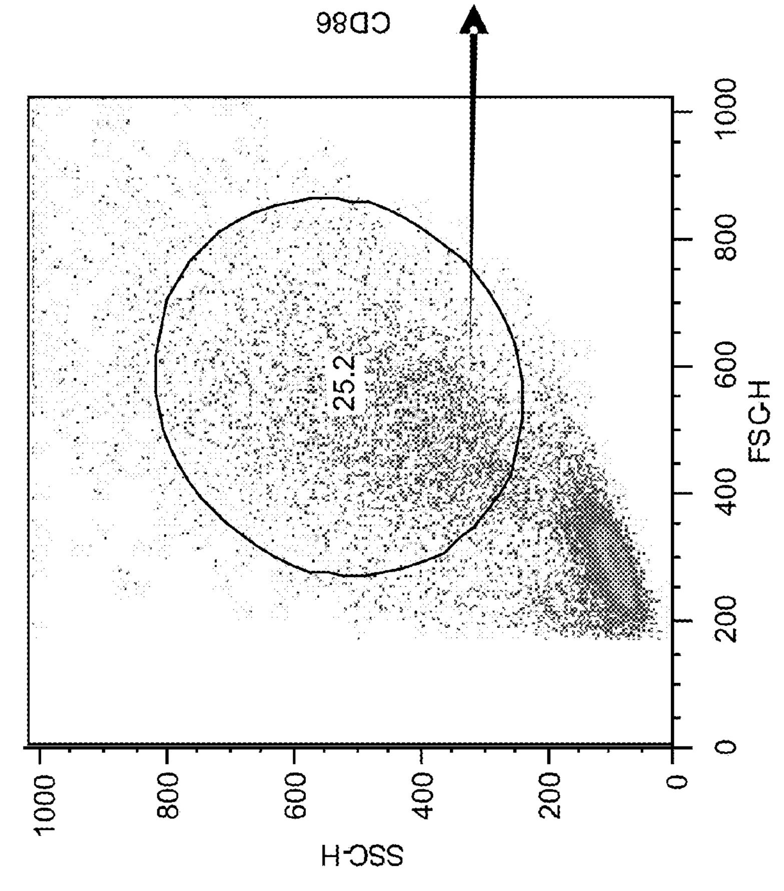
Figures 3, 68B:
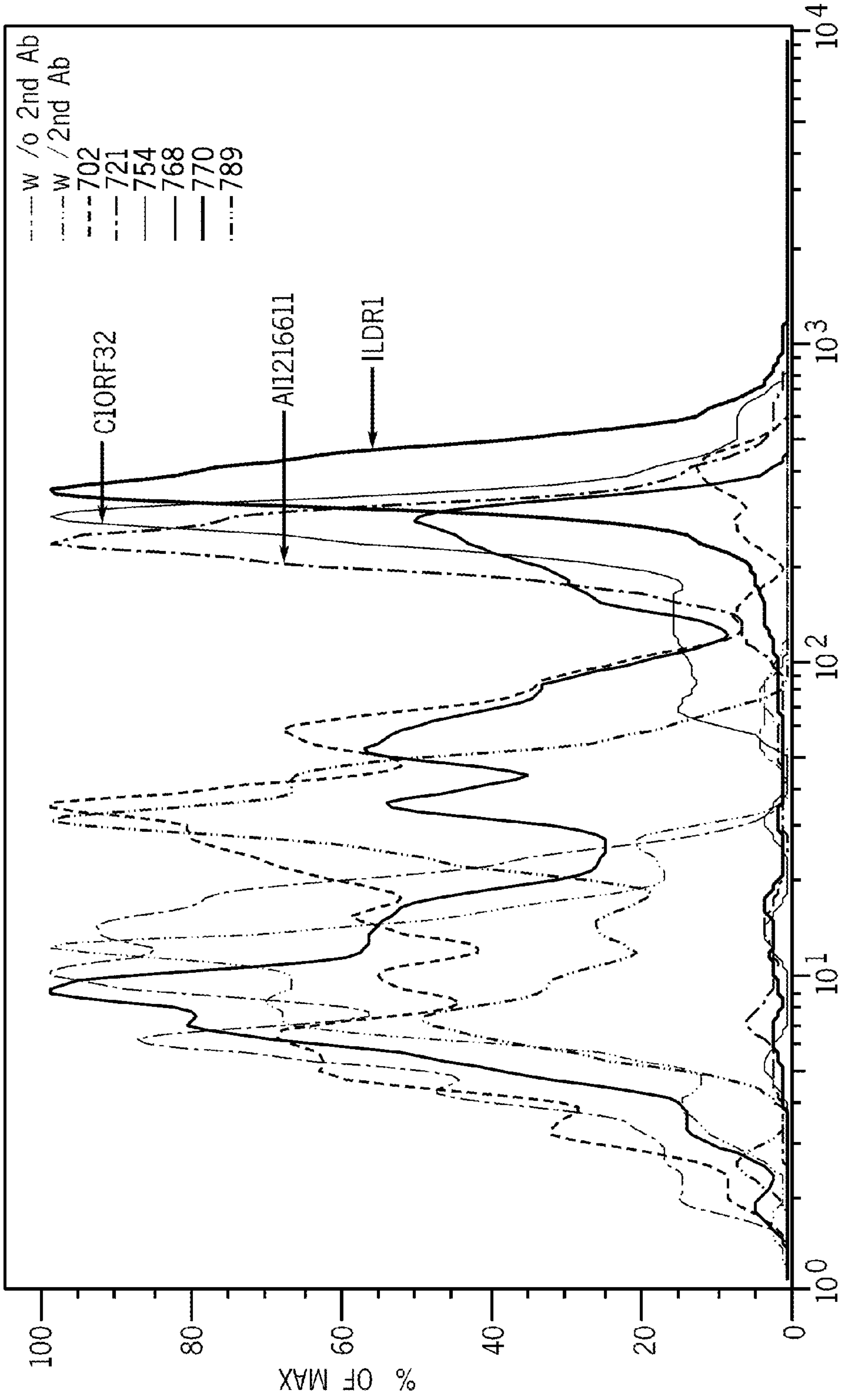

As demonstrated in FIG. 68B, ILDR1-ECD-Fc (SEQ ID NO:107), C1ORF32-ECD-Fc (SEQ ID NO:105) and AI216611-ECD-Fc (SEQ ID NO:104) showed binding to activated B cells.

In order to determine the existence of the counterpart in B cell malignancies, the binding of the ECDs Fc-fused proteins of invention ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) were analysed in B cell lymphoma cell lines. Raji (ATCC# CCL-86) and Daudi (ATCC# CCL-213) cells were purchased from ATCC and maintained in RPMI+10% FBS. The cells were stained with B7s protein or controls at 10 µg/ml and thereafter with FITC-conjugated goat anti-mouse IgG Fc (Jackson Immunol Lab, NJ, USA, cat#115-096-071, lot#71453).

Figures 1, 68C:
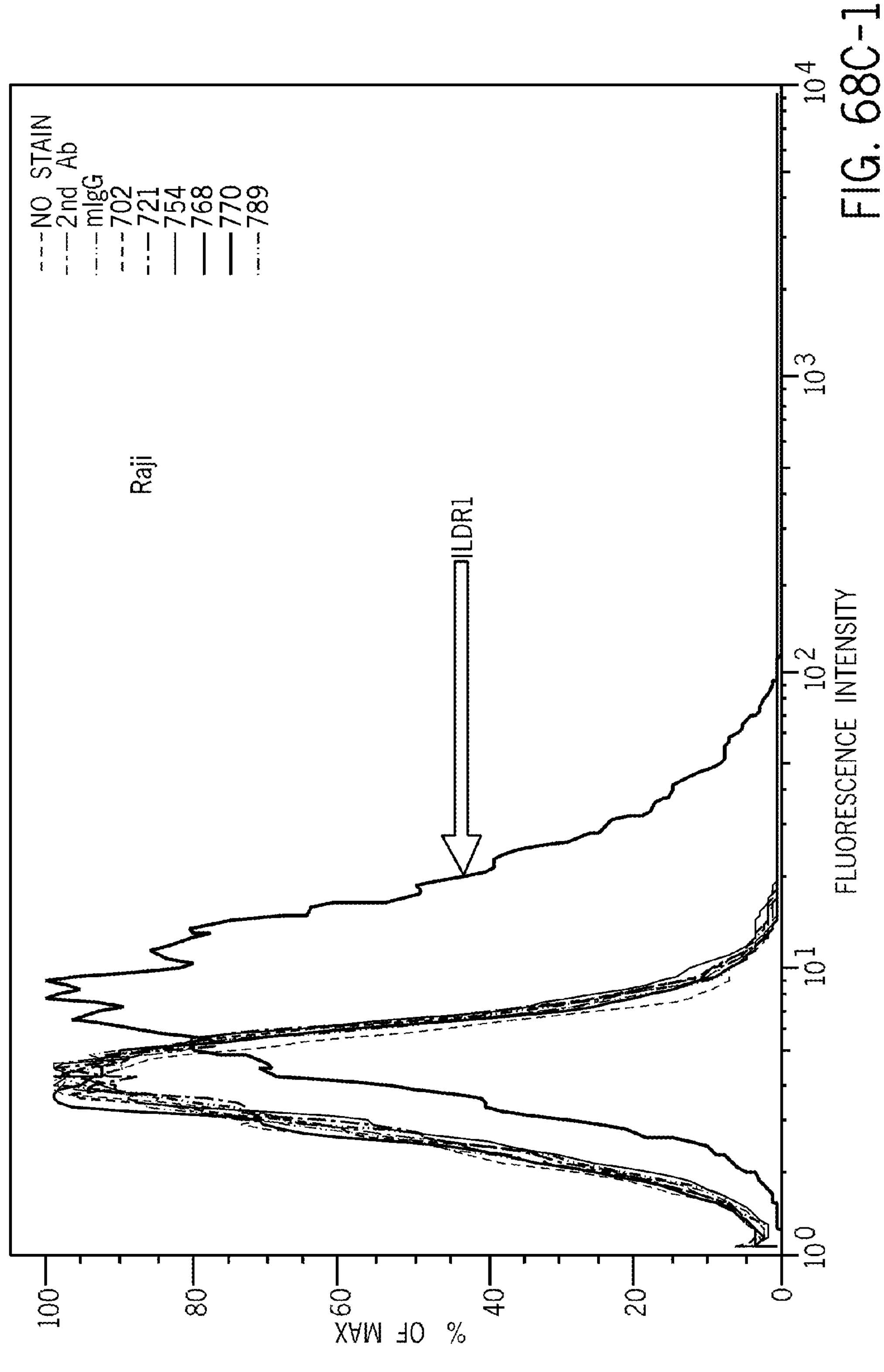
FIG. 68C presents FACS results of binding of ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108) to B lymphoma cell lines.
Figures 2, 68C:
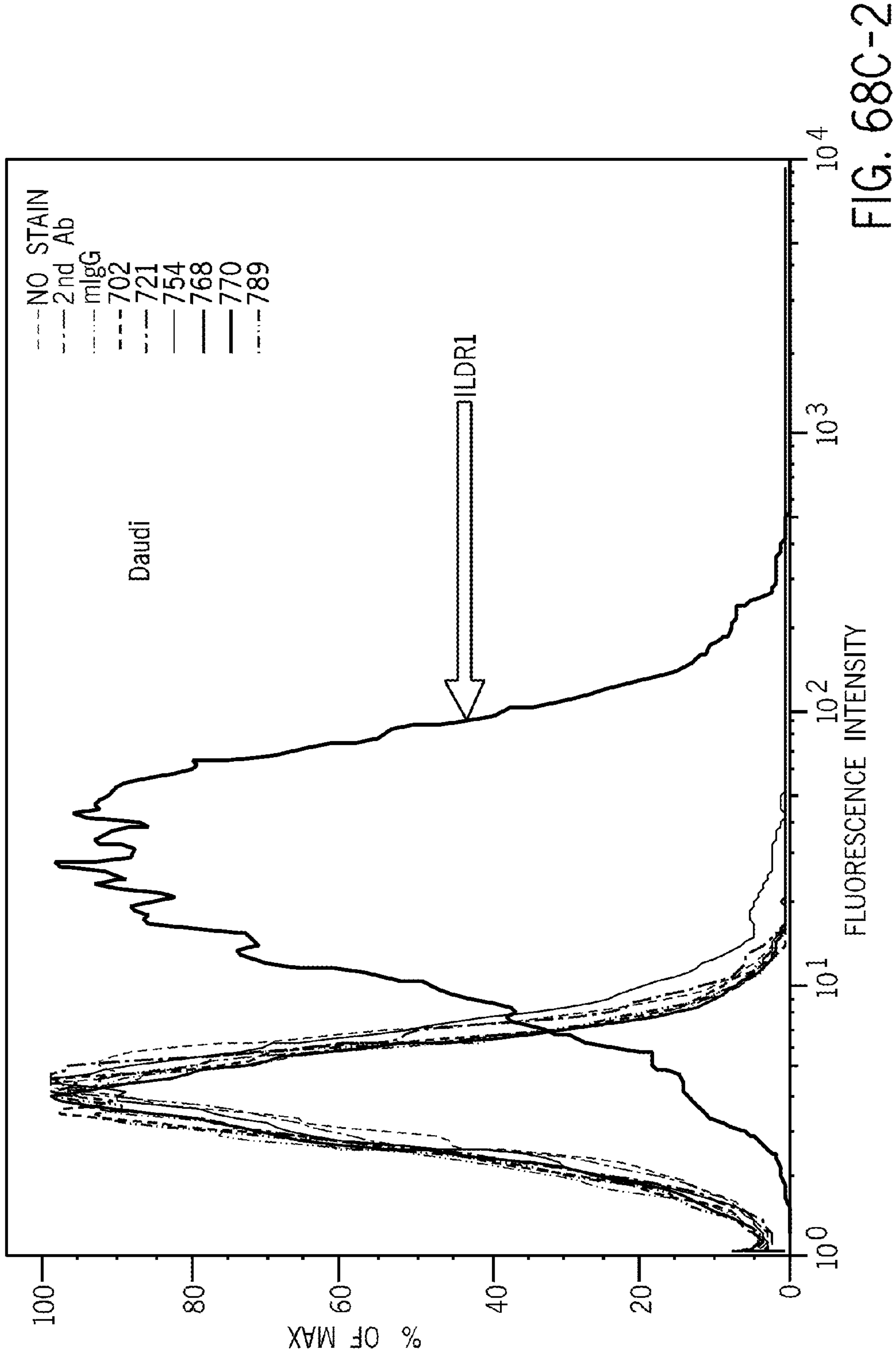

FIG. 68C illustrates the binding of the Fc-fused ECDs of the B7-like proteins of the invention (ILDR1-ECD-Fc (SEQ ID NO:107), C1ORF32-ECD-Fc (SEQ ID NO:105), AI216611-ECD-Fc (SEQ ID NO:104), LOC253012-ECD-Fc (SEQ ID NO:106), FXYD3-ECD-Fc (SEQ ID NO:103), and VSIG1-ECD-Fc (SEQ ID NO:108)) to the B cell lymphoma cell lines. ILDR1-ECD-Fc (SEQ ID NO:107) showed a clear binding the both B cell lymphoma cell lines.

Example 16

Interaction of the ECD-Fc Fused Proteins of the Invention with Known B7

The interaction of AI216611 proteins of the invention with various known ligands of the B7 family was analyzed. Since AI216611 was predicted as a presumed CD28 receptor it was hypothesized to bind to a known B7 ligand, B7H4, which is considered orphan (its counterpart receptor has not yet been recognized).

The analysis of the interaction between B7H4-Ig (R&D Systems, Inc. cat.#4206-B7) and Fc fused AI216611 ECD (SEQ ID NO:104) was conducted using the BIAcore 3000 system (Uppsala, Sweden) (Pharmacia Biosensor, Uppsala, Sweden) that employs surface Plasmon resonance for directly measuring intermolecular interactions. Fc fused AI216611 ECD (SEQ ID NO:104) (400-500 resonance units (RU)) was immobilized directly to the sensor CM5 chip. Solution containing two different concentrations of B7H4-Ig (5 and 10 micro molar) was injected. As control, the solutions were also injected onto an empty flow cell with no ligand immobilized.

Data was analyzed using BIAevaluation software (GraphPad Software Inc., San Diego Calif.). A zero baseline level was obtained by subtracting the background responses from injection of the analytes through a control flow cell with no ligand immobilized.

Figure 69:
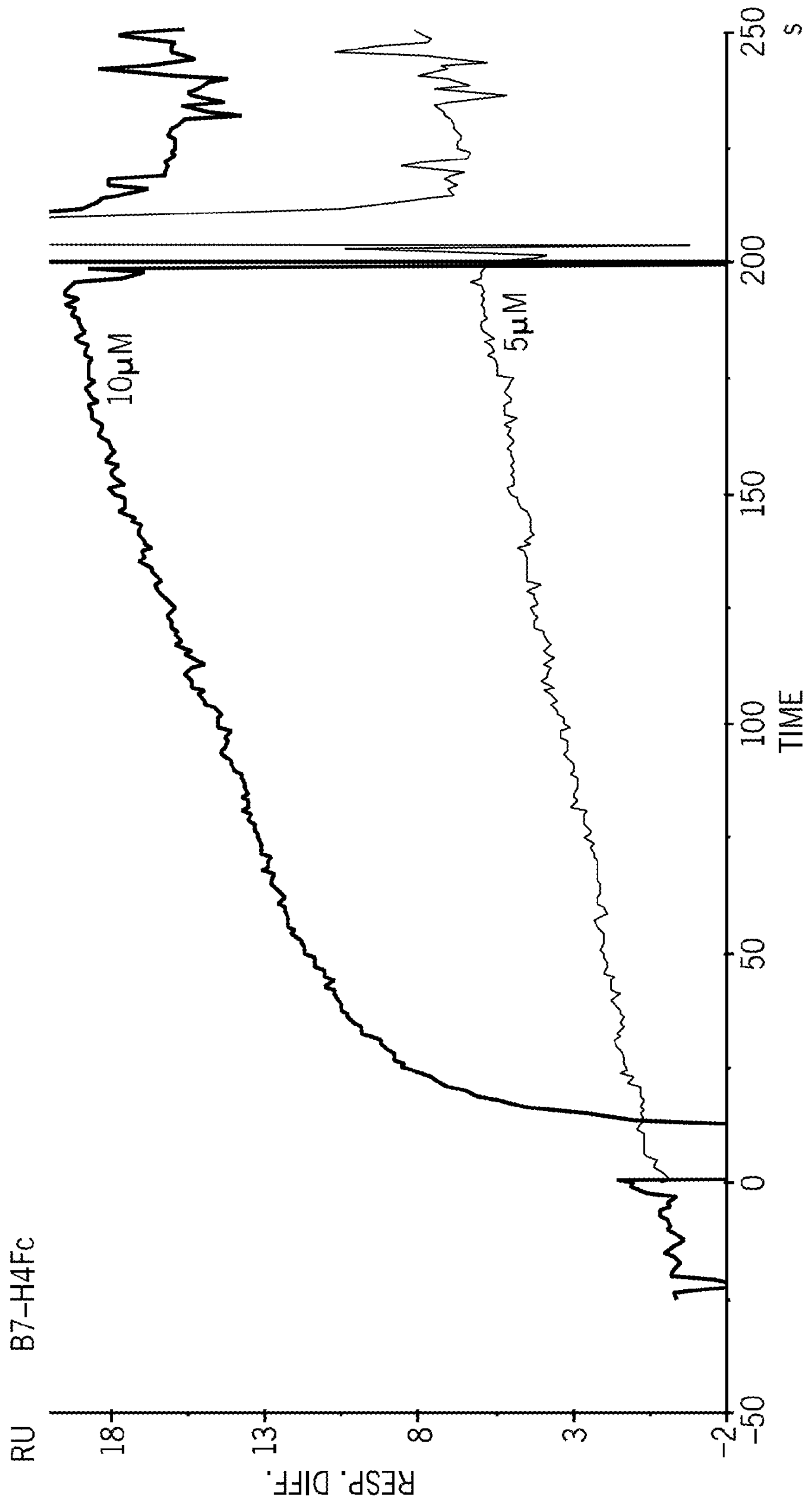
FIG. 69 shows BIACORE results demonstrating interaction between AI216611 and B7H4.

As can be seen from FIG. 69, a slight interaction between Fc fused AI216611 ECD (SEQ ID NO:104) and B7H4 was found in 5 and 10 µM of AI216611.

Example 17

Development of Mouse Monoclonal Anti-VSIG1, Anti-ILDR1, Anti-LOC253012, Anti-AI216611, Anti-C1ORF32 and Anti-FXYD3 Antibodies In order to test the expression of B7-Like proteins in different cancer tissues by immunohistochemistry, monoclonal mouse antibodies specific for Fc-fused ECDs of the proteins of invention were developed.

Development of Mouse Monoclonal Antibodies:

Four groups of the Balb/c mice (3 mice per group) were immunized with 4 Fc-fused ECDs proteins of the invention: VSIG1 (SEQ ID NO:108), LOC253012 (SEQ ID NO:106), C1ORF32 (SEQ ID NO:105) and FXYD3 (SEQ ID NO:103). The immunizations were performed 8 times at one week intervals in multiple sites, subcutaneous and intraperitoneal. Mice were bled ten days following the 4th and 8th immunizations. Serum was screened for antibody titer using a Direct ELISA protocol described below.

ELISA plates were coated with 50 μl/well of 2.5 μg/mL Fc-fused proteins (VSIG1, LOC253012, C1ORF32, FXYD3 ECDs fused to mouse IgG2 Fc, SEQ ID NOs: 108, 106, 105, 103, respectively) diluted in DPBS for 1 hour at room temperature (RT). Human IgG fused to mouse Fc region was used as a negative control. After that, plates were blocked with 300 μl/well of 1% BSA/DPBS for 15 min at RT. Following the blocking step, serially diluted sera from immunized mice and irrelevant mouse IgG were transferred to the blocked ELISA plates and incubated for 1 hour at RT. Afterwards, plates were washed 3 times with 300 μl/well washing buffer (DPBS with 0.05% Tween 20, pH 7.2-7.4). For detection, plates were incubated for 1 hour at RT with 50 μl/well of Goat anti-Mouse Kappa Light Chain Antibody at 1:1000 dilution followed by an extensive wash (6 times with 300 μl/well of washing buffer) and incubation with the substrate. The substrate, 2,2'-Azino-bis-(3-ethylbenzthiazoline-6-sulfonic acid (ABTS), at 100 μL/well was added and incubated for about 5 min at RT before plates were read at 414 nm using a Molecular Devices SPECTRAmax 340 PC plate reader and SOFTmax PRO software.

Serum antibody titer was defined as the dilution of serum that produces a signal that was twice that of the background.

Results of the ELISA test of the immunized sera after 4 immunizations are summarized in the Table 140. Data show that after 4 immunizations, 2 mice groups (immunized with LOC253012 and VSIG1 Fc fused proteins ECDs) developed antibody titers sufficient for hybridoma production.

The mice that showed highest antibody serum titers, were selected for hybridoma production. The splenocytes were fused with mouse myeloma cell line Ag8.653. The supernatant of the hybridoma clones were tested by direct ELISA (as described above) using plates coated with relevant and irrelevant coatings. The results are summzarised in Table 141A and Table 141B.

The results demonstrate that production of hybridoma cell lines resulted in 14 clones specifically recognizing LOC253012 (Table 141A, bold) and 14 clones specifically recognizing VSIG1 (Table 141B, bold).

For the rest of the proteins, four additional immunizations were performed in order to facilitate the serum antibody titers development for the rest of the proteins. The sera titers after the 8th immunization were tested by direct ELISA. Results are summarized in Table 142. The results demonstrate that after 8 immunizations the mice immunized with FXYD-Fc fused ECD (SEQ ID NO:103) and C1ORF32-Fc fused ECD (SEQ ID NO:103) developed sufficient antibody titers for hybridoma production. In the next step, the best responders will be selected for hybridoma production and monoclonal antibody manufacturing.

Mouse monoclonal anti-ILDR1 and anti-AI216611 antibodies are developed similarly.

The Monoclonal Antibodies for each of the antigens of the invention (VSIG1, LOC253012, C1ORF32, FXYD3, AI216611 and ILDR1, SEQ ID NOs: 108, 106, 105, 103, 104 and 107, respectively) are used for Immunohistochemistry analysis in order to verify the expression profile of each of these putative proteins in cancer and healthy tissues.

TABLE 140

Antibody sera titers of the immunized mice after 4 immunizations.

| | | ELISA Plates Coatings. | | | | |
|---|---|---|---|---|---|---|
| Immunogen | Mouse # | C1ORF32 | FXYD3 | LOC253012 | VSIG1 | human IgG-moFc |
| C1ORF32 | 167229 | 378 | 212 | <50 | 181 | 152 |
| | 167230 | 612 | 319 | <50 | 383 | 159 |
| | 167231 | 599 | 445 | 276 | 934 | 398 |
| FXYD3 | 167232 | 1,409 | 2,532 | 962 | 2,229 | 1,433 |
| | 167233 | 1,379 | 2,320 | 695 | 2,777 | 1,211 |
| | 167234 | 1,585 | 4,604 | 615 | 3,625 | 1,751 |
| LOC253012 | 167223 | <50 | 51 | 18,869 | <50 | 68 |
| | 167224 | <50 | 93 | 9,939 | 73 | 156 |
| | 167225 | 93 | 560 | 3,025 | 268 | 116 |
| VSIG1 | 167226 | <50 | <50 | <50 | 10,653 | <50 |
| | 167227 | 158 | 603 | <50 | 18,085 | 58 |
| | 167228 | 412 | 751 | 58 | 93,059 | 83 |

TABLE 141A

Post fusional clones resulted from mouse #167223, immunized with LOC253012

| | ELISA Plates Coatings | | | | |
|---|---|---|---|---|---|
| Clone ID | C1ORF32 | FXYD3 | LOC253012 OD at 441 nm | VSIG1 | moFC |
| 2G2 | 0.188 | 0.214 | 2.296 | 0.216 | 0.278 |
| 3A8 | 2.053 | 2.450 | 1.926 | 1.787 | 0.326 |
| 4A8 | 0.201 | 0.225 | 2.553 | 0.222 | 0.279 |
| 6B10 | 0.227 | 0.206 | 2.335 | 0.227 | 0.293 |
| 8G10 | 0.476 | 0.346 | 1.562 | 0.267 | 0.487 |
| 8G11 | 0.192 | 0.200 | 2.178 | 0.220 | 0.274 |
| 10A3 | 0.189 | 0.190 | 1.654 | 0.215 | 0.272 |
| 10F2 | 0.246 | 0.247 | 1.720 | 0.242 | 0.350 |
| 12D5 | 0.198 | 0.190 | 1.619 | 0.224 | 0.291 |
| 13A4 | 0.252 | 0.221 | 1.847 | 0.228 | 0.312 |
| 13F11 | 0.219 | 0.194 | 1.865 | 0.223 | 0.296 |
| 13H2 | 0.216 | 0.229 | 1.404 | 0.255 | 0.300 |
| 14D11 | 0.199 | 0.230 | 2.183 | 0.225 | 0.294 |
| 16A10 | 1.285 | 2.130 | 1.239 | 0.972 | 0.277 |
| 16C10 | 2.159 | 2.516 | 1.927 | 1.908 | 0.273 |
| 16F10 | 0.183 | 0.179 | 0.235 | 0.203 | 0.271 |
| 17E5 | 0.188 | 0.193 | 1.943 | 0.214 | 0.270 |
| 18G4 | 0.202 | 0.209 | 1.843 | 0.216 | 0.284 |

TABLE 141B

Post fusional clones resulted from mouse #167228 immunized with VSIG1

| Clone ID | C1ORF32 | FXYD3 | LOC253012 | VSIG1 | moFC |
|---|---|---|---|---|---|
| | ELISA Plates Coatings. OD at 441 nm | | | | |
| 3F8 | 0.192 | 0.193 | 0.240 | 2.279 | 0.283 |
| 4D5 | 0.220 | 0.206 | 0.251 | 2.174 | 0.299 |
| 4D6 | 0.206 | 0.207 | 0.227 | 2.808 | 0.279 |
| 5B6 | 0.197 | 0.188 | 0.208 | 0.380 | 0.261 |
| 6G2 | 0.227 | 0.208 | 0.198 | 1.880 | 0.294 |
| 7C1 | 0.208 | 0.212 | 0.209 | 2.392 | 0.278 |
| 7E3 | 2.284 | 2.804 | 1.495 | 2.278 | 0.398 |
| 7H3 | 0.207 | 0.232 | 0.197 | 1.530 | 0.295 |
| 9F4 | 0.226 | 0.274 | 0.175 | 1.965 | 0.372 |
| 10B10 | 0.228 | 0.274 | 0.219 | 0.407 | 0.330 |
| 11B2 | 0.214 | 0.247 | 0.207 | 2.733 | 0.316 |
| 11F3 | 2.638 | 3.052 | 1.919 | 2.575 | 0.313 |
| 11G10 | 0.244 | 0.249 | 0.191 | 2.076 | 0.337 |
| 13A1 | 0.240 | 0.239 | 0.195 | 2.469 | 0.316 |
| 13H5 | 2.782 | 2.886 | 1.963 | 2.305 | 0.293 |
| 14D8 | 0.218 | 0.230 | 0.187 | 2.660 | 0.294 |
| 15E8 | 0.211 | 0.240 | 0.180 | 1.966 | 0.293 |
| 17E6 | 0.602 | 0.547 | 0.271 | 0.341 | 0.662 |
| 19G6 | 0.439 | 0.490 | 0.245 | 1.279 | 0.318 |

TABLE 142

Antibody sera titers of the immunized mice after 8 immunizations.

| Immunogen | Mouse # | C1ORF32 | FXYD3 | LOC253012 | VSIG1 | human IgG-moFc |
|---|---|---|---|---|---|---|
| | | ELISA Plates Coatings | | | | |
| C1ORF32 | 167229 | 21,760 | 2,192 | 295 | 300 | 2,287 |
| | 167230 | 69,543 | 613 | 59 | 265 | 693 |
| | 167231 | 23,100 | 1,952 | 756 | 1,645 | 2,487 |
| FXYD3 | 167232 | 3,237 | 58,240 | 1,564 | 2,622 | 6,515 |
| | 167233 | 5,061 | 10,786 | 2,125 | 4,959 | 7,664 |
| | 167234 | 3,445 | 122,929 | 811 | 2,267 | 7,061 |
| LOC253012 | 167223 | Fused | | | | |
| | 167224 | 2,641 | 18,011 | 328,050 | 5,491 | 260 |
| | 167225 | 6,132 | 23,589 | 173,452 | 7,662 | 90 |
| VSIG1 | 167226 | 819 | 6,096 | 207 | 471,316 | 89 |
| | 167227 | 39,852 | 102,238 | 18,463 | 532,487 | 256 |
| | 167228 | Fused | | | | |

Immunohistochemical Analysis

Immunohistochemistry enables the visualization (using light or confocal microscopy) of the tissue distribution of specific antigens (or epitopes). The process localizes protein targets of interest by applying specific monoclonal or polyclonal antibodies to tissue surfaces in a process called antibody incubation.

This method involves detection of a substrate in situ in fixed cells by substrate specific antibodies. The substrate specific antibodies may be enzyme linked or linked to fluorophores. Detection is carried out by microscopy and subjective evaluation. If enzyme linked antibodies are employed, a colorimetric reaction may be required.

The immunohistochemical analysis performed for the antigens of the invention (VSIG1, LOC253012, C1ORF32, FXYD3, AI216611 and ILDR1, SEQ ID NOs: 108, 106, 105, 103, 104 and 107, respectively) consist of two phases:

Phase I: Antibody calibration: A dilution series of each of the antibodies developed against the specific protein antigens is run using selected formalin-fixed paraffin-embedded (FFPE) control tissues and cell lines. The best performing antibody is selected for Phase II.

Phase II: Protein distribution and localization analysis: Using the optimal antibody concentration selected in Phase I, the distribution and localization of VSIG1, LOC253012, C1ORF32, FXYD3, AI216611 and ILDR1 proteins is analyzed in Tissue Arrays consisting of cancer and healthy tissues, looking for differential expression of the in some of the cancer samples, as compared with healthy samples.

Example 17

Development of Fully Human Anti-VSIG1, Anti-ILDR1, Anti-LOC253012, Anti-AI216611, Anti-C1ORF32 and Anti-FXYD3 Antibodies Generation Of Human Monoclonal Antibodies Against VSIG1, ILDR1, LOC253012, AI216611, C1ORF32 and FXYD3 Antigen Fusion proteins composed of the extracellular domain of the VSIG1, ILDR1, LOC253012, AI216611, C1ORF32 and FXYD3 linked to a mouse IgG2 Fc polypeptide are generated by standard recombinant methods and used as antigen for immunization.

Transgenic HuMab Mouse.

Fully human monoclonal antibodies to VSIG1, ILDR1, LOC253012, AI216611, C1ORF32 and FXYD3 are prepared using mice from the HCo7 strain of the transgenic HuMab Mouse. RTM., which expresses human antibody genes. In this mouse strain, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al. (1996) Nature Biotechnology 14:845-851, and a human heavy chain transgene, HCo7, as described in U.S. Pat. Nos. 5,545,806; 5,625,825; and 5,545,807.

HuMab Immunizations:

To generate fully human monoclonal antibodies to VSIG1, ILDR1, LOC253012, AI216611, C1ORF32 and FXYD3, mice of the HCo7 HuMab Mouse. RTM. (strain can be immunized with purified recombinant VSIG1 fusion protein derived from mammalian cells that are transfected with an expression vector containing the gene encoding the fusion protein. General immunization schemes for the HuMab Mouse. RTM. are described in Lonberg, N. et al (1994) Nature 368(6474): 856-859; Fishwild, D. et al.

(1996) Nature Biotechnology 14: 845-851 and PCT Publication WO 98/24884. The mice are 6-16 weeks of age upon the first infusion of antigen. A purified recombinant VSIG1 antigen preparation (5-50 .mu.g, purified from transfected mammalian cells expressing VSIG1 fusion protein) is used to immunize the HuMab mice intraperitoneally.

Transgenic mice are immunized twice with antigen in complete Freund's adjuvant or Ribi adjuvant IP, followed by 3-21 days IP (up to a total of 11 immunizations) with the antigen in incomplete Freund's or Ribi adjuvant. The immune response is monitored by retroorbital bleeds. The plasma is screened by ELISA (as described below), and mice with sufficient titers of anti-VSIG1 human immunoglobulin are used for fusions. Mice are boosted intravenously with antigen 3 days before sacrifice and removal of the spleen.

Selection of HuMab mice.TM. Producing Anti-VSIG1, ILDR1, LOC253012, AI216611, C1ORF32 and FXYD3 Antibodies:

To select HuMab mice.TM. producing antibodies that bind VSIG1, ILDR1, LOC253012, AI216611, C1ORF32 or FXYD3 sera from immunized mice is tested by a modified ELISA as originally described by Fishwild, D. et al. (1996). Briefly, microtiter plates are coated with purified recombinant VSIG1 fusion protein at 1-2 .mu.g/ml in PBS, 50 .mu.l/wells incubated 4 degrees C. overnight then blocked with 200 .mu.l/well of 5% BSA in PBS. Dilutions of plasma from VSIG1, ILDR1, LOC253012, AI216611, C1ORF32 or FXYD3-immunized mice are added to each well and incubated for 1-2 hours at ambient temperature. The plates are washed with PBS/Tween and then incubated with a goat-anti-human kappa light chain polyclonal antibody conjugated with alkaline phosphatase for 1 hour at room temperature. After washing, the plates are developed with pNPP substrate and analyzed by spectrophotometer at OD 415-650. Mice that developed the highest titers of anti-VSIG1, anti-ILDR1, anti-LOC253012, anti-AI216611, anti-C1ORF32 or anti-FXYD3 antibodies are used for fusions. Fusions are performed as described below and hybridoma supernatants are tested for anti-VSIG1, anti-ILDR1, anti-LOC253012, anti-AI216611, anti-C1ORF32 or anti-FXYD3 activity by ELISA.

Generation of Hybridomas Producing Human Monoclonal Antibodies to VSIG1, ILDR1, LOC253012, AI216611, C1ORF32 or FXYD3

The mouse splenocytes, isolated from the HuMab mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of P3X63 Ag8.6.53 (ATCC CRL 1580) nonsecreting mouse myeloma cells with 50% PEG (Sigma). Cells are plated at approximately 1×10-5/well in flat bottom microtiter plate, followed by about two week incubation in selective medium containing 10% fetal calf serum, supplemented with origen (IGEN) in RPMI, L-glutamine, sodium pyruvate, HEPES, penicillin, streptamycin, gentamycin, 1×HAT, and beta-mercaptoethanol. After 1-2 weeks, cells are cultured in medium in which the HAT is replaced with HT. Individual wells are then screened by ELISA (described above) for human anti-VSIG1, anti-ILDR1, anti-LOC253012, anti-AI216611, anti-C1ORF32 or anti-FXYD3 monoclonal IgG antibodies. Once extensive hybridoma growth occurred, medium is monitored usually after 10-14 days. The antibody secreting hybridomas are replated, screened again and, if still positive for human IgG, anti-VSIG1, anti-ILDR1, anti-LOC253012, anti-AI216611, anti-C1ORF32 or anti-FXYD3 monoclonal antibodies are subcloned at least twice by limiting dilution. The stable subclones are then cultured in vitro to generate small amounts of antibody in tissue culture medium for further characterization.

Hybridoma clones are selected for further analysis.

Structural Characterization Of Desired Anti-VSIG1, anti-ILDR1, anti-LOC253012, anti-AI216611, anti-C1ORF32 or anti-FXYD3 Human Monoclonal Antibodies The cDNA sequences encoding the heavy and light chain variable regions of the obtained anti-VSIG1, anti-ILDR1, anti-LOC253012, anti-AI216611, anti-C1ORF32 or anti-FXYD3 monoclonal antibodies are obtained from the resultant hybridomas, respectively, using standard PCR techniques and are sequenced using standard DNA sequencing techniques.

The nucleotide and amino acid sequences of the heavy chain variable region and of the light chain variable region are identified. These sequences may be compared to known human germline immunoglobulin light and heavy chain sequences and the CDRs of each heavy and light of the obtained anti-VSIG1, anti-ILDR1, anti-LOC253012, anti-AI216611, anti-C1ORF32 or anti-FXYD3 sequences identified.

Characterization of Binding Specificity and Binding Kinetics of Anti-VSIG1, Anti-ILDR1, Anti-LOC253012, Anti-AI216611, Anti-C1ORF32 or Anti-FXYD3 Human Monoclonal Antibodies The binding affinity, binding kinetics, binding specificity, and cross-competition of anti-VSIG1, anti-ILDR1, anti-LOC253012, anti-AI216611, anti-C1ORF32 or anti-FXYD3 antibodies are examined by Biacore analysis. Also, binding specificity is examined by flow cytometry.

Binding Affinity and Kinetics

Anti-VSIG1, anti-ILDR1, anti-LOC253012, anti-AI216611, anti-C1ORF32 or anti-FXYD3 antibodies produced according to the invention are characterized for affinities and binding kinetics by Biacore analysis (Biacore AB, Uppsala, Sweden). Purified recombinant human VSIG1, ILDR1, LOC253012, AI216611, C1ORF32 or FXYD3 fusion protein is covalently linked to a CM5 chip (carboxy methyl dextran coated chip) via primary amines, using standard amine coupling chemistry and kit provided by Biacore. Binding is measured by flowing the antibodies in HBS EP buffer (provided by BIAcore AB) at a concentration of 267 nM at a flow rate of 50 .mu.l/min. The antigen-association antibodies association kinetics is followed for 3 minutes and the dissociation kinetics is followed for 7 minutes. The association and dissociation curves are fit to a 1:1 Langmuir binding model using BIAevaluation software (Biacore AB). To minimize the effects of avidity in the estimation of the binding constants, only the initial segment of data corresponding to association and dissociation phases are used for fitting.

Epitope Mapping of Obtained Anti-VSIG1, Anti-ILDR1, Anti-LOC253012, Anti-AI216611, Anti-C1ORF32 or Anti-FXYD3 Antibodies Biacore is used to determine epitope grouping of anti-VSIG1, anti-ILDR1, anti-LOC253012, anti-AI216611, anti-C1ORF32 or anti-FXYD3 HuMAbs. Obtained anti-VSIG1, anti-ILDR1, anti-LOC253012, anti-AI216611, anti-C1ORF32 or anti-FXYD3 antibodies are used to map their epitopes on the VSIG1, ILDR1, LOC253012, AI216611, C1ORF32 or FXYD3 antigen, respectively. These different antibodies are coated on three different surfaces of the same chip to 8000 RUs each. Dilutions of each of the mAbs are made, starting at 10 mu.g/mL and is incubated with Fc fused VSIG1, ILDR1, LOC253012, AI216611, C1ORF32 or FXYD3 (50 nM) for one hour. The incubated complex is injected over all the three surfaces (and a blank surface) at the same time for 1.5 minutes at a flow rate of 20 .mu.L/min. Signal from each surface at end of 1.5 minutes, after subtraction of appropriate blanks, has been plotted against concentration of mAb in the complex. Upon analysis of the data, the anti-VSIG1, anti-ILDR1, anti-LOC253012, anti-AI216611, anti-C1ORF32 or anti-FXYD3 antibodies are categorized into different epitope groups depending on the epitope mapping results. The functional properties thereof are also compared.

Chinese hamster ovary (CHO) cell lines that express VSIG1, ILDR1, LOC253012, AI216611, C1ORF32 or FXYD3 protein at the cell surface are developed and used to determine the specificity of the VSIG1, ILDR1, LOC253012, AI216611, C1ORF32 or FXYD3 HuMAbs by flow cytometry. CHO cells are transfected with expression plasmids containing full length cDNA encoding a transmembrane forms of VSIG1, ILDR1, LOC253012, AI216611, C1ORF32 or FXYD3 antigen or a variant thereof. The transfected proteins contained an epitope tag at the N-terminus are used for detection by an antibody specific for the epitope. Binding of a anti-VSIG1, anti-ILDR1, anti-LOC253012, anti-AI216611, anti-C1ORF32 or anti-FXYD3 MAb is assessed by incubating the transfected cells with each of the VSIG1, ILDR1, LOC253012, AI216611, C1ORF32 or FXYD3 Abs at a concentration of 10 mu.g/ml. The cells are washed and binding is detected with a FITC-labeled anti-human IgG Ab. A murine anti-epitope tag Ab, followed by labeled anti-murine IgG, is used as the positive control. Non-specific human and murine Abs are used as negative controls. The obtained data is used to assess the specificity of the HuMAbs for the VSIG1, ILDR1, LOC253012, AI216611, C1ORF32 or FXYD3. antigen target.

These antibodies and other antibodies specific to VSIG1, ILDR1, LOC253012, AI216611, C1ORF32 or FXYD3 may be used in the afore-described anti-VSIG1, ILDR1, LOC253012, AI216611, C1ORF32 or FXYD3 related therapies such as treatment of cancers wherein VSIG1, ILDR1, LOC253012, AI216611, C1ORF32 or FXYD3 antigen is differentially expressed such as lung cancer, colon cancer and ovarian cancer and/or for modulating (enhancing or inhibiting) B7 immune co-stimulation involving the VSIG1, ILDR1, LOC253012, AI216611 or C1ORF32 antigen such as in the treatment of cancers and autoimmune diseases wherein such antibodies will e.g., prevent negative stimulation of T cell activity against desired target cancer cells or prevent the positive stimulation of T cell activity thereby eliciting a desired anti-autoimmune effect.

The invention has been described and prophetic embodiments provided relating to manufacture and selection of desired anti-VSIG1, ILDR1, LOC253012, AI216611, C1ORF32 or FXYD3 antibodies for use as therapeutics and diagnostic methods wherein the disease or condition is associated with VSIG1, ILDR1, LOC253012, AI216611, C1ORF32 or FXYD3 antigen. The invention is now further described by the claims which follow.

What is claimed is:

1. An isolated polypeptide comprising the polypeptide of amino acid sequence SEQ ID NO: 299.

2. An isolated polypeptide comprising a sequence of amino acid residues having at least 95% sequence identity with amino acid residues 21-184 of SEQ ID NO:299.

3. An isolated polypeptide comprising the polypeptide of amino acid sequence SEQ ID NO: 299 and a functional group that improves stability, penetration through cellular membranes, penetration through tissue barriers, tissue localization, efficacy, or causes decreased clearance, decreased toxicity, improved selectivity, or improved resistance to expulsion by cellular pumps.

4. The isolated polypeptide of claim 3, having at least one peptidomimetic organic moiety.

5. An isolated polypeptide comprising the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, wherein the polypeptide has been chemically modified, and wherein the chemical modification is selected from acetylation, acylation, amidation, ADP-ribosylation, glycosylation, GPI anchor formation, covalent attachment of a lipid or lipid derivative, methylation, myristylation, pegylation, prenylation, phosphorylation, and ubiquitination.

6. A fusion protein comprising an isolated polypeptide comprising the polypeptide of amino acid sequence SEQ ID NO: 299; the polypeptide of amino acid sequence SEQ ID NO: 299 and a functional group that improves stability, penetration through cellular membranes, penetration through tissue barriers, tissue localization, efficacy, or causes decreased clearance, decreased toxicity, improved selectivity, or improved resistance to expulsion by cellular pumps; or the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, wherein the polypeptide has been chemically modified, and wherein the chemical modification is selected from acetylation, acylation, amidation, ADP-ribosylation, glycosylation, GPI anchor formation, covalent attachment of a lipid or lipid derivative, methylation, myristylation, pegylation, prenylation, phosphorylation, and ubiquitination; joined to a heterologous polypeptide.

7. The fusion protein of claim 6, comprising a sequence of amino acid residues having at least 95% sequence identity with amino acid residues 21-184 of SEQ ID NO: 299 joined to a heterologous polypeptide.

8. The fusion protein of claim 6, wherein the heterologous sequence comprises a VASP domain.

9. The fusion protein of claim 6, wherein the heterologous sequence comprises at least a portion of an immunoglobulin molecule.

10. The fusion protein of claim 9, wherein said at least a portion of said immunoglobulin molecule comprises an immunoglobulin heavy chain constant region.

11. The fusion protein of claim 10, wherein the immunoglobulin heavy chain constant region is an Fc fragment.

12. The fusion protein of claim 11, wherein the immunoglobulin heavy chain constant region is an isotype selected from the group consisting of an IgG1, IgG2, IgG3, IgG4, IgM, IgE, IgA and IgD.

13. The fusion protein of claim 6, wherein the fusion protein modulates lymphocyte activation in vitro or in vivo.

14. A method of producing a fusion protein according to claim 6 or a protein comprising at least one of the polypeptide of amino acid sequence SEQ ID NO: 299; the polypeptide of amino acid sequence SEQ ID NO: 299 and a functional group that improves stability, penetration through cellular membranes, penetration through tissue barriers, tissue localization, efficacy, or causes decreased clearance, decreased toxicity, improved selectivity, or improved resistance to expulsion by cellular pumps; or the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, wherein the polypeptide has been modified, and wherein the modification is selected from acetylation, acylation, amidation, ADP-ribosylation, glycosylation, GPI anchor formation, covalent attachment of a lipid or lipid derivative, methylation, myristylation, prenylation, phosphorylation, and ubiquitination; the method comprising introducing a vector comprising a polynucleotide encoding for said protein to a recombinant cell; and producing the protein with the recombinant cell.

15. The method of claim 14, wherein the recombinant cell is a prokaryotic or eukaryotic cell.

16. The method of claim 15, wherein the recombinant cell is a mammalian cell, yeast cell, insect cell or bacterial cell.

17. The method of claim 16, wherein the recombinant cell is a CHO cell, a COS cell, or a 293 cell or *E. coli* cell.

18. A pharmaceutical composition comprising the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, and a pharmaceutically acceptable diluent or carrier.

19. A pharmaceutical composition comprising a fusion polypeptide comprising the polypeptide of amino acid sequence SEQ ID NO: 299 and a heterologous amino acid sequence, a polypeptide comprising amino acid residues 21-184 of SEQ ID NO: 299 and a heterologous amino acid sequence, or a polypeptide comprising a sequence of amino acid residues having at least 95% sequence identity with amino acid residues 21-184 of SEQ ID NO:299 and a heterologous amino acid sequence; or the polypeptide of amino acid sequence SEQ ID NO: 299 and a functional group that improves stability, penetration through cellular membranes, penetration through tissue barriers, tissue localization, efficacy, or causes decreased clearance, decreased toxicity, improved selectivity, or improved resistance to expulsion by cellular pumps and a heterologous amino acid sequence; or the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, wherein the polypeptide has been chemically modified, and wherein the chemical modification is selected from acetylation, acylation, amidation, ADP-ribosylation, glycosylation, GPI anchor formation, covalent attachment of a lipid or lipid derivative, methylation, myristylation, pegylation, prenylation, phosphorylation, and ubiquitination, and a heterologous amino acid sequence; and a pharmaceutically acceptable diluent or carrier.

20. A method for treating an autoimmune disease or preventing transplant rejection or graft versus host disease in a subject in need thereof comprising administering to the subject a therapeutically effective amount of any of polypeptide comprising the polypeptide of amino acid sequence SEQ ID NO: 299, polypeptide comprising amino acid residues 21-184 of SEQ ID NO: 299, or a polypeptide comprising a sequence of amino acid residues having at least 95% sequence identity with amino acid residues 21-184 of SEQ ID NO:299, or the pharmaceutical composition of claim 18.

21. A method for treating an autoimmune disease or preventing transplant rejection or graft versus host disease in a subject in need thereof comprising administering to the subject a therapeutically effective amount of any of a fusion polypeptide comprising the polypeptide of amino acid sequence SEQ ID NO: 299 and a heterologous amino acid sequence, a polypeptide comprising amino acid residues 21-184 of SEQ ID NO: 299 and a heterologous amino acid sequence, or a polypeptide comprising a sequence of amino acid residues having at least 95% sequence identity with amino acid residues 21-184 of SEQ ID NO:299 and a heterologous amino acid sequence; or the polypeptide of amino acid sequence SEQ ID NO: 299 and a functional group that improves stability, penetration through cellular membranes, penetration through tissue barriers, tissue localization, efficacy, or causes decreased clearance, decreased toxicity, improved selectivity, or improved resistance to expulsion by cellular pumps and a heterologous amino acid sequence; or the polypeptide of amino acid sequence SEQ ID NO: 299, a polypeptide comprising amino acid residues 21-184 of SEQ ID NO: 299, or a polypeptide comprising a sequence of amino acid residues having at least 95% sequence identity with amino acid residues 21-184 of SEQ ID NO:299, wherein the polypeptide has been chemically modified, and wherein the chemical modification is selected from acetylation, acylation, amidation, ADP-ribosylation, glycosylation, GPI anchor formation, covalent attachment of a lipid or lipid derivative, methylation, myristylation, pegylation, prenylation, phosphorylation, and ubiquitination, and a heterologous amino acid sequence; or the pharmaceutical composition of claim 19.

22. The method of claim 20, further comprising administering a moiety useful for treating an autoimmune disease, transplant rejection or graft versus host disease.

23. The method of claim 22, wherein the moiety is a cytokine antibody, cytokine receptor antibody, drug, or another immunomodulatory agent.

24. The method of claim 23, wherein the autoimmune disease is selected from a group consisting of multiple sclerosis; psoriasis; rheumatoid arthritis; systemic lupus erythematosus; Crohn's disease, ulcerative colitis; benign lymphocytic angiitis, lupus erythematosus, Hashimoto's thyroiditis, primary myxedema, Graves disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

25. The method of claim 21, further comprising administering a moiety useful for treating an autoimmune disease, transplant rejection or graft versus host disease.

26. The method of claim 25, wherein the moiety is a cytokine antibody, cytokine receptor antibody, drug, or another immunomodulatory agent.

27. The method of claim 26, wherein the autoimmune disease is selected from a group consisting of multiple sclerosis; psoriasis; rheumatoid arthritis; systemic lupus erythematosus; Crohn's disease, ulcerative colitis; benign lymphocytic angiitis, lupus erythematosus, Hashimoto's thyroiditis, primary myxedema, Graves disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

* * * * *